US012636290B2

(12) United States Patent
Meyers et al.

(10) Patent No.: US 12,636,290 B2
(45) Date of Patent: May 26, 2026

(54) BET INHIBITORS FOR MODULATING DUX4 EXPRESSION IN FSHD

(71) Applicant: Saint Louis University, St. Louis, MO (US)

(72) Inventors: Marvin J. Meyers, Wentzville, MO (US); Francis M. Sverdrup, Lake Saint Louis, MO (US); Timothy Caldwell, Lawrence, KS (US); Jonathan Oliva, Manchester, MO (US)

(73) Assignee: Saint Louis University, St. Louis, MO (US)

( * ) Notice: Subject to any disclaimer, the term of this patent is extended or adjusted under 35 U.S.C. 154(b) by 1096 days.

(21) Appl. No.: 17/416,378

(22) PCT Filed: Dec. 18, 2019

(86) PCT No.: PCT/US2019/067076
§ 371 (c)(1),
(2) Date: Jun. 18, 2021

(87) PCT Pub. No.: WO2020/132004
PCT Pub. Date: Jun. 25, 2020

(65) Prior Publication Data

US 2022/0079951 A1 Mar. 17, 2022

Related U.S. Application Data

(60) Provisional application No. 62/782,853, filed on Dec. 20, 2018.

(51) Int. Cl.

| | |
|---|---|
| ***A61K 31/551*** | (2006.01) |
| ***A61K 31/137*** | (2006.01) |
| ***A61K 31/4353*** | (2006.01) |
| ***A61K 31/44*** | (2006.01) |
| ***A61K 31/444*** | (2006.01) |
| ***A61K 31/4704*** | (2006.01) |
| ***A61K 31/4706*** | (2006.01) |
| ***A61K 31/4745*** | (2006.01) |
| ***A61K 31/496*** | (2006.01) |
| ***A61K 31/517*** | (2006.01) |
| ***A61K 31/5377*** | (2006.01) |
| ***A61K 31/5513*** | (2006.01) |
| ***A61K 31/5517*** | (2006.01) |
| ***A61P 21/00*** | (2006.01) |
| ***C07D 471/04*** | (2006.01) |
| ***C07D 519/00*** | (2006.01) |

(52) U.S. Cl.

CPC .......... *A61K 31/551* (2013.01); *A61K 31/137* (2013.01); *A61K 31/4353* (2013.01); *A61K 31/44* (2013.01); *A61K 31/444* (2013.01); *A61K 31/4704* (2013.01); *A61K 31/4706* (2013.01); *A61K 31/4745* (2013.01); *A61K 31/496* (2013.01); *A61K 31/517* (2013.01); *A61K 31/5377* (2013.01); *A61K 31/5513* (2013.01); *A61K 31/5517* (2013.01); *A61P 21/00* (2018.01); *C07D 471/04* (2013.01); *C07D 519/00* (2013.01)

(58) Field of Classification Search

CPC ..... C07D 471/04; C07D 519/00; A61P 21/00; A61K 31/137; A61K 31/4353; A61K 31/44; A61K 31/444; A61K 31/4704; A61K 31/4706; A61K 31/4745; A61K 31/496; A61K 31/517; A61K 31/5377; A61K 31/5513; A61K 31/5517

See application file for complete search history.

(56) References Cited

U.S. PATENT DOCUMENTS

| | | | |
|---|---|---|---|
| 5,945,418 | A | 8/1999 | Bemis et al. |
| 9,296,741 | B2 | 3/2016 | Wang et al. |
| 2002/0118671 | A1 | 8/2002 | Staples et al. |
| 2003/0232831 | A1 | 12/2003 | Dyckman et al. |
| 2004/0102636 | A1 | 5/2004 | Miller et al. |
| 2004/0132729 | A1 | 7/2004 | Salituro et al. |
| 2004/0254236 | A1 | 12/2004 | Dong et al. |
| 2004/0267012 | A1 | 12/2004 | Angell et al. |

(Continued)

FOREIGN PATENT DOCUMENTS

| | | |
|---|---|---|
| WO | WO 1999/000357 | 1/1999 |
| WO | WO 1999/032463 | 7/1999 |

(Continued)

OTHER PUBLICATIONS

Bosnakovski et al., "An isogenetic myoblast expression screen identifies DUX4-mediated FSHD-associated molecular pathologies", *EMBO J*, 27:2766-2779, 2008.

(Continued)

*Primary Examiner* — Kortney L. Klinkel
*Assistant Examiner* — Richard Grant Peckham
(74) *Attorney, Agent, or Firm* — pH IP Law

(57) ABSTRACT

The present disclosure provides BET inhibitors of the formula: wherein the variables are defined herein, as well as pharmaceutical compositions thereof. The present disclosure also provides methods of treating a patient comprising administering a bromo- and extra-terminal (BET) domain inhibitor for the treatment of FSHD which modulates DUX4 expression. In some embodiments, the present methods comprise using one or more BET inhibitors as a therapeutic agent for the treatment of FSHD patients including patients who are being treated with one or more palliative treatments such as therapy and/or agents which lead to increased muscle mass.

19 Claims, 1 Drawing Sheet

(56) References Cited

U.S. PATENT DOCUMENTS

| | | | |
|---|---|---|---|
| 2005/0020540 | A1 | 1/2005 | Angell et al. |
| 2005/0020590 | A1 | 1/2005 | Lang et al. |
| 2006/0122221 | A1 | 6/2006 | Angell et al. |
| 2007/0185175 | A1 | 8/2007 | Liu et al. |
| 2007/0213300 | A1 | 9/2007 | Liu et al. |
| 2008/0171741 | A1 | 7/2008 | Wrobleski et al. |
| 2009/0118272 | A1 | 5/2009 | Liu et al. |
| 2009/0136596 | A1 | 5/2009 | Munson et al. |
| 2009/0143422 | A1 | 6/2009 | Munson et al. |
| 2011/0077243 | A1 | 3/2011 | Hynes |
| 2011/0190292 | A1 | 8/2011 | Dhar et al. |
| 2017/0340605 | A1 | 11/2017 | Albrecht et al. |
| 2017/0342067 | A1 | 11/2017 | Albrecht et al. |

FOREIGN PATENT DOCUMENTS

| | | | |
|---|---|---|---|
| WO | WO 2000/012074 | 3/2000 | |
| WO | WO 2000/012497 | 3/2000 | |
| WO | WO 2003/068747 | 8/2003 | |
| WO | WO 2003/093248 | 11/2003 | |
| WO | WO 2004/010995 | 2/2004 | |
| WO | WO 2005/012241 | 2/2005 | |
| WO | WO 2005/073189 | 8/2005 | |
| WO | WO 2009/155388 | 12/2009 | |
| WO | WO 2010/067131 | 6/2010 | |
| WO | WO 2012/031057 | 3/2012 | |
| WO | WO 2014/125408 | 8/2014 | |
| WO | WO-2014206150 A1 * | 12/2014 | A61K 31/437 |
| WO | WO 2015/081203 | 6/2015 | |
| WO | WO-2016077378 A1 * | 5/2016 | A61K 31/40 |
| WO | WO-2016077380 A1 * | 5/2016 | A61K 31/437 |
| WO | WO-2016118951 A2 * | 7/2016 | A61K 31/437 |

OTHER PUBLICATIONS

Cuadrado et al., "Mechanisms and function of p38 MAPK signaling", *Biochem J.*; 429(3):403-17, 2010.
Das & Chadwick, "Influence of Repressive Histone and DNA Methylation upon D4Z4 Transcription in Non-Myogenic Cells", *PLoS One*, 11:e0160022, 2016.
De Iaco et al., "DUX-family transcription factors regulate zygotic genome activation in placental mammals", *Nat Genet*, 49:941-945, 2017.
Feng et al., "A general strategy to construct small molecule biosensors in eukaryotes", *Elife*, 4:e10606, 2015.
Gangwal et al., "p38 Mitogen-Activated Protein Kinase Inhibitors: A Review on Pharmacophore Mapping and QSAR Studies", *Current Topics in Medicinal Chemistry*, 13(9):1015-1035, 2013.
Geng et al., "DUX4 activates germline genes, retroelements, and immune mediators: implications for facioscapulohumeral dystrophy", *Dev Cell*, 22:38-51, 2012.
Hardy et al., "Comparative Study of Injury Models for Studying Muscle Regeneration in Mice", *PLoS One*, 11:e0147198, 2016.
Hendrickson et al., "Conserved roles of mouse DUX and human DUX4 in activating cleavage-stage genes and MERVL/HERVL retrotransposons", *Nat Genet*, 49:925-934, 2017.
Hucklenbroich et al., "Aromatic-turmerone induces neural stem cell proliferation in vitro and in vivo", *Stem Cell Research & Therapy*, 5:100, 2014.
International Preliminary Report on Patentability for PCT/US2019/067076, dated Jun. 16, 2021, 8 pages.
International Search Report and Written Opinion for PCT/US2019/067076, dated Mar. 31, 2020, 11 pages.
Invitation to Pay Additional Fees for PCT/US2019/067076, dated Feb. 5, 2020, 3 pages.
Karcher and Laufer, "Aza-Analogue Dibenzepinone Scaffolds as p38 Mitogen-Activated Protein Kinase Inhibitors: Design, Synthesis, and Biological Data of Inhibitors with Improved Physicochemical Properties", *J. Med. Chem.*, 52, 1778-1782, 2009.
Kimble et al., "Simultaneous Block of Interleukin-1 and Tumor Necrosis Factor Is Required to Completely Prevent Bone Loss in the Early Postovariectomy Period", *Endocrinol.*, 136:3054-61, 1995.
Koeberle et al., "Design, Synthesis, and Biological Evaluation of Novel Disubstituted Dibenzosuberones as Highly Potent and Selective Inhibitors of p38 Mitogen Activated Protein Kinase", *J. Med. Chem.*, 55, 5868-5877, 2012.
Kostenko et al., "Physiological roles of mitogen-activated-protein-kinase-activated p38-regulated/activated protein kinase", *World J Biol Chem.* 26; 2(5):73-89, 2011.
Kowaljow et al., "The DUX4 gene at the FSHDIA locus encodes a pro-apoptotic protein", *Neuromuscul Disord*, 17:611-623, 2007.
Kumar et al., "p38 MAP kinases: key signalling molecules as therapeutic targets for inflammatory diseases", *Nat. Rev. Drug Discov.*, 2(9):717-726, 2003.
Lee et al., "Inhibition of p38 MAP kinase as a therapeutic strategy", *Immunopharmacology*, 47(2-3):185-201, 2000.
Lemmers et al., "A Unifying Genetic Model for Facioscapulohumeral Muscular Dystrophy", *Science*, 329:1650-1653, 2010.
Lemmers et al., "Digenic inheritance of an SMCHD1 mutation an dan FSHD-permissive D4Z4 allel causes facioscapulohumeral muscular dystrophy type 2", *Nat. Genet.*, 44:1370-1374, 2012.
Marber et al., "The p38 mitogen-activated protein kinase pathway-a potential target for intervention in infarction, hypertrophy, and heart failure", *J Mol Cell Cardiol.*; 51(4):485-90, 2011.
Norman, "Investigational p38 inhibitors for the treatment of chronic obstructive pulmonary disease", *Expert Opin. Investig. Drugs*, 24(3):383-392, 2015.
Rickard et al., "Endogenous DUX4 expression in FSHD myotubes is sufficient to cause cell death and disrupts RNA splicing and cell migration pathways", *Hum Mol Genet*, 24:5901-5914, 2015.
Shadle et al., "DUX4-induced dsRNA and MYC mRNA stabilizing activate apoptotic pathways in human cell models of facioscapulohumeral dystrophy", *PLoS Genet*, 13:e1006658, 2017.
Snider et al., "Facioscapulohumeral Dystrophy: Incomplete Suppression of a Retrotransposed Gene", *PLoS Genet*, 6:e1001181, 2010.
Snider et al., "RNA transcripts, miRNA-sized fragments and proteins produced from D4Z4 units: new candidates for the pathophysiology of facioscapulohumeral dystrophy", *Hum Mol Genet*, 18:2414-2430, 2009.
Tawil et al., "Facioscapulohumeral dystrophy: the path to consensus on pathophysiology", *Skeletal Muscle*, 4:12, 2014.
Van den Boogaard et al., "Mutations in $DNMT_3B$ Modify Epigenetic Repression of the $D_4Z_4$ Repeat and the Penetrance of Facioscapulohumeral Dystrophy", *Am. J. Hum. Genet.*, 98:1020-1029, 2016.
Van Overveld et al., "Hypomethylation of $D_4Z_4$ in 4q-linked and non-4q-linked facioscapulohumeral muscular dystrophy", *Nat Genet*, 35(4):315-317, 2003.
Wallace et al., "$DUX_4$, a candidate gene for facioscapulohumeral muscular dystrophy, causes p53-dependent myopathy in vivo", *Ann Neurol*, 69:540-552, 2011.
Whiddon et al., "Conservation and innovation in the DUX4-family gene network", *Nat Genet*, 49:935-940, 2017.
Winokur et al., "Expression profiling of FSHD muscle supports a defect in specific stages of myogenic differentiation", *Hum Mol Genet*, 12:2895-2907, 2003.
Yong et al., "The p38 MAPK inhibitors for the treatment of inflammatory diseases and cancer", *Expert Opin. Investig. Drugs*, 18(12):1893-1905, 2009.
Young et al., "DUX4 binding to retroelements creates promoters that are active in FSHD muscle and testis", *PLoS Genet*, 9:e1003947, 2013.
Zeng et al., Specific Loss of Histone H3 Lysine 9 Trimethylation and HP1y/Cohesion Binding at D4Z4 Repeats is Associated with Facioscapulohumeral Dystrophy (FSHD), *PLoS Genet*, 5:e1000559, 2009.

* cited by examiner

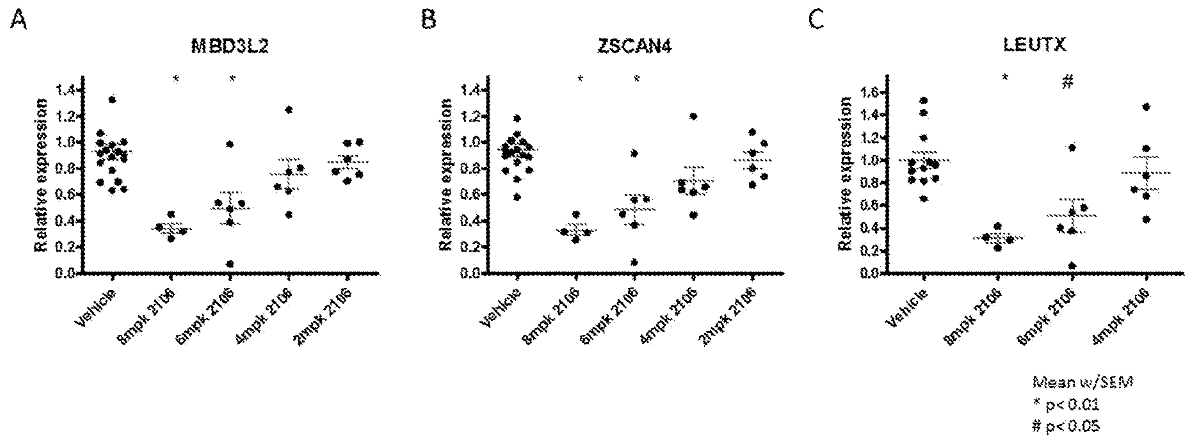
FIG. 1A-C

BET INHIBITORS FOR MODULATING DUX4 EXPRESSION IN FSHD

This application is a national phase application under 35 U.S.C. § 371 of International Application No. PCT/US2019/067076, filed Dec. 18, 2019, which claims the benefit of priority to U.S. Provisional Application No. 62/782,853, filed on Dec. 20, 2018, the entire contents of each of which are hereby incorporated by reference.

BACKGROUND

This invention was made with government support under Grant No. NS069539 awarded by the National Institutes of Health. The government has certain rights in the invention.

I. FIELD

The present disclosure relates to the fields of pharmaceuticals, medicine and cell biology. More specifically, it relates to pharmaceutical agents (compounds) which are useful as in the treatment of facioscapulohumeral muscular dystrophy (FSHD) through the modulation of expression of DUX4.

II. DESCRIPTION OF RELATED ART

Facioscapulohumeral dystrophy (FSHD) is a prevalent muscular dystrophy affecting over 800,000 individuals worldwide. The disease typically presents in young adults as facial and upper extremity weakness and progresses to involve nearly all skeletal muscle groups (Tawil et al., 2014). FSHD is caused by the mis-expression of the double homeobox 4 (DUX4) transcription factor in skeletal muscle. Because of its causative role in FSHD, suppressing DUX4 expression is a primary therapeutic approach for halting disease progression. However, the mechanisms responsible for DUX4 expression are poorly understood and limited drug targets have been identified. Consequently, there is currently no treatment available for FSHD and few clinical trials of promising therapies are ongoing. Therefore, there remains a need to identify new therapeutic agents that may be used in the treatment of FSHD through the modulation of DUX4 expression.

SUMMARY

In some aspects, the present disclosure provides BET inhibitors and methods of using BET inhibitors to treat facioscapulohumeral muscular dystrophy (FSHD). Without wishing to be bound by any theory, it is believed that the BET inhibitors may modulate the expression of DUX4 and thus exert their therapeutic activity.

In one aspect, the present disclosure provides methods of treating a patient with facioscapulohumeral muscular dystrophy (FSHD) comprising administering to the patient a therapeutically effective amount of an inhibitor of BET inhibitor defined by:

In some aspects, the present disclosure provides compounds of the formula:

(I)

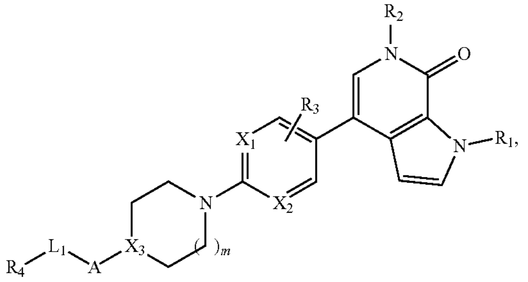

wherein:

m is 0 or 1;

$R_1$ and $R_2$ are each independently hydrogen; or alkyl$_{(C\leq12)}$, alkenyl$_{(C\leq12)}$, alkynyl$_{(C\leq12)}$, cycloalkyl$_{(C\leq12)}$, aralkyl$_{(C\leq12)}$, acyl$_{(C\leq12)}$, —S(O)$_2$-aryl$_{(C\leq12)}$, or a substituted version of any of these groups;

$X_1$, $X_2$, and $X_3$ are each independently CH or N;

$R_3$ is hydrogen, hydroxy, amino, or halo; or alkoxy$_{(C\leq12)}$, alkylamino$_{(C\leq12)}$, dialkylamino$_{(C\leq2)}$, or a substituted version of any of these groups;

A is a covalent bond, arenediyl$_{(C\leq12)}$, substituted arenediyl$_{(C\leq12)}$, heteroarenediyl$_{(C\leq12)}$, or substituted heteroarenediyl$_{(C\leq12)}$;

$L_1$ is a covalent bond; or alkanediyl$_{(C\leq12)}$, —O-alkanediyl$_{(C\leq12)}$-, —C(O)-alkanediyl$_{(C\leq12)}$-, —OC(O)-alkanediyl$_{(C\leq12)}$-, —C(O)-alkanediyl$_{(C\leq12)}$-O-alkanediyl$_{(C\leq12)}$-, —OC(O)-alkanediyl$_{(C\leq12)}$-O-alkanediyl$_{(C\leq12)}$-, or a substituted version of any of these groups; and $R_4$ is hydrogen, hydroxy, or amino; or alkoxy$_{(C\leq12)}$, alkylamino$_{(C\leq12)}$, dialkylamino$_{(C\leq12)}$, cycloalkyl$_{(C\leq12)}$, heterocycloalkyl$_{(C\leq12)}$, aryl$_{(C\leq12)}$, heteroaryl$_{(C\leq12)}$, or a substituted version of any of these groups; or a group of the formula:

(Ia)

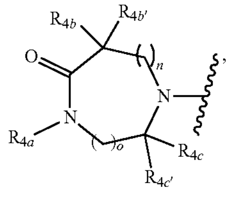

wherein:

n is 0 or 1;

o is 1 or 2;

$R_{4a}$ is hydrogen; or alkyl$_{(C\leq12)}$, alkenyl$_{(C\leq12)}$, alkynyl$_{(C\leq12)}$, acyl$_{(C\leq12)}$, or a substituted version of any of these groups;

$R_{4b}$, $R_{4b'}$, $R_{4c}$, and $R_{4c'}$ are each independently hydrogen, alkyl$_{(C\leq12)}$, or substituted alkyl$_{(C\leq12)}$; or compounds of the formula:

(II)

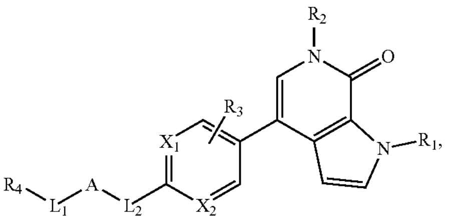

wherein:

$R_1$, $R_2$, $R_3$, $R_4$, $X_1$, $X_2$, A, and $L_1$ are as defined above; and $L_2$ is a covalent bond; or alkanediyl$_{(C\leq12)}$, alkenediyl$_{(C\leq12)}$, alkynediyl$_{(C\leq12)}$, cycloalkanediyl$_{(C\leq12)}$, or a substituted version of any of these groups; or a group of the formula:

(IIa)

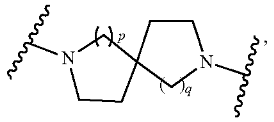

wherein:

p is 1, 2, or 3;

q is 1, 2, or 3;

provided that A is not a covalent bond when $L_2$ is a covalent bond, alkanediyl$_{(C\leq12)}$, substituted alkanediyl$_{(C\leq12)}$, alkenediyl$_{(C\leq12)}$, substituted alkenediyl$_{(C\leq12)}$, alkynediyl$_{(C\leq12)}$, or substituted alkynediyl$_{(C\leq12)}$; or compounds of the formula:

(III)

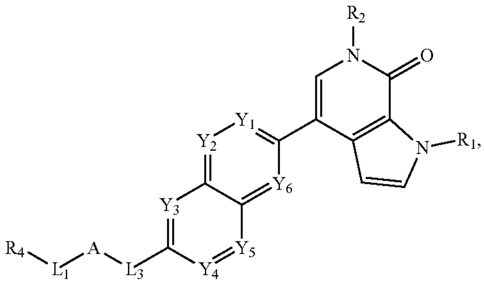

wherein:

$R_1$, $R_2$, $R_4$, A, and $L_1$ are as defined above;

$L_3$ is a covalent bond; or alkanediyl$_{(C\leq12)}$, alkenediyl$_{(C\leq12)}$, alkynediyl$_{(C\leq12)}$, cycloalkanediyl$_{(C\leq12)}$, heterocycloalkanediyl$_{(C\leq12)}$, or a substituted version of any of these groups; or a group of formula (IIa) as defined above; and $Y_1$, $Y_2$, $Y_3$, $Y_4$, $Y_5$, and $Y_6$ are each independently CH or N;

or a pharmaceutically acceptable salt of any one of these formulas.

In some embodiments, the compounds are of formula (I). In further embodiments, the compounds are further defined as:

(IV)

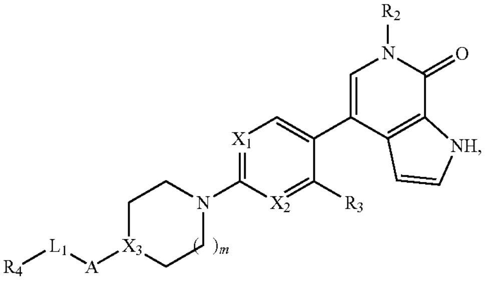

wherein:

m is 0 or 1;

$R_2$ is hydrogen, alkyl$_{(C\leq12)}$, substituted alkyl$_{(C\leq12)}$, alkenyl$_{(C\leq12)}$, or substituted alkenyl$_{(C\leq12)}$;

$X_1$, $X_2$, and $X_3$ are each independently CH or N;

$R_3$ is hydrogen, alkoxy$_{(C\leq12)}$, or substituted alkoxy$_{(C\leq12)}$;

A is a covalent bond, arenediyl$_{(C\leq12)}$, substituted arenediyl$_{(C\leq12)}$, heteroarenediyl$_{(C\leq12)}$, or substituted heteroarenediyl$_{(C\leq12)}$;

$L_1$ is a covalent bond; or alkanediyl$_{(C\leq12)}$, —O-alkanediyl$_{(C\leq12)}$-, —C(O)-alkanediyl$_{(C\leq12)}$-, —OC(O)-alkanediyl$_{(C\leq12)}$-, —C(O)-alkanediyl$_{(C\leq12)}$-O-alkanediyl$_{(C\leq12)}$-, —OC(O)-alkanediyl$_{(C\leq12)}$-O-alkanediyl$_{(C\leq12)}$-, or a substituted version of any of these groups; and $R_4$ is hydrogen, hydroxy, or amino; or alkoxy$_{(C\leq12)}$, alkylamino$_{(C\leq12)}$, dialkylamino$_{(C\leq12)}$, cycloalkyl$_{(C\leq12)}$, heterocycloalkyl$_{(C\leq12)}$, aryl$_{(C\leq12)}$, heteroaryl$_{(C\leq12)}$, or a substituted version of any of these groups; or a group of the formula:

(Ia)

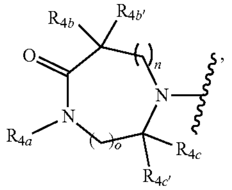

wherein:

n is 0 or 1;

is 1 or 2;

$R_{4a}$ is hydrogen; or alkyl$_{(C\leq12)}$, alkenyl$_{(C\leq12)}$, alkynyl$_{(C\leq12)}$, acyl$_{(C\leq12)}$, or a substituted version of any of these groups;

$R_{4b}$, $R_{4b'}$, $R_{4c}$, and $R_{4c'}$ are each independently hydrogen, alkyl$_{(C\leq12)}$, or substituted alkyl$_{(C\leq12)}$;

or a pharmaceutically acceptable salt thereof.

In other embodiments, the compounds are of formula (II). In further embodiments, the compounds are further defined as:

(V)

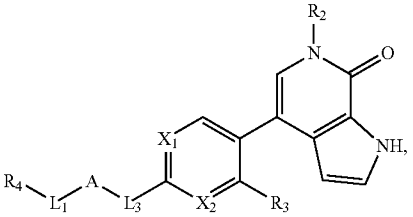

wherein:

$R_2$ is hydrogen, alkyl$_{(C\le12)}$, substituted alkyl$_{(C\le12)}$, alkenyl$_{(C\le12)}$, or substituted alkenyl$_{(C\le12)}$;

$X_1$ and $X_2$ are each independently CH or N;

$R_3$ is hydrogen, alkoxy$_{(C\le12)}$, or substituted alkoxy$_{(C\le12)}$;

A is a covalent bond, arenediyl$_{(C\le12)}$, substituted arenediyl$_{(C\le12)}$, heteroarenediyl$_{(C\le12)}$, or substituted heteroarenediyl$_{(C\le12)}$;

$L_1$ is a covalent bond; or alkanediyl$_{(C\le12)}$, —O-alkanediyl$_{(C\le12)}$-, —C(O)-alkanediyl$_{(C\le12)}$-, —OC(O)-alkanediyl$_{(C\le12)}$-, —C(O)-alkanediyl$_{(C\le12)}$-O-alkanediyl$_{(C\le12)}$-, —OC(O)-alkanediyl$_{(C\le12)}$-O-alkanediyl$_{(C\le12)}$-, or a substituted version of any of these groups; and $R_4$ is hydrogen, hydroxy, or amino; or alkoxy$_{(C\le12)}$, alkylamino$_{(C\le12)}$, dialkylamino$_{(C\le12)}$, cycloalkyl$_{(C\le12)}$, heterocycloalkyl$_{(C\le12)}$, aryl$_{(C\le12)}$, heteroaryl$_{(C\le12)}$, or a substituted version of any of these groups; or a group of the formula:

(Ia)

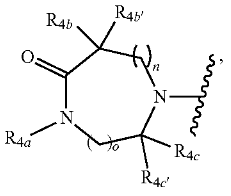

wherein:

n is 0 or 1;

o is 1 or 2;

$R_{4a}$ is hydrogen; or alkyl$_{(C\le12)}$, alkenyl$_{(C\le12)}$, alkynyl$_{(C\le12)}$, acyl$_{(C\le12)}$, or a substituted version of any of these groups;

$R_{4b}$, $R_{4b'}$, $R_{4c}$, and $R_{4c'}$ are each independently hydrogen, alkyl$_{(C\le12)}$, or substituted alkyl$_{(C\le12)}$; and $L_2$ is a covalent bond; or alkanediyl$_{(C\le12)}$, alkenediyl$_{(C\le12)}$, alkynediyl$_{(C\le12)}$, cycloalkanediyl$_{(C\le12)}$, or a substituted version of any of these groups; or a group of the formula:

(IIa)

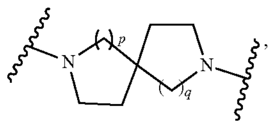

wherein:

p is 1, 2, or 3;

q is 1, 2, or 3;

provided that A is not a covalent bond when $L_2$ is a covalent bond, alkanediyl$_{(C\le12)}$, substituted alkanediyl$_{(C\le12)}$, alkenediyl$_{(C\le12)}$, substituted alkenediyl$_{(C\le12)}$, alkynediyl$_{(C\le12)}$, or substituted alkynediyl$_{(C\le12)}$;

or a pharmaceutically acceptable salt thereof.

In some embodiments, the compounds are further defined as:

(V)

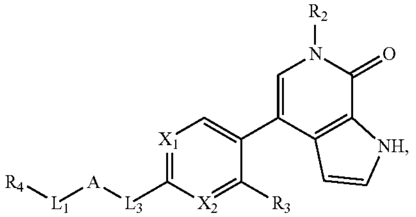

wherein:

$R_2$ is hydrogen, alkyl$_{(C\le12)}$, substituted alkyl$_{(C\le12)}$, alkenyl$_{(C\le12)}$, or substituted alkenyl$_{(C\le12)}$;

$X_1$ and $X_2$ are each independently CH or N;

$R_3$ is hydrogen, alkoxy$_{(C\le12)}$, or substituted alkoxy$_{(C\le12)}$;

A is arenediyl$_{(C\le12)}$, substituted arenediyl$_{(C\le12)}$, heteroarenediyl$_{(C\le12)}$, or substituted heteroarenediyl$_{(C\le12)}$;

$L_1$ is a covalent bond; or alkanediyl$_{(C\le12)}$, —O-alkanediyl$_{(C\le12)}$-, —C(O)-alkanediyl$_{(C\le12)}$-, —OC(O)-alkanediyl$_{(C\le12)}$-, —C(O)-alkanediyl$_{(C\le12)}$-O-alkanediyl$_{(C\le12)}$-, —OC(O)-alkanediyl$_{(C\le12)}$-O-alkanediyl$_{(C\le12)}$-, or a substituted version of any of these groups; and $R_4$ is hydrogen, hydroxy, or amino; or alkoxy$_{(C\le12)}$, alkylamino$_{(C\le12)}$, dialkylamino$_{(C\le12)}$, cycloalkyl$_{(C\le12)}$, heterocycloalkyl$_{(C\le12)}$, aryl$_{(C\le12)}$, heteroaryl$_{(C\le12)}$, or a substituted version of any of these groups; or a group of the formula:

(Ia)

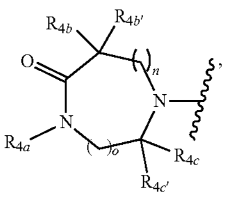

wherein:

n is 0 or 1;

o is 1 or 2;

$R_{4a}$ is hydrogen; or alkyl$_{(C\le12)}$, alkenyl$_{(C\le12)}$, alkynyl$_{(C\le12)}$, acyl$_{(C\le12)}$, or a substituted version of any of these groups;

$R_{4b}$, $R_{4b'}$, $R_{4c}$, and $R_{4c'}$ are each independently hydrogen, alkyl$_{(C\le12)}$, or substituted alkyl$_{(C\le12)}$; and $L_2$ is a covalent bond; or alkanediyl$_{(C\le12)}$, alkenediyl$_{(C\le12)}$, alkynediyl$_{(C\le12)}$, cycloalkanediyl$_{(C\le12)}$, or a substituted version of any of these groups; or a group of the formula:

(IIa)

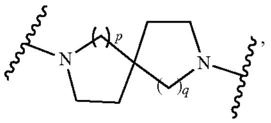

wherein:

p is 1, 2, or 3;

q is 1, 2, or 3;

or a pharmaceutically acceptable salt thereof.

In some embodiments, the compounds are further defined as:

(V)

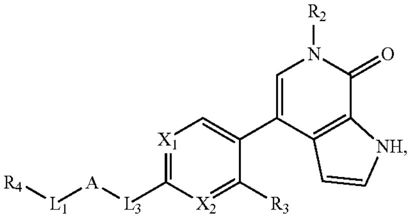

wherein:

$R_2$ is hydrogen, alkyl$_{(C\leq12)}$, substituted alkyl$_{(C\leq12)}$, alkenyl$_{(C\leq12)}$, or substituted alkenyl$_{(C\leq12)}$;

$X_1$ and $X_2$ are each independently CH or N;

$R_3$ is hydrogen, alkoxy$_{(C\leq12)}$, or substituted alkoxy$_{(C\leq12)}$;

A is a covalent bond, arenediyl$_{(C\leq12)}$, substituted arenediyl$_{(C\leq12)}$, heteroarenediyl$_{(C\leq12)}$, or substituted heteroarenediyl$_{(C\leq12)}$;

$L_1$ is a covalent bond; or alkanediyl$_{(C\leq12)}$, —O-alkanediyl$_{(C\leq12)}$-, —C(O)-alkanediyl$_{(C\leq12)}$-, —OC(O)-alkanediyl$_{(C\leq12)}$-, —C(O)-alkanediyl$_{(C\leq12)}$-O-alkanediyl$_{(C\leq12)}$-, —OC(O)-alkanediyl$_{(C\leq12)}$-O-alkanediyl$_{(C\leq12)}$-, or a substituted version of any of these groups; and $R_4$ is hydrogen, hydroxy, or amino; or alkoxy$_{(C\leq12)}$, alkylamino$_{(C\leq12)}$, dialkylamino$_{(C\leq12)}$, cycloalkyl$_{(C\leq12)}$, heterocycloalkyl$_{(C\leq12)}$, aryl$_{(C\leq12)}$, heteroaryl$_{(C\leq12)}$, or a substituted version of any of these groups; or a group of the formula:

(Ia)

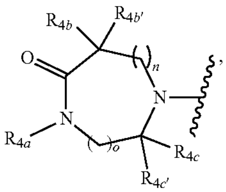

wherein:

n is 0 or 1;

o is 1 or 2;

$R_{4a}$ is hydrogen; or alkyl$_{(C\leq12)}$, alkenyl$_{(C\leq12)}$, alkynyl$_{(C\leq12)}$, acyl$_{(C\leq12)}$, or a substituted version of any of these groups;

$R_{4b}$, $R_{4b'}$, $R_{4c}$, and $R_{4c'}$ are each independently hydrogen, alkyl$_{(C\leq12)}$, or substituted alkyl$_{(C\leq12)}$; and $L_2$ is cycloalkanediyl$_{(C\leq12)}$ or substituted cycloalkanediyl$_{(C\leq12)}$; or a group of the formula:

(IIa)

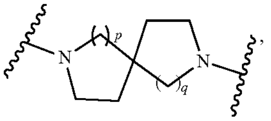

wherein:

p is 1, 2, or 3;

q is 1, 2, or 3;

or a pharmaceutically acceptable salt thereof.

In still other embodiments, the compounds are of formula (III). In further embodiments, the compounds are further defined as:

(VI)

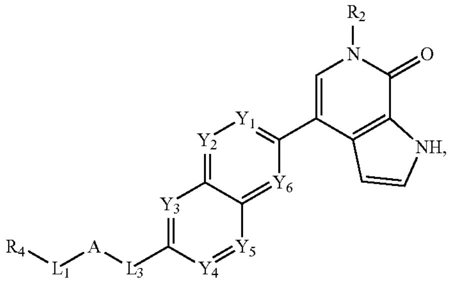

wherein:

$R_2$ is hydrogen, alkyl$_{(C\leq12)}$, substituted alkyl$_{(C\leq12)}$, alkenyl$_{(C\leq12)}$, or substituted alkenyl$_{(C\leq12)}$;

A is a covalent bond, arenediyl$_{(C\leq12)}$, substituted arenediyl$_{(C\leq12)}$, heteroarenediyl$_{(C\leq12)}$, or substituted heteroarenediyl$_{(C\leq12)}$;

$L_1$ is a covalent bond; or alkanediyl$_{(C\leq12)}$, —O-alkanediyl$_{(C\leq12)}$-, —C(O)-alkanediyl$_{(C\leq12)}$-, —OC(O)-alkanediyl$_{(C\leq12)}$-, —C(O)-alkanediyl$_{(C\leq12)}$, —O-alkanediyl$_{(C\leq12)}$-, —OC(O)-alkanediyl$_{(C\leq12)}$-O-alkanediyl$_{(C\leq12)}$-, or a substituted version of any of these groups; and $R_4$ is hydrogen, hydroxy, or amino; or alkoxy$_{(C\leq12)}$, alkylamino$_{(C\leq12)}$, dialkylamino$_{(C\leq12)}$, cycloalkyl$_{(C\leq12)}$, heterocycloalkyl$_{(C\leq12)}$, aryl$_{(C\leq12)}$, heteroaryl$_{(C\leq12)}$, or a substituted version of any of these groups; or a group of the formula:

(Ia)

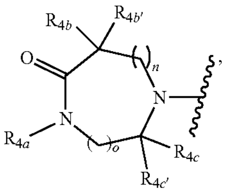

wherein:

n is 0 or 1;

o is 1 or 2;

$R_{4a}$ is hydrogen; or alkyl$_{(C\leq12)}$, alkenyl$_{(C\leq12)}$, alkynyl$_{(C\leq12)}$, acyl$_{(C\leq12)}$, or a substituted version of any of these groups;

$R_{4b}$, $R_{4b'}$, $R_{4c}$, and $R_{4c'}$ are each independently hydrogen, alkyl$_{(C\leq12)}$, or substituted alkyl$_{(C\leq12)}$;

$L_3$ is a covalent bond; or alkanediyl$_{(C\leq12)}$, alkenediyl$_{(C\leq12)}$, alkynediyl$_{(C\leq12)}$, cycloalkanediyl$_{(C\leq12)}$, heterocycloalkanediyl$_{(C\leq12)}$, or a substituted version of any of these groups; or a group of formula (IIa) as defined above; and $Y_1$, $Y_2$, $Y_3$, $Y_4$, $Y_5$, and $Y_6$ are each independently CH or N;

or a pharmaceutically acceptable salt thereof.

In still further embodiments, the compounds are further defined as:

(VII)

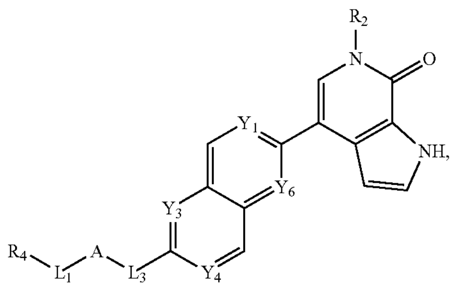

wherein:

$R_2$ is hydrogen, alkyl$_{(C\leq12)}$, substituted alkyl$_{(C\leq12)}$, alkenyl$_{(C\leq12)}$, or substituted alkenyl$_{(C\leq12)}$;

A is a covalent bond, arenediyl$_{(C\leq12)}$, substituted arenediyl$_{(C\leq12)}$, heteroarenediyl$_{(C\leq12)}$, or substituted heteroarenediyl$_{(C\leq12)}$;

$L_1$ is a covalent bond; or alkanediyl$_{(C\leq12)}$, —O-alkanediyl$_{(C\leq12)}$-, —C(O)-alkanediyl$_{(C\leq12)}$-, —OC(O)-alkanediyl$_{(C\leq12)}$-, —C(O)-alkanediyl$_{(C\leq12)}$-O-alkanediyl$_{(C\leq12)}$-, —OC(O)-alkanediyl$_{(C\leq12)}$-O-alkanediyl$_{(C\leq12)}$-, or a substituted version of any of these groups; and $R_4$ is hydrogen, hydroxy, or amino; or alkoxy$_{(C\leq12)}$, alkylamino$_{(C\leq12)}$, dialkylamino$_{(C\leq12)}$, cycloalkyl$_{(C\leq12)}$, heterocycloalkyl$_{(C\leq12)}$, aryl$_{(C\leq12)}$, heteroaryl$_{(C\leq12)}$, or a substituted version of any of these groups; or a group of the formula:

(Ia)

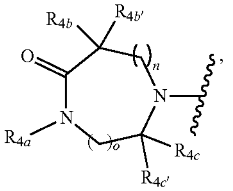

wherein:

n is 0 or 1;

o is 1 or 2;

$R_{4a}$ is hydrogen; or alkyl$_{(C\leq12)}$, alkenyl$_{(C\leq12)}$, alkynyl$_{(C\leq12)}$, acyl$_{(C\leq12)}$, or a substituted version of any of these groups;

$R_{4b}$, $R_{4b'}$, $R_{4c}$, and $R_{4c'}$ are each independently hydrogen, alkyl$_{(C\leq12)}$, or substituted alkyl$_{(C\leq12)}$;

$L_3$ is a covalent bond; or alkanediyl$_{(C\leq12)}$, alkenediyl$_{(C\leq12)}$, alkynediyl$_{(C\leq12)}$, cycloalkanediyl$_{(C\leq12)}$, heterocycloalkanediyl$_{(C\leq12)}$, or a substituted version of any of these groups; or a group of formula (IIa) as defined above; and $Y_1$, $Y_3$, $Y_4$, and $Y_6$ are each independently CH or N;

or a pharmaceutically acceptable salt thereof.

In some embodiments, $R_1$ is hydrogen. In some embodiments, $R_2$ is hydrogen. In other embodiments, $R_2$ is alkyl$_{(C\leq12)}$, substituted alkyl$_{(C\leq12)}$, alkenyl$_{(C\leq12)}$, or substituted alkenyl$_{(C\leq12)}$. In further embodiments, $R_2$ is alkyl$_{(C\leq12)}$ or substituted alkyl$_{(C\leq12)}$. In still further embodiments, $R_2$ is alkyl$_{(C\leq12)}$, such as ethyl or methyl. In other embodiments, $R_2$ is substituted alkyl$_{(C\leq12)}$, such as difluoromethyl. In some embodiments, $R_2$ is alkenyl$_{(C\leq12)}$, or substituted alkenyl$_{(C\leq12)}$. In further embodiments, $R_2$ is alkenyl$_{(C\leq12)}$, such as allyl. In some embodiments, A is a covalent bond. In other embodiments, A is arenediyl$_{(C\leq12)}$, substituted arenediyl$_{(C\leq12)}$, heteroarenediyl$_{(C\leq12)}$, or substituted heteroarenediyl$_{(C\leq12)}$. In further embodiments, A is arenediyl$_{(C\leq12)}$ or substituted arenediyl$_{(C\leq12)}$. In still further embodiments, A is arenediyl$_{(C\leq12)}$, such as benzene-1,4-diyl or benzene-1,3-diyl. In other embodiments, A is heteroarenediyl$_{(C\leq12)}$, or substituted heteroarenediyl$_{(C\leq12)}$. In further embodiments, A is heteroarenediyl$_{(C\leq12)}$, such as quinoline-2,6-diyl.

In some embodiments, $L_1$ is a covalent bond. In other embodiments, $L_1$ is alkanediyl$_{(C\leq12)}$, —O-alkanediyl$_{(C\leq12)}$-, —C(O)-alkanediyl$_{(C\leq12)}$-, —C(O)-alkanediyl$_{(C\leq12)}$-O-alkanediyl$_{(C\leq12)}$-, or a substituted version of any of these groups. In further embodiments, $L_1$ is alkanediyl$_{(C\leq12)}$ or substituted alkanediyl$_{(C\leq12)}$. In still further embodiments, $L_1$ is alkanediyl$_{(C\leq12)}$, such as propanediyl. In some embodiments, $L_1$ is —O-alkanediyl$_{(C\leq12)}$- or substituted —O-alkanediyl$_{(C\leq12)}$-. In further embodiments, $L_1$ is —O-alkanediyl$_{(C\leq12)}$-, such as —$OCH_2$—, —$OCH_2CH_2$—, —$OCH_2CH_2CH_2$—, or —$OCH_2CH(CH_3)CH_2$—. In other embodiments, $L_1$ is —C(O)-alkanediyl$_{(C\leq12)}$- or substituted —C(O)-alkanediyl$_{(C\leq12)}$-. In further embodiments, $L_1$ is —C(O)-alkanediyl$_{(C\leq12)}$-, such as —C(O)$CH_2$—. In still other embodiments, $L_1$ is —C(O)-alkanediyl$_{(C\leq12)}$-O-alkanediyl$_{(C\leq12)}$- or substituted —C(O)-alkanediyl$_{(C\leq12)}$-O-alkanediyl$_{(C\leq12)}$-. In further embodiments, $L_1$ is —C(O)-alkanediyl$_{(C\leq12)}$-O-alkanediyl$_{(C\leq12)}$-, such as —C(O)$CH_2OCH_2CH_2$—.

In some embodiments, $R_4$ is hydrogen. In other embodiments, $R_4$ is hydroxy. In still other embodiments, $R_4$ is dialkylamino$_{(C\leq12)}$ or substituted dialkylamino$_{(C\leq12)}$. In further embodiments, $R_4$ is dialkylamino$_{(C\leq12)}$, such as dimethylamino. In yet other embodiments, $R_4$ is heteroaryl$_{(C\leq12)}$ or substituted heteroaryl$_{(C\leq12)}$. In further embodiments, $R_4$ is heteroaryl$_{(C\leq12)}$, such as 1H-1,2,4-triazol-1-yl. In still other embodiments, $R_4$ is heterocycloalkyl$_{(C\leq12)}$ or substituted heterocycloalkyl$_{(C\leq12)}$. In further embodiments, $R_4$ is heterocycloalkyl$_{(C\leq12)}$, such as piperidin-1-yl, 2,6-dimethylpiperidin-1-yl, morpholin-4-yl, 1-methyl-piperazin-4-yl, In other embodiments, substituted heterocycloalkyl$_{(C\leq12)}$, such as 4,4-difluoropiperidin-1-yl.

In still other embodiments, $R_4$ is a group having the formula:

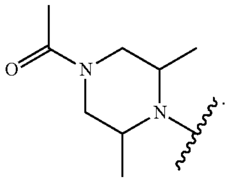 [SMILES: *N1C(C)CN(C(C)=O)CC1C]

In other embodiments, $R_4$ is a group of formula (Ia). In some embodiments, $R_{4a}$ is hydrogen. In other embodiments, $R_{4a}$ is alkyl$_{(C\leq 12)}$ or substituted alkyl$_{(C\leq 12)}$. In further embodiments, $R_{4a}$ is alkyl$_{(C\leq 12)}$, such as methyl, ethyl, or n-propyl. In still other embodiments, $R_{4a}$ is alkynyl$_{(C\leq 12)}$ or substituted alkynyl$_{(C\leq 12)}$. In further embodiments, $R_{4a}$ is alkynyl$_{(C\leq 12)}$, such as prop-1-yn-3-yl. In some embodiments, $R_{4b}$ is hydrogen. In other embodiments, $R_{4b}$ is alkyl$_{(C\leq 12)}$ or substituted alkyl$_{(C\leq 12)}$. In further embodiments, $R_{4b}$ is alkyl$_{(C\leq 12)}$, such as methyl. In some embodiments, $R_{4b'}$ is hydrogen. In other embodiments, $R_{4b'}$ is alkyl$_{(C\leq 12)}$ or substituted alkyl$_{(C\leq 12)}$. In further embodiments, $R_{4b'}$ is alkyl$_{(C\leq 12)}$, such as methyl. In some embodiments, $R_{4c}$ is hydrogen. In other embodiments, $R_{4c}$ is alkyl$_{(C\leq 12)}$ or substituted alkyl$_{(C\leq 12)}$. In further embodiments, $R_{4c}$ is alkyl$_{(C\leq 12)}$, such as methyl. In some embodiments, $R_{4c'}$ is hydrogen. In other embodiments, $R_{4c'}$ is alkyl$_{(C\leq 12)}$ or substituted alkyl$_{(C\leq 12)}$. In further embodiments, $R_{4c'}$ is alkyl$_{(C\leq 12)}$, such as methyl. In some embodiments, n is 0. In other embodiments, n is 1. In some embodiments, o is 1. In other embodiments, o is 2.

In some embodiments, $R_4$ is a group having the formula:

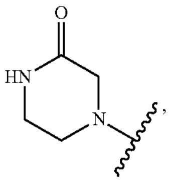
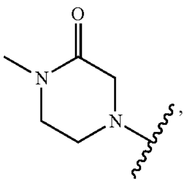
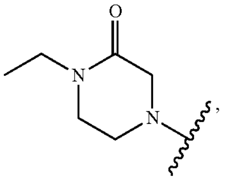
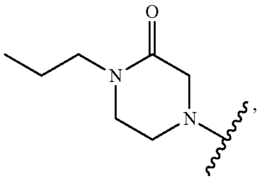
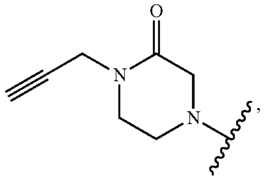
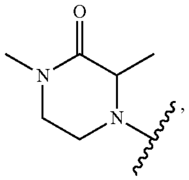
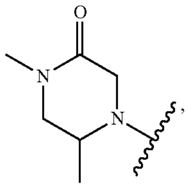
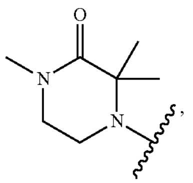
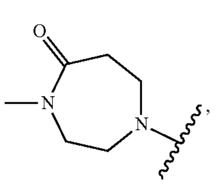
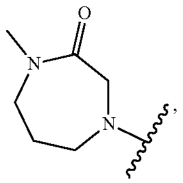
or -continued

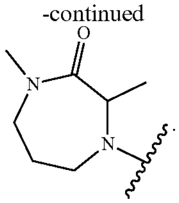

In some embodiments, $R_3$ is hydrogen. In other embodiments, $R_3$ is alkoxy$_{(C\leq 12)}$ or substituted alkoxy$_{(C\leq 12)}$. In further embodiments, $R_3$ is alkoxy$_{(C\leq 12)}$, such as methoxy. In some embodiments, $X_1$ is CH. In other embodiments, $X_1$ is N. In some embodiments, $X_2$ is CH. In other embodiments, $X_2$ is N. In some embodiments, m is 1. In some embodiments, $X_3$ is CH. In other embodiments, $X_3$ is N.

In some embodiments, $L_2$ is a group of formula (IIa). In some embodiments, p is 1. In other embodiments, p is 2. In some embodiments, q is 1. In other embodiments, q is 2. In some embodiments, $L_2$ is a group having the formula:

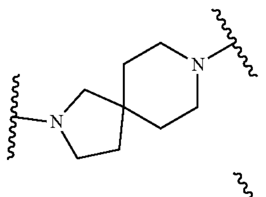
or
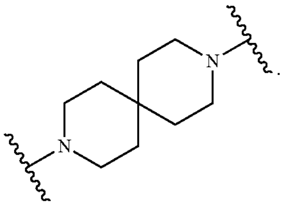

In some embodiments, $L_2$ is a covalent bond. In other embodiments, $L_2$ is alkanediyl$_{(C\leq 12)}$ or substituted alkanediyl$_{(C\leq 12)}$. In further embodiments, $L_2$ is alkanediyl$_{(C\leq 12)}$, such as ethanediyl. In still other embodiments, $L_2$ is alkynediyl$_{(C\leq 12)}$ or substituted alkynediyl$_{(C\leq 12)}$. In further embodiments, $L_2$ is alkynediyl$_{(C\leq 12)}$, such as ethynediyl. In some embodiments, $Y_1$ is CH. In other embodiments, $Y_1$ is N. In some embodiments, $Y_2$ is CH. In some embodiments, $Y_3$ is CH. In other embodiments, $Y_3$ is N. In some embodiments, $Y_4$ is CH. In other embodiments, $Y_4$ is N. In some embodiments, $Y_5$ is CH. In some embodiments, $Y_6$ is CH. In other embodiments, $Y_6$ is N. In some embodiments, no more than three of $Y_1$, $Y_2$, $Y_3$, $Y_4$, $Y_5$, and $Y_6$ is N. In further embodiments, no more than two of $Y_1$, $Y_2$, $Y_3$, $Y_4$, $Y_5$, and $Y_6$ is N. In still further embodiments, no more than one of $Y_1$, $Y_2$, $Y_3$, $Y_4$, $Y_5$, and $Y_6$ is N. In yet further embodiments, one and only one of $Y_1$, $Y_2$, $Y_3$, $Y_4$, $Y_5$, and $Y_6$ is N. In other embodiments, $Y_1$, $Y_2$, $Y_3$, $Y_4$, $Y_5$, and $Y_6$ are each CH.

In some embodiments, $L_3$ is a covalent bond. In other embodiments, $L_3$ is heterocycloalkanediyl$_{(C\leq 12)}$ or substituted heterocycloalkanediyl$_{(C\leq 12)}$. In further embodiments, $L_3$ is heterocycloalkanediyl$_{(C\leq 12)}$, such as piperazin-1,4-diyl.

In some embodiments, the compound is further defined as:

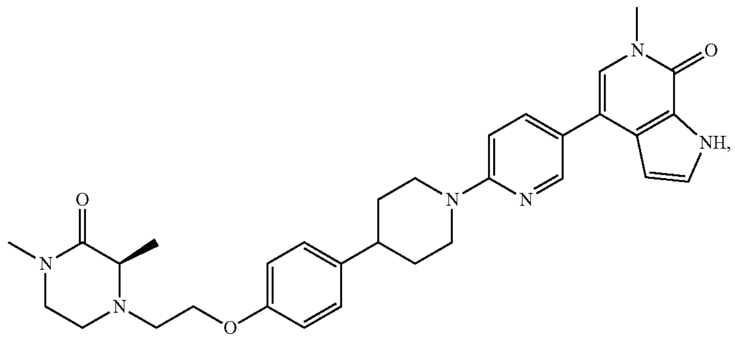
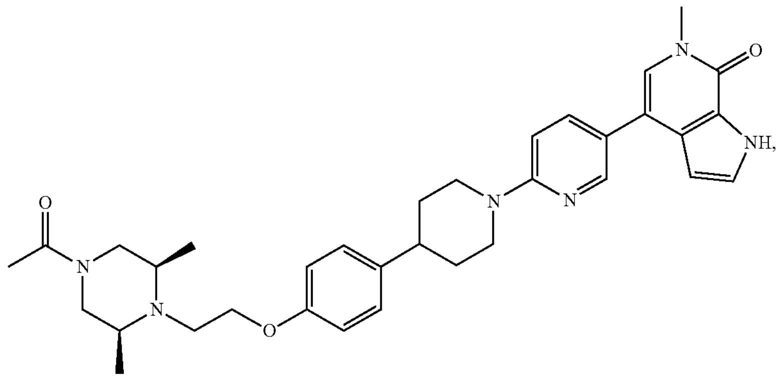
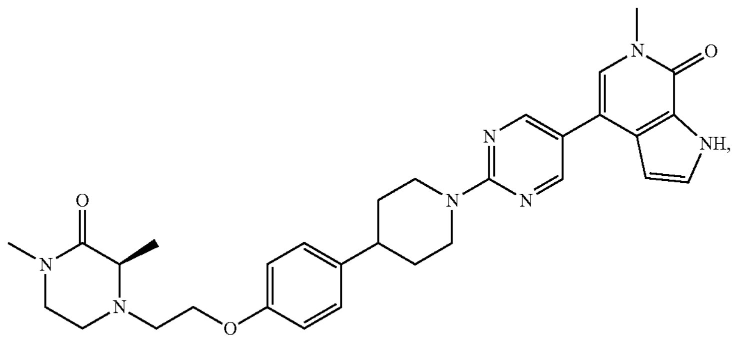
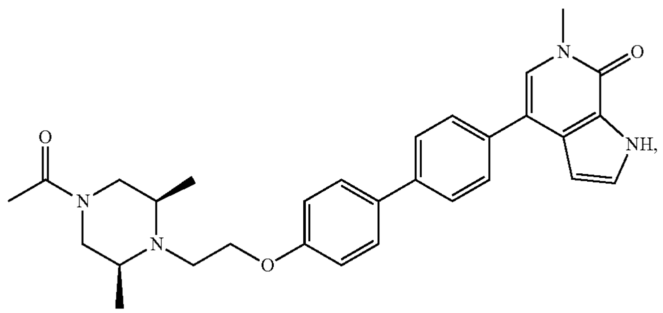
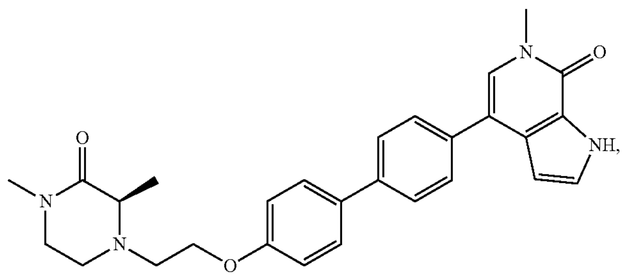

-continued
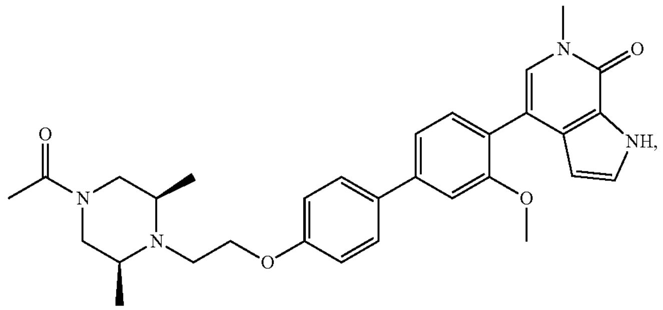
,
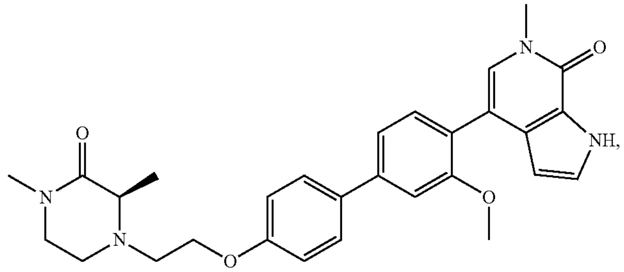
,
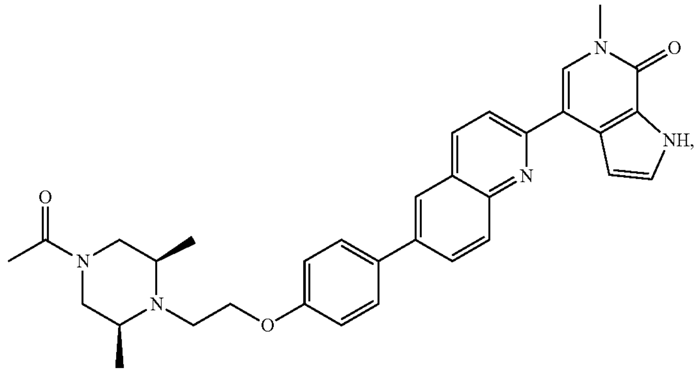
,
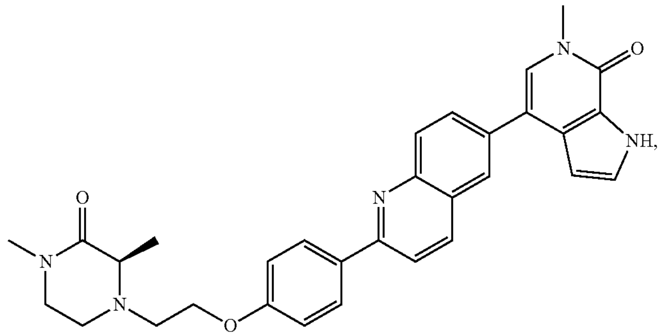
,
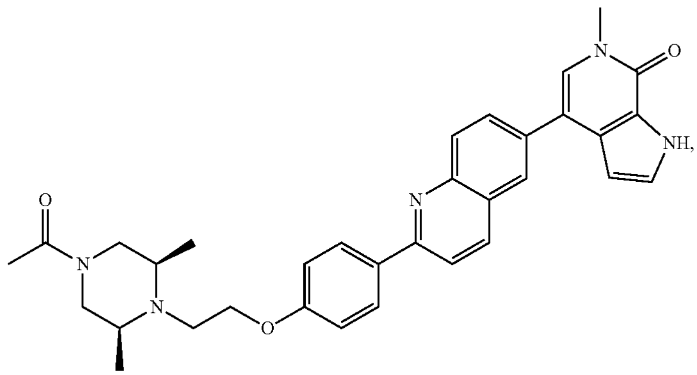
,

-continued
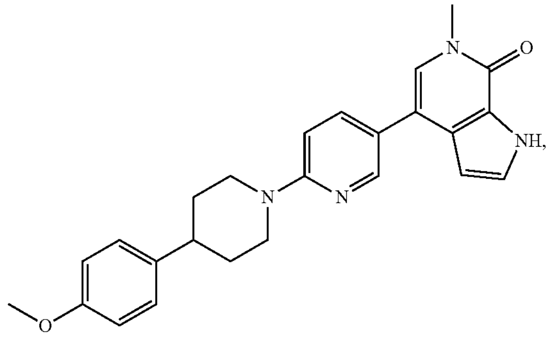
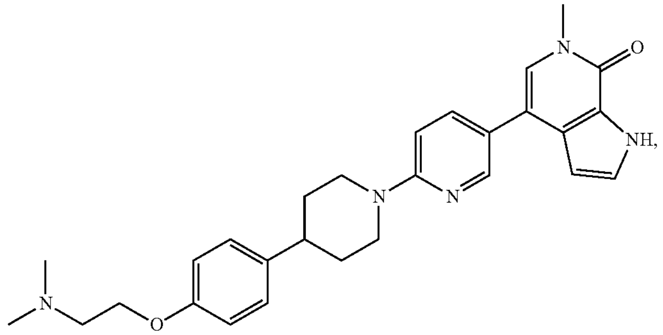
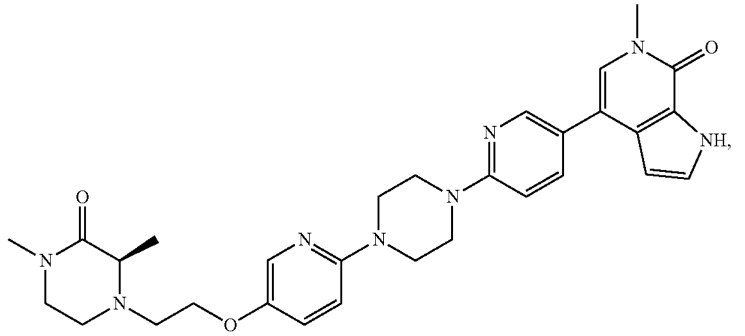
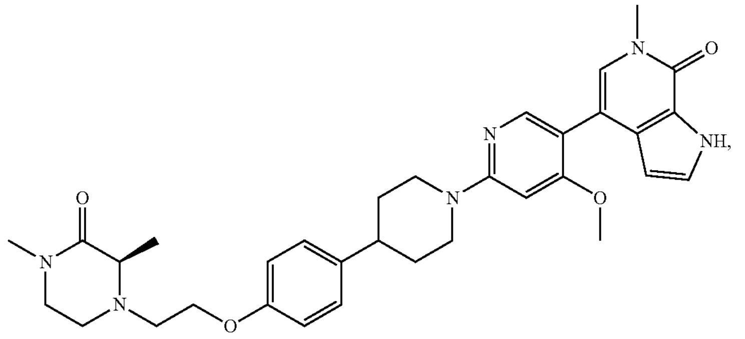
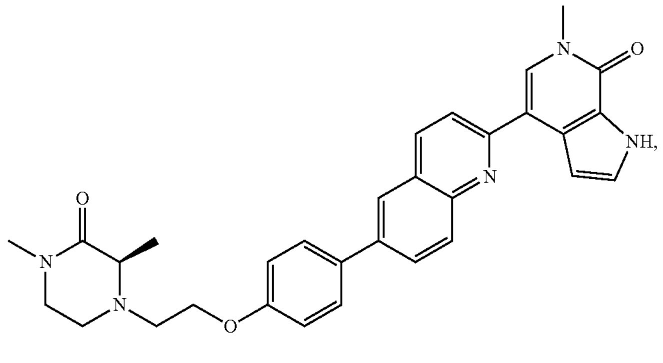

-continued
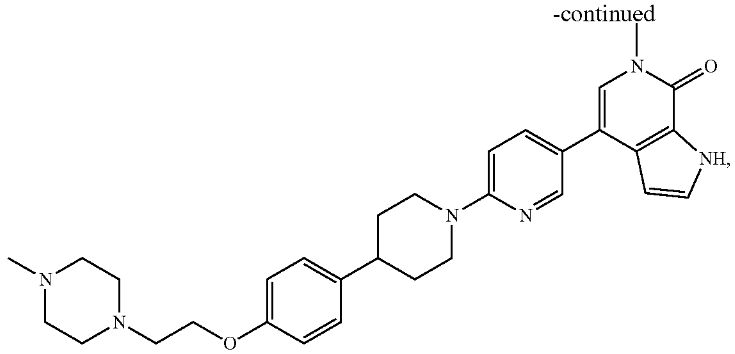
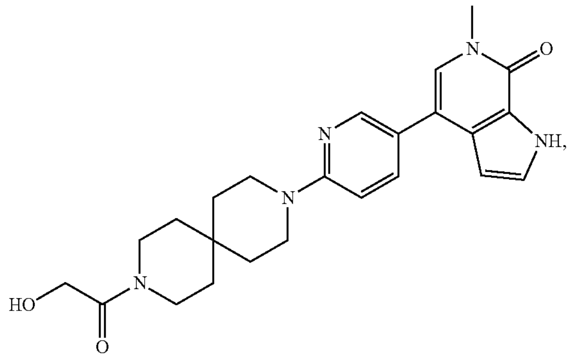
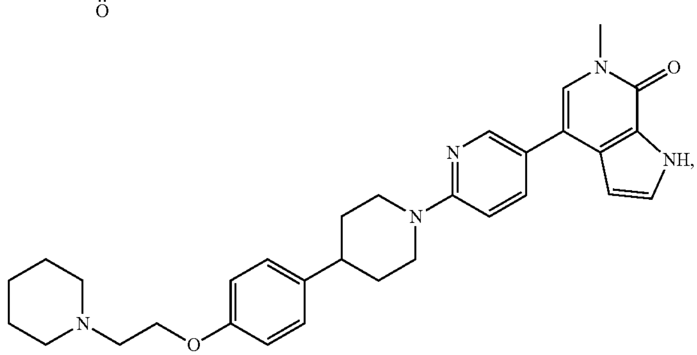
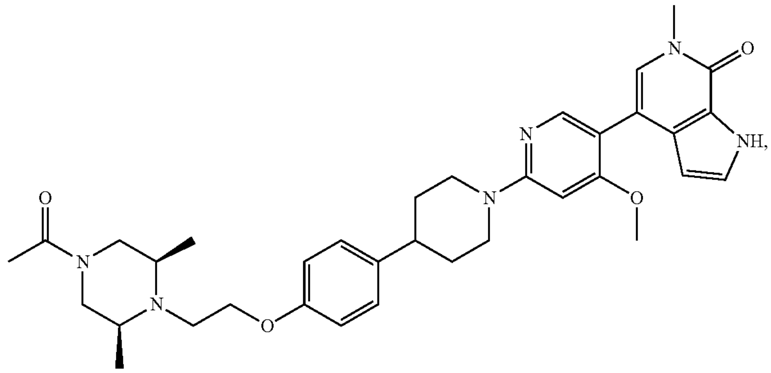
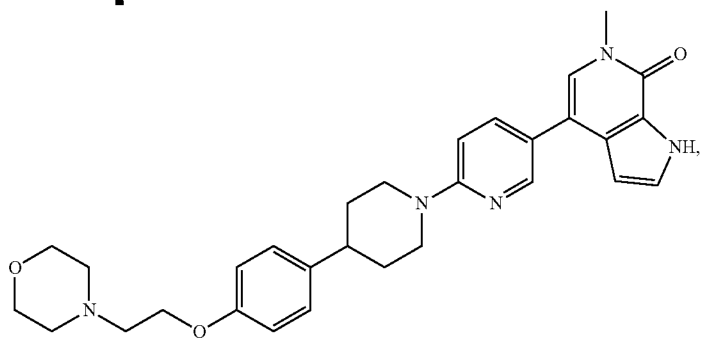

-continued
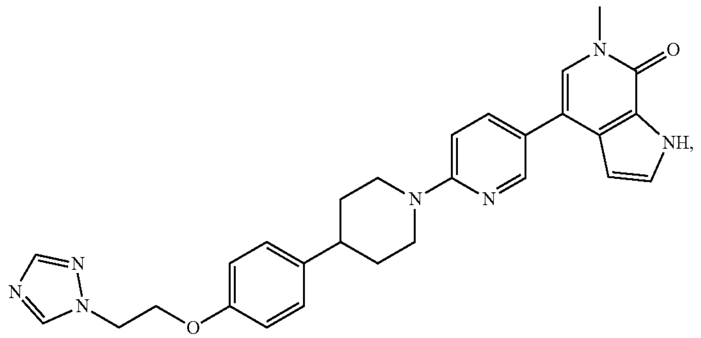
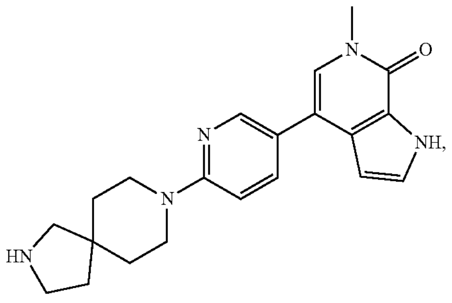
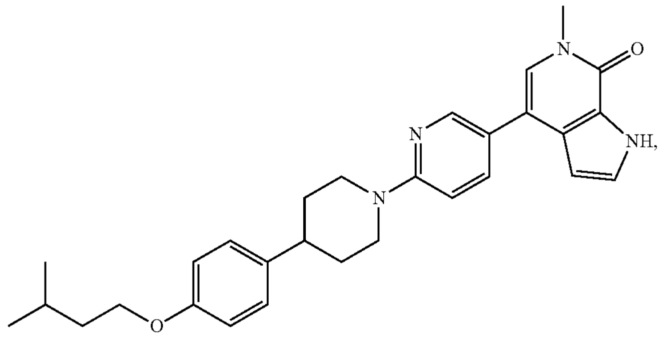
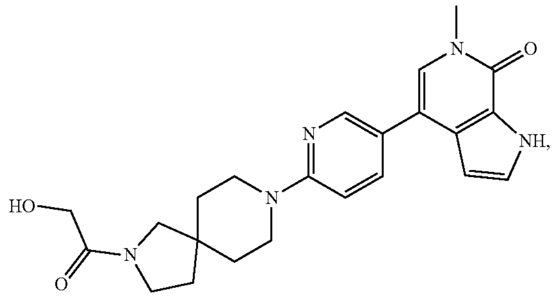
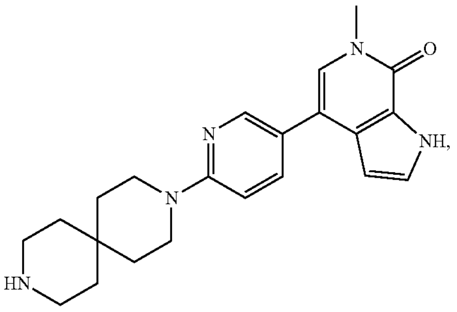
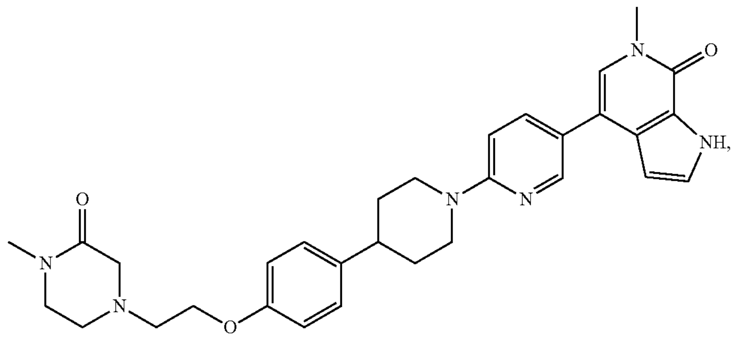
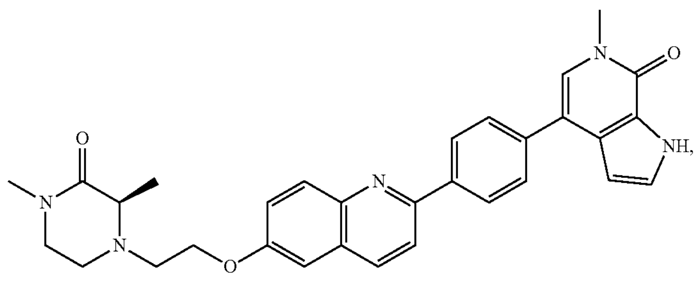

-continued
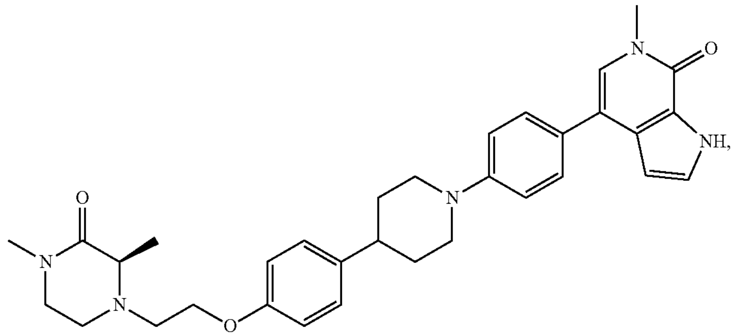
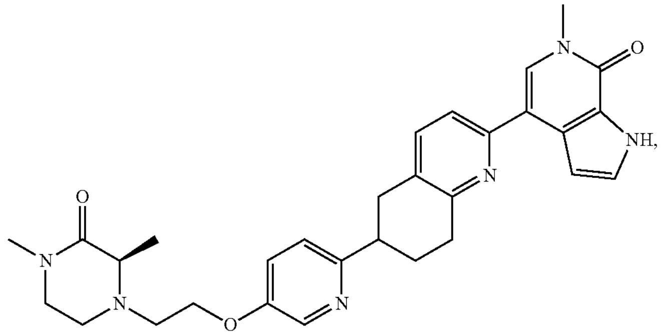
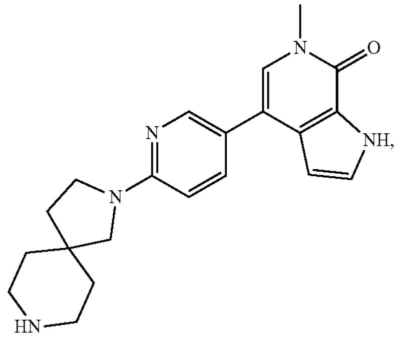
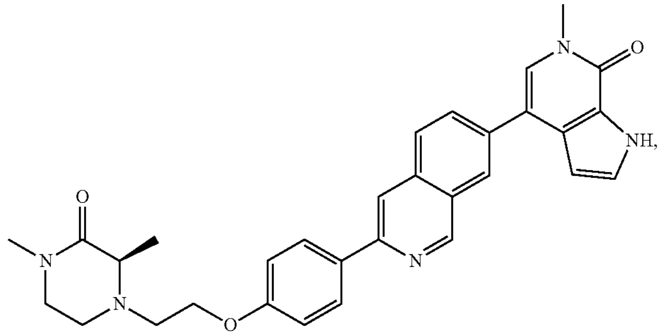
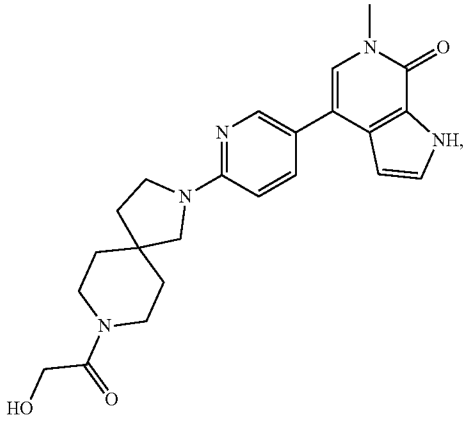
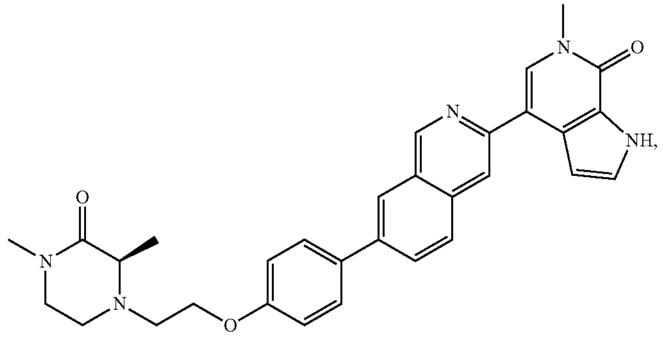

-continued
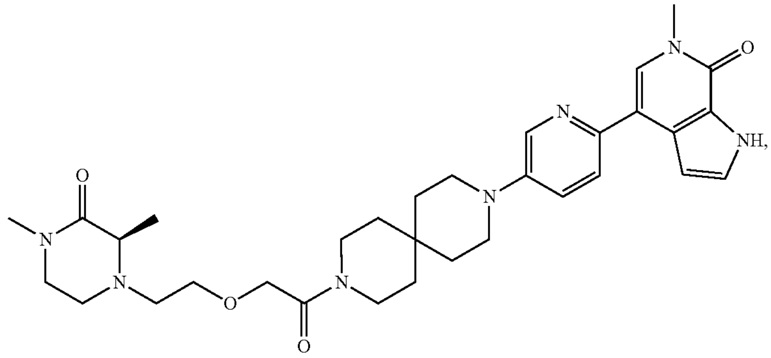
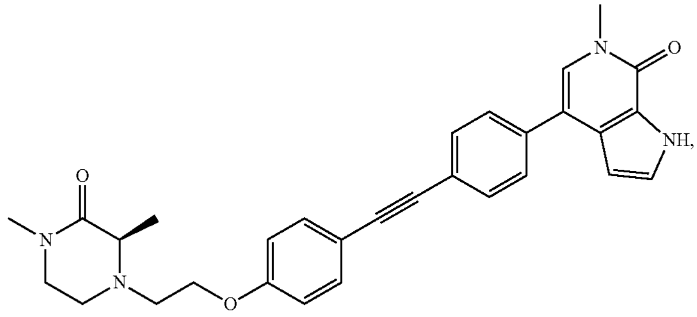
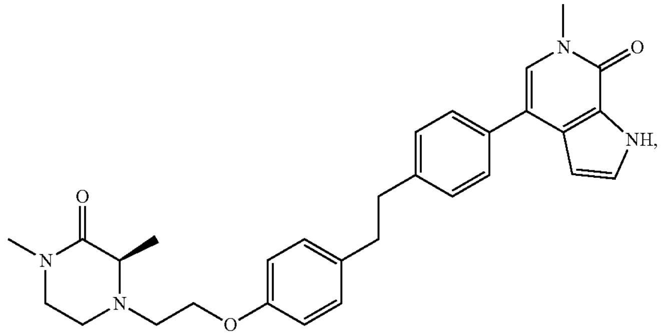
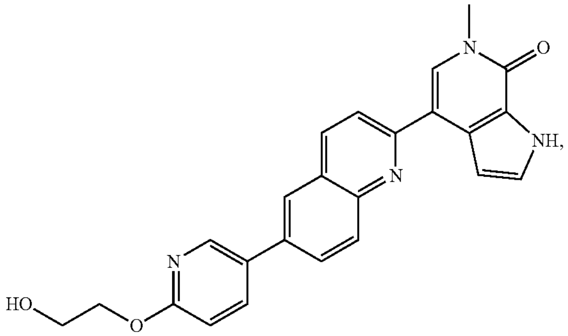
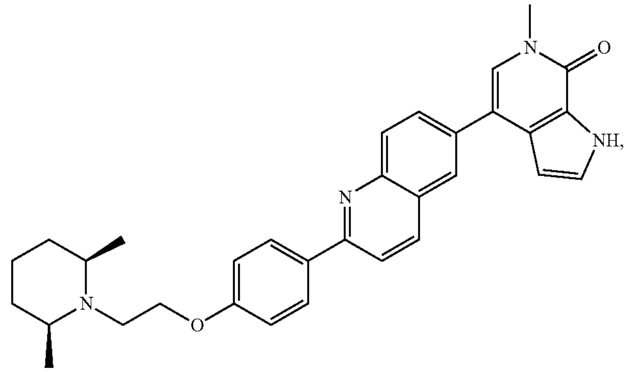
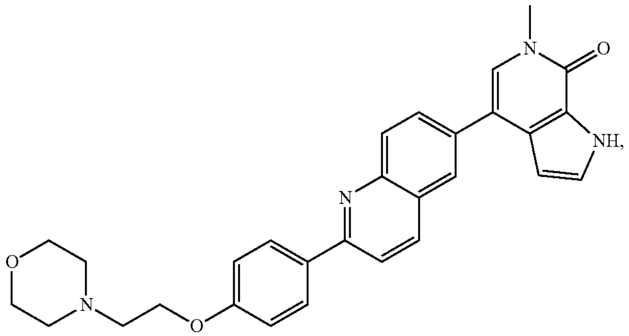

-continued
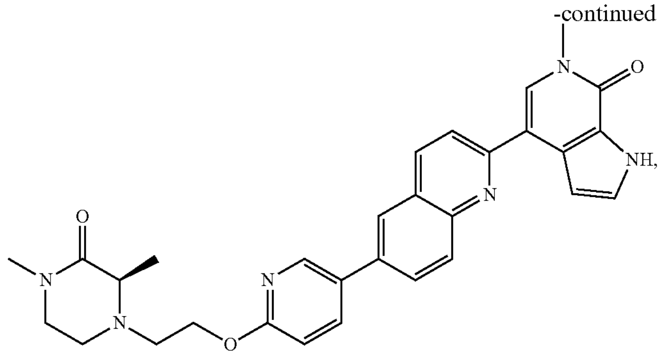
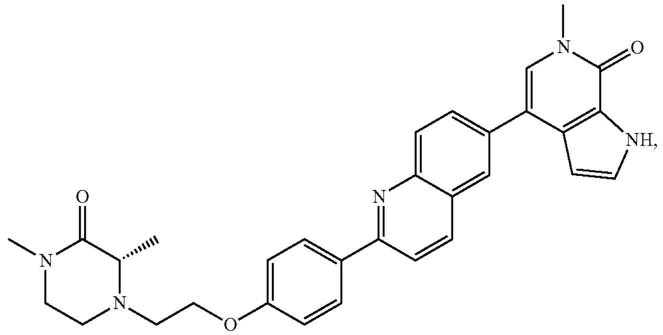
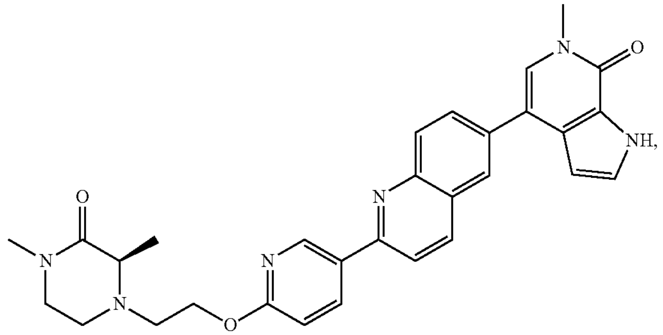 [SMILES: C[C@@H]1C(=O)N(C)CCN1CCOc1ccc(-c2ccc3cc(-c4cn(C)c(=O)c5[nH]ccc45)ccc3n2)cn1]
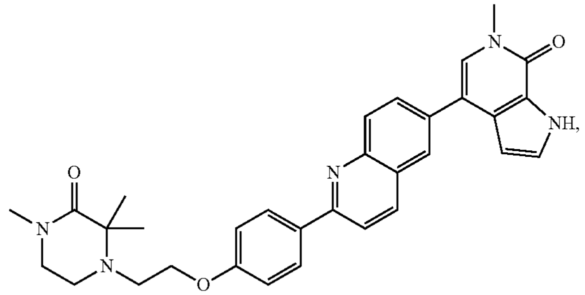
-continued
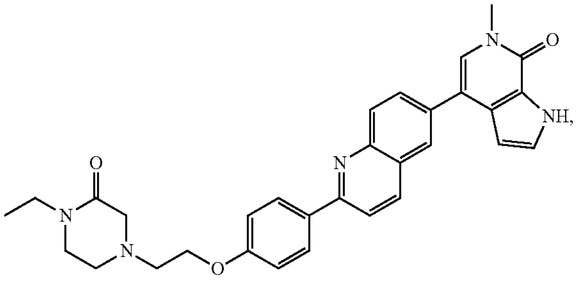
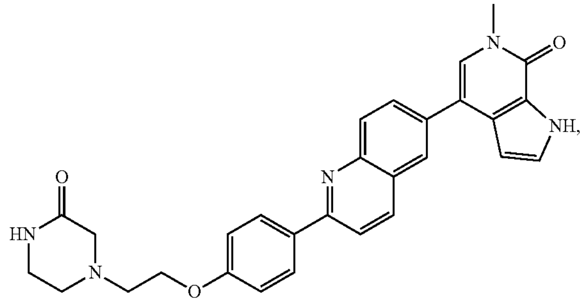
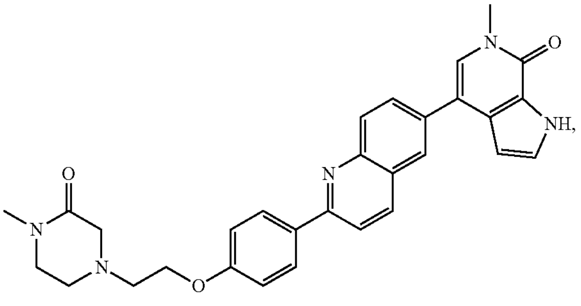

-continued
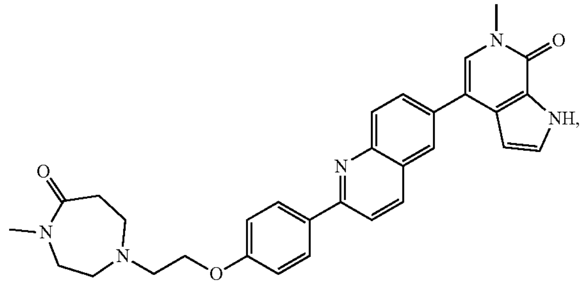
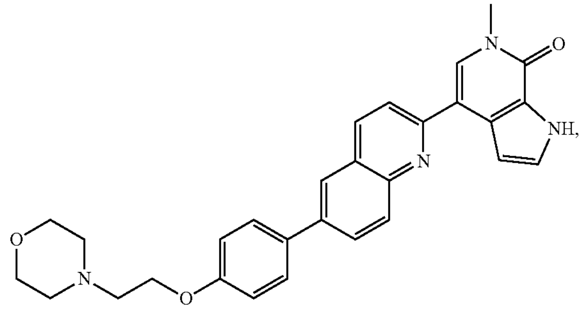
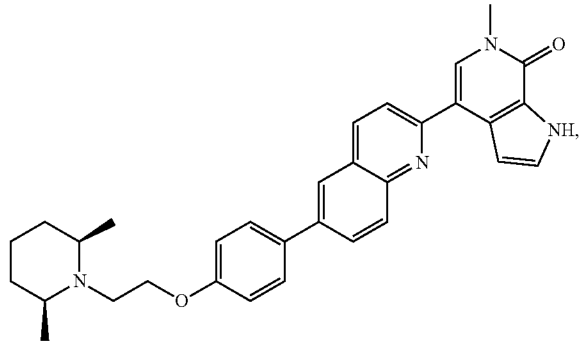
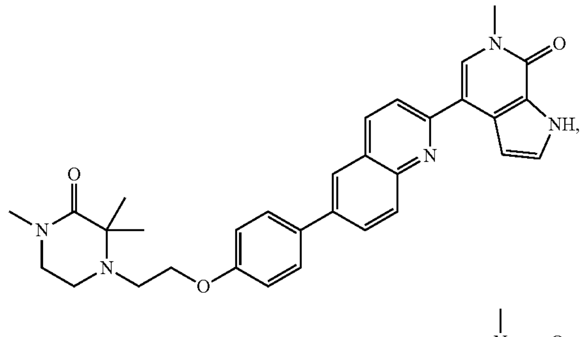
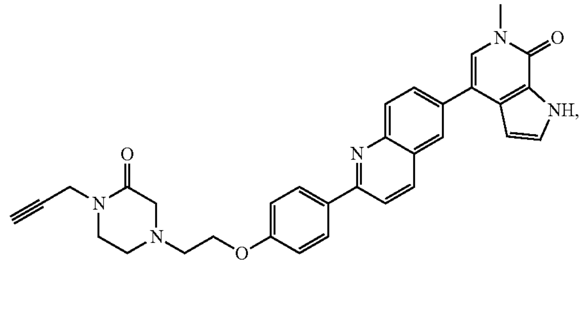
-continued
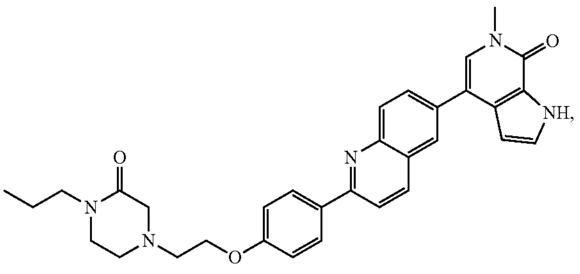
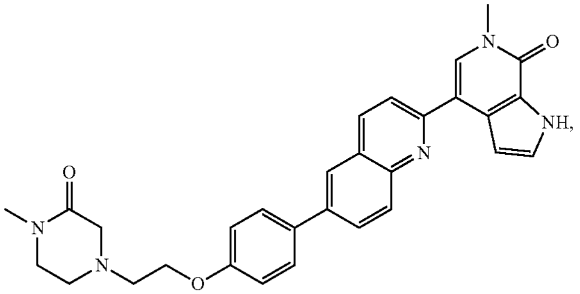
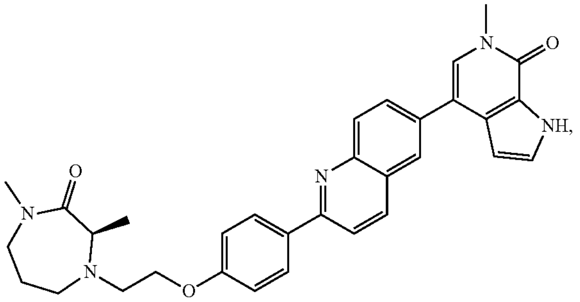
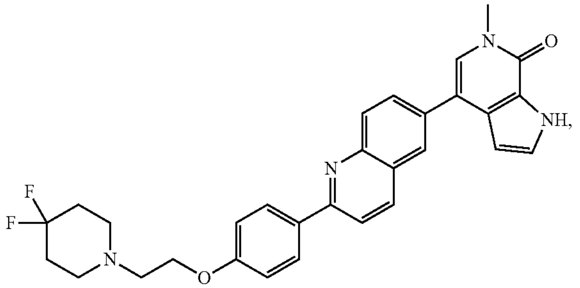
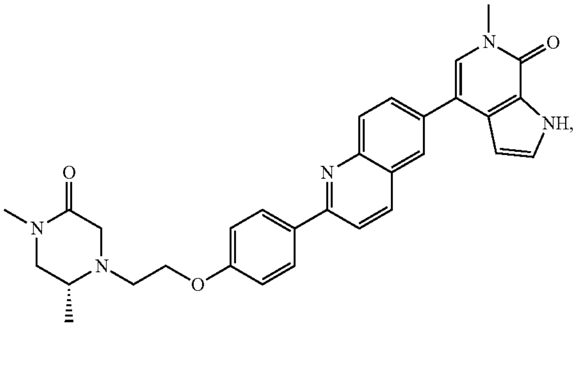

-continued
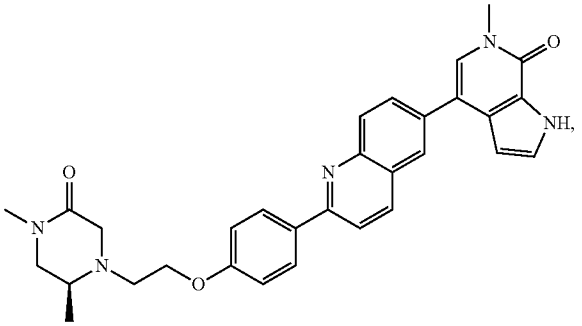
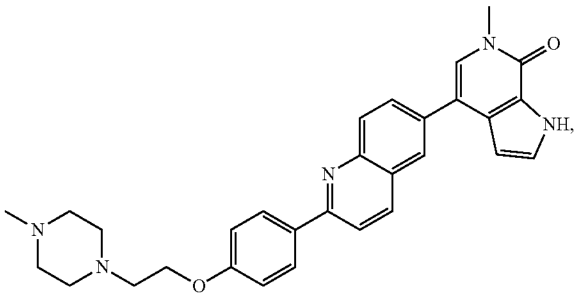
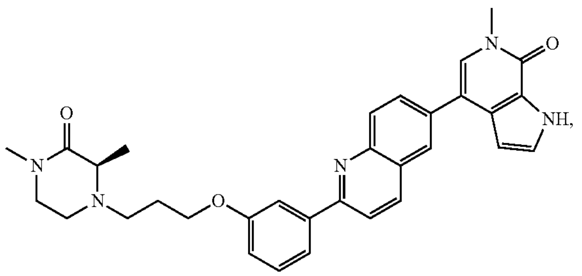
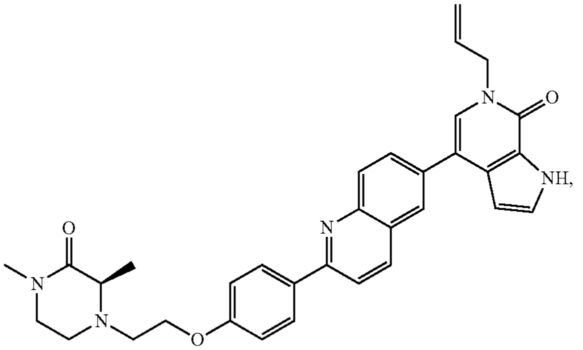
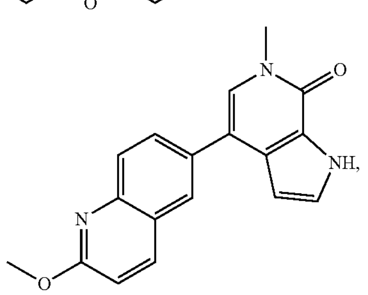
-continued
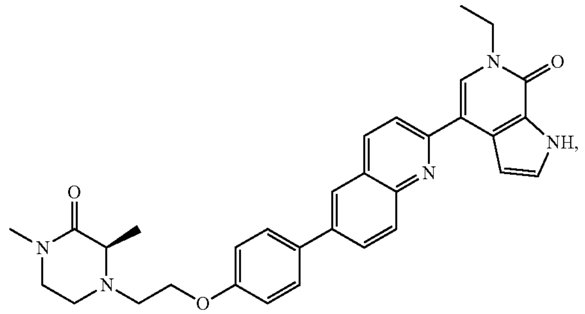
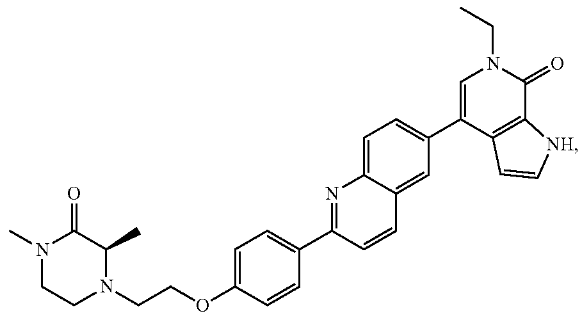
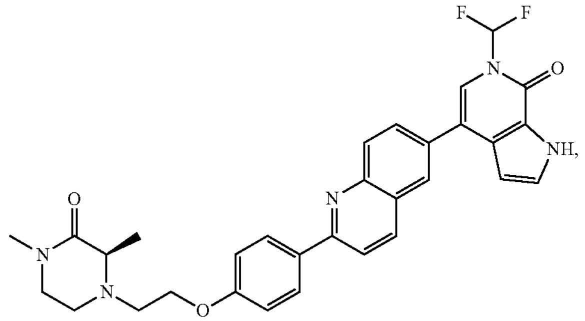
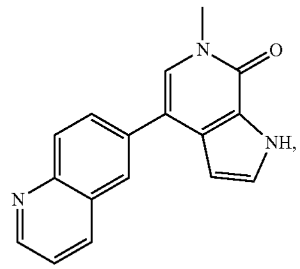
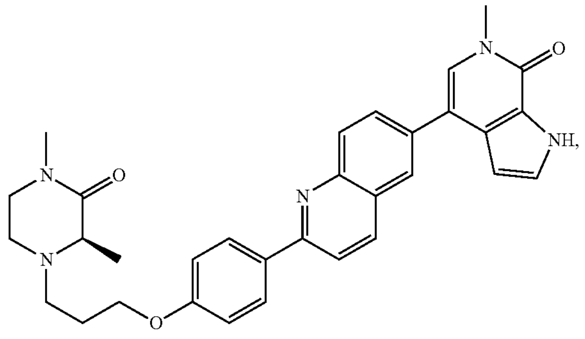

-continued

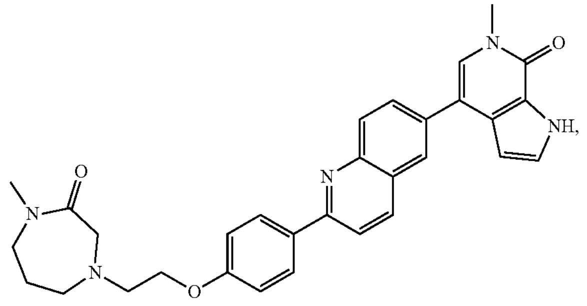

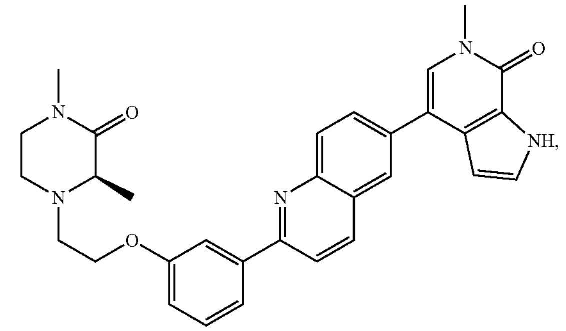

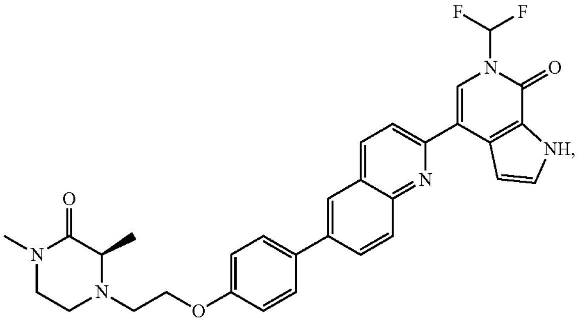

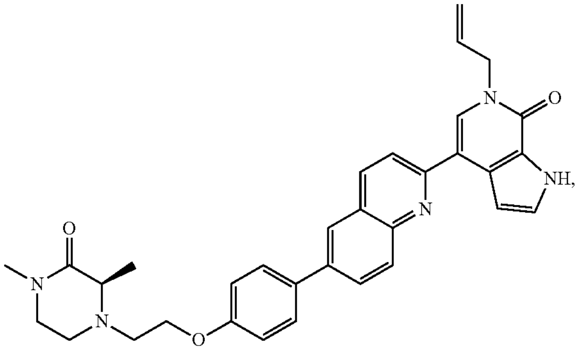

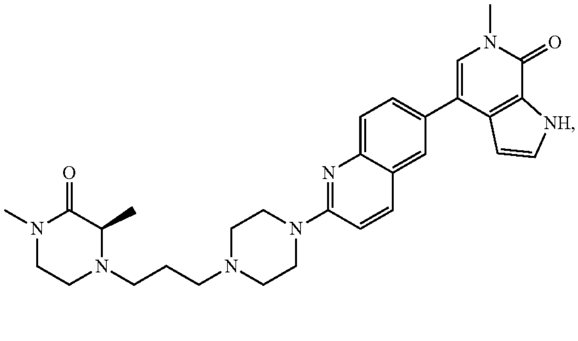

-continued

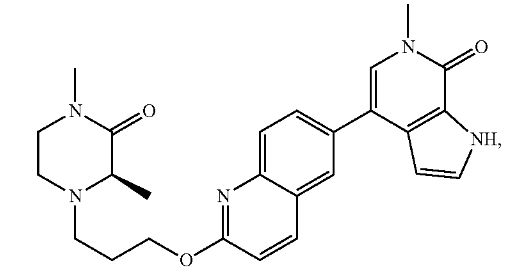

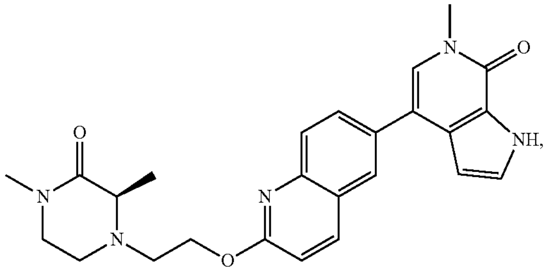

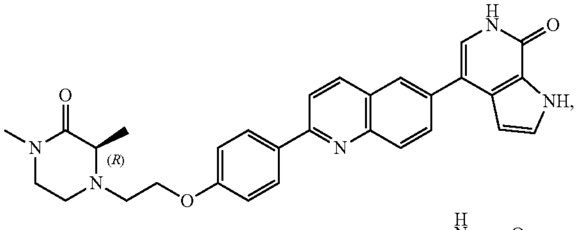

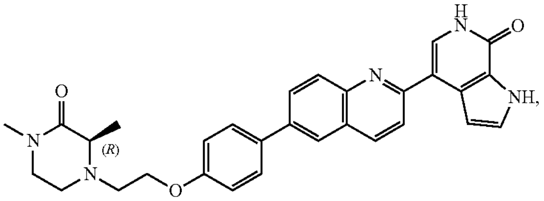

or

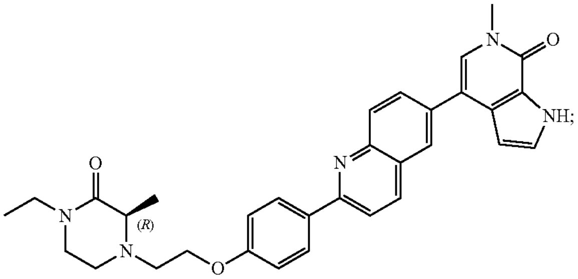

or a pharmaceutically acceptable salt thereof.

In another aspect, the present disclosure provides pharmaceutical compositions comprising:

a) a compound described herein; and b) an excipient and/or a pharmaceutically acceptable carrier.

In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In further embodiments, the composition is formulated for administration orally or via injection. In some embodiments, the composition is formulated for administration via intravenous, subcutaneous, or intramuscular injection. In some embodiments, the composition is formulated as a unit dose.

In still another aspect, the present disclosure provides methods of treating a patient with facioscapulohumeral muscular dystrophy (FSHD) comprising administering to the patient a therapeutically effective amount of an inhibitor of a bromo- and extra-terminal (BET) domain protein, wherein the inhibitor is a compound or composition described herein. In further embodiments, the BET domain protein is BRD2, BRD3, BRD4 or BRDT. In some embodiments, the FSHD has been diagnosed. In other embodiments, the FSHD has not been diagnosed. In some embodiments, the FSHD is adult-onset FSHD. In other embodiments, the FSHD is infantile-onset FSHD. In some embodiments, the FSHD is Type 1 FSHD. In other embodiments, the FSHD is Type 2 FSHD. In some embodiments, the patient is a mammal, non-human mammal, or a human. In some embodiments, the patient exhibits one or more symptoms of FSHD. In further embodiments, the symptoms of FSHD are facial muscle weakness, shoulder weakness, hearing loss, abnormal heart rhythm, unequal weakening of muscles in the upper body, loss of strength in the abdominal muscles, or foot drop. In still further embodiments, the symptom of FSHD is facial muscle weakness. In some embodiments, the unequal weakening of muscles in the upper body is unequal weakening of muscles in the biceps, triceps, deltoids, or lower arm muscles.

In some embodiments, the method further comprises administering a second therapy for FSHD. In further embodiments, the second therapy is administered before the inhibitor of BET. In some embodiments, the second therapy is administered concurrently with the inhibitor of BET. In other embodiments, the second therapy is administered after the inhibitor of BET. In some embodiments, the second therapy is a second BET inhibitor, such as I-BET762, I-BET726, I-BET151, RVX-208, CPI-203, CPI-232, CPI-0610, (+) JQ1, OTX-015, GW-841819X, BET-BAY-022, SRX-2523, or ABBV-075. In some embodiments, the second therapy is a β-2 adrenergic receptor agonist, such as bitolterol, fenoterol, isoprenaline, levosalbutamol, orciprenaline, pirbuterol, procaterol, ritodrine, salbutamol, bambuterol, formoterol, arformoterol, clenbuterol, salmeterol, abediterol, indacaterol, or olodaterol. In some embodiments, the second therapy is an inhibitor of p38 is an inhibitor of p38α and p38β. In some embodiments, the inhibitor of p38 is a selective In further embodiments, the inhibitor of p38 does not inhibit either p38δ or p38γ. In some embodiments, the inhibitor of p38 is selected from acumapimod, ARRY-371797, BMS-582949, dilmapimod, dorimapimod, losmapimod, LY222820, LY3007113, pamapimod, PH-797804, SB202190, SB203580, TAK-715, talmapimod, VX-702, and VX-745. In some embodiments, the second therapy comprises the p38 inhibitor and the β-2 adrenergic receptor agonist.

In some embodiments, the second therapy is a therapy to increase muscle mass, physical therapy, or occupational therapy. In some embodiments, the second therapy is a therapy which improves quality of life. In some embodiments, the second therapy is scapular fusion or scapular bracing. In other embodiments, the second therapy is an anti-inflammatory compounds. In further embodiments, the anti-inflammatory compound is an NSAID. In other embodiments, the anti-inflammatory compound is a glucocorticoid receptor modulator (glucocorticoid). In some embodiments, the compound is administered systemically. In further embodiments, the compound is administered systemically via injection or oral administration. In some embodiments, the inhibitor of BET is administered once. In other embodiments, the inhibitor of BET is administered two or more times.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-1C show the modulation of DUX4 target gene expression by SLU-2106 in a mouse xenograft model of FSHD. Human MB200 FSHD2 xenografts were created by co-injecting MB200 FSHD2 myoblasts with barium chloride into the tibialis anterior (TA) muscles of immunodeficient mice (Hardy et al., 2016). SLU-2106 was administered by oral gavage at 2, 4, 6 or 8 mpk BID starting immediately after FSHD myoblast implantation. Four days after implantation, RNA was isolated from TA muscles and analyzed for human-specific gene expression using qRT-PCR. FIG. 1A. hMBD3L2 gene expression. FIG. 1B. hZSCAN gene expression. FIG. 1C. hLEUTX gene expression. Relative mRNA levels for each gene were normalized to that in the Vehicle control group, which was set to 1. Error bars indicate the standard error of the mean of biological replicates. P-values were calculated using one-way analysis of variance. *, $p<0.01$. #, $p<0.05$.

DESCRIPTION OF ILLUSTRATIVE EMBODIMENTS

Provided herein are inhibitors of BET that show modulation of DUX4 expression and may be used in the treatment of facioscapulohumeral muscular dystrophy (FSHD). While Wnt/β-catenin pathway activators and estrogen have been shown to effect DUX4 expression, both of these molecules have potential to lead to off-target activities in other pathways. Inhibitors of BET may be used to modulate the expression of DUX4 without triggering these other pathways. These and other embodiments will be described in more detail herein.

I. FACIOSCAPULOHUMERAL MUSCULAR DYSTROPHY (FSHD)

Facioscapulohumeral dystrophy (FSHD or FSH) is a progressive muscle disease and a prevalent form of muscular dystrophy. The disease typically presents in young adults as facial and upper extremity weakness, and progresses to involve nearly all skeletal muscle groups (Tawil, et al., 2014). FSHD is caused by the mis-expression of the double homeobox 4 (DUX4) transcription factor in skeletal muscle. DUX4 is encoded by a retrogene located in each unit of the D4Z4 macrosatellite repeat array in the subtelomeric region of chromosomes 4q and 10q. FSHD results from a contraction at 4q35 resulting in too few D4Z4 repeats for efficient repeat-mediated epigenetic repression (FSHD type 1, FSHD1) or from the presence of mutations in trans-acting chromatin factors necessary for epigenetic repression of the D4Z4 array (FSHD type 2, FSHD2) (Lemmers, et al., 2012, Lemmers, et al., 2010, and van den Boogaard, et al., 2016). Inefficient D4Z4 repression, when combined with a permissive chromosome 4qA haplotype that provides a polyadenylation site for the DUX4 messenger RNA (mRNA), results in the ectopic expression of DUX4 protein in muscle cells (Lemmers, et al., 2010, Snider, et al., 2010, Tawil, et al., 2014). DUX4 is normally expressed in the pre-implantation embryo and in germline tissues, where it activates early developmental and stem cell genes (De Iaco, et al., 2017, Hendrickson, et al., 2017, Tawil, et al., 2014, Whiddon, et al., 2017). In most somatic tissues, including skeletal muscle, the D4Z4 arrays and DUX4 are epigenetically silenced through multiple mechanisms that suppress repetitive elements in the genome (Das and Chadwick, 2016, Daxinger, et al., 2015, Snider, et al., 2010, van Overveld, et al., 2003, and Zeng, et al., 2009). DUX4 mis-expression in skeletal muscle induces early embryo, stem cell and germline genes; activates repetitive elements; suppresses innate immune response and nonsense-mediated RNA decay pathways; inhibits myogenesis; and causes cell death through mechanisms that include the accumulation of aberrant and double-stranded RNAs (Bosnakovski, et al., 2008, Feng, et al., 2015, Geng, et al., 2012, Kowaljow, et al., 2007, Rickard, et al., 2015, Shadle, et al., 2017, Snider, et al., 2009, Wallace, et al., 2011, Winokur, et al., 2003, and Young, et al., 2013).

FSHD gets its name from the major muscle groups which are involved, namely the face, shoulders and upper arms. In general, muscle weakness starts in the face and moves down the body to the shoulders and upper arms followed by the weakening of the lower arms, abdominal muscles, and the hips and leg muscles. Additionally, patients with FSHD may also experience abnormal heart rhythm, hearing loss, and foot drop. FSHD, as a genetic disease, is typically and definitively diagnosed with a genetic test. Other tests such as creatine kinase levels, electromyogram, nerve conduction velocity, and muscle biopsy may be used to test for FSHD in some clinical situations but none of these tests are as accurate or specific for FSHD as genetic testing. Currently, there are no treatments for FSHD specifically, but palliative treatments which target pain and loss of function associated with muscle wasting. These treatments may include therapy such as physical therapy or occupational therapy, and non-steroidal anti-inflammatory or opioid pain medications. Alternatively, surgical interventions such as scapular fusion or bracing may be used to improve the patient's quality of life. Therapeutic agents in current clinical trials target only general increases in muscle mass (e.g., ACE-083) or a potential immune component (e.g., Resolaris/ATYR1940) without addressing the underlying cause of muscle degeneration, DUX4 expression.

In some embodiments, the FSHD has been diagnosed. In other embodiments, the FSHD has not been diagnosed. In some embodiments, the FSHD is adult-onset FSHD. In other embodiments, the FSHD is infantile-onset FSHD. In some embodiments, the FSHD is Type 1 FSHD. In other embodiments, the FSHD is Type 2 FSHD. In some embodiments, the patient is a mammal such as a human, or a non-human mammal such as a rat, a mouse, a rabbit, a dog or a cat. In some embodiments, the patient exhibits one or more symptoms of FSHD such as facial muscle weakness, shoulder weakness, hearing loss, abnormal heart rhythm, unequal weakening of muscles in the upper body, loss of strength in the abdominal muscles, or foot drop. In some embodiments, the symptom of FSHD is facial muscle weakness. In some embodiments, the unequal weakening of muscles in the upper body is unequal weakening of muscles in the biceps, triceps, deltoids, or lower arm muscles.

II. BET AND BET INHIBITORS

A. Bromo- and Extra-Terminal Domain Family

A bromodomain is an approximately 110 amino acid protein domain that recognizes acetylated lysine residues, such as those on the N-terminal tails of histones. Bromodomains, as the "readers" of lysine acetylation, are responsible in transducing the signal carried by acetylated lysine residues and translating it into various normal or abnormal phenotypes. Their affinity is higher for regions where multiple acetylation sites exist in proximity. This recognition is often a prerequisite for protein-histone association and chromatin remodeling. The domain itself adopts an all-α protein fold, a bundle of four alpha helices each separated by loop regions of variable lengths that form a hydrophobic pocket that recognizes the acetyl lysine.

The bromodomain was identified as a novel structural motif by John W. Tamkun and colleagues studying the *Drosophila* gene Brahma/brm, and showed sequence similarity to genes involved in transcriptional activation. The name "bromodomain" is derived from the relationship of this domain with Brahma and is unrelated to the chemical element bromine. The role of bromodomains in translating a deregulated cell acetylome into disease phenotypes was recently unveiled by the development of small molecule bromodomain inhibitors. This breakthrough discovery highlighted bromodomain-containing proteins as key players in cancer biology, as well as inflammation and remyelination in multiple sclerosis.

Bromodomain-containing proteins can have a wide variety of functions, ranging from histone acetyltransferase activity and chromatin remodeling to transcriptional mediation and co-activation. Of the 43 known in 2015, 11 had two bromodomains, and one protein had 6 bromodomains. Preparation, biochemical analysis, and structure determination of the bromodomain containing proteins have been described in detail. Members of the BET family have been implicated as targets in both human cancer and multiple sclerosis. BET inhibitors have shown therapeutic effects in multiple preclinical models of cancer and are currently in clinical trials in the United States. Their application in multiple sclerosis is still in the preclinical stage. A well-known example of a bromodomain family is the BET (Bromodomain and extraterminal domain) family. Members of this family include BRD2, BRD3, BRD4 and BRDT. Not considered part of the BET family (yet containing a bromodomain) are BRD7, and BRD9. Small molecule inhibitors of non-BET bromodomain proteins BRD7 and BRD9 have also been developed.

B. BET Inhibitors of the Disclosure
| Compound # | Structure | DUX4* MT FSHD2: IC50 (nM) |
| --- | --- | --- |
| SLU-2089 | 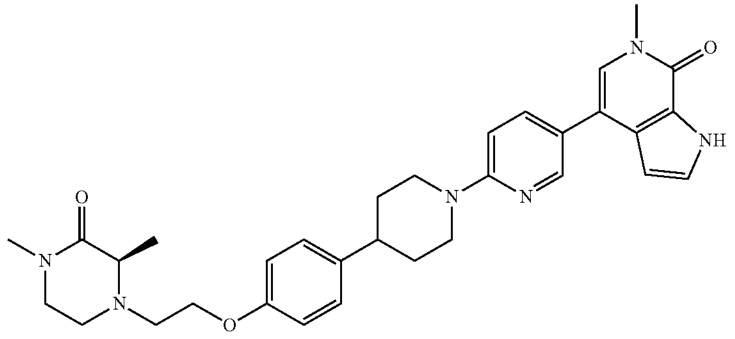 [SMILES: C[C@@H]1C(=O)N(C)CCN1CCOc1ccc(C2CCN(c3ccc(-c4cn(C)c(=O)c5[nH]ccc45)cn3)CC2)cc1] | 4.8 |
| SLU-2090 | 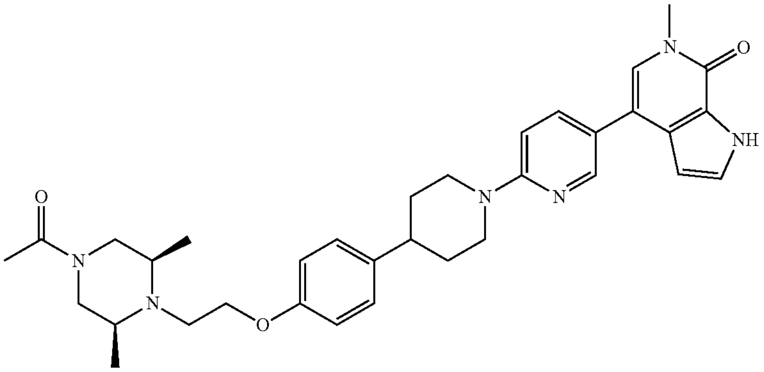 [SMILES: CC(=O)N1C[C@@H](C)N(CCOc2ccc(C3CCN(c4ccc(-c5cn(C)c(=O)c6[nH]ccc56)cn4)CC3)cc2)[C@@H](C)C1] | 43 |
| SLU-2091 | 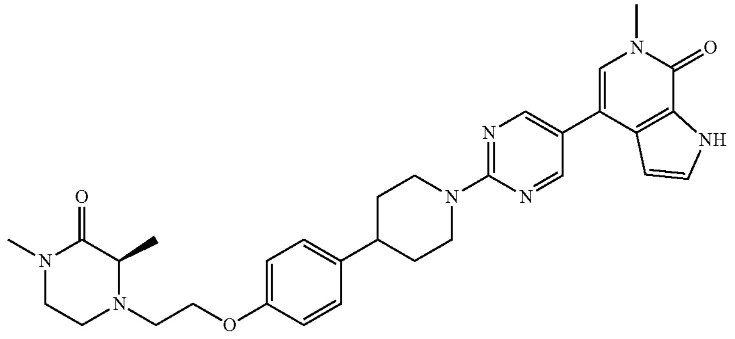 [SMILES: C[C@@H]1C(=O)N(C)CCN1CCOc1ccc(C2CCN(c3ncc(-c4cn(C)c(=O)c5[nH]ccc45)cn3)CC2)cc1] | 20 |
| SLU-2096 | 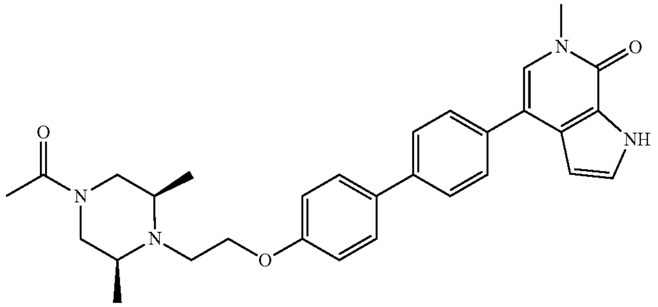 [SMILES: CC(=O)N1C[C@@H](C)N(CCOc2ccc(-c3ccc(-c4cn(C)c(=O)c5[nH]ccc45)cc3)cc2)[C@@H](C)C1] | 180 |

-continued
| Compound # | Structure | DUX4* MT FSHD2: IC50 (nM) |
|---|---|---|
| SLU-2097 | 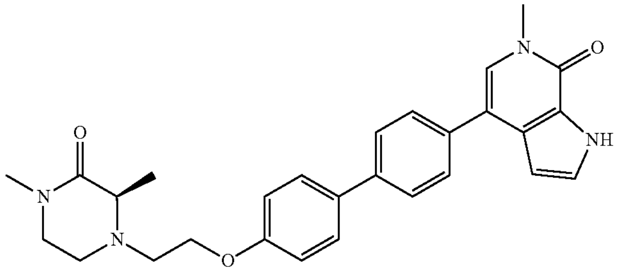 [SMILES: C[C@@H]1C(=O)N(C)CCN1CCOc1ccc(-c2ccc(-c3cn(C)c(=O)c4[nH]ccc34)cc2)cc1] | 120 |
| SLU-2098 | 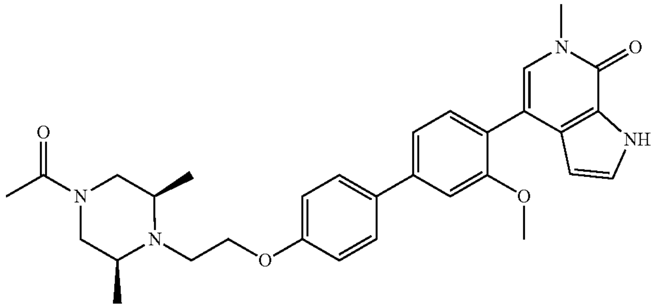 [SMILES: COc1cc(-c2ccc(OCCN3[C@H](C)CN(C(C)=O)C[C@@H]3C)cc2)ccc1-c1cn(C)c(=O)c2[nH]ccc12] | 310 |
| SLU-2102 | 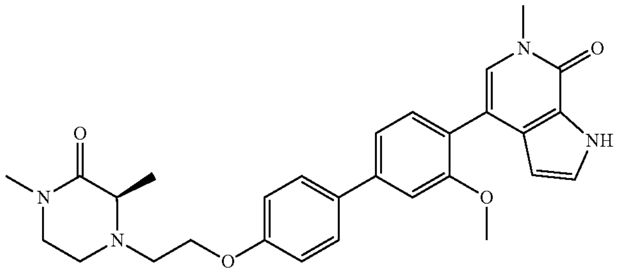 [SMILES: COc1cc(-c2ccc(OCCN3CCN(C)C(=O)[C@H]3C)cc2)ccc1-c1cn(C)c(=O)c2[nH]ccc12] | 130 |
| SLU-2104 | 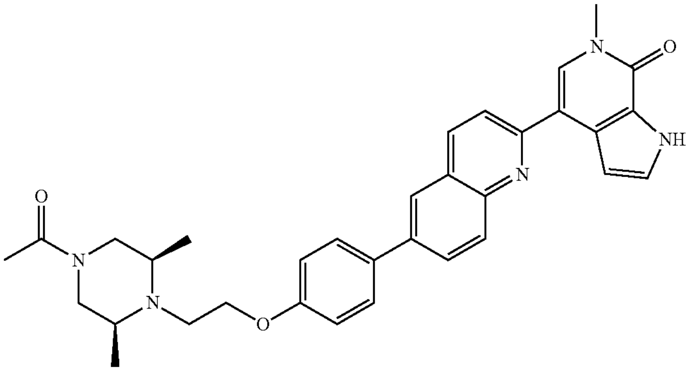 [SMILES: CC(=O)N1C[C@@H](C)N(CCOc2ccc(-c3ccc4nc(-c5cn(C)c(=O)c6[nH]ccc56)ccc4c3)cc2)[C@@H](C)C1] | 43 |

-continued
| Compound # | Structure | DUX4* MT FSHD2: IC50 (nM) |
|---|---|---|
| SLU-2106 | 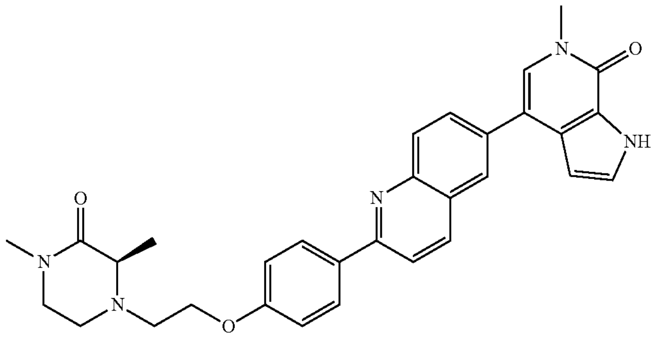 [SMILES: C[C@@H]1C(=O)N(C)CCN1CCOc1ccc(-c2ccc3cc(-c4cn(C)c(=O)c5[nH]ccc45)ccc3n2)cc1] | 24 |
| SLU-2107 | 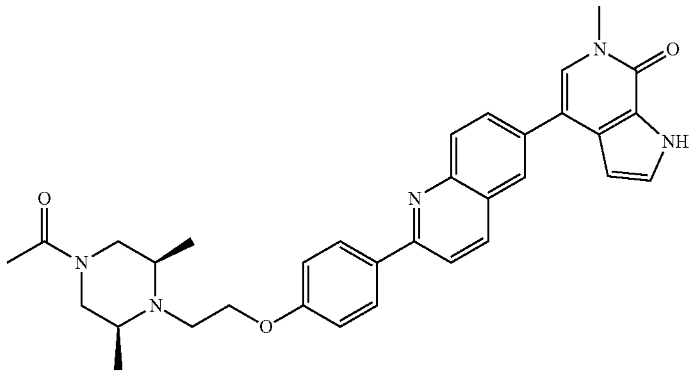 [SMILES: CC(=O)N1C[C@@H](C)N(CCOc2ccc(-c3ccc4cc(-c5cn(C)c(=O)c6[nH]ccc56)ccc4n3)cc2)[C@@H](C)C1] | 48 |
| SLU-2108 | 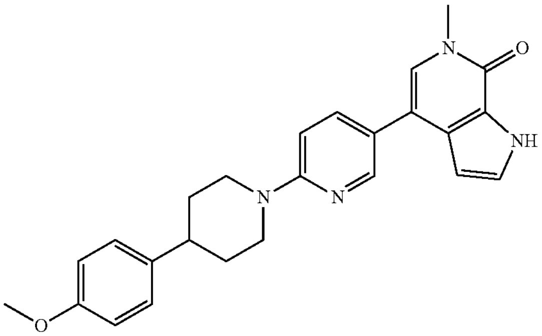 [SMILES: COc1ccc(C2CCN(c3ccc(-c4cn(C)c(=O)c5[nH]ccc45)cn3)CC2)cc1] | 280 |
| SLU-2109 | 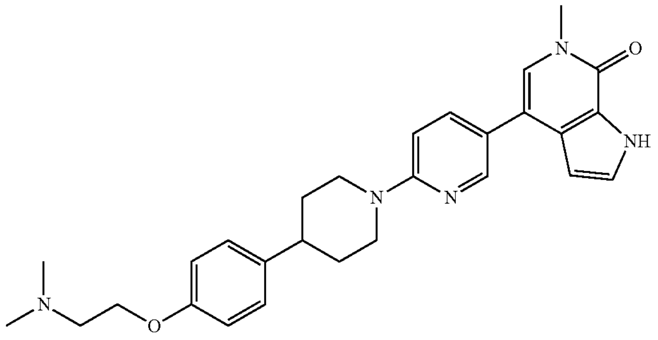 [SMILES: CN(C)CCOc1ccc(C2CCN(c3ccc(-c4cn(C)c(=O)c5[nH]ccc45)cn3)CC2)cc1] | 33 |

-continued
| Compound # | Structure | DUX4* MT FSHD2: IC50 (nM) |
| --- | --- | --- |
| SLU-2110 | 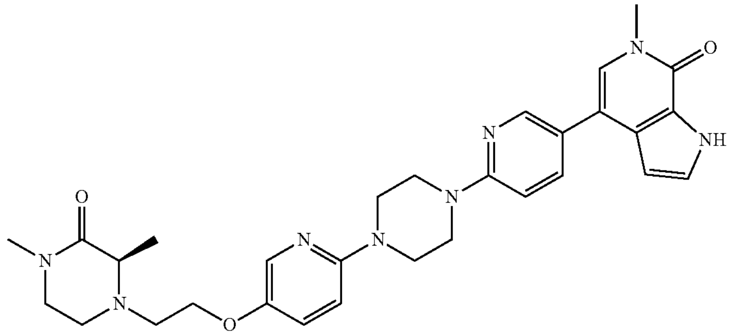 [SMILES: C[C@@H]1C(=O)N(C)CCN1CCOc1ccc(N2CCN(c3ccc(-c4cn(C)c(=O)c5[nH]ccc45)cn3)CC2)nc1] | 16 |
| SLU-2111 | 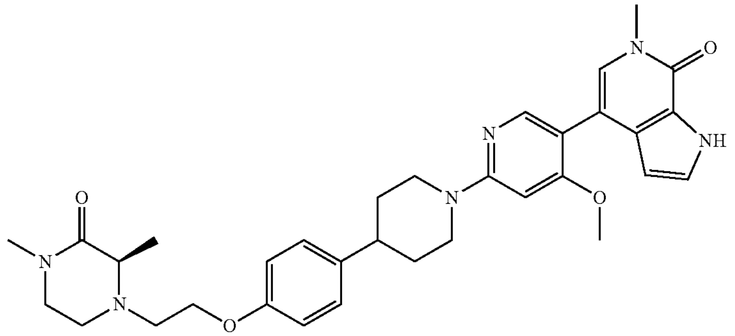 [SMILES: COc1cc(N2CCC(c3ccc(OCCN4CCN(C)C(=O)[C@H]4C)cc3)CC2)ncc1-c1cn(C)c(=O)c2[nH]ccc12] | 29 |
| SLU-2112 | 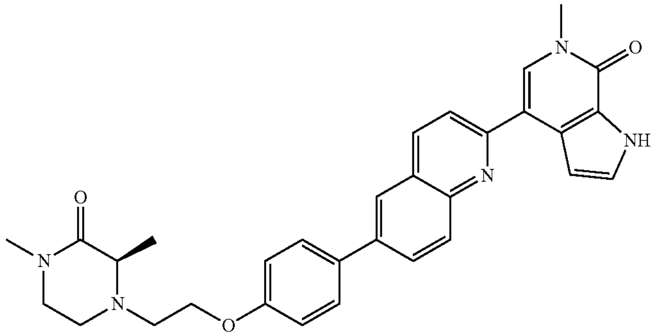 [SMILES: C[C@@H]1C(=O)N(C)CCN1CCOc1ccc(-c2ccc3nc(-c4cn(C)c(=O)c5[nH]ccc45)ccc3c2)cc1] | 40 |
| SLU-2114 | 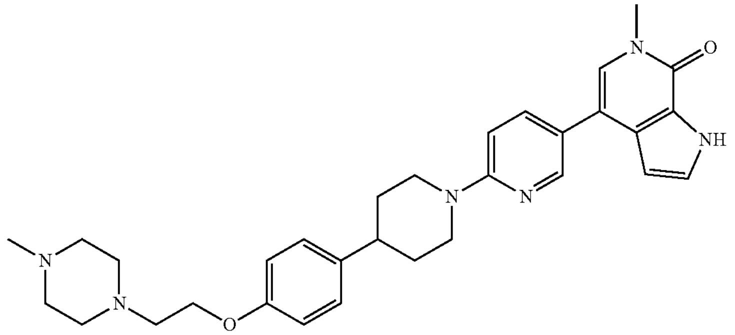 [SMILES: CN1CCN(CCOc2ccc(C3CCN(c4ccc(-c5cn(C)c(=O)c6[nH]ccc56)cn4)CC3)cc2)CC1] | 330 |

-continued
| Compound # | Structure | DUX4* MT FSHD2: IC50 (nM) |
|---|---|---|
| SLU-2115 | 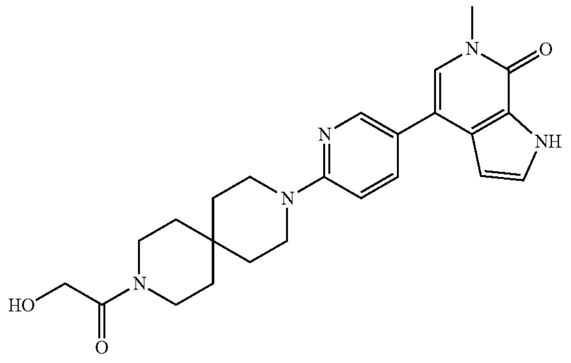 [SMILES: Cn1cc(-c2ccc(N3CCC4(CCN(C(=O)CO)CC4)CC3)nc2)c2cc[nH]c2c1=O] | 97 |
| SLU-2116 | 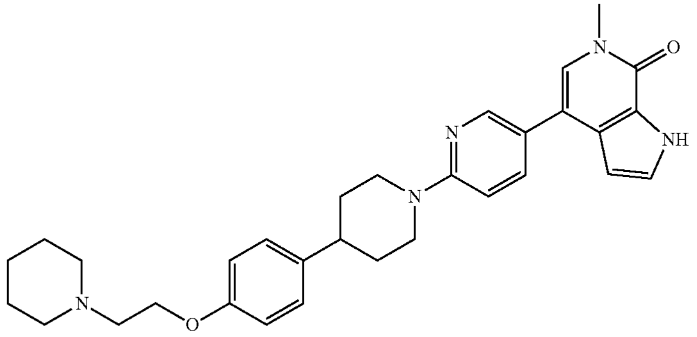 [SMILES: Cn1cc(-c2ccc(N3CCC(c4ccc(OCCN5CCCCC5)cc4)CC3)nc2)c2cc[nH]c2c1=O] | 270 |
| SLU-2117 | 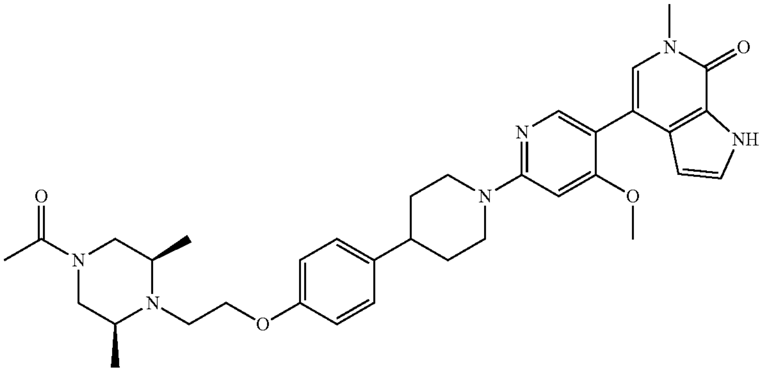 [SMILES: COc1cc(N2CCC(c3ccc(OCCN4[C@H](C)CN(C(C)=O)C[C@@H]4C)cc3)CC2)ncc1-c1cn(C)c(=O)c2[nH]ccc12] | 91 |
| SLU-2118 | 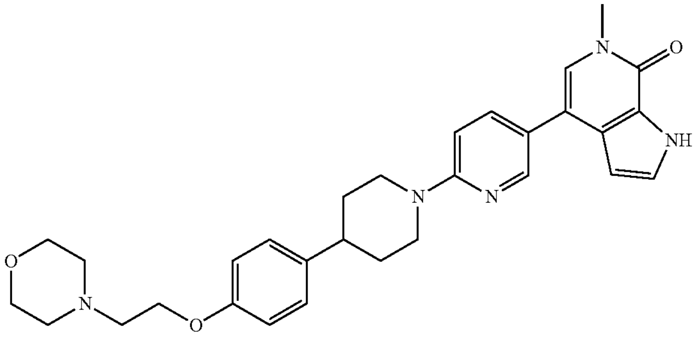 [SMILES: Cn1cc(-c2ccc(N3CCC(c4ccc(OCCN5CCOCC5)cc4)CC3)nc2)c2cc[nH]c2c1=O] | 261 |

-continued
| Compound # | Structure | DUX4* MT FSHD2: IC50 (nM) |
| --- | --- | --- |
| SLU-2119 | 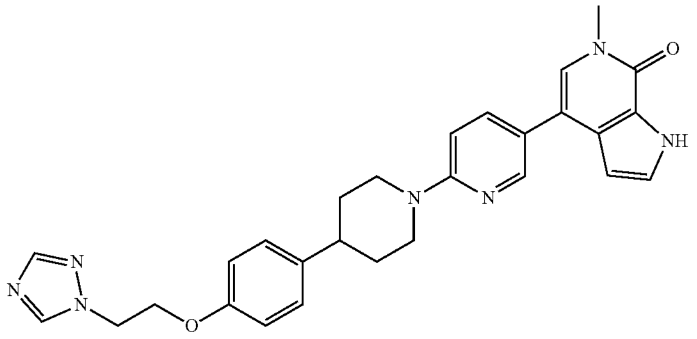 [SMILES: Cn1cc(-c2ccc(N3CCC(c4ccc(OCCn5cncn5)cc4)CC3)nc2)c2cc[nH]c2c1=O] | 130 |
| SLU-2120 | 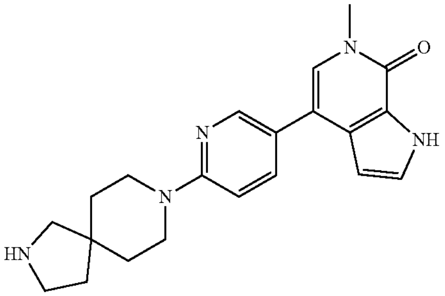 [SMILES: Cn1cc(-c2ccc(N3CCC4(CCNC4)CC3)nc2)c2cc[nH]c2c1=O] | 350 |
| SLU-2124 | 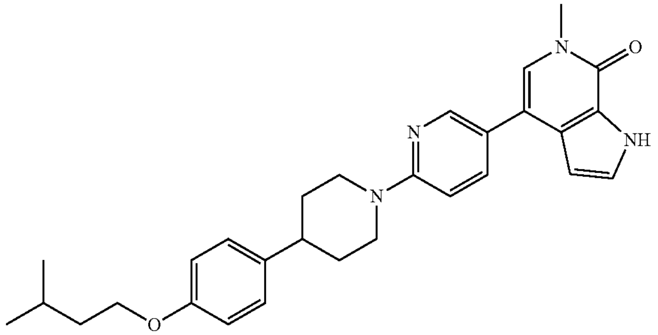 [SMILES: CC(C)CCOc1ccc(C2CCN(c3ccc(-c4cn(C)c(=O)c5[nH]ccc45)cn3)CC2)cc1] | 1300 |
| SLU-2127 | 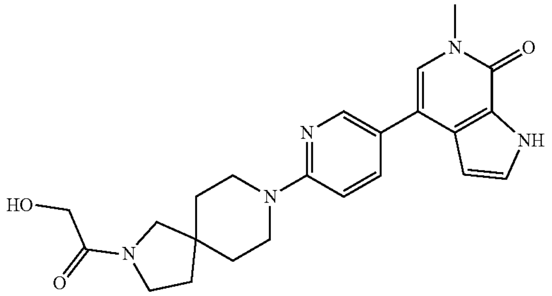 [SMILES: Cn1cc(-c2ccc(N3CCC4(CCN(C(=O)CO)C4)CC3)nc2)c2cc[nH]c2c1=O] | 37 |

-continued
| Compound # | Structure | DUX4* MT FSHD2: IC50 (nM) |
| --- | --- | --- |
| SLU-2130 | 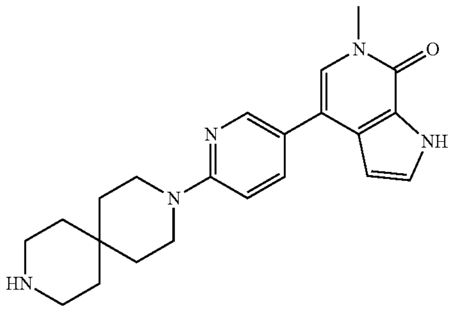 [SMILES: Cn1cc(-c2ccc(N3CCC4(CCNCC4)CC3)nc2)c2cc[nH]c2c1=O] | 120 |
| SLU-2131 | 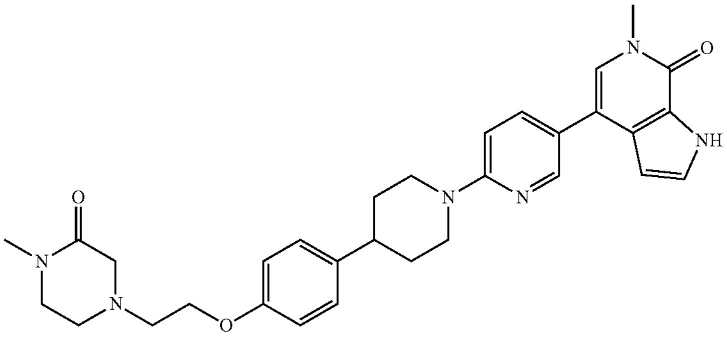 [SMILES: CN1CCN(CCOc2ccc(C3CCN(c4ccc(-c5cn(C)c(=O)c6[nH]ccc56)cn4)CC3)cc2)CC1=O] | 62 |
| SLU-2211 | 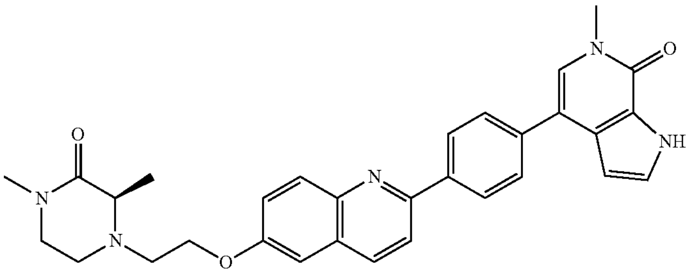 [SMILES: C[C@@H]1C(=O)N(C)CCN1CCOc1ccc2nc(-c3ccc(-c4cn(C)c(=O)c5[nH]ccc45)cc3)ccc2c1] | 62 |
| SLU-2212 | 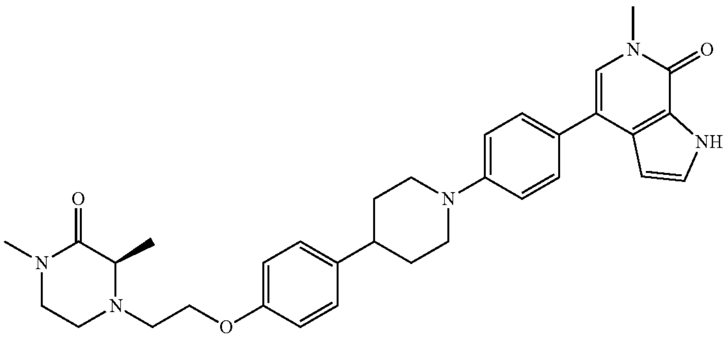 [SMILES: C[C@@H]1C(=O)N(C)CCN1CCOc1ccc(C2CCN(c3ccc(-c4cn(C)c(=O)c5[nH]ccc45)cc3)CC2)cc1] | 86 |

-continued
| Compound # | Structure | DUX4* MT FSHD2: IC50 (nM) |
|---|---|---|
| SLU-2213 | 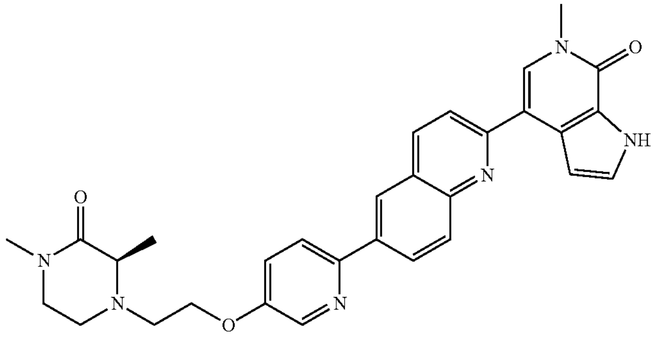 | 41 |
| SLU-2214 | 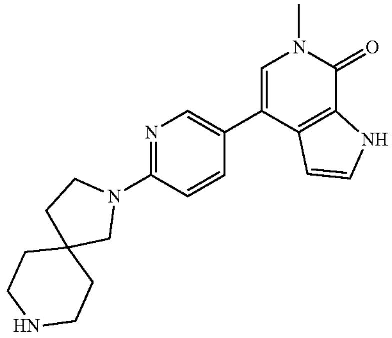 [SMILES: Cn1cc(-c2ccc(N3CCC4(CCNCC4)C3)nc2)c2cc[nH]c2c1=O] | 95 |
| SLU-2217 | 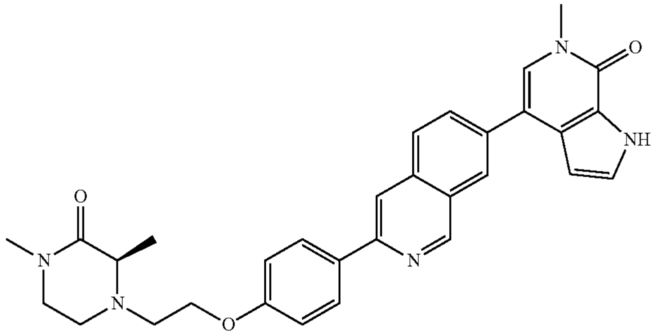 | 22 |
| SLU-2218 | 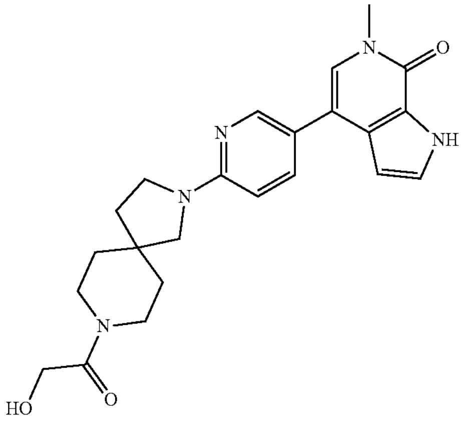 [SMILES: Cn1cc(-c2ccc(N3CCC4(CCN(C(=O)CO)CC4)C3)nc2)c2cc[nH]c2c1=O] | 41 |

-continued
| Compound # | Structure | DUX4* MT FSHD2: IC50 (nM) |
|---|---|---|
| SLU-2219 | 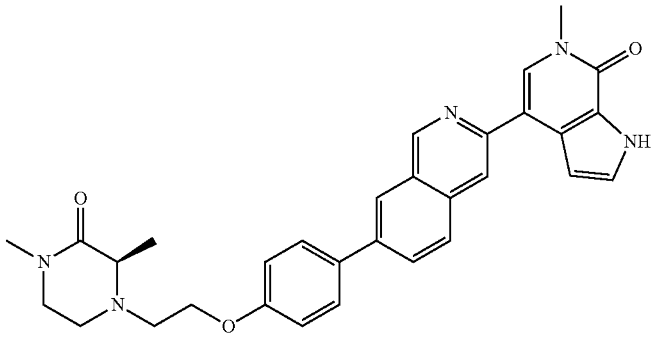 | 95 |
| SLU-2225 | 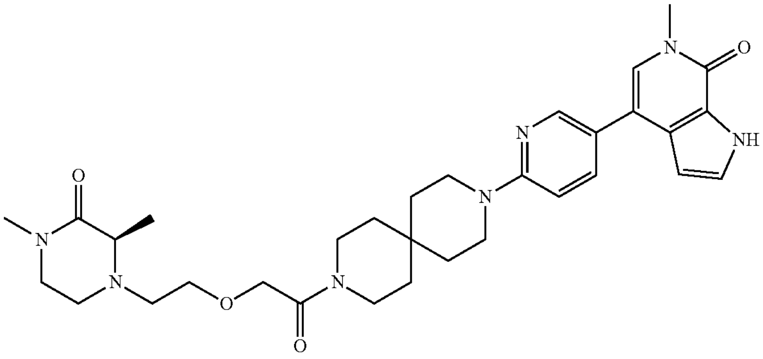 [SMILES: C[C@@H]1C(=O)N(C)CCN1CCOCC(=O)N1CCC2(CC1)CCN(c1ccc(-c3cn(C)c(=O)c4[nH]ccc34)cn1)CC2] | 35 |
| SLU-2226 | 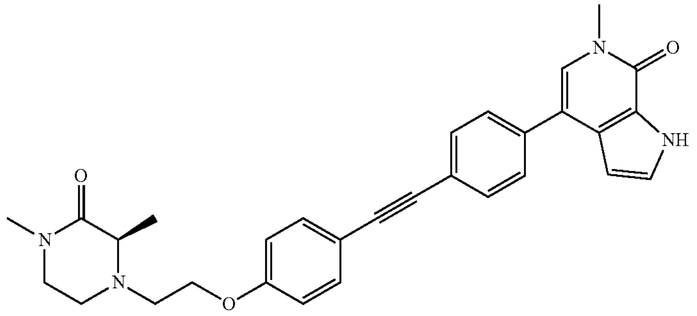 [SMILES: C[C@@H]1C(=O)N(C)CCN1CCOc1ccc(C#Cc2ccc(-c3cn(C)c(=O)c4[nH]ccc34)cc2)cc1] | 47 |
| SLU-2227 | 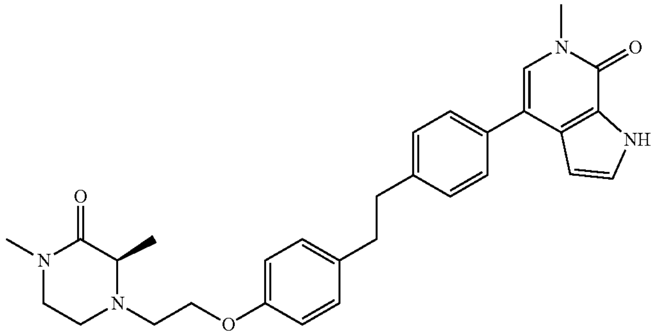 [SMILES: C[C@@H]1C(=O)N(C)CCN1CCOc1ccc(CCc2ccc(-c3cn(C)c(=O)c4[nH]ccc34)cc2)cc1] | 69 |

-continued
| Compound # | Structure | DUX4* MT FSHD2: IC50 (nM) |
| --- | --- | --- |
| SLU-2232 | 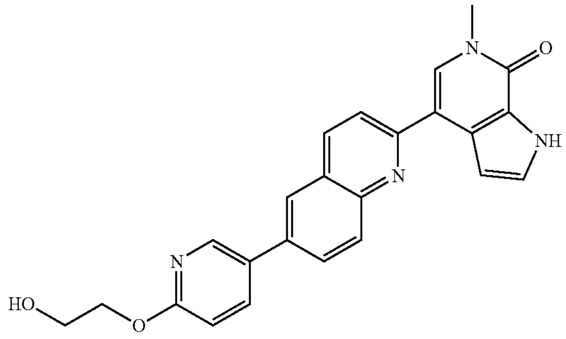 [SMILES: Cn1cc(-c2ccc3cc(-c4ccc(OCCO)nc4)ccc3n2)c2cc[nH]c2c1=O] | 97 |
| SLU-2233 | 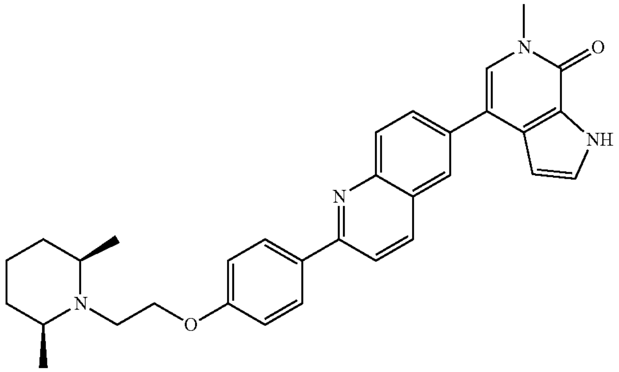 [SMILES: C[C@@H]1CCC[C@H](C)N1CCOc1ccc(-c2ccc3cc(-c4cn(C)c(=O)c5[nH]ccc45)ccc3n2)cc1] | 290 |
| SLU-2234 | 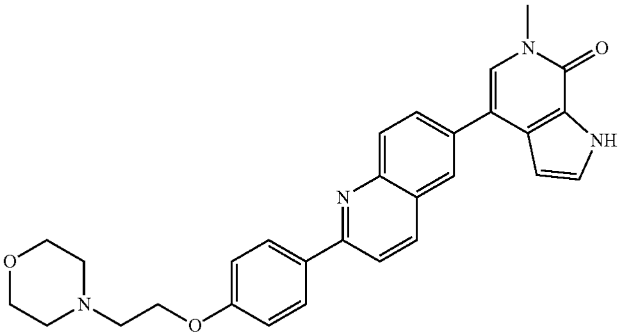 [SMILES: Cn1cc(-c2ccc3nc(-c4ccc(OCCN5CCOCC5)cc4)ccc3c2)c2cc[nH]c2c1=O] | 69 |
| SLU-2235 | 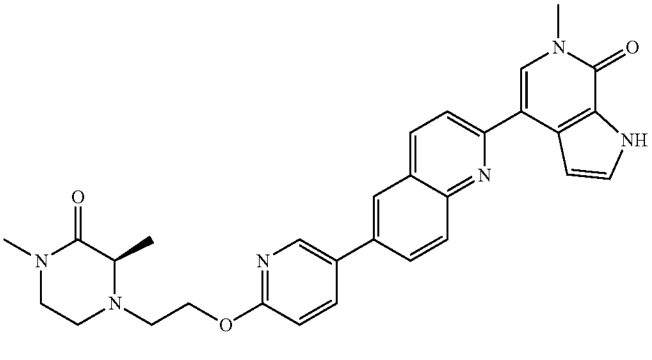 | 12 |

-continued
| Compound # | Structure | DUX4* MT FSHD2: IC50 (nM) |
|---|---|---|
| SLU-2236 | 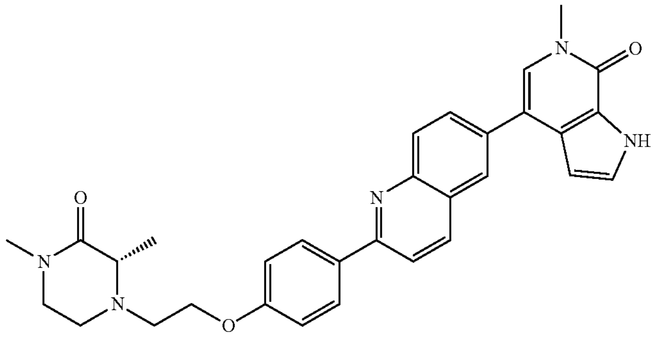 [SMILES: C[C@H]1C(=O)N(C)CCN1CCOc1ccc(-c2ccc3cc(-c4cn(C)c(=O)c5[nH]ccc45)ccc3n2)cc1] | 13 |
| SLU-2240 | 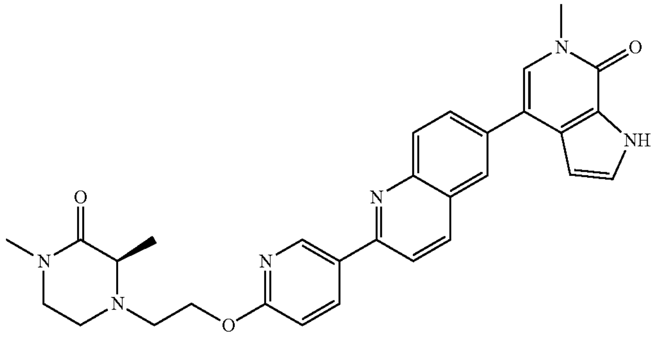 | 35 |
| SLU-2241 | 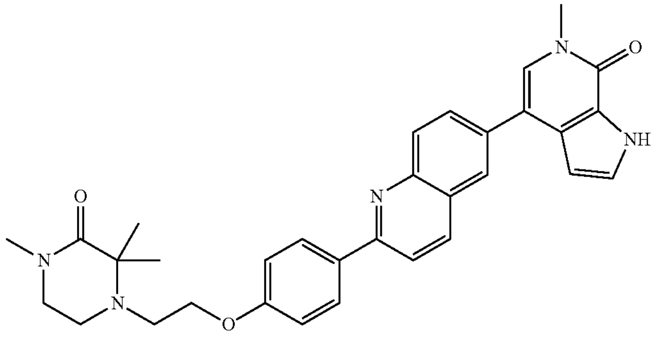 [SMILES: CN1CCN(CCOc2ccc(-c3ccc4cc(-c5cn(C)c(=O)c6[nH]ccc56)ccc4n3)cc2)C(C)(C)C1=O] | 110 |
| SLU-2242 | 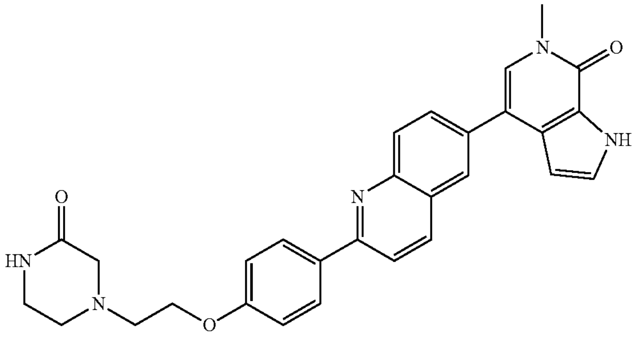 [SMILES: Cn1cc(-c2ccc3nc(-c4ccc(OCCN5CCNC(=O)C5)cc4)ccc3c2)c2cc[nH]c2c1=O] | 93 |

-continued
| Compound # | Structure | DUX4* MT FSHD2: IC50 (nM) |
| --- | --- | --- |
| SLU-2243 | 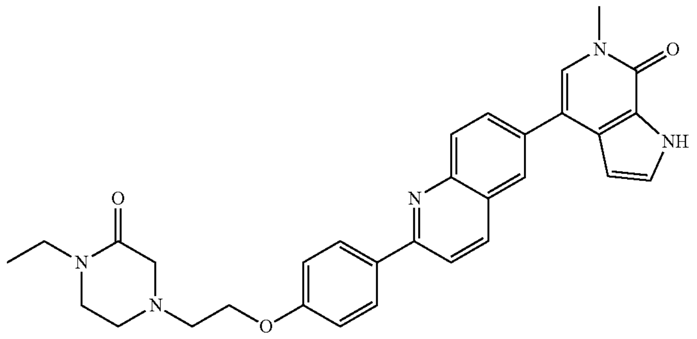 [SMILES: CCN1CCN(CCOc2ccc(-c3ccc4cc(-c5cn(C)c(=O)c6[nH]ccc56)ccc4n3)cc2)CC1=O] | 110 |
| SLU-2244 | 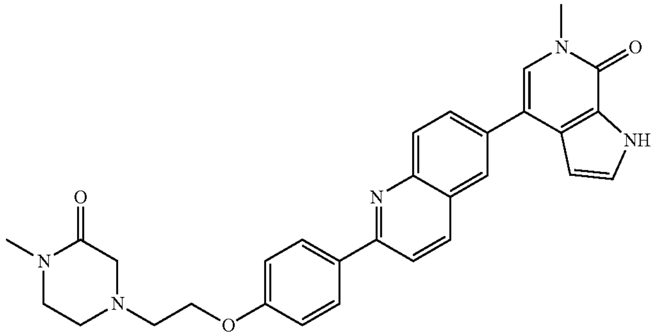 [SMILES: CN1CCN(CCOc2ccc(-c3ccc4cc(-c5cn(C)c(=O)c6[nH]ccc56)ccc4n3)cc2)CC1=O] | 28 |
| SLU-2277 | 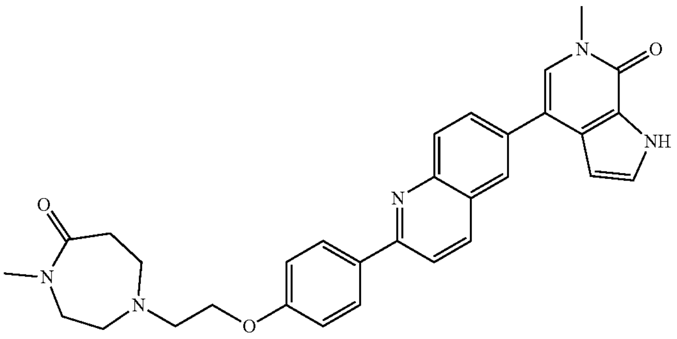 [SMILES: CN1CCN(CCOc2ccc(-c3ccc4cc(-c5cn(C)c(=O)c6[nH]ccc56)ccc4n3)cc2)CCC1=O] | 20 |
| SLU-2278 | 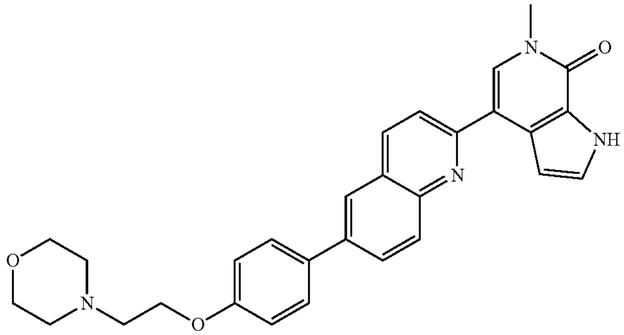 [SMILES: Cn1cc(-c2ccc3cc(-c4ccc(OCCN5CCOCC5)cc4)ccc3n2)c2cc[nH]c2c1=O] | 120 |

-continued
| Compound # | Structure | DUX4* MT FSHD2: IC50 (nM) |
|---|---|---|
| SLU-2279 | 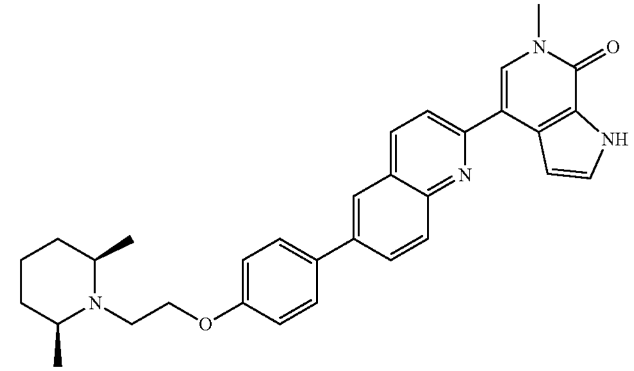 [SMILES: C[C@@H]1CCC[C@H](C)N1CCOc1ccc(-c2ccc3nc(-c4cn(C)c(=O)c5[nH]ccc45)ccc3c2)cc1] | 420 |
| SLU-2280 | 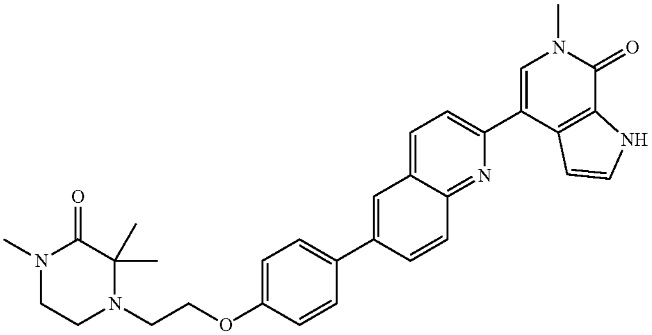 [SMILES: CN1CCN(CCOc2ccc(-c3ccc4nc(-c5cn(C)c(=O)c6[nH]ccc56)ccc4c3)cc2)C(C)(C)C1=O] | 120 |
| SLU-2281 | 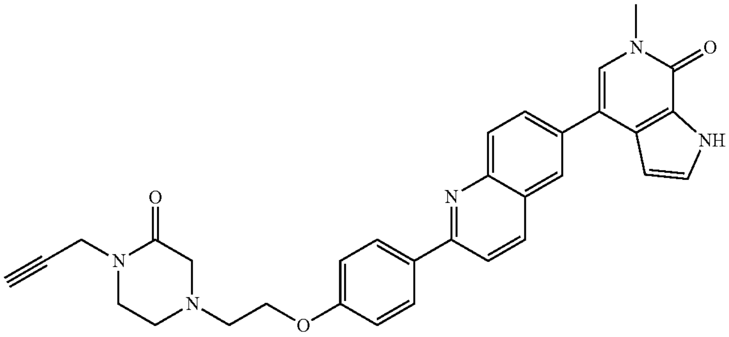 [SMILES: C#CCN1CCN(CCOc2ccc(-c3ccc4cc(-c5cn(C)c(=O)c6[nH]ccc56)ccc4n3)cc2)CC1=O] | 130 |
| SLU-2282 | 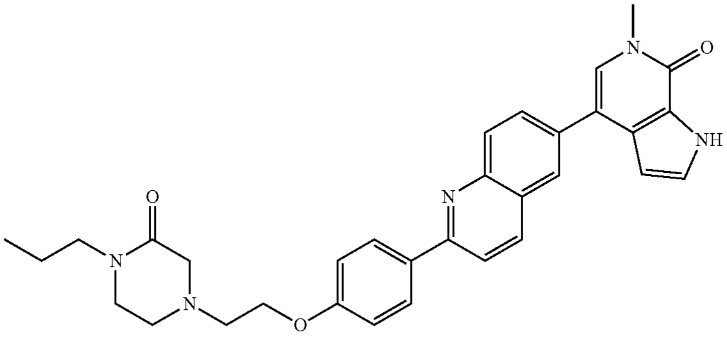 [SMILES: CCCN1CCN(CCOc2ccc(-c3ccc4cc(-c5cn(C)c(=O)c6[nH]ccc56)ccc4n3)cc2)CC1=O] | 54 |

-continued
| Compound # | Structure | DUX4* MT FSHD2: IC50 (nM) |
| --- | --- | --- |
| SLU-2283 | 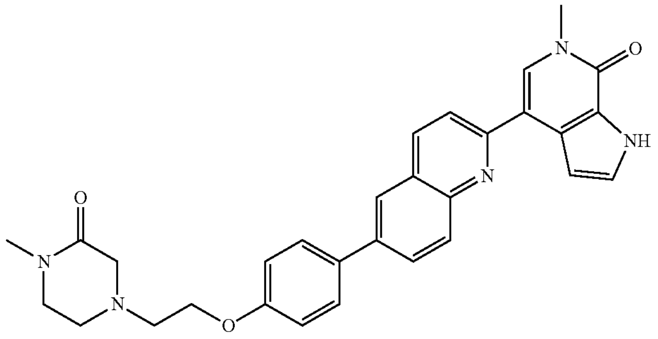 [SMILES: CN1CCN(CCOc2ccc(-c3ccc4nc(-c5cn(C)c(=O)c6[nH]ccc56)ccc4c3)cc2)CC1=O] | 160 |
| SLU-2284 | 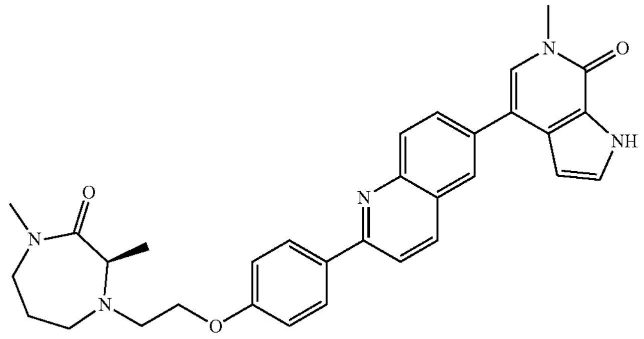 [SMILES: C[C@@H]1C(=O)N(C)CCCN1CCOc1ccc(-c2ccc3cc(-c4cn(C)c(=O)c5[nH]ccc45)ccc3n2)cc1] | 90 |
| SLU-2285 | 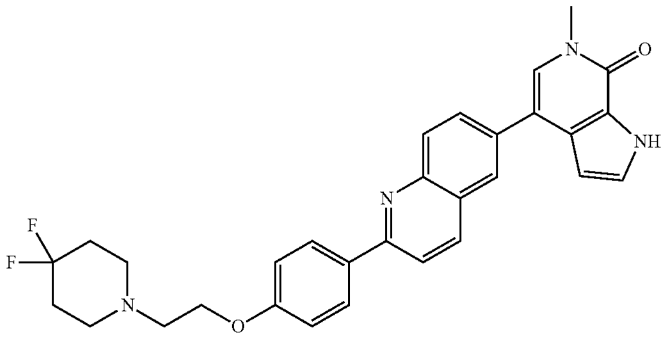 [SMILES: Cn1cc(-c2ccc3nc(-c4ccc(OCCN5CCC(F)(F)CC5)cc4)ccc3c2)c2cc[nH]c2c1=O] | 570 |
| SLU-2286 | 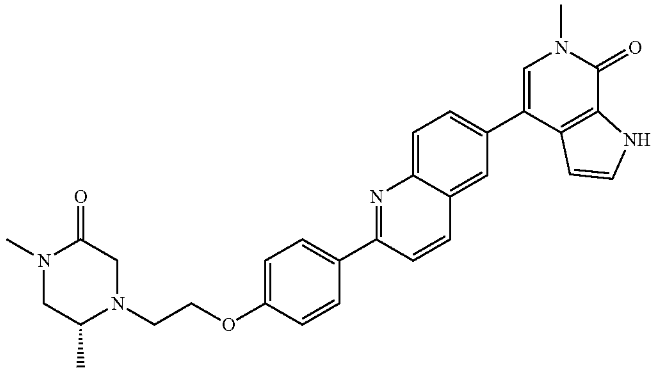 [SMILES: C[C@@H]1CN(C)C(=O)CN1CCOc1ccc(-c2ccc3cc(-c4cn(C)c(=O)c5[nH]ccc45)ccc3n2)cc1] | 63 |

-continued
| Compound # | Structure | DUX4* MT FSHD2: IC50 (nM) |
|---|---|---|
| SLU-2287 | 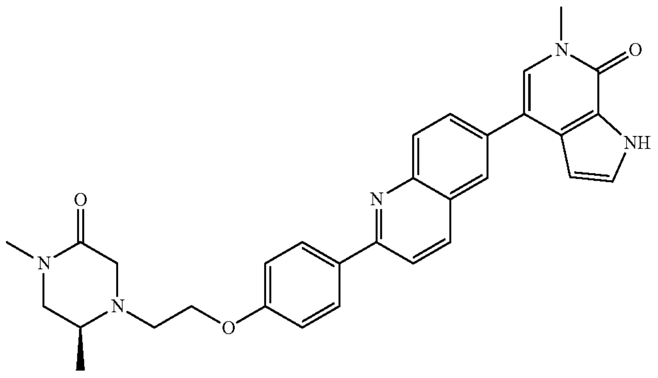 [SMILES: C[C@H]1CN(C)C(=O)CN1CCOc1ccc(-c2ccc3cc(-c4cn(C)c(=O)c5[nH]ccc45)ccc3n2)cc1] | 108 |
| SLU-2288 | 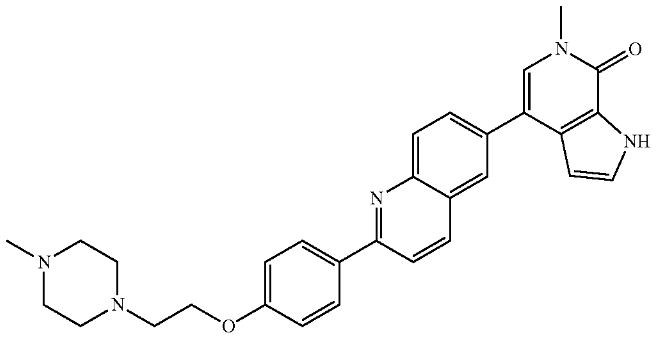 [SMILES: CN1CCN(CCOc2ccc(-c3ccc4cc(-c5cn(C)c(=O)c6[nH]ccc56)ccc4n3)cc2)CC1] | 250 |
| SLU-2292 | 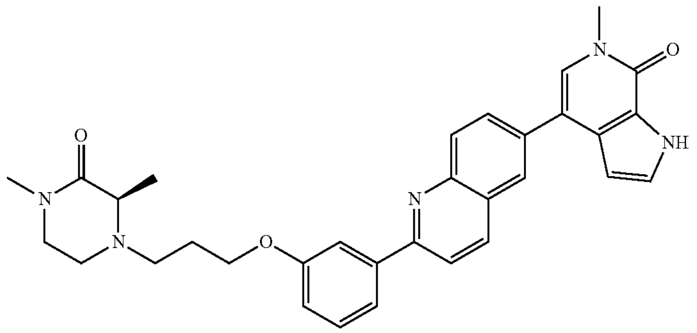 [SMILES: C[C@@H]1C(=O)N(C)CCN1CCCOc1cccc(-c2ccc3cc(-c4cn(C)c(=O)c5[nH]ccc45)ccc3n2)c1] | 25 |
| SLU-2293 | 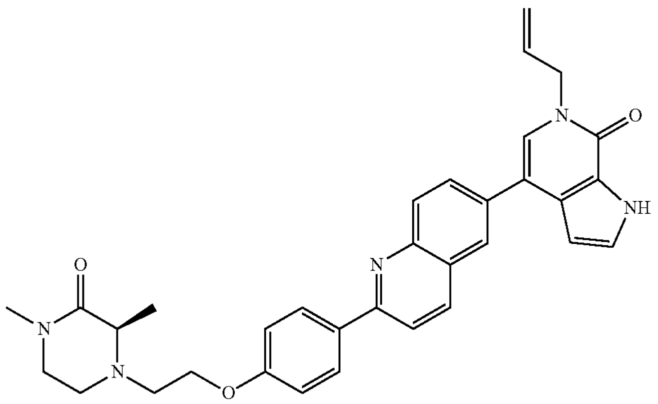 [SMILES: C=CCn1cc(-c2ccc3nc(-c4ccc(OCCN5CCN(C)C(=O)[C@H]5C)cc4)ccc3c2)c2cc[nH]c2c1=O] | 18 |

-continued
| Compound # | Structure | DUX4* MT FSHD2: IC50 (nM) |
| --- | --- | --- |
| SLU-2294 | 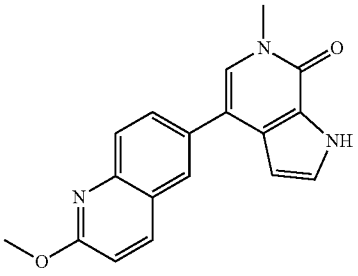 [SMILES: COc1ccc2cc(-c3cn(C)c(=O)c4[nH]ccc34)ccc2n1] | 59 |
| SLU-2295 | 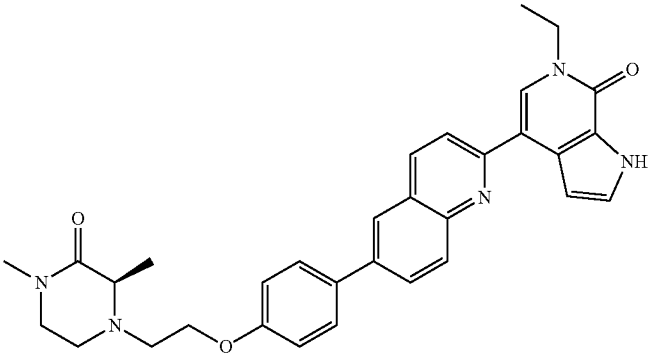 [SMILES: CCn1cc(-c2ccc3cc(-c4ccc(OCCN5CCN(C)C(=O)[C@H]5C)cc4)ccc3n2)c2cc[nH]c2c1=O] | 51 |
| SLU-2296 | 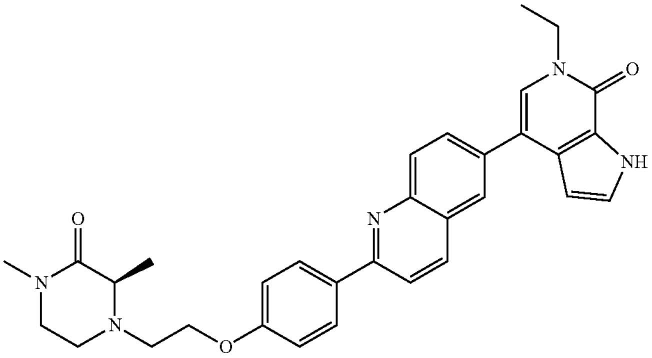 [SMILES: CCn1cc(-c2ccc3nc(-c4ccc(OCCN5CCN(C)C(=O)[C@H]5C)cc4)ccc3c2)c2cc[nH]c2c1=O] | 58 |
| SLU-2297 | 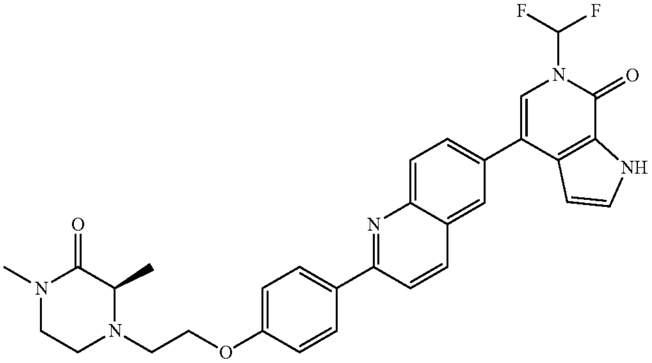 [SMILES: C[C@@H]1C(=O)N(C)CCN1CCOc1ccc(-c2ccc3cc(-c4cn(C(F)F)c(=O)c5[nH]ccc45)ccc3n2)cc1] | 1600 |

-continued
| Compound # | Structure | DUX4* MT FSHD2: IC50 (nM) |
| --- | --- | --- |
| SLU-2298 | 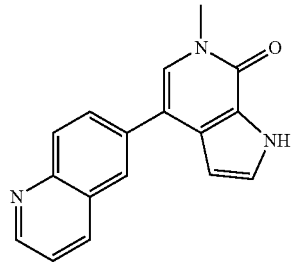 [SMILES: Cn1cc(-c2ccc3ncccc3c2)c2cc[nH]c2c1=O] | 113 |
| SLU-2299 | 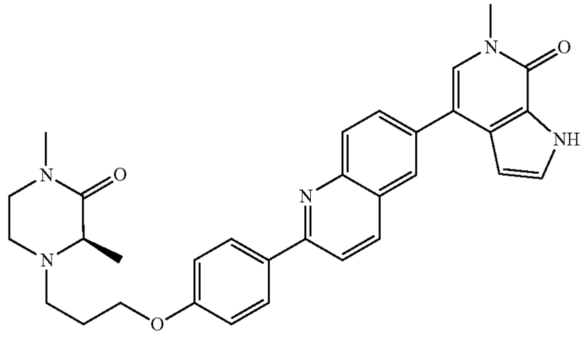 [SMILES: C[C@@H]1C(=O)N(C)CCN1CCCOc1ccc(-c2ccc3cc(-c4cn(C)c(=O)c5[nH]ccc45)ccc3n2)cc1] | 3.4 |
| SLU-2300 | 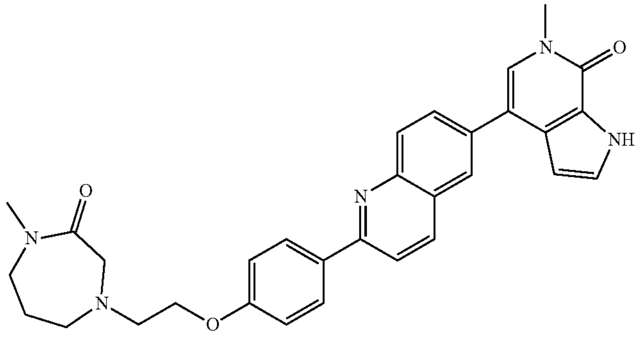 [SMILES: CN1CCCN(CCOc2ccc(-c3ccc4cc(-c5cn(C)c(=O)c6[nH]ccc56)ccc4n3)cc2)CC1=O] | 49 |
| SLU-2301 | 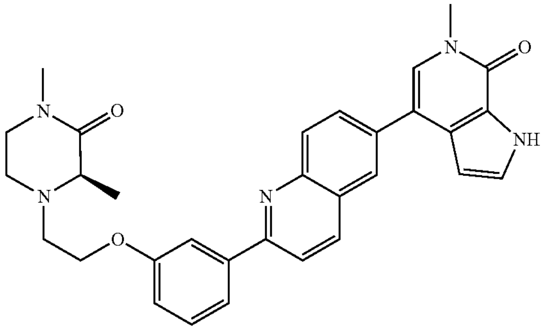 [SMILES: C[C@@H]1C(=O)N(C)CCN1CCOc1cccc(-c2ccc3cc(-c4cn(C)c(=O)c5[nH]ccc45)ccc3n2)c1] | 13 |
| SLU-2302 | 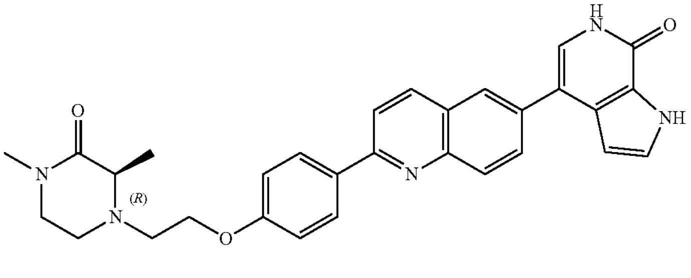 | 1800 |

-continued
| Compound # | Structure | DUX4* MT FSHD2: IC50 (nM) |
|---|---|---|
| SLU-2325 | 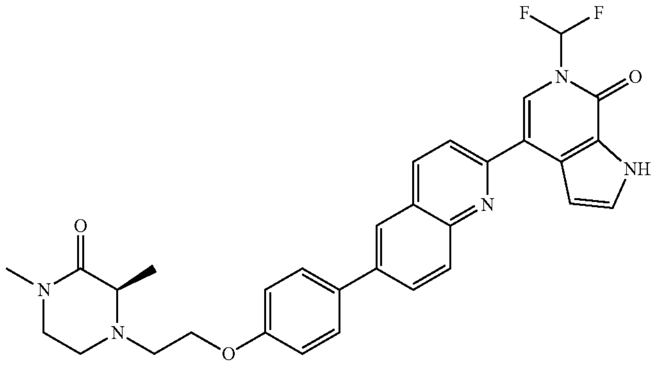 [SMILES: C[C@@H]1C(=O)N(C)CCN1CCOc1ccc(-c2ccc3nc(-c4cn(C(F)F)c(=O)c5[nH]ccc45)ccc3c2)cc1] | 290 |
| SLU-2326 | 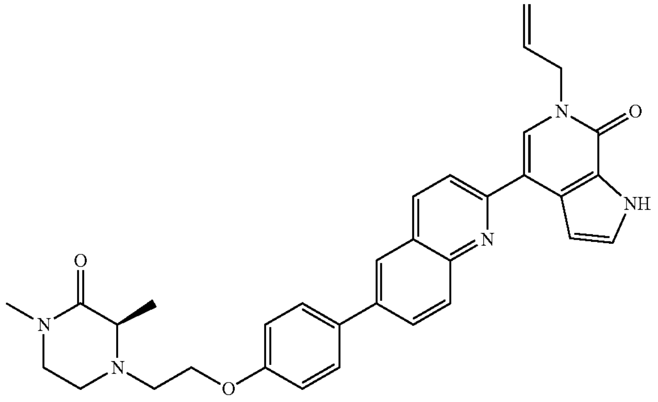 [SMILES: C=CCn1cc(-c2ccc3cc(-c4ccc(OCCN5CCN(C)C(=O)[C@H]5C)cc4)ccc3n2)c2cc[nH]c2c1=O] | 130 |
| SLU-2327 | 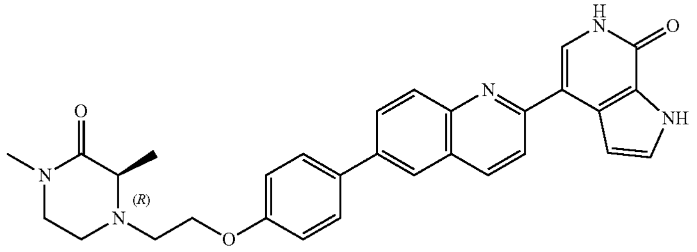 | 1100 |
| SLU-2346 | 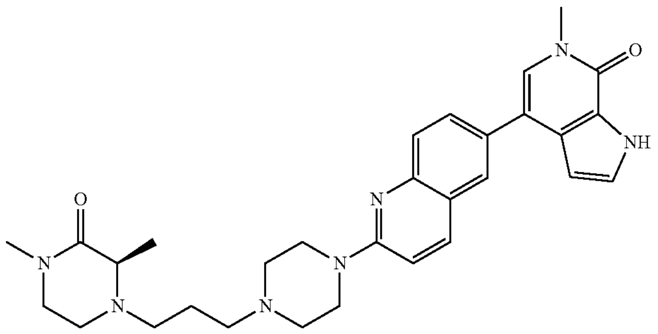 [SMILES: C[C@@H]1C(=O)N(C)CCN1CCCN1CCN(c2ccc3cc(-c4cn(C)c(=O)c5[nH]ccc45)ccc3n2)CC1] | 41 |

-continued

| Compound # | Structure | DUX4* MT FSHD2: IC50 (nM) |
| --- | --- | --- |
| SLU-2347 | 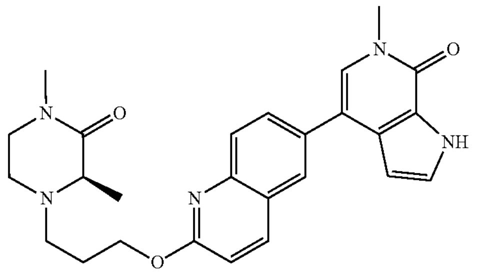 [SMILES: C[C@@H]1C(=O)N(C)CCN1CCCOc1ccc2cc(-c3cn(C)c(=O)c4[nH]ccc34)ccc2n1] | 85 |
| SLU-2348 | 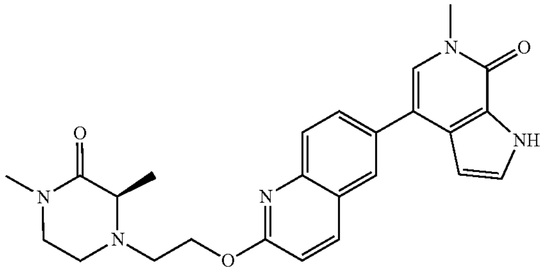 [SMILES: C[C@@H]1C(=O)N(C)CCN1CCOc1ccc2cc(-c3cn(C)c(=O)c4[nH]ccc34)ccc2n1] | 140 |
| SLU-2611 | 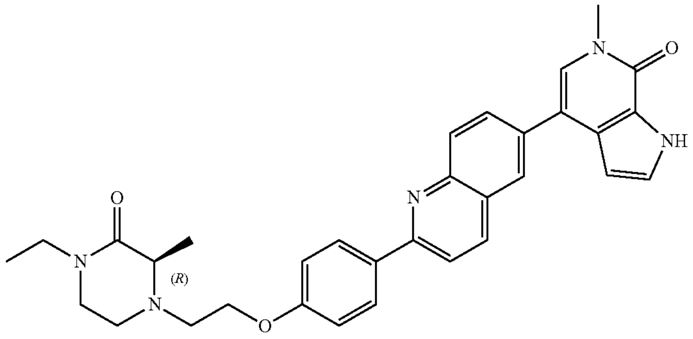 | 41 |

*DUX4 expression inferred from surrogate marker MBD3L2 expression (see Example 2)

The BET inhibitors of the present disclosure (also referred to as "compounds of the present disclosure") are shown, for example, above, in the summary section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All the compounds of the present disclosure may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present disclosure are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present disclosure have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration. In some embodiments, the present compounds may contain two or more atoms which have a defined stereochemical orientation.

Chemical formulas used to represent compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, compounds of the present disclosure function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

C. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; imino means=NH; "cyano" means —CN; "isocyanyl" means —N=C=O; "azido" means —$N_3$; in a monovalent context "phosphate" means —OP(O)$(OH)_2$ or a deprotonated form thereof; in a divalent context "phosphate" means —OP(O)(OH)O— or a deprotonated form thereof, "mercapto" means —SH; and "thio" means =S; "sulfonyl" means —$S(O)_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⩶" represents a single bond or a double bond. Thus, the formula

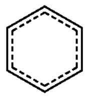

covers, for example,

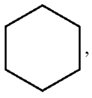, 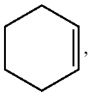, 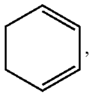, 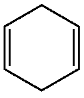 and 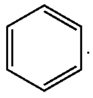.

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿", when drawn perpendicularly across a bond (e.g, , 

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "ıııııı" means a single bond where the group attached to the thick end of the wedge is "into the page". The symbol "∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

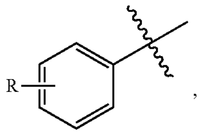

, then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

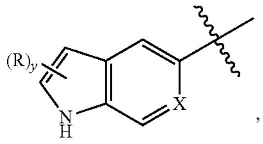

, then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C\leq8)}$", "cycloalkanediyl$_{(C\leq8)}$", "heteroaryl$_{(C\leq8)}$", and "acyl$_{(C\leq8)}$" is one, the minimum number of carbon atoms in the groups "alkenyl$_{(C\leq8)}$", "alkynyl$_{(C\leq8)}$", and "heterocycloalkyl$_{(C\leq8)}$" is two, the minimum number of carbon atoms in the group "cycloalkyl$_{(C\leq8)}$" is three, and the minimum number of carbon atoms in the groups "aryl$_{(C\leq8)}$" and "arenediyl$_{(C\leq8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefinc$_5$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

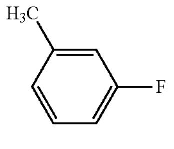

is also taken to refer to

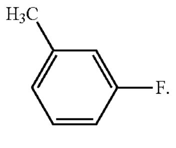

.

Aromatic compounds may also be depicted using a circle to represent the delocalized nature of the electrons in the fully conjugated cyclic π system, two non-limiting examples of which are shown below:

 and 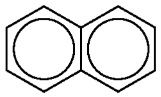.

The term "alkyl" refers to a monovalent saturated aliphatic group with a carbon atom as the point of attachment, a linear or branched acyclic structure, and no atoms other than carbon and hydrogen. The groups $-CH_3$ (Me), $-CH_2CH_3$ (Et), $-CH_2CH_2CH_3$ (n-Pr or propyl), $-CH(CH_3)_2$ (i-Pr, $^i$Pr or isopropyl), $-CH_2CH_2CH_2CH_3$ (n-Bu), $-CH(CH_3)CH_2CH_3$ (sec-butyl), $-CH_2CH(CH_3)_2$ (isobutyl), $-C(CH_3)_3$ (tert-butyl, t-butyl, t-Bu or $^t$Bu), and $-CH_2C(CH_3)_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups $-CH_2-$ (methylene), $-CH_2CH_2-$, $-CH_2C(CH_3)_2CH_2-$, and $-CH_2CH_2CH_2-$are non-limiting examples of alkanediyl groups. The term "alkylidene" refers to the divalent group $=CRR'$ in which R and R' are independently hydrogen or alkyl. Non-limiting examples of alkylidene groups include: $=CH_2$, $=CH(CH_2CH_3)$, and $=C(CH_3)_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: $-CH(CH_2)_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

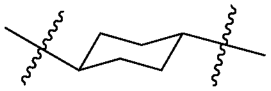 [SMILES: *C1CCC(*)CC1]

is a non-limiting example of cycloalkanediyl group. A "cycloalkane" refers to the class of compounds having the formula H—R, wherein R is cycloalkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: $-CH=CH_2$ (vinyl), $-CH=CHCH_3$, $-CH=CHCH_2CH_3$, $-CH_2CH=CH_2$ (allyl), $-CH_2CH=CHCH_3$, and $-CH=CHCH=CH_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups $-CH=CH-$, $-CH=C(CH_3)CH_2-$, $-CH=CHCH_2-$, and $-CH_2CH=CHCH_2-$ are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups $-C\equiv CH$, $-C\equiv CCH_3$, and $-CH_2C\equiv CCH_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, $-NH_2$, $-NO_2$, $-CO_2H$, $-CO_2CH_3$, —CN, —SH, $-OCH_3$, $-OCH_2CH_3$, $-C(O)CH_3$, $-NHCH_3$, $-NHCH_2CH_3$, $-N(CH_3)_2$, $-C(O)NH_2$, $-C(O)NHCH_3$, $-C(O)N(CH_3)_2$, $-OC(O)CH_3$, $-NHC(O)CH_3$, $-S(O)_2OH$, or $-S(O)_2NH_2$.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, $-C_6H_4CH_2CH_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

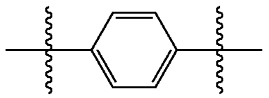, 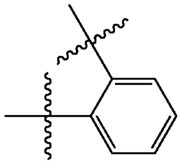,

-continued

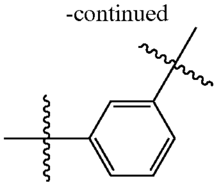

,

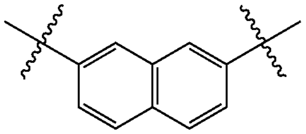

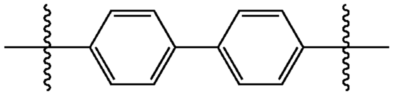

, and

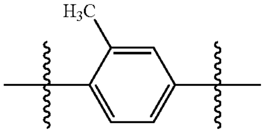

.

An "arene" refers to the class of compounds having the formula H—R, wherein R is aryl as that term is defined above. Benzene and toluene are non-limiting examples of arenes.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

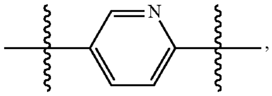

,

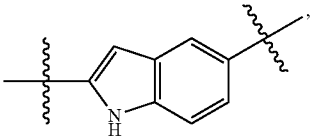

,

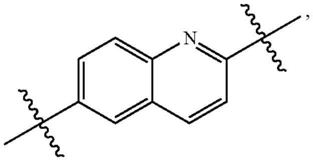

, and

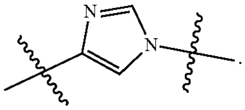

.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group.

The term "heterocycloalkanediyl" refers to a divalent cyclic group, with two carbon atoms, two nitrogen atoms, or one carbon atom and one nitrogen atom as the two points of attachment, said atoms forming part of one or more ring structure(s) wherein at least one of the ring atoms of the non-aromatic ring structure(s) is nitrogen, oxygen or sulfur, and wherein the divalent group consists of no atoms other than carbon, hydrogen, nitrogen, oxygen and sulfur. If more than one ring is present, the rings are fused. As used herein, the term heterocycloalkanediyl does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkanediyl groups include:

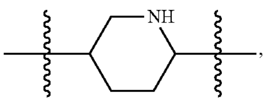,
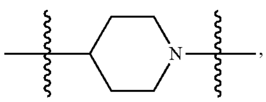,
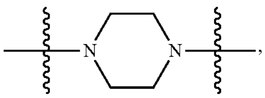,
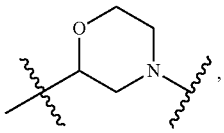, and
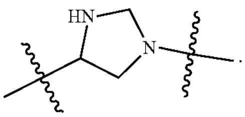.

The term "acyl" refers to the group —C(O)R, in which R is a hydrogen, alkyl, cycloalkyl, or aryl as those terms are defined above. The groups, —CHO, —C(O)$CH_3$ (acetyl, Ac), —C(O)$CH_2CH_3$, —C(O)CH($CH_3$)$_2$, —C(O)CH ($CH_2$)$_2$, —C(O)$C_6H_5$, and —C(O)$C_6H_4CH_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —OCH($CH_3$)$_2$ (isopropoxy), or —OC($CH_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

The term "alkylamino" refers to the group —NHR, in which R is an alkyl, as that term is defined above. Non-limiting examples include: —$NHCH_3$ and —$NHCH_2CH_3$. The term "dialkylamino" refers to the group —NRR', in which R and R' can be the same or different alkyl groups. Non-limiting examples of dialkylamino groups include: —N($CH_3$)$_2$ and —N($CH_3$)($CH_2CH_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —$NHC_6H_5$. The terms "dicycloalkylamino", "dialkenylamino", "dialkynylamino", "diarylamino", "diaralkylamino", "diheteroarylamino", "diheterocycloalkylamino", and "dialkoxyamino", refers to groups, defined as —NRR', in which R and R' are both cycloalkyl, alkenyl, alkynyl, aryl, aralkyl, heteroaryl, heterocycloalkyl, and alkoxy, respectively. Similarly, the term alkyl(cycloalkyl)amino refers to a group defined as —NRR', in which R is alkyl and R' is cycloalkyl. The term "amido" (acylamino), when used without the "substituted" modifier, refers to the group —NHR, in which R is acyl, as that term is defined above. A non-limiting example of an amido group is —NHC(O)$CH_3$.

When a chemical group is used with the "substituted" modifier, one or more hydrogen atom has been replaced, independently at each instance, by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —N($CH_3$)$_2$, —C(O)$NH_2$, —C(O)$NHCH_3$, —C(O)N($CH_3$)$_2$, —OC(O)$CH_3$, —NHC(O)$CH_3$, —S(O)$_2$OH, or —S(O)$_2NH_2$. For example, the following groups are non-limiting examples of substituted alkyl groups: —$CH_2OH$, —$CH_2Cl$, —$CF_3$, —$CH_2CN$, —$CH_2$C(O)OH, —$CH_2$C(O)$OCH_3$, —$CH_2$C(O)$NH_2$, —$CH_2$C(O)$CH_3$, —$CH_2OCH_3$, —$CH_2$OC(O)$CH_3$, —$CH_2NH_2$, —$CH_2$N($CH_3$)$_2$, and —$CH_2CH_2Cl$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —$CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —$CH_2F$, —$CF_3$, and —$CH_2CF_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)$CH_2CF_3$, —$CO_2H$ (carboxyl), —$CO_2CH_3$ (methylcarboxyl), —$CO_2CH_2CH_3$, —C(O)$NH_2$ (carbamoyl), and —CON($CH_3$)$_2$, are non-limiting examples of substituted acyl groups. The groups —NHC(O)$OCH_3$ and —NHC(O)$NHCH_3$ are non-limiting examples of substituted amido groups.

When a chemical group is used with the "substituted" modifier, one or more hydrogen atom has been replaced, independently at each instance, by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —N($CH_3$)$_2$, —C(O)$NH_2$, —C(O)$NHCH_3$, —C(O)N($CH_3$)$_2$, —OC(O)$CH_3$, —NHC(O)$CH_3$, —S(O)$_2$OH, or —S(O)$_2NH_2$. For example, the following groups are non-limiting examples of substituted alkyl groups: —$CH_2OH$, —$CH_2Cl$, —$CF_3$, —$CH_2CN$, —$CH_2$C(O)OH, —$CH_2$C(O)$OCH_3$, —$CH_2$C(O)$NH_2$, —$CH_2$C(O)$CH_3$, —$CH_2OCH_3$, —$CH_2$OC(O)$CH_3$, —$CH_2NH_2$, —$CH_2$N($CH_3$)$_2$, and —$CH_2CH_2Cl$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —$CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —$CH_2F$, —$CF_3$, and —$CH_2CF_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)$CH_2CF_3$, —$CO_2H$ (carboxyl), —$CO_2CH_3$ (methylcarboxyl), —$CO_2CH_2CH_3$, —C(O)$NH_2$ (carbamoyl), and —CON($CH_3$)$_2$, are non-limiting examples of substituted acyl groups. The groups —NHC(O)$OCH_3$ and —NHC(O)$NHCH_3$ are non-limiting examples of substituted amido groups.

In some embodiments, a generic chemical formula may include a chain of variables. A non-limiting example is shown below:

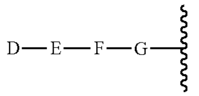

In some embodiments, two or more adjacent and non-terminal variables, i.e. selected in the above example from E, F, and G, may each be a covalent bond. When two or more adjacent, non-terminal variables are defined as a covalent bond, it is understood that only a single covalent bond will be the result. For example, in the example above, if E and F are both defined as a covalent bond, then one of skill in the art would recognize that the resulting group is the following:

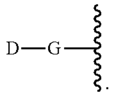

III. COMBINATION THERAPIES

It is envisioned that the BET inhibitors disclosed herein may be used in combination therapies with an additional agent or therapy that mitigates one or more of the symptoms of FSHD. The following is a general discussion of therapies that may be used in conjunction with the therapies of the present disclosure.

To treat FSHD using the methods and compositions of the present disclosure, one may contact a subject with a compound and at least one other therapy. These therapies would be provided in a combined amount effective to achieve a reduction in one or more disease parameter(s). This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the inhibitors may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Exemplary agents or factors suitable for use in a combined therapy with agents according to the present disclosure are described above in the section on FSHD, and below.

A. p38 Inhibitors

As used herein, the abbreviation "p38" refers to any of the p38 mitogen-activated protein (MAP) kinases. p38 is a mammalian protein kinase involved cell proliferation, cell death and response to extracellular stimuli. Activation of p38 has been observed in cells stimulated by stresses, such as treatment of lipopolysaccharides (LPS), UV, anisomycin, or osmotic shock, and by cytokines, such as IL-1 and TNF. Inhibition of p38 kinase leads to a blockade on the production of both IL-1 and TNF. IL-1 and TNF stimulate the production of other proinflammatory cytokines such as IL-6 and IL-8 and have been implicated in acute and chronic inflammatory diseases and in postmenopausal osteoporosis (R. B. Kimble et al., 1995). Several p38 MAP kinases have been identified, including p38-α (also known as MAPK14), p38-β (also known as MAPK11), p38-γ (also known as MAPK12/ERK6) and p38-δ (also known as MAPK13/SAPK4). The nucleic acid sequences of the genes encoding p38, including, but not limited to, the nucleic acid sequences of the open reading frames of the genes, are known in the art. The amino acid sequences of p38 polypeptides and proteins, including, but not limited to, the amino acid sequences of the human p38 polypeptides and proteins, are known in the art. The accession number of the nucleic acid sequence of *Mus musculus* p38-α (MAPK14) is NM_011951.3 and the accession number of the nucleic acid sequence of human p38-α (MAPK14) is NM_001315.2. The accession number of the amino acid sequence of *Mus musculus* p38-α (MAPK14) is NP_036081.1 and the accession number of the amino acid sequence of human p38-α (MAPK14) is NP_001306.1. For additional information on p38, see Marber et al., 2011; see also Kostenko et al., 2011 and Cuadrado et al., 2010, all of which are incorporated by reference herein.

Both pan p38 inhibitors and specific inhibitors of one isoform of p38 are contemplated herein and may be used to treat FSpD. A non-limiting selections selection of different inhibitors of p38 or related pathways are shown in Table 1 below.

TABLE 1

Non-limiting List of Inhibitors in differentiating cultures of FSHD1 and FHD2 muscle cells

| Inhibitor | Mechanism/Selectivity |
|---|---|
| Acumapimod | p38α/β |
| ARRY-371797 | p38α |
| BMS-582949 | p38α, 5X selective over p38β |
| Dilmapimod | p38α/β |
| Dorimapimod | p38α; 20X selective over B-Raf |
| eFT-508 | MNK 1/2 |
| Losmapimod | p38α/β |
| LY2228820 | p38α/β |
| LY3007113 | p38 |
| Pamapimod | p38α, 34X selective over p38β |
| PF-3644022 | MAPKAPK2 (MK2) |
| PH-797804 | p38α, 4X selective over p38β |
| SB202190 | p38α/β |
| SB203580 | P38α/β |
| TAK-715 | p38α, 28X selective over p38β |
| Talmapimod | p38α, 10X selective over p38β |
| VX-702 | p38α, 14X selective over p38β |
| VX-745 | p38α, 22X selective over p38β |

Additional p38 inhibitors which may be used herein include those described in Lee et al., 2000, Kumar et al., 2003, Gangwal et al., 2013, Karcher and Laufer, 2009, Yong et al., 2009, Fink et al., 2014, Norman, 2015, WO 2003/068747, WO 2003/093248, US 2005/0020540, US 2006/0122221, US 2004/0267012, WO 2005/012241, WO 2004/010995, WO 2005/073189, US 2004/0102636, US 2004/0132729, US 2005/0020590, WO 1999/032463, US 2003/0232831, WO 2000/012497, US 2002/0118671, WO 2000/012074, WO 2010/067131, WO 1999/000357, US 2004/0254236, U.S. Pat. No. 5,945,418, US 2009/0143422, US 2009/0136596, US 2007/0185175, US 2009/0118272, US 2007/0213300, US 2008/0171741, US 2011/0190292, WO 2009/155388, US 2011/0077243, WO 2012/031057, and WO 2009/155388, the entirety of which are herein by incorporated by reference.

B. Beta-2 Adrenergic Receptor Agonists $\beta_2$ (beta$_2$) adrenergic receptor agonists, also known as adrenergic $\beta_2$ receptor agonists, are a class of drugs that act on the $\beta_2$ adrenergic receptor. Like other β adrenergic agonists, they cause smooth muscle relaxation. $\beta_2$ adrenergic agonists' effects on smooth muscle cause dilation of bronchial passages, vasodilation in muscle and liver, relaxation of uterine muscle, and release of insulin. They are primarily used to treat asthma and other pulmonary disorders. Activation of β adrenergic receptors leads to relaxation of smooth muscle in the lung, and dilation and opening of the airways.

β adrenergic receptors are coupled to a stimulatory G protein of adenylyl cyclase. This enzyme produces the second messenger cyclic adenosine monophosphate (cAMP). In the lung, cAMP decreases calcium concentrations within cells and activates protein kinase A. Both of these changes inactivate myosin light-chain kinase and activate myosin light-chain phosphatase. In addition, $\beta_2$ agonists open large conductance calcium-activated potassium channels and thereby tend to hyperpolarize airway smooth muscle cells. The combination of decreased intracellular calcium, increased membrane potassium conductance, and decreased myosin light chain kinase activity leads to smooth muscle relaxation and bronchodilation.

Findings indicate that $\beta_2$ stimulants, especially in parenteral administration such as inhalation or injection, can induce adverse effects, such as Tachycardia secondary to peripheral vasodilation and cardiac stimulation, palpitations, tremor, excessive sweating, anxiety, insomnia, and agitation. More severe effects, such as pulmonary edema, myocardial ischemia, and cardiac arrhythmia, are exceptional. Asthma aggravation has been observed in patients using large doses of $\beta_2$ agonists, but if it results from spontaneous course of the disease or adverse effect of the drugs is not known. The excipients, in particular sulfite, could contribute to the adverse effects. The possible loss of the bronchodilator activity of $\beta_2$ mimetics could be attenuated by inhaled corticosteroid intake.

All $\beta_2$ agonists are available in inhaler form, either metered-dose inhalers, which aerosolize the drug, or dry powder inhalers, which dispense powder which can be inhaled.

Salbutamol (INN) or albuterol (USAN) and some other $\beta_2$ agonists, such as formoterol, also are sold in a solution form for nebulization, which is more commonly used than inhalers in emergency rooms. Salbutamol and terbutaline are also both available in oral forms. The nebulizer form is as effective as administering the drug intravenously.

In addition, several of these medications are available in intravenous forms, including both salbutamol and terbutaline. It can be used in this form in severe cases of asthma, but it is more commonly used to suppress premature labor because it also relaxes uterine muscle, thereby inhibiting contractions.

On Nov. 18, 2005, the U.S. Food and Drug Administration (FDA) alerted healthcare professionals and patients that several long-acting bronchodilator medicines have been associated with possible increased risk of worsening wheezing in some people, and requested that manufacturers update warnings in their existing product labeling.

On Jun. 29, 2006, Cornell University and Stanford University researchers reported that a meta-analysis they conducted found that "regularly inhaled β agonists (orciprenaline/metaproterenol (Alupent), formoterol (Foradil), fluticasone+salmeterol (Serevent, Advair), and salbutamol/albuterol (Proventil, Ventolin, Volmax, and others)) increased the risk of respiratory death more than two-fold, compared with a placebo," while used to treat chronic obstructive pulmonary disease.

On Dec. 11, 2008, a panel of experts convened by the FDA voted to ban the drugs Serevent and Foradil from use in the treatment of asthma. When these two drugs are used without steroids, they increase the risks of more severe attacks. The experts said that two other much more popular asthma drugs containing long-acting β agonists, Advair and Symbicort, should continue to be used.

They can be divided into short-acting, long-acting, and ultra-long-acting β (more specifically, $\beta_2$) adrenoreceptor agonists. Short-acting $\beta_2$ agonists include bitolterol (Tornalate), fenoterol (Berotec), isoprenaline (INN) or isoproterenol (USAN) (Isuprel), levosalbutamol (INN) or levalbuterol (USAN) (Xopenex), orciprenaline (INN) or metaproterenol (USAN) (Alupent), pirbuterol (Maxair), procaterol, ritodrine (Yutopar), salbutamol (INN) or albuterol (USAN) (Ventolin), and terbutaline (Bricanyl). Long-acting $\beta_2$ agonists include arformoterol (Brovana) (some consider it to be an ultra-LABA), bambuterol (Bambec), Oxeol, clenbuterol (Dilaterol), Spiropent, formoterol (Foradil), Oxis, Perforomist, and salmeterol (Serevent). Ultra-long-acting 32 agonists include abediterol, carmoterol, indacaterol (Arcapta) Neohaler (U.S.), Onbrez Breezhaler (EU, RU), olodaterol (Striverdi Respimat), and vilanterol with umeclidinium bromide (Anoro Ellipta), or with fluticasone furoate (Breo Ellipta, U.S.; Relvar Ellipta, EU, RU). Unknown duration of action agonists include isoxsuprine, mabuterol, and zilpaterol (Zilmax).

IV. THERAPEUTIC METHODS

In another aspect, this disclosure provides methods of modulating DUX4 expression using BET inhibitors such as one or more of the compounds disclosed herein, as well as pharmaceutical compositions thereof. Such pharmaceutical compositions further comprise one or more non-toxic, pharmaceutically acceptable carriers and/or diluents and/or adjuvants (collectively referred to herein as "carrier" materials) and if desired other active ingredients. In some embodiments, the compound is administered as part of a pharmaceutical composition further comprising a pharmaceutically acceptable carrier. In some embodiments, the compounds and/or pharmaceutical compositions thereof may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitoneally. In some embodiments, the compounds of the present disclosure are administered by any suitable route in the form of a pharmaceutical composition adapted to such a route, and in a dose effective for the treatment intended. Therapeutically effective doses of the compounds required to prevent or arrest the progress of or to treat a medical condition are readily ascertained by one of ordinary skill in the art using preclinical and clinical approaches familiar to the medicinal arts.

Based upon standard laboratory experimental techniques and procedures well known and appreciated by those skilled in the art, as well as comparisons with compounds of known usefulness, the compounds described above can be used in the treatment of patients suffering from the above pathological conditions. One skilled in the art will recognize that selection of the most appropriate compound of the disclosure is within the ability of one with ordinary skill in the art and will depend on a variety of factors including assessment of results obtained in standard assay and animal models.

V. PHARMACEUTICAL FORMULATIONS AND ROUTES OF ADMINISTRATION

For administration to a primate, especially a human, in need of such treatment, the compounds in a therapeutically effective amount are ordinarily combined with one or more excipients appropriate to the indicated route of administration. The compounds of the present disclosure are contemplated to be formulated in a manner ameniable to treatment of a veterinary patient as well as a human patient. In some embodiments, the veterinary patient may be a non-human primate. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art and may be adapted to the type of primate being treated.

The pharmaceutical compositions useful in the present disclosure may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g., subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions may be suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it may be useful to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the methods of preparation include vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard- or soft-shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general a human equivalent dose (HED) in mg/kg can be calculated in accordance with the following formula (see, e.g., Reagan-Shaw et al., *FASEB J.,* 22(3):659-661, 2008, which is incorporated herein by reference):

$$HED\text{(mg/kg)=Animal dose(mg/kg)}\times\text{(Animal } K_m\text{/Human } K_m\text{)}$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 1% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may be taken orally and that the timing of which is or is not dependent upon food intake. Thus, for example, the agent can be taken every morning and/or every evening, regardless of when the subject has eaten or will eat.

VI. DEFINITIONS

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

An "active ingredient" (AI) (also referred to as an active compound, active substance, active agent, pharmaceutical agent, agent, biologically active molecule, or a therapeutic compound) is the ingredient in a pharmaceutical drug that is biologically active. The similar terms active pharmaceutical ingredient (API) and bulk active are also used in medicine.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular active ingredient or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a compound or composition used to diagnose, cure, treat, or prevent disease. An active ingredient (AI) (defined above) is the ingredient in a pharmaceutical drug. The similar terms active pharmaceutical ingredient (API) and bulk active are also used in medicine. Some medications products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an active ingredient according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-p-hydroxynaphthoate, gentisates, isethionates, di-p-toluoyltartrates, methanesulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

VII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Synthesis

General. Reagents and solvents were purchased from commercial sources and were used as received. Microwave assisted synthesis was performed with an Anton Parr Monowave 300. $^{1}H$ NMR spectra were obtained on a Bruker AVANCE 300 spectrometer at 300 MHz and Bruker AVANCE 400 spectrometer at 400 MHz with tetramethylsilane used as an internal standard. Thin-layer chromatography was performed using Merck TLC silica-gel 60 $F_{254}$ plates. Visualization of TLC plates was performed using UV light (254 nm). The mass spectra were obtained on a Shimadzu LCMS-2010EV spectrometer using electrospray ionization and atmospheric-pressure chemical ionization. HPLC analysis was performed using Method A to Method H.

HPLC Methods

Method A

Column: Polaris C18-A 100×3.0 mm, 2.6 μm.
Mobile Phase A: 0.05% TFA in Water.
Mobile Phase B: 0.05% TFA in Acetonitrile.

| Method A Gradient | | | |
|---|---|---|---|
| Time (min) | Flow (mL/min) | % A | % B |
| 0 | 1.0 | 95.0 | 5.0 |
| 3 | 1.0 | 95.0 | 5.0 |
| 6 | 1.0 | 10.0 | 90.0 |
| 12 | 1.0 | 5.0 | 90.0 |
| 12.1 | 1.0 | 95.0 | 5.0 |
| 15 | 1.0 | 95.0 | 5.0 |

Method B

Column: Zodiac C18 100×4.6 mm, 3.0 μm.
Mobile Phase A: 0.05% TFA in Water.
Mobile Phase B: 0.05% TFA in Acetonitrile.

| Method B Gradient | | | |
|---|---|---|---|
| Time (min) | Flow (mL/min) | % A | % B |
| 0 | 1.0 | 95.0 | 5.0 |
| 3 | 1.0 | 95.0 | 5.0 |
| 6 | 1.0 | 10.0 | 90.0 |
| 12 | 1.0 | 10.0 | 90.0 |
| 12.1 | 1.0 | 95.0 | 5.0 |
| 15 | 1.0 | 95.0 | 5.0 |

Method C

Column: Zodiac C18 150×4.6 mm, 5.0 μm.
Mobile Phase A: 0.05% TFA in Water.
Mobile Phase B: 0.05% TFA in Acetonitrile.

| Method C Gradient | | | |
|---|---|---|---|
| Time (min) | Flow (mL/min) | % A | % B |
| 0 | 1.0 | 95.0 | 20.0 |
| 3 | 1.0 | 80.0 | 20.0 |
| 6 | 1.0 | 10.0 | 90.0 |
| 12 | 1.0 | 10.0 | 90.0 |
| 12.1 | 1.0 | 80.0 | 20.0 |
| 15 | 1.0 | 80.0 | 20.0 |

Method D

Column: Eclipse XDB C18 100×4.6 mm, 3.5 μm.
Mobile Phase A: 0.05% TFA in Water.
Mobile Phase B: 0.05% TFA in Acetonitrile.

| Method D Gradient | | | |
|---|---|---|---|
| Time (min) | Flow (mL/min) | % A | % B |
| 0 | 1.0 | 95.0 | 5.0 |
| 3 | 1.0 | 95.0 | 5.0 |
| 6 | 1.0 | 10.0 | 90.0 |
| 12 | 1.0 | 10.0 | 90.0 |

-continued

| Method D Gradient | | | |
|---|---|---|---|
| Time (min) | Flow (mL/min) | % A | % B |
| 12.1 | 1.0 | 95.0 | 5.0 |
| 15 | 1.0 | 95.0 | 5.0 |

Method E

Column: Xbridge C18 100×4.6 mm, 3.5 μm.
Mobile Phase A: 0.05% TFA in Water.
Mobile Phase B: 0.05% TFA in Acetonitrile.

| Method E Gradient | | | |
|---|---|---|---|
| Time (min) | Flow (mL/min) | % A | % B |
| 0 | 1.0 | 95.0 | 5.0 |
| 3 | 1.0 | 95.0 | 5.0 |
| 6 | 1.0 | 10.0 | 90.0 |
| 12 | 1.0 | 10.0 | 90.0 |
| 12.1 | 1.0 | 95.0 | 5.0 |
| 16 | 1.0 | 95.0 | 5.0 |

Method F

Column: Eclipse Plus C18 100×4.6 mm, 3.5 μm.
Mobile Phase A: 0.05% TFA in Water.
Mobile Phase B: 0.05% TFA in Acetonitrile.

| Method F Gradient | | | |
|---|---|---|---|
| Time (min) | Flow (mL/min) | % A | % B |
| 0 | 1.0 | 95.0 | 5.0 |
| 3 | 1.0 | 95.0 | 5.0 |
| 6 | 1.0 | 10.0 | 90.0 |
| 12.1 | 1.0 | 10.0 | 90.0 |
| 12.1 | 1.0 | 95.0 | 5.0 |
| 15 | 1.0 | 95.0 | 5.0 |

Method G

Column: Agilent Eclipse Plus-C18, 3.5 μm 4.6×100 mm.
Mobile Phase A: 0.05% TFA in Water.
Mobile Phase B: 0.05% TFA in Acetonitrile.

| Method G Gradient | | | |
|---|---|---|---|
| Time (min) | Flow (mL/min) | % A | % B |
| 0 | 1.0 | 95.0 | 5.0 |
| 3 | 1.0 | 95.0 | 5.0 |
| 6 | 1.0 | 10.0 | 90.0 |
| 12 | 1.0 | 10.0 | 90.0 |
| 12.1 | 1.0 | 95.0 | 5.0 |
| 15 | 1.0 | 95.0 | 5.0 |

Method H

Column: Luna C18 100A, 150×4.6 mm, 3.0 μm.
Mobile Phase A: 0.05% TFA in Water.
Mobile Phase B: 0.05% TFA in Acetonitrile.

| Method H Gradient | | | |
|---|---|---|---|
| Time (min) | Flow (mL/min) | % A | % B |
| 0 | 0.8 | 95.0 | 5.0 |
| 5 | 0.8 | 95.0 | 5.0 |
| 15 | 0.8 | 30.0 | 70.0 |
| 20 | 0.8 | 5.0 | 95.0 |
| 20.1 | 0.8 | 95.0 | 5.0 |
| 25 | 0.8 | 95.0 | 5.0 |

Synthesis of (R)-1,3-dimethylpiperazin-2-one (Intermediate-1)

Scheme 1

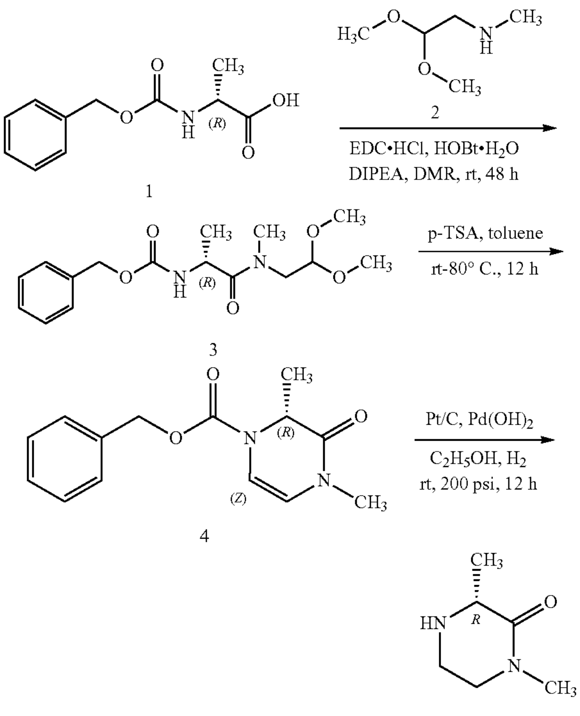

1
2
3
4

Intermediate-1

(R)-benzyl {1-[(2,2-dimethoxyethyl)(methyl) amino]-1-oxopropan-2-yl}carbamate (3)

To a stirred solution of 1 (100 g, 448.2 mmol) in DMF (1000 mL), 2,2-dimethoxy-N-methylethanamine 2 (58.69 g, 493 mmol) was added followed by addition of DIPEA (148.0 g, 896 mmol), EDC·HCl (128.8 g, 672 mmol) and HOBt·$H_2O$ (90.8 g, 672 mmol). The reaction mixture was stirred at ambient temperatures for 48 h. The reaction mixture was poured into water (2000 mL) and extracted with EtOAc (5×1000 mL). Combined organic layers were washed with ice cold water (5×300 mL), brine (2×300 mL), dried over anhydrous $Na_2SO_4$ and concentrated under reduced pressure to afford 3 (102.0 g, 72%) as brown colored gum. $^1$H NMR (400 MHz, $CDCl_3$): δ ppm 7.51 (dd, J=8.0, 30.0 Hz, 1H), 7.28-7.38 (m, 5H), 5.01 (s, 2H), 4.39-4.57 (m, 2H), 3.61 (dd, J=6.8, 15.6 Hz, 1H), 3.43 (dd, J=5.6, 13.6 Hz, 1H), 3.33 (s, 3H), 3.26-3.25 (m, 4H), 3.18 (t, J=6.8 Hz, 1H), 2.10 (t, J=4.8 Hz, 1H), 1.16 (d, J=7.2 Hz, 3H).

(R)-benzyl 2,4-dimethyl-3-oxo-3,4-dihydropyrazine-1(2H)-carboxylate (4)

To a stirred solution of 3 (102.0 g, 315 mmol) in toluene (500 mL), P-TSA (30.1 g, 157 mmol) was added portion wise for 15 min at room temperature and heated at 80° C. for 12 h. The reaction mixture was cooled to temperature and toluene was evaporated under reduced pressure. The crude was dissolved in EtOAc (3000 mL) and washed with water (2x500 mL) followed by saturated $NaHCO_3$ (3x500 mL) solution. Combined organic layers were dried over anhydrous $Na_2SO_4$ and concentrated under reduced pressure to afford 4 (58.0 g, 71%) as an off-white solid.

$^1$H NMR (400 MHz, DMSO-$d_6$): δ ppm 7.35-7.36 (m, 5H), 6.28 (dd, J=5.6, 6.0 Hz, 1H), 5.47-5.53 (m, 1H), 5.20 (s, 2H), 4.81-4.91 (m, 1H), 3.08 (s, 3H), 1.30 (t, J=7.6 Hz, 3H).

(R)-1,3-dimethylpiperazin-2-one (Intermediate-1)

In a 1.0 L capacity auto clave vessel, to a stirred solution of 4 (58.0 g, 223 mmol) in ethanol (500 mL), 5% platinum on carbon (5.80 g) was added at room temperature followed by addition of 20% palladium hydroxide on charcoal (8.70 g). The reaction mixture was stirred at room temperature at 200 psi under hydrogen atmosphere for 12 h. The reaction mixture was filtered through celite pad and washed with methanol (2000 mL). Filtrate was concentrated under reduced pressure. The crude material was purified by combiflash column chromatography ($CH_2Cl_2$:$CH_3OH$=90:10) to afford Intermediate-1 (19.0 g, 68%) as a colourless gum. $^1$H NMR (400 MHz, DMSO-$d_6$): δ ppm 3.20-3.33 (m, 2H), 3.10-3.16 (m, 1H), 2.93-2.98 (m, 2H), 2.80-2.92 (m, 1H), 2.80 (s, 3H), 1.16 (d, J=6.8 Hz, 3H).

Synthesis of (R)-4-{2-[4-(6-chloroquinolin-2-yl) phenoxy]ethyl}-1,3-dimethylpiperazin-2-one (Intermediate-4)

Scheme 2

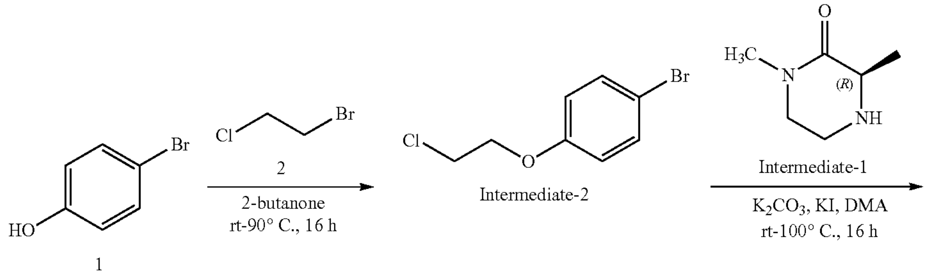

1
2
Intermediate-2
Intermediate-1

-continued

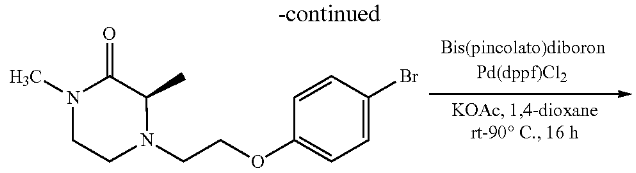

2

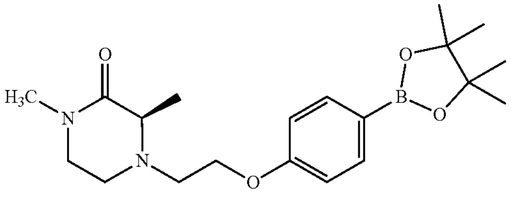

Intermediate-3

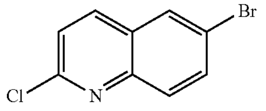

3

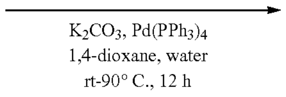

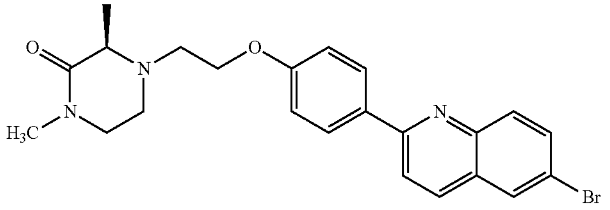

Intermediate-4

1-bromo-4-(2-chloroethoxy)benzene (Intermediate-2)

To a stirred solution of 4-bromo phenol 1 (30.0 g, 173 mmol) in 2-butanone (500 mL), $K_2CO_3$ (95 g, 686 mmol) and 1-bromo-2-chloroethane 2 (82 mL, 867 mmol) were added at room temperature and heated at 90° C. for 16 h. The reaction mixture was allowed to room temperature and diluted with EtOAc (200 mL). Organic layer was washed with water (3×200 mL), brine (1×100 mL). Organic layer was dried over anhydrous $Na_2SO_4$ and concentrated under reduced pressure to afford Intermediate-2 (37.0 g, 91%) as a white solid.

$^1$H NMR (400 MHz, $CDCl_3$): δ ppm 7.38 (d, J=9.2 Hz, 2H), 6.80 (d, J=8.8 Hz, 2H), 4.19 (t, J=5.6 Hz, 2H), 3.80 (t, J=6.0 Hz, 2H).

(R)-4-[2-(4-bromophenoxy)ethyl]-1,3-dimethylpiperazin-2-one (2)

To a stirred solution of Intermediate-2 (5.0 g, 21.5 mmol) in dimethylacetamide (50 mL), Intermediate-1 (3.38 g, 25.8 mmol), KI (1.78 g, 10.7 mmol), $K_2CO_3$ (8.9 g, 64.5 mmol) were added at room temperature and heated at 100° C. for 16 h. The reaction mixture was diluted with water (100 mL) and extracted with EtOAc (3×350 mL). The combined organic layers were dried over anhydrous $Na_2SO_4$, concentrated under reduced pressure and purified by combiflash chromatography (EtOAc:Hexanes=80:20) to afford 2 (5.10 g, 67%) as an off-white solid.

$^1$H NMR (400 MHz, DMSO-$d_6$) δ ppm 7.43 (d, J=9.0 Hz, 2H), 6.91 (d, J=8.7 Hz, 2H), 4.06 (t, J=5.7 Hz, 2H), 3.22-3.25 (m, 2H), 3.06-3.16 (m, 2H), 3.01-3.04 (m, 1H), 2.92 (s, 3H), 2.63-2.88 (m, 2H), 1.22 (d, J=6.6 Hz, 3H).

(R)-1,3-dimethyl-4-{2-[4-(4,4,5,5-tetramethyl-1,3,2-dioxaborolan-2-yl)phenoxy]ethyl}piperazin-2-one (Intermediate-3)

To a stirred solution of 2 (0.20 g, 0.61 mmol) in 1,4-dioxane (5 mL), Bis(pincolato)diboron (0.23 g, 0.92 mmol) and Pd(dppf)$Cl_2$ (0.05 g, 0.06 mmol) and KOAc (0.09 g, 0.92 mmol) were added at room temperature and heated at 90° C. for 16 h. The reaction mixture was diluted with water (20 mL) and extracted with EtOAc (3×20 mL). The combined organic layers were dried over anhydrous $Na_2SO_4$, concentrated under reduced pressure and crude product was purified by combiflash chromatography ($CH_2Cl_2$: $CH_3OH$=97:3) to afford Intermediate-3 (0.016 g, 67%) as a colourless gum.

$^1$H NMR (400 MHz, DMSO-$d_6$) δ ppm 7.59 (d, J=8.4 Hz, 2H), 6.93 (d, J=8.4 Hz, 2H), 4.08-4.11 (m, 2H), 3.23-3.28 (m, 2H), 3.16-3.23 (m, 1H), 3.02-3.08 (m, 1H), 2.90-2.97 (m, 1H), 2.80 (s, 3H), 2.55-2.62 (m, 2H), 1.27 (s, 12H), 1.26 (s, 3H).

(R)-4-{2-[4-(6-chloroquinolin-2-yl)phenoxy]ethyl}-1,3-dimethylpiperazin-2-one (Intermediate-4)

A solution of Intermediate-3 (0.250 g, 0.66 mmol) in 1,4-dioxane (5 mL) and $H_2O$ (2 mL) were charged with 6-bromo-2-chloroquinoline 3 (0.162 g, 0.66 mmol), and potassium carbonate (0.182 g, 1.32 mmol) at room temperature and degassed it with argon for 5 min. Pd($PPh_3$)$_4$ (0.031 g, 0.02 mmol) was added to the reaction mixture and stirred at 90° C. for 12 h. The reaction mixture was diluted with water (20 mL), extracted with EtOAc (2×30 mL). The combined organic layers were dried over anhydrous $Na_2SO_4$, concentrated under reduced pressure and crude material was purified by combiflash chromatography ($CH_2Cl_2$:MeOH=95:5) to afford Intermediate-4 (0.2 g, 66%) as an off-white solid.

$^1$H NMR (400 MHz, $CDCl_3$): δ ppm 8.00-8.06 (m, 3H), 7.91 (d, J=9.0 Hz, 1H), 7.89 (d, J=2.1 Hz, 1H),), 7.78 (d, J=8.6 Hz, 1H), 7.69 (dd, J=2.4, 8.9 Hz, 1H), 6.96 (d, J=8.8 Hz, 2H), 4.06 (m, 2H), 3.19-3.33 (m, 3H), 3.07-3.13 (m, 1H), 2.98-3.04 (m, 1H), 2.81-2.88 (m, 4H), 2.71-2.77 (m, 1H), 1.36 (d, J=6.8 Hz, 3H).

Synthesis of 6-methyl-4-[6-(4,4,5,5-tetramethyl-1,3,2-dioxaborolan-2-yl)quinolin-2-yl]-1-tosyl-1H-pyrrolo[2,3-c]pyridin-7(6H)-one (Intermediate-7)

Scheme 3

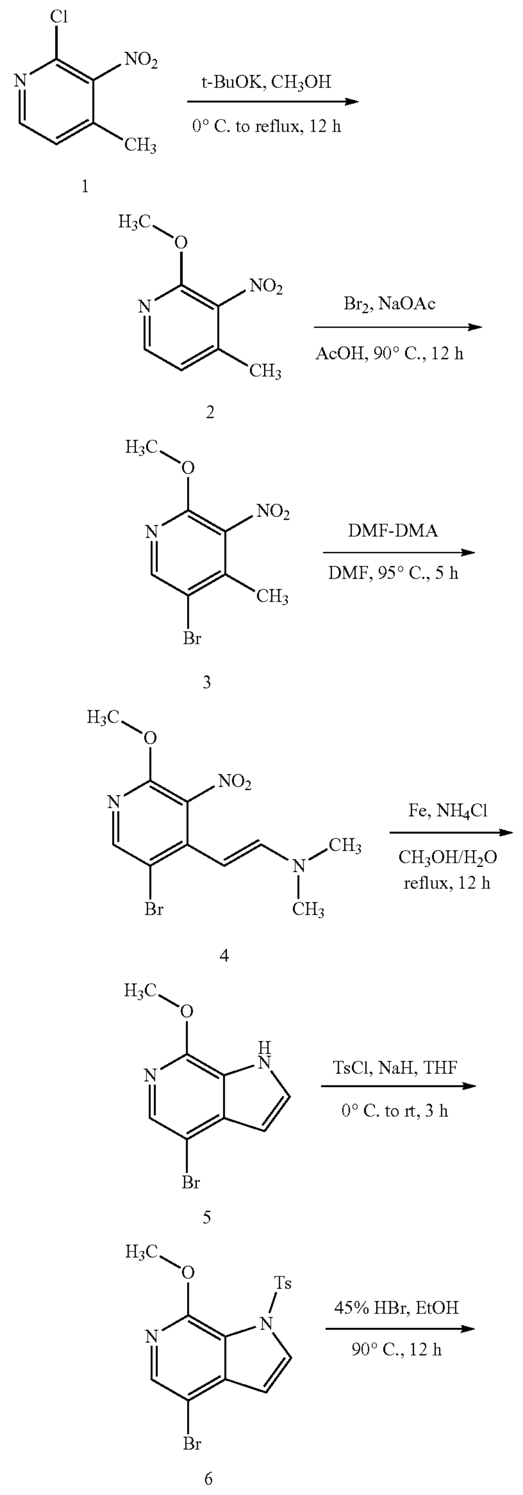

-continued

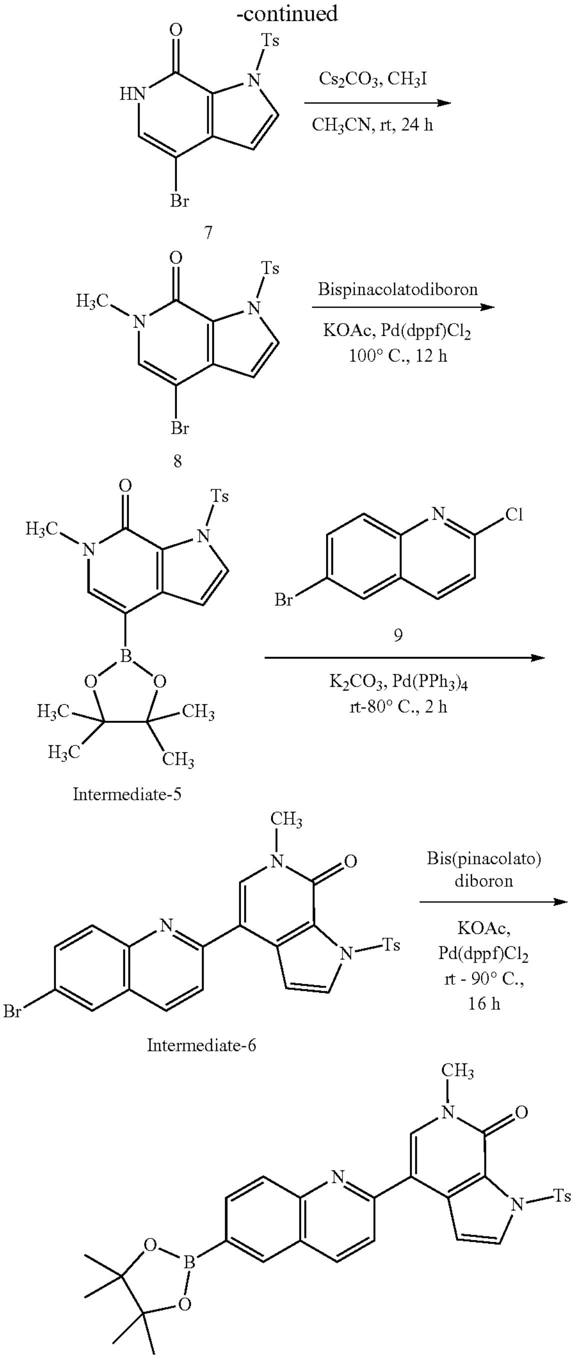

2-methoxy-4-methyl-3-nitropyridine (2)

To a stirred solution of 2-chloro-4-methyl-3-nitropyridine 1 (25.0 g, 145.30 mmol) in methanol (300 mL) at 0° C., t-BuOK (32.5 g, 290.60 mmol) was charged portion wise and slowly heated to reflux for 12 h. The reaction mixture concentrated under reduced pressure to a volume of (250 mL) and quenched by addition of $H_2O$ (200 mL). The resulting solid was collected by filtration, washed with water and dried under pressure to afford 2 (24.0 g, 48.0%) as a brown solid.

$^1$H NMR (400 MHz, DMSO-$d_6$): δ 8.25 (d, J=5.2 Hz, 1H), 7.13 (d, J=5.2 Hz, 1H), 3.96 (s, 3H), 2.30 (s, 3H).

5-bromo-2-methoxy-4-methyl-3-nitropyridine (3)

Sodium acetate (43.9 g, 535.60 mmol) was charged to a stirred solution of 2-methoxy-4-methyl-3-nitropyridine 2 (24.0 g, 148.80 mmol) in acetic acid (200 mL) at ambient temperature and $Br_2$ (61.5 g, 386.90 mmol) was added dropwise for 30 min. Upon addition, the mixture was heated at 90° C. for 12 h. TLC indicated at which time the reaction gone to completion, the reaction mixture was cooled to 0° C. and quenched by sequential addition of 10% saturated aqueous sodium sulphite (300 mL). The resulting solid was collected by filtration, washed with water and dried under reduced pressure to afford 3 (29.0 g, 82%) as a light yellow solid.

$^1$H NMR (400 MHz, DMSO-$d_6$): δ ppm 8.57 (s, 1H), 3.97 (s, 3H), 2.32 (s, 3H).

(E)-2-(5-bromo-2-methoxy-3-nitropyridin-4-yl)-N,N-dimethylethenamine (4)

DMF-DMA (300 mL) was charged to a solution of 5-Bromo 2-methoxy-4-methyl-3-nitro pyridine 3 (58.0 g, 236.70 mmol) in DMF (500 mL) at room temperature. Upon addition, the mixture was heated at 95° C. for 5 h. The reaction mixture was cooled to room temperature and poured into ice cold water (1.0 L). The resulting red solid was collected by filtration, washed with water and dried under reduced pressure to afford 4 (60.0 g, 84.0%) as a red solid.

$^1$H NMR (400 MHz, DMSO-$d_6$): δ ppm 8.24 (s, 1H), 7.04 (d, J=13.6 Hz, 1H), 4.80 (d, J=13.6 Hz, 1H), 3.88 (s, 3H), 2.90 (s, 6H).

4-bromo-7-methoxy-1H-pyrrolo[2,3-c]pyridine (5)

A mixture of 4 (20.0 g, 66.20 mmol), Fe (20.0 g, 357.60 mmol) and $NH_4Cl$ (20.0 g, 377.60 mmol) in $CH_3OH/H_2O$ (400/100 mL) was reflux for 7 h. TLC indicated at which time the reaction gone to completion, the reaction mixture was filtered while hot and the cake was washed with methanol (3×300 mL). The combined filtrates were concentrated under reduced pressure and the resulting residue was triturated with acetonitrile to afford 5 (20.0 g, 90.0%) as a light brown solid.

$^1$H NMR (400 MHz, DMSO-$d_6$): ppm δ 12.1 (br.s., 1H), 7.75 (s, 1H), 7.55 (t, J=2.8 Hz, 1H), 6.43 (t, J=2.4 Hz, 1H), 4.01 (s, 3H).

4-bromo-7-methoxy-1-tosyl-1H-pyrrolo[2,3-c]pyridine (6)

A solution of 5 (17.0 g, 74.50 mmol) in tetrahydrofuran (300 mL), sodium hydride (60%, 5.3 g, 223.60 mmol) was charged portion wise at 0° C. Upon addition, the mixture was stirred at room temperature and again cooled to 0° C. Tosyl chloride (21.2 g, 111.80 mmol) in THF (200 mL) was added dropwise and the resulting mixture was stirred at ambient temperature for 3 h. The reaction was quenched with saturated aqueous $NH_4Cl$ (500 mL) and extracted with EtOAc (3×200 mL). The combined organic layers were dried over $Na_2SO_4$, concentrated under reduced pressure and the residue was triturated with acetonitrile to afford 6 (25.0 g, 87%) as a brown solid.

$^1$H NMR (400 MHz, $CDCl_3$): ppm δ 7.97 (d, J=3.6 Hz, 1H), 7.89 (s, 1H), 7.77 (d, J=8.4 Hz, 2H), 7.29 (d, J=8.0 Hz, 2H), 6.68 (d, J=3.6 Hz, 1H), 3.88 (s, 3H), 2.40 (s, 3H).

4-bromo-1-tosyl-1H-pyrrolo[2,3-c]pyridin-7(6H)-one (7)

Hydrogen bromide (40% aqueous, 500 mL) was added to a solution of 6 (50.0 g, 131.90 mmol) in Ethanol (100 mL). Upon addition, the mixture was heated at 90° C. for 12 h, at which time TLC indicated the reaction had gone to completion. The mixture was cooled to 0° C. and the resulting white solid was collected by filtration, washed with water and dried under vacuum to afford 7 (45.0 g, 93%) as an off-white solid.

$^1$H NMR (400 MHz, DMSO-$d_6$): ppm δ 11.5 (br. s., 1H), 8.03 (d, J=3.4 Hz, 1H), 7.93 (d, J=8.4 Hz, 2H), 7.41 (d, J=8.0 Hz, 2H), 7.36 (d, J=4.48 Hz, 1H), 6.59 (d, J=3.4 Hz, 1H), 2.37 (s, 3H).

4-bromo-6-methyl-1-tosyl-1H-pyrrolo[2,3-c]pyridin-7(6H)-one (8)

Methyl iodide (29.5 g, 207.8 mmol) was charged dropwise to stirred suspension of 7 (20.0 g, 54.70 mmol) and cesium carbonate (53.3 g, 164.10 mmol) in 1,4-dioxane (300 mL). Upon addition, reaction mixture was stirred at room temperature for 24 h. Then, the solvent was evaporated under reduced pressure from the reaction mixture, diluted with $H_2O$ (200 mL) and extracted with EtOAc (5×150 mL). The combined organic layers dried over anhydrous $Na_2SO_4$ and concentrated under reduced pressure to afford 8 (20.0 g, 96%) as an off-white solid.

$^1$H NMR (400 MHz, $CDCl_3$): ppm δ 8.03 (d, J=8.3 Hz, 2H), 7.93 (d, J=3.4 Hz, 1H), 7.30 (d, J=8.3 Hz, 2H), 7.17 (s, 1H), 6.50 (d, J=3.4 Hz, 1H), 3.49 (s, 3H), 2.40 (s, 3H).

6-methyl-4-(4,4,5,5-tetramethyl-1,3,2-dioxaborolan-2-yl)-1-tosyl-1H-pyrrolo[2,3-c]pyridin-7(6H)-one (Intermediate-5)

A mixture of 8 (6.0 g, 15.80 mmol) and Bis(pinacolato) diboron (4.8 g, 18.90 mmol) in 1,4-dioxane (100 mL) was added potassium acetate (2.3 g, 23.70 mmol) and degassed it with argon for 10 min. Pd(dppf)$Cl_2$ (0.577 g, 0.71 mmol) was added to the reaction mixture and heated at 100° C. for 12 h. Upon cooled, the mixture was diluted with $H_2O$ (150 mL) and extracted with EtOAc (3×100 mL), combined organic layers were dried over sodium sulphate and concentrated under reduced pressure. The crude product was purified by combiflash chromatography (Hexanes:EtOAc=1:1) to afford compound Intermediate-5 (2.00 g, 29%) as a yellow semi solid.

$^1$H NMR (400 MHz, $CDCl_3$): ppm δ 7.96 (d, J=8.4 Hz, 2H), 7.88 (d, J=3.4 Hz, 1H), 7.51 (s, 1H), 7.32 (d, J=3.1 Hz, 2H), 6.69 (d, J=3.4 Hz, 1H), 3.52 (s, 3H), 2.38 (s, 3H), 1.32 (s, 12H).

4-(6-bromoquinolin-2-yl)-6-methyl-1-tosyl-1H-pyrrolo[2,3-c]pyridin-7(6H)-one (Intermediate-6)

To a stirred mixture of Intermediate-5 (2.50 g, 5.84 mmol) and 6-bromo-2-chloroquinoline (1.41 g, 5.84 mmol) in 4:1 mixture of 1,4-dioxane, $H_2O$ (125 mL), $K_2CO_3$ (1.60 g, 11.68 mmol) was added at room temperature. The solution was purged with argon for 10 min followed by addition of $Pd(PPh_3)_4$ (0.660 g, 0.58 mmol) and reaction mixture was heated at 80° C. for 2 h. The solvent was evaporated under reduced pressure and crude product was purified by combiflash chromatography ($CH_2Cl_2$:$CH_3OH$=97:3) to afford Intermediate-6 (1.90 g, 63%) as an off-white solid.

$^1$H NMR (400 MHz, DMSO-$d_6$): δ ppm 8.39 (d, J=2.0 Hz, 1H), 8.36 (s, 1H), 8.25 (d, J=2.0 Hz, 1H), 8.09 (d, J=3.2 Hz, 1H), 7.95-8.06 (m, 4H), 7.88 (dd, J=2.4, 9.2 Hz, 1H), 7.72 (d, J=3.2 Hz, 1H), 7.43 (d, J=8.0 Hz, 2H), 3.92 (s, 3H), 2.38 (s, 3H).

ESI-MS m/z $[C_{24}H_{18}BrN_3O_3S+H]^+$ 508.0

6-methyl-4-[6-(4,4,5,5-tetramethyl-1,3,2-dioxaborolan-2-yl)quinolin-2-yl]-1-tosyl-1H-pyrrolo[2,3-c]pyridin-7(6H)-one (Intermediate-7)

To a stirred solution of Intermediate-6 (0.3 g, 0.63 mmol), Bis(pincolato)diboron (0.19 g, 0.75 mmol) and KOAc (0.12 g, 1.26 mmol) in dioxane (15 mL) at room temperature and degassed it with argon for 5 min. Pd(dppf)$Cl_2$ (0.046 g, 0.06 mmol) was added to the reaction mixture and degassed it again with argon for 5 min and stirred at 90° C. for 16 h. The reaction mixture was diluted with water (20 mL) and extracted with EtOAc (3×20 mL). The combined organic layers were dried over anhydrous $Na_2SO_4$, concentrated under reduced pressure and crude product was purified by combiflash chromatography (EtOAc:Hexanes=70:30) to afford Intermediate-7 (0.175 g, 50%) as a light brown solid.

$^1$H NMR (400 MHz, DMSO-$d_6$) δ ppm 8.35 (s, 1H), 8.22 (d, J=8.4 Hz, 1H), 8.09 (d, J=4.4 Hz, 2H), 7.99-8.06 (m, 3H), 7.64-7.72 (m, 2H), 7.27-7.44 (m, 3H), 3.64 (s, 3H), 2.41 (s, 3H), 1.40 (s, 12H).

Synthesis of (2R,6S)-2,6-dimethyl-1-{2-[4-(4,4,5,5-tetramethyl-1,3,2-dioxaborolan-2-yl)phenoxy]ethyl}piperidine (Intermediate-8)

Scheme 4

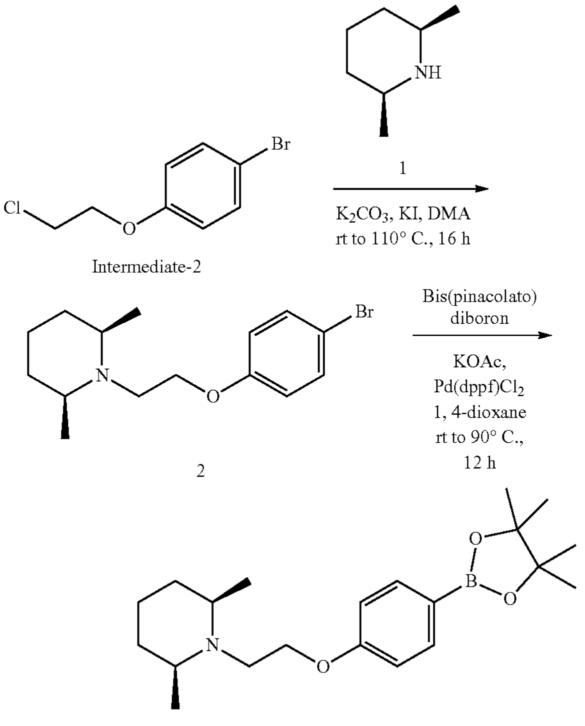

Intermediate-8

(2R,6S)-1-[2-(4-bromophenoxy)ethyl]-2,6-dimethylpiperidine (2)

To a solution of Intermediate-2 (2.0 g, 8.58 mmol) in DMA (20 mL) were charged with potassium carbonate (2.80 g, 1.71 mmol), potassium iodide (0.588 g, 4.26 mmol), and (2R,6S)-2,6-dimethylpiperidine 1 (1.16 g 10.3 mmol) at room temperature and heated at 110° C. for 16 h. The reaction mixture was diluted with water (20 mL) and extracted with EtOAc (3×30 mL). The combined organic layers were washed with $H_2O$ (2×30 mL), brine (2×20 mL), dried over anhydrous $Na_2SO_4$ and concentrated under reduced pressure afford 2 (1.50 g) as an off-white solid. The crude compound was used for the next step without purification.

$^1$H NMR (400 MHz, $CDCl_3$): δ ppm 7.35 (d, J=9.0 Hz, 2H), 6.76 (d, J=8.9 Hz, 2H), 3.94 (t, J=7.2 Hz, 2H), 3.03 (t, J=7.0 Hz, 2H), 2.49-2.59 (m, 2H), 1.64-1.70 (m, 1H), 1.52-1.59 (m, 1H), 1.20-1.38 (m, 3H), 1.16 (d, J=6.27 Hz, 6H).

(2R,6S)-2,6-dimethyl-1-{2-[4-(4,4,5,5-tetramethyl-1,3,2-dioxaborolan-2-yl)phenoxy]ethyl}piperidine (Intermediate-8)

To a solution of 2 (1.10 g, 3.53 mmol) in 1,4-dioxane (20 mL), potassium acetate (0.677 g, 7.06 mmol) and bis(pinacolato)diboron (1.07 g, 4.24 mmol) were added at room temperature and degassed it with argon for 10 min. Pd(dppf)$Cl_2$ (0.258 g, 0.35 mmol) was added to the reaction mixture at room temperature and heated at 90° C. for 12 h. The reaction mixture was filtered through a pad of celite and the filtrate was diluted with water (20 mL) and extracted with EtOAc (3×30 mL). Combined organic layers were dried over anhydrous $Na_2SO_4$, concentrated under reduced pressure and purified by combiflash chromatography (100% EtOAc) to afford Intermediate-8 (0.4 g, 33%) as brown semi solid.

$^1$H NMR (400 MHz, $CDCl_3$): δ ppm 7.74 (d, J=8.3 Hz, 2H), 6.87 (d, J=8.4 Hz, 2H), 4.04 (t, J=6.8 Hz, 2H), 3.13 (t, J=6.9 Hz, 2H), 2.60-2.69 (m, 2H), 1.65-1.70 (m, 1H), 1.55-1.61 (m, 2H), 1.33 (s, 12H), 1.20 (d, J=6.2 Hz, 6H).

Synthesis of 1,3,3-trimethyl-4-{2-[4-(4,4,5,5-tetramethyl-1,3,2-dioxaborolan-2-yl)phenoxy]ethyl}piperazin-2-one (Intermediate-9)

Scheme 5

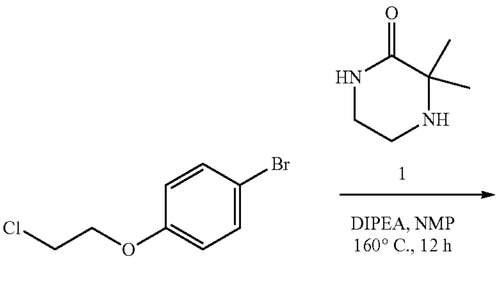

Intermediate-2

-continued

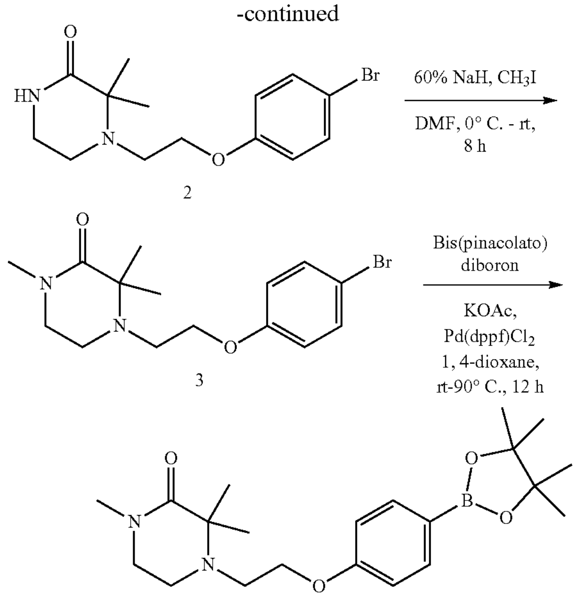

2
3

Intermediate-9

4-[2-(4-bromophenoxy)ethyl]-3,3-dimethylpiperazin-2-one (2)

A solution of Intermediate-2 (2.00 g, 8.58 mmol) in NMP (5 mL) was charged with DIPEA (5.5 mL, 34.30 mmol) and 3,3-dimethylpiperazin-2-one 1 (1.09 g, 8.58 mmol) in a sealed tube and heated at 160° C. for 12 h. The reaction mixture was diluted with water (20 mL) and extracted with EtOAc (3x30 mL). Combined organic layers were washed with water (2x30 mL), brine (2x20 mL), dried over anhydrous $Na_2SO_4$, concentrated under reduced pressure and purified by combiflash chromatography ($CH_2Cl_2$: MeOH=95:5) to afford 2 (1.30 g, 44%) as an off-white semi solid.

$^1$H NMR (400 MHz, $CDCl_3$): δ ppm 7.55 (br.s., 1H), 7.43 (d, J=8.9 Hz, 1H), 6.90 (d, J=9.1 Hz, 1H), 3.99 (t, J=6.3 Hz, 2H), 3.62 (s, 3H), 3.04-3.08 (m, 2H), 2.79 (t, J=5.6 Hz, 2H), 2.73 (t, J=6.1 Hz, 2H), 1.10 (s, 6H).

4-[2-(4-bromophenoxy)ethyl]-1,3,3-trimethylpiperazin-2-one (3)

A solution of 2 (1.20 g, 3.68 mmol) in DMF (20 mL) was charged with 60% NaH (0.22 g, 9.20 mmol) portion wise at 0° C. Upon 30 min stirring, MeI (1.04 g, 7.63 mmol) was added and stirred for 8 h at room temperature. The reaction mixture was quenched with ice cold water, diluted with water (20 mL) and extracted with EtOAc (3x30 mL). Combined organic layers were dried over anhydrous $Na_2SO_4$ and concentrated under reduced pressure to afford 3 (1.00 g) as light brown solid. The crude material was used for next step without any further purification.

$^1$H NMR (400 MHz, $CDCl_3$): δ ppm 7.37(d, J=8.8, 2H), 6.77 (d, J=9.2 Hz, 2H), 3.92 (t, J=6.0 Hz, 2H), 3.27 (t, J=4.8 Hz, 2H), 2.92-2.97 (m, 5H), 2.80 (t, J=3.6 Hz, 2H), 1.31 (s, 6H).

1,3,3-trimethyl-4-{2-[4-(4,4,5,5-tetramethyl-1,3,2-dioxaborolan-2-yl)phenoxy]ethyl}piperazin-2-one (Intermediate-9)

To a solution of 3 (1.00 g, 3.02 mmol) in 1,4-dioxane (15 mL) potassium acetate (0.579 g, 6.04 mmol) and bis(pinacolato)diboron (0.920 g, 3.62 mmol) were added at room temperature and degassed it with argon for 10 min. Pd(dppf)$Cl_2$ (0.220 g, 0.30 mmol) was added to the reaction mixture at room temperature and heated at 90° C. for 12 h. The reaction mixture was filtered through a pad of celite; the filtrate was diluted with water (20 mL) and extracted with EtOAc (3x30 mL). Combined organic layers were dried over anhydrous $Na_2SO_4$, concentrated under reduced pressure and purified by combiflash chromatography (EtOAc: Hexanes=90:10) to afford Intermediate-9 (1.0 g, 90%) as dark brown semi solid.

$^1$H NMR (400 MHz, DMSO-$d_6$): δ ppm 7.59 (d, J=8.5 Hz, 2H), 6.92 (d, J=8.6 Hz, 2H), 4.03 (t, J=5.9 Hz, 2H), 3.20 (t, J=5.1 Hz, 2H), 2.87 (t, J=5.5 Hz, 2H), 2.78 (s, 3H), 2.73 (t, J=6.1 Hz, 2H), 1.27 (s, 12H), 1.18 (s, 6H).

Synthesis of 4-{2-[4-(4,4,5,5-tetramethyl-1,3,2-dioxaborolan-2-yl)phenoxy]ethyl}morpholine (Intermediate-10)

Scheme 6

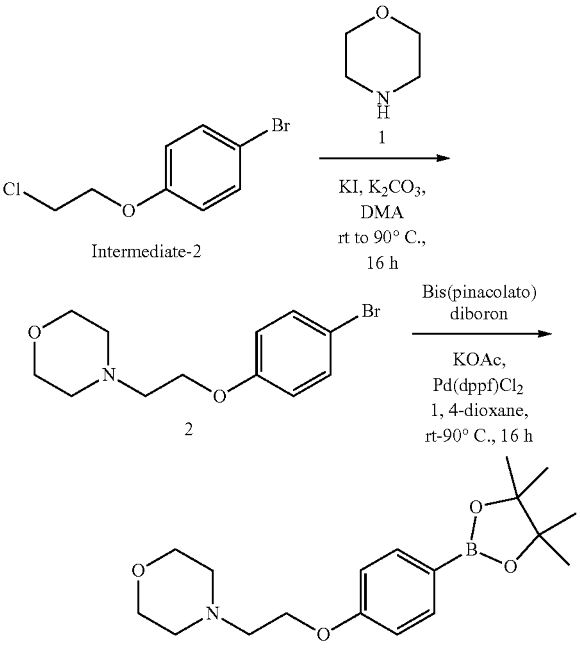

1
Intermediate-2
2

Intermediate-10

4-[2-(4-bromophenoxy)ethyl]morpholine (2)

A solution of Intermediate-2 (1.0 g, 20 mmol) in DMA (10 mL) were charged with morpholine 1 (0.370 g, 4.20 mmol), KI (0.410 g, 2.10 mmol) and $K_2CO_3$ (1.160 g, 8.40 mmol) at room temperature and was heated at 90° C. for 16 h, TLC indicated at which time the reaction gone to completion. The mixture was diluted with water (70 mL) and extracted with EtOAc (3x90 mL). Combined organic layers were dried over anhydrous $Na_2SO_4$ and concentrated under reduced pressure. The crude product was purified by combiflash chromatography (EtOAc:Hexanes=1:1) to afford 2 (0.780 g, 57%) as colourless liquid.

$^1$H NMR (400 MHz, $CDCl_3$) δ ppm 7.37 (d, J=8.8 Hz, 2H), 6.78 (dd, J=2.0, 6.8 Hz, 2H), 4.07 (t, J=5.6 Hz, 2H), 3.73 (t, J=4.8 Hz, 4H), 2.79 (t, J=5.6 Hz, 2H), 2.57 (t, J=4.4 Hz, 4H).

4-{2-[4-(4,4,5,5-tetramethyl-1,3,2-dioxaborolan-2-yl)phenoxy]ethyl}morpholine (Intermediate-10)

To a stirred solution of 2 (0.780 g, 2.63 mmol) in dioxane (10 mL), KOAc (0.515 g, 5.26 mmol), Bis(pincolato)diboron (0.8 g, 3.15 mmol) and KOAc (0.515 g, 5.26 mmol) were added at room temperature and degassed it with argon for 5 min. $Pd(dppf)Cl_2 \cdot CH_2Cl_2$ (0.190 g, 0.26 mmol) was added to the reaction mixture and was heated at 90° C. for 16 h. The reaction mixture was diluted with water (80 mL) and extracted with EtOAc (3×80 mL). Combined organic layers were dried over anhydrous $Na_2SO_4$, concentrated under reduced pressure and purified by combiflash chromatography (EtOAc:Hexanes=60:40) to afford Intermediate-10 (0.5 g, 55%) as an off-white solid.

$^1$H NMR (400 MHz, DMSO-$d_6$) δ ppm 7.59 (d, J=8.4 Hz, 2H), 6.93 (d, J=8.4 Hz, 2H), 4.10 (t, J=6.0 Hz, 2H), 3.57 (t, J=4.4 Hz, 4H), 2.68 (t, J=5.6 Hz, 2H), 2.46-2.47 (m, 4H), 1.27 (s, 12H).

Synthesis of (R)-4-{2-[(6-bromopyridin-3-yl)oxy]ethyl}-1,3-dimethylpiperazin-2-one (Intermediate-11)

Scheme 7

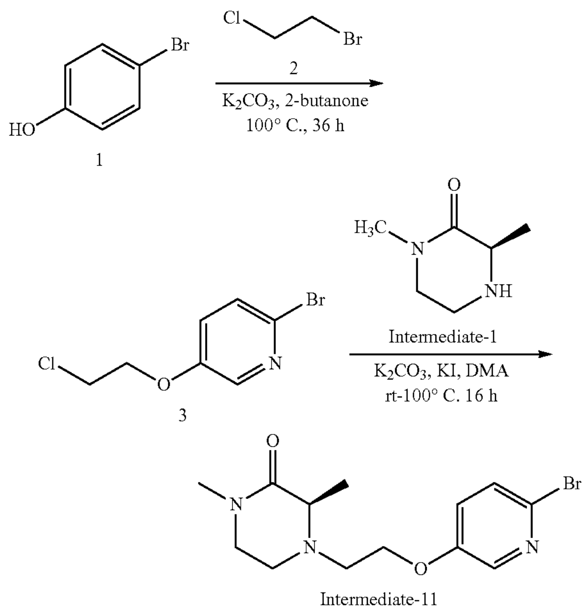

2-bromo-5-(2-chloroethoxy)pyridine (3)

To a stirred solution of 6-bromopyridin-3-ol 1 (5.00 g, 29.0 mmol) and $K_2CO_3$ (12.5 g, 87.2 mmol) in 2-butanone (25 mL), 1-bromo-2-chloroethane 2 (25 mL) was added and stirred at 100° C. for 36 h. The reaction mixture was diluted with water (40 mL) and extracted with EtOAc (3×25 mL). Combined organic layers were dried over anhydrous $Na_2SO_4$ and concentrated under reduced pressure. The crude product was purified by combiflash chromatography (Hexane:EtOAc=85:15) to afford 3 (6.00 g, 88%) as an off-white solid.

$^1$H NMR (400 MHz, $CDCl_3$) δ ppm 8.07 (d, J=3.1 Hz, 1H), 7.39 (d, J=8.6 Hz, 1H), 7.13 (dd, J=3.1, 8.6 Hz, 1H), 4.26 (t, J=5.6 Hz, 2H), 3.83 (t, J=5.7 Hz, 2H).

(R)-4-{2-[(6-bromopyridin-3-yl)oxy]ethyl}-1,3-dimethylpiperazin-2-one: (Intermediate-11)

To a stirred solution of 3 (1.00 g, 4.20 mmol) in DMA (20 mL), Intermediate-1 (0.559 g, 4.20 mmol), KI (0.348 g, 2.1 mmol) and $K_2CO_3$ (1.73 g, 12.6 mmol) were charged at room temperature and stirred for 100° C. for 16 h, TLC indicated at which the reaction gone to completion. The reaction mixture was diluted with water (100 mL) and extracted with EtOAc (3×250 mL). Combined organic layers were dried over anhydrous $Na_2SO_4$, concentrated under reduced pressure and purified by reverse phase combiflash chromatography ($CH_3CN$:$H_2O$=70:30) to afford Intermediate-11 (0.700 g, 53%) as light yellow liquid.

$^1$H NMR (400 MHz, DMSO-$d_6$) δ ppm 8.12 (d, J=3.1 Hz, 1H), 7.54 (d, J=8.7 Hz, 1H), 7.40 (dd, J=3.3, 8.7 Hz, 1H), 4.12-4.20 (m, 2H), 3.23 (t, J=5.1 Hz, 2H), 3.13 (q, J=6.8 Hz, 1H), 3.02-3.07 (m, 1H), 2.91-2.97 (m, 1H), 2.74-2.80 (m, 4H), 2.62-2.70 (m, 1H), 1.22 (d, J=6.8 Hz, 3H).

Synthesis of HCl Salt of (R)-1,3-dimethyl-4-[2-(4-(piperidin-4-yl)phenoxy)ethyl]piperazin-2-one (Intermediate-14)

Scheme 8

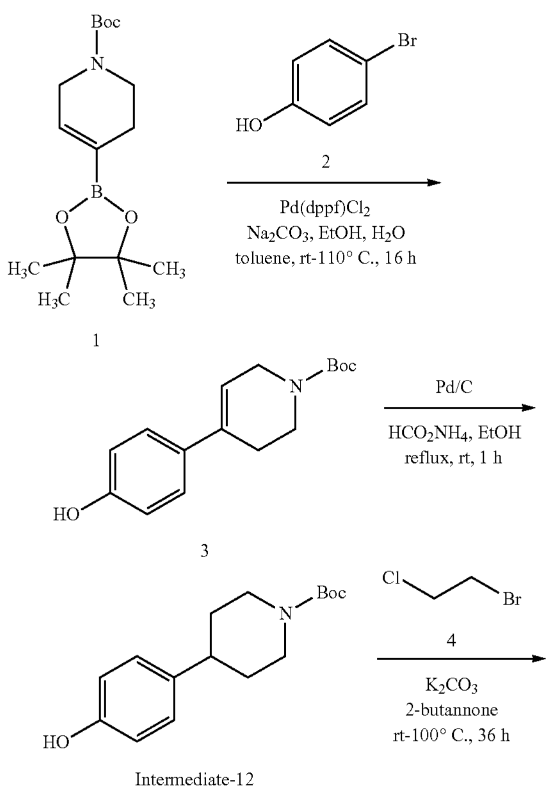

-continued

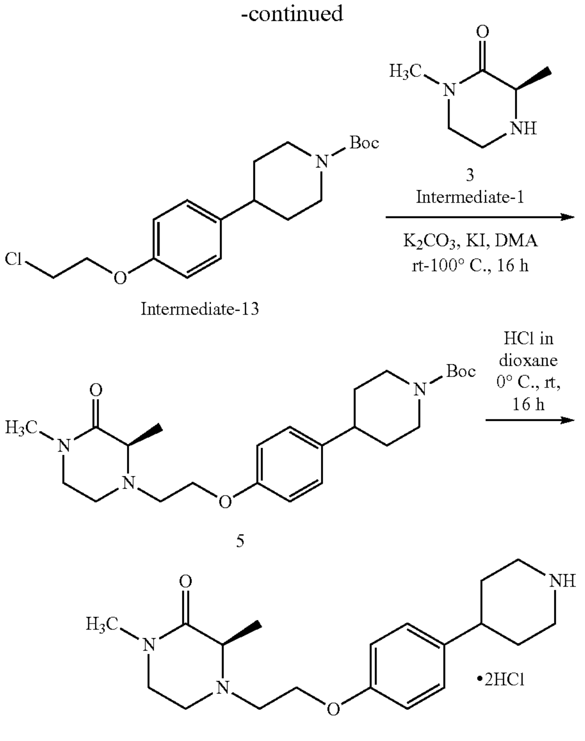

3

Intermediate-13

5

Intermediate-14 tert-butyl 4-(4-hydroxyphenyl)-5,6-dihydropyridine-1(2H)-carboxylate (3)

A solution of tert-butyl 4-(4,4,5,5-tetramethyl-1,3,2-dioxaborolan-2-yl)-5,6-dihydropyridine-1(2H)-carboxylate 1 (20.0 g, 64.0 mmol), 4-bromo phenol 2 (13.4 g, 74.0 mmol) and $Na_2CO_3$ (20.0 g, 192.0 mmol) in ethanol (50 mL), toluene (100 mL), water (50 mL) at room temperature was degassed with argon for 5 min and Pd(dppf)$Cl_2$ (4.6 g, 6.4 mmol) was added at room temperature. The reaction mixture was subjected to heating at 110° C. for 16 h, diluted with water (200 mL) and extracted with EtOAc (3×600 mL). Combined organic layers were dried over anhydrous $Na_2SO_4$, concentrated under reduced pressure and purified by combiflash chromatography (Hexanes:EtOAc=70:30) to afford tert-butyl 4-(4-hydroxyphenyl)-5,6-dihydropyridine-1(2H)-carboxylate 3 (10.01 g, 56%).as an off-white solid.

$^1$H NMR (400 MHz, $CDCl_3$) δ ppm 7.25 (d, J=7.6 Hz, 2H), 6.8 (d, J=8.8 Hz, 2H), 5.91 (br. s, 1H), 5.30 (s, 1H), 4.05 (d, J=2.0 Hz, 2H), 3.62 (t, J=5.6 Hz, 2H), 2.48 (br.s., 2H), 1.49 (s, 9H).

tert-butyl 4-(4-hydroxyphenyl)piperidine-1-carboxylate (Intermediate-12)

A solution of tert-butyl 4-(4-hydroxyphenyl)-5,6-dihydropyridine-1(2H)-carboxylate 3 (10.0 g, 36.2 mmol), Pd/C (1.5 g) and $HCOONH_4$ (22.8 g, 362.0 mmol) in ethanol (150 mL) was refluxed for 1 h. The reaction mixture was filtered through celite bed, washed with ethanol (2×70 mL), concentrated and diluted with water (200 mL) and extracted with EtOAc (3×350 mL). Combined organic layers were dried over anhydrous $Na_2SO_4$ and concentrated under reduced pressure to afford Intermediate-12 (7.70 g, 77%) as an off-white solid.

$^1$H NMR (400 MHz, $CDCl_3$) δ ppm 7.05 (d, J=8.8 Hz, 2H), 6.78 (d, J=8.8 Hz, 2H), 4.22 (br.s., 2H), 2.78 (br.s., 2H), 2.53-2.61 (m, 1H), 1.78 (d, J=13.2 Hz, 2H), 1.53-1.61 (m, 2H), 1.47 (s, 9H).

tert-butyl 4-[4-(2-chloroethoxy)phenyl]piperidine-1-carboxylate (Intermediate-13)

To a stirred solution of Intermediate-12 (0.4 g, 1.43 mmol), 1-bromo-2-chloroethane 4 (2.0 g, 14.3 mmol) and $K_2CO_3$ (0.59 g, 4.29 mmol) in 2-butanone (10 mL) at room temperature was stirred at 100° C. for 36 h. TLC indicated at which time the reaction gone to completion. The mixture was diluted with water (40 mL) and extracted with EtOAc (3×25 mL), combined organic layers were dried over anhydrous $Na_2SO_4$ and concentrated under reduced pressure. The crude product was purified by combiflash chromatography (Hexanes:EtOAc=85:15) to afford Intermediate-13 (0.250 g, 53%) as an off-white solid.

$^1$H NMR (400 MHz, DMSO-$d_6$) δ ppm 7.15 (d, J=8.8 Hz, 2H), 6.88 (d, J=8.8 Hz, 2H), 4.21 (t, J=4.8 Hz, 2H), 4.01-4.05 (m, 2H), 3.92 (t, J=4.0 Hz, 2H), 2.77 (br.s., 2H), 2.58-2.67 (m, 1H), 1.71 (d, J=12.4 Hz, 2H), 1.48-1.51 (m, 2H), 1.41 (s, 9H).

(R)-tert-butyl 4-{4-[2-(2,4-dimethyl-3-oxopiperazin-1-yl)ethoxy]phenyl}piperidine-1-carboxylate (5)

To a stirred solution of Intermediate-13 (2.5 g, 14.7 mmol), Intermediate-1 (2.30 g, 17.6 mmol) in DMA(30 mL), KI (1.20 g, 7.35 mmol) and $K_2CO_3$ (6.00 g, 44.1 mmol) was added at room temperature and stirred for 100° C. for 16 h. TLC indicated at which time the reaction gone to completion. The mixture was diluted with water (100 mL) and extracted with EtOAc (3×250 mL), combined organic layers were dried over anhydrous $Na_2SO_4$ and concentrated under reduced pressure. The crude product was purified by combiflash chromatography ($CH_2Cl_2$:$CH_3OH$=97:3) to afford 5 (1.30 g, 41%) as colourless liquid.

$^1$H NMR (300 MHz, DMSO-$d_6$) δ ppm 7.13 (d, J=11.2 Hz, 2H), 6.85 (d, J=11.2 Hz, 2H), 4.01-4.12 (m, 5H), 3.23 (t, J=7.2 Hz, 2H), 3.01-3.12 (m, 2H), 2.87-2.95 (m, 1H), 2.80 (s, 4H), 2.56-2.73 (m, 4H) 1.68-1.72 (m, 2H), 1.42-1.50 (m, 1H), 1.41 (s, 9H), 1.23 (d, J=6.4 Hz, 3H).

HCl Salt of (R)-1,3-dimethyl-4-[2-(4-(piperidin-4-yl)phenoxy)ethyl]piperazin-2-one (Intermediate-14)

To a stirred solution of 5 (1.3 g, 5.1 mmol) in HCl in dioxane (20 mL) at 0° C. and stirred for 16 h at room temperature. TLC indicated at which time the reaction gone to completion. The mixture was concentrated to afford Intermediate-14 (1.15 g) as a gummy solid. This crude was used for next step.

$^1$H NMR (400 MHz, DMSO-$d_6$) δ ppm 12.16 (s, 1H), 9.07-9.1 (m, 2H) 7.18 (d, J=8.4 Hz, 2H), 6.97 (d, J=8.4 Hz, 2H), 4.43-4.48 (m, 2H), 4.00-4.07 (m, 4H) 3.74-3.84 (m, 2H), 3.56 (s, 3H), 3.31 (d, J=13.5 Hz, 2H), 2.94-2.98 (m, 1H), 2.86 (s, 3H), 2.76-2.82 (m, 1H) 1.82-1.87 (m, 4H), 1.63 (d, J=6.4 Hz, 2H).

Synthesis of 5-bromo-2-{4-[4-(2-chloroethoxy)phenyl]piperidin-1-yl}pyridine (Intermediate-15)

Scheme 9

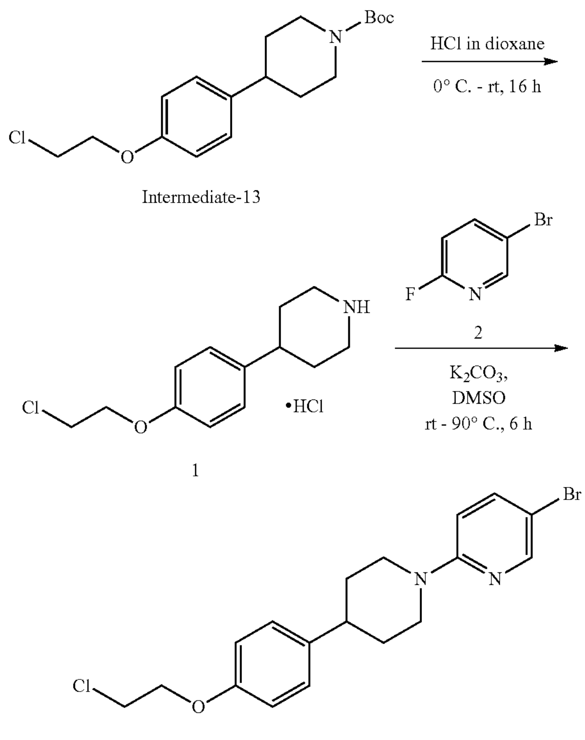

Intermediate-13

1

Intermediate-15

4-[4-(2-chloroethoxy)phenyl]piperidine·Hydrochloride (1)

To a stirred solution of Intermediate-13 (2.0 g, 5.89 mmol) in 1,4-dioxane (10 mL) at 0° C. under inert atmosphere a solution of HCl in dioxane (5.0 mL, 4 M solution) was charged at 0° C. and stirred at room temperature for 16 h. The reaction mixture was concentrated under reduced pressure and washed with MTBE (1×100 mL) to afford 1 [4.0 g, (crude)] as an off-white solid.

$^1$H NMR (300 MHz, DMSO-$d_6$): δ ppm 8.69-8.80 (m, 2H), 7.14 (d, J=8.4, 2H), 7.93 (d, J=8.4 Hz, 2H), 4.22 (d, J=4.5 Hz, 2H), 3.93 (d, J=5.1 Hz, 2H), 2.94-2.97 (m, 4H), 1.71-1.98 (m, 4H).

5-bromo-2-{4-[4-(2-chloroethoxy)phenyl]piperidin-1-yl}pyridine (Intermediate-15)

To a stirred mixture of 4-(4-(2-chloroethoxy)phenyl)piperidine 1 (0.10 g, 0.37 mmol) and 5-bromo-2-fluoropyridine (0.06 g, 0.37 mmol) in DMSO (15 mL), $K_2CO_3$ (0.10 g, 0.73 mmol) was charged at room temperature and heated at 90° C. for 6 h. The reaction mixture was allowed to room temperature and diluted with water (50 mL) followed by extraction into EtOAc (2×50 mL). Combined organic layers were washed with brine (2×10 mL), was dried over anhydrous $Na_2SO_4$ and concentrated under reduced pressure. Crude product was purified by combiflash chromatography (EtOAc:n-hexanes=70:30) to afford Intermediate-15 (0.07 g, 50%) as a colourless gum.

ESI-MS m/z $[C_{18}H_{20}BrClN_2O+H]^+$ 395.0.

Synthesis of 1-[(3S,5R)-3,5-dimethylpiperazin-1-yl]ethanone (Intermediate-16)

Scheme 10

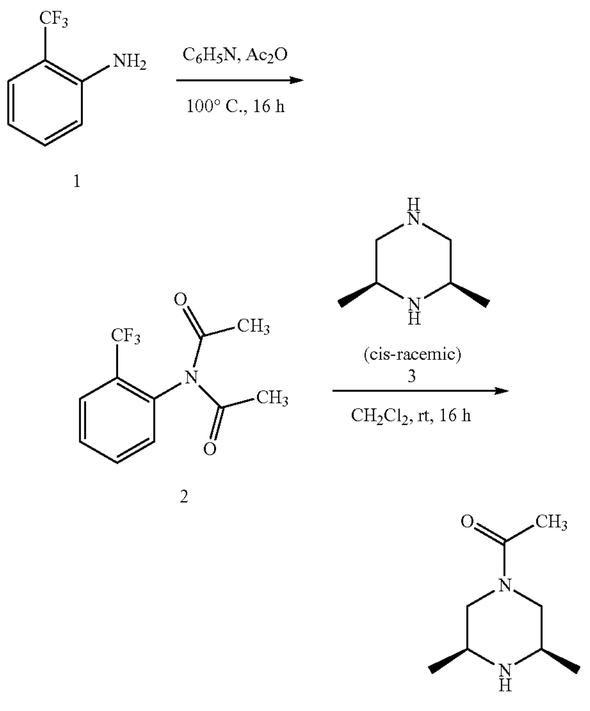

(cis-racemic)
Intermediate-16

N-acetyl-N-[2-(trifluoromethyl)phenyl]acetamide (2)

To a stirred solution of 2-(trifluoromethyl)aniline 1 (10.0 g, 62.11 mmol) in $C_6H_5N$ (100 mL), at 0° C. and acetic anhydride (45 mL, 465 mmol) was added slowly as dropwise for 10 min. The reaction mixture was heated at 100° C. for 16 h. The reaction mixture was evaporated under reduced pressure. Crude obtained was washed with n-hexanes (2×200 mL) and filtered followed by drying under high vacuum to afford N-acetyl-N-[2-(trifluoromethyl)phenyl]acetamide 2 (9.50 g, 65%) as an off-white solid.

ESI-MS m/z $[C_{11}H_{10}F_3NO_2+H]^+$ 246.1.

1-[(3S,5R)-3,5-dimethylpiperazin-1-yl]ethanone (Intermediate-16)

To a stirred solution N-acetyl-N-(2-(trifluoromethyl)phenyl)acetamide 2 (9.50 g, 38.0 mmol) in $CH_2Cl_2$ (150 mL), (2S,6R)-2,6-dimethylpiperazine 3 (4.42 g, 38.0 mmol) was charged portion wise for 15 min. The reaction mixture was stirred at ambient temperature for 16 h and concentrated under reduced pressure. This crude material was purified by combiflash column chromatography ($CH_2Cl_2$:$CH_3OH$=90:10) to afford Intermediate-16 (3.42 g, 57%) as colourless liquid.

$^1$H NMR (300 MHz, DMSO-$d_6$): δ ppm 4.19-4.24 (m, 1H), 3.61 (d, J=12.3 Hz, 1H), 2.58-2.64 (m, 1H), 2.44-2.51 (m, 4H), 1.96 (s, 3H), 0.94 (t, J=5.7 Hz, 6H).

Synthesis of 1-{(3R,5S)-3,5-dimethyl-4-[2-(4-(piperidin-4-yl)phenoxy)ethyl]piperazin-1-yl}ethanone (Intermediate-17)

Scheme 11

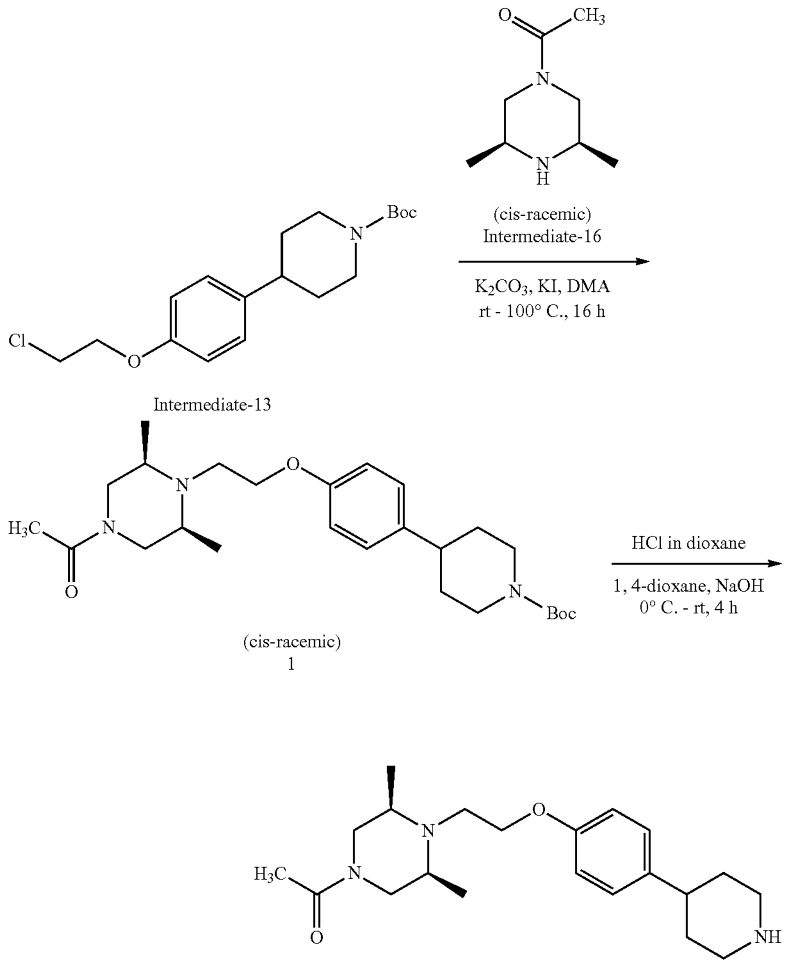

(cis-racemic) Intermediate-16

Intermediate-13

(cis-racemic) 1

(cis-racemic) Intermediate-17 tert-butyl 4-{4-[2-((2R,6S)-4-acetyl-2,6-dimethylpiperazin-1-yl)ethoxy]phenyl}piperidine-1-carboxylate (1)

A stirred mixture of Intermediate-13 (4.28 g, 12.8 mmol) (0.07 g, 0.79 mmol) and Intermediate-16 in N,N-dimethylacetamide (40 mL) was charged with $K_2CO_3$ (8.28 g, 64.1 mmol) followed by KI (0.99 g, 6.41 mmol) at room temperature and heated at 100° C. for 16 h. Then, the reaction mixture was allowed to room temperature and poured into water (50 mL) and extracted with EtOAc (3×200 mL). Combined organic layers were washed with ice-cold water (3×50 mL), brine (1×40 mL), dried over anhydrous $Na_2SO_4$, concentrated under reduced pressure and purified by combiflash chromatography ($CH_2Cl_2$:$CH_3OH$=97:3) to afford 1 (2.00 g, 34%) as a colourless gum.

$^1$H NMR (300 MHz, $CDCl_3$): δ ppm 7.44 (d, J=8.4, 2H), 6.74 (d, J=8.4 Hz, 2H), 4.33 (d, J=13.2 Hz, 1H), 4.14 (br.s., 2H), 3.89 (d, J=3.9 Hz, 2H), 3.49 (d, J=12.9 Hz, 1H), 3.05 (t, J=6.0 Hz, 2H), 2.51-2.75 (m, 4H), 2.32 (t, J=11.4 Hz, 1H), 2.00 (s, 3H), 1.69 (t, J=12.9 Hz, 4H), 1.47-1.55 (m, 2H), 1.40 (s, 9H), 1.10 (t, J=6.0 Hz, 6H).

ESI-MS m/z $[C_{26}H_{41}N_3O_4+H]^+$ 460.3.

1-{(3R,5S)-3,5-dimethyl-4-[2-(4-(piperidin-4-yl)phenoxy)ethyl]piperazin-1-yl}ethanone (Intermediate-17)

To a stirred solution of 1 (0.5 g, 1.08 mmol) in 1,4-dioxane (2 mL), HCl in 1,4-dioxane (1.0 mL, 4 M solution) was added at 0° C. under inert atmosphere and stirred at room temperature for 4 h. The reaction mixture was concentrated under reduced pressure, crude was dissolved in 10 mL of $H_2O$ and $p^H$ of the solution was adjusted to 9-10 with NaOH solution (1 N). Then, $H_2O$ and azeotrope done with toluene (5×20 mL) was evaporated to afford Intermediate-17 (0.33 g, 76%) as a brown gum.

ESI-MS m/z $[C_{21}H_{33}N_3O_2+H]^+$ 360.2.

Synthesis of 1-(3R,5S)-3,5-dimethyl-{4-[2-(4-(4,4,5,5-tetramethyl-1,3,2-dioxaborolan-2-yl)phenoxy)ethyl]piperazin-1-yl}ethanone (Intermediate-18)

Scheme 12

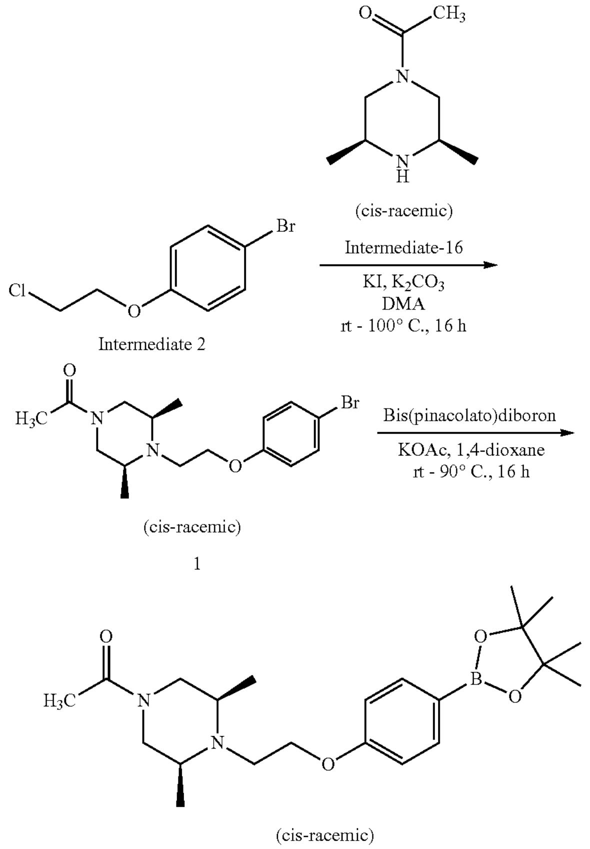

(cis-racemic)

Intermediate 2

(cis-racemic)

1

(cis-racemic)

Intermediate-18

1-[(3R,5S)-4-(2-(4-bromophenoxy)ethyl]-3,5-dimethylpiperazin-1-yl]ethanone (1)

To a stirred mixture of Intermediate-2 (4.80 g, 20.6 mmol) and Intermediate-16 (3.20 g, 20.6 mmol) in N,N-dimethylacetamide (20 mL), $K_2CO_3$ (5.52 g, 41.3 mmol), KI (1.66 g, 10.3 mmol) were added at room temperature and stirred at 100° C. for 16 h. After completion of the reaction, the reaction mixture was cooled to room temperature, poured into water (300 mL) and extracted with EtOAc (3×200 mL). Combined organic layers were washed with ice-cold water (3×50 mL), brine (1×40 mL), dried over anhydrous $Na_2SO_4$, concentrated under reduced pressure and crude residue was purified by combiflash chromatography ($CH_2Cl_2$: $CH_3OH$=97:3) to afford 1 (4.10 g, 56%) as a colourless gum.

$^1H$ NMR (400 MHz, $CDCl_3$): δ ppm 7.36 (d, J=8.8 Hz, 2H), 6.75 (d, J=9.2 Hz, 2H), 4.38-4.42 (m, 1H), 3.90-3.99 (m, 2H), 3.54-3.58 (m, 1H), 3.09 (t, J=6.4 Hz, 2H), 2.86-2.94 (m, 1H), 2.58-2.68 (m, 2H), 2.35-2.41 (m, 1H), 2.07 (s, 3H), 1.14-1.18 (m, 6H).

ESI-MS m/z $[C_{16}H_{23}BrN_2O_2+H]^+$ 355.1.

1-(3R,5S)-3,5-dimethyl-{4-[2-(4-(4,4,5,5-tetramethyl-1,3,2-dioxaborolan-2-yl)phenoxy)ethyl]piperazin-1-yl}ethanone (Intermediate-18)

A solution of 1 (3.0 g, 8.45 mmol) in 1,4-dioxane (60 mL) was charged with potassium acetate (1.24 g, 12.67 mmol), Bis(pinacolato)diboron (2.35 g, 9.29 mmol) and purged with argon for 5 min. $Pd(dppf)Cl_2 \cdot CH_2Cl_2$ (0.68 g, 0.84 mmol) was added at room temperature and the reaction mixture was heated at 90° C. for 16 h. The reaction mixture was filtered through celite pad and washed with EtOAc (500 mL). Filtrate was washed with water (2×100 mL), brine (1×100 mL). Combined organic layers were dried over anhydrous $Na_2SO_4$, concentrated under reduced pressure and purified by combiflash chromatography ($CH_2Cl_2$:$CH_3OH$=92:8) to afford Intermediate-18 (2.25 g, 68%) as a brown solid.

$^1H$ NMR (300 MHz, DMSO-$d_6$): δ ppm 7.59 (d, J=11.2 Hz, 2H), 6.92 (d, J=11.2 Hz, 2H), 4.18 (t, J=10.8 Hz, 1H), 4.00 (t, J=8.0 Hz, 2H), 3.64 (d, J=16.8 Hz, 1H), 3.01 (t, J=8.0 Hz, 2H), 2.74 (t, J=15.2 Hz, 1H), 2.59-2.61 (m, 2H), 2.25 (t, J=16.0 Hz, 1H), 1.97 (s, 3H), 1.27 (s, 12H), 1.05-1.08 (m, 6H).

Synthesis of 4-[6-(3,9-diazaspiro[5.5]undecan-3-yl)pyridin-3-yl]-6-methyl-1-tosyl-1H-pyrrolo[2,3-c]pyridin-7(6H)-one·hydrochloride (Intermediate-20)

Scheme 13

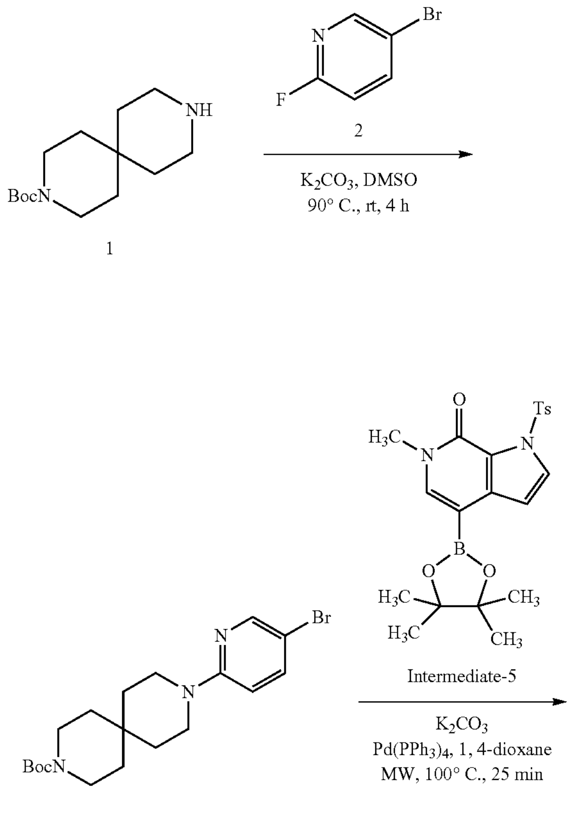

1

3

-continued

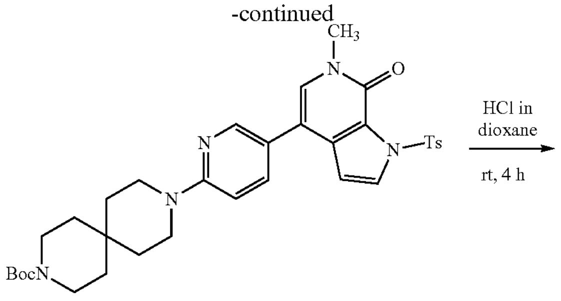

Intermediate-19

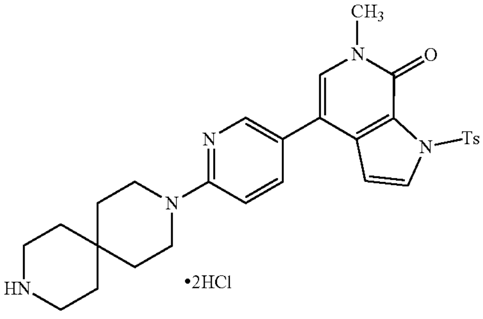

Intermediate-20 tert-butyl 9-(5-bromopyridin-2-yl)-3,9-diazaspiro [5.5]undecane-3-carboxylate of (3)

To a stirred mixture of tert-butyl 3,9-diazaspiro[5.5]undecane-3-carboxylate 1 (0.5 g, 1.96 mmol) and 5-bromo-2-fluoropyridine 2 (0.376 g, 2.16 mmol) in DMSO (20 mL), $K_2CO_3$ (0.678 g, 4.92 mmol) was charged and heated at 90° C. for 4 h. The reaction mixture was cooled to room temperature, poured into water (50 mL) and extracted into EtOAc (5×50 mL). Combined organic layers were washed with ice cold water (2×50 mL), .brine (1×30 mL). Organic layer was dried over anhydrous $Na_2SO_4$ and concentrated under reduced pressure and crude product was purified by combiflash chromatography (n-Hexanes:EtOAc=90:10) to afford 3 (0.560 g, 70%) as an off-white solid.

$^1$H NMR (400 MHz, $CDCl_3$): δ ppm 8.17 (d, J=2.0 Hz, 1H), 7.50 (dd, J=2.4, 9.2 Hz, 1H), 6.54 (d, J=8.8 Hz, 1H), 3.49 (t, J=6.0 Hz, 4H), 3.41 (t, J=5.6 Hz, 4H), 1.48-1.59 (m, 8H), 1.46 (s, 9H).

tert-butyl 9-[5-(6-methyl-7-oxo-1-tosyl-6,7-dihydro-1H-pyrrolo[2,3-c]pyridin-4-yl)pyridin-2-yl]-3,9-diazaspiro[5.5]undecane-3-carboxylate (Intermediate-19)

In a microwave vial, to a stirred solution of 3 (0.560 g, 1.36 mmol) in 4:1 of 1,4-dioxane in $H_2O$ (10 mL), Intermediate-5 (0.580 g, 1.36 mmol) and $K_2CO_3$ (0.470 g, 3.42 mmol) were charged and purged with argon for 5 min. $Pd(PPh_3)_4$ (0.157 g, 0.13 mmol) was added to the reaction mixture and heated at 100° C. for 25 min. The reaction mixture was filtered through celite pad, washed with EtOAc (2×50 mL). Filtrate was concentrated under reduced pressure and crude product was purified by combiflash chromatography (Hexanes:EtOAc=90:10) to afford Intermediate-19 (0.350 g, 42%) as an off-white solid.

$^1$H NMR (400 MHz, $CDCl_3$): δ ppm 8.22 (d, J=2.4 Hz, 1H), 8.03 (d, J=8.4 Hz, 2H), 7.92 (d, J=3.6 Hz, 1H) 7.64-7.69 (m, 1H), 7.31 (d, J=8.4 Hz, 2H), 6.96 (s, 1H), 6.71 (d, J=8.8 Hz, 1H), 6.52 (d, J=3.6 Hz, 1H), 3.58-3.59 (m, 4H), 3.56 (s, 3H), 3.43 (t, J=5.2 Hz, 4H), 1.62 (t, J=5.6 Hz, 4H), 1.51-1.49 (m, 4H), 1.46 (s, 9H).

ESI-MS m/z $[C_{34}H_{41}N_5O_5S+H]^+$ 632.3.

4-[6-(3,9-diazaspiro[5.5]undecan-3-yl)pyridin-3-yl]-6-methyl-1-tosyl-1H-pyrrolo[2,3-c]pyridin-7(6H)-one·hydrochloride (Intermediate-20)

To a stirred solution of Intermediate-19 (0.350 g, 11.5 mmol) in dioxane (8.0 mL), a solution of HCl in dioxane (3.5 mL, 4 M solution) was added at 0° C. and stirred at room temperature for 4 h. The reaction mixture was concentrated under reduced pressure and triturated with MTBE (2×50 mL) to afford Intermediate-20 [0.450 g, (crude)] as a brown solid.

$^1$H NMR (400 MHz, DMSO-$d_6$): δ ppm 8.82 (br.s., 2H), 8.08 (t, J=3.6, 3H), 7.97 (d, J=8.4 Hz, 2H), 7.68 (s, 1H), 7.43 (d, J=8.0, 3H), 6.63 (d, J=9.0 Hz, 1H), 3.73 (br.s., 4H), 3.46 (s, 3H), 3.07 (br.s., 4H), 2.39 (s, 3H), 1.59-1.71 (m, 8H).

ESI-MS m/z $[C_{29}H_{33}N_5O_3S+H]^+$ 532.2.

Synthesis of 6-methyl-4-{2-[4-(2-(3-oxopiperazin-1-yl)ethoxy)phenyl]quinolin-6-yl}-1-tosyl-1H-pyrrolo [2,3-c]pyridin-7(6H)-one (Intermediate-23)

Scheme 14

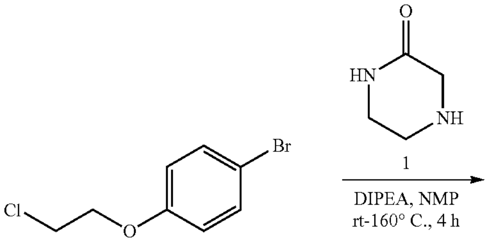

Intermediate-2

-continued

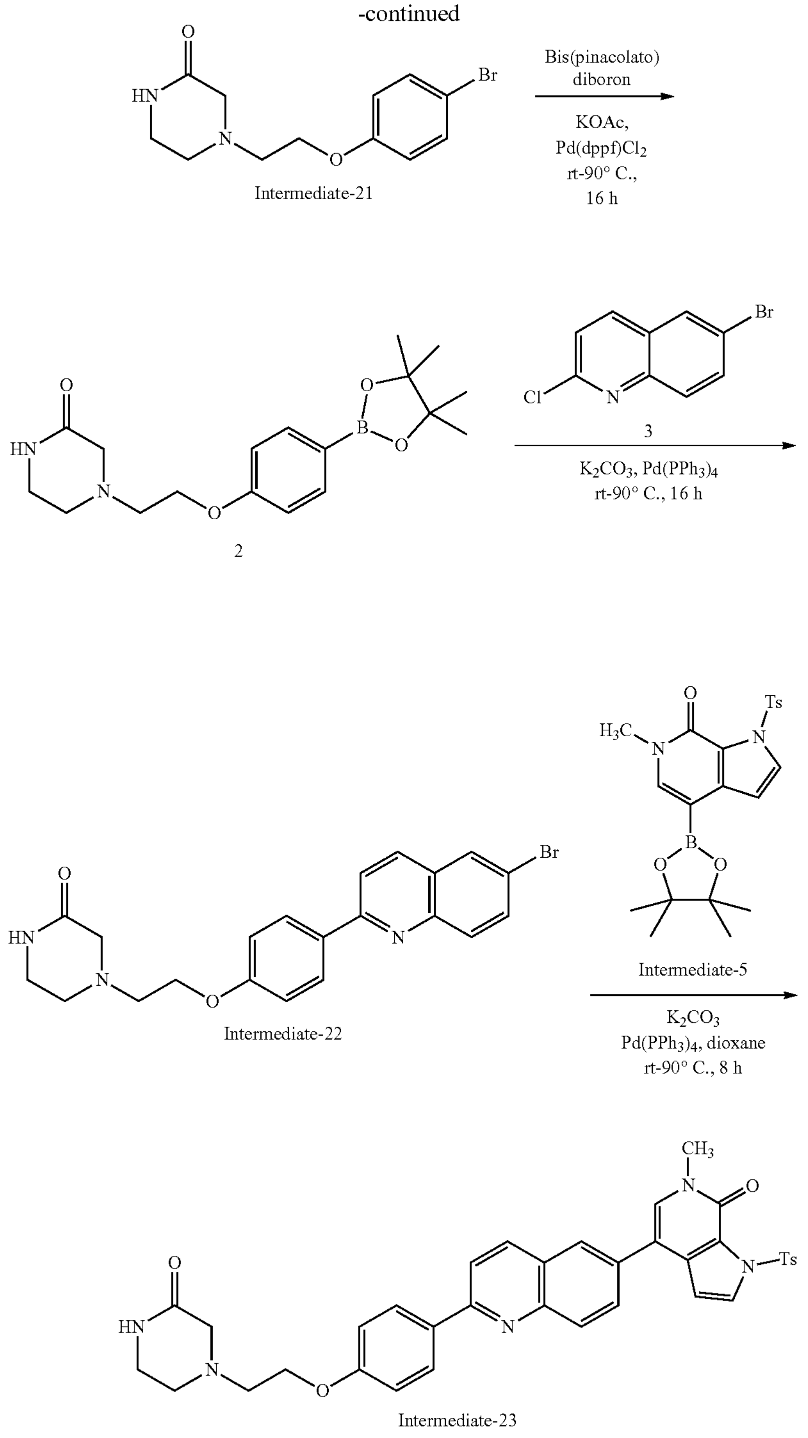

4-[2-(4-bromophenoxy)ethyl]piperazin-2-one (Intermediate-21)

To a stirred solution of Intermediate-2 (6.0 g, 25 mmol) and piperazin-2-one 1 (2.55 g, 25 mmol) in N-methyl-2-pyrrolidone (40 mL), DIPEA (16.5 mL, 10 mmol) was charged at room temperature in a sealed tube and heated at 160° C. on a sand bath for 4 h. The reaction mixture was allowed to room temperature and poured into water (300 mL). Organic compound was extracted into EtOAc (3×500 mL). Combined organic layers were washed with ice-cold water (3×200 mL), brine (1×100 mL), dried over anhydrous $Na_2SO_4$ and concentrated under reduced pressure. The solid obtained was washed with n-hexanes (1×100 mL) and dried under vacuum to afford Intermediate-21 (6.00 g, 78%) as an off-white solid.

$^1$H NMR (400 MHz, DMSO-$d_6$): δ ppm 7.77 (br.s., 1H), 7.43 (d, J=9.2 Hz, 2H), 6.92 (dd, J=2.0, 9.2 Hz, 2H), 4.08 (t, J=5.6 Hz, 2H), 3.12-3.16 (m, 2H), 3.02 (s, 2H), 2.75 (t, J=10.4 Hz, 2H), 2.65 (t, J=5.6 Hz, 2H)

ESI-MS m/z $[C_{12}H_{15}BrN_2O_2+H]^+$ 299.26.

4-{2-[4-(4,4,5,5-tetramethyl-1,3,2-dioxaborolan-2-yl)phenoxy]ethyl}piperazin-2-one (2)

A solution of Intermediate-21 (6.0 g, 20 mmol) in 1,4-dioxane (200 mL) was charged with potassium acetate (3.92 g, 40 mmol), Bis(pinacolato)diboron (7.11 g, 28 mmol) at room temperature followed by purging with argon for 15 min. Pd(dppf)$Cl_2$ (1.46 g, 2.0 mmol) was added and purged with argon for 15 min. Reaction was heated at 90° C. for 16 h. The reaction mixture was filtered through celite pad and washed with EtOAc (500 mL). Filtrate was washed with water (3×200 mL), brine (2×200 mL), dried over anhydrous $Na_2SO_4$, concentrated under reduced pressure and purified by combiflash chromatography ($CH_2Cl_2$:$CH_3OH$=95:5) to afford 2 (4.50 g, 66%) as a brown solid.

$^1H$ NMR (400 MHz, DMSO-$d_6$): δ ppm 7.73 (s, 1H), 7.60 (dd, J=1.6, 6.0 Hz, 2H), 6.94 (dd, J=1.6, 6.0 Hz, 2H), 4.12 (t, J=5.6 Hz, 2H), 3.13-3.16 (m, 2H), 3.03 (s, 2H), 2.77 (t, J=5.6 Hz, 2H), 2.66 (t, J=5.6 Hz, 2H), 1.27 (s, 12H).

ESI-MS m/z $[C_{18}H_{27}BN_2O_4+H]^+$ 347.1.

4-{2-[4-(6-bromoquinolin-2-yl)phenoxy]ethyl}piperazin-2-one (Intermediate-22)

To a stirred solution of 2 (4.50 g, 13 mmol) in 4:1 of dioxane, $H_2O$ (150 mL), 6-bromo-2-chloroquinoline 3 (3.14 g, 13 mmol) and $K_2CO_3$ (3.58 g, 26 mmol) were added at room temperature and purged with argon for 15 min followed by addition of $Pd(PPh_3)_4$ (1.50 g, 1.30 mmol) at room temperature. Then, reaction mixture was heated at 90° C. for 16 h and was filtered through celite pad, washed with EtOAc (2×250 mL). Filtrate was washed with water (2×100 mL), brine (1×100 mL), dried over anhydrous $Na_2SO_4$, concentrated under reduced pressure and purified by combiflash chromatography ($CH_2Cl_2$:$CH_3OH$=95:5). The semi solid obtained was triturated with n-hexanes (100 mL) and filtered-off to afford Intermediate-22 (2.70 g, 50%) as an off-white solid.

$^1H$ NMR (400 MHz, DMSO-$d_6$): δ ppm 8.38 (d, J=8.0 Hz, 1H), 8.23-8.26 (m, 3H), 8.17 (d, J=8.8 Hz, 1H), 7.96 (d, J=8.8 Hz, 1H), 7.86 (dd, J=2.4, 8.8 Hz, 1H), 7.76 (s, 1H), 7.12 (d, J=8.8 Hz, 2H), 4.20 (t, J=5.6 Hz, 2H), 3.16-3.19 (m, 2H), 3.07 (s, 2H), 2.82 (t, J=5.6 Hz, 2H), 2.70 (t, J=5.2 Hz, 2H).

ESI-MS m/z $[C_{21}H_{20}BrN_3O_2+H]^+$ 426.2.

6-methyl-4-{2-[4-(2-(3-oxopiperazin-1-yl)ethoxy)phenyl]quinolin-6-yl}-1-tosyl-1H-pyrrolo[2,3-c]pyridin-7(6H)-one (Intermediate-23)

To a stirred mixture of Intermediate-22 (0.2 g, 0.46 mmol) and Intermediate-5 (0.220 g, 0.51 mmol) in 4:1 of 1,4-dioxane:$H_2O$ (20 mL), $K_2CO_3$ (0.120 g, 0.92 mmol) was charged at room temperature and purged with argon for 5 min. $Pd(PPh_3)_4$ (0.053 g, 0.046 mmol) was added at room temperature and heated at 90° C. for 8 h. The reaction mixture was evaporated under reduced pressure and crude product was purified by combiflash chromatography ($CH_2Cl_2$:$CH_3OH$=93:7) to afford Intermediate-23 (0.110 g, 37%) as an off-white solid.

$^1H$ NMR (400 MHz, DMSO-$d_6$): δ ppm 8.45 (d, J=8.0 Hz, 1H), 8.27 (d, J=8.4 Hz, 2H), 8.15 (d, J=8.8 Hz, 1H), 8.09-8.11 (m, 3H), 7.99 (d, J=8.8 Hz, 2H), 7.89-7.92 (m, 1H), 7.80 (s, 1H), 7.76 (br.s., 1H), 7.45 (d, J=8.4 Hz, 2H), 7.13 (d, J=8.0 Hz, 2H), 6.87 (d, J=3.6 Hz, 1H), 4.21 (br.s., 2H), 3.51 (s, 3H), 3.17 (br.s., 2H), 3.07 (s, 2H), 2.82 (br.s., 2H), 2.69 (t, J=4.4 Hz, 2H), 2.40 (s, 3H).

ESI-MS m/z $[C_{29}H_{27}N_5O_3+H]^+$ 648.2.

Synthesis of (R)-4-{2-[4-(1-(5-bromopyridin-2-yl)piperidin-4-yl)phenoxy]ethyl}-1,3-dimethylpiperazin-2-one (Intermediate-24)

Scheme 15

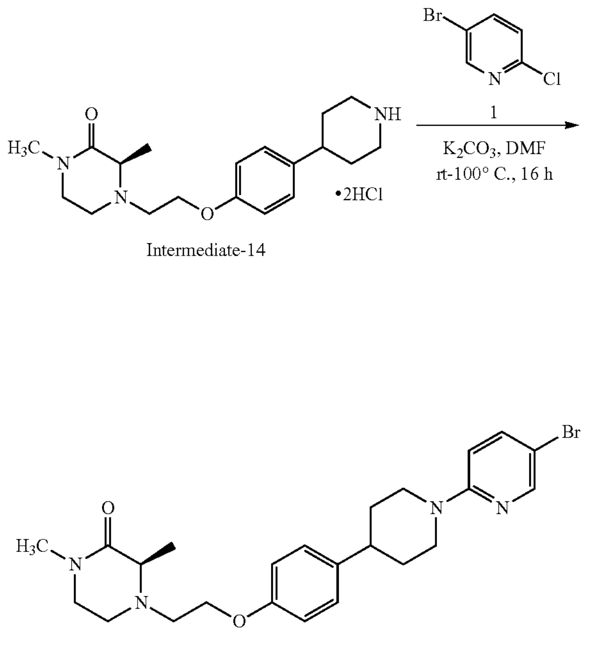

Intermediate-14

Intermediate-24

(R)-4-{2-[4-(1-(5-bromopyridin-2-yl)piperidin-4-yl)phenoxy]ethyl}-1,3-dimethylpiperazin-2-one (Intermediate-24)

To a stirred solution of Intermediate-14 (0.500 g, 1.50 mmol) in DMF (5.0 mL) were charged with 5-bromo-2-chloropyridine 1 (0.350 g, 1.80 mmol) and $K_2CO_3$ (0.620 g, 4.5 mmol) at room temperature and was heated at 100° C. for 16 h. TLC indicated at which time the reaction gone to completion. The mixture was diluted with water (20 mL) and extracted with EtOAc (3×50 mL). Combined organic layers were dried over anhydrous $Na_2SO_4$ and concentrated under reduced pressure. The crude product was purified by combiflash chromatography ($CH_2Cl_2$:$CH_3OH$=97:3) to afford Intermediate-24 (0.230 g, 17%) as colourless liquid.

$^1H$ NMR (300 MHz, DMSO-$d_6$): δ ppm 8.15 (d, J=2.4 Hz, 1H), 7.65 (d, J=2.4, 8.8 Hz, 1H), 7.14 (d, J=8.8 Hz, 2H), 6.84-6.87 (m, 3H), 4.38 (d, J=13.2 Hz, 2H), 4.03 (t, J=6.0 Hz, 2H), 3.22-3.25 (m, 2H), 3.11-3.17 (m, 2H), 3.02-3.07 (m, 1H), 2.87 (s, 1H) 2.82-2.84 (m, 1H), 2.78 (s, 3H), 2.70-2.77 (m, 1H), 2.66-2.69 (m, 2H), 1.79 (d, J=12.0 Hz, 2H), 1.49-1.59 (m, 2H), 1.22 (d, J=6.8 Hz, 3H).

Synthesis of 4-{6-[4-(4-(2-((2R,6S)-4-acetyl-2,6-dimethylpiperazin-1-yl)ethoxy)phenyl)piperidin-1-yl]pyridin-3-yl}-6-methyl-1H-pyrrolo[2,3-c]pyridin-7(6H)-one (SLU-2090)
Scheme 16
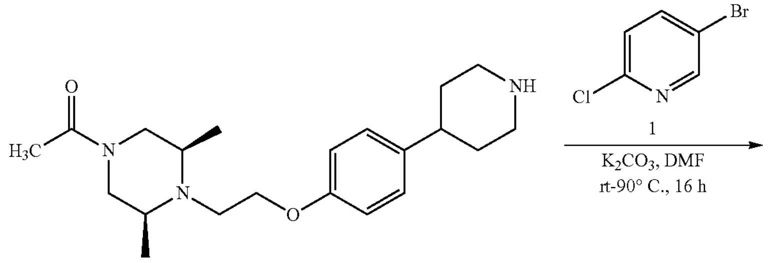
(cis-racemic)
Intermediate-17
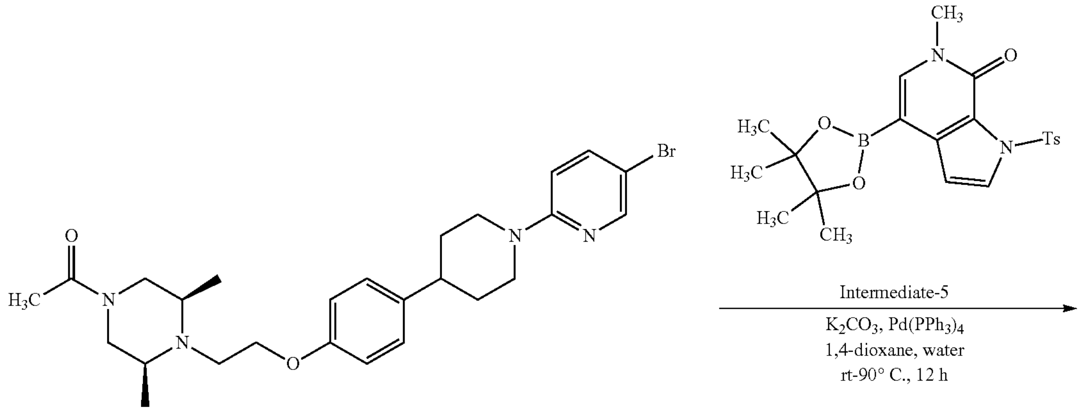
(cis-racemic)
2

-continued

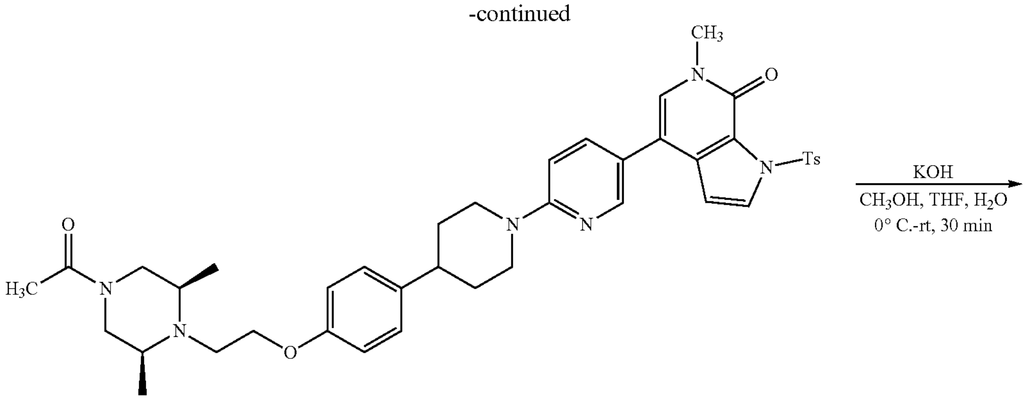

(cis-racemic)
3

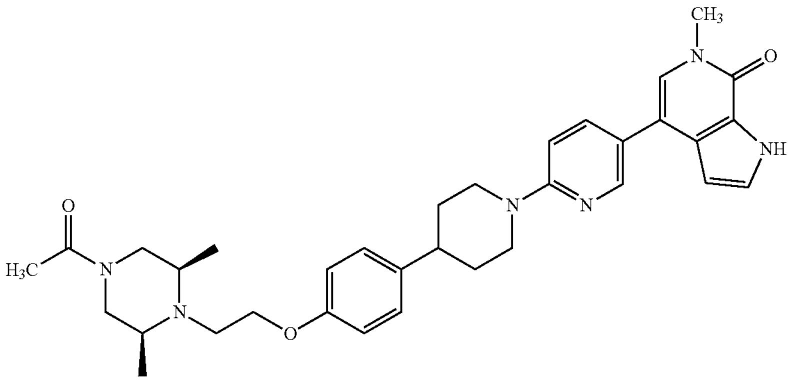

(cis-racemic)
SLU-2090

1[(3R,5S)-4-{2-[4-(1-(5-bromopyridin-2-yl)piperidin-4-yl)phenoxy)ethyl]-3,5-dimethylpiperazin-1-yl}ethanone (2)

To a stirred solution of Intermediate-17 (0.33 g, 0.91 mmol) and 5-bromo-2-chloropyridine 1 (0.19 g, 1.01 mmol) in DMF (8 mL), $K_2CO_3$ (0.37 g, 2.73 mmol) was added at room temperature and stirred at 90° C. for 16 h. The reaction mixture was cooled to room temperature, poured into water (50 mL) and organic compound was extracted into EtOAc (2×100 mL). Combined organic layers were washed with ice-cold water (2×10 mL), brine (1×15 mL), dried over anhydrous $Na_2SO_4$ and concentrated under reduced pressure. The crude product was purified by combiflash chromatography ($CH_2Cl_2$:$CH_3OH$=95:5) to afford 2 (0.06 g, 12%) as an off-white solid.

ESI-MS m/z $[C_{26}H_{35}BrN_4O_2+H]^+$ 515.1.

4-{6-[4-(4-(2-((2R,6S)-4-acetyl-2,6-dimethylpiperazin-1-yl)ethoxy)phenyl)piperidin-1-yl]pyridin-3-yl}-6-methyl-1-tosyl-1H-pyrrolo[2,3-c]pyridin-7(6H)-one (3)

To a solution of 2 (0.06 g, 0.11 mmol) in 4:1 mixture of dioxane, $H_2O$ (10 mL), Intermediate-5 (0.05 g, 0.11 mmol) and $K_2CO_3$ (0.03 g, 0.24 mmol) were charged at room temperature and purged with argon for 5 min. $Pd(PPh_3)_4$ (0.01 g, 0.01 mmol) was added to the reaction mixture and purged with argon for 5 min. The reaction mixture was allowed to stir at 90° C. for 12 h and filtered through celite pad, washed with EtOAc (2×50 mL). Filtrate was concentrated under reduced pressure and crude residue was purified by combiflash chromatography ($CH_2Cl_2$:$CH_3OH$=95:5) to afford 3 (0.01 g, 15%); ESI-MS m/z $[C_{41}H_{48}N_6O_5S+H]^+$ 737.3.

4-{6-[4-(4-(2-((2R,6S)-4-acetyl-2,6-dimethylpiperazin-1-yl)ethoxy)phenyl)piperidin-1-yl]pyridin-3-yl}-6-methyl-1H-pyrrolo[2,3-c]pyridin-7(6H)-one (SLU-2090)

To a stirred solution of 3 (0.12 g, 0.39 mmol) in 2:2:1 solvent mixture of $CH_3OH$, THF, $H_2O$ (25 mL), KOH (0.04 g, 0.78 mmol) was added at 0° C. and stirred at room temperature. After 30 min, the reaction mixture was concentrated under reduced pressure and crude product was purified by reverse phase combiflash chromatography ($CH_3CN$:$H_2O$=80:20) to afford SLU-2090 (0.05 g, 51%) as a white solid.

$^1H$ NMR (400 MHz, DMSO-$d_6$): δ ppm 12.12 (s, 1H), 8.33 (d, J=2.8 Hz, 1H), 7.74 (dd, J=2.4, 8.8 Hz, 1H), 7.38 (t, J=2.8 Hz, 1H), 7.30 (s, 1H), 7.16 (d, J=8.8 Hz, 2H), 6.97 (d, J=8.8 Hz, 1H), 6.85 (d, J=8.4 Hz, 2H), 6.40 (t, J=2.0 Hz, 1H), 4.48 (d, J=13.2 Hz, 2H), 4.16 (d, J=12.0 Hz, 1H), 3.94 (t, J=6.4 Hz, 2H), 3.64 (d, J=12.8 Hz, 1H), 3.56 (s, 3H), 2.99 (t, J=6.0 Hz, 2H), 2.89 (t, J=12.0 Hz, 2H), 2.74 (t, J=10.8 Hz, 2H), 2.60-2.71 (m, 1H), 2.32 (t, J=1.2 Hz, 1H), 2.24 (t, J=12.0 Hz, 1H), 1.97 (s, 3H), 1.82 (d, J=13.2 Hz, 2H), 1.55-1.64 (m, 2H), 1.06 (d, J=12.0 Hz, 6H).

ESI-MS m/z $[C_{34}H_{42}N_6O_3+H]^+$ 583.2;

HPLC (Method D) 93.9% (AUC), $t_R$=6.21 min.

Synthesis of 4-{4'-[2-((2R,6S)-4-acetyl-2,6-dimethylpiperazin-1-yl)ethoxy)-3-methoxy-[1,1'-biphenyl]-4-yl}-6-methyl-1H-pyrrolo[2,3-c]pyridin-7(6H)-one (SLU-2098)
Scheme 17
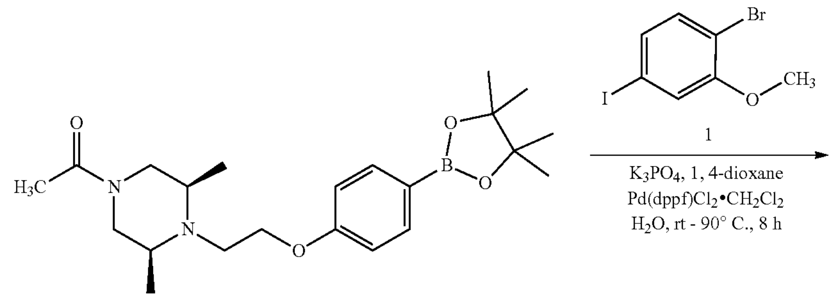
(cis-racemic)
Intermediate-18
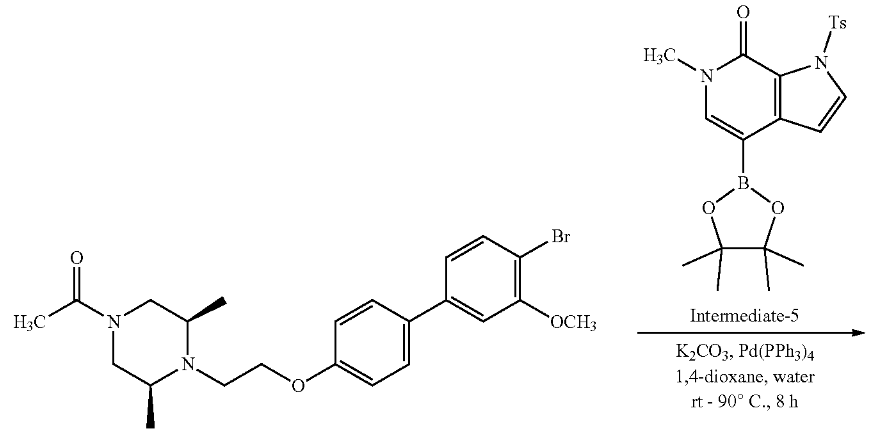
2
(cis-racemic)
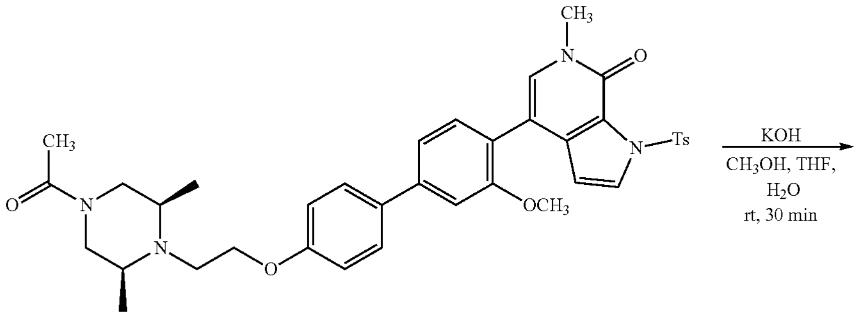
3
(cis-racemic)

-continued

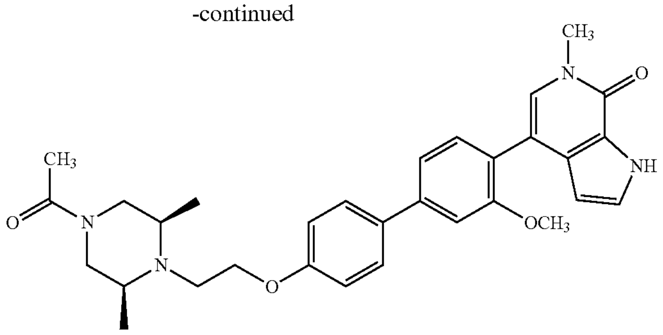

(cis-racemic)
SLU-2098

(R)-4-{2-[(4'-bromo-3'-methoxy-[1,1'-biphenyl]-4-yl)oxy]ethyl}-1,3-dimethylpiperazin-2-one (2)

To a stirred mixture of Intermediate-18 (0.40 g, 0.99 mmol) and 1-bromo-4-iodo-2-methoxybenzene 1 (0.31 g, 0.99 mmol) in 4:1 mixture of dioxane, $H_2O$ (12.5 mL), $K_3PO_4$ (0.40 g, 1.90 mmol) was charged at room temperature and purged with argon for 5 min followed by addition of $Pd(dppf)Cl_2 \cdot CH_2Cl_2$ (0.08 g, 0.09 mmol). The reaction mixture was allowed to stir at 90° C. for 8 h and the reaction mixture was filtered through celite pad, washed with EtOAc (2×100 mL). Filtrate was concentrated under reduced pressure and crude residue was purified by combiflash chromatography ($CH_2Cl_2$:$CH_3OH$=98:2) to afford 2 (0.18 g, 40%) as an off-white solid.

$^1$H NMR (400 MHz, $CDCl_3$): δ ppm 7.55 (d, J=8.4 Hz, 1H), 7.47-7.49 (m, 2H), 7.04 (d, J=1.6 Hz, 1H), 7.00 (dd, J=1.6, 8.0 Hz, 1H), 6.93-6.95 (m, 2H), 4.39-4.44 (m, 1H), 4.03 (q, J=6.4 Hz, 2H), 3.95 (s, 3H), 3.55-3.60 (m, 1H), 3.14 (t, J=6.4 Hz, 2H), 2.88-2.94 (m, 1H), 2.62-2.71 (m, 2H), 2.40 (t, J=12.8 Hz, 1H), 2.09 (s, 3H), 1.17-1.21 (m, 6H).

ESI-MS m/z $[C_{23}H_{29}BrN_2O_3+H]^+$ 461.1.

4-{4'-[2-((2R,6S)-4-acetyl-2,6-dimethylpiperazin-1-yl)ethoxy)-3-methoxy-[1,1'-biphenyl]-4-yl}-6-methyl-1-tosyl-1H-pyrrolo[2,3-c]pyridin-7(6H)-one (3)

To a stirred mixture of 2 (0.18 g, 0.41 mmol) and Intermediate-5 (0.17 g, 0.43 mmol) in 4:1 of dioxane, $H_2O$ (25 mL), $K_2CO_3$ (0.11 g, 0.82 mmol) was charged at room temperature and purged with argon for 5 min followed by addition of $Pd(PPh_3)_4$ (0.04 g, 0.04 mmol). The reaction mixture was heated at 90° C. for 8 h. The reaction mixture was filtered through celite pad and washed with EtOAc (2×100 mL). Filtrate was concentrated under reduced pressure and crude product was purified by combiflash chromatography ($CH_2Cl_2$:$CH_3OH$=94:6) to afford 3 (0.06 g, 23%) as an off-white solid. No analysis was taken.

4-{4'-[2-((2R,6S)-4-acetyl-2,6-dimethylpiperazin-1-yl)ethoxy)-3-methoxy-[1,1'-biphenyl]-4-yl}-6-methyl-1H-pyrrolo[2,3-c]pyridin-7(6H)-one (SLU-2098)

To a stirred solution 3 (0.06 g, 0.08 mmol) in 2:2:1 mixture of $CH_3OH$, THF, $H_2O$ (5 mL), KOH (0.02 g, 0.17 mmol) was added at 0° C. and left to room temperature for 30 min. The reaction mixture was concentrated under reduced pressure and crude product was purified by reverse phase combiflash chromatography ($H_2O$:$CH_3CN$=65:35) to afford SLU-2098 (0.03 g, 71%) as an off-white solid.

$^1$H NMR (300 MHz, DMSO-$d_6$): δ ppm 11.98 (s, 1H), 7.69 (d, J=8.7 Hz, 2H), 7.37 (d, J=8.1 Hz, 2H), 7.29-7.24 (m, 2H), 7.20 (s, 1H), 7.03 (d, J=8.7 Hz, 2H), 6.08 (s, 1H), 4.18 (d, J=13.5 Hz, 1H), 4.05 (t, J=6.6 Hz, 2H), 3.82 (s, 3H), 3.67 (d, J=12.6 Hz, 1H), 3.55 (s, 3H), 3.04 (t, J=6.6 Hz, 2H), 2.72-2.76 (m, 4H), 1.98 (s, 3H), 1.10 (t, J=5.1 Hz, 6H).

ESI-MS m/z $[C_{31}H_{36}N_4O_4+H]^+$ 529.2;

HPLC (Method D) 95.7% (AUC), $t_R$=8.50 min.

Synthesis of (R)-4-{4'-[2-(2,4-dimethyl-3-oxopiperazin-1-yl)ethoxy]-3-methoxy-[1,1'-biphenyl]-4-yl}-6-methyl-1H-pyrrolo[2,3-c]pyridin-7(6H)-one (SLU-2102)

Scheme 18

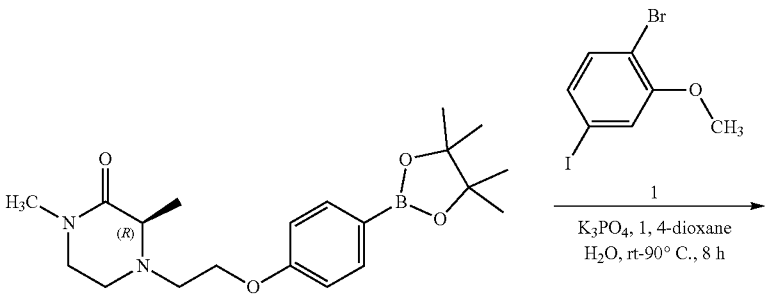

Intermediate-3

-continued

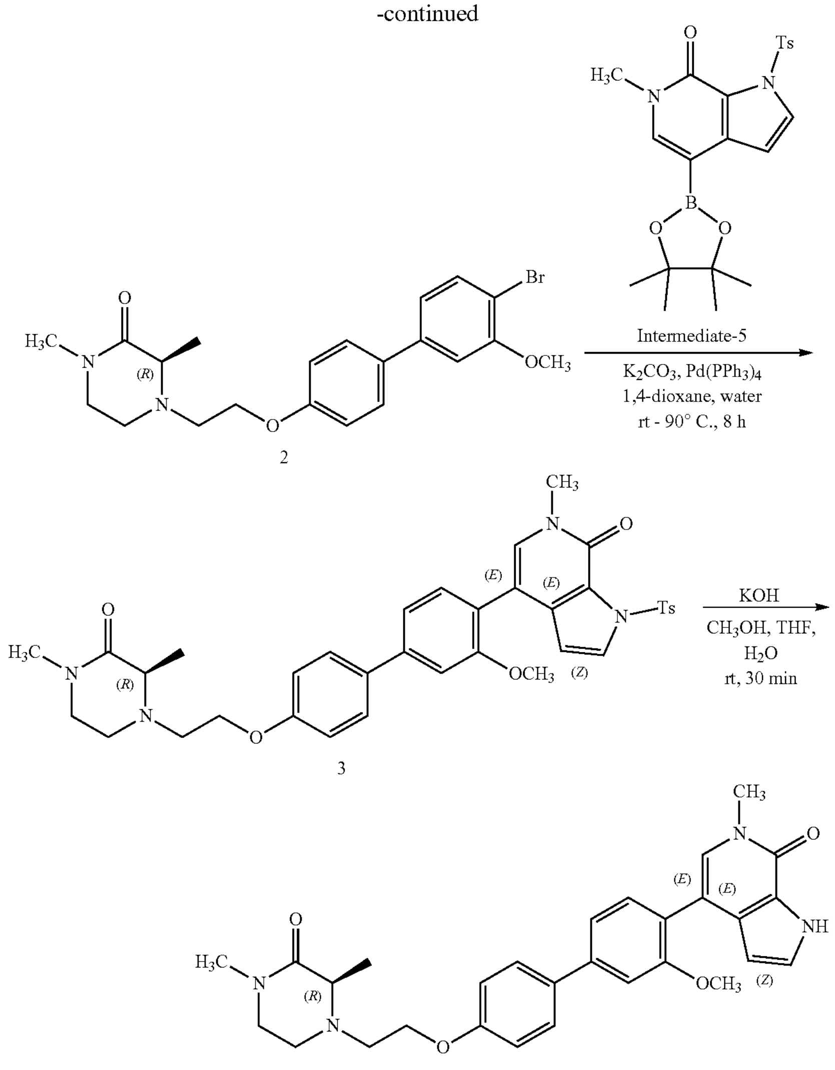

2

3

SLU-2102

(R)-4-{2-[(4'-bromo-3'-methoxy-[1,1'-biphenyl]-4-yl)oxy]ethyl}-1,3-dimethylpiperazin-2-one (2)

To a stirred mixture of Intermediate-3 (0.40 g, 1.06 mmol) and 1-bromo-4-iodo-2-methoxybenzene 1 (0.33 g, 1.06 mmol) in 4:1 mixture of dioxane, $H_2O$ (12.5 mL), $K_3PO_4$ (0.22 g, 2.13 mmol) was charged at room temperature and purged with argon for 5 min. Then, $Pd(dppf)Cl_2 \cdot CH_2Cl_2$ (0.08 g, 0.10 mmol) was added to the reaction micture at room temperature and stirred at 90° C. for 8 h. The reaction mixture was filtered through celite pad, washed with EtOAc (2×100 mL) and filtrate was concentrated under reduced pressure. The crude product was purified by combiflash chromatography ($CH_2Cl_2$:$CH_3OH$=96:4) to afford 2 (0.19 g, 42%) as an off-white solid.

ESI-MS m/z $[C_{21}H_{25}BrN_2O_3+H]^+$ 433.0.

(R)-4-{2-[(4'-bromo-3'-methoxy-[1,1'-biphenyl]-4-yl)oxy]ethyl}-1,3-dimethylpiperazin-2-one (3)

To a stirred mixture of 2 (0.19 g, 0.43 mmol) and Intermediate-5 (0.18 g, 0.43 mmol) in 4:1 mixture of dioxane, $H_2O$ (25 mL), $K_2CO_3$ (0.12 g, 0.87 mmol) was charged at room temperature and purged with argon for 5 min. $Pd(PPh_3)_4$ (0.05 g, 0.04 mmol) was added to the reaction mixture at room temperature and allowed stir at 90° C. for 8 h. The reaction mixture was filtered through celite pad, washed with EtOAc (2×100 mL). Filtrate was concentrated under reduced pressure and crude residue was purified by combiflash chromatography ($CH_2Cl_2$:$CH_3OH$=94:6) to afford (R)-4-{2-[(4'-bromo-3'-methoxy-[1,1'-biphenyl]-4-yl)oxy]ethyl}-1,3-dimethylpiperazin-2-one 3 (0.07 g, 26%) as an off-white solid.

(R)-4-{4'-[2-(2,4-dimethyl-3-oxopiperazin-1-yl)ethoxy]-3-methoxy-[1,1'-biphenyl]-4-yl}-6-methyl-1H-pyrrolo[2,3-c]pyridin-7(6H)-one (SLU-2102)

To a stirred solution 3 (0.07 g, 0.25 mmol) in 2:2:1 mixture of $CH_3OH$, THF, $H_2O$ (5 mL), KOH (0.02 g, 0.42 mmol) was charged at 0° C. and left to room temperature for 30 min. The reaction mixture was concentrated under reduced pressure and purified by reverse phase combiflash chromatography ($CH_3CN$:$H_2O$=65:35) to afford SLU-2102 (0.02 g, 40%) as an off-white solid.

$^1H$ NMR (400 MHz, DMSO-$d_6$): δ ppm 11.97 (s, 1H), 7.69 (d, J=8.8 Hz, 2H), 7.35 (d, J=8.0 Hz, 1H), 7.26-7.27 (m, 1H), 7.25 (d, J=2.8 Hz, 1H), 7.2 (s, 1H), 7.05 (d, J=8.8 Hz, 2H), 6.08 (t, J=2.4 Hz, 1H), 3.82 (s, 3H), 3.55 (s, 3H), 3.25-3.28 (m, 2H), 3.16 (q, J=6.8 Hz, 1H), 3.06-3.12 (m, 1H), 2.94-3.0 (m, 1H), 2.78-2.84 (m, 1H), 2.81 (s, 3H), 2.66-2.74 (m, 1H), 1.25 (d, J=6.8 Hz, 3H).
ESI-MS m/z $[C_{29}H_{32}N_4O_4+H]^+$ 501.2;
HPLC (Method D) 95.2% (AUC), $t_R$=6.56 min.
Synthesis of 4-{6-[4-(2-((2R,6S)-4-acetyl-2,6-dimethylpiperazin-1-yl)ethoxy)phenyl]quinolin-2-yl}-6-methyl-1H-pyrrolo[2,3-c]pyridin-7(6H)-one (SLU-2104)
Scheme 19
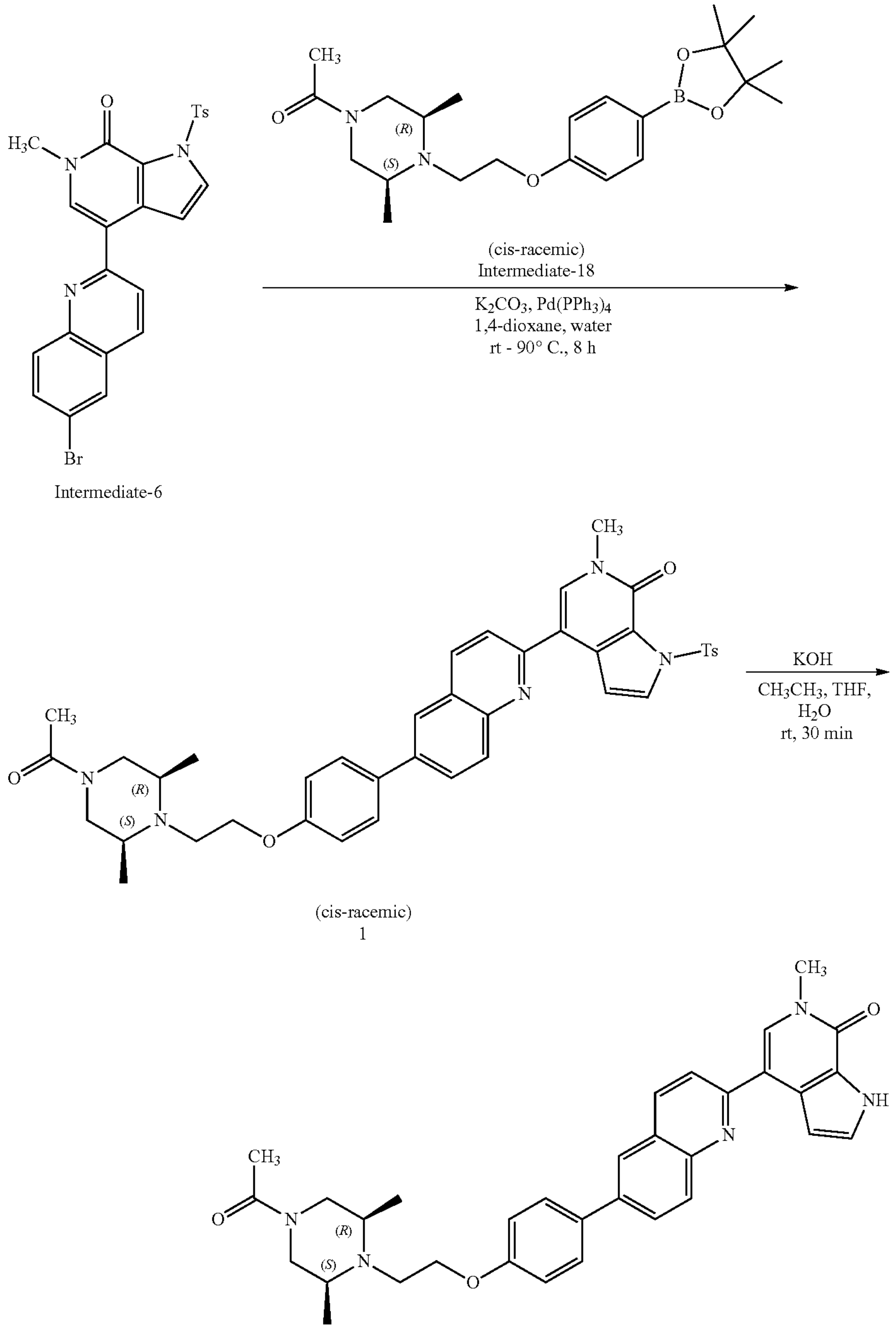
Intermediate-6
(cis-racemic)
1
(cis-racemic)
SLU-2104

4-{6-[4-(2-((2R,6S)-4-acetyl-2,6-dimethylpiperazin-1-yl)ethoxy)phenyl]quinolin-2-yl}-6-methyl-1-tosyl-1H-pyrrolo[2,3-c]pyridin-7(6H)-one (1)

To a stirred mixture of Intermediate-6 (0.20 g, 0.39 mmol) and Intermediate-18 (0.15 g, 0.39 mmol) in 4:1 mixture of dioxane, $H_2O$ (24 mL), $K_2CO_3$ (0.08 g, 0.58 mmol) was charged at room temperature and purged with argon for 5 min followed by addition of $Pd(PPh_3)_4$ (0.04 g, 0.03 mmol). Then, the reaction mixture was heated at 90° C. for 8 h. The reaction mixture was filtered through celite pad and washed with EtOAc (2×100 mL). Filtrate was concentrated under reduced pressure and crude product was purified by combiflash chromatography ($CH_2Cl_2$:$CH_3OH$=98:2) to afford 1 (0.18 g, 52%) as an off-white solid.

$^1$H NMR (300 MHz, DMSO-$d_6$): δ ppm 8.41-8.45 (m, 1H), 8.37-8.39 (m, 1H), 8.20-8.21 (m, 1H), 8.09-8.10 (m, 3H), 7.98-8.02 (m, 3H), 7.74-7.80 (m, 3H), 7.42-7.45 (m, 2H), 7.07-7.10 (m, 2H), 4.16-4.20 (m, 2H), 4.07-4.09 (m, 4H), 3.68-3.64 (m, 2H), 3.55 (s, 3H), 3.51 (br.s., 1H), 2.39 (s, 3H), 1.98 (s, 3H), 1.10-1.11 (m, 6H).

ESI-MS m/z $[C_{40}H_{41}N_5O_5S+H]^+$ 704.2.

4-{6-[4-(2-((2R,6S)-4-acetyl-2,6-dimethylpiperazin-1-yl)ethoxy)phenyl]quinolin-2-yl}-6-methyl-1H-pyrrolo[2,3-c]pyridin-7(6H)-one (SLU-2104)

To a stirred solution 1 (0.18 g, 0.25 mmol) in 2:2:1 mixture of $CH_3OH$, THF, $H_2O$ (10 mL), KOH (0.07 g, 1.27 mmol) was charged at 0° C. and allowed to room temperature for 30 min. The reaction mixture was concentrated under reduced pressure and crude product was purified by combiflash chromatography ($CH_2Cl_2$:$CH_3OH$=95:5) to afford SLU-2104 (0.06 g, 42%) as an off-white solid.

$^1$H NMR (300 MHz, DMSO-$d_6$) δ ppm 12.16 (br.s., 1H), 8.40 (d, J=8.7 Hz, 1H), 8.19 (s, 2H), 8.06 (d, J=5.1 Hz, 3H), 7.78-7.80 (m, 2H), 7.34-7.40 (m, 2H), 7.08 (d, J=6.9 Hz, 2H), 4.06-4.16 (m, 3H), 3.65-3.68 (m, 4H), 3.28 (s, 3H), 3.04 (d, J=5.1 Hz, 3H), 1.94-1.99 (m, 3H), 1.09 (d, J=3.9 Hz, 6H).

ESI-MS m/z $[C_{33}H_{35}N_5O_3+H]^+$ 550.2;

HPLC (Method D) 92.5% (AUC), $t_R$=6.33 min.

Synthesis of (R)-4-{6-[4-(2-(2,4-dimethyl-3-oxopiperazin-1-yl)ethoxy)phenyl]quinolin-2-yl}-6-methyl-1H-pyrrolo[2,3-c]pyridin-7(6H)-one (SLU-2112)

Scheme 20

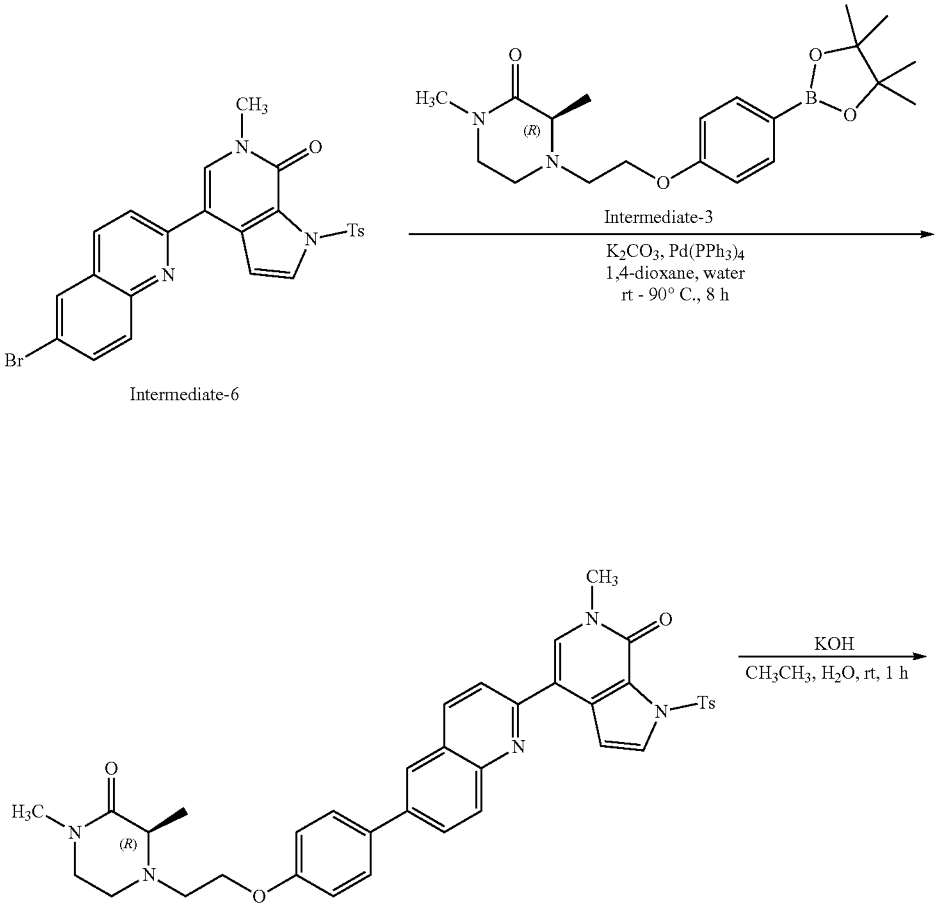

Intermediate-6

Intermediate-3

1

-continued

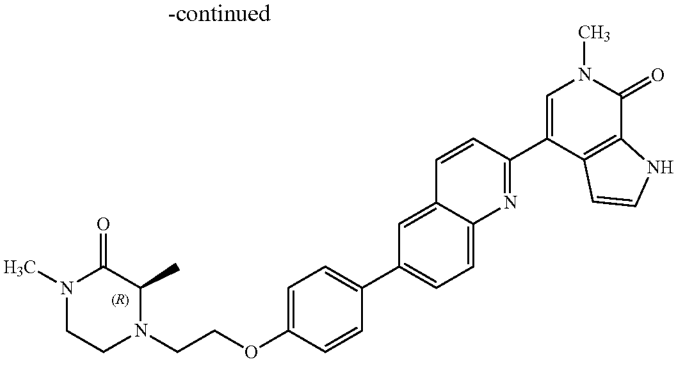

SLU-2112

(R)-4-{6-[4-(2-(2,4-dimethyl-3-oxopiperazin-1-yl)ethoxy)phenyl]quinolin-2-yl}-6-methyl-1-tosyl-1H-pyrrolo[2,3-c]pyridin-7(6H)-one (1)

To a stirred mixture of Intermediate-6 (0.24 g, 4.72 mmol) and Intermediate-3 (0.17 g, 4.72 mmol) in 4:1 mixture of 1,4-dioxane, $H_2O$ (25 mL), $K_2CO_3$ (0.13 g, 0.944 mmol) was charged at room temperature and purged with argon for 5 min. $Pd(PPh_3)_4$ (0.05 g, 0.47 mmol) was added to the reaction micture at room temperature and allowed to stir at 90° C. for 8 h. The reaction mixture was filtered through celite pad and the celite pad was washed with EtOAc (2×100 mL). Filtrate was concentrated under reduced pressure and crude residue was purified by combiflash chromatography ($CH_2Cl_2$:$CH_3OH$=95:5) to afford 1 (0.08 g, 23%) as an off-white solid.

ESI-MS m/z $[C_{38}H_{37}N_5O_5S+H]^+$ 676.1.

(R)-4-{6-[4-(2-(2,4-dimethyl-3-oxopiperazin-1-yl)ethoxy)phenyl]quinolin-2-yl}-6-methyl-1H-pyrrolo[2,3-c]pyridin-7(6H)-one (SLU-2112)

To a stirred solution 1 (0.08 g, 0.11 mmol) in 2:2:1 mixture of $CH_3OH$, THF, $H_2O$ (12 mL), KOH (0.017 g, 0.35 mmol) was charged at 0° C. and left to room temperature for 1 h. The reaction mixture was concentrated under reduced pressure and crude product was purified by combiflash chromatography ($CH_2Cl_2$:$CH_3OH$=94:6). Further it was purified by mass triggered preparative HPLC to afford SLU-2112 (0.017 g, 14%) as an off-white solid.

$^1H$ NMR (300 MHz, DMSO-$d_6$) δ ppm 12.15 (s, 1H), 8.40 (d, J=11.7 Hz, 1H), 8.19 (s, 2H), 8.08 (t, J=9.6 Hz, 3H), 7.79 (d, J=8.7 Hz, 2H), 7.41 (s, 1H), 7.34 (s, 1H), 7.60 (d, J=8.7 Hz, 2H), 4.16 (t, J=5.7 Hz, 2H), 3.68 (s, 3H), 3.25-3.27 (m, 2H), 3.07-3.19 (m, 1H), 3.01-3.02 (m, 1H), 2.96-2.98 (m, 2H), 2.84-2.85 (m, 1H), 2.82 (s, 3H), 1.25 (t, J=6.0 Hz, 3H).

ESI-MS m/z $[C_{31}H_{31}N_5O_3+H]^+$ 522.1;

HPLC (Method D) 98.4% (AUC), $t_R$=6.27 min.

Synthesis of 6-methyl-4-{6-[4-(4-(2-(4-methylpiperazin-1-yl)ethoxy)phenyl)piperidin-1-yl]pyridin-3-yl}-1H-pyrrolo[2,3-c]pyridin-7(6H)-one (SLU-2114)

Scheme 21

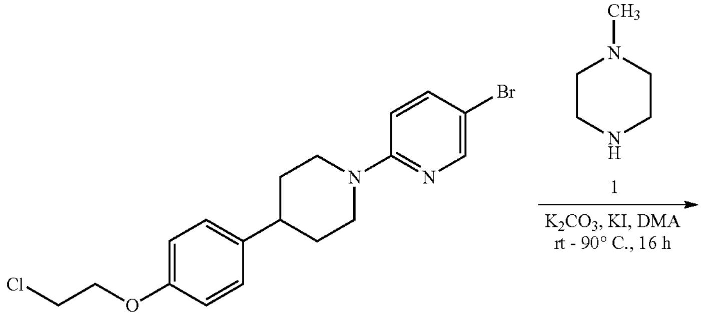

Intermediate-15

-continued

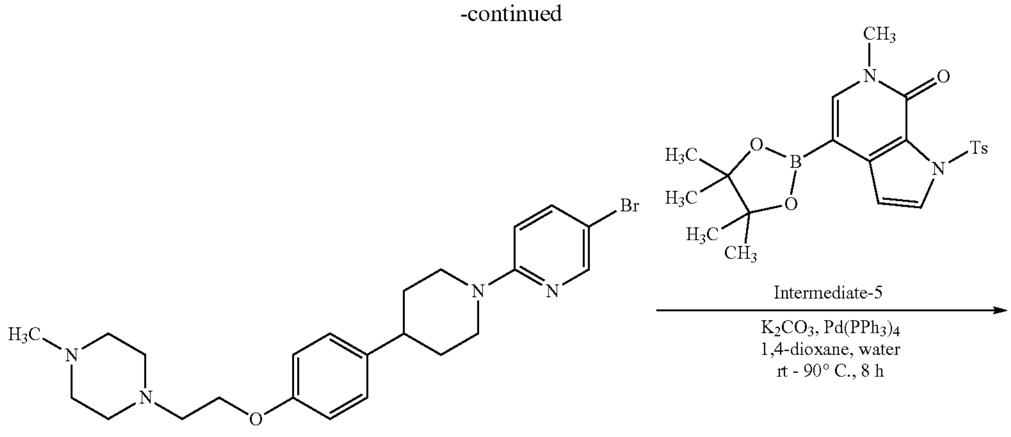

2

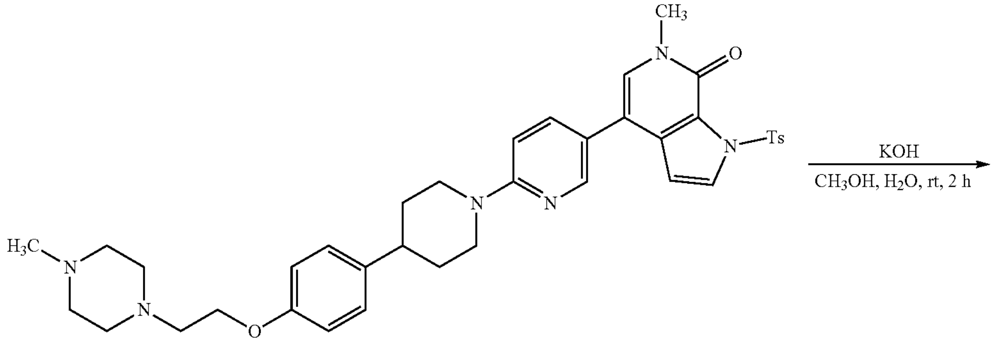

3

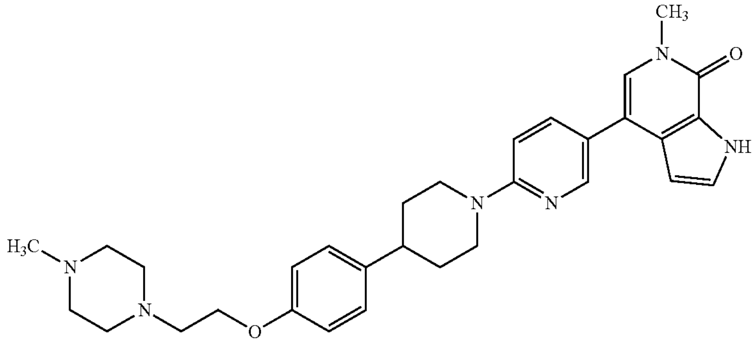

SLU-2114

4-{2-[4-(1-(5-bromopyridin-2-yl)piperidin-4-yl)phenoxy]ethyl}-1-methylpiperazin-2-one (2)

A solution of Intermediate-15 (0.25 g, 0.63 mmol) and 1-methylpiperazine 1 (0.07 g, 0.79 mmol) in N,N-dimethylacetamide (10 mL) was charged with $K_2CO_3$ (0.17 g, 1.26 mmol) and KI (0.05 g, 0.31 mmol) at room temperature. The reaction mixture was heated at 90° C. for 16 h. The reaction mixture was cooled to room temperature, poured into water (50 mL) and organic compound was extracted into EtOAc (3×100 mL). Combined organic layers were washed with ice-cold water (3×10 mL), brine (1×10 mL), dried over anhydrous $Na_2SO_4$, concentrated under reduced pressure and crude residue was purified by combiflash chromatography ($CH_2Cl_2$:$CH_3OH$=97:3) to afford 2 (0.16 g, 56%) as an off-white solid.

ESI-MS m/z $[C_{23}H_{31}BrN_4O+H]^+$ 459.1.

6-methyl-4-{6-[4-(4-(2-(4-methylpiperazin-1-yl)ethoxy)phenyl)piperidin-1-yl]pyridin-3-yl}-1-tosyl-1H-pyrrolo[2,3-c]pyridin-7(6H)-one (3)

To a solution of 2 (0.16 g, 0.35 mmol) in 4:1 mixture of dioxane, $H_2O$ (12.5 mL), Intermediate-5 (0.17 g, 0.39 mmol) and $K_2CO_3$ (0.10 g, 0.71 mmol) were charged at room temperature and purged with argon for 5 min followed by addition of $Pd(PPh_3)_4$ (0.04 g, 0.07 mmol). The reaction mixture was allowed stir at 90° C. for 8 h. The reaction mixture was filtered through celite pad, washed with EtOAc (2×50 mL) and filtrate was concentrated under reduced pressure. The crude product was purified by combiflash chromatography ($CH_2Cl_2$:$CH_3OH$=95:5) to afford 3 (0.09 g, 36%).

ESI-MS m/z $[C_{38}H_{44}N_6O_4S+H]^+$ 681.3.

6-methyl-4-{6-[4-(4-(2-(4-methylpiperazin-1-yl)ethoxy)phenyl)piperidin-1-yl]pyridin-3-yl}-1H-pyrrolo[2,3-c]pyridin-7(6H)-one (SLU-2114)

To a stirred solution 3 (0.09 g, 0.014 mmol) in 2:2:1 mixture of $CH_3OH$, THF, $H_2O$ (5 mL), KOH (0.02 g, 0029 mmol) was charged at 0° C. and left to room temperature for 2 h. The reaction mixture was concentrated under reduced pressure and crude product was purified by reverse phase combiflash chromatography ($CH_3CN$:$H_2O$=65:35) to afford SLU-2114 (0.06 g, 6%) as an off-white solid.

$^1H$ NMR (400 MHz, MeOD) δ ppm 8.19 (d, J=2.0 Hz, 1H), 7.75 (d, J=9.5 Hz, 1H), 7.30 (d, J=3.5 Hz, 1H), 7.15 (s, 1H), 7.09 (d, J=8.4 Hz, 2H), 6.95 (d, J=9.2 Hz, 1H), 6.78 (d, J=8.8 Hz, 2H), 6.40 (d, J=2.8 Hz, 1H), 4.34 (d, J=13.2 Hz, 2H), 4.05 (d, J=4.4 Hz, 2H), 3.60 (s, 3H), 3.24 (s, 3H), 2.85-2.98 (m, 8H), 2.73-2.67 (m, 5H), 1.82 (d, J=12.8 Hz, 2H), 1.61-1.70 (m, 2H).

ESI-MS m/z $[C_{31}H_{38}N_6O_2+H]^+$ 527.3;

HPLC (Method D) 98.2% (AUC), $t_R$=6.12 min.

Synthesis of 4-{6-[9-(2-hydroxyacetyl)-3,9-diazaspiro[5.5]undecan-3-yl]pyridin-3-yl}-6-methyl-1H-pyrrolo[2,3-c]pyridin-7(6H)-one (SLU-2115)

Scheme 22

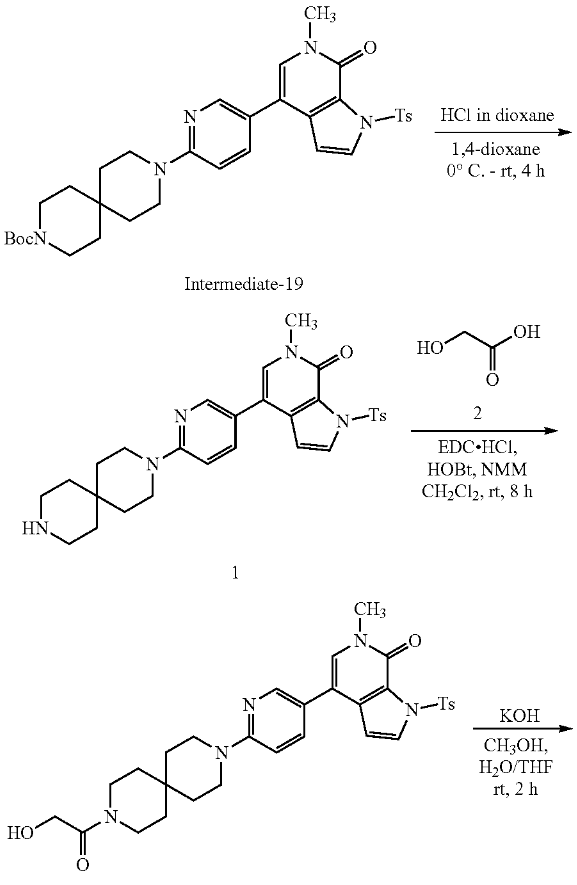

Intermediate-19

1

3

-continued

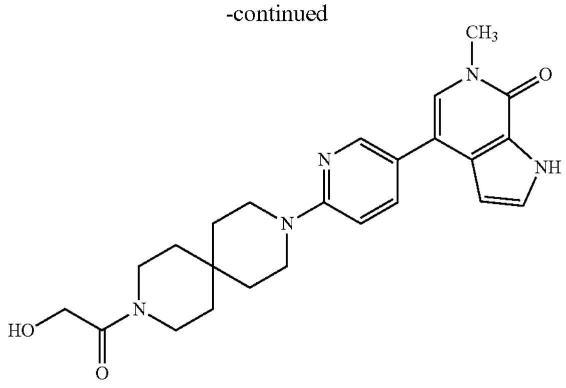

SLU-2115

4-[6-(3,9-diazaspiro[5.5]undecan-3-yl)pyridin-3-yl]-6-methyl-1-tosyl-1H-pyrrolo[2,3-c]pyridin-7(6H)-one (1)

To a stirred solution of Intermediate-19 (0.35 g, 0.55 mmol) in 1,4-dioxane (10.0 mL), a solution of HCl in 1,4-dioxane (5.0 mL, 4 M solution) was charged at 0° C. and stirred at room temperature for 4 h. The reaction mixture was poured into $H_2O$ (15 mL) and EtOAc (100 mL). Basified with $NaHCO_3$, organic layer was separated out, dried over anhydrous $Na_2SO_4$ and concentrated under reduced pressure. Crude product was purified by combiflash chromatography ($CH_2Cl_2$:$CH_3OH$=97:3) to afford 1 (0.20 g, 71%) as an off-white solid.

ESI-MS m/z $[C_{29}H_{33}N_5O_3+H]^+$ 532.1.

4-{6-[9-(2-hydroxyacetyl)-3,9-diazaspiro[5.5]undecan-3-yl]pyridin-3-yl}-6-methyl-1-tosyl-1H-pyrrolo[2,3-c]pyridin-7(6H)-one (3)

To a stirred solution of 1 (0.30 g, 0.56 mmol) in $CH_2Cl_2$ (12 mL), glycolic acid 2 (0.05 g, 0.67 mmol), NMM (0.18 mL, 1.12 mmol) and EDC·HCl (0.16 g, 0.84 mmol) were added at room temperature followed by addition of HoBt (0.11 g, 0.84 mmol). The reaction mixture was stirred at ambient temperatures for 8 h. The reaction mixture was poured into $H_2O$ (50 mL) and extracted into $CH_2Cl_2$ (3×100 mL). Combined organic layers were washed with brine (1×30 mL), dried over anhydrous $Na_2SO_4$, concentrated under reduced pressure and crude product was purified by combiflash chromatography ($CH_2Cl_2$:$CH_3OH$=95:5) to afford 3 (0.16 g, 43%) as an off-white solid.

$^1H$ NMR (400 MHz, DMSO-$d_6$): δ ppm 8.21 (d, J=1.6 Hz, 1H), 8.01 (d, J=4.0 Hz, 1H), 7.96 (d, J=8.4 Hz, 2H), 7.631 (d, J=9.2 Hz, 1H), 7.51 (s, 1H), 7.42 (d, J=8.0 Hz, 2H), 6.91 (d, J=8.8 Hz, 1H), 6.65 (d, J=3.6 Hz, 1H), 4.44 (t, J=4.8 Hz, 1H), 4.07 (d, J=4.8 Hz, 2H), 3.49-3.55(m, 8H), 3.44 (s, 3H), 2.38 (s, 3H), 1.44-1.52 (m, 8H).

4-{6-[9-(2-hydroxyacetyl)-3,9-diazaspiro[5.5]undecan-3-yl]pyridin-3-yl}-6-methyl-1H-pyrrolo[2,3-c]pyridin-7(6H)-one (SLU-2115)

To a stirred solution 3 (0.09 g, 0.15 mmol) in 2:2:1 mixture of $CH_3OH$, THF, $H_2O$ (8 mL), KOH (0.01 g, 0.30 mmol) was charged at 0° C. and left to room temperature for 2 h. The reaction mixture was concentrated under reduced pressure and crude product was purified by reverse phase combiflash chromatography (ACN:$H_2O$=65:35) to afford SLU-2115 (0.04 g, 62%) as an off-white solid.

1H NMR (300 MHz, DMSO-$d_6$) δ ppm 12.11 (s, 1H), 8.31 (d, J=2.1 Hz, 1H), 7.72 (dd, J=2.4, 9.0 Hz, 1H), 7.32 (d, J=2.7 Hz, 1H), 7.29 (s, 1H), 6.92 (d, J=8.7 Hz, 1H), 6.38 (s, 1H), 4.45 (s, 1H), 4.07 (d, J=2.4 Hz, 2H), 3.49-3.56 (m, 11H), 1.46-1.53 (m, 8H).

ESI-MS m/z $[C_{24}H_{29}N_3O+H]^+$ 436.2;

HPLC (Method D) 95.7% (AUC), $t_R$=6.17 min.

Synthesis of 4-[6-(3,9-diazaspiro[5.5]undecan-3-yl)pyridin-3-yl]-6-methyl-1H-pyrrolo[2,3-c]pyridin-7(6H)-one (SLU-2130)

Scheme 23

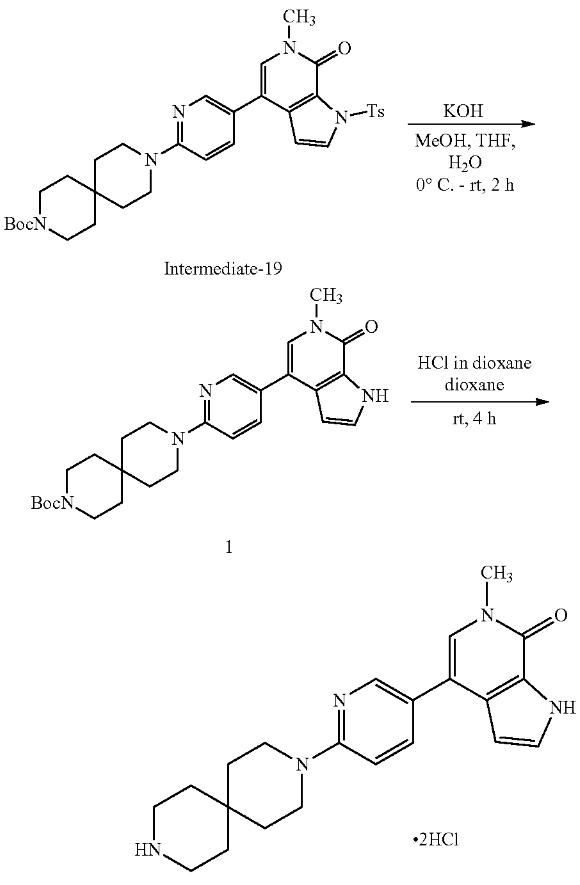

Intermediate-19

1

SLU-2130 tert-butyl 9-[5-(6-methyl-7-oxo-6,7-dihydro-1H-pyrrolo[2,3-c]pyridin-4-yl)pyridin-2-yl]-3,9-diazaspiro[5.5]undecane-3-carboxylate (1)

To a stirred solution Intermediate-19 (0.15 g, 0.23 mmol) in 2:2:1 mixture of $CH_3OH$, THF, $H_2O$ (10 mL), KOH (0.026 g, 0.47 mmol) was charged at 0° C. and left to room temperature for 2 h. The reaction mixture was concentrated under reduced pressure and crude product was purified by combiflash chromatography ($CH_2Cl_2$:$CH_3OH$=98:2) to afford 1 (0.08 g, 70%) as a white solid.

$^1H$ NMR (300 MHz, DMSO-$d_6$): δ ppm 12.11 (s, 1H), 8.31 (d, J=1.8 Hz, 1H), 7.71 (dd, J=2.1, 8.7 Hz, 1H), 7.33 (t, J=2.4 Hz, 1H), 7.29 (s, 1H), 6.91 (d, J=8.7 Hz, 1H), 6.38 (s, 1H), 3.55-3.57 (m, 8H), 3.55 (s, 3H), 1.41-1.54 (m, 8H), 1.39 (s, 9H).

ESI-MS m/z $[C_{27}H_{35}N_5O_3+H]^+$ 378.0.

4-[6-(3,9-diazaspiro[5.5]undecan-3-yl)pyridin-3-yl]-6-methyl-1H-pyrrolo[2,3-c]pyridin-7(6H)-one·hydrochloride (SLU-2130)

To a stirred solution of 1 (0.08 g, 0.16 mmol) in dioxane (5.0 mL), a solution of HCl in dioxane (2.0 mL, 4 M solution) was charged at 0° C. and stirred at room temperature for 4 h. The reaction mixture was concentrated under reduced pressure and washed with MTBE (2×10 mL) to afford SLU-2130 (0.020 g, 69%) as an off-white solid.

$^1H$ NMR (300 MHz, DMSO-$d_6$): δ ppm 12.29 (br.s., 1H), 8.89 (br.s., 2H), 8.08-8.19 (m, 2H), 7.52 (d, J=12.0 Hz, 2H), 7.39 (d, J=9.0 Hz, 1H), 6.35 (d, J=10.2 Hz, 1H), 3.74-3.75 (m, 5H), 3.52-3.58 (m, 3H), 3.06 (br.s., 4H), 1.66 (br.s., 8H).

ESI-MS m/z $[C_{22}H_{27}N_5O+H]^+$ 378.1;

HPLC (Method D) 95.0% (AUC), $t_R$=5.67 min.

Synthesis of 6-methyl-4-{6-[4-(4-(2-(4-methyl-3-oxopiperazin-1-yl)ethoxy)phenyl)piperidin-1-yl]pyridin-3-yl}-1H-pyrrolo[2,3-c]pyridin-7(6H)-one (SLU-2131)

Scheme 24

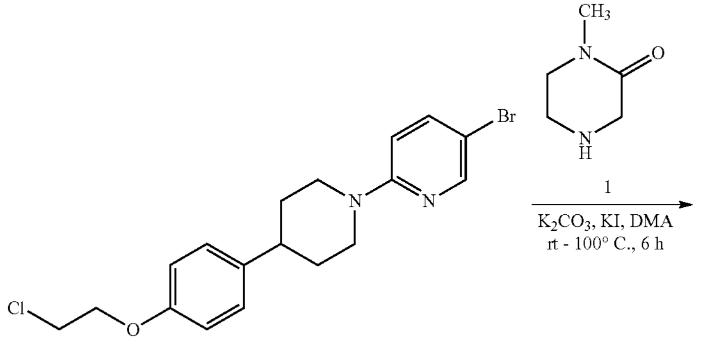

Intermediate-15

-continued

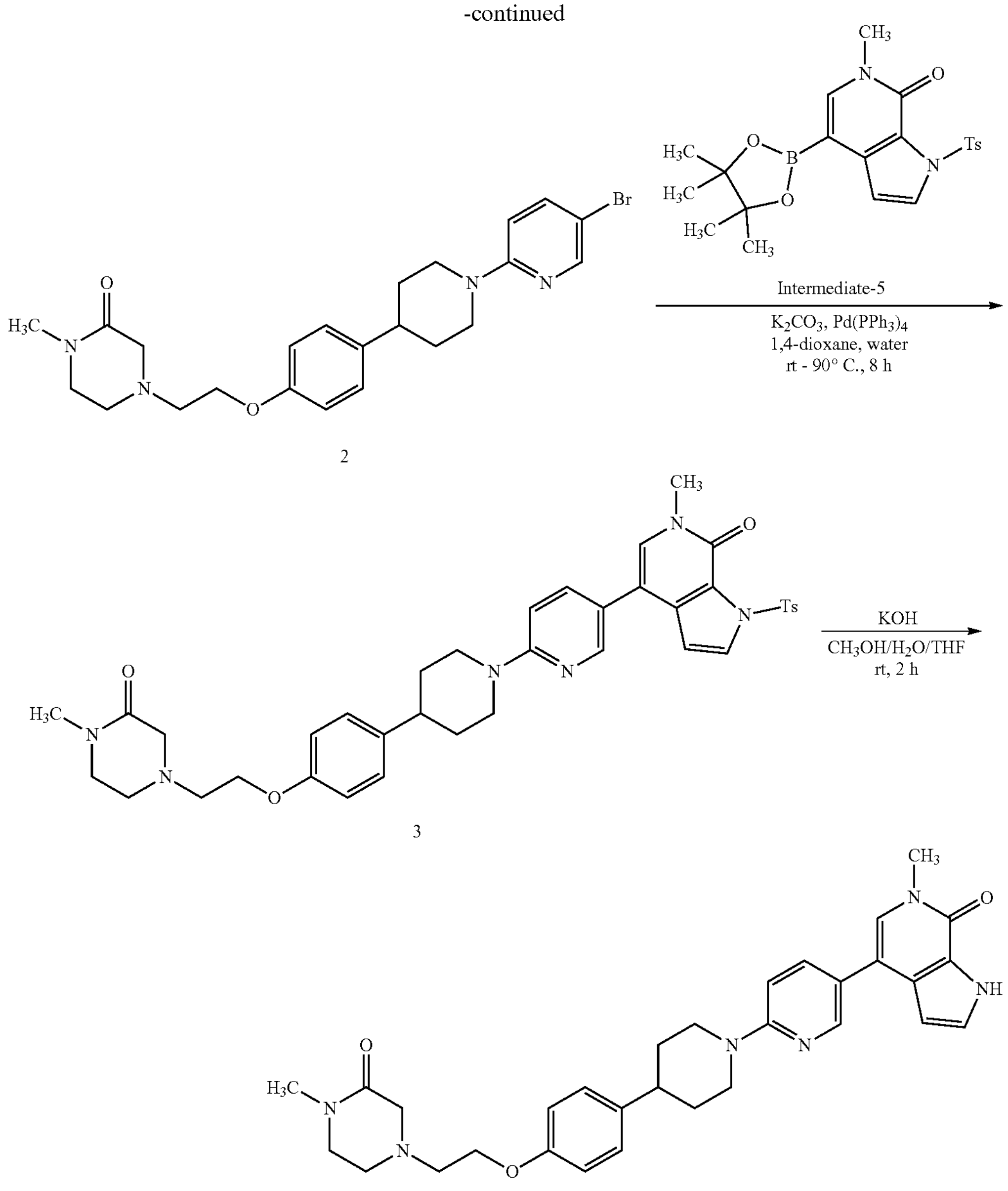

SLU-2131

4-{2-[4-(1-(5-bromopyridin-2-yl)piperidin-4-yl)phenoxy]ethyl}-1-methylpiperazin-2-one (2)

A solution of Intermediate-15 (0.05 g, 0.12 mmol) and 1-methylpiperazin-2-one 1 (0.01 g, 0.13 mmol) in N,N-dimethylacetamide (10 mL) was charged with $K_2CO_3$ (0.03 g, 0.25 mmol) and KI (0.01 g, 0.069 mmol) at room temperature. The reaction mixture was heated at 100° C. for 6 h. The reaction mixture was cooled to room temperature, poured into water (50 mL) and organic compound was extracted into EtOAc (3×100 mL). Combined organic layers were washed with ice-cold water (3×10 mL) followed by brine (1×10 mL). Combined organic layers were dried over anhydrous $Na_2SO_4$, concentrated under reduced pressure and crude residue was purified by combiflash chromatography ($CH_2Cl_2$:$CH_3OH$=97:3) to afford 2 (0.03 g, 58%) as off-white solid.

$^1$H NMR (400 MHz, DMSO-$d_6$): δ ppm 8.15 (d, J=2.4 Hz, 1H), 7.65 (dd, J=2.8, 9.2 Hz, 1H), 7.14 (d, J=8.4 Hz, 2H), 6.86 (dd, J=3.2, 9.6 Hz, 3H), 4.38 (t, J=13.2 Hz, 2H), 4.05 (t, J=5.2 Hz, 2H), 3.25 (t, J=5.2 Hz, 2H), 3.07 (s, 2H), 2.87 (t, J=12.4 Hz, 2H), 2.80 (s, 3H), 2.72-2.75 (m, 5H), 1.79 (d, J=8.8 Hz, 2H), 1.49-1.59 (m, 2H).

ESI-MS m/z $[C_{23}H_{29}BrN_4O_2+H]^+$ 475.1.

6-methyl-4-{6-[4-(4-(2-(4-methyl-3-oxopiperazin-1-yl)ethoxy)phenyl)piperidin-1-yl]pyridin-3-yl}-1-tosyl-1H-pyrrolo[2,3-c]pyridin-7(6H)-one (3)

To a solution of 2 (0.35 g, 0.73 mmol) in 4:1 mixture of dioxane, $H_2O$ (12.5 mL), Intermediate-5 (0.33 g, 0.73 mmol) and $K_2CO_3$ (0.20 g, 1.47 mmol) were charged at room temperature and purged with argon for 5 min followed by addition of $Pd(PPh_3)_4$ (0.08 g, 0.07 mmol). Then, the reaction mixture was allowed to stir at 90° C. for 8 h. The reaction mixture was filtered through celite pad, washed with EtOAc (2×50 mL) and filtrate was concentrated under reduced pressure. The crude product was purified by combiflash chromatography ($CH_2Cl_2$:$CH_3OH$=95:5) to afford title compound 3 (0.20 g, 39%) as an off-white solid.

ESI-MS m/z $[C_{38}H_{42}N_6O_5S+H]^+$ 695.2.

6-methyl-4-{6-[4-(4-(2-(4-methyl-3-oxopiperazin-1-yl)ethoxy)phenyl)piperidin-1-yl]pyridin-3-yl}-1H-pyrrolo[2,3-c]pyridin-7(6H)-one (SLU-2131)

To a stirred solution 3 (0.20 g, 0.28 mmol) in 2:2:1 mixture of $CH_3OH$, THF, $H_2O$ (12 mL) KOH (0.03 g, 0.57 mmol) was added at 0° C. and left to room temperature for 2 h. The reaction mixture was concentrated under reduced pressure and crude product was purified by reverse phase combiflash chromatography ($CH_3CN$:$H_2O$=65:35) to afford SLU-2131 (0.06 g, 6%) as an off-white solid.

$^1H$ NMR (300 MHz, DMSO-$d_6$) δ ppm 12.13 (s, 1H), 8.32 (s, 1H), 7.72 (dd, J=7.2, 10.8 Hz, 1H), 7.33 (s, 1H), 7.31 (s, 1H), 7.17 (d, J=8.4 Hz, 2H), 6.97 (d, J=8.7 Hz, 1H), 6.87 (d, J=8.4 Hz, 2H), 6.40 (s, 1H), 4.48 (d, J=12.6 Hz, 2H), 4.04 (t, J=5.1 Hz, 2H), 3.56 (s, 3H), 3.24 (d, J=6.0 Hz, 2H), 3.08 (s, 2H), 2.89 (t, J=13.8 Hz, 2H), 2.80 (s, 3H), 2.72 (br.s., 5H), 1.81-1.85 (m, 2H), 1.58-1.65 (m, 2H).

ESI-MS m/z $[C_{31}H_{36}N_6O_3+H]^+$ 541.2.

HPLC (Method D) 97.3% (AUC), $t_R$=6.16 min.

Synthesis of (R)-4-{4-[6-(2-(2,4-dimethyl-3-oxopiperazin-1-yl)ethoxy)quinolin-2-yl]phenyl}-6-methyl-1H-pyrrolo[2,3-c]pyridin-7(6H)-one (SLU-2211)

Scheme 25

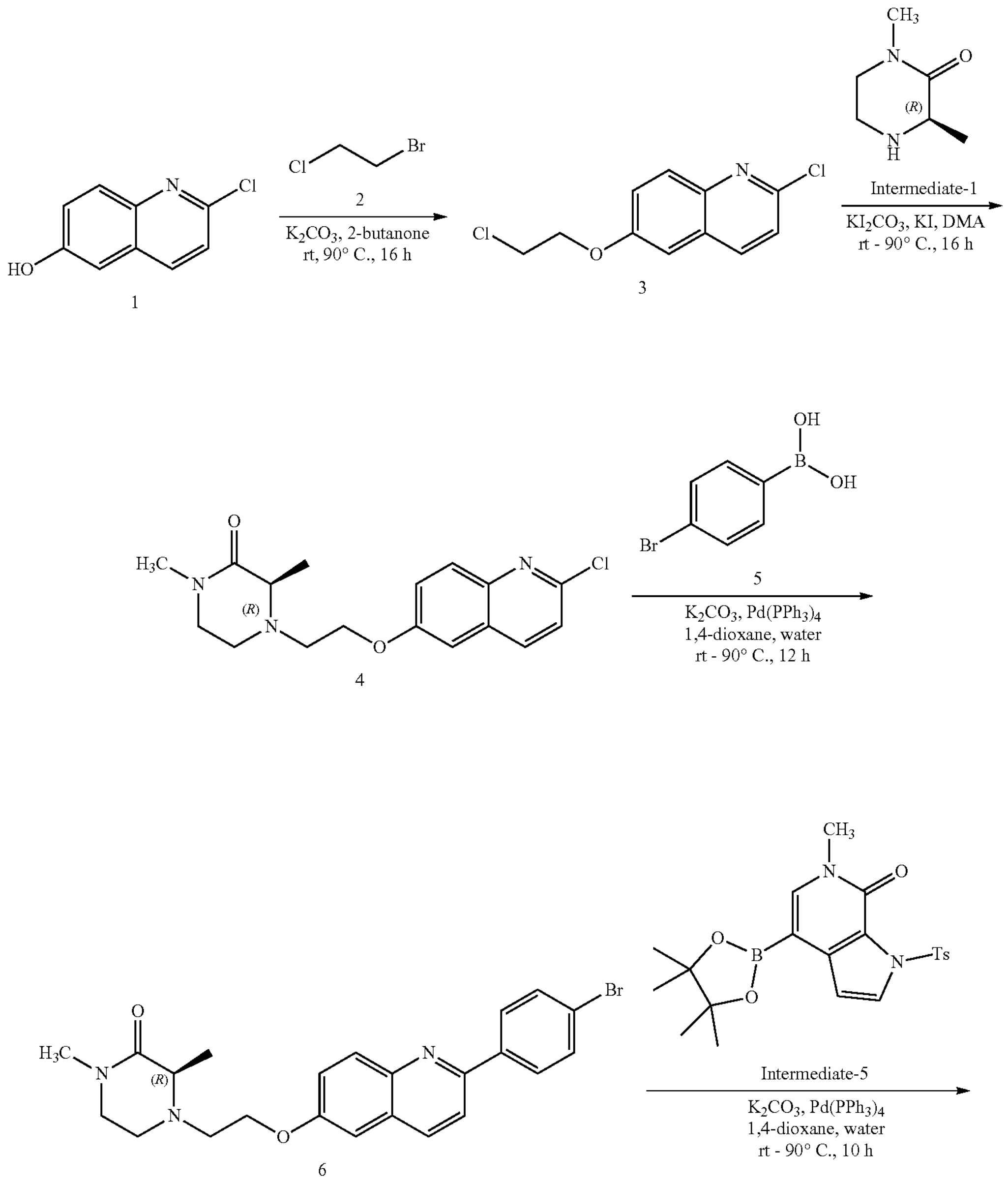

-continued

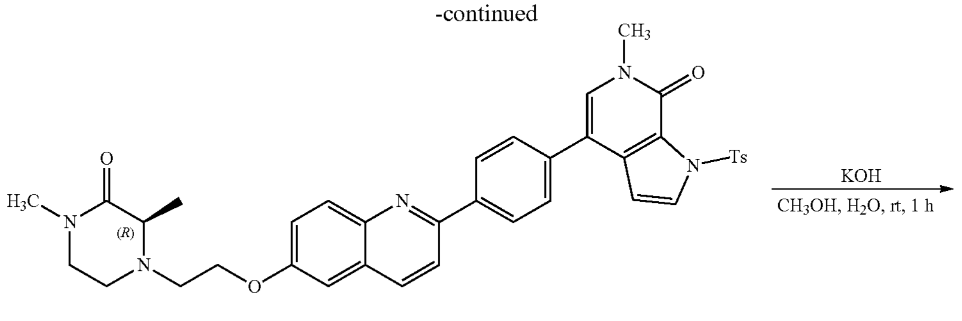

7

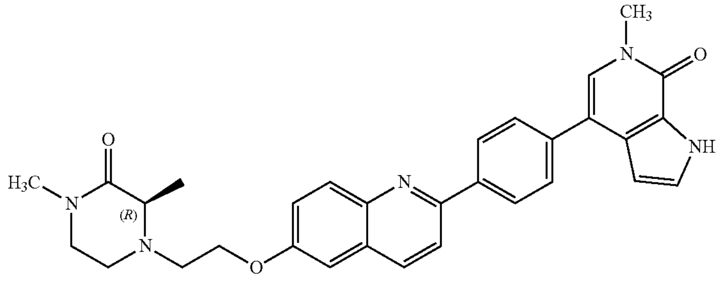

SLU- 2211

2-chloro-6-(2-chloroethoxy)quinolone (3)

To a stirred solution of 1 (0.50 g, 2.79 mmol) in 2-butanone (20 mL), $K_2CO_3$ (0.55 g, 5.58 mmol) was charged followed by the addition of 1-bromo-2-chloroethane 2 (1.19 g, 8.37 mmol) at room temperature and the reaction mixture was allowed to stir at 90° C. for 16 h. The reaction mixture was cooled to room temperature, diluted with EtOAc (100 mL). Organic layer was washed with water (3×50 mL), brine (1×50 mL), dried over anhydrous $Na_2SO_4$ and concentrated under reduced pressure to afford 3 (0.59 g, crude) as an off-white solid.

$^1$H NMR (400 MHz, $CDCl_3$): δ ppm 7.99 (d, J=8.4 Hz, 1H), 7.94 (d, J=9.2 Hz, 1H), 7.42 (dd, J=2.0, 9.2 Hz, 1H), 7.35 (d, J=8.4 Hz, 1H), 7.90 (d, J=2.0 Hz, 1H), 4.35 (t, J=5.6 Hz, 2H), 3.89 (t, J=6.0 Hz, 2H).

ESI-MS m/z $[C_{11}H_9Cl_2NO+H]^+$ 242.1.

(R)-4-{2-[(2-chloroquinolin-6-yl)oxy]ethyl}-1,3-dimethylpiperazin-2-one (4)

To a stirred solution of 3 (0.59 g, 2.44 mmol) and Intermediate-1 (0.31 g, 2.44 mmol) in N,N-dimethylacetamide (20 mL), $K_2CO_3$ (0.55 g, 4.48 mmol) was added at room temperature and heated at 90° C. for 16 h. The reaction mixture was cooled to room temperature poured into water (100 mL) and organic compound was extracted into EtOAc (3×200 mL). Combined organic layers were washed with ice-cold water (3×50 mL), brine (1×50 mL), dried over anhydrous $Na_2SO_4$ and concentrated under reduced pressure. The crude product was purified by combiflash chromatography ($CH_2Cl_2$:$CH_3OH$=95:5) to afford 4 (0.23 g, 29%) as light brown solid.

$^1$H NMR (400 MHz, $CDCl_3$): δ ppm 7.98 (d, J=8.4 Hz, 1H), 7.91 (d, J=9.2 Hz, 1H), 7.33-7.42 (m, 2H), 7.07-7.09 (m, 1H), 4.20 (t, J=4.4 Hz, 2H), 4.05-4.18 (m, 1H), 3.27-3.39 (m, 3H), 3.08-3.21 (m, 2H), 2.94 (s, 3H), 2.79-2.85 (m, 1H), 1.43 (d, J=6.8 Hz, 3H).

ESI-MS m/z $[C_{17}H_{20}ClN_3O_2+H]^+$ 334.1.

(R)-4-{2-[(2-(4-bromophenyl)quinolin-6-yl)oxy]ethyl}-1,3-dimethylpiperazin-2-one (6)

To a stirred solution of 4 (0.23 g, 0.69 mmol) in 4:1 of dioxane, $H_2O$ (12 mL), 4-Bromophenylboronic acid 5 (0.13 g, 0.69 mmol) and $K_2CO_3$ (0.14 g, 1.03 mmol) were charged at room temperature and purged with argon for 5 min. $Pd(PPh_3)_4$ (0.079 g, 1.0 mmol) was added at room temperature and purged with argon for 5 min. The reaction mixture was heated at 90° C. for 12 h. The reaction mixture was filtered through celite pad, washed with EtOAc (2×100 mL) and filtrate was concentrated under reduced pressure. The crude product was purified by combiflash chromatography ($CH_2Cl_2$:$CH_3OH$=95:5) to afford 6 (0.17 g, 56%) as an off-white solid.

$^1$H NMR (300 MHz, DMSO-$d_6$): δ ppm 8.34 (d, J=8.7 Hz, 1H), 8.20 (d, J=8.4 Hz, 1H), 8.11 (d, J=8.4 Hz, 1H), 7.97 (d, J=8.7 Hz, 1H), 7.85 (d, J=8.4 Hz, 1H), 7.73 (d, J=8.7 Hz, 2H), 7.41-7.44 (m, 2H), 4.24 (t, J=5.1 Hz, 2H), 3.23-3.27 (m, 2H), 3.19 (d, J=6.6 Hz, 1H), 3.09-3.16 (m, 1H), 3.01-3.07 (m, 1H), 2.87-2.89 (m, 1H), 2.81 (s, 3H), 2.72-2.78 (m, 1H), 1.27 (d, J=6.9 Hz, 3H).

ESI-MS m/z $[C_{23}H_{24}BN_3O_2+H]^+$ 456.0.

(R)-4-{4-[6-(2-(2,4-dimethyl-3-oxopiperazin-1-yl)ethoxy)quinolin-2-yl]phenyl}-6-methyl-1-tosyl-1H-pyrrolo[2,3-c]pyridin-7(6H)-one (7)

To a solution of 6 (0.2 g, 0.44 mmol) in 4:1 mixture of dioxane, $H_2O$ (12 mL), Intermediate-5 (0.20 g, 0.44 mmol) and $K_2CO_3$ (0.12 g, 0.88 mmol) were charged and purged with argon for 5 min followed by addition of $Pd(PPh_3)_4$ (0.16 g, 0.04 mmol). The reaction mixture was heated at 90° C. for 10 h. The reaction mixture was filtered through celite pad, washed with EtOAc (2×250 mL) and filtrate was concentrated under reduced pressure. The crude product was purified by combiflash chromatography ($CH_2Cl_2$:$CH_3OH$=95:5) to afford 7 (0.10 g, 34%).

ESI-MS m/z $[C_{38}H_{37}N_5O_5S+H]^+$ 676.2;

(R)-4-{4-[6-(2-(2,4-dimethyl-3-oxopiperazin-1-yl)ethoxy)quinolin-2-yl]phenyl}-6-methyl-1H-pyrrolo[2,3-c]pyridin-7(6H)-one (SLU-2211)

To a stirred solution 7 (0.10 g, 0.15 mmol) in 2:2:1 mixture of $CH_3OH$, THF, $H_2O$ (15 mL, KOH (0.017 g, 0.30 mmol) was charged at 0° C. and left to room temperature for 1 h. The reaction mixture was concentrated under reduced pressure crude residue was purified by combiflash chromatography ($CH_2Cl_2$:$CH_3OH$=94:6). The obtained solid was re-purified by mass triggered preparative-HPLC to afford SLU-2211 (0.012 g, 15%) as an off-white solid.

$^1H$ NMR (400 MHz, DMSO-$d_6$): δ ppm 12.20 (s, 1H), 8.34 (d, J=8.4 Hz, 3H), 8.16 (d, J=8.4 Hz, 1H), 7.99 (d, J=9.2 Hz, 1H, H), 7.77 (d, J=8.4 Hz, 2H), 7.52 (s, 1H), 7.38-7.44 (m, 3H), 6.54 (s, 1H), 4.25 (t, J=5.6 Hz, 2H), 3.62 (s, 3H), 3.27 (t, J=4.0 Hz, 2H), 3.20 (q, J=6.4, 13.2 Hz, 1H), 3.09-3.15 (m, 1H), 3.01-3.07 (m, 1H), 2.85-2.91 (m, 1H), 2.82 (s, 3H), 2.67-2.77 (m, 1H), 1.27 (d, 6.8 Hz, 3H).

ESI-MS m/z $[C_{31}H_{31}N_5O_3+H]^+$ 522.1.

HPLC (Method D) 99.8% (AUC), $t_R$=6.28 min.

Synthesis of (R)-4-{6-[9-(2-(2-(2,4-dimethyl-3-oxopiperazin-1-yl)ethoxy)acetyl)-3,9-diazaspiro[5.5]undecan-3-yl]pyridin-3-yl}-6-methyl-1H-pyrrolo[2,3-c]pyridin-7(6H)-one (SLU-2225)

Scheme 26

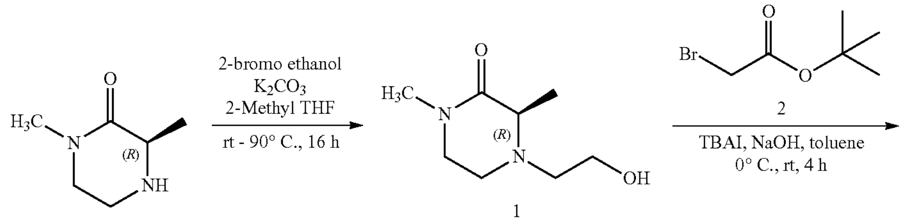

Intermediate-1

1

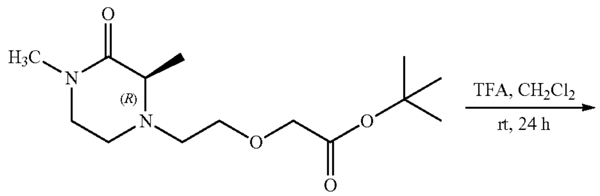

3

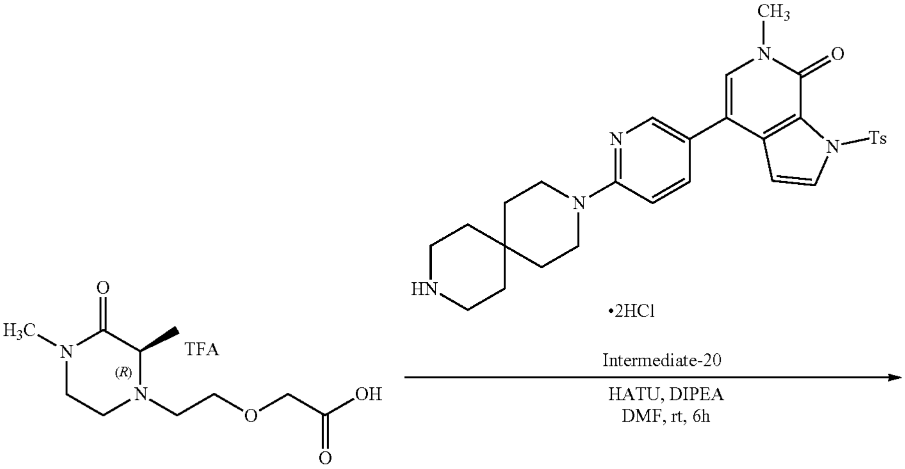

4

-continued

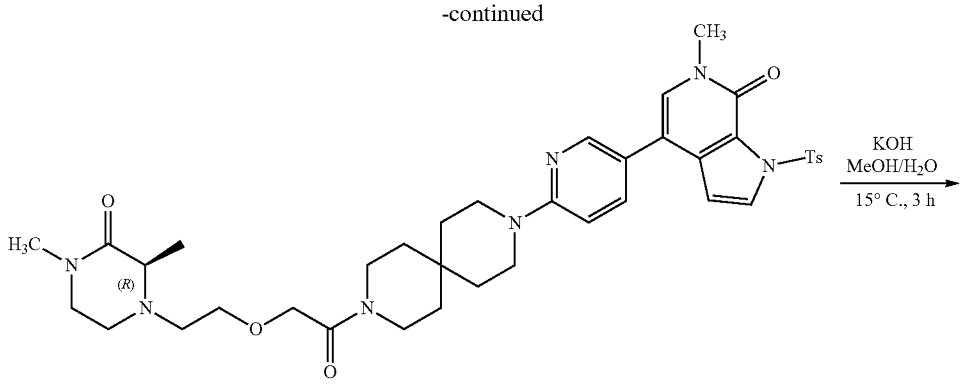

5

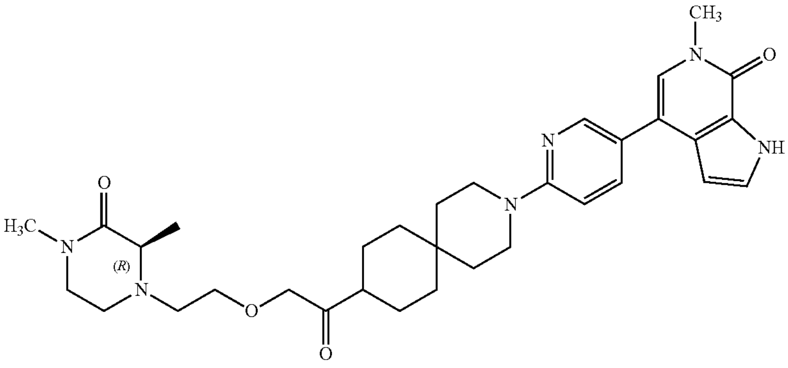

SLU-2225

(R)-4-(2-hydroxyethyl)-1,3-dimethylpiperazin-2-one (1)

To a stirred solution of Intermediate-1 (3.0 g, 23.45 mmol) and 2-bromo ethanol (11.6 g, 93.75 mmol) in 2-methyl THF (30 mL), $K_2CO_3$ (6.34 g, 46.87 mmol) was charged at room temperature and stirred at 90° C. for 16 h. The reaction mixture was concentrated under reduced pressure and crude residue was purified by combiflash chromatography ($CH_2Cl_2$:$CH_3OH$=95:5) to afford 1 (2.00 g, 51%) as a brown gum.

$^1$H NMR (400 MHz, $CDCl_3$): δ ppm 3.81-3.84 (m, 1H), 3.74-3.76 (m, 1H), 3.70 (s, 3H), 3.60-3.66 (m, 2H), 3.33 (t, J=5.6 Hz, 2H), 3.06-3.12 (m, 1H), 2.78-2.84 (m, 1H), 2.62-2.68 (m, 1H), 2.54-2.60 (m, 1H).

ESI-MS m/z $[C_8H_{16}N_2O_2+H]^+$ 173.1.

(R)-tert-butyl 2-[2-(2,4-dimethyl-3-oxopiperazin-1-yl)ethoxy]acetate (3)

A solution of 1 (1.0 g, 5.80 mmol) in toluene (15 mL) was charged with TBAI (0.740 g, 2.03 mmol). The reaction mixture was cooled to 0° C. and 35% NaOH (15 mL) was added followed by addition of t-butyl bromo acetate 2 (1.69 g, 8.72 mmol). The reaction mixture was stirred for 4 h at room temperature and diluted with EtOAc (100 mL). Organic layer was dried over anhydrous $Na_2SO_4$, concentrated under reduced pressure and crude product was purified by combiflash chromatography ($CH_2Cl_2$:$CH_3OH$=97:3) to afford 3 (0.480 g mixture) as a brown gum.

ESI-MS m/z $[C_{14}H_{26}N_2O_4+H]^+$ 287.3.

(R)-2-[2-(2,4-dimethyl-3-oxopiperazin-1-yl)ethoxy] acetic acid trifluoro acetic acid (4)

To a stirred solution of 3 (0.480 g, 1.67 mmol) in $CH_2Cl_2$ (10 mL), trifluoroacetic acid (4.0 mL) was added dropwise at 0° C. for 2 min and stirred at room temperature for 24 h. The reaction mixture was concentrated under reduced pressure to afford crude compound of 4 (0.450 g) as a brown gum which was used for next step without further purification.

ESI-MS m/z $[C_{10}H_{18}N_2O_4+H]^+$ 231.1.

(R)-4-{6-[9-(2-(2-(2,4-dimethyl-3-oxopiperazin-1-yl)ethoxy)acetyl)-3,9-diazaspiro[5.5]undecan-3-yl] pyridin-3-yl}-6-methyl-1-tosyl-1H-pyrrolo[2,3-c] pyridin-7(6H)-one (5)

To a stirred solution of 4 (0.310 g, 0.45 mmol) in DMF (10 mL), DIPEA (0.174 g, 1.35 mmol) and Intermediate-20 (0.240 g, 903 mmol) were added followed by addition of HATU (0.257 g, 676 mmol) at room temperature. The reaction mixture was stirred at ambient temperatures for 6 h and poured into ice cold water (100 mL). Organic compound was extracted into EtOAc (5×150 mL). Combined organic layers were washed with ice cold water (3×50 mL), brine (1×50 mL), dried over anhydrous $Na_2SO_4$ and concentrated under reduced pressure. Crude product was purified by combiflash chromatography ($CH_2Cl_2$:$CH_3OH$=93:7) to afford 5 (0.142 g, 42%) as a colourless semi solid.

$^1$H NMR (400 MHz, DMSO-$d_6$): δ ppm 8.21 (d, J=2.4 Hz, 1H), 8.01 (d, J=3.6 Hz, 1H), 7.96 (d, J=8.4 Hz, 2H), 7.63 (dd, J=2.4, 8.8 Hz, 1H), 7.51 (s, 1H), 7.42 (d, J=8.4 Hz, 2H), 6.91 (d, J=8.8 Hz, 1H), 6.65 (d, J=3.6 Hz, 1H), 4.12 (s, 2H), 3.54-3.55 (m, 8H), 3.44 (s, 3H), 3.37-3.38 (m, 2H), 3.21-3.22 (m, 2H), 3.10-3.14 (m, 3H), 2.80 (s, 3H), 2.60-2.67 (m, 2H), 2.38 (s, 3H), 1.42-1.52 (m, 8H), 1.20 (d, J=6.8 Hz, 3H).

ESI-MS m/z $[C_{39}H_{49}N_7O_6S+H]^+$ 744.3.

(R)-4-{6-[9-(2-(2-(2,4-dimethyl-3-oxopiperazin-1-yl)ethoxy)acetyl)-3,9-diazaspiro[5.5]undecan-3-yl]pyridin-3-yl}-6-methyl-1H-pyrrolo[2,3-c]pyridin-7(6H)-one (SLU-2225)

To a stirred solution of 5 (0.1 g, 0.13 mmol) in 1:1 mixture of $CH_3OH$, THF (10 mL) at 0° C., 2 N KOH (2.5 mL) solution was charged and left to 15° C. for 3 h. The reaction mixture was diluted with EtOAc (50 mL) and washed with water (5 mL). Organic layer separated was dried over anhydrous $Na_2SO_4$, concentrated under reduced pressure and crude residue was purified by reverse phase column chromatography ($H_2O$:$CH_3CN$=60:40) to afford SLU-2225 (0.03 g, 39%) as off-white solid.

$^1H$ NMR (400 MHz, DMSO-$d_6$): δ ppm 12.12 (s, 1H), 8.31 (d, J=2.4 Hz, 1H), 7.72 (dd, J=2.0, 8.8 Hz, 1H), 7.33 (t, J=2.4 Hz, 1H), 7.29 (s, 1H), 6.92 (d, J=8.8 Hz, 1H), 6.38 (s, 1H), 4.12 (s, 2H), 3.54-3.56 (m, 10H), 3.42-3.48 (m, 2H), 3.35-3.40 (m, 2H), 3.22 (t, J=5.6 Hz, 2H), 3.11 (q, J=6.8 Hz, 1H), 2.97-3.03 (m, 1H), 2.80 (s, 3H), 2.73 (t, J=5.6 Hz, 1H), 2.59-2.63 (m, 1H), 1.48-1.53 (m, 6H), 1.40-1.46 (m, 2H), 1.20 (t, J=6.8 Hz, 3H).

ESI-MS m/z $[C_{32}H_{43}N_7O_4+H]^+$ 590.6.

HPLC (Method C) 99.9% (AUC), $t_R$=6.55 min.

Synthesis of (S)-4-{2-[4-(2-(2,4-dimethyl-3-oxopiperazin-1-yl)ethoxy)phenyl]quinolin-6-yl}-6-methyl-1H-pyrrolo[2,3-c]pyridin-7(6H)-one (SLU-2236)

Scheme 27

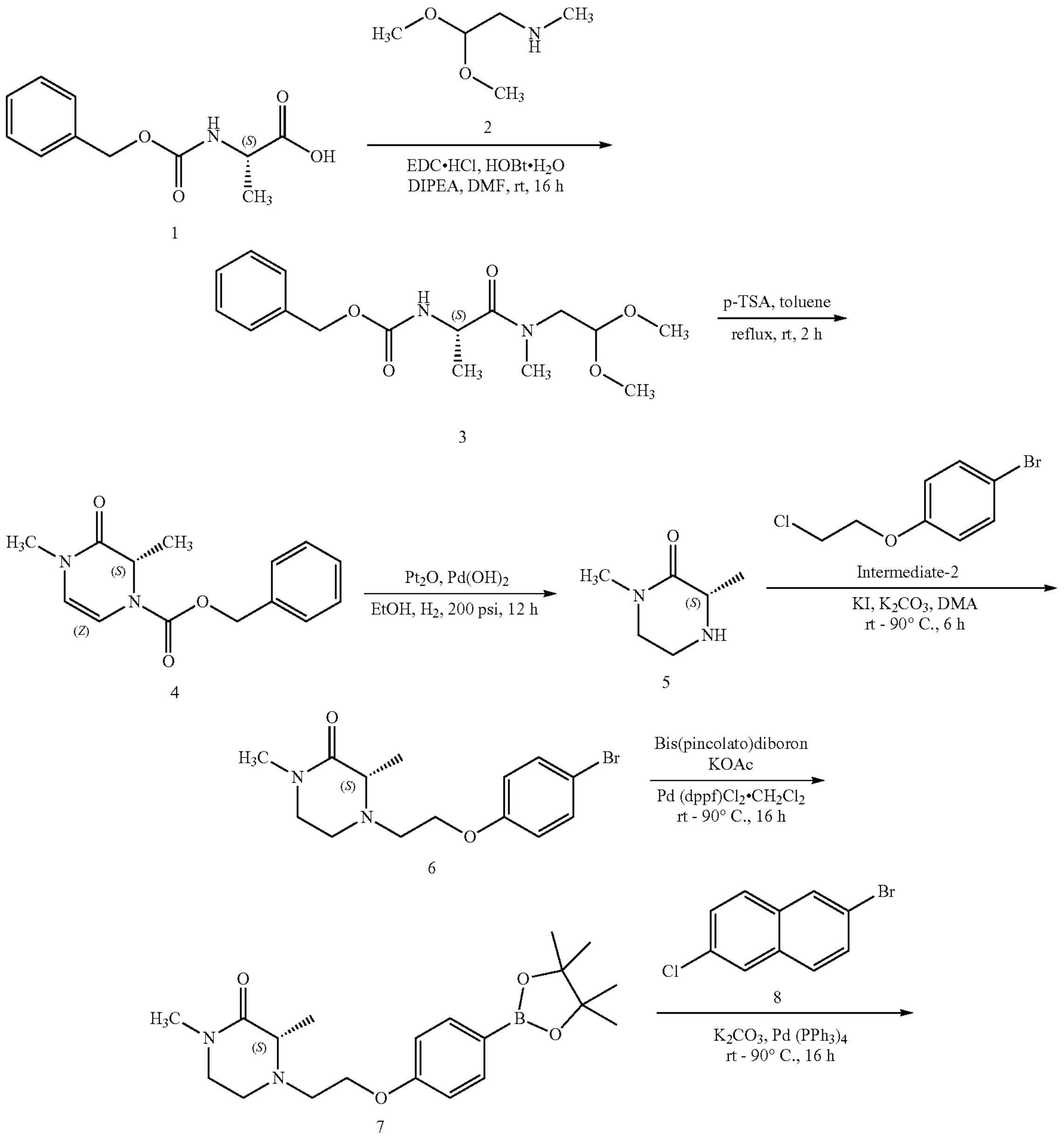

-continued

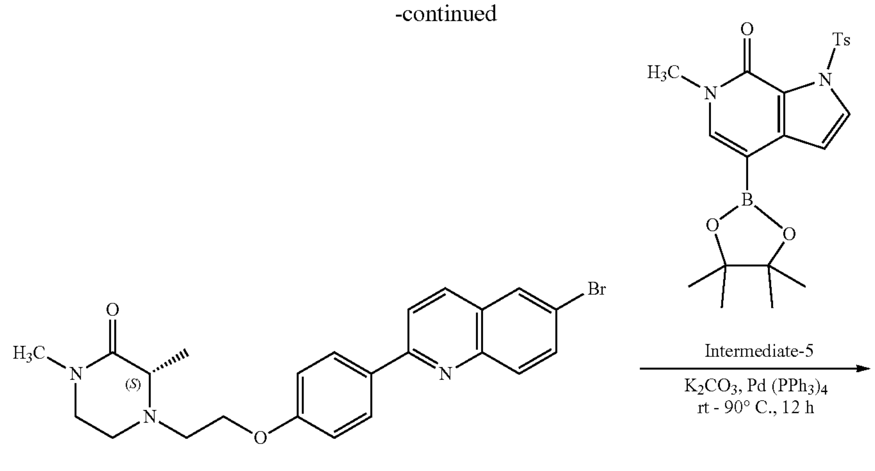

9

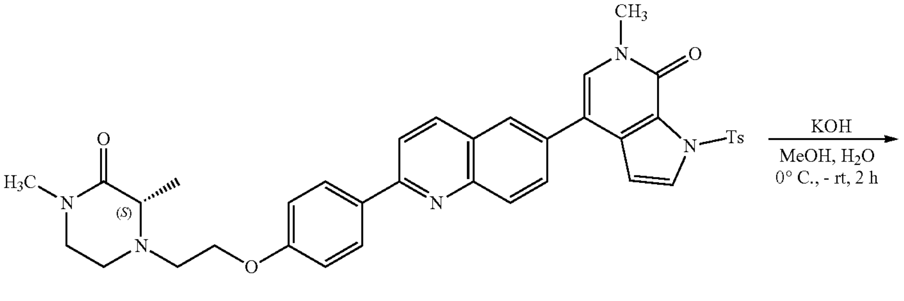

10

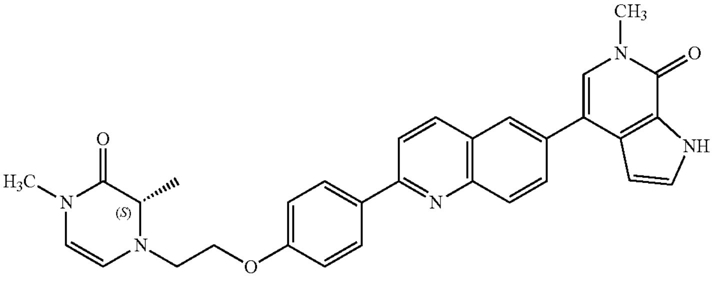

SLU-2236

(S)-benzyl {1-[(2,2-dimethoxyethyl)(methyl)aminol-1-oxopropan-2-yl}carbamate (3)

To a stirred solution of 1 (8.0 g, 35.87 mmol) in DMF (80 mL), 2,2-dimethoxy-N-methylethanamine 2 (4.69 g, 39.46 mmol) was charged followed by addition of DIPEA (9.03 g, 71.74 mmol) at room temperature. EDC·HCl (9.93 g, 53.80 mmol) was added to the reaction mixture followed by addition of HOBt·$H_2O$ (7.08 g, 53.08 mmol) at room temperature and stirred for 16 h. The reaction mixture was poured into water (200 mL) and extracted with EtOAc (5×100 mL). Combined organic layers were washed with ice cold water (5×50 mL), brine (2×30 mL), dried over anhydrous $Na_2SO_4$ and concentrated under reduced pressure to afford 3 (9.0 g, 77%) as a brown gum which was directly used for next step.

$^1$H NMR (400 MHz, $CDCl_3$): δ ppm 7.30-7.35 (m, 6H), 5.65-5.80 (m, 1H), 5.09 (s, 2H), 4.64-4.77 (m, 1H), 4.47 (t, J=5.6 Hz, 1H), 3.38-3.41 (m, 8H), 3.11 (s, 2H), 1.33(d, J=6.8 Hz, 3H).

(S)-benzyl 2,4-dimethyl-3-oxo-3,4-dihydropyrazine-1(2H)-carboxylate (4)

To a stirred solution of 3 (9.0 g, 27 mmol) in toluene (100 mL), P-TSA (2.63 g, 13 mmol) was charged portion wise for 5 min at room temperature and refluxed for 2 h. The reaction mixture was cooled to room temperature; toluene was evaporated under reduced pressure and dissolved in EtOAc (500 mL). Organic layer was washed with water (2×100 mL), saturated $NaHCO_3$ (3×100 mL), dried over anhydrous $Na_2SO_4$ and concentrated under reduced pressure to afford 4 (5.0 g, 69%) as an off-white solid which was used for next step without any purification $^1$H NMR (400 MHz, $CDCl_3$): δ ppm 7.35-7.36 (m, 5H), 6.29 (dd, J=5.6, 9.2 Hz, 1H), 5.47-5.59 (m, 1H), 5.20 (s, 2H), 4.80-4.92 (m, 1H), 3.08 (s, 3H), 1.30 (t, J=8.0 Hz, 3H).

(S)-1,3-dimethylpiperazin-2-one (5)

In a 100 mL capacity auto clave vessel, to a stirred solution of 4 (3.0 g, 11.5 mmol) in ethanol (40 mL), 5% platinum on carbon (0.450 g) and 20% palladium hydroxide on charcoal (0.3 g) were added carefully at room temperature. The reaction mixture was stirred at room temperature at 200 psi for 12 h under hydrogen atmosphere. The reaction mixture was filtered through celite pad, washed with methanol (500 mL) and filtrate was concentrated under reduced pressure to afford 5 (1.12 g, 76%) as colourless liquid which was directly used for next step without further purification.

$^1$H NMR (400 MHz, $CDCl_3$): δ ppm 3.42-3.55 (m, 2H), 3.15-3.24 (m, 2H), 3.03-3.10 (m, 1H), 2.94 (s, 3H), 2.67 (br.s., 1H), 1.39 (d, J=6.8 Hz, 3H).

ESI-MS m/z $[C_6H_{12}N_2O+H]^+$ 128.8.

(S)-4-[2-(4-bromophenoxy)ethyl]-1,3-dimethylpiperazin-2-one (6)

To a stirred solution of Intermediate-2 (1.80 g, 7.65 mmol) and (1.10 g, 7.65 mmol) in N,N-dimethylacetamide (20 mL), KI (0.630 g, 3.82 mmol) was charged followed by $K_2CO_3$ (2.12 g, 15.3 mmol) addition at room temperature and allowed to stir at 90° C. for 6 h. The reaction mixture was allowed to ambient temperature and poured into water (150 mL). Organic compound was extracted into ethyl acetate (4×100 mL). Combined organic layers were washed with ice-cold water (2×50 mL) followed by brine (1×50 mL), dried over anhydrous $Na_2SO_4$ and concentrated under reduced pressure to afford 6 [2.00 g, (crude)] as a brown solid.

$^1$H NMR (400 MHz, $CDCl_3$): δ ppm 7.37 (d, J=9.2 Hz, 2H), 6.77 (d, J=9.2 Hz, 2H), 4.02-4.08 (m, 2H), 3.34-3.39 (m, 1H), 3.24-3.31 (m, 2H), 3.10-3.16 (m, 1H), 3.02-3.06 (m, 1H), 3.01 (s, 3H), 2.82-2.89 (m, 1H), 2.74-2.80 (m, 1H), 1.40 (d, J=9.2 Hz, 3H).

ESI-MS m/z $[C_{14}H_{19}BrN_2O_2+H]^+$ 327.2.

(S)-1,3-dimethyl-4-{2-[4-(4,4,5,5-tetramethyl-1,3,2-dioxaborolan-2-yl)phenoxy]ethyl}piperazin-2-one (7)

To a stirred solution of 6 (2.0 g, 6.10 mmol) in 1,4-dioxane (25 mL) was charged with KOAc (1.19 g 1.22 mmol), Bis(pinacolato)diboron (2.0 g, 7.90 mmol) at room temperature and purged with argon for 10 min. Pd(dppf) $Cl_2$ (0.312 g, 0.4 mmol) was added at room temperature and purged with argon for 10 min. The reaction mixture was heated at 90° C. for 16 h. The reaction mixture was filtered through celite pad and the celite pad was washed with EtOAc (200 mL). Filtrate was concentrated under reduced pressure and crude product was purified by combiflash chromatography ($CH_2Cl_2$:$CH_3OH$=97:3) to afford 7 (1.51 g, 66%) as light brown colour solid.

$^1$H NMR (400 MHz, $CDCl_3$): δ ppm 7.74 (d, J=8.8 Hz, 2H), 6.88 (d, J=8.8 Hz, 2H), 4.08-4.14 (m, 2H), 3.36-3.39 (m, 1H), 3.23-3.31 (m, 2H), 3.11-3.17 (m, 1H), 3.02-3.07 (m, 1H), 2.94 (s, 3H), 2.83-2.90 (m, 1H), 2.74-2.81 (m, 1H), 1.39 (d, J=1.2 Hz, 3H), 1.33 (s, 12H).

ESI-MS m/z $[C_{20}H_{31}BN_2O_4+H]^+$ 375.4.

(S)-4-{2-[4-(6-bromoquinolin-2-yl)phenoxy]ethyl}-1,3-dimethylpiperazin-2-one (9)

To a stirred solution of 7 (1.50 g, 4.0 mmol) in 4:1 of dioxane, $H_2O$ (25 mL), 6-bromo-2-chloroquinoline 8 (0.770 g, 3.22 mmol) and $K_2CO_3$ (1.10 g, 8.00 mmol) were charged at room temperature and purged with argon for 10 min. $Pd(PPh_3)_4$ (0.320 g, 0.28 mmol) was added at room temperature and purged with argon for 10 min. The reaction mixture was heated at 90° C. for 16 h. The reaction mixture was filtered through celite pad and the celite pad was washed with EtOAc (2×250 mL). Combined filtrate was concentrated under reduced pressure. The crude product was purified by combiflash chromatography ($CH_2Cl_2$:$CH_3OH$=94:6) to afford 9 (0.670 g, 37%) as an off-white solid.

$^1$H NMR (400 MHz, $CDCl_3$): δ ppm 8.08-8.13 (m, 1H), 7.96-8.00 (m, 1H), 7.75-7.86 (m, 1H), 7.64-7.69 (m, 1H), 7.45-7.55 (m, 2H), 7.37 (d, J=8.8 Hz, 1H), 7.03 (d, J=8.4 Hz, 1H), 7.77 (d, J=8.8 Hz, 1H), 4.16-4.20 (m, 1H), 4.03-4.09 (m, 1H), 3.33-3.39 (m, 3H), 3.02-3.20 (m, 1H), 2.95 (s, 3H), 2.73-2.94 (m, 2H), 1.23-1.44 (m, 3H).

ESI-MS m/z $[C_{23}H_{24}BrN_3O_2+H]^+$ 454.12.

(S)-4-{2-[4-(2-(2,4-dimethyl-3-oxopiperazin-1-yl)ethoxy)phenyl]quinolin-6-yl}-6-methyl-1-tosyl-1H-pyrrolo[2,3-c]pyridin-7(6H)-one (10)

To a stirred mixture of 9 (0.670 g, 1.47 mmol) and Intermediate-5 (0.630 g, 1.47 mmol IN-NMT-N-44) in 4:1 of dioxane, $H_2O$ (18 mL), $K_2CO_3$ (0.4 g, 2.94 mmol) was charged at room temperature and purged with argon for 5. $Pd(PPh_3)_4$ (0.170 g, 0.014 mmol) was added at room temperature and purged with argon for 5 min. The reaction mixture was heated at 90° C. for 12 h. The reaction mixture was evaporated under reduced pressure. Crude product was purified by combiflash chromatography ($CH_2Cl_2$: $CH_3OH$=96:4) to afford 10 (0.240 g, 41%) as a brown solid.

ESI-MS m/z $[C_{38}H_{37}N_5O_5S+H]^+$ 676.4.

(S)-4-{2-[4-(2-(2,4-dimethyl-3-oxopiperazin-1-yl)ethoxy)phenyl]quinolin-6-yl}-6-methyl-1H-pyrrolo[2,3-c]pyridin-7(6H)-one (SLU-2236)

To a stirred solution of 10 (0.220 g, 0.32 mmol) in 2:2:1 of $CH_3OH$, THF, $H_2O$ (10 mL) at 0° C. and KOH (0.45 g, 0.78 mmol) was charged and left to room temperature for 2 h. The reaction mixture was diluted with EtOAc (100 mL), dried over anhydrous $Na_2SO_4$ and concentrated under reduced pressure. Crude product was purified by combiflash chromatography ($CH_2Cl_2$:$CH_3OH$=94:6) and purified by preparative-HPLC to afford SLU-2236 (0.070 g, 37%) as an off-white solid.

$^1$H NMR (400 MHz, DMSO-$d_6$): δ ppm 12.22 (s, 1H), 8.46 (d, J=8.8 Hz, 1H), 8.26 (d, J=8.8 Hz, 2H), 8.18 (d, J=2.0 Hz, 1H), 8.09-8.14 (m, 2H), 8.01 (dd, J=2.0, 8.8 Hz, 1H), 7.60 (s, 1H), 7.41 (t, J=2.8 Hz, 1H), 7.12 (d, J=8.8 Hz, 2H), 6.62 (t, J=2.0 Hz, 1H), 4.18 (t, J=6.0 Hz, 2H), 3.63 (s, 3H), 3.26-3.29 (m, 2H), 3.18 (q, J=6.8 Hz, 1H), 3.07-3.13 (m, 1H), 2.96-3.02 (m, 1H), 2.75 (s, 3H), 2.69-2.74 (m, 1H), 2.55-2.56 (m, 1H), 1.26 (d, J=6.8 Hz, 3H).

ESI-MS m/z $[C_{31}H_{31}N_5O_3+H]^+$ 522.2.

HPLC (Method A) 97.2% (AUC), $t_R$=6.03 min.

Synthesis of 6-methyl-4-{2-[4-(2-(3-oxopiperazin-1-yl)ethoxy)phenyl]quinolin-6-yl}-1H-pyrrolo[2,3-c]pyridin-7(6H)-one (SLU-2242)

Scheme 28

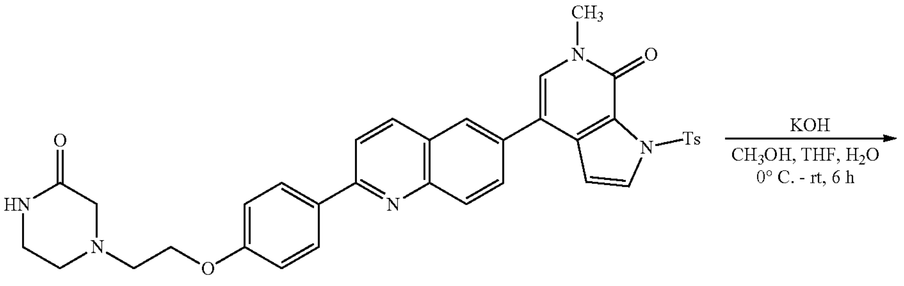

Intermediate-23

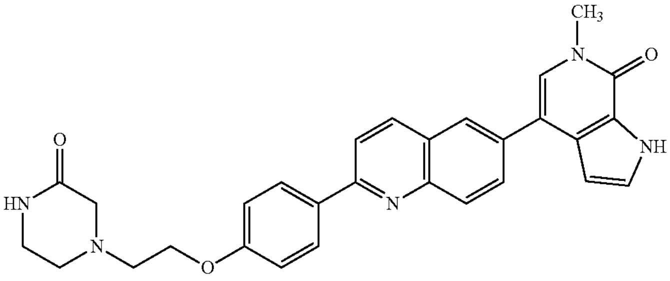

SLU-2242

To a stirred solution of Intermediate-23 (0.1 g, 0.15 mmol) in 2:2:1 of $CH_3OH$, THF, $H_2O$ (10 mL) at 0° C. and KOH (0.050 g, 0.77 mmol) was charged and left to room temperature for 6 h. The reaction mixture was concentrated under reduced pressure. Crude product was purified by combiflash chromatography ($CH_2Cl_2$:$CH_3OH$=92:8). The obtained solid was stirred in acetonitrile (12 mL), filtered and dried under vacuum to afford SLU-2242 (0.065 g, 78%) as an off-white solid.

$^1H$ NMR (400 MHz, DMSO-$d_6$): δ ppm 12.22 (s, 1H), 8.46 (d, J=8.8 Hz, 1H), 8.27 (d, J=8.8 Hz, 2H), 8.09-8.18 (m, 3H), 8.01 (d, J=8.8 Hz, 1H), 7.76 (m, 1H), 7.60 (s, 1H), 7.41 (m, 1H), 7.13 (d, J=8.4 Hz, 2H), 6.62 (m, 1H), 4.21 (t, J=5.6 Hz, 2H), 3.63 (s, 3H), 3.18 (br.s., 2H), 3.08 (s, 2H), 2.82 (t, J=5.6 Hz, 2H), 2.71 (t, J=5.2 Hz, 2H).

ESI-MS m/z $[C_{29}H_{27}N_5O_3+H]^+$ 494.3.

HPLC (Method A) 98.4% (AUC), $t_R$=5.96 min.

Synthesis of 4-{2-[4-(2-(4-ethyl-3-oxopiperazin-1-yl)ethoxy)phenyl]quinolin-6-yl}-6-methyl-1H-pyrrolo[2,3-c]pyridin-7(6H)-one (SLU-2243)

Scheme 29

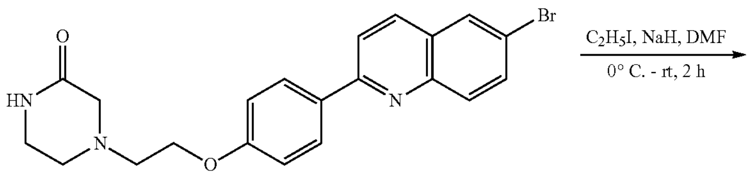

Intermediate-22

-continued

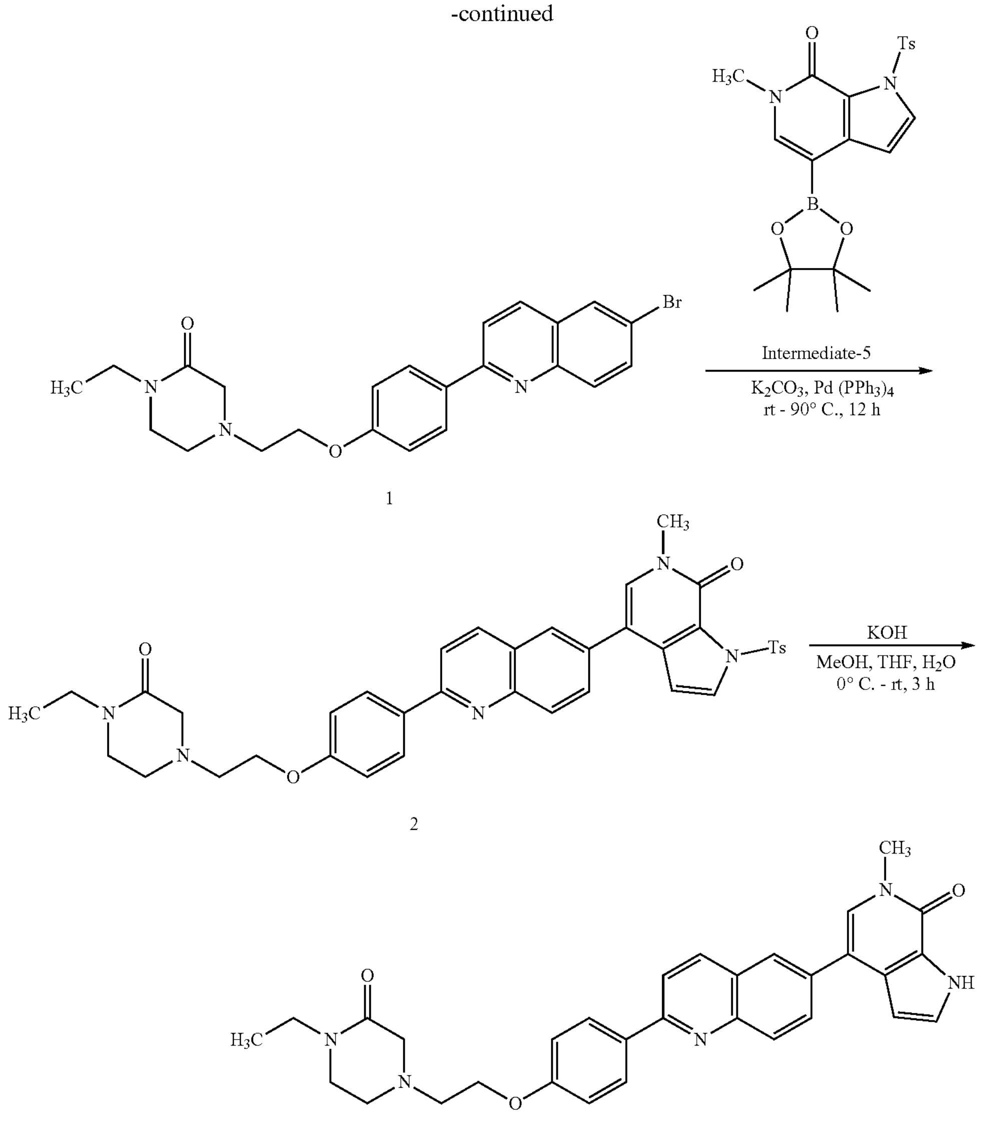

1

2

SLU-2243

4-{2-[4-(6-bromoquinolin-2-yl)phenoxy]ethyl)-1-ethylpiperazin-2-one (1)

To a stirred solution of Intermediate-22 (0.5 g, 1.17 mmol, IN-SKA-Q-68) in DMF (20 mL) at 0° C. under inert atmosphere, NaH (60% in mineral oil, 0.051 g, 1.29 mmol) was charged and stirred for 10 min. $C_2H_5I$ (0.202 g, 1.30 mmol) was added and left to ambient temperature for 2 h. The reaction mixture was poured into ice cold water (100 mL) and extracted into EtOAc (5×100 mL). Combined organic layers were washed with water (5×50 mL) followed by brine (1×50 mL). Organic layer was dried over anhydrous $Na_2SO_4$ and concentrated under reduced pressure. Crude product was purified by combiflash chromatography ($CH_2Cl_2$:$CH_3OH$=96:4) to afford 1 (0.4 g, 75%) as an off-white solid.

$^1$H NMR (400 MHz, DMSO-$d_6$): δ ppm 8.38 (d, J=8.8 Hz, 1H), 8.23-8.26 (m, 3H), 8.17 (d, J=8.8 Hz, 1H), 7.96 (d, J=9.2 Hz, 1H), 7.86 (dd, J=2.4, 8.8 Hz, 1H), 7.12 (d, J=8.8 Hz, 2H), 4.20 (t, J=5.6 Hz, 2H), 3.27-3.34 (m, 4H), 3.12 (s, 2H), 2.77-2.82 (m, 4H), 1.02 (t, J=7.2 Hz, 3H).

ESI-MS m/z $[C_{31}H_{31}N_5O_3+H]^+$ 456.1.

4-{2-[4-(2-(4-ethyl-3-oxopiperazin-1-yl)ethoxy)phenyl]quinolin-6-yl}-6-methyl-1-tosyl-1H-pyrrolo[2,3-c]pyridin-7(6H)-one (2)

To a stirred mixture of 1 (0.2 g, 0.44 mmol) and Intermediate-5 (0.207 g, 0.48 mmol) in 4:1 of dioxane, $H_2O$ (24 mL), $K_2CO_3$ (0.121 g, 0.88 mmol) was charged at room temperature and purged with argon for 5 min. $Pd(PPh_3)_4$ (0.050 g, 0.04 mmol) was added at room temperature and purged with argon for 5 min. The reaction was heated at 90° C. for 12 h. The reaction mixture was evaporated under reduced pressure. Crude product was purified by combiflash chromatography ($CH_2Cl_2$ $CH_3OH$=93:7) to afford 2 (0.120 g, 40%) as an off-white solid.

$^1$H NMR (400 MHz, DMSO-$d_6$): δ ppm 8.44 (d, J=8.8 Hz, 1H), 8.26 (d, J=8.8 Hz, 2H), 8.09-8.15 (m, 4H), 7.99 (d, J=8.0 Hz, 2H), 7.88-7.91 (m, 1H), 7.79 (s, 1H), 7.44 (d, J=8.0 Hz, 2H), 7.12 (d, J=8.8 Hz, 2H), 6.86 (d, J=3.6 Hz, 1H), 4.20 (t, J=5.6 Hz, 2H), 3.51 (s, 3H), 3.29 (t, J=3.6 Hz, 4H), 3.13 (s, 2H), 2.77-2.82 (m, 4H), 2.39 (s, 3H), 1.02 (t, J=7.2 Hz, 3H).

ESI-MS m/z $[C_{38}H_{37}N_5O_5S+H]^+$ 676.4.

4-{2-[4-(2-(4-ethyl-3-oxopiperazin-1-yl)ethoxy) phenyl]quinolin-6-yl}-6-methyl-1H-pyrrolo[2,3-c] pyridin-7(6H)-one (SLU-2243)

To a stirred solution of 2 (0.110 g, 0.16 mmol) in 2:2:1 of $CH_3OH$, THF, $H_2O$ (12 mL) at 0° C. and KOH (0.050 g, 0.832 mmol) was charged and left to room temperature for 3 h. The reaction mixture was concentrated under reduced pressure. Crude product was purified by combiflash chromatography ($CH_2Cl_2$:$CH_3OH$=92:8). The obtained solid was stirred in acetonitrile (12 mL), filtered and dried under vacuum to afford SLU-2243 (0.057 g, 67%) as an off-white solid.

$^1H$ NMR (400 MHz, $CDCl_3$) δ ppm 10.46 (s, 1H), 8.20 (dd, J=2.9, 8.8 Hz, 2H), 8.16 (d, J=10.0 Hz, 2H), 7.92-7.97 (m, 2H), 7.87 (d, J=8.4 Hz, 1H), 7.35 (t, J=2.8 Hz, 1H), 7.16 (s, 1H), 7.06 (d, J=8.8 Hz, 2H), 6.63 (t, J=2.0 Hz, 1H), 4.21 (t, J=5.6 Hz, 2H), 3.77 (s, 3H), 3.45 (q, J=6.8 Hz, 2H), 3.37 (t, J=5.2 Hz, 2H), 3.32 (s, 2H), 2.86-2.92 (m, 4H), 1.15 (t, J=14.4 Hz, 3H).

ESI-MS m/z $[C_{31}H_{31}N_5O_3+H]^+$ 522.

HPLC (Method A) 96.5% (AUC), $t_R$=6.05 min.

Synthesis of 6-methyl-4-{2-[4-(2-(4-methyl-3-oxopiperazin-1-yl)ethoxy)phenyl]quinolin-6-yl}-1H-pyrrolo[2,3-c]pyridin-7(6H)-one (SLU-2244)

Scheme 30

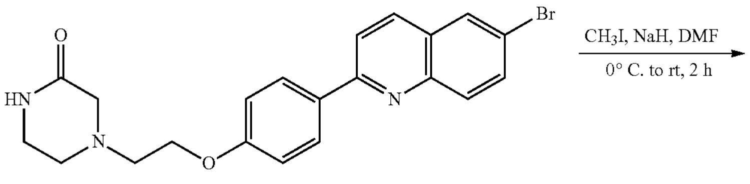

Intermediate-22

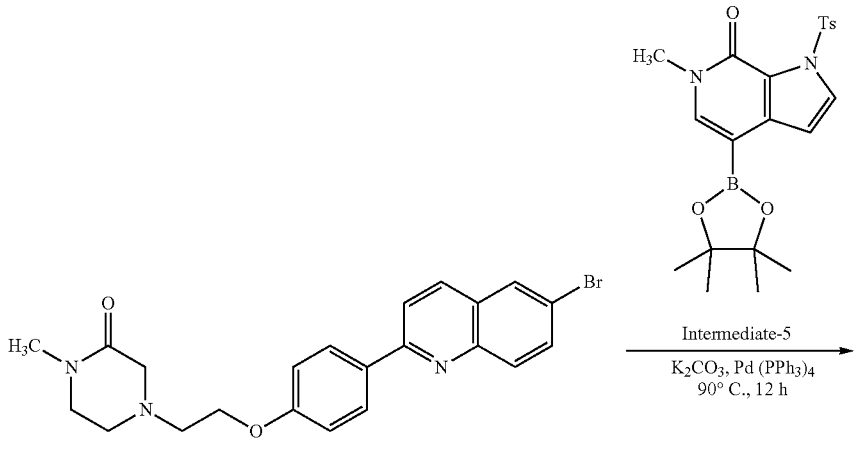

1

-continued

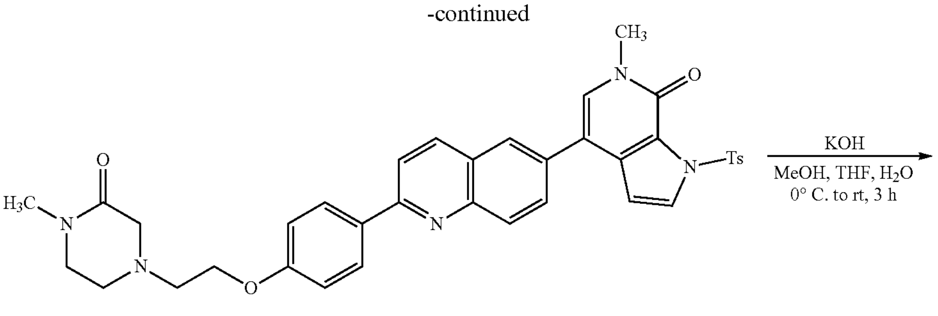

2

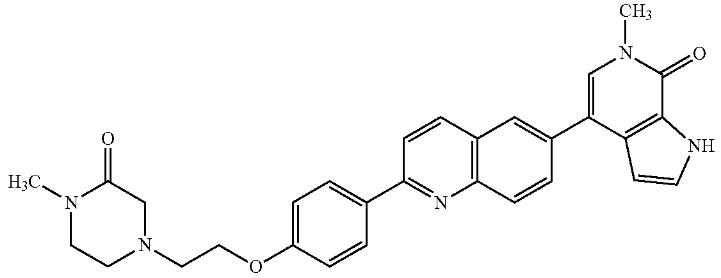

SLU-2244

4-{2-[4-(6-bromoquinolin-2-yl)phenoxy]ethyl}-1-methylpiperazin-2-one (1)

To a stirred solution of Intermediate-22 (0.5 g, 1.17 mmol, IN-SKA-Q-68) in DMF (20 mL) at 0° C. under inert atmosphere, NaH (60% in mineral oil, 0.051 g, 1.29 mmol) was charged and stirred for 10 min. $CH_3I$ (183 mg, 1.29 mmol) was added and left to ambient temperature for 2 h. The reaction mixture was poured into ice cold water (100 mL) and extracted into EtOAc (5×50 mL). Combined organic layers were washed with water (3×50 mL) followed by brine (1×50 mL). Organic layer was dried over anhydrous $Na_2SO_4$ and concentrated under reduced pressure. The solid obtained was washed with MTBE (2×15 mL) and dried under vacuum to afford 1 [0.35 g, (crude)] as a brown solid. This crude was used for next step without any further purification.

$^1$H NMR (400 MHz, DMSO-$d_6$): δ ppm 8.39 (d, J=8.4 Hz, 1H), 8.24-8.27 (m, 3H), 8.17 (d, J=8.8 Hz, 1H), 7.96 (d, J=8.8 Hz, 1H), 7.45-7.87 (m, 1H), 7.12 (d, J=7.6 Hz, 2H), 4.20 (t, J=5.2 Hz, 2H), 3.28 (t, J=5.2 Hz, 2H), 3.12 (s, 2H), 2.82 (s, 3H), 2.77-2.81 (m, 4H).

ESI-MS m/z $[C_{22}H_{22}BrN_3O_2+H]^+$ 440.1.

6-methyl-4-{2-[4-(2-(4-methyl-3-oxopiperazin-1-yl)ethoxy)phenyl]quinolin-6-yl}-1-tosyl-1H-pyrrolo[2,3-c]pyridin-7(6H)-one (2)

To a stirred mixture of 1 (0.320 g, 0.72 mmol) and Intermediate-5 (0.342 g, 0.79 mmol) in in 4:1 of 1,4-dioxane, $H_2O$ (24 mL), $K_2CO_3$ (0.2 g, 1.45 mmol) was charged at room temperature and purged with argon for 5 min. $Pd(PPh_3)_4$ (0.084 g, 0.072 mmol) was added at room temperature and purged with argon for 5 min. The reaction mixture was heated at 90° C. for 12 h. The reaction mixture was evaporated under reduced pressure. Crude product was purified by combiflash chromatography ($CH_2Cl_2$: $CH_3OH$=96:4) to afford 2 (0.110 g, 21%) as an off-white solid.

$^1$H NMR (400 MHz, DMSO-$d_6$): δ ppm 8.45 (d, J=8.8 Hz, 1H), 8.27 (d, J=8.8 Hz, 2H), 8.10-8.16 (m, 4H), 7.99 (d, J=8.4 Hz, 2H), 7.91 (d, J=8.8 Hz, 1H), 7.80 (s, 1H), 7.45 (d, J=8.0 Hz, 2H), 7.13 (d, J=8.4 Hz, 2H), 6.87 (d, J=3.6 Hz, 1H), 4.21 (t, J=5.2 Hz, 2H), 3.51 (s, 3H), 3.28 (t, J=5.2 Hz, 2H), 3.13 (s, 3H), 2.82 (s, 3H), 2.78-2.80 (m, 4H), 2.40 (s, 3H).

ESI-MS m/z $[C_{37}H_{35}N_5O_5S+H]^+$ 662.3.

6-methyl-4-{2-[4-(2-(4-methyl-3-oxopiperazin-1-yl)ethoxy)phenyl]quinolin-6-yl}-1H-pyrrolo[2,3-c]pyridin-7(6H)-one (SLU-2244)

To a stirred solution of 2 (0.1 g, 0.166 mmol) in 2:2:1 of $CH_3OH$, THF, water (12 mL) at 0° C. and KOH (0.046 g, 0.832 mmol) was charged and left to room temperature for 3 h. The reaction mixture was diluted with EtOAc (200 mL) and washed with water (2×25 mL) followed by brine (2×25 mL). Organic layer was dried over anhydrous $Na_2SO_4$ and concentrated under reduced pressure. Crude product was purified by combiflash chromatography ($CH_2Cl_2$: $CH_3OH$=92:8). The obtained solid was stirred in acetonitrile (20 mL), filtered and dried under vacuum to afford SLU-2244 (0.056 g, 62%) an off-white solid $^1$H NMR (400 MHz, DMSO-$d_6$): δ ppm 12.22 (s, 1H), 8.46 (d, J=8.8 Hz, 1H), 8.26 (d, J=8.8 Hz, 2H), 8.09-8.17 (m, 3H), 8.01 (d, J=8.4 Hz, 1H), 7.60 (s, 1H), 7.41 (m, 1H), 7.12 (d, J=8.8 Hz, 2H), 6.62 (m, 1H), 4.20 (t, J=5.2 Hz, 2H), 3.63 (s, 3H), 3.28 (t, J=5.2 Hz, 2H), 3.13 (s, 2H), 2.82 (s, 3H), 2.78-2.82 (m, 3H).

ESI-MS m/z $[C_{30}H_{29}N_5O_3+H]^+$ 508.2.

HPLC (Method A) 98.3% (AUC), $t_R$=6.01 min.

Synthesis of 6-methyl-4-{2-[4-(2-(3-oxopiperazin-1-yl)ethoxy)phenyl]quinolin-6-yl}-1H-pyrrolo[2,3-c]pyridin-7(6H)-one (SLU-2281) and 6-methyl-4-{2-[4-(2-(3-oxo-4-propylpiperazin-1-yl)ethoxy)phenyl]quinolin-6-yl}-1H-pyrrolo[2,3-c]pyridin-7(6H)-one (SLU-2282)

Scheme 31

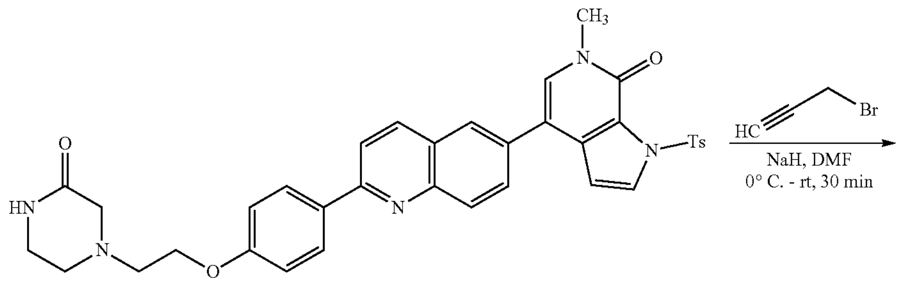

Intermediate-23

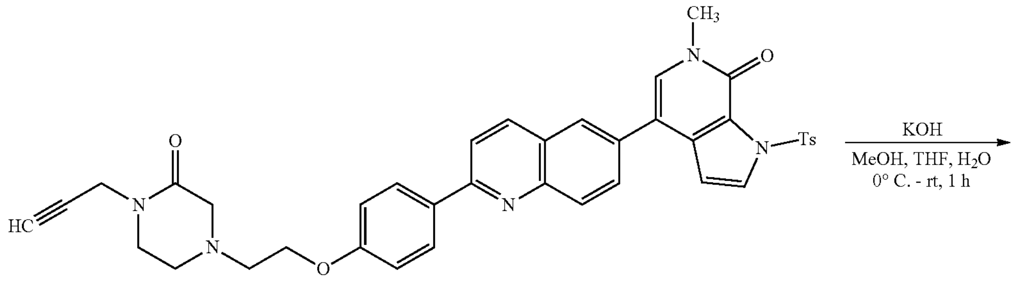

1

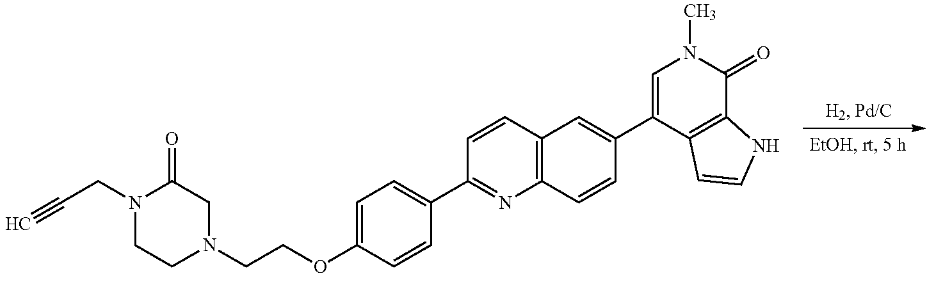

SLU-2281

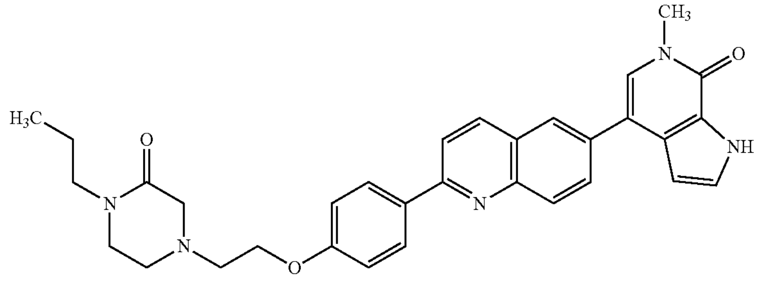

SLU-2282

6-methyl-4-{2-[4-(2-(3-oxo-4-(prop-2-yn-1-yl)piperazin-1-yl)ethoxy)phenyl]quinolin-6-yl}-1-tosyl-1H-pyrrolo[2,3-c]pyridin-7(6H)-one (1)

To a stirred solution of Intermediate-23 (0.350 g, 0.54 mmol) in DMF (10 mL) at 0° C. under inert atmosphere, NaH (60% in mineral oil, 0.032 g, 0.81 mmol) was charged and stirred for 10 min. Propargyl bromide (80% in toluene) (0.080 g, 0.67 mmol) was added and left to ambient temperature for 30 min. The reaction mixture was poured into ice cold water (100 mL). Organic compound was extracted into EtOAc (3×100 mL). Combined organic layer was washed with water (4×20 mL) followed by brine (1×20 mL). Organic layer was dried over anhydrous $Na_2SO_4$ and concentrated under reduced pressure. Crude product was purified by combiflash chromatography ($CH_2Cl_2$:$CH_3OH$=97:3) to afford 1 (0.180 g, 45%2) as an off-white solid.

$^1$H NMR (400 MHz, DMSO-$d_6$): δ ppm 8.45 (d, J=8.8 Hz, 1H), 8.26 (d, J=8.8 Hz, 2H), 8.13-8.16 (m, 1H), 8.09-8.11 (m, 2H), 7.98 (t, J=8.4 Hz, 3H), 7.90 (dd, J=1.6, 8.8 Hz, 1H), 7.13 (d, J=8.8 Hz, 2H), 6.87 (d, J=3.2 Hz, 3H), 5.28 (d, J=2.0 Hz, 1H), 4.21 (t, J=5.2 Hz, 2H), 4.17 (d, J=2.4 Hz, 2H), 3.51 (s, 3H), 3.72 (t, J=5.2 Hz, 2H), 2.89 (s, 2H), 2.82-2.83 (m, 4H), 2.39 (s, 3H).

ESI-MS m/z $[C_{39}H_{35}N_5O_5S+H]^+$ 686.3.

6-methyl-4-{2-[4-(2-(3-oxo-4-(prop-2-yn-1-yl)piperazin-1-yl)ethoxy)phenyl]quinolin-6-yl}-1H-pyrrolo[2,3-c]pyridin-7(6H)-one (SLU-2281)

To a stirred solution of 1 (0.160 g, 0.23 mmol2) in 2:2:1 of $CH_3OH$, THF, $H_2O$ (10 mL) at 0° C. and KOH (0.065 g, 1.16 mmol) was charged and left to room temperature for 1 h. The reaction mixture was concentrated under reduced pressure. Crude product was purified by combiflash chromatography ($CH_2Cl_2$:$CH_3OH$=94:6). The obtained solid was stirred in acetonitrile (10 mL), filtered and dried under vacuum to afford SLU-2281 (0.1 g, 71%) as an off-white solid.

$^1$H NMR (400 MHz, DMSO-$d_6$): δ ppm 12.21 (s, 1H), 8.46 (d, J=9.2 Hz, 1H), 8.27 (d, J=8.8 Hz, 2H), 8.09-8.18 (m, 3H), 8.01 (dd, J=2.0, 8.8 Hz, 1H), 7.60 (s, 1H), 7.41 (t, J=2.8 Hz, 1H), 7.13 (d, J=8.8 Hz, 2H), 6.61 (t, J=2.4 Hz, 1H), 4.21 (t, J=5.6 Hz, 2H), 4.17 (d, J=2.4 Hz, 2H), 3.63 (s, 3H), 3.37 (t, J=5.2 Hz, 2H), 3.22 (t, J=2.4 Hz, 1H), 3.19 (s, 2H), 2.84 (q, J=4.8 Hz, 4H).

ESI-MS m/z $[C_{32}H_{29}N_5O_3+H]^+$ 532.4.

HPLC (Method A) 97.6% (AUC), $t_R$=6.12 min.

6-methyl-4-{2-[4-(2-(3-oxo-4-propylpiperazin-1-yl)ethoxy)phenyl]quinolin-6-yl}-1H-pyrrolo[2,3-c]pyridin-7(6H)-one (SLU-2282)

To a stirred solution of SLU-2281 (0.07 g, 0.14 mmol7) in ethanol (10 mL) 10% Pd/C (0.01 g) was charged and stirred under hydrogen atmosphere with balloon for 5 h. The reaction mixture was diluted with methanol (100 mL) and filtered through celite pad. Filtrate was concentrated under reduced pressure. The obtained solid was stirred in acetonitrile (12 mL), filtered and dried under vacuum to afford SLU-2282 (0.06 g, 89%) as an off-white solid.

$^1$H NMR (400 MHz, DMSO-$d_6$): δ ppm 12.21 (s, 1H), 8.46 (d, J=8.4 Hz, 1H), 8.26 (d, J=8.4 Hz, 2H), 8.09-8.18 (m, 3H), 8.01 (d, J=7.6 Hz, 1H), 7.60 (s, 1H), 7.41 (br.s, 1H), 7.13 (d, J=8.4 Hz, 2H), 6.61 (br.s., 1H), 4.18-4.21 (m, 2H), 3.63 (s, 3H), 3.19-3.30 (m, 4H), 3.14 (s, 2H), 2.79-2.81 (m, 4H), 1.48 (q, J=7.2 Hz, 2H), 0.82 (t, J=7.2 Hz, 3H).

ESI-MS m/z $[C_{29}H_{27}N_5O_3+H]^+$ 536.5.

HPLC (Method A) 97.2% (AUC), $t_R$=6.14 min.

Synthesis of 6-methyl-4-{2-[4-(2-(4-methyl-3-oxopiperazin-1-yl)ethoxy)phenyl]quinolin-6-yl}-1H-pyrrolo[2,3-c]pyridin-7(6H)-one (SLU-2283)

Scheme 32

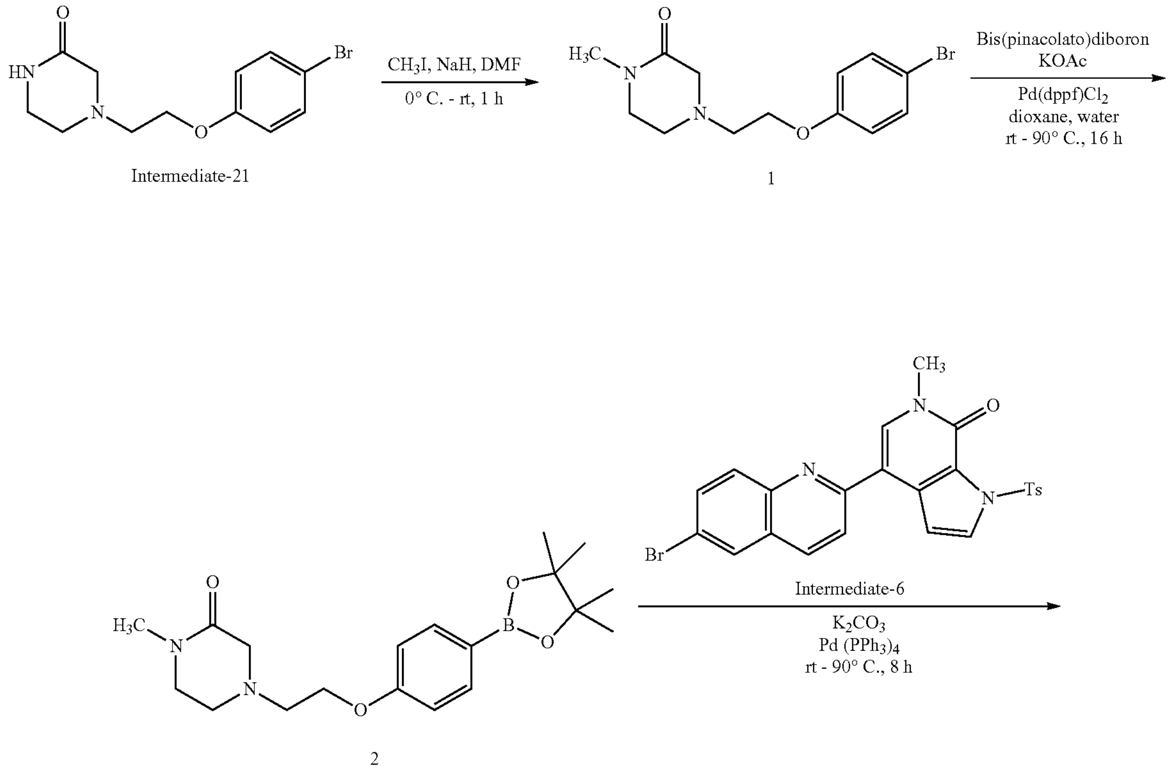

-continued

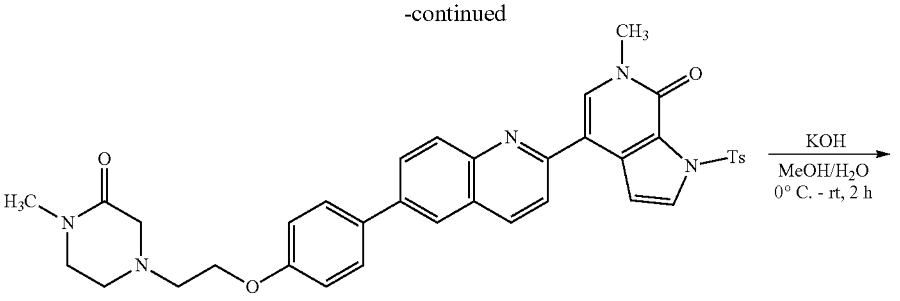

3

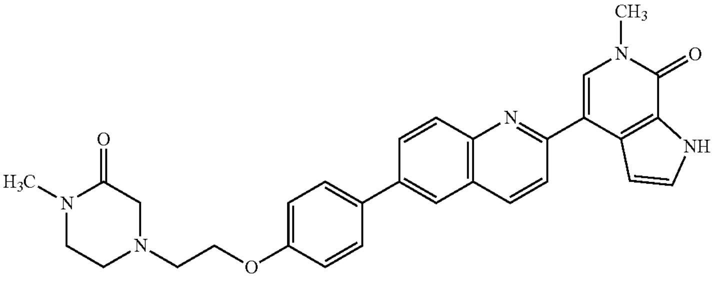

SLU-2283

4-[2-(4-bromophenoxy)ethyl]-1-methylpiperazin-2-one (1)

To a stirred solution of Intermediate-21 (0.90 g, 3.0 mmol5) in DMF (20 mL) at 0° C. under inert atmosphere, NaH (60% in mineral oil, 0.18 g, 4.50 mmol) was charged and stirred for 10 min. $CH_3I$ (0.28 mL, 1.29 mmol) was added and left to ambient temperature for 1 h. The reaction mixture was poured into ice cold water (150 mL), extracted into EtOAc (3×150 mL). Combined organic layer was washed with water (3×50 mL) followed by brine (1×50 mL). Organic layer was dried over anhydrous $Na_2SO_4$ and concentrated under reduced pressure. Crude product was purified by combiflash chromatography ($CH_2Cl_2$:$CH_3OH$=95:5) to afford 1 (0.6 g9) as a brown gum.

$^1H$ NMR (400 MHz, DMSO-$d_6$): δ ppm 7.43 (d, J=9.2 Hz, 2H), 6.92 (d, J=9.2 Hz, 2H), 4.08 (t, J=5.6 Hz, 2H), 3.25 (t, J=5.2 Hz, 2H), 3.08 (s, 2H), 2.89 (s, 3H), 2.73-2.80 (m, 4H).

ESI-MS m/z $[C_{13}H_{17}BrN_2O_2+H]^+$ 313.0.

1-methyl-4-{2-[4-(4,4,5,5-tetramethyl-1,3,2-dioxaborolan-2-yl)phenoxy]ethyl}piperazin-2-one (2)

To a stirred solution of 1 (0.6 g, 1.91 mmol3) in 1,4-dioxane (25 mL) was charged with potassium acetate (0.280 g, 2.85 mmol), Bis(pinacolato)diboron (0.53 g, 2.10 mmol) and purged with argon for 10 min at room temperature. Pd(dppf)$Cl_2$ (0.14 g, 0.19 mmol) was added at room temperature and purged with argon for 15 min. The reaction mixture was heated at 90° C. for 16 h. The reaction mixture was filtered through celite pad and concentrated under reduced pressure. The crude product was purified by combiflash chromatography ($CH_2Cl_2$:$CH_3OH$=95:5) to afford 2 (0.41 g, 60%5).

$^1H$ NMR (400 MHz, DMSO-$d_6$): δ ppm 7.59 (d, J=8.8, 2H), 6.93 (d, J=8.4 Hz, 2H), 4.12 (t, J=5.6 Hz, 2H), 3.25 (t, J=5.2 Hz, 2H), 3.09 (s, 2H), 2.80 (s, 3H), 2.73-2.77 (m, 4H), 1.27 (s, 12H).

ESI-MS m/z $[C_{18}H_{27}BN_2O_4+H]^+$ 361.2.

6-methyl-4-{6-[4-(2-(4-methyl-3-oxopiperazin-1-yl)ethoxy)phenyl]quinolin-2-yl}-1-tosyl-1H-pyrrolo[2,3-c]pyridin-7(6H)-one (3)

To a solution of 2 (0.18 g, 0.72 mmol5) in 4:1 of dioxane, water (24 mL), Intermediate-6 (0.27 g, 0.53 mmol6) and $K_2CO_3$ (0.20 g, 1.45 mmol) were charged at room temperature and purged with argon for 5 min. Pd $(PPh_3)_4$ (0.08 g, 0.07 mmol) was added at room temperature and purged with argon for 5 min. The reaction mixture was heated at 90° C. for 8 h. The reaction mixture was filtered through celite pad and concentrated under reduced pressure. The crude product was purified by combiflash chromatography ($CH_2Cl_2$:$CH_3OH$=95:5) to afford 3 (0.13 g, 38%1) as a brown solid.

$^1H$ NMR (400 MHz, DMSO-$d_6$): δ ppm 8.42 (d, J=8.8 Hz, 1H), 8.37 (s, 1H), 8.21 (br.s., 1H), 8.09-8.11 (m, 3H), 8.01 (d, J=8.8 Hz, 1H), 7.97 (d, J=8.4 Hz, 2H), 7.79 (d, J=8.8 Hz, 2H), 7.75 (d, J=3.6 Hz, 1H), 7.44 (d, J=8.4 Hz, 2H), 7.11 (d, J=8.8 Hz, 2H), 4.18 (t, J=5.2 Hz, 2H), 3.56 (s, 3H), 3.28 (t, J=5.2 Hz, 2H), 3.16 (s, 3H), 2.82 (s, 3H), 2.79 (t, J=6.4 Hz, 4H), 2.39 (s, 3H).

ESI-MS m/z $[C_{37}H_{35}N_5O_5S+H]^+$ 662.3.

6-methyl-4-{6-[4-(2-(4-methyl-3-oxopiperazin-1-yl)ethoxy)phenyl]quinolin-2-yl}-1H-pyrrolo[2,3-c]pyridin-7(6H)-one (SLU-2283)

To a stirred solution of 3 (0.13 g, 0.19 mmol1) in 2:2:1 of $CH_3OH$, THF, $H_2O$ (10 mL) at 0° C. and KOH (0.04 g, 0.78 mmol) was charged and left to room temperature for 2 h. The reaction mixture was diluted with methylene chloride (100 mL), dried over anhydrous $Na_2SO_4$ and concentrated under reduced pressure. Crude product was purified by combiflash chromatography ($CH_2Cl_2$:$CH_3OH$=95:5). The obtained solid was stirred in $CH_3CN$ (5.0 mL) and filtered and dried under vacuum to afford SLU-2283 (0.07 g, 75%) as an off-white solid.

$^1$H NMR (400 MHz, DMSO-$d_6$): δ ppm 12.16 (s, 1H), 8.40 (d, J=8.8 Hz, 1H), 8.19-8.20 (m, 2H), 8.04-8.10 (m, 3H), 7.79 (d, J=8.8 Hz, 2H), 7.41 (d, J=2.4 Hz, 1H), 7.33 (d, J=2.8 Hz, 1H), 7.11 (d, J=8.8 Hz, 2H), 4.18 (t, J=5.6 Hz, 2H), 3.68 (s, 3H), 3.28 (t, J=5.2 Hz, 2H), 3.13 (s, 2H), 2.82 (s, 3H), 2.77-2.80 (m, 4H).
ESI-MS m/z $[C_{30}H_{29}N_5O_3+H]^+$ 508.2.
HPLC (Method A) 97.9% (AUC), $t_R$=6.07 min.
Synthesis of (R)-4-{4-[(4-(2-(2,4-dimethyl-3-oxopiperazin-1-yl)ethoxy)phenyl)ethynyl]phenyl}-6-methyl-1H-pyrrolo[2,3-c]pyridin-7(6H)-one (SLU-2226)
Scheme 33
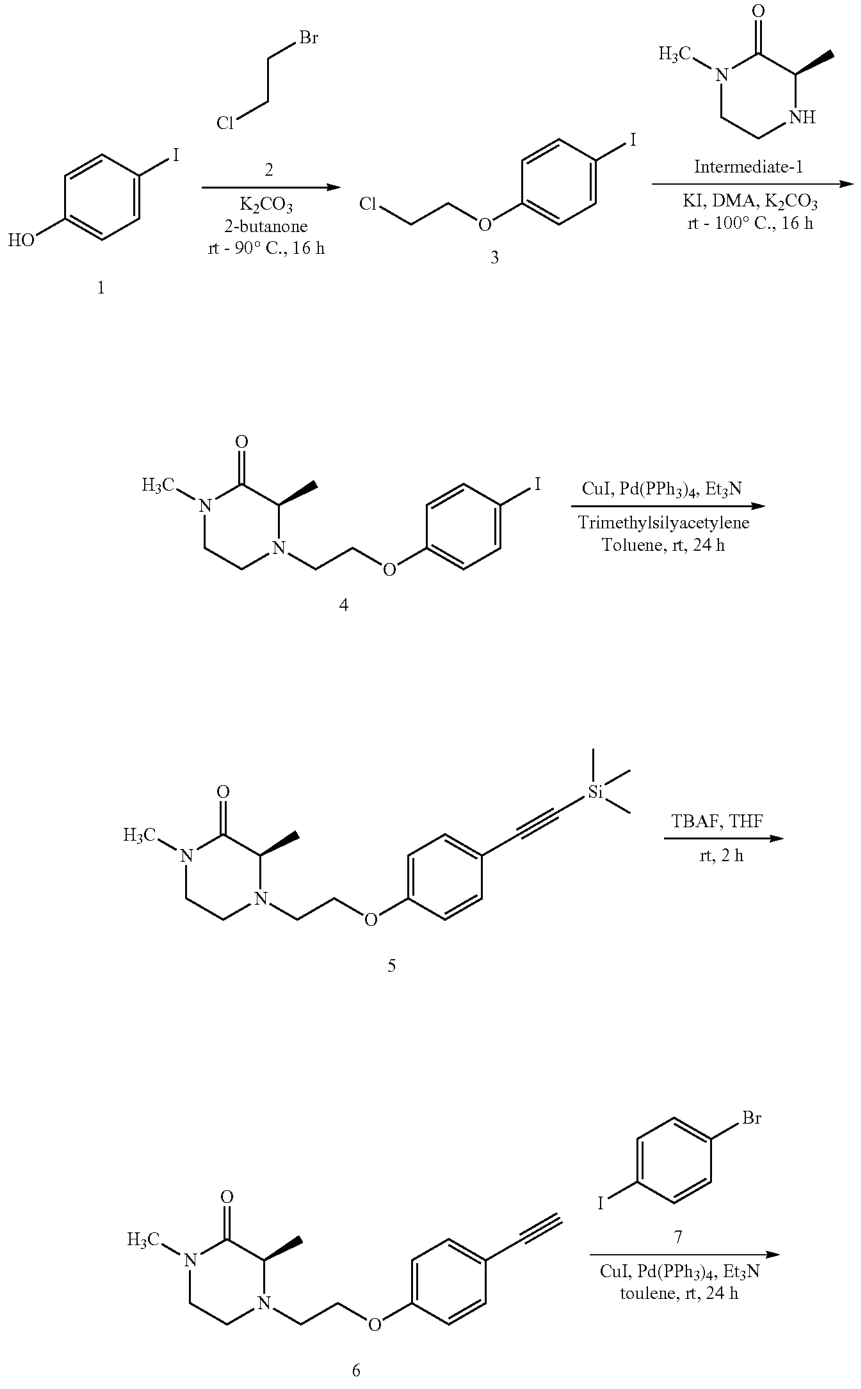

-continued

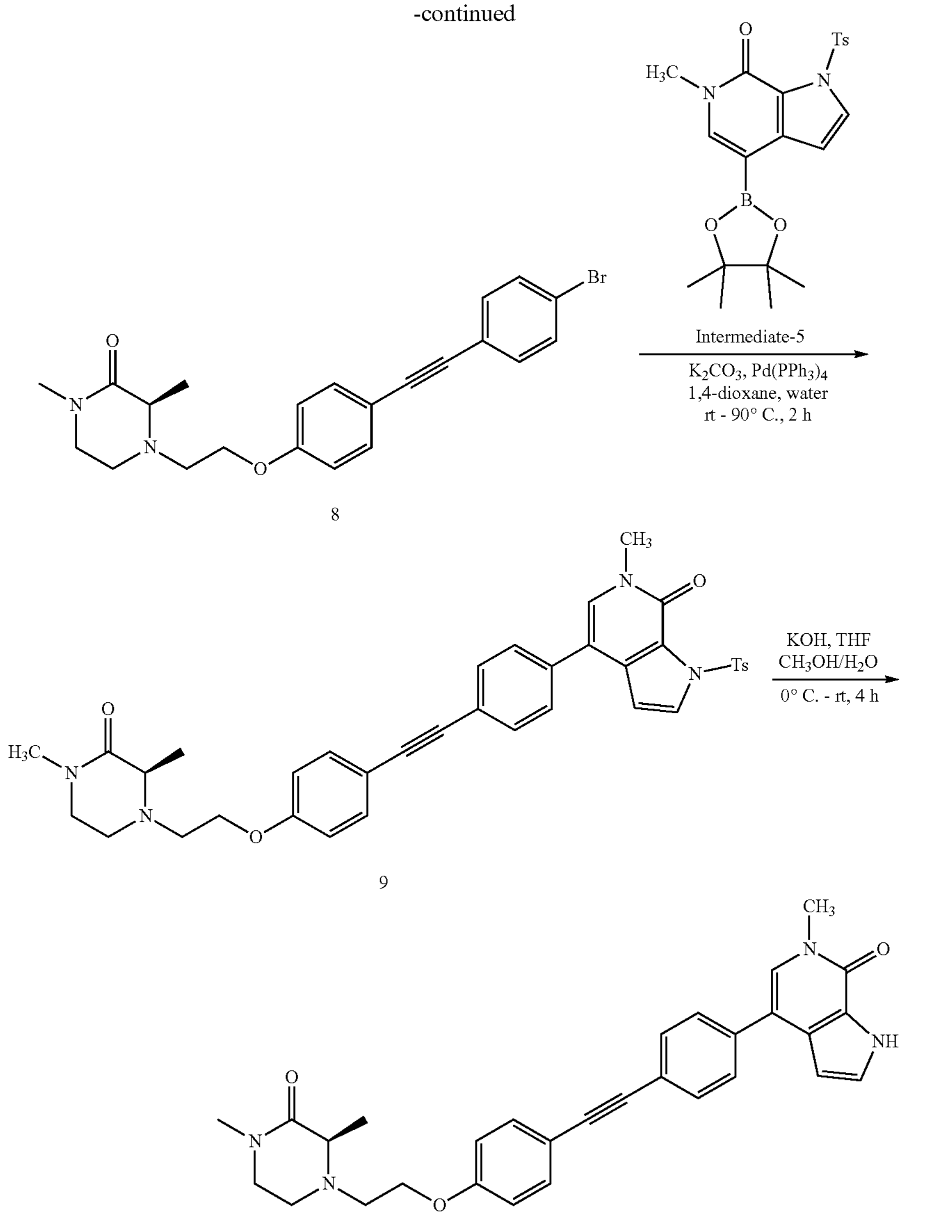

8

9

SLU-2226

1-(2-chloroethoxy)-4-iodobenzene (3)

To a stirred solution of 4-iodo phenol 1 (3.0 g, 13.0 mmol) in 2-butanone (30 mL), $K_2CO_3$ (4.9 g, 36.0 mmol) was charged at room temperature. 1-bromo-2-chloroethane 2 (15 mL, 5.0 vol) was added to the reaction mixture. The reaction mixture was heated at 90° C. for 16 h. The reaction mixture was allowed to ambient temperature and diluted with EtOAc (150 mL). Combined organic layers were washed with water (3×100 mL) followed by brine (1×100 mL). The resulting mixture was dried over anhydrous $Na_2SO_4$ and concentrated under reduced pressure to obtain 3 [3.5 g (crude)] as an off-white solid. This crude material was used for next step without further purification.

$^1$H NMR (400 MHz, $CDCl_3$): δ ppm 7.56 (d, J=8.9 Hz, 2H), 6.69 (d, J=8.9 Hz, 2H), 4.19 (t, J=5.7 Hz, 2H), 3.80 (t, J=5.8 Hz, 2H).

(R)-4-[2-(4-iodophenoxy)ethyl]-1,3-dimethylpiperazin-2-one (4)

To a stirred solution of 3 (12.0 g, 42.4 mmol) in DMA (150 mL), was charged with $K_2CO_3$ (11.6 g, 84.6 mmol) and potassium iodide (3.50 g, 21.20 mmol) at room temperature. Intermediate-1 (5.90 g, 46.6 mmol) was added to the reaction mixture at room temperature. The reaction mixture was heated at 100° C. for 16 h. The reaction mixture was allowed to ambient temperature, diluted with water (20 mL) and extracted with EtOAc (3×30 mL). Combined organic layer dried over anhydrous $Na_2SO_4$ and concentrated under reduced pressure to afford 4 (4.0 g, 26%) as light yellow liquid.

$^1$H NMR (400 MHz, $CDCl_3$): δ ppm 7.55 (d, J=8.7 Hz, 2H), 6.67 (d, J=8.8 Hz, 2H), 4.00-4.09 (m, 2H), 3.23-3.39 (m, 3H), 3.10-3.16 (m, 1H), 2.97-3.05 (m, 1H), 2.94 (s, 3H), 2.82-2.88 (m, 1H), 2.73-2.79 (m, 1H), 1.40 (d, J=6.8 Hz, 3H).

(R)-1,3-dimethyl-4-{2-[4-((trimethylsilyl)ethynyl)phenoxy]ethyl}piperazin-2-one (5)

To a stirred solution of 4 (3.00 g, 0.21 mmol) in toluene (30 mL), were charged with CuI (0.136 g, 0.72 mmol), $Et_3N$ (0.080 g, 8.0 mmol) and trimethylsilylacetylene (0.943 g, 9.60 mL) at room temperature and degassed it with argon for 10 min. $Pd(PPh_3)_4$ (0.277 g, 0.24 mmol) was added to the reaction mixture and stirred for 24 h at room temperature. The reaction mixture was evaporated, diluted with water (40 mL) and extracted with EtOAc (3×40 mL). Combined organic layers were dried over anhydrous $Na_2SO_4$ and concentrated under reduced pressure to afford 5 (2.50 g) as brown liquid ESI-MS m/z $[C_{19}H_{28}N_2O_2Si+H]^+$ 345.3

(R)-4-[2-(4-ethynylphenoxy)ethyl]-1,3-dimethylpiperazin-2-one (6)

To a stirred solution of 5 (1.5 g, 0.21 mmol) in THF (30 mL) was charged with TBAF (1.0 M) in THF (21 mL, 21.7 mmol) at room temperature. The reaction mixture was stirred for 2 h at room temperature. The reaction mixture was evaporated, diluted with water (30 mL) and extracted with EtOAc (3×30 mL). Combined organic layers dried over anhydrous $Na_2SO_4$ and concentrated under reduced pressure to afford 6 (1.20 g) as an off-white solid. The crude material was used for next step without further purification.

$^1$H NMR (400 MHz, $CDCl_3$): δ ppm 7.42 (d, J=8.6 Hz, 2H), 6.83 (d, J=8.8 Hz, 2H), 4.04-4.13 (m, 2H), 3.23-3.39 (m, 3H), 3.11-3.16 (m, 1H), 3.00-3.07 (m, 1H), 2.94 (s, 3H), 2.84-2.91 (m, 1H), 2.74-2.80 (m, 1H), 1.40 (d, J=6.8 Hz, 3H).

(R)-4-{2-[4-((4-bromophenyl)ethynyl)phenoxy]ethyl}-1,3-dimethylpiperazin-2-one (8)

To a stirred solution of 6 (1.0 g, 3.67 mmol) in toluene (15 mL), was charged with CuI (0.062 g, 0.72 mmol), $Et_3N$ (0.0370 g, 3.67 mmol) and 4-bromo iodo benzene 7 (1.03 g, 3.67 mmol) at room temperature and degassed it with argon for 10 min. $Pd(PPh_3)_4$ (0.127 g, 0.11 mmol) was added to the reaction mixture and stirred for 24 h at room temperature. The reaction mixture was evaporated, diluted with water (30 mL) and extracted with EtOAc (3×30 mL). Combined organic layers were dried over anhydrous $Na_2SO_4$ and concentrated under reduced pressure to obtain crude 8 (1.00 g) as brown liquid. The crude material was used for next step without further purification.

$^1$H NMR (400 MHz, $CDCl_3$): δ ppm 7.43-7.47 (m, 4H), 7.35 (d, J=8.3 Hz, 2H), 6.86 (d, J=8.8 Hz, 2H), 4.05-4.15 (m, 2H), 3.23-3.39 (m, 3H), 3.11-3.16 (m, 1H), 3.00-3.07 (m, 1H), 2.94 (s, 3H), 2.84-2.91 (m, 1H), 2.74-2.80 (m, 1H), 1.40 (d, J=6.8 Hz, 3H).

Preparation (R)-4-{4-[(4-(2-(2,4-dimethyl-3-oxopiperazin-1-yl)ethoxy)phenyl)ethynyl]phenyl}-6-methyl-1-tosyl-1H-pyrrolo[2,3-c]pyridin-7(6H)-one (9)

To a stirred solution of 8 (0.5 g, 1.10 mmol) in 1,4-dioxane (20 mL) and $H_2O$ (5.0 mL) were charged with Intermediate-5 (0.269 g, 1.10 mmol) and potassium carbonate (0.3 g, 2.20 mmol) at room temperature and degassed it with argon for 10 min. $Pd(PPh_3)_4$ (0.120 g, 0.11 mmol) was added to the reaction mixture and heated at 90° C. for 2 h. The reaction mixture diluted with water (20 mL) and extracted with EtOAc (2×30 mL). Combined organic layers were dried over anhydrous $Na_2SO_4$ and concentrated under reduced pressure. The crude product was purified by combiflash chromatography ($CH_2Cl_2$:MeOH=95:5) to afford 9 (0.350 g, 46%) as an off-white solid.

$^1$H NMR (400 MHz, $CDCl_3$): δ ppm 8.06 (d, J=3.5 Hz, 1H), 7.96 (d, J=8.3 Hz, 2H), 7.67 (s, 1H), 7.61 (d, J=8.4 Hz, 2H), 7.55 (d, J=8.4 Hz, 2H), 7.50 (d, J=8.7 Hz, 2H), 7.43 (d, J=8.1 Hz, 2H),7.01 (d, J=8.9 Hz, 2H), 6.75 (d, J=3.5 Hz, 1H), 4.14 (t, J=6.0 Hz, 2H), 3.47 (s, 3H), 3.23-3.27 (m, 2H), 3.15 (q, J=6.8 Hz, 1H), 3.04-3.09 (m, 1H), 2.92-2.98 (m, 1H), 2.76-2.82 (m, 4H), 2.67-2.72 (m, 1H), 1.24 (d, J=6.8 Hz, 3H).

Preparation (R)-4-{4-[(4-(2-(2,4-dimethyl-3-oxopiperazin-1-yl)ethoxy)phenyl)ethynyl]phenyl}-6-methyl-1H-pyrrolo[2,3-c]pyridin-7(6H)-one (SLU-2226)

To a stirred solution of 9 (0.240 g, 0.37 mmol) in MeOH (10 mL), $H_2O$ (5.0 mL) and THF (5.0 mL) were charged with potassium hydroxide (0.148 g, 1.89 mmol) at 0° C. and stirred at room temperature for 4 h. The reaction mixture was evaporated, diluted with water (20 mL) and extracted with $CH_2Cl_2$ (3×30 mL). Combined organic layers were dried over anhydrous $Na_2SO_4$ and concentrated under reduced pressure. The crude product was triturated with acetonitrile (5.0 mL), filtered and dried to afford SLU-2226 (0.22 g, 84%) as an off-white solid.

1H NMR (400 MHz, DMSO-$d_6$): δ ppm 12.17 (br.s., 1H), 7.61-7.58 (m, 4H), 7.47-7.51 (m, 3H), 7.37 (s, 1H), 6.84 (d, J=8.8 Hz, 2H), 6.48 (d, J=2.0 Hz, 1H), 4.13 (t, J=6.0 Hz, 2H), 3.59 (s, 3H), 3.24-3.27 (m, 2H), 3.15 (q, J=6.4 Hz, 1H), 3.04-3.09 (m, 1H), 2.92-2.98 (m, 1H), 2.82 (s, 3H), 2.76-2.79 (m, 1H), 2.66-2.72 (m, 1H), 1.24 (d, J=6.8 Hz, 3H).

ESI-MS m/z $[C_{30}H_{30}N_4O_3+H]^+$ 495.2.

HPLC (Method C) 98.8% (AUC), $t_R$=6.99 min.

Synthesis of (R)-4-{4-[4-(2-(2,4-dimethyl-3-oxopiperazin-1-yl)ethoxy)phenethyl]phenyl}-6-methyl-1H-pyrrolo[2,3-c]pyridin-7(6H)-one (SLU-2227)

Scheme 34

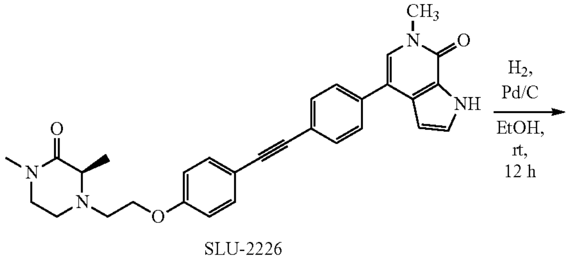

SLU-2226

-continued

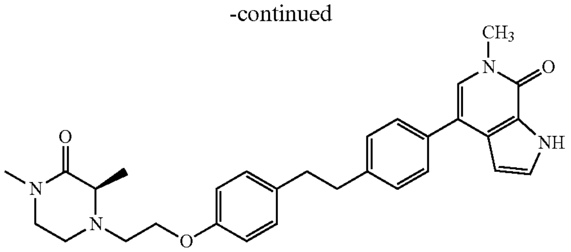

SLU-2227

A solution of SLU-2226 (0.080 g, 0.101 mmol) in EtOH (10 mL) was charged with 10% Pd/C (10 mg) and allowed to stir at room temperature for 12 h under hydrogen atmosphere. The reaction mixture was filtered through celite bed, washed with (30 mL) of MeOH and filtrate was evaporated under reduced pressure to obtain the crude. This crude material was triturated with MTBE (10 mL), filter and dried to afford SLU-2227 (0.060 g, 75%) as an off-white solid.

$^1$H NMR (400 MHz, DMSO-$d_6$) δ ppm 12.13 (br.s., 1H), 7.49 (d, J=7.6 Hz, 2H), 7.29-7.33 (m, 4H), 7.16 (d, J=8.0 Hz, 2H), 6.85 (d, J=8.0 Hz, 2H), 6.42 (s, 1H), 4.00-4.07 (m, 2H), 3.57 (s, 3H), 3.20-3.28 (m, 2H), 3.04-3.19 (m, 2H), 2.86-2.93 (m, 5H), 2.80 (s, 3H), 2.70-2.78 (m, 1H), 2.66-2.69 (m, 1H), 1.24 (d, J=6.4 Hz, 3H).

ESI-MS m/z $[C_{30}H_{34}N_4O_3+H]^+$ 499.4.

HPLC (Method C) 99.8% (AUC), $t_R$=7.03 min.

Synthesis of Compound (R)-4-{6-[5-(2-(2,4-dimethyl-3-oxopiperazin-1-yl)ethoxy)pyridin-2-yl]quinolin-2-yl}-6-methyl-1-tosyl-1H-pyrrolo[2,3-c]pyridin-7(6H)-one (SLU-2213)

Scheme 35

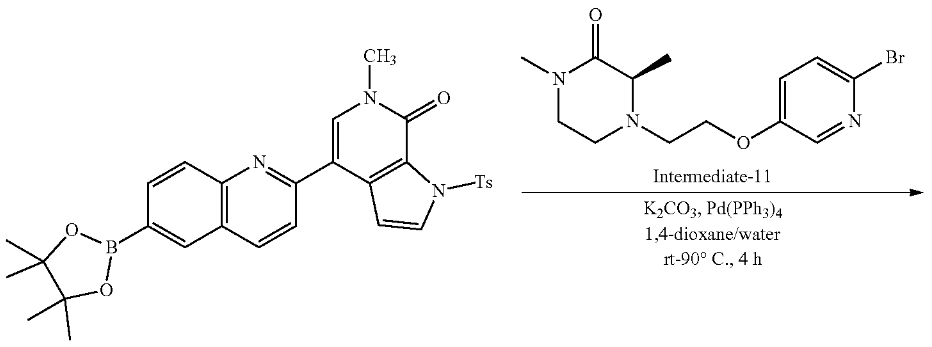

Intermediate-7

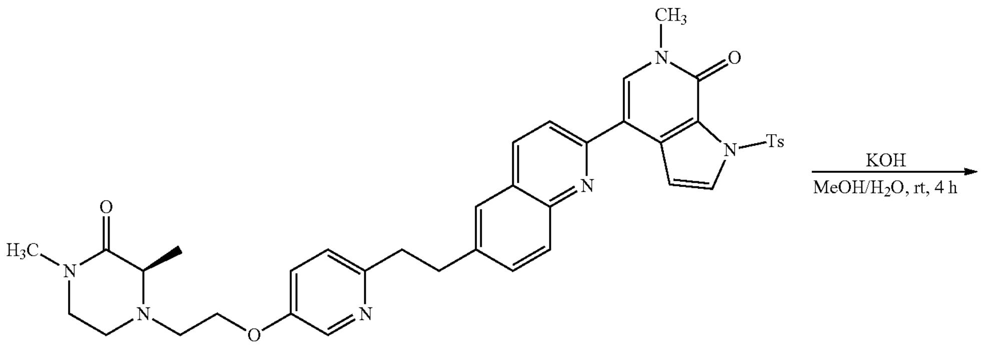

1

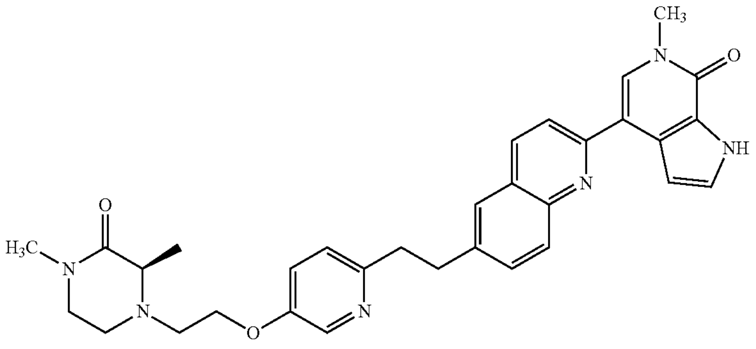

SLU-2213

(R)-4-{6-[5-(2-(2,4-dimethyl-3-oxopiperazin-1-yl) ethoxy)pyridin-2-yl]quinolin-2-yl})-6-methyl-1-tosyl-1H-pyrrolo[2,3-c]pyridin-7(6H)-one (2)

To a stirred solution of Intermediate-7 (0.150 g, 0.45 mmol) in 1,4-dioxane (5 mL) and $H_2O$ (2 mL) were charged with Intermediate-11 (0.253 g, 0.45 mmol) and potassium carbonate (0.124 g, 0.90 mmol), at room temperature and degassed it with argon for 5 min. $Pd(PPh_3)_4$ (0.051 g, 0.04 mmol) was added to the reaction mixture and heated at 90° C. for 4 h. The reaction mixture was diluted with water (20 mL) and extracted with EtOAc (3×20 mL). Combined organic layers were dried over anhydrous $Na_2SO_4$ and concentrated under reduced pressure to obtain crude. The crude product was purified by combiflash chromatography ($CH_2Cl_2$:MeOH=95:5) to afford 1 (0.100 g, 55%) as an off-white solid.

$^1$H NMR (400 MHz, DMSO-$d_6$): δ ppm 8.61 (d, J=1.8 Hz, 1H), 8.44-8.48 (m, 3H), 8.39 (s, 1H), 8.10-8.13 (m, 3H), 8.02 (d, J=8.9 Hz, 1H), 7.97 (d, J=8.3 Hz, 1H), 7.76 (d, J=3.4 Hz, 2H), 7.57 (dd, J=3.0, 8.8 Hz, 1H), 7.44 (d, J=8.1 Hz, 2H), 4.25 (t, J=5.79 Hz, 2H), 3.56 (s, 3H), 3.31-3.33 (m, 2H), 3.27 (t, J=5.0 Hz, 2H), 3.16-3.20 (m, 1H), 3.07-3.13 (m, 1H), 2.69-2.86 (m, 5H), 2.39 (s, 3H), 1.26 (d, J=6.9 Hz, 3H).

(R)-4-{6-[5-(2-(2,4-dimethyl-3-oxopiperazin-1-yl) ethoxy)pyridin-2-yl]quinolin-2-yl}-6-methyl-1-tosyl-1H-pyrrolo[2,3-c]pyridin-7(6H)-one (SLU-2213)

To a stirred solution of 1 (0.1 g, 0.37 mmol) in MeOH (10 mL), $H_2O$ (5.0 mL) and THF (5.0 mL) were charged with potassium hydroxide (0.036 g, 0.66 mmol) at room temperature. The reaction mixture was stirred for 4 h at room temperature. The reaction mixture was evaporated, diluted with water (20 mL) and extracted with $CH_2Cl_2$ (3×30 mL). Combined organic layers were dried over anhydrous $Na_2SO_4$ and concentrated under reduced pressure. The crude product was purified by reverse phase chromatography (ACN:$H_2O$=95:5) to afford SLU-2213 (0.020 g, 28%) as an off white solid.

$^1$H NMR (400 MHz, DMSO-$d_6$): δ ppm 12.16 (br.s., 1H), 8.60 (d, J=1.2 Hz, 1H), 8.43-8.46 (m, 3H), 8.21 (s, 1H), 8.06-8.12 (m, 3H), 7.57 (dd, J=2.8 Hz, 8.8 Hz, 1H), 7.41 (t, J=2.8 Hz, 1H), 7.35 (t, J=2.8 Hz, 1H), 4.25 (t, J=5.6 Hz, 2H), 3.64 (s, 3H), 3.27 (t, J=6.0 Hz, 2H), 3.18 (q, J=6.8 Hz, 1H), 3.07-3.13 (m, 1H), 2.97-3.03 (m, 1H), 2.83-2.86 (m, 1H), 2.82 (s, 3H), 2.69-2.75 (m, 1H), 1.26 (d, J=6.8 Hz, 3H).

ESI-MS m/z $[C_{30}H_{30}N_6O_3+H]^+$ 523.4.

HPLC (Method B) 94.9% (AUC), $t_R$=6.22 min.

Synthesis of 4-{2-[4-(2-((2R,6S)-2,6-dimethylpiperidin-1-yl)ethoxy)phenyl]quinolin-6-yl}-6-methyl-1H-pyrrolo[2,3-c]pyridin-7(6H)-one (SLU-2233)

Scheme 36

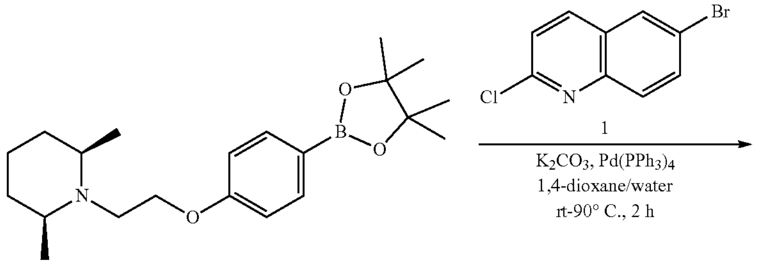

1

Intermediate-8

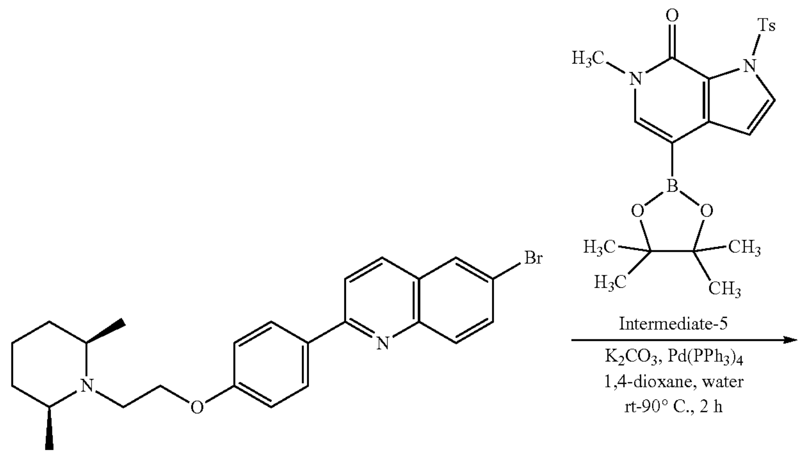

Intermediate-5

2

-continued

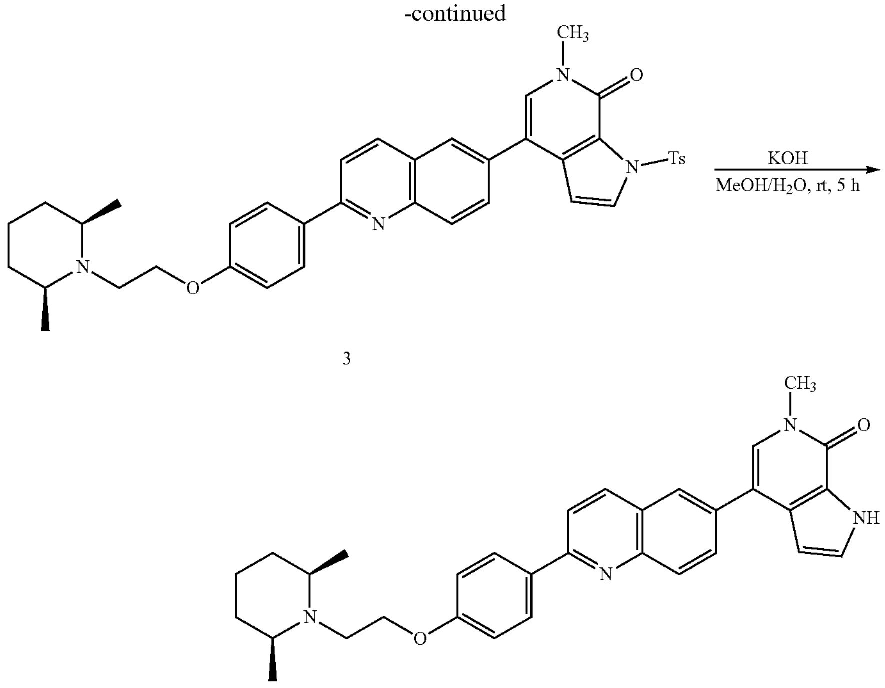

3

SLU-2233

6-bromo-2-{4-[2-((2R,6S)-2,6-dimethylpiperidin-1-yl)ethoxy]phenyl}quinoline (2)

To a stirred solution of Intermediate-8 (0.300 g, 0.83 mmol) in 1,4-dioxane (5 mL) and $H_2O$ (2 mL) was charged with 6-bromo2-chloroquinoline 1 (0.201 g, 0.83 mmol), potassium carbonate (0.229 g, 1.66 mmol) at room temperature and degassed it with argon for 10 min. $Pd(PPh_3)_4$ (0.095 g, 0.08 mmol) was added to the reaction mixture and heated at 90° C. for 2 h. The reaction mixture was diluted with water (20 mL) and extracted with EtOAc (3×20 mL). Combined organic layers were dried over anhydrous $Na_2SO_4$ and concentrated under reduced pressure. The crude product was purified by silica gel chromatography (100% EtOAc) to afford 2 (0.290 g, 60%) an off-white solid.

$^1H$ NMR (400 MHz, $CDCl_3$): δ ppm 8.11 (d, J=8.8 Hz, 2H), 8.07 (d, J=8.7 Hz, 1H), 7.99 (d, J=8.8 Hz, 1H), 7.95 (d, J=2.1 Hz, 1H), 7.85 (d, J=8.6 Hz, 1H), 7.75 (dd, J=2.1, 8.9 Hz, 1H), 7.03 (d, J=8.9 Hz, 2H), 4.07 (t, J=7.1 Hz, 2H), 3.09 (t, J=7.0 Hz, 2H), 2.54-2.62 (m, 2H), 1.65-1.72 (m, 1H), 1.53-1.60 (m, 2H), 1.20-1.38 (m, 3H), 1.20 (d, J=6.1 Hz, 6H).

4-{2-[4-(2-((2R,6S)-2,6-dimethylpiperidin-1-yl)ethoxy)phenyl]quinolin-6-yl}-6-methyl-1-tosyl-1H-pyrrolo[2,3-c]pyridin-7(6H)-one (3)

To a stirred solution of 2 (0.280 g, 0.63 mmol) in 1,4-dioxane (5.0 mL) and $H_2O$ (2.0 mL) was charged with Intermediate-5 (0.269 g, 0.63 mmol), potassium carbonate (0.173 g, 1.26 mmol) at room temperature and degassed it with argon for 10 min. $Pd(PPh_3)_4$ (0.072 g, 0.06 mmol) was added to the reaction mixture and heated at 90° C. for 2 h. The reaction mixture was diluted with water (20 mL) and extracted with EtOAc (2×30 mL). Combined organic layers were dried over anhydrous $Na_2SO_4$ and concentrated under reduced pressure. The crude product was purified by combiflash chromatography ($CH_2Cl_2$:MeOH=95:5) to afford 3 (0.240 g, 56%) as an off-white solid.

$^1H$ NMR (400 MHz, $CDCl_3$): δ ppm 8.14-8.20 (m, 4H), 8.05 (d, J=8.3 Hz, 2H), 7.98 (d, J=3.4 Hz, 1H), 7.88 (d, J=8.7 Hz, 1H), 7.83 (d, J=1.4 Hz, 1H), 7.78 (dd, J=2.0, 8.4 Hz, 1H), 7.33 (d, J=8.1 Hz, 2H), 7.20 (s, 1H), 7.05 (d, J=8.8 Hz, 2H), 6.65 (d, J=3.4 Hz, 1H), 4.11 (t, J=7.0 Hz, 2H), 3.62 (s, 3H), 3.01-3.91 (m, 2H), 1.59-1.61 (m, 1H), 1.20-1.41 (m, 9H).

4-{2-[4-(2-((2R,6S)-2,6-dimethylpiperidin-1-yl)ethoxy)phenyl]quinolin-6-yl}-6-methyl-1H-pyrrolo[2,3-c]pyridin-7(6H)-one (SLU-2233)

To a stirred solution of 3 (0.240 g, 0.37 mmol) in MeOH (10 mL), $H_2O$ (5.0 mL) and THF (5.0 mL) was charged with potassium hydroxide (0.104 g, 1.89 mmol) at room temperature and stirred for 5 h at room temperature. The reaction mixture was evaporated, diluted with water (20 mL) and extracted with $CH_2Cl_2$ (3×30 mL). Combined organic layers were dried over anhydrous $Na_2SO_4$ and concentrated under reduced pressure. The crude product was purified by reverse phase combiflash chromatography (ACN:$H_2O$=95:5) to afford SLU-2233 (0.020 g, 11%) as an off-white solid.

$^1H$ NMR (400 MHz, DMSO-$d_6$) δ ppm 12.2 (br.s., 1H), 8.46 (d, J=8.8 Hz, 1H), 8.26 (d, J=8.4 Hz, 2H), 8.18 (d, J=2.0 Hz, 1H), 8.01 (dd, J=2.0, 8.8 Hz, 1H), 7.99-8.02 (m, 1H), 7.60 (s, 1H), 7.41 (t, J=2.4 Hz, 1H), 7.11 (d, J=8.4 Hz, 2H), 6.61 (t, J=2.4 Hz, 1H), 4.10-3.98 (m, 2H), 3.63 (s, 3H), 2.89-3.10 (m, 2H), 2.58-2.50 (m, 2H), 1.45-1.61 (m, 3H), 1.23-1.38 (m, 3H), 1.10-1.18 (m, 6H).

ESI-MS m/z $[C_{32}H_{34}N_4O_2+H]^+$ 507.2.

HPLC (Method A) 94.2% (AUC), $t_R$=6.25 min.

Synthesis of 6-methyl-4-{2-[4-(2-(2,2,4-trimethyl-3-oxopiperazin-1-yl)ethoxy)phenyl]quinolin-6-yl}-1H-pyrrolo[2,3-c]pyridin-7(6H)-one (SLU-2241)

Scheme 37

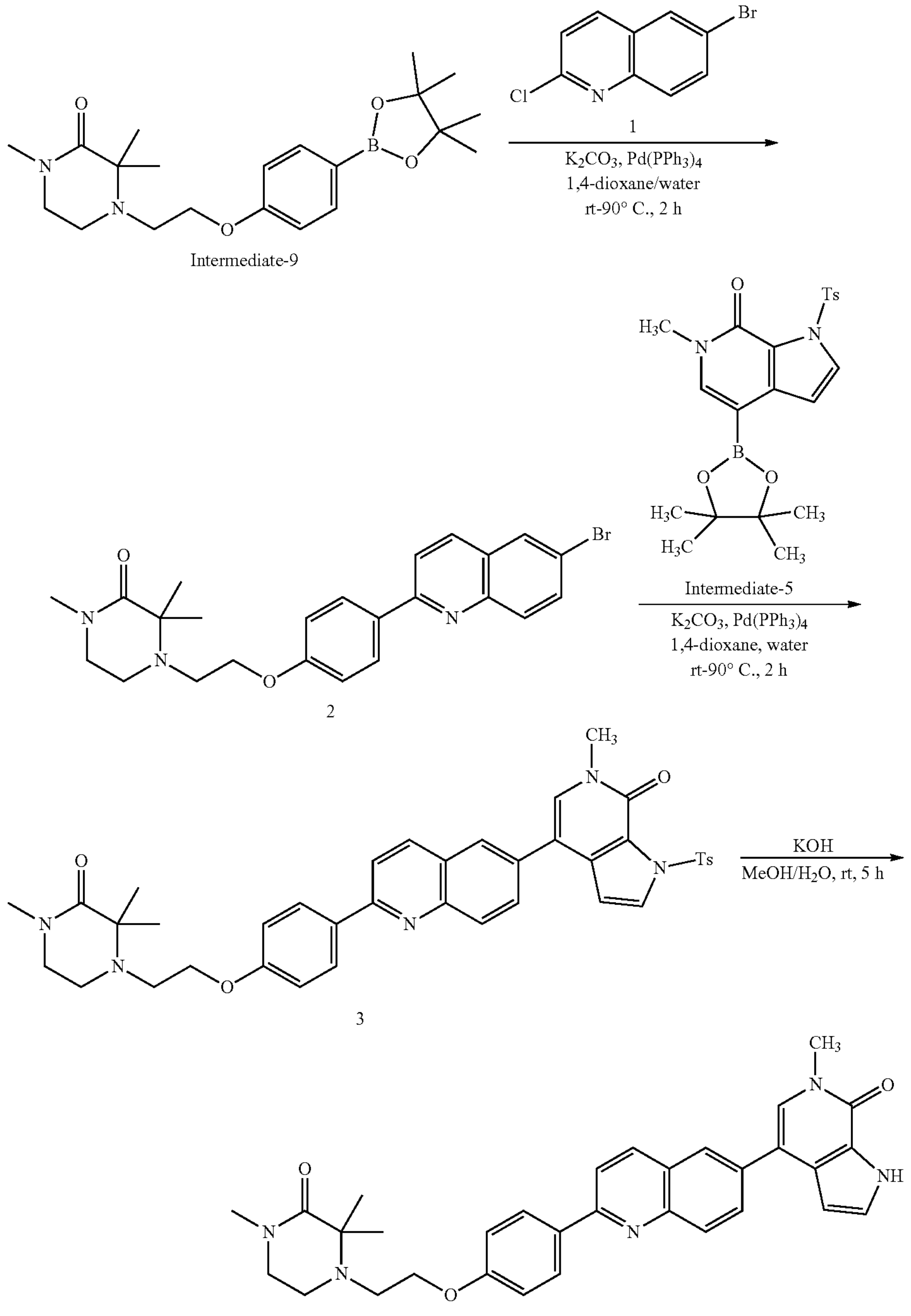

1

Intermediate-9

Intermediate-5

2

3

SLU-2241

4-{2-[4-(6-bromoquinolin-2-yl)phenoxy]ethyl}-1,3,3-trimethylpiperazin-2-one (2)

To a stirred solution of Intermediate-9 (0.40 g, 1.03 mmol3) in 1,4-dioxane (5.0 mL) and $H_2O$ (2.0 mL) were charged with 6-bromo2-chloroquinoline 1 (0.248 g, 1.03 mmol) and potassium carbonate (0.284 g, 2.06 mmol) at room temperature and degassed it with argon for 5 min. $Pd(PPh_3)_4$ (0.118 g, 0.10 mmol) was added to the reaction mixture and heated at 90° C. for 2 h. The reaction mixture was diluted with water (20 mL) and extracted with EtOAc (2×30 mL). Combined organic layers were dried over anhydrous $Na_2SO_4$ and concentrated under reduced pressure. The crude product was purified by combiflash chromatography (100% EtOAc) to afford 2 (0.40 g, 83%) as an off-white solid.

$^1$H NMR (400 MHz, $CDCl_3$): δ ppm 8.12 (d, J=8.5 Hz, 3H), 8.08 (d, J=8.5 Hz, 2H), 7.98 (d, J=8.8 Hz, 1H), 7.96 (d, J=2.6 Hz, 1H), 7.85 (d, J=8.7 Hz, 1H), 7.76 (dd, J=2.2, 8.9 Hz, 1H), 7.03 (d, J=8.8 Hz, 1H), 4.10 (t, J=6.1 Hz, 2H), 3.30 (t, J=5.1 Hz, 2H), 2.97 (t, J=5.8 Hz, 2H), 2.93 (s, 3H), 2.87 (t, J=6.0 Hz, 2H), 1.35 (s, 6H).

6-methyl-1-tosyl-4-{2-[4-(2-(2,2,4-trimethyl-3-oxopiperazin-1-yl)ethoxy)phenyl]quinolin-6-yl}-1H-pyrrolo[2,3-c]pyridin-7(6H)-one (3)

To a stirred solution of 2 (0.20 g, 0.42 mmol6) in 1,4-dioxane (5.0 mL) and $H_2O$ (2.0 mL) were charged with Intermediate-5 (0.183 g, 0.42 mmol), potassium carbonate (0.112 g, 0.84 mmol) at room temperature and degassed it with argon for 5 min. $Pd(PPh_3)_4$ (0.048 g, 0.10 mmol) was added to the reaction mixture and heated at 90° C. for 2 h. The reaction mixture was evaporated, diluted with water (20 mL) and extracted with EtOAc (3×30 mL). Combined organic layers were dried over anhydrous $Na_2SO_4$ and concentrated under reduced pressure. The crude product was purified ($CH_2Cl_2$:MeOH=95:5) to afford 3 (0.20 g, 45%9) as an off-white solid.

$^1$H NMR (400 MHz, $CDCl_3$): δ ppm 8.14-8.20 (m, 4H), 8.06 (d, J=8.3 Hz, 2H), 7.98 (d, J=3.4 Hz, 1H), 7.88 (d, J=8.7 Hz, 1H), 7.83 (d, J=1.5 Hz, 1H), 7.78 (dd, J=1.7, 8.6 Hz, 1H), 7.34 (d, J=8.1 Hz, 1H), 7.20 (s, 1H), 7.05 (d, J=8.7 Hz, 2H), 6.66 (d, J=3.4 Hz, 1H), 4.12 (t, J=6.0 Hz, 2H), 3.62 (s, 3H), 3.31 (t, J=5.2 Hz, 2H), 2.98 (t, J=5.4 Hz, 2H), 2.94 (s, 3H), 2.88 (t, J=6.0 Hz, 2H), 2.42 (s, 3H), 1.36 (s, 6H).

6-methyl-4-{2-[4-(2-(2,2,4-trimethyl-3-oxopiperazin-1-yl)ethoxy)phenyl]quinolin-6-yl}-1H-pyrrolo[2,3-c]pyridin-7(6H)-one (SLU-2241)

To a stirred solution of 3 (0.150 g, 0.22 mmol9) in MeOH (10 mL), $H_2O$ (5.0 mL) and THF (5 mL) was charged with potassium hydroxide (0.062 g, 1.10 mmol) at room temperature. The reaction mixture was stirred for 5 h at room tempetature. The reaction mixture was evaporated, diluted with water (20 mL) and extracted with $CH_2Cl_2$ (3×30 mL). Combined organic layers were dried over anhydrous $Na_2SO_4$ and concentrated under reduced pressure. The crude product was triturated with acetonitrile (5.0 mL), filtered and dried to afford SLU-2241 (0.100 g, 66%) as an off-white solid.

1H NMR (400 MHz, DMSO-$d_6$) δ ppm 12.2 (br.s., 1H), 8.46 (d, J=8.8 Hz, 1H), 8.26 (d, J=8.4 Hz, 2H), 8.18 (br.s., 1H), 8.08-8.14 (m, 2H), 8.01 (d, J=8.4 Hz, 1H), 7.60 (s, 1H), 7.41 (m, 1H), 7.11 (d, J=8.8 Hz, 2H), 6.61 (m, 1H), 4.12 (t, J=6.0 Hz, 2H), 3.63 (s, 3H), 3.24 (t, J=5.2 Hz, 2H), 2.91 (t, J=4.8 Hz, 2H), 2.80 (s, 3H), 2.78-2.81 (m, 2H), 1.22 (s, 6H).

ESI-MS m/z $[C_{30}H_{28}F_2N_4O_2+H]^+$ 536.3.

HPLC (Method A) 96.1% (AUC), $t_R$=6.08 min.

Synthesis of 4-{6-[4-(2-((2R,6S)-2,6-dimethylpiperidin-1-yl)ethoxy)phenyl]quinolin-2-yl}-6-methyl-1H-pyrrolo[2,3-c]pyridin-7(6H)-one (SLU-2279)

Scheme 38

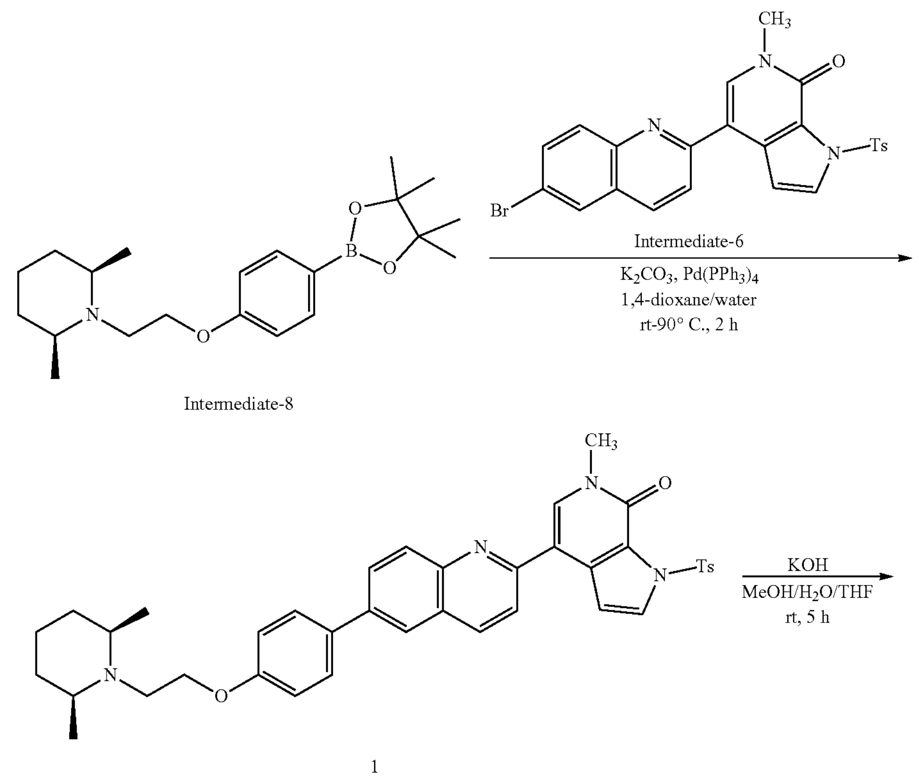

1

-continued

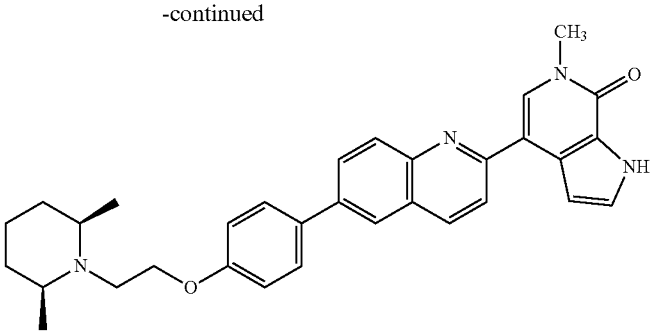

SLU-2279

4-{6-[4-(2-((2R,6S)-2,6-dimethylpiperidin-1-yl)ethoxy)phenyl]quinolin-2-yl}-6-methyl-1-tosyl-1H-pyrrolo[2,3-c]pyridin-7(6H)-one (1)

To a stirred solution of Intermediate-8 (0.100 g, 0.27 mmol0) in 1,4-dioxane (5.0 mL) and $H_2O$ (2.0 mL) were charged with Intermediate-6 (0.136 g, 0.55 mmol6) and potassium carbonate (0.148 g, 1.10 mmol) at room temperature and degassed it with argon for 5 min. $Pd(PPh_3)_4$ (0.031 g, 0.02 mmol) was added to the reaction mixture and heated at 90° C. for 2 h. The reaction mixture was diluted with $H_2O$ (20 mL) and extracted with EtOAc (2x30 mL). Organic layer was dried over anhydrous $Na_2SO_4$ and concentrated under reduced pressure to afford 1 (0.150 g9) as an off-white solid.

ESI-MS m/z $[C_{39}H_{40}N_4O_4S+H]^+$ 661.5.

4-{6-[4-(2-((2R,6S)-2,6-dimethylpiperidin-1-yl)ethoxy)phenyl]quinolin-2-yl}-6-methyl-1H-pyrrolo[2,3-c]pyridin-7(6H)-one (SLU-2279)

To a solution of 1 (0.280 g, 0.42 mmol2) in MeOH (10 mL), $H_2O$ (5.0 mL) and THF (5.0 mL) were charged with potassium hydroxide (0.116 g, 2.1 mmol) at room temperature. The reaction mixture was stirred for 5 h at room temperature. The reaction mixture was evaporated, diluted with $H_2O$ (20 mL) and extracted with $CH_2Cl_2$ (3x30 mL). Combined organic layer was dried over anhydrous $Na_2SO_4$ and concentrated under reduced pressure. The crude product was triturated with acetonitrile (5.0 mL), with MeOH (5.0 mL), filtered and dried to afford SLU-2279 (0.093 g, 44%) as an off-white solid.

$^1H$ NMR (400 MHz, DMSO-$d_6$) δ ppm 12.1 (br.s., 1H), 8.40 (d, J=8.8 Hz, 1H), 8.19 (s, 2H), 8.05-8.11 (m, 3H), 7.70 (d, J=8.0 Hz, 2H), 7.41 (t, J=2.4 Hz, 1H), 7.34 (t, J=2.4 Hz, 1H), 7.08 (d, J=8.0 Hz, 2H), 3.98-4.09 (m, 2H), 3.68 (s, 3H), 2.93-3.10 (m, 2H), 2.58-2.50 (m, 2H), 1.51-1.61 (m, 3H), 1.23-1.38 (m, 3H), 1.10-1.18 (d, J=5.2 Hz, 6H).

ESI-MS m/z $[C_{32}H_{34}N_4O_2+H]^+$ 507.3.

HPLC (Method A) 95.7% (AUC), $t_R$=6.3 min.

Synthesis of (R)-4-{2-[4-(2-(2,4-dimethyl-5-oxopiperazin-1-yl)ethoxy)phenyl]quinolin-6-yl}-6-methyl-1H-pyrrolo[2,3-c]pyridin-7(6H)-one (SLU-2286)

Scheme 39

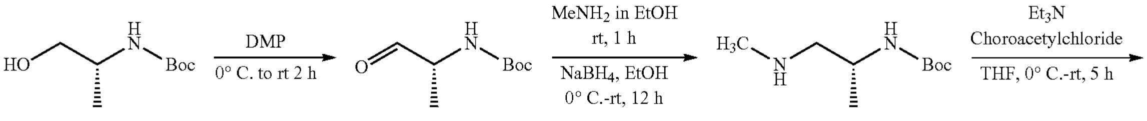

1 2 3

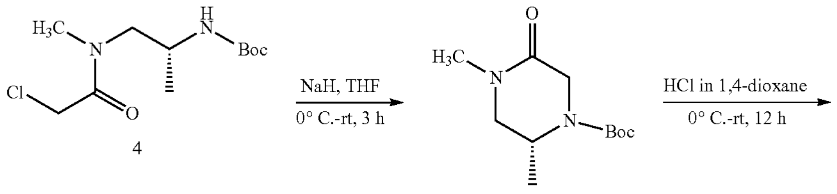

4 5

-continued
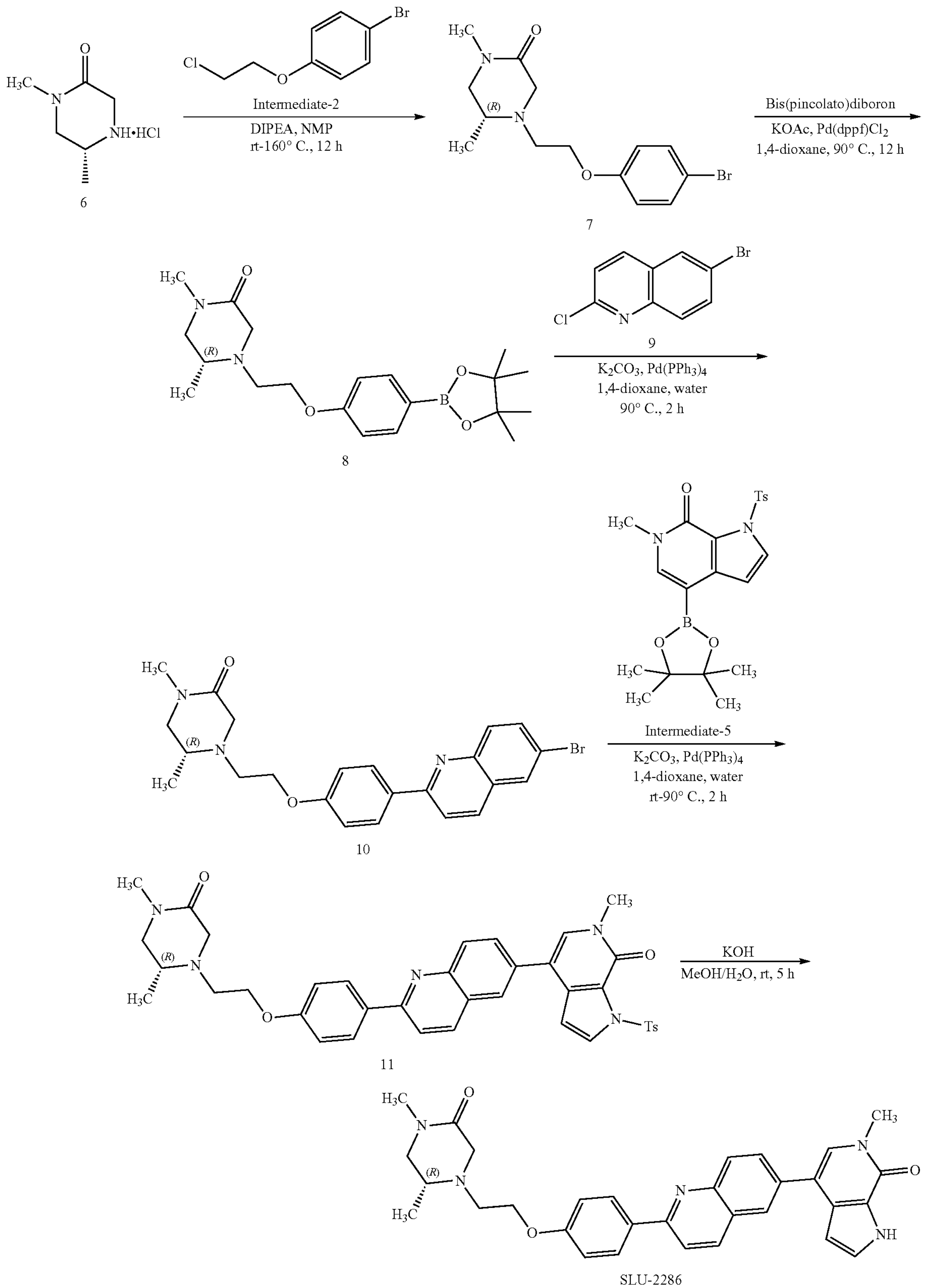
6
7
8
9
10
11
SLU-2286

(R)-tert-butyl (1-oxopropan-2-yl)carbamate (2)

To a stirred solution 1 (0.500 g, 2.85 mmol) in $CH_2Cl_2$ (100 mL), Dess-Martin periodinane (1.33 g, 3.14 mmol) was charged portion wise at room temperature. The reaction mixture was stirred for 2 h at room temperature. TLC indicated at which time the reaction gone to completion. The mixture was filtered through celite bed and washed with $CH_2Cl_2$ (20 mL). The crude product was purified by combiflash chromatography (Hexanes:EtOAc=70:30) to afford 2 (0.400 g, 81%) as an off-white solid.

$^1H$ NMR (400 MHz, $CDCl_3$): δ ppm 9.56 (s, 1H), 5.15 (s, 1H), 4.24 (t, J=6.8 Hz, 1H), 1.45 (s, 9H), 1.34 (d, J=7.2 Hz, 3H).

(R)-tert-butyl [1-(methylamino)propan-2-yl]carbamate (3)

To a stirred solution of 2 (0.400 g, 2.2 mmol) in ethanol (5.0 mL), methylamine in ethanol (2 M, 1.7 mL, 3.4 mmol) was charged dropwise at room temperature and stirred for 1 h. $NaBH_4$ (0.162 g, 3.4 mmol) was added to the reaction mixture portion wise at 0° C. and stirred for 12 h at room temperature. TLC indicated at which time the reaction gone to completion. The reaction mixture was concentrated, diluted with water (20 mL) and extracted with EtOAc (3×20 mL). Combined organic layers were dried over $Na_2SO_4$ and concentrated under reduced pressure. The crude product was used for next for next step without purification of 3 [0.300 g (crude)6] as an colourless liquid.

$^1H$ NMR (400 MHz, $CD_3OD$): δ ppm 3.61-3.68 (m, 1H), 2.42-2.48 (m, 2H), 2.25 (s, 3H), 1.33 (s, 9H), 1.00 (d, J=6.8 Hz, 3H).

(R)-tert-butyl [1-(2-chloro-N-methylacetamido)propan-2-yl]carbamate (4)

To a stirred solution of 3 (4.00 g, 21.2 mmol8) in THF (50 mL), $Et_3N$ (12.8 g, 127.2 mmol) and chloroacetylchloride (7.10 g, 63.8 mmol) was charged dropwise at 0° C. and stirred for 5 h at room temperature. TLC indicated at which time the reaction gone to completion. The mixture was diluted with water (100 mL) and extracted with EtOAc (3×100 mL). Organic layer was separated, dried over anhydrous $Na_2SO_4$ and concentrated under reduced pressure. The crude product was purified by combiflash chromatography (EtOAc:Hexanes=1:1) to afford 4 (4.00 g, 71%) as light brown liquid.

$^1H$ NMR (400 MHz, $CDCl_3$) δ ppm 4.69-4.71 (m, 1H), 3.85-3.90 (m, 1H), 3.75-3.81 (m, 1H), 3.12 (s, 3H), 3.05-3.08 (m, 2H), 1.47 (s, 9H), 1.14 (d, J=6.4 Hz, 3H).

(R)-tert-butyl 2-methyl-5-oxopiperazine-1-carboxylate (5)

To a stirred solution 4 (3.60 g, 13.6 mmol3), in THF (50 mL), 60% NaH (0.981 g, 40.9 mmol) was charged portionwise at 0° C. and stirred for 3 h at room temperature. TLC indicated at which time the reaction gone to completion. The mixture was diluted with ice cold water (250 mL) and extracted with EtAOc (3×150 mL). Organic layer was separated, dried over anhydrous $Na_2SO_4$ and concentrated under reduced pressure. This crude product was used for next step without purification of 5 (2.70 g) as an off-white gum.

$^1H$ NMR (400 MHz, $CDCl_3$) δ ppm 4.46 (br.s., 1H), 4.28 (d, J=18.4 Hz, 1H), 3.78 (d, J=18.5 Hz, 1H), 3.68 (dd, J=4.2, 12.2 Hz, 1H), 3.00 (s, 3H), 2.97 (d, J=1.7 Hz, 1H), 1.46 (s, 9H), 1.23 (d, J=6.9 Hz, 3H).

(R)-1,5-dimethylpiperazin-2-one hydrochloride (6)

To a stirred solution 5 (1.50 g, 6.5 mmol8), in dioxane (15 mL), HCl in dioxane (15 mL) was charged dropwise at 0° C. and stirred for 12 h at room temperature. TLC indicated at which time the reaction gone to completion. The mixture was concentrated under reduced pressure. This crude product was used for next step without purification of 6 (1.50 g2) as an off-white gum.

$^1H$ NMR (400 MHz, DMSO-$d_6$): δ ppm 10.3 (br.s., 1H), 10.20 (br.s., 1H), 5.42 (br.s., 2H), 3.68-3.74 (m, 1H), 3.60-3.65 (m, 1H), 3.46 (d, J=2.68 Hz, 2H), 2.85 (s, 3H), 1.31 (d, J=6.4 Hz, 3H).

(R)-4-[2-(4-bromophenoxy)ethyl]-1,5-dimethylpiperazin-2-one (7)

To a stirred solution of Intermediate-2 (2.30 g, 10.15 mmol1) in NMP was charged with 6 (1.30 g, 10.15 mmol2), DIPEA (7.80 g, 60.9 mmol) at room temperature and heated at 160° C. for 6 h in sand bath. TLC indicated at which time the reaction gone to completion. The reaction mixture was diluted with water (100 mL) and extracted with EtOAc (3×150 mL). Organic layer was separated, dried over anhydrous $Na_2SO_4$ and concentrated under reduced pressure. The crude product was purified by combiflash chromatography ($CH_2Cl_2$:$CH_3OH$=95:5) to afford 7 (1.80 g, 54%4) as an off-white gum.

$^1H$ NMR (400 MHz, $CDCl_3$) δ ppm 7.36 (d, J=8.9 Hz, 2H), 6.77 (d, J=8.8 Hz, 2H), 4.03 (t, J=5.6 Hz, 2H), 3.49 (d, J=16.7 Hz, 2H), 3.23-3.31 (m, 2H), 3.00-3.11 (m, 3H), 2.94 (s, 3H), 2.74-2.81 (m, 1H), 1.17 (d, J=6.4 Hz, 3H).

(R)-1,5-dimethyl-4-{2-[4-(4,4,5,5-tetramethyl-1,3,2-dioxaborolan-2-yl)phenoxy]ethyl}piperazin-2-one (8)

To a stirred solution 7 (1.80 g, 5.50 mmol4), bis(pincolato)diboron (1.68 g, 6.60 mmol) and Pd(dppf)$Cl_2$ (0.402 g, 0.55 mmol) and KOAc (1.05 g, 1.10 mmol) in dioxane (20 mL) was heated at 90° C. for 12 h. TLC indicated at which time the reaction gone to completion. The mixture was diluted with water (30 mL) and extracted with EtOAc (3×50 mL). Organic layer was separated, dried over anhydrous $Na_2SO_4$ and concentrated under reduced pressure. The crude product was purified by combiflash chromatography ($CH_2Cl_2$:$CH_3OH$=96:4) to afford 8 (1.80 g, 90%) as a brown gummy solid.

$^1H$ NMR (400 MHz, $CDCl_3$) δ ppm 7.73 (d, J=8.7 Hz, 2H), 6.87 (d, J=8.6 Hz, 2H), 4.08-4.11 (m, 2H), 3.50 (d, J=17.2 Hz, 2H) 3.25-3.31 (m, 2H), 2.98-3.10 (m, 3H), 2.93 (s, 3H), 2.78-2.81 (m, 1H), 1.33 (s, 12H), 1.16 (d, J=6.1 Hz, 3H).

(R)-4-{2-[4-(6-bromoquinolin-2-yl)phenoxy]ethyl}-1,5-dimethylpiperazin-2-one (10)

To a stirred solution 8 (0.200 g, 0.53 mmol0), 6-bromo 2-chloroquinoline 9 (0.128 g, 0.53 mmol) and $K_2CO_3$ (0.146 g, 1.06 mmol) in dioxane (20 mL) and water (5 mL) and degassed it with argon. $(PPh_3)_4$ (0.092 g, 0.08 mmol) was added to the reaction mixture and heated at 90° C. for 2 h.

TLC indicated at which time the reaction gone to completion. The mixture was diluted with water (20 mL) and extracted with EtOAc (3×30 mL). Organic layer was separated, dried over anhydrous $Na_2SO_4$ and concentrated under reduced pressure. The crude product was purified by combiflash chromatography ($CH_2Cl_2$:$CH_3OH$=96:4) to afford 10 (0.080 g, 33%0) as an off-white gum.

$^1$H NMR (300 MHz, DMSO-$d_6$) δ ppm 8.39 (d, J=8.6 Hz, 1H), 8.23-8.27 (m, 3H), 8.17 (d, J=8.8 Hz, 1H), 7.96 (d, J=8.9 Hz, 1H), 7.86 (dd, J=2.3, 8.9 Hz, 1H), 7.11 (d, J=8.9 Hz, 2H), 4.16 (t, J=5.8 Hz, 2H), 3.27-3.35 (m, 1H), 3.13 (d, J=16.6 Hz, 1H), 2.93-3.04 (m, 3H), 2.81 (s, 3H), 2.72-2.78 (m, 1H), 1.06 (d, J=6.1 Hz, 1H).

(R)-4-{2-[4-(2-(2,4-dimethyl-5-oxopiperazin-1-yl)ethoxy)phenyl]quinolin-6-yl}-6-methyl-1-tosyl-1H-pyrrolo[2,3-c]pyridin-7(6H)-one (11)

To a stirred solution of 10 (0.130 g, 0.28 mmol0), Intermediate-5 (0.122 g, 0.28 mmol) and $K_2CO_3$ (0.077 g, 0.56 mmol) in dioxane (5.0 mL) and water (2.0 mL) at room temperature and degassed it with argon for 5 min. $Pd(PPh_3)_4$ (0.032 g, 0.02 mmol) was added to the reaction mixture and heated at 90° C. for 2 h. TLC indicated at which time the reaction gone to completion. The mixture was diluted with water (10 mL) and extracted with EtOAc (3×25 mL). Organic layer was separated, dried over anhydrous $Na_2SO_4$ and concentrated under reduced pressure. The crude product was purified by combiflash chromatography ($CH_2Cl_2$:$CH_3OH$=96:4) to afford 11 (0.130 g1) as an off-white solid. This crude product was used for next step without purification.

ESI-MS m/z $[C_{38}H_{37}N_5O_5S+H]^+$ 676.3.

(R)-4-{2-[4-(2-(2,4-dimethyl-5-oxopiperazin-1-yl)ethoxy)phenyl]quinolin-6-yl}-6-methyl-1H-pyrrolo[2,3-c]pyridin-7(6H)-one (SLU-2286)

To a stirred solution 11 (0.130 g, 0.19 mmol) in MeOH (3 mL), water (1.0 mL), THF (2.0 mL) was charged with potassium hydroxide (0.052 g, 0.96 mmol) at room temperature and stirred for 5 h at room temperature. The reaction mixture was evaporated, diluted with water (10 mL) and extracted with EtOAc (3×20 mL). Organic layer was dried over anhydrous $Na_2SO_4$ and concentrated under reduced pressure. The crude product was purified by combiflash chromatography ($CH_2Cl_2$:$CH_3OH$=96:4) to afford SLU-2286 (0.039 g, 39%) as an off-white solid.

$^1$H NMR (400 MHz, DMSO-$d_6$) δ ppm 12.2 (br.s., 1H), 8.46 (d, J=8.4 Hz, 1H), 8.26 (d, J=8.8 Hz, 2H), 8.09-8.17 (m, 3H), 8.01 (dd, J=1.6, 8.8 Hz, 1H), 7.60 (s, 1H), 7.41 (t, J=2.4 Hz, 1H), 7.12 (d, J=9.2 Hz, 2H), 6.60-6.62 (m, 1H), 4.17 (t, J=5.2 Hz, 2H), 3.63 (s, 3H), 3.29-3.39 (m, 2H), 3.14 (d, J=16.8 Hz, 1H), 2.97-3.05 (m, 3H), 2.81 (s, 3H), 2.71-2.79 (m, 1H), 1.09 (d, J=6.0 Hz, 3H).

ESI-MS m/z $[C_{31}H_{31}N_5O_3+H]^+$ 522.2.

HPLC (Method A) 95.7% (AUC), $t_R$=6.05 min.

Synthesis of 4-{2-[4-(2-(4,4-difluoropiperidin-1-yl)ethoxy)phenyl]quinolin-6-yl}-6-methyl-1H-pyrrolo[2,3-c]pyridin-7(6H)-one (SLU-2285)

Scheme 40

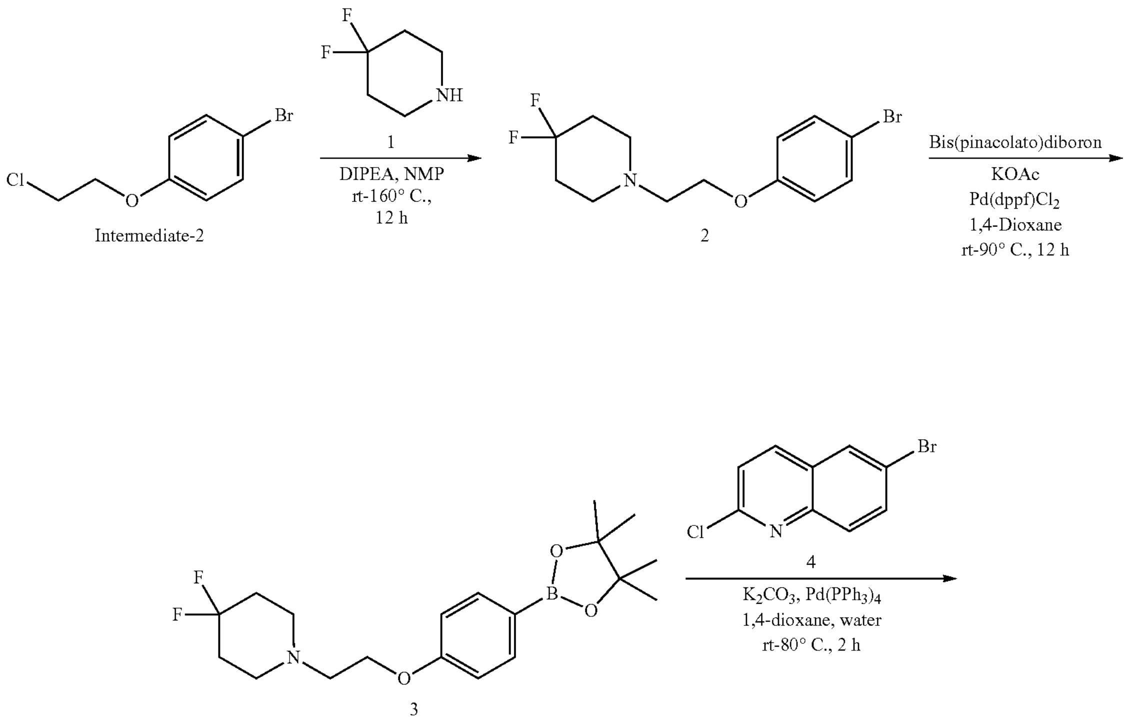

-continued

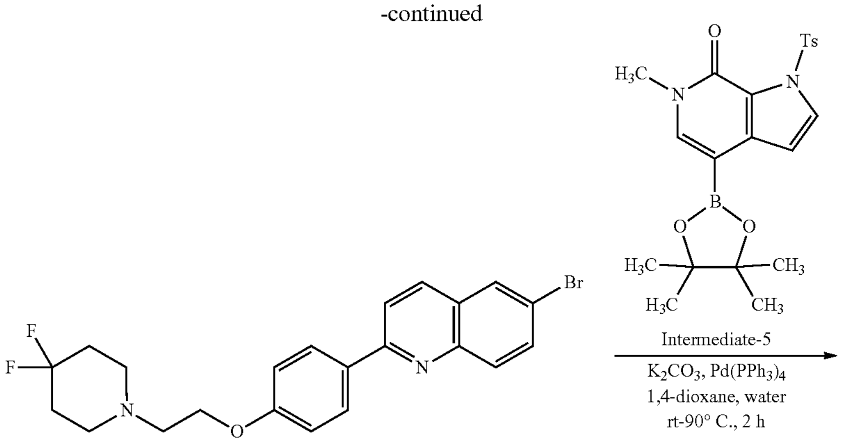

5

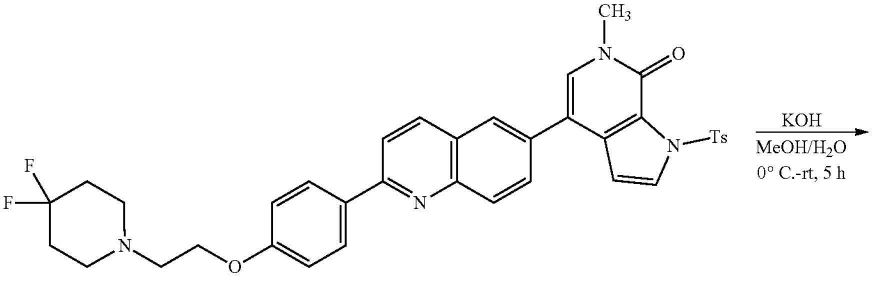

6

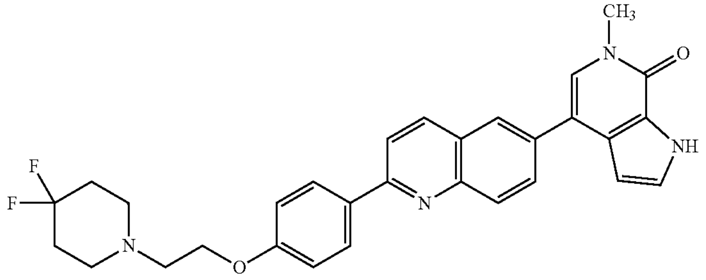

SLU-2285

1-[2-(4-bromophenoxy)ethyl]-4,4-difluoropiperidine (2)

To a stirred solution of Intermediate-2 (1.50 g, 6.4 mmol) in NMP (5.0 mL) were charged with DIPEA (0.3 mL, 1.71 mmol) and 4,4-difluoropiperidine 1 (0.778 g, 6.4 mmol) in a sealed tube at room temperature and was heated at 160° C. for 12 h. The reaction mixture was diluted with water (20 mL) and extracted with MTBE (3×30 mL). Combined organic layers were washed with water (2×30 mL), brine (2×20 mL), dried over anhydrous $Na_2SO_4$ and concentrated under reduced pressure to afford 2 (1.50 g0) as a light yellow solid. The crude compound used for the next step without purification.

$^1$H NMR (400 MHz, $CDCl_3$): δ ppm 7.37 (d, J=9.1 Hz, 2H), 6.78 (d, J=8.93 Hz, 2H), 4.05 (t, J=5.6 Hz, 2H), 2.84 (t, J=5.9 Hz, 2H), 2.67 (t, J=5.5 Hz, 4H), 1.93-2.06 (m, 4H).

4,4-difluoro-1-{2-[4-(4,4,5,5-tetramethyl-1,3,2-dioxaborolan-2-yl)phenoxy]ethyl}piperidine (3)

To a stirred solution of 2 (1.50 g, 5.50 mmol0) in 1,4-dioxane (20 mL) were charged with potassium acetate (1.09 g, 11.0 mmol), bis(pinacolato)diboron (1.40 g, 5.50 mmol) at room temperature and degassed it with argon for 10 min. Pd(dppf)$Cl_2$ (0.402 g, 0.55 mmol) was added to the reaction mixture and heated at 90° C. for 12 h. The reaction mixture was filtered through a pad of celite, filtrate was diluted with water (20 mL) and extracted with EtOAc (3×30 mL). Combined organic layers were dried over anhydrous $Na_2SO_4$ and concentrated under reduced pressure. The crude product was purified by combiflash chromatography (100% EtOAc) to afford 3 (1.00 g, 58%) as a thick brown solid.

$^1$H NMR (400 MHz, $CDCl_3$): δ ppm 7.74 (d, J=8.6 Hz, 2H), 6.88 (d, J=8.6 Hz, 2H), 4.13 (t, J=5.6 Hz, 2H), 2.87 (t, J=5.6 Hz, 2H), 2.71 (t, J=5.5 Hz, 4H), 1.95-2.08 (m, 4H), 1.33 (s, 12H).

6-bromo-2-{4-[2-(4,4-difluoropiperidin-1-yl)ethoxy]phenyl}quinolone (5)

To a stirred solution of 3 (0.20 g, 0.54 mmol5) in 1,4-dioxane (5.0 mL) and $H_2O$ (2.0 mL) were charged with 6-bromo 2-chloroquinoline 4 (0.130 g, 0.54 mmol), potassium carbonate (0.148 g, 1.08 mmol) at room temperature and degassed it with argon for 5 min. $Pd(PPh_3)_4$ (0.062 g, 0.05 mmol) was added to the reaction mixture and heated at 80° C. for 2 h. The reaction mixture was diluted with water (20 mL) and extracted with EtOAc (3×20 mL). Combined organic layers were dried over anhydrous $Na_2SO_4$ and concentrated under reduced pressure to afford 5 (0.20 gl) as an off-white solid. The crude compound used for the next step without purification.

1H NMR (400 MHz, $CDCl_3$): δ ppm 8.12 (d, J=8.9 Hz, 2H), 8.09 (d, J=8.6 Hz, 1H), 7.99 (d, J=8.8 Hz, 1H), 7.96 (d, J=2.4 Hz, 1H), 7.88-7.93 (m, 1H), 7.85 (d, J=8.8 Hz, 1H), 7.78 (dd, J=2.0, 8.4 Hz, 1H), 7.04 (d, J=9.0 Hz, 2H), 4.18 (t, J=5.8 Hz, 2H), 2.90 (t, J=5.7 Hz, 2H), 1.99-2.08 (m, 4H).

4-{2-[4-(2-(4,4-difluoropiperidin-1-yl)ethoxy)phenyl]quinolin-6-yl}-6-methyl-1-tosyl-1H-pyrrolo[2,3-c]pyridin-7(6H)-one (6)

To a stirred solution of 5 (0.150 g, 0.33 mmoll) in 1,4-dioxane (5.0 mL) and $H_2O$ (2.0 mL) were charged with Intermediate-5 (0.154 g, 0.36 mmoll) potassium carbonate (0.091 g, 0.66 mmol) at room temperature and degassed it with argon for 5 min. $Pd(PPh_3)_4$ (0.038 g, 0.03 mmol) was added to the reaction mixture and heated at 90° C. for 2 h. The reaction mixture was diluted with water (20 mL) and extracted with EtOAc (2×30 mL). Combined organic layers were dried over anhydrous $Na_2SO_4$ and concentrated under reduced pressure. The crude product was purified by silica gel chromatography ($CH_2Cl_2$:$CH_3OH$=95:5) to afford 6 (0.170 g, 77%) as an off-white solid.

$^1$H NMR (400 MHz, $CDCl_3$): δ ppm 8.20 (d, J=3.0 Hz, 1H), 8.18 (d, J=3.2 Hz, 1H), 8.15 (d, J=8.8 Hz, 2H), 8.06 (d, J=8.3 Hz, 2H), 7.98 (d, J=3.4 Hz, 1H), 7.88 (d, J=8.8 Hz, 1H), 7.83 (d, J=1.8 Hz, 1H), 7.78 (dd, J=2.0, 8.4 Hz, 1H), 7.33 (d, J=8.6 Hz, 1H), 7.20 (s, 1H), 7.06 (d, J=2.0 Hz, 2H), 6.65 (d, J=3.4 Hz, 1H), 4.19 (t, J=5.6 Hz, 2H), 3.62 (s, 3H), 2.91 (t, J=5.6 Hz, 2H), 2.69-2.74 (m, 4H), 1.98-2.14 (m, 4H).

4-{2-[4-(2-(4,4-difluoropiperidin-1-yl)ethoxy)phenyl]quinolin-6-yl}-6-methyl-1H-pyrrolo[2,3-c]pyridin-7(6H)-one (SLU-2285)

To a stirred solution of 6 (0.170 g, 0.22 mmol7) in MeOH (10 mL), water (5.0 mL) and THF (5.0 mL) was charged with potassium hydroxide (0.62 g, 1.10 mmol) at 0° C. The reaction mixture was stirred for 5 h at room temperature, evaporated, diluted with water (20 mL) and extracted with $CH_2Cl_2$ (3×30 mL). Combined organic layers were dried over anhydrous $Na_2SO_4$ and concentrated under reduced pressure. The crude product was purified by reverse phase chromatography (ACN:$H_2O$=95:5) to afford SLU-2285 (0.170 g, 52%) as an off-white solid.

$^1$H NMR (400 MHz, DMSO-$d_6$) δ ppm 12.2 (br.s., 1H), 8.46 (d, J=8.8 Hz, 1H), 8.26 (d, J=8.8 Hz, 2H), 8.08-8.19 (m, 3H), 8.01 (dd, J=1.6, 8.4 Hz, 1H), 7.59 (s, 1H), 7.41 (t, J=2.4 Hz, 1H), 7.12 (d, J=8.8 Hz, 2H), 6.60-6.62 (m, 1H), 4.19 (t, J=6.0 Hz, 2H), 3.63 (s, 3H), 2.83 (t, J=5.6 Hz, 2H), 2.65 (t, J=5.2 Hz, 4H), 1.90-2.15 (m, 4H).

ESI-MS m/z $[C_{32}H_{33}N_5O_3+H]^+$ 515.4.

HPLC (Method A) 92.0% (AUC), $t_R$=8.81 min.

Synthesis of (R)-4-{2-[4-(2-(2,4-dimethyl-3-oxo-1,4-diazepan-1-yl)ethoxy)phenyl]quinolin-6-yl}-6-methyl-1H-pyrrolo[2,3-c]pyridin-7(6H)-one (SLU-2284)

Scheme 41

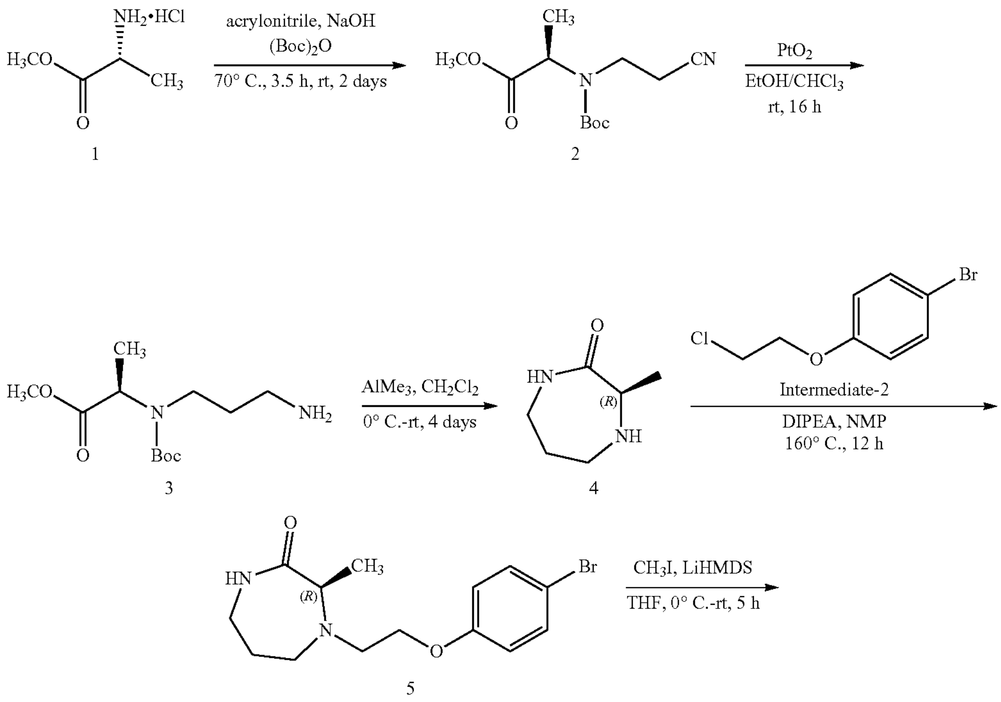

1

2

3

4

5

-continued
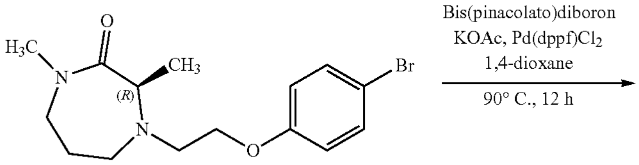
6
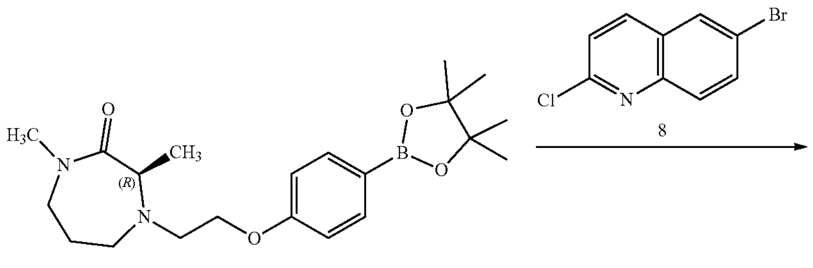
7
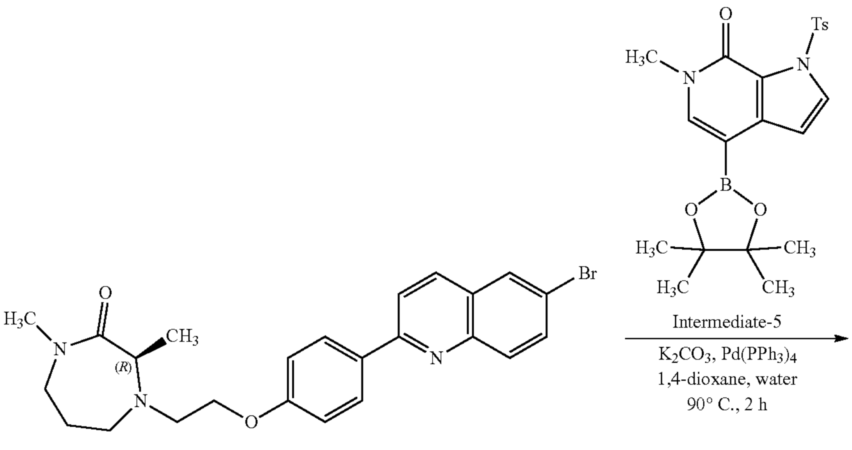
9
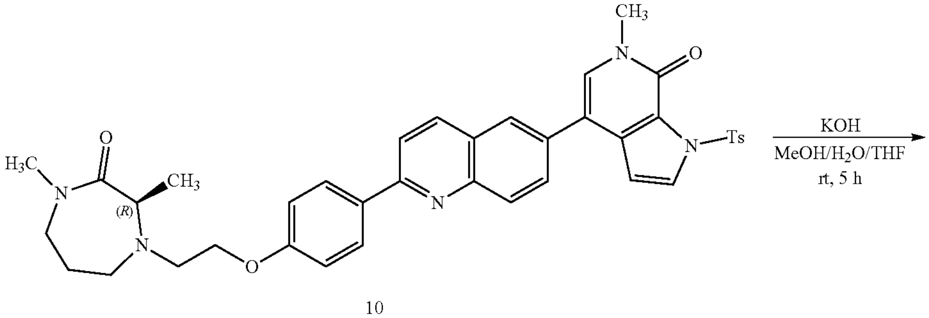
10
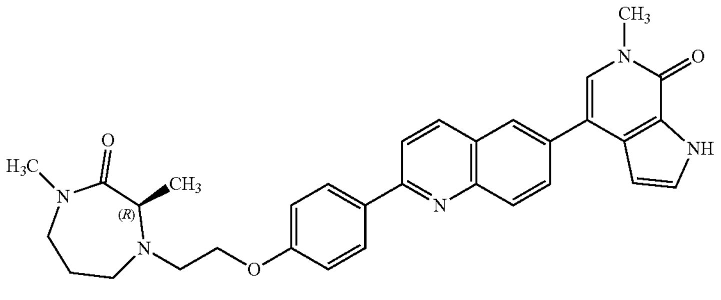
SLU-2284

(S)-methyl 2-[(tert-butoxycarbonyl)(2-cyanoethyl) amino]propanoate (2)

To a solution of 1 (0.1 g, 57.55 mmol) in NaOH (5 N, 12 mL), $H_2O$ (60 mL) at 0° C. was charged with acrylonitrile (14.4 mL, 83.01 mmol) dropwise and heated at 70° C. for 3.5 h. The reaction mixture was cooled to room temperature. Boc anhydride was added to the reaction mixture and stirred for 2 days at room temperature. The reaction mixture was diluted with $H_2O$ (50 mL) and extracted with EtOAc (3×60 mL). The combined organic layers were dried over anhydrous $Na_2SO_4$ and concentrated under reduced pressure. The crude product was purified by combiflash chromatography (EtOAc:Hexanes=60:40) to afford 2 (4.80 g, 34%2) as colourless liquid.

$^1$H NMR (400 MHz, $CDCl_3$): ppm δ 4.21-4.66 (m, 1H), 3.73 (s, 3H), 3.55-3.66 (m, 1H), 3.37-3.48 (m, 1H), 2.66-2.72 (m, 2H), 142-1.51 (m, 12H).

(S)-methyl 2-[(tert-butoxycarbonyl)(2-cyanoethyl) amino]propanoate (3)

To a solution of 2 (4.80 g2) in EtOH (330 mL) and $CHCl_3$ (10 mL) was charged with $PtO_2$ (1.50 g) at room temperature. The reaction mixture was stirred for 16 h under $H_2$ bladder pressure. The reaction mixture was filtered through celite bed and washed with 10% $CH_3OH/CH_2Cl_2$ (500 mL). The filtrate was concentrated under reduced pressure to obtain 3 [5.00 g (crude)2] as an off-white liquid. This crude material was used for next step without any further purification.

$^1$H NMR (400 MHz, DMSO-$d_6$): ppm δ 8.12 (br.s., 2H), 4.15-4.31 (m, 1H), 3.64 (s, 3H), 3.35-3.44 (m, 3H), 2.67-2.85 (m, 2H), 1.78-1.83 (m, 2H), 1.33-1.40 (m, 12H).

(R)-3-methyl-1,4-diazepan-2-one (4)

To a solution of 3 [5.00 g (crude)2] in $CH_2Cl_2$ (50 mL) at 0° C. was charged with $AlMe_3$ in toluene (2.0 M, 16 mL) dropwise and stirred for 4 days. The reaction mixture was poured into celite (15.0 g) in a glass conical and saturated ammonium chloride (10 mL) was added to the reaction mixture at 0° C. $Na_2SO_4$ (10.0 g) and MeOH (50 mL) were added to the reaction mixture dropwise at 0° C. and stirred for 1 h. The reaction mixture was filtered through celite bed and washed with 10% $MeOH/CH_2Cl_2$ (500 mL). The filtrate was concentrated under reduced pressure and the crude product was purified by combiflash chromatography ($MeOH:CH_2Cl_2$:Aqueous $NH_3$=90:9:1) to afford 4 (1.00 g, 45%8) as a brown gum.

$^1$H NMR (400 MHz, DMSO-$d_6$): ppm δ 7.35 (br.s., 1H), 3.17-3.33 (m, 3H), 3.02-3.12 (m, 2H), 2.70-2.74 (m, 1H), 1.32-1.43 (m, 1H), 1.03 (d, J=6.7 Hz, 3H).

(R)-4-[2-(4-bromophenoxy)ethyl]-3-methyl-1,4-diazepan-2-one (5)

To a solution of Intermediate-2 (1.80 g, 7.80 mmol) in NMP (5.00 mL), DIPEA (3.8 mL, 23.40 mmol) was charged with 4 (1.00 g, 7.80 mmol8) in a sealed tube and heated at 160° C. for 12 h. The reaction mixture was diluted with water (10 mL) and extracted with EtOAc (3×30 mL). The combined organic layers were washed with water (2×30 mL), brine (2×20 mL), dried over anhydrous $Na_2SO_4$ and concentrated under reduced pressure. The crude product was purified by silica gel chromatography ($CH_2Cl_2$:MeOH=90:10) to afford 5 (1.00 g, 40%) as an off-white solid.

$^1$H NMR (400 MHz, $CDCl_3$): δ ppm 7.35 (d, J=9.0 Hz, 2H), 6.76 (d, J=9.0 Hz, 2H), 5.85 (br.s., 1H), 3.89-4.02 (m, 2H), 3.07 (q, J=6.9 Hz, 1H), 3.38-3.45 (m, 2H), 3.23-3.27 (m, 1H), 3.03-3.10 (m, 1H), 2.83-2.97 (m, 2H), 1.89-1.99 (m, 1H), 1.45-1.49 (m, 1H), 1.28 (d, J=6.09 Hz, 3H).

(R)-4-[2-(4-bromophenoxy)ethyl]-3-methyl-1,4-diazepan-2-one (6)

To a solution of 5 (1.00 g, 3.00 mmol7) in THF (15 mL) was charged with LiHMDS (6.0 mL, 6.00 mmol) dropwise at 0° C. and stirred for 30 min. Upon stirring, Mel (0.435 g, 6.00 mmol) was added and stirred for 5 h at room temperature. The reaction mixture was quenched with ice cold water, diluted with water (20 mL) and extracted with EtOAc (3×50 mL). The combined organic layers were dried over anhydrous $Na_2SO_4$ and concentrated under reduced pressure to afford 6 (0.85 g, 83%) as light yellow liquid.

$^1$H NMR (400 MHz, $CDCl_3$): δ ppm 7.34 (d, J=9.0 Hz, 2H), 6.75 (d, J=8.9 Hz, 2H), 3.87-3.99 (m, 2H), 3.70-3.81 (m, 2H), 3.35-3.39 (m, 1H), 3.21-3.26 (m, 1H), 3.01-3.08 (m, 4H), 2.88-2.95 (m, 1H), 2.68-2.75 (m, 1H), 1.92-2.04 (m, 1H), 1.40-1.45 (m, 1H), 1.26 (d, J=6.8 Hz, 3H).

(R)-1,3-dimethyl-4-{2-[4-(4,4,5,5-tetramethyl-1,3,2-dioxaborolan-2-yl)phenoxy]ethyl}-1,4-diazepan-2-one (7)

To a solution of 6 (0.7 g, 2.02 mmol) in 1,4-dioxane (15 mL) was charged with potassium acetate (0.384 g, 4.04 mmol), bis(pinacolato)diboron (0.627 g, 2.40 mmol) and degassed with argon for 10 min. Pd(dppf)$Cl_2$ (0.146 g, 0.20 mmol) was added to the reaction mixture and heated at 90° C. for 12 h. The reaction mixture was filtered through a pad of celite and the filtrate was diluted with water (20 mL). The resulting mixture was extracted with EtOAc (3×30 mL). The organic layers obtained were dried over anhydrous $Na_2SO_4$ and concentrated under reduced pressure. The crude product was purified by combiflash chromatography ($CH_2Cl_2$:MeOH=90:10) to afford 7 (0.2 g, 77%1) as an off-white solid.

$^1$H NMR (400 MHz, $CDCl_3$): δ ppm 7.72 (d, J=8.7 Hz, 2H), 6.86 (d, J=8.6 Hz, 2H), 3.93-4.06 (m, 2H), 3.70-3.82 (m, 2H), 3.38-3.39 (m, 1H), 3.21-3.26 (m, 1H), 3.01-3.08 (m, 4H), 2.90-2.96 (m, 1H), 2.71-2.77 (m, 1H), 1.94-2.04 (m, 1H), 1.39-1.45 (m, 1H), 1.32-1.26 (m, 15H).

Preparation (R)-4-{2-[4-(6-bromoquinolin-2-yl)phenoxy]ethyl}-1,3-dimethyl-1,4-diazepan-2-one (9)

To a solution 7 (0.7 g, 1.80 mmol1) in 1,4-dioxane (10 mL), $H_2O$ (3.0 mL) was charged with 6-bromo-2-chloroquinoline (8, 0.434 g, 1.80 mmol), potassium carbonate (0.496 g, 3.60 mmol) and degassed with argon for 10 min. Pd$(PPh_3)_4$ (0.207 g, 0.18 mmol) was added to the reaction mixture and heated at 90° C. for 2 h. The reaction mixture was diluted with water (20 mL) and extracted with EtOAc (2×30 mL). The combined organic layers were dried over anhydrous $Na_2SO_4$ and concentrated under reduced pressure. The crude product was purified by combiflash chromatography ($CH_2Cl_2$:MeOH=90:10) to afford 9 (0.2 g, 40%0) as an off-white solid.

$^1$H NMR (400 MHz, $CDCl_3$): δ ppm 8.07-8.11 (m, 3H), 8.00 (d, J=8.8 Hz, 1H), 7.95 (d, J=2.1 Hz, 1H), 7.85 (d, J=8.6 Hz, 1H), 7.75 (dd, J=2.1, 8.9 Hz, 1H), 7.01 (d, J=8.8 Hz, 2H), 3.99-4.12 (m, 2H), 3.72-3.84 (m, 2H), 3.39-3.46 (m, 1H), 3.23-3.28 (m, 1H), 2.90-3.12 (m, 5H), 2.75-2.81 (m, 1H), 1.96-2.06 (m, 1H), 1.43-1.46 (m, 1H), 1.19 (d, J=6.7 Hz, 3H).

Preparation (R)-4-{2-[4-(2-(2,4-dimethyl-3-oxo-1,4-diazepan-1-yl)ethoxy)phenyl]quinolin-6-yl}-6-methyl-1-tosyl-1H-pyrrolo[2,3-c]pyridin-7(6H)-one (10)

To a solution of 9 (0.175 g, 0.37 mmol0) in 1,4-dioxane (5.0 mL) and $H_2O$ (2.0 mL) was charged with Intermediate-5 (0.177 g, 0.41 mmol), $K_2CO_3$ (0.102 g, 0.74 mmol) and degassed with argon for 10 min. $Pd(PPh_3)_4$ (0.042 g, 0.03 mmol) was added to the reaction mixture and heated at 90° C. for 2 h. The reaction mixture was evaporated, diluted with water (20 mL) and extracted with EtOAc (3×30 mL). The organic layer was dried over anhydrous $Na_2SO_4$ and concentrated under reduced pressure to obtain 10 (0.175 g4) as an off-white solid. The crude material was used for next step without any further purification.

ESI-MS m/z $[C_{39}H_{39}N_5O_5S+H]^+$ 690.3.

(R)-4-{2-[4-(2-(2,4-dimethyl-3-oxo-1,4-diazepan-1-yl)ethoxy)phenyl]quinolin-6-yl}-6-methyl-1H-pyrrolo[2,3-c]pyridin-7(6H)-one (SLU-2284)

To a solution of 10 (0.170 g, 0.24 mmol4) in MeOH (10 mL), $H_2O$ (5.0 mL) and THF (5.0 mL) was charged with potassium hydroxide (0.067 g, 1.23 mmol) and stirred for 5 h at room temperature. The reaction mixture was evaporated, diluted with water (20 mL) and extracted with $CH_2Cl_2$ (3×30 mL). The combined organic layers were dried over anhydrous $Na_2SO_4$ and concentrated under reduced pressure. The crude product was purified by reverse phase chromatography (ACN:$H_2O$=90:10) to afford SLU-2284 (0.035 g, 26%) as an off-white solid.

1H NMR (400 MHz, DMSO-$d_6$) δ ppm 12.2 (br.s., 1H), 8.45 (d, J=8.8 Hz, 1H), 8.25 (d, J=8.8 Hz, 2H), 8.08-8.17 (m, 3H), 8.01 (dd, J=2.0, 8.8 Hz, 1H), 7.59 (s, 1H), 7.41 (t, J=2.8 Hz, 1H), 7.08 (d, J=8.8 Hz, 2H), 6.61 (t, J=6.0 Hz, 1H), 4.04 (t, J=6.0 Hz, 2H), 3.88 (q, J=6.8 Hz, 1H), 3.75-3.81 (m, 1H), 3.63 (s, 3H), 3.19-3.27 (m, 2H), 2.98 (t, J=12.4 Hz, 1H), 2.89 (s, 3H), 2.71-2.78 (m, 1H), 2.60-2.67 (m, 1H), 1.93 (q, J=11.6 Hz, 1H), 1.32 (d, J=10.0 Hz, 1H), 1.08 (d, J=6.8 Hz, 3H).

ESI-MS m/z $[C_{32}H_{33}N_5O_3+H]^+$ 536.3.

HPLC (Method A) 99.7% (AUC), $t_R$=6.08 min.

Synthesis of 6-methyl-4-{6-[4-(2-(2,2,4-trimethyl-3-oxopiperazin-1-yl)ethoxy)phenyl]quinolin-2-yl}-1H-pyrrolo[2,3-c]pyridin-7(6H)-one (SLU-2280)

Scheme 42

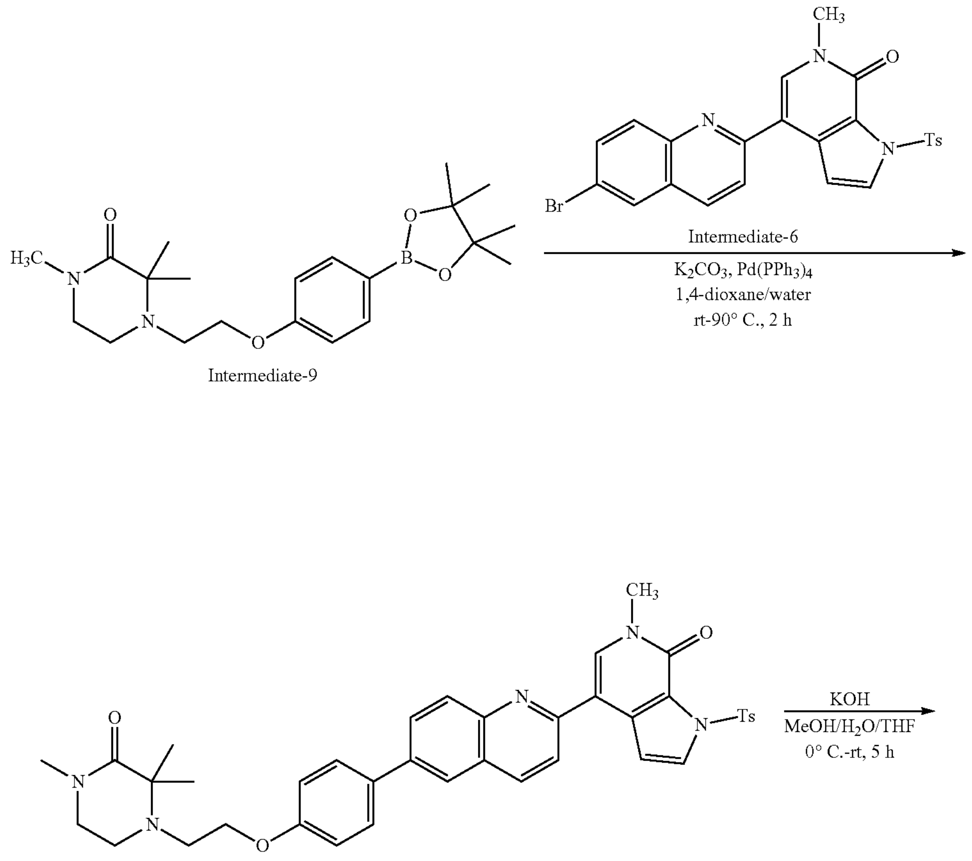

1

-continued

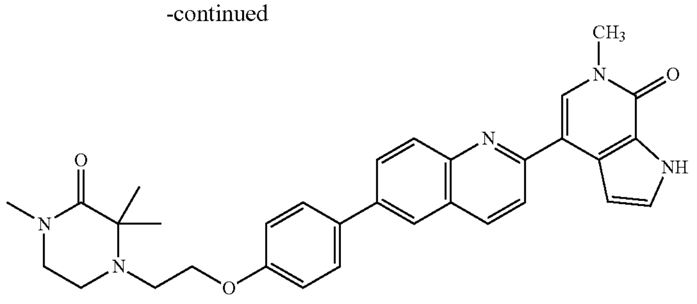

SLU-2280

6-methyl-1-tosyl-4-{6-[4-(2-(2,2,4-trimethyl-3-oxopiperazin-1-yl)ethoxy)phenyl]quinolin-2-yl}-1H-pyrrolo[2,3-c]pyridin-7(6H)-one (1)

To a stirred solution of Intermediate-9 (0.100 g, 0.25 mmol3) in 1,4-dioxane (5.0 mL) and $H_2O$ (2.0 mL) were charged with Intermediate-6 (0.130 g, 0.25 mmol6), potassium carbonate (0.069 g, 0.50 mmol) at room temperature and degassed it with argon for 5 min. $Pd(PPh_3)_4$ (0.028 g, 0.02 mmol) was added to the reaction mixture and heated at 90° C. for 2 h. The reaction mixture diluted with water (20 mL) and extracted with EtOAc (2x30 mL). Combined organic layers were dried over anhydrous $Na_2SO$ and concentrated under reduced pressure. The crude product was purified by combiflash chromatography (100% EtOAc) to afford 1 (0.150 g) as an off-white solid.

ESI-MS m/z $[C_{39}H_{39}N_5O_5S+H]^+$ 690.3

6-methyl-4-{6-[4-(2-(2,2,4-trimethyl-3-oxopiperazin-1-yl)ethoxy)phenyl]quinolin-2-yl}-1H-pyrrolo[2,3-c]pyridin-7(6H)-one (SLU-2280)

To a stirred solution of 1 (0.150 g, 0.21 mmol2) in MeOH (10 mL), $H_2O$ (5.0 mL), THF (5.0 mL) was charged with potassium hydroxide (0.059 g, 1.00 mmol) at 0° C. The reaction mixture was stirred for 5 h at room temperature. The reaction mixture was evaporated, diluted with water (20 mL) and extracted with $CH_2C_2$ (3x30 mL). Combined organic layers were dried over anhydrous $Na_2SO_4$ and concentrated under reduced pressure. The crude product was triturated with acetonitrile (5.0 mL), with MeOH (5.0 mL), filtered and dried to afford SLU-2280 (0.097 g, 85%) as an off-white solid.

$^1H$ NMR (400 MHz, DMSO-$d_6$) δ ppm 12.1 (br.s., 1H), 8.40 (d, J=8.8 Hz, 1H), 8.19 (s, 2H), 8.04-8.08 (m, 3H), 7.79 (d, J=8.8 Hz, 2H), 7.41 (t, J=2.8 Hz, 1H), 7.34 (t, J=2.4 Hz, 1H), 7.09 (d, J=8.8 Hz, 2H), 4.09 (t, J=6.0 Hz, 2H), 3.68 (s, 3H), 3.23 (t, J=5.2 Hz, 2H), 2.91 (t, J=5.2 Hz, 2H), 2.80 (s, 3H), 2.78 (t, J=6.0 Hz, 2H), 1.22 (s, 6H).

ESI-MS m/z $[C_{32}H_{33}N_5O_3+H]^+$ 536.4.

HPLC (Method A) 97.2% (AUC), $t_R$=6.16 min.

Synthesis of (R)-4-{6-[4-(5-(2-(2,4-dimethyl-3-oxopiperazin-1-yl)ethoxy)pyridin-2-yl)piperazin-1-yl]pyridin-3-yl}-6-methyl-1H-pyrrolo[2,3-c]pyridin-7(6H)-one (SLU-2110)

Scheme 43

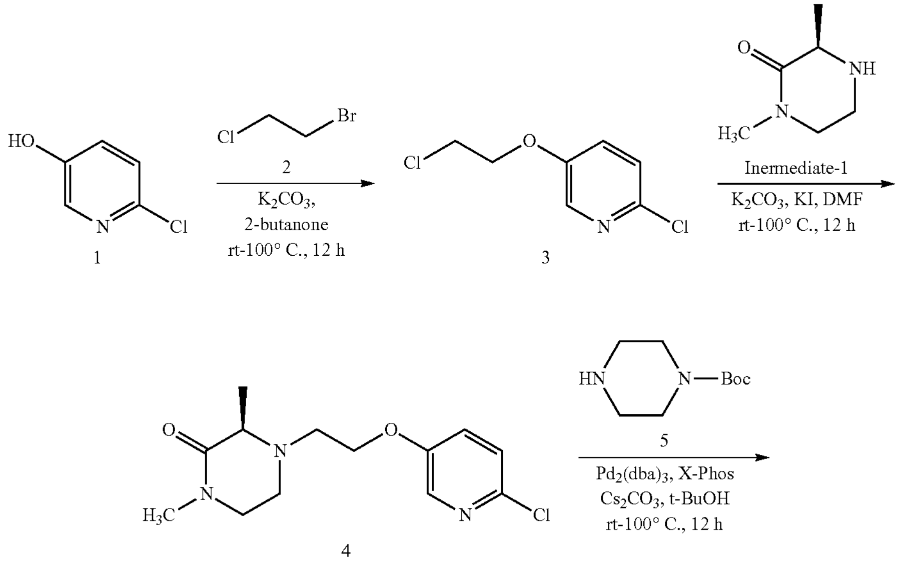

-continued
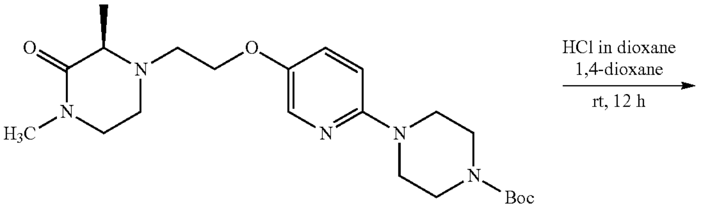
6
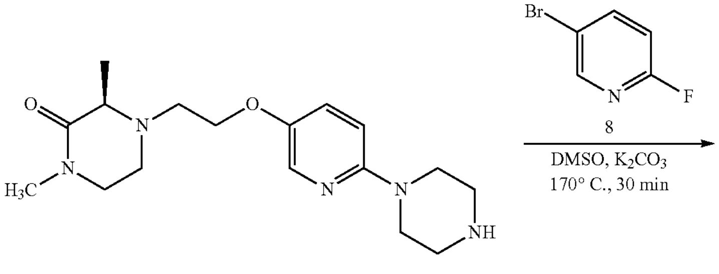
7
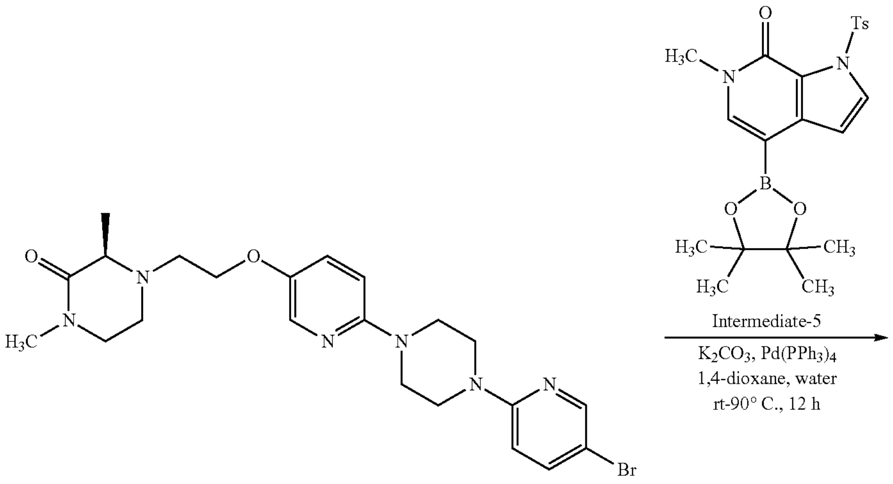
9
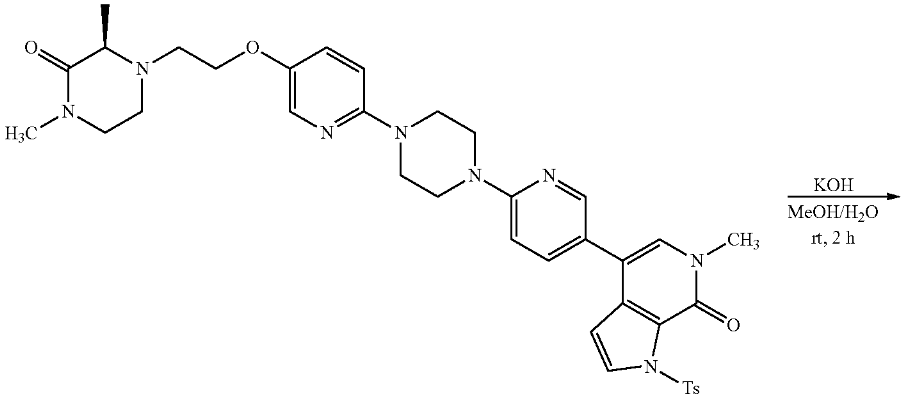
10

-continued

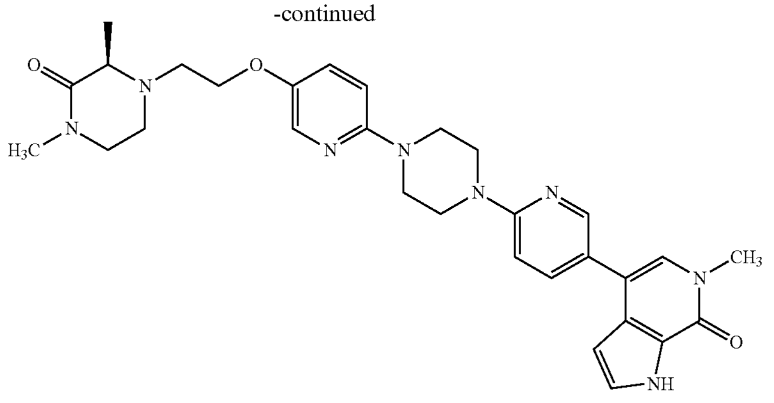

SLU-2110

Preparation 2-chloro-5-(2-chloroethoxy)pyridine (3)

To a stirred solution of 1 (0.100 g, 0.77 mmol) in 2-butanone (2.0 mL) was charged with $K_2CO_3$ (0.318 g, 2.31 mmol) and 1-bromo-2-chloroethane 2 (1.0 mL, 10 vol) at room temperature was heated at 100° C. for 12 h. The reaction mixture diluted with $H_2O$ (10 mL) and extracted with EtOAc (2×10 mL). Combined organic layers were washed with water (2×30 mL), brine (2×20 mL), dried over anhydrous $Na_2SO_4$ and concentrated under reduced pressure to afford 3 (0.170 g, (crude)0) as an off-white semi solid which was used for next step without further purification $^1$H NMR (300 MHz, $CDCl_3$): δ ppm 8.07 (s, 1H), 7.23-7.27 (m, 2H), 4.25-4.29 (m, 2H), 3.81-3.85 (m, 2H).

Preparation (R)-4-{2-[(6-chloropyridin-3-yl)oxy] ethyl}-1,3-dimethylpiperazin-2-one (4)

To a stirred solution of 3 (1.5 g, 7.8 mmol5) in DMF (40 mL) was charged with $K_2CO_3$ (3.2 g, 23.40 mmol), KI (0.640 g, 3.9 mmol), and Intermediate-1 (1.03 g, 7.8 mmol5) at room temperature and stirred for 12 h at 100° C. The reaction mixture was dissolved in $H_2O$ (50 mL) and extracted with EtOAc (3×30 mL). Combined organic layers were dried over anhydrous $Na_2SO_4$ and concentrated under reduced pressure. The crude product was purified by reverse phase combiflash chromatography (ACN:$H_2O$=80:20) to afford 4 (1.20 g, 40%7) as light yellow liquid $^1$H NMR (400 MHz, DMSO-$d_6$): δ ppm 8.12(d, J=3.0, 1H), 7.49 (dd, J=3.1, 8.7, 1H), 7.42 (d, J=8.7 Hz, 1H), 4.14-4.18 (m, 2H), 3.23 (t, J=5.0 Hz, 2H), 3.14 (q, J=6.7 Hz, 1H), 3.02-3.08 (m, 1H), 2.91-2.97 (m, 1H), 2.74-2.80 (m, 4H), 2.62-2.71 (m, 1H), 1.22 (d, J=6.8, 3H).

(R)-tert-butyl 4-{5-[2-(2,4-dimethyl-3-oxopiperazin-1-yl)ethoxy]pyridin-2-yl}piperazine-1-carboxylate (6)

To a stirred solution of 4 (0.500 g, 1.74 mmol2) in t-BuOH (5.0 mL) was charged with tert-butyl piperazine-1-carboxylate 5 (0.650 g, 3.61 mmol), cesium carbonate (1.65 g, 5.34 mmol), X-Phos (0.160 g, 0.37 mmol) at room temperature and degassed it with argon for 10 min. $Pd_2(dba)_3$ (0.150 g, 0.17 mmol) was added to the reaction mixture and heated at 100° C. for 12 h. The reaction mixture diluted with $H_2O$ (20 mL) and extracted with EtOAc (2×30 mL). Combined organic layers were dried over anhydrous $Na_2SO_4$ and concentrated under reduced pressure. The crude product was purified by reverse combiflash (ACN:$H_2O$=80:20) to afford 6 (0.35 g, 40%9) as light yellow liquid.

ESI-MS m/z $[C_{22}H_{35}N_5O_4+H]^+$ 434.2.

(R)-1,3-dimethyl-4-{2-[(6-(piperazin-1-yl)pyridin-3-yl)oxy]ethyl}piperazin-2-one (7)

To a stirred solution 6 (0.300 g9) in 1,4-dioxane (5.0 mL) was charged with HCl in dioxane (10 mL) at room temperature and stirred for 12 h at room temperature. The reaction mixture was directly evaporated under reduced pressure to afford 7 [0.250 g (crude)0] as colourless liquid which was used for next step without further purification.

ESI-MS m/z $[C_{17}H_{27}N_5O_2+H]^+$ 334.1.

(R)-4-{2-[(6-(4-(5-bromopyridin-2-yl)piperazin-1-yl)pyridin-3-yl)oxy]ethyl}-1,3-dimethylpiperazin-2-one (9)

To a solution 7 (0.4 g, 1.20 mmol in DMSO (5.0 mL) was charged with $K_2CO_3$ (0.496 g, 3.60 mmol) and 5-bromo-2-fluoropyridine 8 (0.317 g, 1.80 mmol) in a microwave vial was heated at 170° C. for 30 min. The reaction mixture was diluted with $H_2O$ (20 mL) and extracted with EtOAc (3×30 mL). Combined organic layers were washed with water (2×30 mL), brine (2×20 mL), dried over anhydrous $Na_2SO_4$ and concentrated under reduced pressure. The crude product was purified by combiflash chromatography ($CH_2Cl_2$:MeOH=90:10) to afford 9 (0.300 g, 51% as an off-white solid.

$^1$H NMR (400 MHz, DMSO-$d_6$): δ ppm 8.19 (s, 1H), 7.91 (s, 1H), 7.71 (d, J=9.1 Hz, 1H), 7.30 (d, J=9.6 Hz, 1H), 6.8 (t, J=6.4 Hz, 2H), 4.05 (t, J=5.9 Hz, 2H), 3.95 (br.s., 4H), 3.45 (br.s., 4H), H), 3.23 (t, J=4.9 Hz, 2H), 3.03-3.24 (m, 2H), 2.91-2.97 (m, 1H), 2.74-2.80 (m, 4H), 2.62-2.71 (m, 1H), 1.22 (d, J=6.6, 3H).

(R)-4-{6-[4-(5-(2-(2,4-dimethyl-3-oxopiperazin-1-yl)ethoxy)pyridin-2-yl)piperazin-1-yl]pyridin-3-yl}-6-methyl-1-tosyl-1H-pyrrolo[2,3-c]pyridin-7(6H)-one (10)

To a stirred solution of 9 (0.2 g, 0.41 mmol) in 1,4-dioxane (5.0 mL), $H_2O$ (2.0 mL) was charged with Intermediate-5 (0.174 g, 0.41 mmol6), potassium carbonate (0.169 g, 1.23 mmol) at room temperature and degassed it with argon for 10 min. $Pd(PPh_3)_4$ (0.023 g, 0.20 mmol) was added to the reaction mixture and heated at 90° C. for 12 h.

The reaction mixture diluted with $H_2O$ (20 mL) and extracted with EtOAc (2x30 mL). Combined organic layers were dried over anhydrous $Na_2SO_4$ and concentrated under reduced pressure. The crude product was purified by combiflash chromatography ($CH_2Cl_2$:MeOH=90:10) to afford 10 (0.2 g, 68%) as an off-white solid.

$^1$H NMR (400 MHz, DMSO-$d_6$) δ ppm 8.26 (d, J=2.4 Hz, 1H), 8.03 (d, J=8.4 Hz, 2H), 7.96 (d, J=2.9 Hz, 1H), 7.93 (d, J=3.5 Hz, 1H), 7.64-7.69 (m, 2H), 7.54-7.58 (m, 2H), 7.44-7.48 (m, 2H), 7.31 (d, J=8.3 Hz, 2H), 7.20 (dd, J=3.0, 9.0 Hz, 1H), 6.98 (s, 1H), 6.77 (d, J=8.9 Hz, 1H), 6.70 (d, J=9.1 Hz, 1H), 6.51 (d, J=3.5 Hz, 1H), 4.04-4.10 (m, 2H), 3.73 (t, J=4.4, 4H), 3.55-3.59 (m, 7H), 3.34-3.40 (m, 1H), 3.25-3.32 (m, 2H), 3.12-3.17 (m, 1H), 2.97-3.05 (m, 1H), 2.95 (s, 3H), 2.7-2.87 (m, 2H), 2.40 (s, 3H), 1.40 (d, J=6.8 Hz, 3H).

(R)-4-{6-[4-(5-(2-(2,4-dimethyl-3-oxopiperazin-1-yl)ethoxy)pyridin-2-yl)piperazin-1-yl]pyridin-3-yl}-6-methyl-1H-pyrrolo[2,3-c]pyridin-7(6H)-one (SLU-2110)

To a stirred solution of 10 (0.2 g, 0.28 mmol) in MeOH (10 mL), $H_2O$ (5.0 mL), THF (5.0 mL) was charged with potassium hydroxide (0.091 g, 1.40 mmol) and stirred for 2 h at room temperature. The reaction mixture was evaporated, diluted with water (20 mL) and extracted with $CH_2Cl_2$ (3x30 mL). Combined organic layers were dried over anhydrous $Na_2SO_4$ and concentrated under reduced pressure. The crude product was purified by reverse phase combiflash chromatography (ACN:$H_2O$=80:20) to afford SLU-2110 (0.130 g, 73%) as an off-white solid.

1H NMR (400 MHz, DMSO-$d_6$) δ ppm 12.13 (br.s., 1H), 8.36 (d, J=2.4 Hz, 1H), 7.92 (d, J=3.2 Hz, 1H), 7.78 (dd, J=2.4, 8.8 Hz, 1H), 7.30-7.33 (m, 3H), 7.00 (d, J=8.8 Hz, 1H), 6.89 (d, J=9.2 Hz, 1H), 6.39 (d, J=2.0 Hz, 1H), 4.05 (t, J=5.6 Hz, 2H), 3.64-3.65 (m, 4H), 3.56 (s, 3H), 3.49-3.50 (m, 4H), 3.23-3.25 (m, 2H), 3.13 (q, J=6.8 Hz, 1H), 3.02-3.08 (m, 1H), 2.88-2.94 (m, 1H), 2.80 (s, 3H), 2.64-2.77 (m, 2H), 1.23 (d, J=6.8 Hz, 3H).

ESI-MS m/z $[C_{30}H_{36}N_8O_3+H]^+$ 557.2.

HPLC (Method D) 96.6% (AUC), $t_R$=5.85 min.

Synthesis of 6-methyl-4-{6-[4-(4-(2-(piperidin-1-yl)ethoxy)phenyl)piperidin-1-yl]pyridin-3-yl}-1H-pyrrolo[2,3-c]pyridin-7(6H)-one (SLU-2116)

Scheme 44

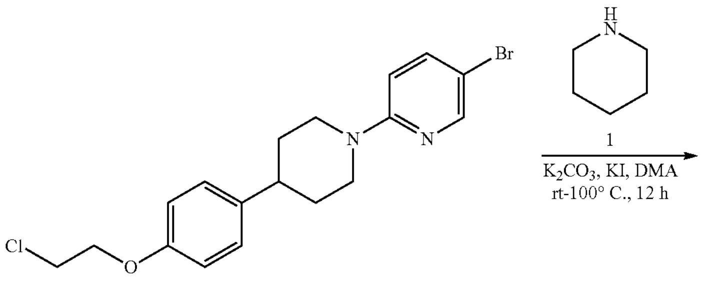

Intermediate-15

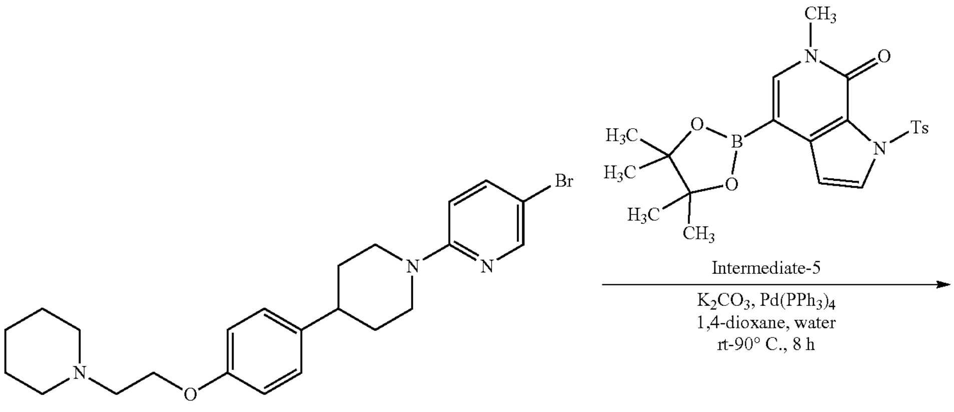

2

-continued

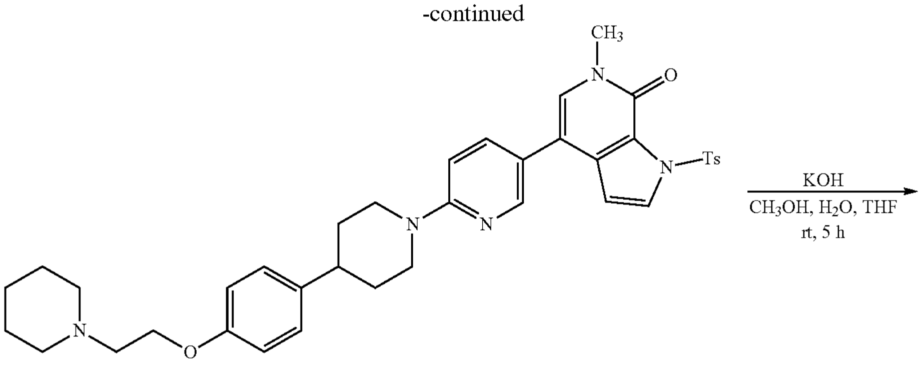

3

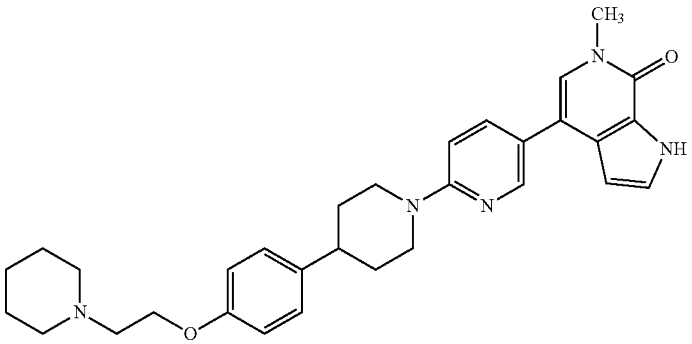

SLU-2116

5-bromo-2-(4-(4-(2-(piperidin-1-yl)ethoxy)phenyl)piperidin-1-yl)pyridine (2)

To a stirred solution of Intermediate-15 (0.250 g, 0.64 mmol) in DMA (5 mL) was charged with $K_2CO_3$ (0.260 g, 1.89 mmol), KI (0.0058 g, 0.03 mmol), piperidine 1 (0.059 g, 0.69 mmol) at room temperature and heated at 100° C. for 12 h. The reaction mixture diluted with water (10 mL) and extracted with EtOAc (3×15 mL). Combined organic layers were washed with water (2×30 mL), brine (2×20 mL), dried over anhydrous $Na_2SO_4$ and concentrated under reduced pressure to afford 2 [0.150 g, (crude)] as an off-white solid.

$^1$H NMR (400 MHz, $CDCl_3$): δ ppm 8.18 (d, J=2.39 Hz, 1H), 7.52 (dd, J=2.2, 9.0 Hz, 1H), 7.12 (d, J=8.5 Hz, 2H), 6.85 (d, J=8.4 Hz, 2H), 6.59 (d, J=9.1 Hz, 1H), 4.36 (d, J=13.0 Hz, 2H), 4.10 (t, J=5.9 Hz, 2H), 2.91 (t, J=13.0 Hz, 2H), 2.78 (t, J=6.0 Hz, 2H), 2.66-2.72 (m, 1H), 2.52 (br.s., 4H), 1.90 (d, J=12.9 Hz, 2H), 1.59-1.75 (m, 6H), 1.44-1.46 (m, 2H).

6-methyl-4-{6-[4-(4-(2-(piperidin-1-yl)ethoxy)phenyl)piperidin-1-yl]pyridin-3-yl}-1-tosyl-1H-pyrrolo[2,3-c]pyridin-7(6H)-one (3)

To a stirred solution of 2 (0.150 g, 0.33 mmol) in 1,4-dioxane (5.0 mL), $H_2O$ (2.0 mL) was charged with Intermediate-5 (0.144 g, 0.33 mmol), potassium carbonate (0.136 g, 0.99 mmol) at room temperature and degassed it with argon for 10 min. $Pd(PPh_3)_4$ (0.019 g, 0.016 mmol) was added to the reaction mixture and heated at 90° C. for 8 h. The reaction mixture diluted with water (15 mL) and extracted with EtOAc (2×20 mL). Organic layer was dried over anhydrous $Na_2SO_4$ and concentrated under reduced pressure to 3 [0.2 g (crude)] as an off-white solid.

ESI-MS m/z $[C_{38}H_{43}N_5O_4S+H]^+$ 666.3.

6-methyl-4-{6-[4-(4-(2-(piperidin-1-yl)ethoxy)phenyl)piperidin-1-yl]pyridin-3-yl}-1H-pyrrolo[2,3-c]pyridin-7(6H)-one (SLU-2116)

To a solution of 3 [0.150 g (crude), 0.22 mmol] in MeOH (10 mL), $H_2O$ (5.0 mL), THF (5.0 mL) was charged with potassium hydroxide (0.073 g, 1.10 mmol) and stirred for 5 h at room temperature. The reaction mixture was evaporated, diluted with water (20 mL) and extracted with $CH_2Cl_2$ (3×30 mL). Combined organic layers were dried over anhydrous $Na_2SO_4$ and concentrated under reduced pressure. The crude products were triturated with acetonitrile (5.0 mL), filtered and dried to afford SLU-2116 (0.030 g, 26%) as an off-white solid.

$^1$H NMR (400 MHz, DMSO-$d_6$) δ ppm 12.12 (s, 1H), 8.33 (s, 1H), 7.74 (dd, J=2.0, 8.8 Hz, 1H), 7.33 (br.s., 1H), 7.30 (s, 1H), 7.15 (d, J=8.4 Hz, 2H), 6.97 (d, J=8.8 Hz, 1H), 6.86 (d, J=2.0 Hz, 2H), 6.40 (s, 1H), 4.48 (d, J=12.4 Hz, 2H), 4.01 (br.s., 2H), 3.56 (s, 3H), 2.90 (t, J=11.6 Hz, 2H), 2.73 (t, J=12.4 Hz, 1H), 2.45 (br.s., 4H), 1.83 (d, J=12.8 Hz, 2H), 1.53-1.64 (m, 2H), 1.48 (br.s., 5H), 1.36 (br.s., 3H).

ESI-MS m/z $[C_{31}H_{37}N_5O_2+H]^+$ 512.3.

HPLC (Method D) 97.3% (AUC), $t_R$=6.32 min.

Synthesis of 6-methyl-4-{2-[4-(2-(2,2,4-trimethyl-3-oxopiperazin-1-yl)ethoxy)phenyl]quinolin-6-yl}-1H-pyrrolo[2,3-c]pyridin-7(6H)-one (SLU-2212)
Scheme 45
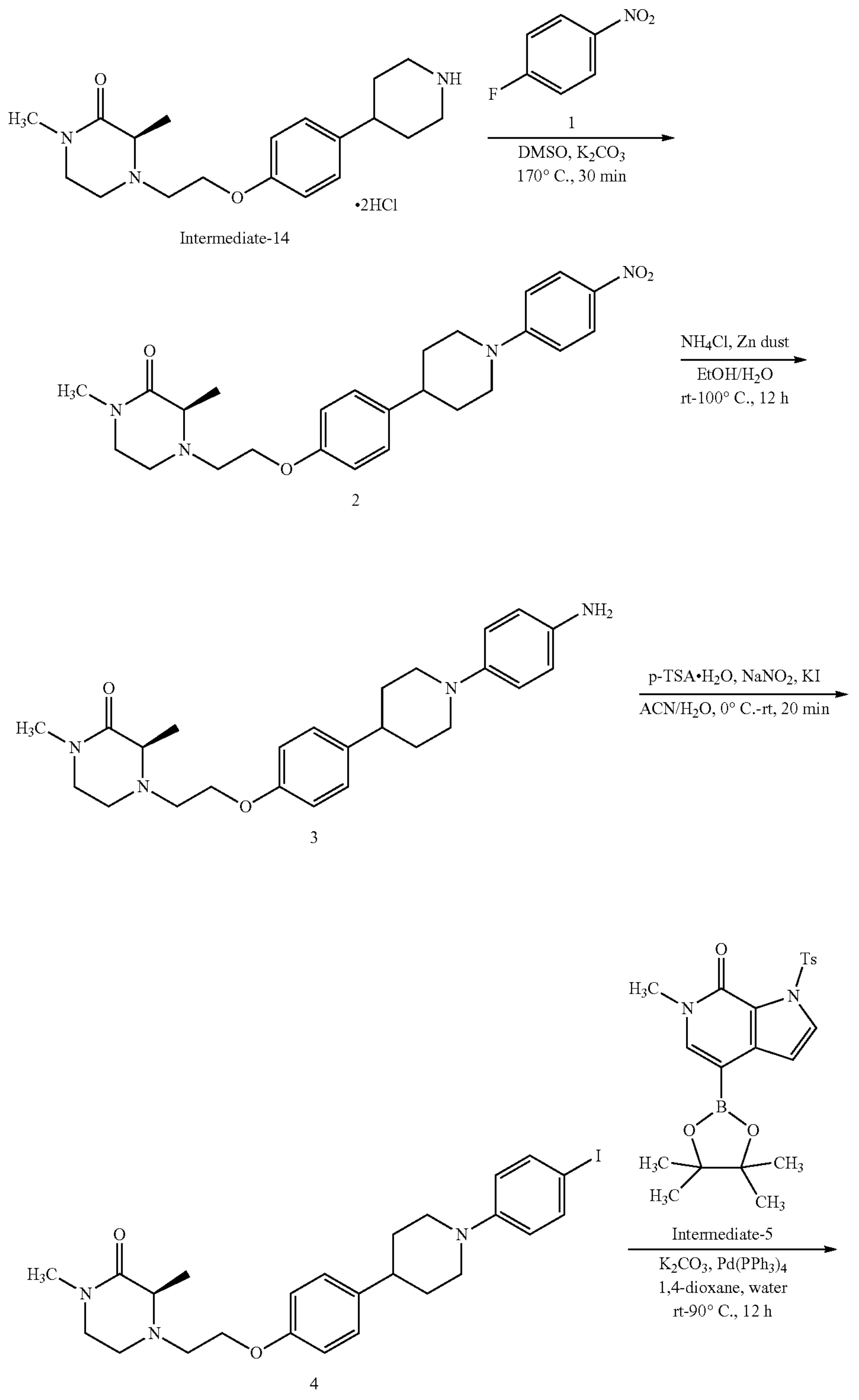

-continued

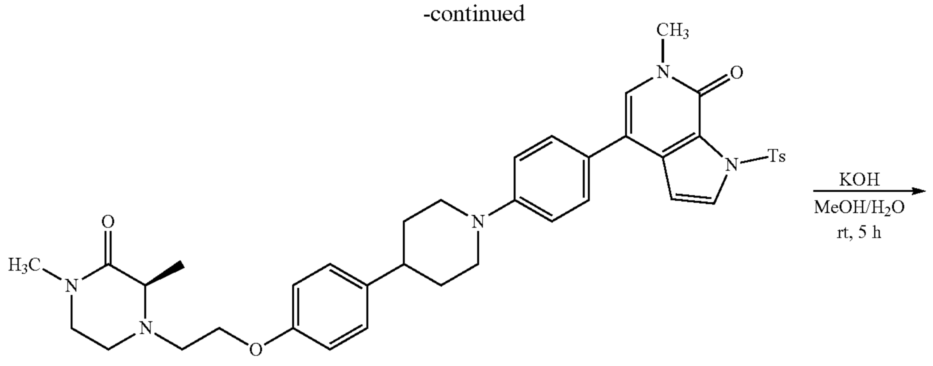

5

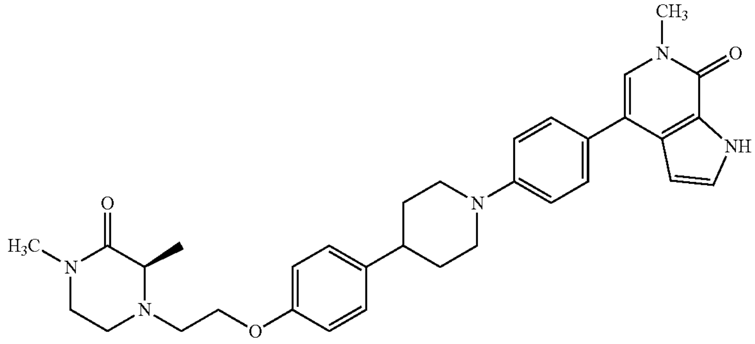

SLU-2212

(2R)-2,4-dimethyl-1-{2-[4-(1-(4-nitrophenyl)piperidin-4-yl)phenoxy]ethyl}piperidin-3-one (2)

To a solution of Intermediate-14 (0.020 g, 0.06 mmol7) in DMSO (1.0 mL) was charged with $K_2CO_3$ (0.016 g, 0.12 mmol) and 1-fluoro-4-nitrobenzene 1 (0.008 g, 0.06 mmol) in a microwave vial was heated at 170° C. for 20 min. The reaction mixture diluted with water (5 mL) and extracted with EtOAc (2x5 mL). Combined organic layers were was washed with water (2x5 mL), brine (2x5 mL), dried over anhydrous $Na_2SO_4$ and concentrated under reduced pressure to afford 2 [0.020 g (crude)2] as an off-white solid.

ESI-MS m/z $[C_{25}H_{32}N_4O_4+H]^+$ 453.2.

(2R)-1-{2-[4-(1-(4-aminophenyl)piperidin-4-yl)phenoxy]ethyl}-2,4-dimethylpiperidin-3-one (3)

To a solution of 2 (0.700 g, 1.54 mmol) in EtOH (10 mL), water (5.0 mL) was charged with $NH_4Cl$ (0.816 g, 15.4 mmol), Zn dust (1.0 g, 15.4 mmol) at room temperature and stirred at 100° C. for 12 h. The reaction mixture was filter through celite bed and washed with $CH_2Cl_2$ (30 mL). The filtrate was concentrated, the crude material was dissolved in $H_2O$ (50 mL) and extracted with $CH_2Cl_2$ (3x30 mL). Combined organic layers were dried over anhydrous $Na_2SO_4$ and concentrated under reduced pressure to afford 3 [0.600 g (crude)] as an off-white solid. The crude material was used for next step without any further purification.

$^1H$ NMR (400 MHz, $CDCl_3$): δ ppm 7.17 (d, J=8.5 Hz, 2H), 6.86 (t, J=8.4 Hz, 4H), 6.66 (d, J=8.5 Hz, 1H), 4.03-4.12 (m, 2H), 3.57 (d, J=11.9 Hz, 2H), 3.32-3.39 (m, 1H), 3.23-3.30 (m, 2H), 3.12-3.18 (m, 1H), 3.00-3.08 (m, 1H), 2.94 (s, 3H), 2.75-2.90 (m, 2H), 2.67-2.73 (m, 2H), 2.50-2.58 (m, 1H), 1.83-1.92 (m, 4H), 1.40 (d, J=6.7 Hz, 3H).

(2R)-1-{2-[4-(1-(4-iodophenyl)piperidin-4-yl)phenoxy]ethyl}-2,4-dimethylpiperidin-3-one (4)

To a solution of 3 (0.250 g, 0.58 mmol) in acetonitrile (5.0 mL), water (2) was charged with p-TSA·$H_2O$ (0.335 g, 1.76 mmol) at 0° C. and stirred for 20 min. Precipitate formation was observed and $NaNO_2$ (0.080 g, 01.16 mmol), KI (0.240 g, 1.45 mmol) in water (5.0 mL) was added to the reaction mixture dropwise for 20 min without raising internal temperature above 0° C. and stirred for another one hour at room temperature, diluted with $H_2O$ (20 mL) and extracted with EtOAc (3x30 mL). Combined organic layers were dried over anhydrous $Na_2SO_4$, concentrated under reduced pressure. The crude product was purified by combiflash chromatography ($CH_2Cl_2$:MeOH=90:10) to afford 4 (0.040 g, 12%) as an off-white solid.

ESI-MS m/z $[C_{25}H_{32}IN_3O_2+H]^+$ 534.1

(R)-4-{4-[4-(4-(2-(2,4-dimethyl-3-oxopiperazin-1-yl)ethoxy)phenyl)piperidin-1-yl]phenyl}-6-methyl-1-tosyl-1H-pyrrolo[2,3-c]pyridin-7(6H)-one (5)

To a solution of 4 (0.060 g, 0.11 mmol2) in 1,4-dioxane (2.0 mL), water (0.5 mL) was charged with Intermediate-5 (0.047 g, 1.03 mmol), potassium carbonate (0.030 g, 0.22 mmol) at room temperature and degassed it with argon for 10 min. $Pd(PPh_3)_4$ (0.0063 g, 0.005 mmol) was added to the reaction mixture and heated at 90° C. for 12 h. The reaction mixture was diluted with water (10 mL) and extracted with EtOAc (2x20 mL). Combined organic layers were dried over anhydrous $Na_2SO_4$, and concentrated under reduced pressure. The crude product was purified by combiflash chromatography ($CH_2Cl_2$:MeOH=90:10) to afford 5 (0.030 g, 37%5) as an off-white solid.

(R)-4-{4-[4-(4-(2-(2,4-dimethyl-3-oxopiperazin-1-yl)ethoxy)phenyl)piperidin-1-yl]phenyl}-6-methyl-1H-pyrrolo[2,3-c]pyridin-7(6H)-one (SLU-2212)

To a solution of 5 (0.030 g, 0.04 mmol5) in MeOH (3.0 mL), $H_2O$ (2.0 mL), THF (2.0 mL) was charged with potassium hydroxide (0.013 g, 0.21 mmol) at room temperature and stirred for 5 h at room temperature. The reaction mixture was evaporated, diluted with water (20 mL) and extracted with $CH_2Cl_2$ (3×30 mL). Combined organic layers were dried over anhydrous $Na_2SO_4$ and concentrated under reduced pressure. The crude products were triturated with acetonitrile (2.0 mL), filtered and dried to afford SLU-2212 (0.016 g, 69%) as an off-white solid.

$^1$H NMR (400 MHz, DMSO-$d_6$) δ ppm 12.08 (br.s., 1H), 7.44 (d, J=8.8 Hz, 2H), 7.32 (t, J=2.8 Hz, 1H), 7.25 (s, 1H), 7.19 (d, J=8.8 Hz, 2H), 7.06 (d, J=8.8 Hz, 2H), 6.88 (d, J=8.8 Hz, 2H), 6.42 (t, J=2.4 Hz, 1H), 4.04 (t, J=6.0 Hz, 2H), 3.86 (d, J=12.4 Hz, 2H), 3.56 (s, 3H), 3.23-3.26 (m, 2H), 3.14 (q, J=6.8 Hz, 1H), 3.05-3.08 (m, 1H), 2.89-2.92 (m, 1H), 2.80 (s, 3H), 2.73-2.79 (m, 3H), 2.60-2.71 (m, 2H), 1.85 (d, J=12.4 Hz, 2H), 1.69-1.77 (m, 2H), 1.23 (d, J=10.4 Hz, 3H).

ESI-MS m/z $[C_{33}H_{39}N_5O_3+H]^+$ 554.4.

HPLC (Method B) 99.2% (AUC), $t_R$=6.25 min.

Synthesis of (R)-4-{2-[4-(4-(2-(2,4-dimethyl-3-oxopiperazin-1-yl)ethoxy)phenyl)piperidin-1-yl]pyrimidin-5-yl}-6-methyl-1H-pyrrolo[2,3-c]pyridin-7(6H)-one (SLU-2091)

Scheme 46

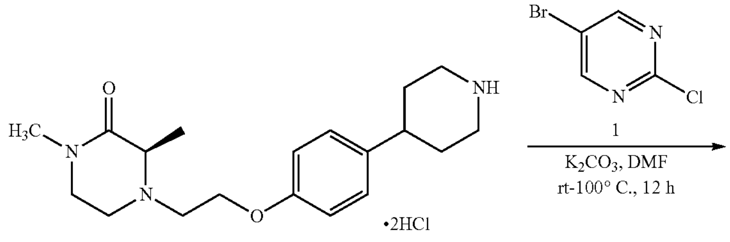

Intermediate-14

1

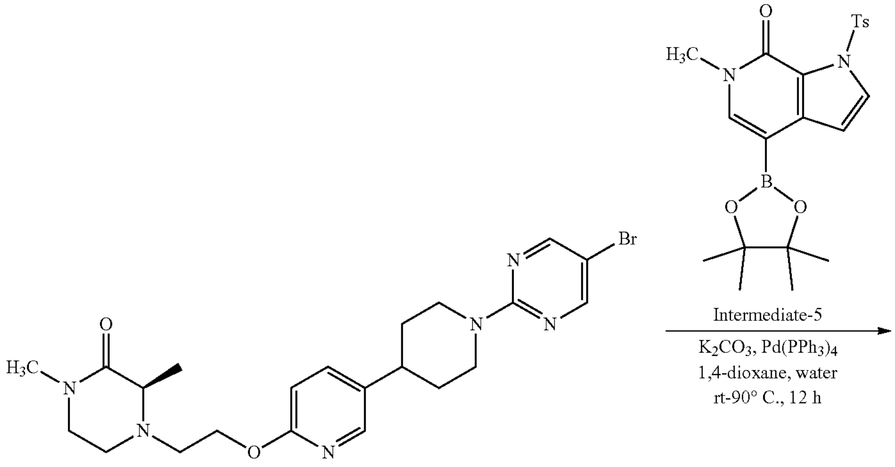

2

Intermediate-5

-continued

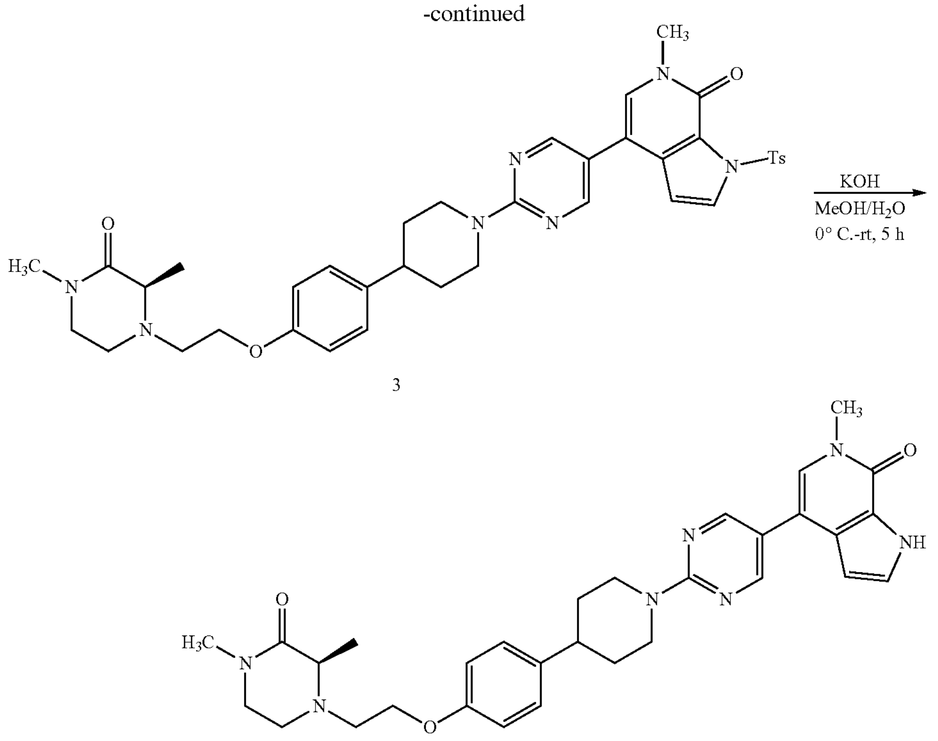

3

SLU-2091

(R)-4-{2-[(5-(1-(5-bromopyrimidin-2-yl) piperidin-4-yl) pyridin-2-yl)oxy]ethyl}-1,3-dimethylpiperazin-2-one (2)

To a solution of Intermediate-14 (0.50 g, 1.51 mmol) in DMF (5.0 mL) were charged with 5-bromo-2-chloropyrimidine 1 (0.291 g, 1.51 mmol), $K_2CO_3$ (0.833 g, 6.04 mmol) at room temperature and heated at 100° C. for 12 h. The reaction mixture was diluted with water (20 mL) and extracted with EtOAc (2×30 mL). Combined organic layers were dried over anhydrous $Na_2SO_4$ and concentrated under reduced pressure to obtain crude. This crude material was purified by combiflash chromatography ($CH_2Cl_2$: MeOH=95:5) to afford 2 (0.250 g, 41%7) as an off-white solid.

$^1$H NMR (400 MHz, $CDCl_3$): δ ppm 8.28 (s, 2H), 7.12 (d, J=8.6 Hz, 2H), 6.83 (d, J=8.7 Hz, 2H), 4.86 (d, J=13.2 Hz, 2H), 4.07-4.09 (m, 2H), 3.24-3.39 (m, 3H), 3.11-3.18 (m, 1H), 3.01-3.08 (m, 1H), 2.88-2.97 (m, 4H), 2.69-2.82 (m, 2H), 1.84 (d, J=11.6 Hz, 2H), 1.58-1.68 (m, 2H), 1.41 (d, J=6.9 Hz, 3H).

(R)-4-{2-[4-(4-(2-(2,4-dimethyl-3-oxopiperazin-1-yl)ethoxy)phenyl)piperidin-1-yl]pyrimidin-5-yl}-6-methyl-1-tosyl-1H-pyrrolo[2,3-c]pyridin-7(6H)-one (3)

To a stirred solution of 2 (0.2 g, 0.40 mmol7) in 1,4-dioxane (5.0 mL), water (2.0 mL) were charged with Intermediate-5 (0.175 g, 0.40 mmol), potassium carbonate (0.112 g, 1.65 mmol) at room temperature and degassed it with argon for 5 min. $Pd(PPh_3)_4$ (0.023 g, 0.02 mmol) was added to the reaction mixture and heated at 90° C. for 12 h. The reaction mixture was diluted with water (20 mL) and extracted with EtOAc (2×30 mL). Combined organic layers were dried over anhydrous $Na_2SO_4$ and concentrated under reduced pressure. The crude product was purified by reverse phase chromatography (ACN:$H_2O$=95:5) to afford 3 (0.160 g, 55%) as an off-white solid.

ESI-MS m/z $[C_{38}H_{43}N_7O_5S_2+H]^+$ 710.2.

(R)-4-{2-[4-(2-(2,4-dimethyl-3-oxopiperazin-1-yl) ethoxy)phenyl]quinolin-6-yl}-6-methyl-1H-pyrrolo [2,3-c]pyridin-7(6H)-one (SLU-2091)

To a solution of 3 (0.160 g, 0.28 mmol4) in MeOH (10 mL), $H_2O$ (5.0 mL), THF (5.0 mL) was charged with potassium hydroxide (0.078 g, 1.39 mmol) at 0° C. The reaction mixture was stirred for 5 h at room temperature. The reaction mixture was evaporated, diluted with water (20 mL) and extracted with $CH_2Cl_2$ (3×30 mL). Combined organic layers were dried over anhydrous $Na_2SO_4$ and concentrated under reduced pressure. The crude product was purified by reverse phase chromatography (ACN:$H_2O$=95:5) to afford SLU-2091 (0.070 g, 44%) as an off-white solid.

$^1$H NMR (400 MHz, DMSO-$d_6$) δ ppm 12.17 (br.s., 1H), 8.58 (s, 2H), 7.37 (s, 1H), 7.34 (t, J=2.8 Hz, 1H), 7.17 (d, J=8.8 Hz, 2H), 6.80 (d, J=8.8 Hz, 2H), 6.42 (t, J=2.4 Hz, 1H), 4.86 (d, J=13.2 Hz, 2H), 4.04 (t, J=5.6 Hz, 2H), 3.56 (s, 3H), 3.22-3.25 (m, 2H), 3.13 (q, J=6.4 Hz, 1H), 2.88-3.08 (m, 4H), 2.80 (s, 3H), 2.65-2.77 (m, 3H), 1.84 (d, J=11.6 Hz, 2H), 1.51-1.59 (m, 2H), 1.23 (d, J=6.8 Hz, 3H).

ESI-MS m/z $[C_{31}H_{37}N_7O_3+H]^+$ 556.2.

HPLC (Method E) 99.1% (AUC), $t_R$=6.39 min.

Synthesis of (R)-4-{2-[4-(2-(2,4-dimethyl-3-oxopiperazin-1-yl)ethoxy)phenyl]quinolin-6-yl}-6-methyl-1H-pyrrolo[2,3-c]pyridin-7(6H)-one (SLU-2106)

Scheme 47

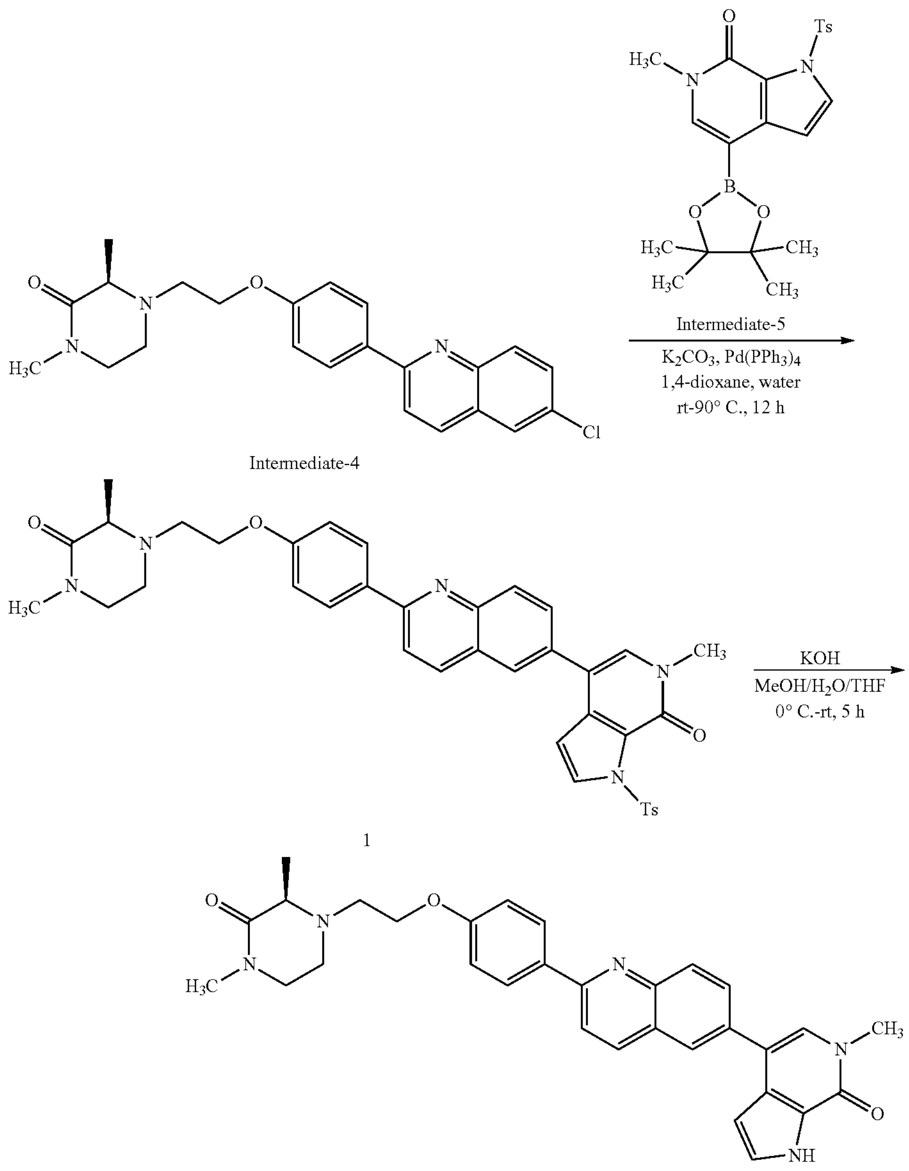

Intermediate-5

Intermediate-4

1

SLU-2106

(R)-4-{2-[4-(2-(2,4-dimethyl-3-oxopiperazin-1-yl)ethoxy)phenyl]quinolin-6-yl}-6-methyl-1-tosyl-1H-pyrrolo[2,3-c]pyridin-7(6H)-one (1)

To a stirred solution of Intermediate-4 (0.050 g, 0.11 mmol0) in 1,4-dioxane (2.0 mL), $H_2O$ (0.5 mL) were charged with Intermediate-5 (0.047 g, 0.55 mmol9), $K_2CO_3$ (0.045 g, 0.33 mmol) at room temperature and degassed it with argon for 5 min. $Pd(PPh_3)_4$ (0.006 g, 0.05 mmol) was added to the reaction mixture and heated at 90° C. for 12 h. The reaction mixture was diluted with water (20 mL) and extracted with EtOAc (2×30 mL). Combined organic layers were dried over anhydrous $Na_2SO_4$ and concentrated under reduced pressure to afford 1 [0.050 g (crude)2] as an off-white solid. This crude material was used for next step without further purification.

ESI-MS m/z $[C_{38}H_{37}N_5O_5S+H]^+$ 704.2

(R)-4-{2-[4-(2-(2,4-dimethyl-3-oxopiperazin-1-yl)ethoxy)phenyl]quinolin-6-yl}-6-methyl-1H-pyrrolo[2,3-c]pyridin-7(6H)-one (SLU-2106)

To a stirred solution of 1 (0.150 g, 0.22 mmol3) in MeOH (10 mL), $H_2O$ (5.0 mL), THF (5.0 mL) were charged with potassium hydroxide (0.062 g, 1.10 mmol) at 0° C. The reaction mixture was stirred for 5 h at room temperature, evaporated, diluted with water (20 mL) and extracted with $CH_2Cl_2$ (3×30 mL). Combined organic layers were dried over anhydrous $Na_2SO_4$ and concentrated under reduced pressure. The crude product was purified by combiflash chromatography ($CH_2Cl_2$:$CH_3OH$=95:5) to afford SLU-2106 (0.040 g, 36%) as an off-white solid.

$^1H$ NMR (300 MHz, DMSO-$d_6$): δ ppm 12.22 (br.s., 1H), 8.46 (d, J=8.7 Hz, 1H), 8.26 (d, J=8.7 Hz, 2H), 8.08-8.17 (m, 3H), 8.03 (d, J=10.5 Hz, 1H), 7.60 (s, 1H), 7.41 (t, J=2.4 Hz, 1H), 7.12 (d, J=9.0 Hz, 2H), 6.62 (s, 1H), 4.18 (t, J=5.4 Hz, 2H), 3.63 (s, 3H), 3.26 (t, J=6.0 Hz, 2H), 3.12-3.21 (m, 1H), 2.95-3.09 (m, 2H), 2.79-2.87 (m, 4H), 2.68-2.76 (m, 1H), 1.26 (d, J=6.9 Hz, 3H).

ESI-MS m/z $[C_{31}H_{31}N_5O_3+H]^+$ 522.2.

HPLC (Method D) 98.3% (AUC), $t_R$=6.22 min.

Synthesis of 4-{6-[4-(2-((2R,6S)-2,6-dimethylpiperidin-1-yl)ethoxy)phenyl]quinolin-2-yl}-6-methyl-1H-pyrrolo[2,3-c]pyridin-7(6H)-one (SLU-2107)

Scheme 48

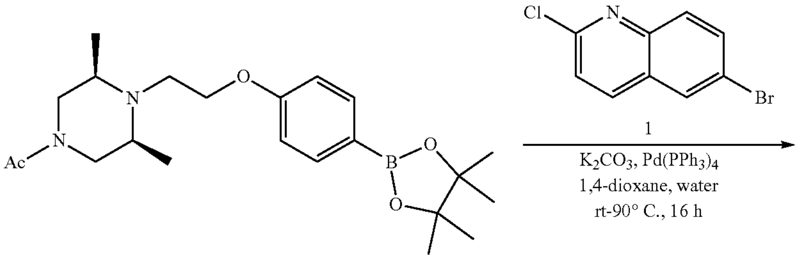

Intermediate-18
(cis-racemic)

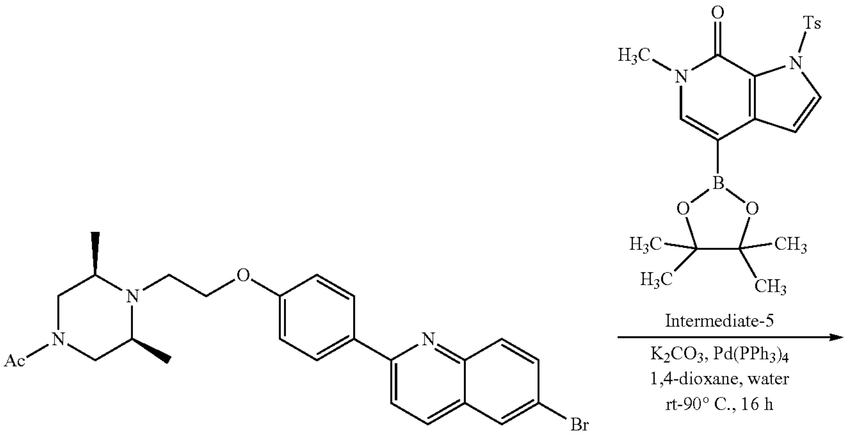

2
(cis-racemic)

-continued

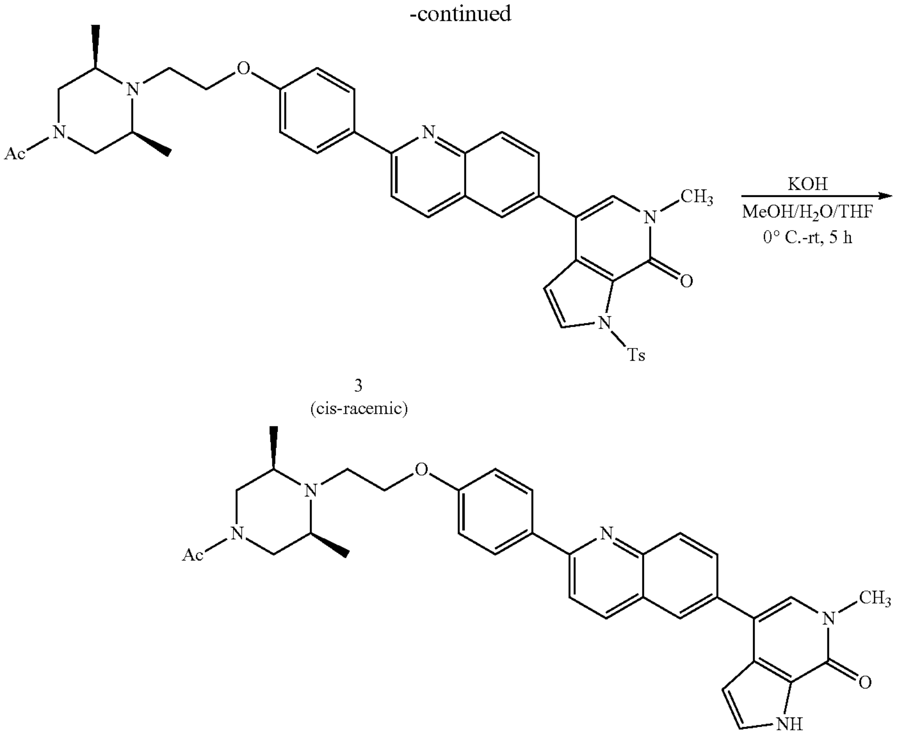

3
(cis-racemic)

SLU-2107
(cis-racemic)

1-(3R,5S)-4-{2-[4-(6-bromoquinolin-2-yl)phenoxy)ethyl]-3,5-dimethylpiperazin-1-yl}ethanone (2)

To a stirred solution of Intermediate-18 (0.050 g, 0.11 mmol) in 1,4-dioxane (5.0 mL) and $H_2O$ (2.0 mL) were charged with 6-bromo2-chloroquinoline 1 (0.022 g, 0.11 mmol), potassium carbonate (0.030 g, 1.38 mmol) at room temperature and degassed it with argon for 5 min. $Pd(PPh_3)_4$ (0.005 g, 0.005 mmol) was added to the reaction mixture and heated at 90° C. for 16 h. The reaction mixture was diluted with water (10 mL) and extracted with EtOAc (2×20 mL). Combined organic layers were dried over anhydrous $Na_2SO_4$ and concentrated under reduced pressure to obtain crude. The crude product was purified by combiflash chromatography (100% EtOAc) to afford 2 (0.020 g, 36%7) as an off-white solid.

$^1$H NMR (300 MHz, DMSO-$d_6$): δ ppm 8.38 (d, J=8.6 Hz, 1H), 8.25 (d, J=8.6 Hz, 2H), 8.17 (d, J=8.7 Hz, 1H), 8.10 (d, J=2.26 Hz, 1H), 8.03 (d, J=8.9 Hz, 1H), 7.75 (dd, J=2.3, 8.9 Hz, 1H), 7.09 (d, J=8.7 Hz, 2H), 4.18 (d, J=13.1 Hz, 1H), 4.08 (t, J=6.1 Hz, 2H), 3.67 (d, J=12.8 Hz, 1H), 3.05 (t, J=6.0 Hz, 2H), 2.75 (t, J=12.7 Hz, 1H), 2.27 (t, J=12.2 Hz, 1H), 1.10 (t, J=5.4 Hz, 6H).

4-{2-[4-(2-((2R,6S)-4-acetyl-2,6-dimethylpiperazin-1-yl)ethoxy)phenyl]quinolin-6-yl}-6-methyl-1-tosyl-1H-pyrrolo[2,3-c]pyridin-7(6H)-one (3)

To a stirred solution of 2 (0.050 g, 0.103 mmol8) in 1,4-dioxane (2.0 mL), $H_2O$ (0.5 mL) were charged with Intermediate-5 (0.044 g, 0.103 mmol9), potassium carbonate (0.042 g, 0.309 mmol) at room temperature, degassed it with argon for 5 min. $Pd(PPh_3)_4$ (0.0053 g, 0.005 mmol) was added to the reaction mixture and heated at 90° C. for 16 h. The reaction mixture was diluted with water (10 mL) and extract with EtOAc (2×10 mL). Combined organic layers were dried over anhydrous $Na_2SO_4$ and concentrated under reduced pressure to afford 3 [0.050 g (crude)1] as an off-white solid. The crude product was used for next step without further purification.

ESI-MS m/z $[C_{40}H_{41}N_5O_5S+H]^+$ 704.2.

4-{2-[4-(2-((2R,6S)-4-acetyl-2,6-dimethylpiperazin-1-yl)ethoxy)phenyl]quinolin-6-yl}-6-methyl-1H-pyrrolo[2,3-c]pyridin-7(6H)-one (SLU-2107)

To a stirred solution 3 (0.150 g, 0.21 mmol8) in MeOH (10 mL), $H_2O$ (5.0 mL), THF (5.0 mL) was charged with potassium hydroxide (0.059 g, 1.0 mmol) at 0° C. The reaction mixture was stirred for 5 h at room temperature, evaporated, diluted with water (20 mL) and extracted with $CH_2Cl_2$ (3×30 mL). Combined organic layers were dried over anhydrous $Na_2SO_4$ and concentrated under reduced pressure. The crude products were triturated with acetonitrile (5.0 mL), with MeOH (5.0 mL), filtered and dried to afford SLU-2107 (0.093 g, 44%) as an off-white solid.

$^1$H NMR (400 MHz, DMSO-$d_6$): δ ppm 12.22 (br. s., 1H), 8.46 (d, J=8.8 Hz, 1H), 8.26 (d, J=8.4 Hz, 2H), 8.18 (s, 1H), 8.09-8.14 (m, 2H), 8.01 (d, J=8.4 Hz, 1H), 7.60 (s, 1H), 7.41 (s, 1H), 7.11 (d, J=8.8 Hz, 2H), 6.62 (s, 1H), 4.18 (d, J=12.4 Hz, 1H), 4.09 (t, J=6.4 Hz, 2H), 3.66-3.68 (m, 2H), 3.63 (s, 3H), 3.06 (t, J=6.0 Hz, 2H), 2.77 (t, J=11.2 Hz, 1H), 2.60-2.65 (m, 1H), 2.28 (t, J=12.0 Hz, 1H), 1.99 (s, 3H), 1.11 (t, J=6.0 Hz, 6H).

ESI-MS m/z $[C_{33}H_{35}N_5O_3+H]^+$ 550.2.

HPLC (Method E) 97.6% (AUC), $t_R$=6.9 min.

Synthesis of (R)-4-{6-[4-(4-(2-(2,4-dimethyl-3-oxopiperazin-1-yl)ethoxy)phenyl)piperidin-1-yl]pyridin-3-yl}-6-methyl-1H-pyrrolo[2,3-c]pyridin-7(6H)-one (SLU-2089)

Scheme 49

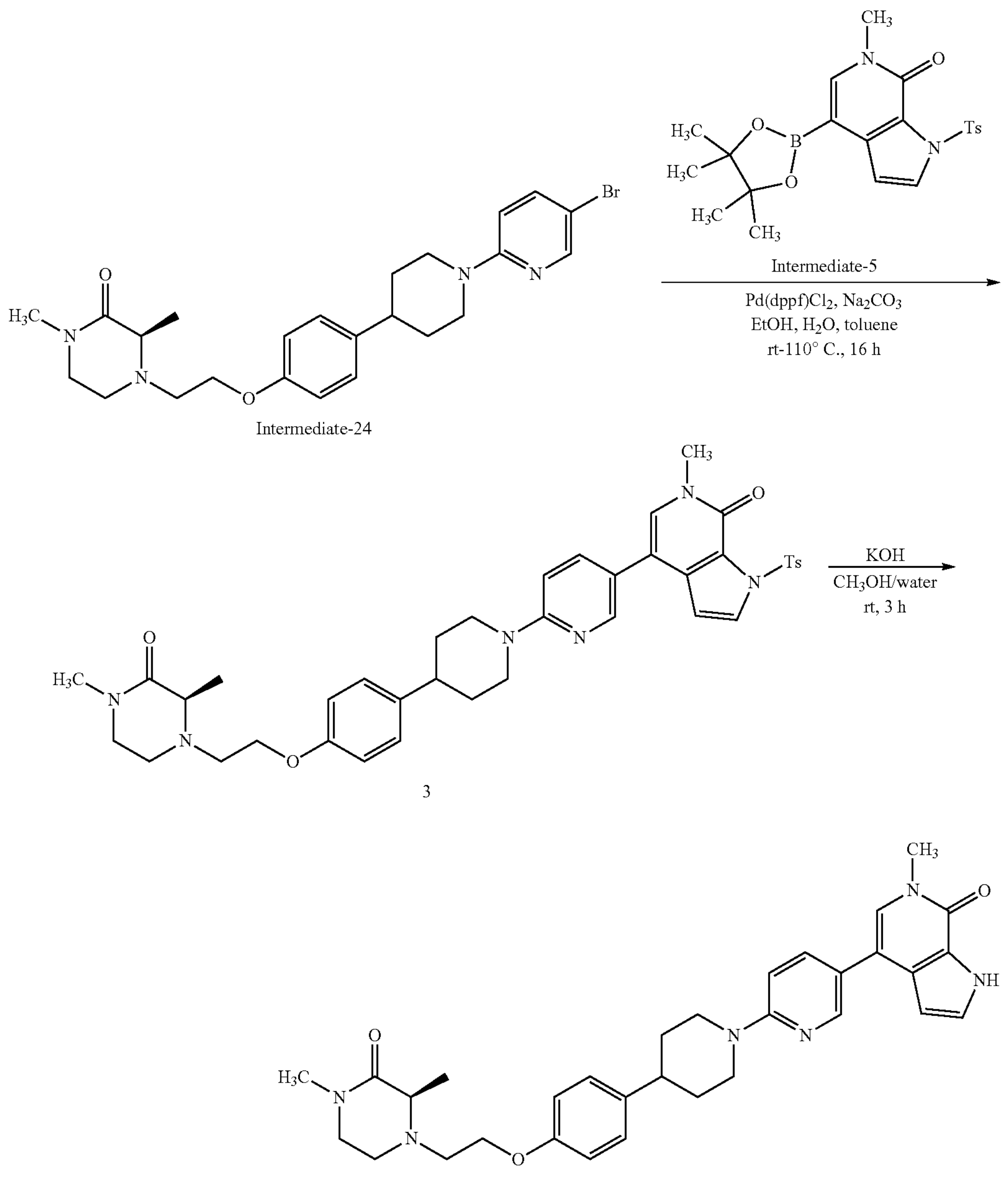

Intermediate-24

3

SLU-2089

(R)-4-{2-[4-(1-(5-bromopyridin-2-yl)piperidin-4-yl)phenoxy]ethyl}-1,3-dimethylpiperazin-2-one (2)

To a stirred solution of Intermediate-14 (0.500 g, 1.50 mmol) in DMF (5.0 mL) were charged with 5-bromo-2-chloropyridine 1 (0.350 g, 1.80 mmol) and $K_2CO_3$ (0.620 g, 4.5 mmol) at room temperature and was heated at 100° C. for 16 h. TLC indicated at which time the reaction gone to completion. The mixture was diluted with water (20 mL) and extracted with EtOAc (3×50 mL). Combined organic layers were dried over anhydrous $Na_2SO_4$ and concentrated under reduced pressure. The crude product was purified by combiflash chromatography ($CH_2Cl_2$:$CH_3OH$=97:3) to afford 2 (0.230 g, 17%9) as colourless liquid.

$^1$H NMR (300 MHz, DMSO-d$_6$): δ ppm 8.15 (d, J=2.4 Hz, 1H), 7.65 (d, J=2.4, 8.8 Hz, 1H), 7.14 (d, J=8.8 Hz, 2H), 6.84-6.87 (m, 3H), 4.38 (d, J=13.2 Hz, 2H), 4.03 (t, J=6.0 Hz, 2H), 3.22-3.25 (m, 2H), 3.11-3.17 (m, 2H), 3.02-3.07 (m, 1H), 2.87 (s, 1H) 2.82-2.84 (m, 1H), 2.78 (s, 3H), 2.70-2.77 (m, 1H), 2.66-2.69 (m, 2H), 1.79 (d, J=12.0 Hz, 2H), 1.49-1.59 (m, 2H), 1.22 (d, J=6.8 Hz, 3H).

(R)-4-{6-[4-(4-(2-(2,4-dimethyl-3-oxopiperazin-1-yl)ethoxy)phenyl)piperidin-1-yl]pyridin-3-yl}-6-methyl-1-tosyl-1H-pyrrolo[2,3-c]pyridin-7(6H)-one (3)

To a stirred solution of 2 (0.010 g, 0.02 mmol5) in ethanol (2.0 mL), toluene (2.0 mL), $H_2O$ (1.0 mL) were charged with Intermediate-5 (0.010 g, 0.024 mmol8), $Na_2CO_3$ (0.006 g, 0.06 mmol) at room temperature and degassed it with argon for 5 min. $Pd(dppf)Cl_2$ (0.002 g, 0.002 mmol) was added to the reaction mixture at room temperature and heated at 110° C. for 16 h. TLC indicated at which time the reaction gone to completion. The mixture was diluted with water (5.0 mL) and extracted with EtOAc (2x5 mL). Combined organic layers were dried over anhydrous $Na_2SO_4$ and concentrated under reduced pressure. The crude product was purified by combiflash chromatography ($CH_2Cl_2$: $CH_3OH$=97:3) to afford 5 [0.015 g (crude)7] as an off-white solid.

ESI-MS m/z $[C_{39}H_{44}N_6O_5S+H]^+$ 709.2.

(R)-4-{6-[4-(4-(2-(2,4-dimethyl-3-oxopiperazin-1-yl)ethoxy)phenyl)piperidin-1-yl]pyridin-3-yl}-6-methyl-1H-pyrrolo[2,3-c]pyridin-7(6H)-one (SLU-2089)

To a stirred solution of 5 (0.070 g, 0.09 mmol2) in $CH_3OH$ (3.0 mL), water (1.5 mL) was charged with potassium hydroxide (0.112 g, 1.97 mmol) and the reaction mixture was stirred for 3 h at room tempetature. The reaction mixture was evaporated, diluted with water (5.0 mL) and extracted with EtOAc (3x20 mL). Combined organic layers were dried over anhydrous $Na_2SO_4$ and concentrated under reduced pressure. The crude product was purified by reverse phase chromatography (2 times) (ACN:$H_2O$=80:20) to afford SLU-2089 (0.018 g, 33%4) as a white solid.

$^1$H NMR (400 MHz, DMSO-$d_6$): δ ppm 12.12 (s, 1H), 8.33 (d, J=2.4 Hz, 1H), 7.74 (dd, J=2.4, 11.2 Hz, 1H), 7.33 (t, J=2.8 Hz, 1H), 7.30 (s, 1H), 7.17 (d, J=8.8 Hz, 2H), 6.97 (d, J=8.8 Hz, 1H), 6.87 (d, J=8.8 Hz, 2H), 6.40 (t, J=4.8 Hz, 1H), 4.48 (d, J=12.8 Hz, 2H), 4.04 (t, J=5.6 Hz, 2H), 3.56 (s, 3H), 3.23 (d, J=4.8 Hz, 2H), 3.13-3.16 (m, 1H), 3.03-3.07 (m, 1H), 2.90 (t, J=12.8 Hz, 3H) 2.80 (s, 3H), 2.60-2.67 (m, 3H), 1.83 (d, J=12.8 Hz, 2H), 1.56-1.64 (m, 2H), 1.23 (d, J=6.8 Hz, 3H).

ESI-MS m/z $[C_{32}H_{38}N_6O_3+H]^+$ 555.3.

HPLC (Method D) 93.3% (AUC), $t_R$=6.2 min.

Synthesis of 4-{4'-[2-((2R,6S)-4-acetyl-2,6-dimethylpiperazin-1-yl)ethoxy]-[1,1'-biphenyl]-4-yl}-6-methyl-1H-pyrrolo[2,3-c]pyridin-7(6H)-one (SLU-2096)

Scheme 50

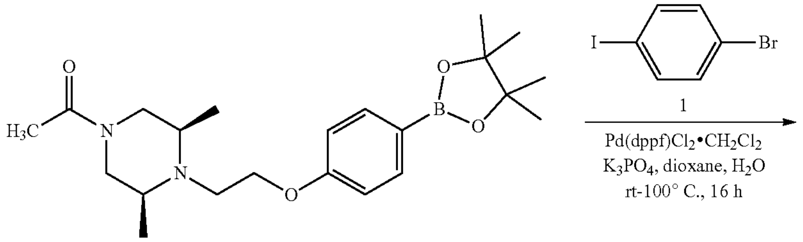

(cis-racemic)
Intermediate-18

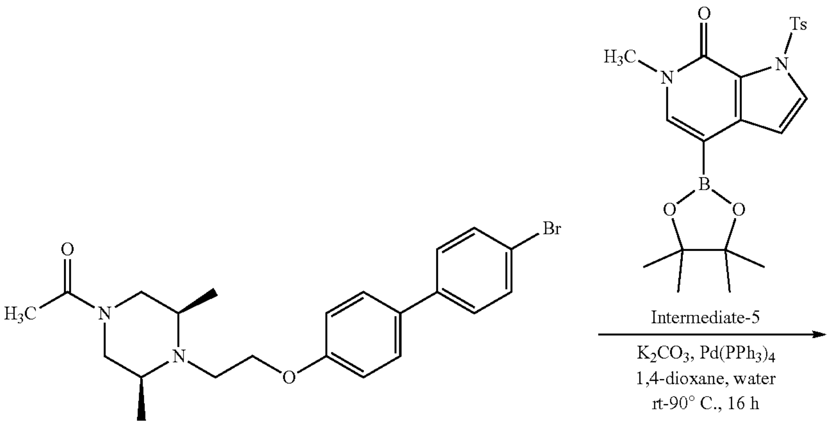

2
(cis-racemic)

-continued

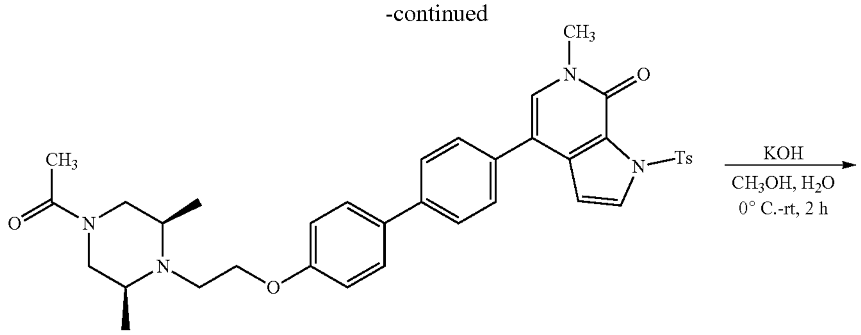

3
(cis-racemic)

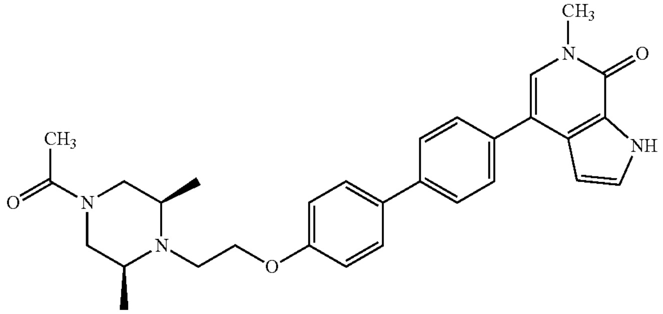

(cis-racemic)
SLU-2096

1-(3R,5S)-4-{2-[(4'-bromo-[1,1'-biphenyl]-4-yl)oxy) ethyl]-3,5-dimethyl piperazin-1-yl}ethanone (2)

To a stirred solution of Intermediate-18 (0.30 g, 0.72 mmol) in dioxane (8.0 mL), $H_2O$ (2.0 mL) were charged with 1-bromo-4-iodobenzene 1 (0.210 g, 0.72 mmol), $K_3PO_4$ (0.699 g, 2.88 mmol) at room temperature and it degassed with argon for 5 min. $Pd(dppf)Cl_2 \cdot CH_2Cl_2$ (0.060 g, 0.072 mmol) was added to the reaction mixture at room temperature and was heated at 100° C. for 16 h. TLC indicated at which time the reaction gone to completion. The reaction mixture was diluted with water (20 mL) and extracted with EtOAc (3×30 mL). Combined organic layers were dried over anhydrous $Na_2SO_4$ and concentrated under reduced pressure. The crude product was purified by combiflash chromatography ($CH_2Cl_2$:$CH_3OH$=95:5) to afford 2 (0.205 g, 64%) as an off-white solid.

$^1H$ NMR (400 MHz, $CDCl_3$): δ ppm 7.53 (d, J=8.4 Hz, 2H), 7.47 (d, J=8.8 Hz, 2H), 7.40 (d, J=8.4 Hz, 2H), 6.94 (d, J=8.4 Hz, 2H), 4.36-4.47 (m, 1H), 3.70-4.05 (m, 2H), 3.55-3.59 (m, 1H), 3.14 (t, J=6.4 Hz, 2H), 2.87-2.93 (m, 1H), 2.63-2.71 (m, 2H), 2.39-2.62 (m, 1H), 2.08 (s, 3H), 1.17-1.20 (m, 6H).

4-{4'-[2-((2R,6S)-4-acetyl-2,6-dimethylpiperazin-1-yl)ethoxy]-[1,1'-biphenyl]-4-yl}-6-methyl-1-tosyl-1H-pyrrolo[2,3-c]pyridin-7(6H)-one (3)

To a stirred solution of 2 (0.020 g, 0.04 mmol) in dioxane (2.0 mL), $H_2O$ (0.5 mL) were charged with Intermediate-5 (0.017 g, 0.04 mmol8), $K_2CO_3$ (0.011 g, 0.08 mmol) at room temperature and degassed it with argon for 5 min. $Pd(PPh_3)_4$ (0.002 g, 0.002 mmol) was added to the reaction mixture at room temperature and heated at 90° C. for 16 h. TLC indicated at which time the reaction gone to completion. The mixture was diluted with water (5.0 mL) and extracted with EtOAc (2×5 mL). Combined organic layers were dried over anhydrous $Na_2SO_4$ and concentrated under reduced pressure. The crude product was purified by combiflash chromatography ($CH_2Cl_2$:$CH_3OH$=95:5) to afford 3 [0.025 g (crude)7] as an off-white solid.

ESI-MS m/z $[C_{37}H_{40}N_4O_5S+H]^+$ 653.2.

4-{4'-[2-((2R,6S)-4-acetyl-2,6-dimethylpiperazin-1-yl)ethoxy]-[1,1'-biphenyl]-4-yl}-6-methyl-1H-pyrrolo[2,3-c]pyridin-7(6H)-one (SLU-2096)

To a stirred solution of 3 (0.080 g, 0.09 mmol9) in $CH_3OH$ (3.0 mL), $H_2O$ (1.5 mL) was charged with potassium hydroxide (0.167 g, 2.99 mmol) at 0° C. and stirred for 2 h at room temperature. The reaction mixture was evaporated, diluted with water (5.0 mL) and extracted with EtOAc (3×10 mL). Combined organic layers were dried over anhydrous $Na_2SO_4$ and concentrated under reduced pressure. The crude product was purified by reverse phase chromatography (ACN:$H_2O$=70:30) to afford SLU-2096 (0.024 g, 39%) as an off-white solid.

$^1H$ NMR (400 MHz, DMSO-$d_6$): δ ppm 12.16 (s, 1H), 7.71 (d, J=8.4 Hz, 3H), 7.65 (d, J=6.4 Hz, 3H), 7.43 (s, 1H), 7.37 (s, 1H), 7.03 (d, J=8.4 Hz, 2H), 6.49 (s, 1H), 4.18 (d, J=12.8 Hz, 1H), 4.04 (t, J=6.0 Hz, 2H), 3.66 (d, J=13.2 Hz, 1H), 3.59 (s, 3H), 3.04 (t, J=6.0 Hz, 2H), 2.76 (t, J=10.8 Hz, 2H), 2.24-2.33 (m, 2H), 1.98 (s, 3H), 1.09 (t, J=6.0 Hz, 6H).

ESI-MS m/z $[C_{30}H_{34}N_4O_3+H]^+$ 499.2.

HPLC (Method D) 96.7% (AUC), $t_R$=8.53 min.

Synthesis of (R)-4-{4'-[2-(2,4-dimethyl-3-oxopiperazin-1-yl)ethoxy]-[1,1'-biphenyl]-4-yl}-6-methyl-1H-pyrrolo[2,3-c]pyridin-7(6H)-one (SLU-2097)

Scheme 51

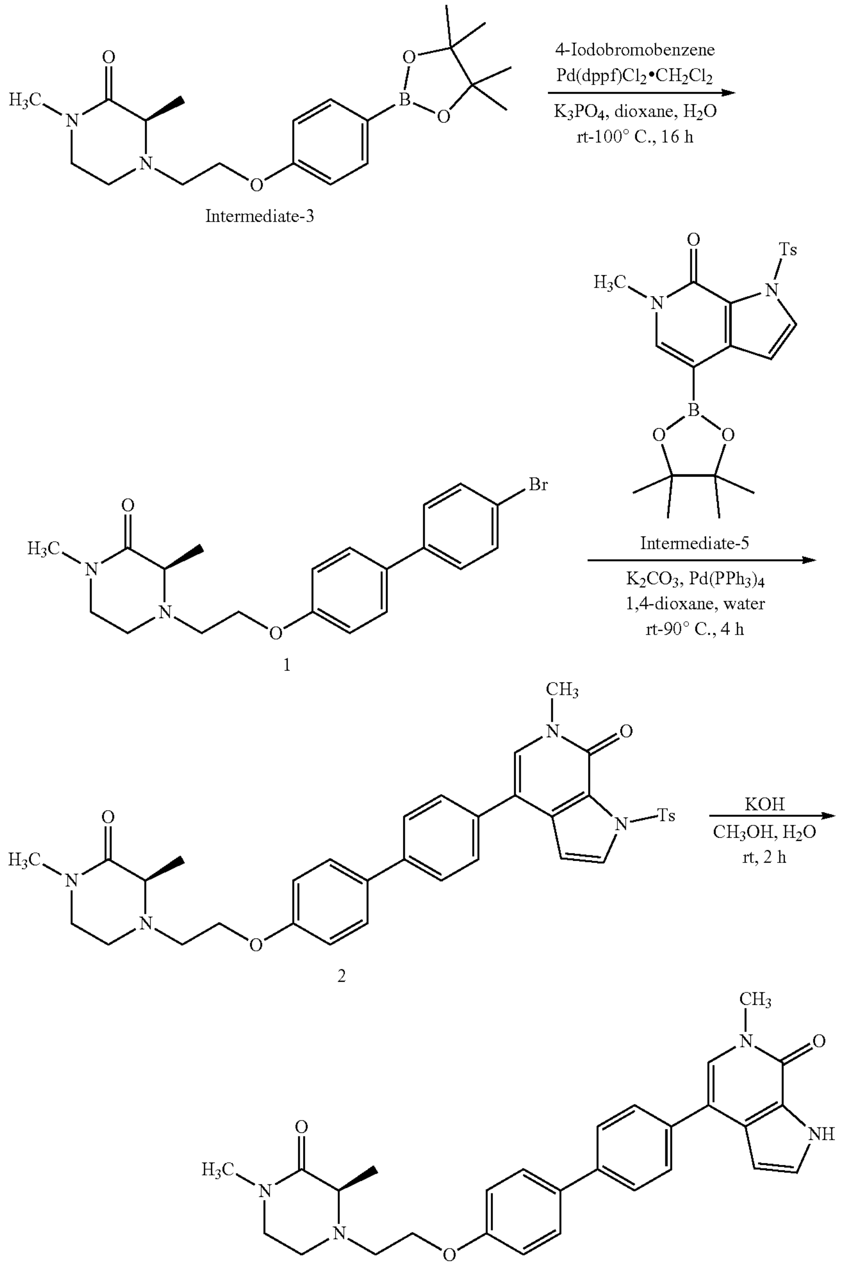

Intermediate-3

1

2

SLU-2097

(R)-4-{2-[(4'-bromo-[1,1'-biphenyl]-4-yl)oxy]ethyl}-1,3-dimethylpiperazin-2-one (1)

To a stirred solution of Intermediate-3 (0.4 g, 1.06 mmol2) in dioxane (10 mL), $H_2O$ (2.0 mL) were charged with 4-iodobromobenzene (0.283 g, 1.06 mmol), $K_3PO_4$ (1.03 g, 4.24 mmol) at room temperature and degassed it with argon for 5 min. $Pd(dppf)Cl_2 \cdot CH_2Cl_2$ (0.082 g, 0.1 mmol) was added to the reaction mixture at room temperature and heated at 100° C. for 16 h. TLC indicated at which time the reaction gone to completion. The reaction mixture was diluted with water (20 mL) and extracted with EtOAc (3×50 mL). Combined organic layers were dried over anhydrous $Na_2SO_4$ and concentrated under reduced pressure. The crude product was purified by combiflash chromatography ($CH_2Cl_2$:$CH_3OH$=95:5) to afford 1 (0.220 g, 42%1) as an off-white solid.

$^1$H NMR (400 MHz, $CDCl_3$): δ ppm 7.53 (d, J=8.8 Hz, 2H), 7.47 (d, J=6.8 Hz, 2H), 7.41 (d, J=6.4 Hz, 3H), 6.90 (d, J=8.8 Hz, 1H), 4.71 (d, J=2.0 Hz, 1H), 3.35-3.39 (m, 1H), 3.28-3.34 (m, 1H), 3.13-3.19 (m, 1H), 2.95-3.09 (m, 1H), 2.93 (s, 3H), 2.83-2.91 (m, 1H), 2.77-2.82 (m, 1H), 1.76 (s, 2H), 1.42 (d, J=6.8 Hz, 3H).

(R)-4-{4'-[2-(2,4-dimethyl-3-oxopiperazin-1-yl) ethoxy]-[1,1'-biphenyl]-4-yl}-6-methyl-1-tosyl-1H-pyrrolo[2,3-c]pyridin-7(6H)-one (2)

To a stirred solution of 1 (0.020 g, 0.04 mmol) in dioxane (2.0 mL), $H_2O$ (0.5 mL) were charged with Intermediate-5 (0.017 g, 0.04 mmol), $K_2CO_3$ (0.011 g, 0.08 mmol) at room temperature and degassed it with argon for 5 min. $Pd(PPh_3)_4$ (0.002 g, 0.002 mmol) was added to the reaction mixture at room temperature and heated at 90° C. for 4 h. TLC indicated at which time the reaction gone to completion. The mixture was diluted with water (5.0 mL) and extracted with EtOAc (2×5 mL). Combined organic layers were dried over anhydrous $Na_2SO_4$ and concentrated under reduced pressure. The crude product was purified by combiflash chromatography ($CH_2Cl_2$:$CH_3OH$=95:5) to afford 2 [0.025 g (crude)6] as an off-white solid.

ESI-MS m/z $[C_{35}H_{36}N_4O_5S+H]^+$ 625.2.

(R)-4-{4'-[2-(2,4-dimethyl-3-oxopiperazin-1-yl) ethoxy]-[1,1'-biphenyl]-4-yl}-6-methyl-1H-pyrrolo [2,3-c]pyridin-7(6H)-one (SLU-2097)

To a stirred solution of 2 (0.075 g, 0.12 mmol0) in $CH_3OH$ (3.0 mL), $H_2O$ (1.5 mL) was charged with potassium hydroxide (0.201 g, 3.6 mmol) and stirred for 2 h at room temperature. The reaction mixture was evaporated, diluted with water (5.0 mL) and extracted with EtOAc (3×20 mL). Combined organic layers were dried over anhydrous $Na_2SO_4$ and concentrated under reduced pressure. The crude product was purified by reverse phase chromatography (ACN:$H_2O$=70:30) to afford SLU-2097 (0.020 g, 36%) as a white solid.

$^1$H NMR (300 MHz, DMSO-$d_6$): δ ppm 12.16 (s, 1H), 7.72 (d, J=8.4 Hz, 3H), 7.65 (d, J=6.0 Hz, 3H), 7.43 (s, 1H), 7.36 (t, J=2.7 Hz, 1H), 7.05 (d, J=8.7 Hz, 2H), 6.49 (s, 1H), 4.13 (t, J=5.7 Hz, 2H), 3.59 (s, 3H), 3.26 (t, J=5.7 Hz, 2H), 3.08-3.18 (m, 2H), 2.95-3.06 (m, 2H), 2.81 (s, 3H), 2.72 (d, J=4.5 Hz, 1H), 1.25 (d, J=6.9 Hz, 3H).

ESI-MS m/z $[C_{28}H_{30}N_4O_3+H]^+$ 471.2.

HPLC (Method D) 96.2% (AUC), $t_R$=8.48 min.

Synthesis of 4-{6-[4-(4-methoxyphenyl)piperidin-1-yl]pyridin-3-yl}-6-methyl-1H-pyrrolo[2,3-c]pyridin-7(6H)-one (SLU-2108)

Scheme 52

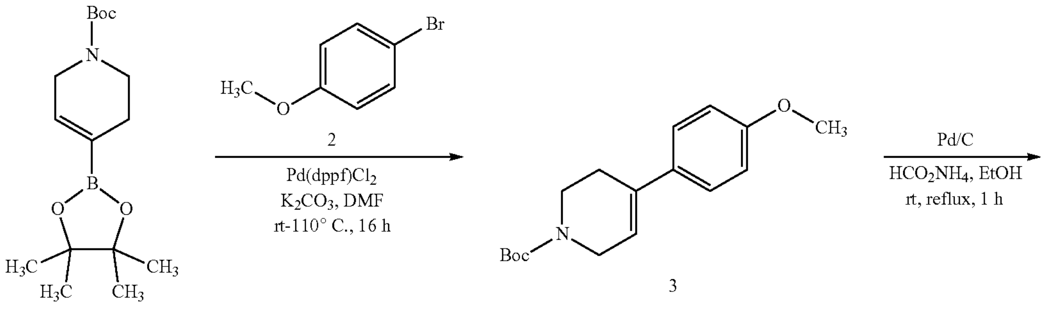

1 3

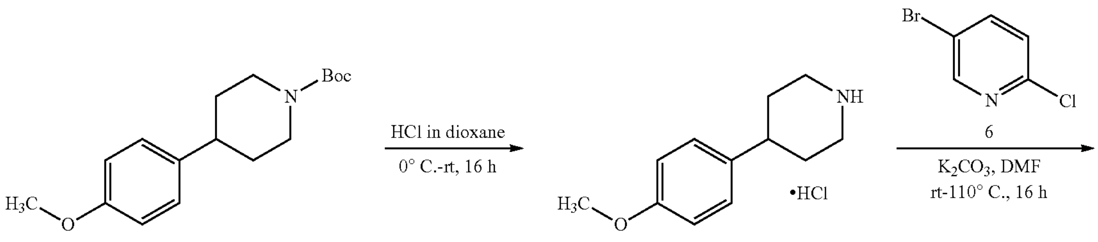

4 5

-continued

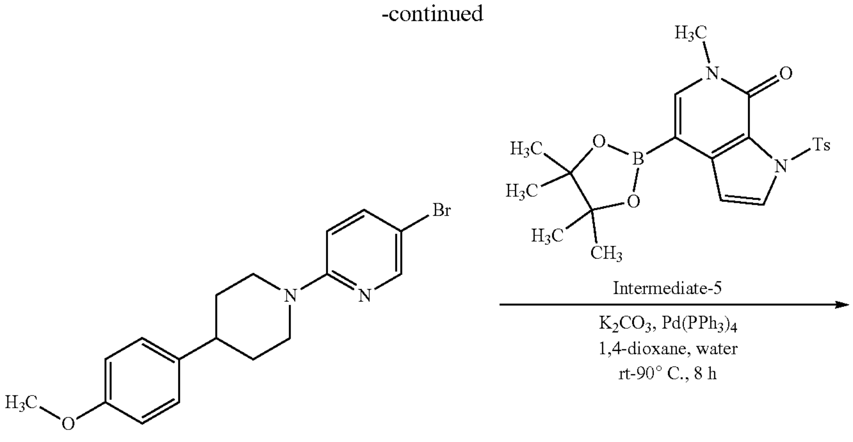

7

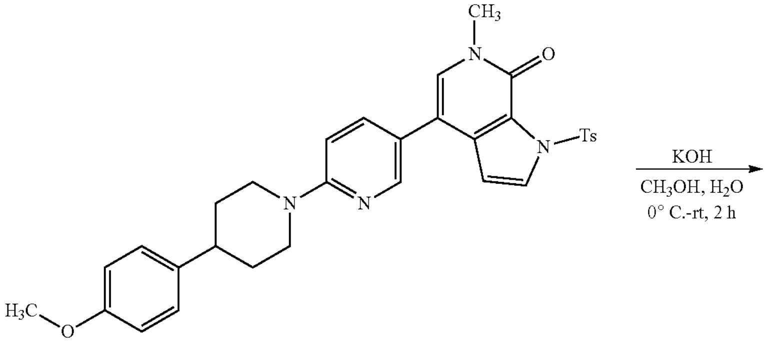

8

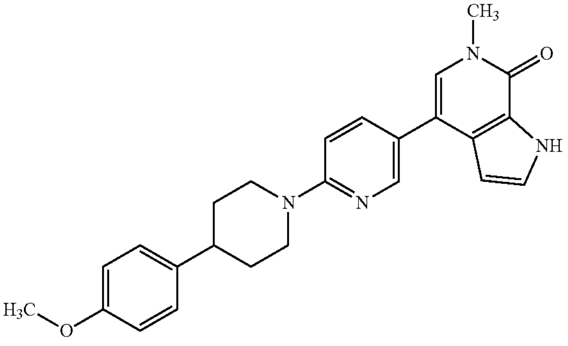

SLU-2108 tert-butyl 4-(4-methoxyphenyl)-5,6-dihydropyridine-1(2H)-carboxylate (3)

To a stirred solution of 1 (3.0 g, 9.7 mmol) in DMF (30 mL) were charged with 1-bromo-4-methoxybenzene 2 (2.2 g, 11.6 mmol), $K_2CO_3$ (20.0 g, 192.0 mmol) at room temperature and degassed it with argon for 10 min. Pd(dppf) $Cl_2$ (0.791 g, 0.97 mmol) was added to the reaction mixture at room temperature and was heated at 110° C. for 16 h. TLC indicated at which time the reaction gone to completion. The reaction mixture was diluted with water (200 mL) and extracted with EtOAc (3x600 mL). Combined organic layers were dried over anhydrous $Na_2SO_4$ and concentrated under reduced pressure. The crude product was purified by combiflash chromatography (Hexanes:EtOAc=70:30) to afford 3 (1.4 g, 43%0) as an off-white solid.

$^1H$ NMR (400 MHz, $CDCl_3$): δ ppm 7.31 (d, J=8.8 Hz, 2H), 6.87 (d, J=8.8 Hz, 2H), 5.93 (br.s., 1H), 4.05 (br.s., 2H), 3.81 (s, 3H), 3.62 (t, J=5.6 Hz, 2H), 2.49 (br.s., 2H), 1.48 (s, 9H).

tert-butyl 4-(4-methoxyphenyl)piperidine-1-carboxylate (4)

To a stirred solution 3 (1.4 g, 4.8 mmol0) in ethanol (150 mL) was charged with Pd/C (0.4 g), $HCOONH_4$ (3.05 g, 48.4 mmol) at room temperature and was refluxed for 1 h. TLC indicated at which time the reaction gone to completion. The reaction mixture was filtered through celite bed, washed with ethanol (2x70 mL) and concentrated. The reaction mixture was diluted with water (200 mL) and extracted with EtOAc (3x350 mL). Combined organic layers were dried over anhydrous $Na_2SO_4$ and concentrated under reduced pressure to afford 4 (1.0 g1) as a gummy solid. This crude was used for next step.

4-(4-methoxyphenyl)piperidine·hydrochloride (5)

To a stirred solution of 4 (1.0 g, 3.4 mmol1) in HCl in dioxane (10 mL) at 0° C. and stirred for 16 h at room temperature. TLC indicated at which time the reaction gone to completion. The mixture was concentrated to afford 5 (0.8 g3) as a gummy solid. This crude was used for next step.

ESI-MS m/z $[C_{12}H_{17}NO+H]^+$ 192.2.

5-bromo-2-[4-(4-methoxyphenyl)piperidin-1-yl] pyridine (7)

To a stirred solution of 5 (0.8 g, 2.61 mmol3) in DMF (10 mL) were charged with 5-bromo-2-chloropyridine 6 (0.504 g, 2.61 mmol), $K_2CO_3$ (1.08 g, 7.85 mmol) at room temperature and was heated at 100° C. for 16 h. TLC indicated at which time the reaction gone to completion. The reaction mixture was diluted with water (20 mL) and extracted with EtOAc (3x50 mL). Combined organic layers were dried over anhydrous $Na_2SO_4$ and concentrated under reduced pressure. The crude product was purified by combiflash chromatography (Hexanes:EtOAc=70:30) to afford 7 (0.180 g, 17%4) as an off-white solid.

$^1$H NMR (400 MHz, $CDCl_3$): δ ppm 8.19 (d, J=2.4 Hz, 1H), 7.52 (d, J=2.4, 8.8 Hz, 1H), 7.14 (d, J=8.4 Hz, 2H), 6.85 (d, J=8.8 Hz, 2H), 6.60 (d, J=8.8 Hz, 1H), 4.37 (dd, J=2.0, 10.8 Hz, 2H), 3.82 (s, 3H), 2.87-2.94 (m, 2H), 2.67-2.73 (m, 1H), 1.91 (d, J=12.8 Hz, 2H), 1.66-1.74 (m, 2H).

4-{6-[4-(4-methoxyphenyl)piperidin-1-yl]pyridin-3-yl}-6-methyl-1-tosyl-1H-pyrrolo[2,3-c]pyridin-7(6H)-one (8)

To a stirred solution of 7 (0.180 g, 0.63 mmol4) in dioxane (4.0 mL) were charged with Intermediate-5 (0.270 g, 0.63 mmol), $K_2CO_3$ (0.173 g, 1.26 mmol) at room temperature and degassed it with for 10 min. $Pd(PPh_3)_4$ (0.036 g, 0.03 mmol) was added to the reaction mixture at room temperature and heated at 90° C. for 8 h. TLC indicated at which time the reaction gone to completion. The reaction mixture was diluted with water (10 mL) and extracted with EtOAc (3x20 mL). Combined organic layers were dried over anhydrous $Na_2SO_4$ and concentrated under reduced pressure. The crude product was purified by combiflash chromatography (Hexanes:EtOAc=70:30) to afford 8 (0.070 g, 22%6) as an off-white solid.

ESI-MS m/z $[C_{32}H_{32}N_4O_4S+H]^+$ 569.1.

4-{6-[4-(4-methoxyphenyl)piperidin-1-yl]pyridin-3-yl}-6-methyl-1H-pyrrolo[2,3-c]pyridin-7(6H)-one (SLU-2108)

To a stirred solution of 8 (0.065 g, 0.09 mmol6) in $CH_3OH$ (3.0 mL), $H_2O$ (1.5 mL) was charged with potassium hydroxide (0.162 g, 1.97 mmol) at 0° C. and stirred for 2 h at room temperature. The reaction mixture was evaporated, diluted with water (5.0 mL) and extracted with EtOAc (3x20 mL). Organic layer was dried over anhydrous $Na_2SO_4$ and concentrated under reduced pressure. The crude product was purified by reverse phase chromatography (2 times) (ACN:$H_2O$=80:20) to afford SLU-2108 (0.009 g, 20%) as an off-white solid.

$^1$H NMR (400 MHz, $CDCl_3$): δ ppm 10.12 (s, 1H), 8.39 (d, J=2.4 Hz, 1H), 7.68 (dd, J=2.4, 8.8 Hz, 1H), 7.29 (t, J=2.8 Hz, 1H), 7.17 (d, J=8.8 Hz, 2H), 6.94 (s, 1H), 6.87 (d, J=8.4 Hz, 2H), 6.80 (d, J=8.8 Hz, 1H), 6.51 (t, J=2.4 Hz, 1H), 4.49 (d, J=13.2 Hz, 2H), 3.80 (s, 3H), 3.71 (s, 3H), 2.94-3.01 (m, 2H), 2.71-2.78 (m, 1H), 1.96 (d, J=11.6 Hz, 2H), 1.72-1.82 (m, 2H).

ESI-MS m/z $[C_{25}H_{26}N_4O_2+H]^+$ 415.2.

HPLC (Method E) 95.1% (AUC), $t_R$=7.4 min.

Synthesis of 4-{6-[4-(4-(2-(dimethylamino)ethoxy)phenyl)piperidin-1-yl]pyridin-3-yl}-6-methyl-1H-pyrrolo[2,3-c]pyridin-7(6H)-one (SLU-2109)

Scheme 53

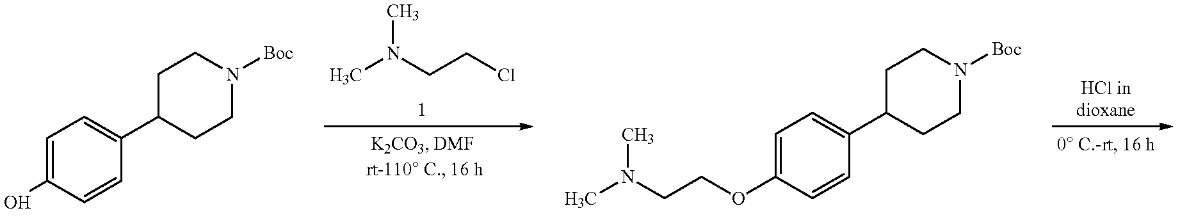

Intermediate-12

2

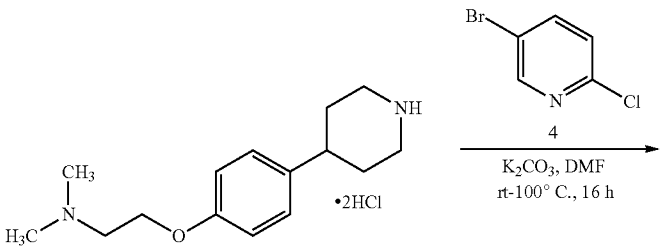

3

-continued

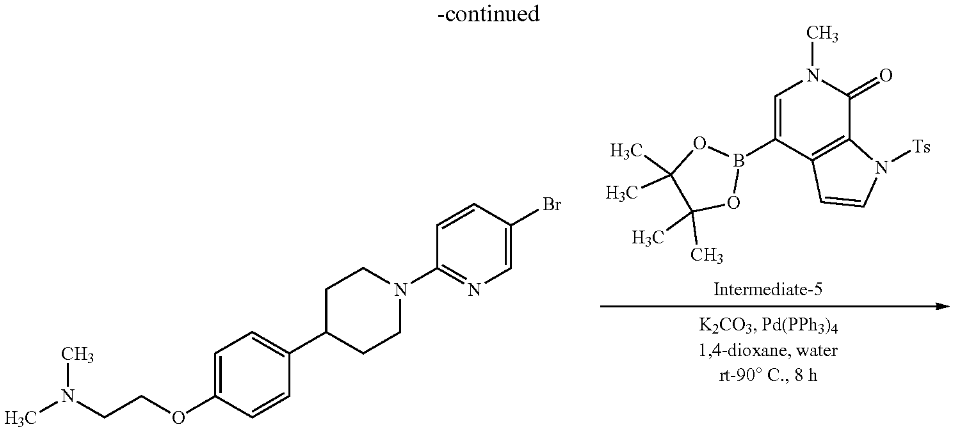

5

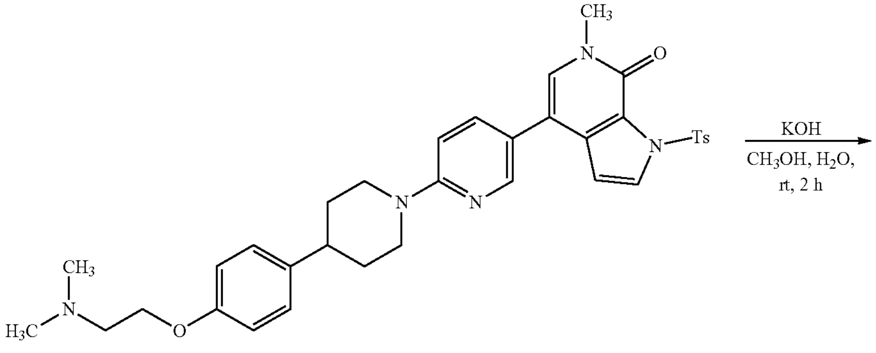

6

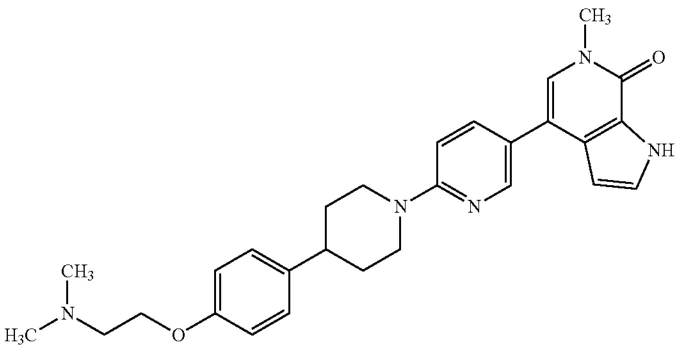

SLU-2109 tert-butyl 4-{4-[2-(dimethylamino)ethoxy]phenyl}piperidine-1-carboxylate (2)

To a stirred solution of Intermediate-12 (1.0 g, 3.5 mmol) 2-chloro-N,N-dimethylethanamine 1 (0.62 g, 4.3 mmol), $K_2CO_3$ (1.4 g, 10.5 mmol) in DMF (15 mL) at room temperature and heated at 110° C. for 16 h. TLC indicated at which time the reaction gone to completion. The reaction mixture was diluted with water (50 mL) and extracted with EtOAc (3×100 mL). Organic layer was separated, dried over anhydrous $Na_2SO_4$ and concentrated under reduced pressure. The crude product was purified by combiflash chromatography (Hexanes:EtOAc=90:10) to afford 2 (0.51 g, 41%) as an off-white solid.

N,N-dimethyl-2-[4-(piperidin-4-yl)phenoxy]ethanamine·hydrochloride (3)

To a stirred solution of 2 (0.51 g, 1.46 mmol) in HCl in dioxane (10 mL) at 0° C. and was stirred for 16 h at room temperature. TLC indicated at which time the reaction gone to completion. The mixture was concentrated to afford 3 (0.45 g) as a gummy solid. This crude was used for next step.

2-{4-[1-(5-bromopyridin-2-yl)piperidin-4-yl]phenoxy}-N,N-dimethylethanamine (5)

To a stirred solution of 3 (0.45 g, 1.80 mmol) 5-bromo-2-chloropyridine 4 (0.38 g, 1.80 mmol), $K_2CO_3$ (0.828 g, 5.4 mmol) in DMF (10 mL) at room temperature and was heated at 100° C. for 16 h. TLC indicated at which time the reaction gone to completion. The mixture was diluted with water (40 mL) and extracted with EtOAc (3×60 mL). Organic layer was separated, dried over anhydrous $Na_2SO_4$ and concentrated under reduced pressure. The crude product was purified by combiflash chromatography (Hexanes:EtOAc=90:10) to afford 5 (0.10 g, 12%) as an off-white solid.

$^1H$ NMR (300 MHz, DMSO-$d_6$): δ ppm 8.15 (d, J=1.5 Hz, 1H), 7.65 (d, J=8.4 Hz, 1H), 7.13 (d, J=8.1 Hz, 2H), 6.83-6.88 (m, 3H), 4.38 (d, J=13.8 Hz, 2H), 3.99 (t, J=5.7 Hz, 2H), 2.83-2.91 (m, 5H), 2.20 (s, 6H), 1.79 (d, J=11.4 Hz, 2H), 1.53-1.60 (m, 2H).

4-{6-[4-(4-(2-(dimethylamino)ethoxy)phenyl)piperidin-1-yl])pyridin-3-yl}-6-methyl-1-tosyl-1H-pyrrolo[2,3-c]pyridin-7(6H)-one (6)

To a stirred solution of 5 (0.10 g, 0.24 mmol) Intermediate-5 (0.106 g, 0.24 mmol), $K_2CO_3$ (0.099 g, 0.72 mmol) in dioxane (4.0 mL), water (1.0 mL) and degassed it with argon for 5 min. $Pd(PPh_3)_4$ (0.014 g, 0.012 mmol) degassed it with argon for 2 min at room temperature and was heated at 90° C. for 8 h. TLC indicated at which time the reaction gone to completion. The mixture was diluted with water (10 mL) and extracted with EtOAc (3x20 mL). Organic layer was separated, dried over anhydrous $Na_2SO_4$ and concentrated under reduced pressure ($CH_2Cl_2$:$CH_3OH$=95:5) to afford 6 (0.12 g) as a gummy solid.

ESI-MS m/z $[C_{35}H_{39}N_5O_4S+H]^+$ 626.2.

4-{6-[4-(4-(2-(dimethylamino)ethoxy)phenyl)piperidin-1-yl]pyridin-3-yl}-6-methyl-1H-pyrrolo[2,3-c]pyridin-7(6H)-one (SLU-2109)

To a stirred solution 6 (0.12 g, 0.19 mmol) in $CH_3OH$ (3.0 mL), water (1.5 mL) was charged with potassium hydroxide (0.106 g, 1.9 mmol) and stirred for 2 h at room temperature. The reaction mixture was evaporated, diluted with water (5.0 mL) and extracted with EtOAc (3x20 mL). Organic layer was dried over anhydrous $Na_2SO_4$ and concentrated under reduced pressure. The crude product was purified by reverse phase chromatography (ACN:$H_2O$=70:30) to afford SLU-2109 (0.017 g, 19%) as an off-white solid.

$^1H$ NMR (300 MHz, DMSO-$d_6$): δ ppm 12.12 (s, 1H), 8.33 (s, 1H), 7.73 (d, J=9.0 Hz, 1H), 7.32 (d, J=8.7 Hz, 2H), 7.16 (d, J=7.8 Hz, 2H), 6.97 (d, J=8.4 Hz, 1H), 6.86 (d, J=8.1 Hz, 2H), 6.40 (s, 1H), 4.48 (d, J=11.4 Hz, 2H), 4.00 (t, J=5.4 Hz, 2H), 3.56 (s, 3H), 2.85-2.94 (m, 5H), 2.20 (s, 6H), 1.83 (d, J=12.0 Hz, 2H), 1.53-1.66 (m, 2H).

ESI-MS m/z $[C_{28}H_{33}N_5O_2+H]^+$ 472.2.

HPLC (Method D) 94.7% (AUC), $t_R$=6.1 min.

Synthesis of (R)-4-{6-[4-(4-(2-(2,4-dimethyl-3-oxopiperazin-1-yl)ethoxy)phenyl)piperidin-1-yl]-4-methoxypyridin-3-yl}-6-methyl-1,6-dihydro-7H-pyrrolo[2,3-c]pyridin-7-one (SLU-2111)

Scheme 54

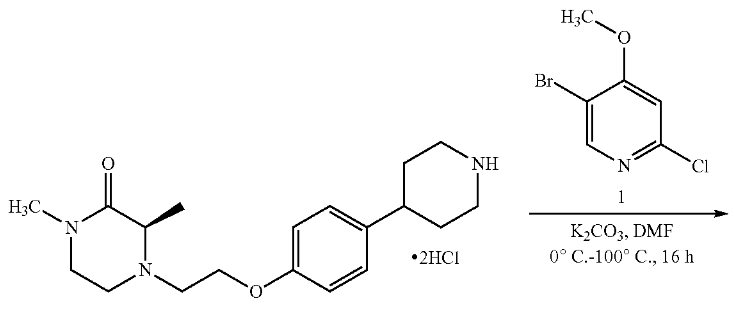

Intermediate-14

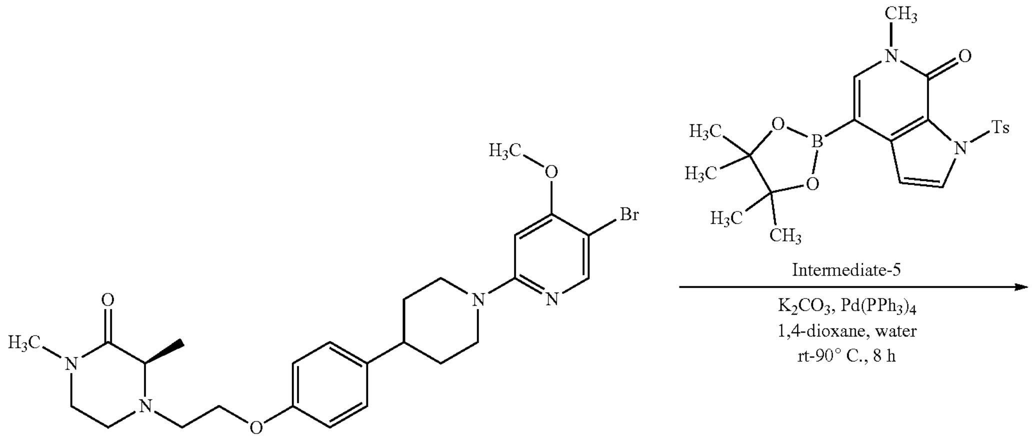

2

-continued

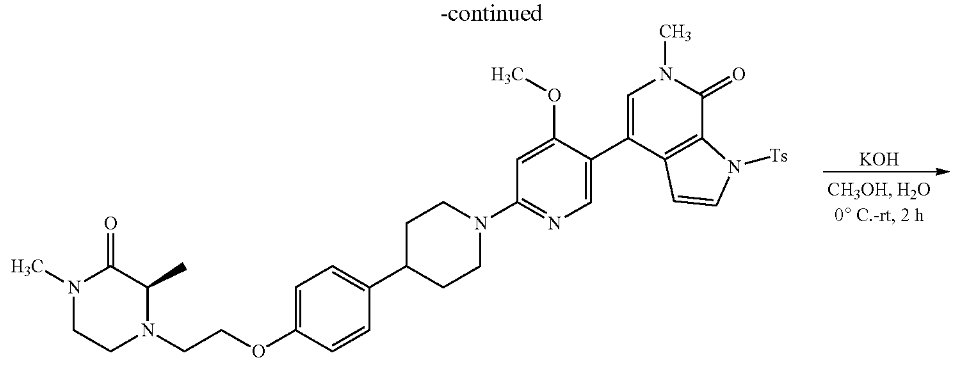

3

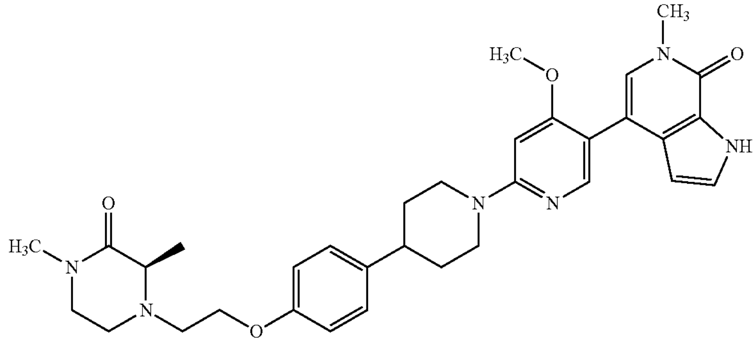

SLU-2111

(R)-4-{2-[4-(1-(5-bromo-4-methoxypyridin-2-yl)piperidin-4-yl)phenoxy]ethyl}-1,3-dimethylpiperazin-2-one (2)

To a stirred solution of Intermediate-14 (1.0 g, 13.0 mmol) in DMF (15 mL) were charged with 5-bromo-2-chloro-4-methoxypyridine 1 (0.642 g, 3.0 mmol), $K_2CO_3$ (1.24 g, 9.0 mmol) at 0° C. and was heated at 100° C. for 16 h. TLC indicated at which time the reaction gone to completion. The reaction mixture was diluted with water (50 mL) and extracted with EtOAc (4×50 mL). Combined organic layers were dried over anhydrous $Na_2SO_4$ and concentrated under reduced pressure. The crude product was purified by combiflash chromatography ($CH_2Cl_2$:$CH_3OH$=96:4) to afford 2 (0.080 g, 6%) as a gummy solid.

$^1$H NMR (400 MHz, DMSO-$d_6$): δ ppm 8.02 (s, 1H), 7.15 (d, J=8.8 Hz, 2H), 6.85 (d, J=8.4 Hz, 2H), 6.46 (s, 1H), 4.44 (d, J=13.2 Hz, 2H), 4.03 (t, J=5.7 Hz, 2H), 3.89 (s, 3H), 3.22-3.27 (m, 2H), 3.11-3.17 (m, 1H), 3.02-3.07 (m, 1H), 2.85-2.95 (m, 3H), 2.80 (s, 3H), 2.64-2.71 (m, 3H), 1.79 (d, J=12.4 Hz, 2H), 1.54-1.57 (m, 2H), 1.22 (d, J=6.4 Hz, 3H).

(R)-4-{6-[4-(4-(2-(2,4-dimethyl-3-oxopiperazin-1-yl)ethoxy)phenyl)piperidin-1-yl]-4-methoxypyridin-3-yl}-6-methyl-1-tosyl-1,6-dihydro-7H-pyrrolo[2,3-c]pyridin-7-one (3)

To a stirred solution of 2 (0.080 g, 0.07 mmol) in dioxane (4.0 mL), $H_2O$ (1.0 mL) were charged with Intermediate-5 (0.033 g, 0.07 mmol), $K_2CO_3$ (0.019 g, 0.14 mmol) at room temperature and degassed it with argon for 5 min. $Pd(PPh_3)_4$ (0.008 g, 0.003 mmol) was added to the reaction mixture at room temperature and heated at 90° C. for 8 h. TLC indicated at which time the reaction gone to completion. The reaction mixture was diluted with water (10 mL) and extracted with EtOAc (3×20 mL). Combined organic layers were dried over anhydrous $Na_2SO_4$ and concentrated under reduced pressure ($CH_2Cl_2$:$CH_3OH$=95:5) to afford 3 (0.060 g) as a gummy solid.

(R)-4-{6-[4-(4-(2-(2,4-dimethyl-3-oxopiperazin-1-yl)ethoxy)phenyl)piperidin-1-yl]-4-methoxypyridin-3-yl}-6-methyl-1,6-dihydro-7H-pyrrolo[2,3-c]pyridin-7-one (SLU-2111)

To a stirred solution of 3 (0.060 g, 0.08 mmol) in $CH_3OH$ (3.0 mL), water (1.5 mL) was charged with potassium hydroxide (0.138 g, 2.47 mmol) at 0° C. The reaction mixture was stirred for 2 h at room temperature, evaporated, diluted with water (5 mL) and extracted with EtOAc (3×20 mL). Combined organic layers were dried over anhydrous $Na_2SO_4$ and concentrated under reduced pressure. The crude product was purified by reverse phase chromatography (ACN:$H_2O$=70:30) to afford SLU-2111 (0.012 g, 25%) as an off-white solid.

1H NMR (300 MHz, DMSO-$d_6$): δ ppm 11.93 (s, 1H), 7.89 (s, 1H), 7.23 (br.s., 1H), 7.17 (d, J=8.4 Hz, 2H), 7.09 (s, 1H), 6.87 (d, J=8.4 Hz, 2H), 6.46 (s, 1H), 6.03 (s, 1H), 4.52 (d, J=12.3 Hz, 2H), 4.04 (t, J=6.0 Hz, 2H), 3.78 (s, 3H), 3.53 (s, 3H), 3.24 (t, J=6.0 Hz, 2H), 3.15 (t, J=5.4 Hz, 2H), 2.90 (d, J=12.0 Hz, 2H), 2.80 (s, 3H), 2.71 (d, J=9.6 Hz, 3H), 1.81-1.88 (m, 3H), 1.55-1.66 (m, 2H), 1.23 (d, J=6.6 Hz, 3H).

ESI-MS m/z $[C_{33}H_{40}N_6O_4+H]^+$ 585.3.

HPLC (Method D) 92.9% (AUC), $t_R$=6.2 min.

Synthesis of 4-{6-[4-(4-(2-((2R,6S)-4-acetyl-2,6-dimethylpiperazin-1-yl)ethoxy)phenyl)piperidin-1-yl]-4-methoxypyridin-3-yl}-6-methyl-1H-pyrrolo[2,3-c]pyridin-7(6H)-one (SLU-2117)
Scheme 55
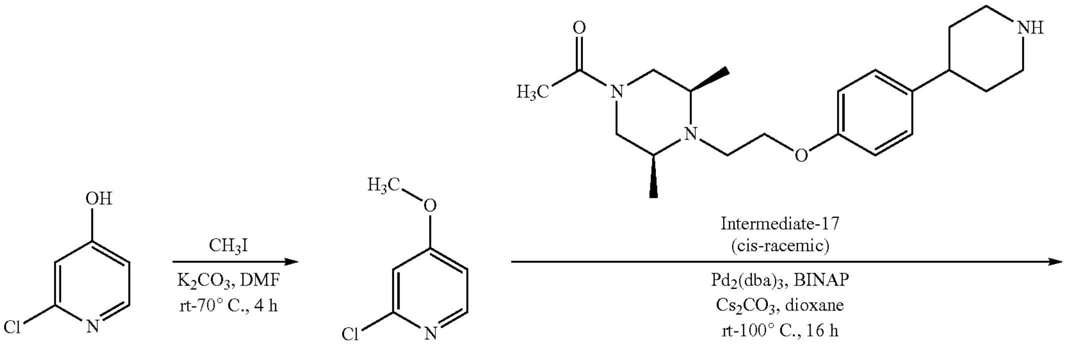
1
2
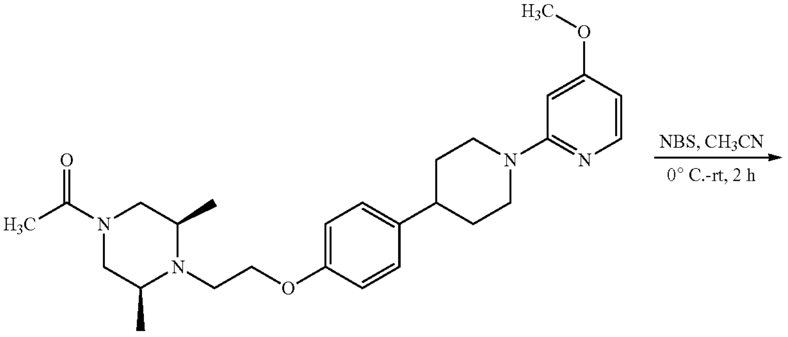
3
(cis-racemic)
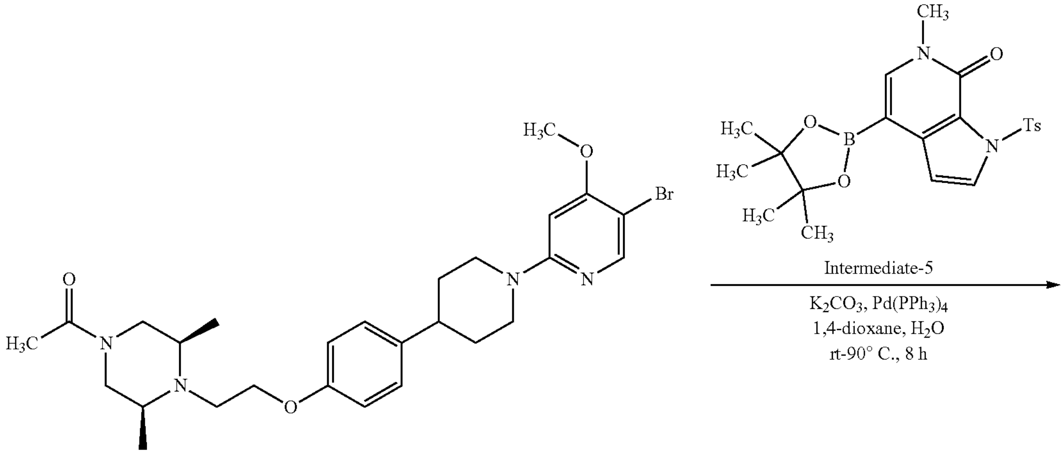
4
(cis-racemic)

-continued

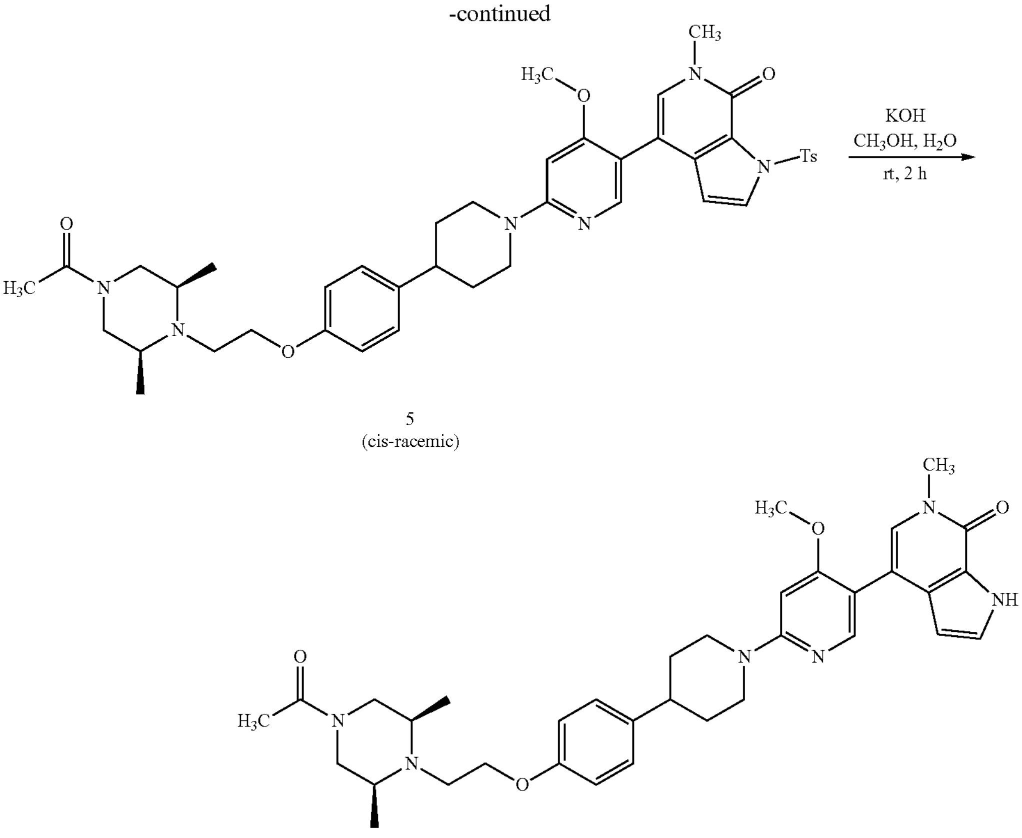

5
(cis-racemic)

SLU-2117
(cis-racemic)

2-chloro-4-methoxypyridine (2)

To a stirred solution of 1 (2.0 g, 15.5 mmol), $CH_3I$ (2.4 g, 17.0 mmol), $K_2CO_3$ (4.27 g, 31.0 mmol) in DMF (30 mL) was charged at room temperature and heated at 70° C. for 4 h. TLC indicated at which time the reaction gone to completion. The reaction mixture was diluted with water (100 mL) and extracted with EtOAc (4×150 mL). Organic layer was separated, dried over anhydrous $Na_2SO_4$ and concentrated under reduced pressure. The crude product was purified by combiflash chromatography (Hexanes:EtOAc=80:20) to afford 2 (1.85 g, 81%) as an off-white solid.

$^1$H NMR (300 MHz, $CDCl_3$): δ ppm 8.19 (d, J=5.6 Hz, 1H), 6.84 (d, J=2.0 Hz, 1H), 6.76 (dd, J=2.4, 6.0 Hz, 1H), 3.86 (s, 3H).

1-{[(3R,5S)-4-(2-(4-(1-(4-methoxypyridin-2-yl)piperidin-4-yl)phenoxy)ethyl)-3,5-dimethylpiperazin-1-yl]}ethanone (3)

To a stirred solution of 2 (0.3 g, 2.08 mmol), Intermediate-17 (0.75 g, 2.08 mmol), $Cs_2CO_3$ (2.02 g, 6.24 mmol) in dioxane (15 mL) and degassed it with argon for 5 min. BINAP (0.124 g, 0.20 mmol), $Pd_2(dba)_3$ (0.183 g, 0.20 mmol) was added to the reaction mixture and degassed it with argon for 2 min at room temperature and was heated at 100° C. for 16 h. TLC indicated at which time the reaction gone to completion. The reaction mixture was diluted with water (80 mL) and extracted with EtOAc (3×150 mL). Combined organic layers were dried over anhydrous $Na_2SO_4$ and concentrated under reduced pressure. The crude product was purified by reverse phase chromatography (ACN:$H_2O$=70:30) to afford 3 (0.12 g, 13%) as an off-white solid.

$^1$H NMR (400 MHz, DMSO-$d_6$): δ ppm 7.92 (d, J=5.6 Hz, 1H), 7.40 (d, J=8.8 Hz, 2H), 6.82-6.85 (m, 3H), 6.25 (d, J=2.0, 6.0 Hz, 1H), 4.41 (d, J=13.1 Hz, 2H), 4.15 (d, J=12.4 Hz, 2H), 3.94 (t, J=6.4 Hz, 2H), 3.77 (s, 3H), 3.64 (d, J=13.2 Hz, 2H), 2.99 (d, J=12.4 Hz, 4H), 2.69-2.89 (m, 2H), 2.21-2.27 (m, 2H), 1.97 (s, 3H), 1.77 (d, J=10.8 Hz, 2H), 1.49-1.60 (m, 2H), 1.06 (t, J=6.4 Hz, 6H).

1-{[(3R,5S)-4-(2-(4-(1-(5-bromo-4-methoxypyridin-2-yl)piperidin-4-yl)phenoxy)ethyl)-3,5-dimethylpiperazin-1-yl]}ethanone (4)

To a stirred solution of 3 (0.25 g, 0.53 mmol) in $CH_3CN$ (8.0 mL) was cooled to 0° C. and N-bromosuccinimide (0.10 g, 0.59 mmol) was added portion wise at 0° C. and stirred for 2 h at room temperature. TLC indicated at which time the reaction gone to completion. The reaction mixture was diluted with water (30 mL) and extracted with EtOAc (3×50 mL). Combined organic layers were dried over anhydrous $Na_2SO_4$ and concentrated under reduced pressure. The crude product was purified by combiflash chromatography ($CH_2Cl_2$:$CH_3OH$=95:5) to afford 4 (0.15 g, 51%) as an off-white solid.

$^1$H NMR (400 MHz, DMSO-$d_6$): δ ppm 8.02 (s, 1H), 7.14 (d, J=8.8 Hz, 2H), 6.84 (d, J=8.8 Hz, 2H), 6.46 (s, 1H), 4.44 (d, J=12.8 Hz, 2H), 4.16 (d, J=11.6 Hz, 1H), 3.94 (t, J=6.0 Hz, 2H), 3.89 (s, 3H), 3.64 (d, J=12.8 Hz, 1H), 2.99 (br.s., 4H), 2.86 (t, J=12.8 Hz, 2H), 2.67-2.74 (m, 2H), 2.13-2.27 (m, 2H), 1.97 (s, 3H), 1.78 (d, J=12.8 Hz, 2H), 1.53-1.57 (m, 2H), 1.06 (t, J=6.0 Hz, 6H).

4-{6-[4-(4-(2-((2R,6S)-4-acetyl-2,6-dimethylpiperazin-1-yl)ethoxy)phenyl)piperidin-1-yl]-4-methoxypyridin-3-yl}-6-methyl-1-tosyl-1H-pyrrolo[2,3-c]pyridin-7(6H)-one (5)

To a stirred solution of 4 (0.15 g, 0.20 mmol), Intermediate-5 (0.094 g, 0.20 mmol), $K_2CO_3$ (0.082 g, 0.6 mmol) in dioxane (4.0 mL), water (1.0 mL) and degassed it with argon for 5 min at room temperature. $Pd(PPh_3)_4$ (0.011 g, 0.01 mmol) and degassed it with argon for 5 min at room temperature and was heated at 90° C. for 8 h. TLC indicated at which time the reaction gone to completion. The reaction mixture was diluted with water (20 mL) and extracted with EtOAc (3×25 mL). Combined organic layers were washed with water (10 mL), dried over anhydrous $Na_2SO_4$ and concentrated under reduced pressure. The crude product was purified by combiflash chromatography ($CH_2Cl_2$: $CH_3OH$=94:6) to afford 5 (0.075 g, 32%) as an off-white solid.

$^1$H NMR (400 MHz, DMSO-$d_6$): δ ppm 7.98 (d, J=8.4 Hz, 2H), 7.91 (d, J=3.6 Hz, 1H), 7.83 (s, 1H), 7.43 (d, J=8.4 Hz, 2H), 7.35 (s, 1H), 7.16 (d, J=8.8 Hz, 2H), 6.85 (d, J=8.8 Hz, 2H), 6.46 (s, 1H), 6.30 (d, J=3.6 Hz, 1H), 4.52 (d, J=12.8 Hz, 2H), 4.16 (d, J=12.4 Hz, 1H), 3.93-3.96 (m, 2H), 3.77 (s, 3H), 3.64 (d, J=12.8 Hz, 1H), 3.42 (s, 3H), 2.99 (t, J=6.0 Hz, 2H), 2.89 (t, J=12.0 Hz, 2H), 2.71-2.77 (m, 3H), 2.39 (s, 3H), 1.97 (s, 3H), 1.82 (d, J=12.0 Hz, 2H), 1.57-1.60 (m, 2H), 1.06 (t, J=6.0 Hz, 8H).

4-{6-[4-(4-(2-((2R,6S)-4-acetyl-2,6-dimethylpiperazin-1-yl)ethoxy)phenyl)piperidin-1-yl]-4-methoxypyridin-3-yl}-6-methyl-1H-pyrrolo[2,3-c]pyridin-7(6H)-one (SLU-2117)

To a stirred solution of 5 (0.075 g, 0.09 mmol) in $CH_3OH$ (3.0 mL), water (1.0 mL) was charged with potassium hydroxide (0.116 g, 2.93 mmol) and the reaction mixture was stirred for 2 h at room temperature. The reaction mixture was evaporated, diluted with water (10 mL) and extracted with EtOAc (3×20 mL). Combined organic layers were dried over anhydrous $Na_2SO_4$ and concentrated under reduced pressure. The crude product was purified by reverse phase chromatography (ACN:$H_2O$=80:20) to afford SLU-2117 (0.033 g, 55%) as an off-white solid.

$^1$H NMR (300 MHz, DMSO-$d_6$): δ ppm 11.95 (s, 1H), 7.89 (s, 1H), 7.23 (br.s., 1H), 7.17 (d, J=8.4 Hz, 2H), 7.09 (s, 1H), 6.85 (d, J=8.4 Hz, 2H), 6.46 (s, 1H), 6.03 (br.s., 1H), 4.52 (d, J=11.7 Hz, 2H), 4.16 (d, J=12.0 Hz, 1H), 3.95 (t, J=6.0 Hz, 2H), 3.78 (s, 3H), 3.65 (d, J=11.7 Hz, 1H), 3.53 (s, 3H), 2.99 (t, J=6.0 Hz, 2H), 2.88 (t, J=13.2 Hz, 2H), 2.70-2.88 (m, 3H), 2.25-2.27 (m, 2H), 1.97 (s, 3H), 1.83 (d, J=10.2 Hz, 2H), 1.58-1.66 (m, 2H), 1.06 (t, J=5.1 Hz, 6H).

ESI-MS m/z $[C_{33}H_{44}N_6O_4+H]^+$ 613.3.

HPLC (Method D) 99.1% (AUC), $t_R$=6.3 min.

Synthesis of 6-methyl-4-{6-[4-(4-(2-morpholinoethoxy)phenyl)piperidin-1-yl]pyridin-3-yl}-1H-pyrrolo[2,3-c]pyridin-7(6H)-one (SLU-2118)

Scheme 56

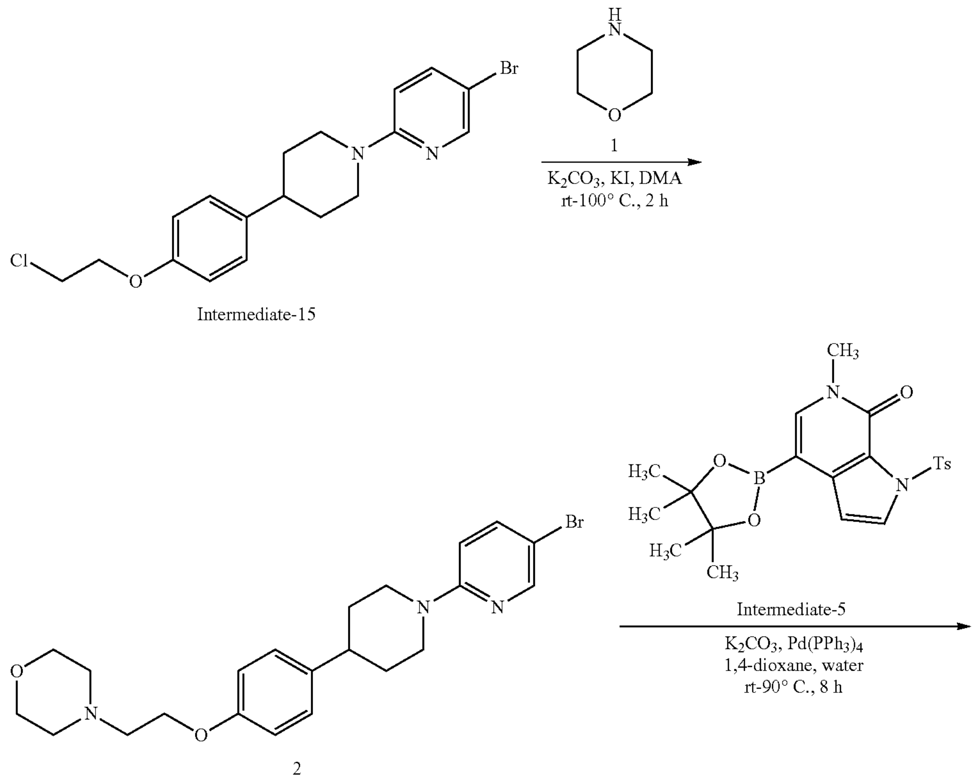

2

-continued

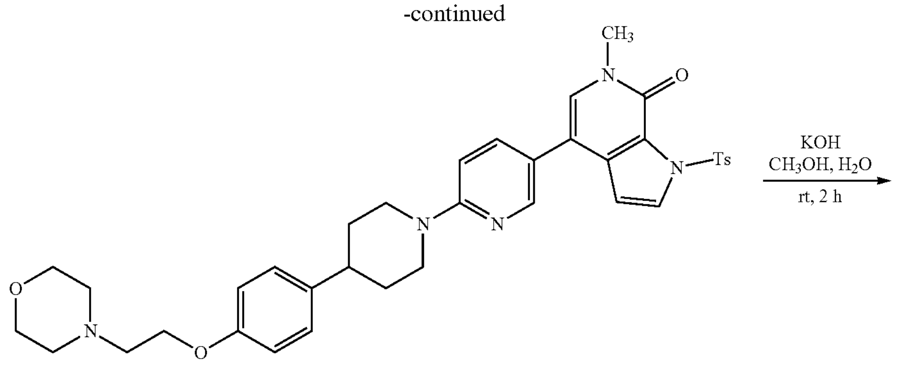

3

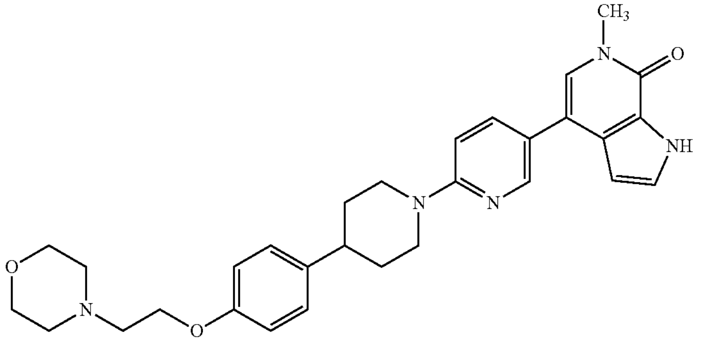

SLU-2118

4-{2-[4-(1-(5-bromopyridin-2-yl)piperidin-4-yl)phenoxy]ethyl}morpholine (2)

To a stirred solution of Intermediate-15 (0.15 g, 0.38 mmol), morpholine 1 (0.04 g, 0.46 mmol), KI (0.03 g, 0.19 mmol), $K_2CO_3$ (0.157 g, 1.14 mmol) in DMA (5.0 mL) at room temperature and heated at 100° C. for 2 h. TLC indicated at which time the reaction gone to completion. The reaction mixture was diluted with water (15 mL) and extracted with EtOAc (3×20 mL). Combined organic layers were dried over anhydrous $Na_2SO_4$ and concentrated under reduced pressure. The crude product was purified by combiflash chromatography (Hexanes:EtOAc=70:30) to afford 2 (0.095 g, 56%) as colourless liquid.

$^1$H NMR (300 MHz, DMSO-$d_6$): δ ppm 8.00 (d, J=2.8 Hz, 1H), 7.49 (d, J=2.4, 9.2 Hz, 1H), 7.04 (d, J=8.8 Hz, 2H), 6.76 (d, J=8.8 Hz, 2H), 6.69 (d, J=9.2 Hz, 1H), 4.28 (d, J=13.2 Hz, 2H), 4.00 (t, J=5.6 Hz, 2H), 3.60 (d, J=4.8 Hz, 4H), 3.20-3.21 (m, 3H), 2.68 (t, J=5.2 Hz, 2H), 2.49 (t, J=4.4 Hz, 4H), 1.76 (d, J=12.8 Hz, 2H), 1.51-1.61 (m, 2H).

6-methyl-4-{6-[4-(4-(2-morpholinoethoxy)phenyl) piperidin-1-yl]pyridin-3-yl}-1-tosyl-1H-pyrrolo[2,3-c]pyridin-7(6H)-one (3)

To a stirred solution of 2 (0.095 g, 0.19 mmol), Intermediate-5 (0.082 g, 0.24 mmol), $K_2CO_3$ (0.07 g, 0.57 mmol) in dioxane (4.0 mL), water (1.0 mL) and degassed it with argon for 5 min. $Pd(PPh_3)_4$ (0.011 g, 0.09 mmol) was added to the reaction mixture and degassed it with argon for 2 min at room temperature and heated at 90° C. for 8 h. TLC indicated at which time the reaction gone to completion. The reaction mixture was diluted with water (10 mL) and extracted with EtOAc (3×20 mL). Combined organic layers were dried over anhydrous $Na_2SO_4$ and concentrated under reduced pressure. The crude product was purified by reverse phase chromatography (ACN:$H_2O$=60:40) to afford 3 (0.045 g) as a gummy solid.

$^1$H NMR (300 MHz, DMSO-$d_6$): δ ppm 8.23 (br.s., 1H), 8.01 (d, J=5.2 Hz, 1H), 7.97 (d, J=10.8 Hz, 1H), 7.66 (d, J=10.4 Hz, 2H), 7.53 (s, 1H), 7.43 (d, J=10.8 Hz, 2H), 7.15 (d, J=11.2 Hz, 2H), 6.97 (d, J=11.2 Hz, 1H), 6.86 (d, J=11.2 Hz, 2H), 6.67 (d, J=4.8 Hz, 1H), 4.46-4.50 (m, 2H), 4.04 (t, J=7.6 Hz, 2H), 3.53-3.55 (m, 4H), 3.45 (s, 4H), 2.86-2.94 (m, 4H), 2.66 (t, J=7.2 Hz, 4H), 2.38 (s, 3H), 1.80-1.84 (m, 2H), 1.56-1.60 (m, 2H).

6-methyl-4-{6-[4-(4-(2-morpholinoethoxy)phenyl) piperidin-1-yl]pyridin-3-yl}-1H-pyrrolo[2,3-c]pyridin-7(6H)-one (SLU-2118)

To a stirred solution of 3 (0.045 g, 0.06 mmol) in $CH_3OH$ (2.0 mL), water (1.0 mL) was charged with potassium hydroxide (0.113 g, 2.02 mmol) and the reaction mixture was stirred for 2 h at room temperature. The reaction mixture was evaporated, diluted with water (5.0 mL) and extracted with EtOAc (3×20 mL). Combined organic layers were dried over anhydrous $Na_2SO_4$ and concentrated under reduced pressure. The crude product was purified by reverse phase chromatography (ACN:$H_2O$=70:30) to afford SLU-2118 (0.016 g, 41%) as a white solid.

$^1$H NMR (300 MHz, DMSO-$d_6$): δ ppm 12.1 (s, 1H), 8.33 (s, 1H), 7.74 (d, J=9.0 Hz, 1H), 7.32 (d, J=8.4 Hz, 2H), 7.16 (d, J=8.1 Hz, 2H), 6.97 (d, J=8.7 Hz, 1H), 6.86 (d, J=8.1 Hz, 2H), 6.40 (s, 1H), 4.48 (d, J=11.4 Hz, 2H), 4.04 (t, J=5.4 Hz, 2H), 3.56 (s, 7H), 2.85 (t, J=12.6 Hz, 4H), 2.66 (t, J=5.4 Hz, 5H), 1.83 (d, J=11.1 Hz, 2H), 1.54-1.66 (m, 2H).

ESI-MS m/z $[C_{30}H_{35}N_5O_3+H]^+$ 514.3.

HPLC (Method D) 98.7% (AUC), $t_R$=6.1 min.

Synthesis of 4-{6-[4-(4-(2-(1H-1,2,4-triazol-1-yl)ethoxy)phenyl)piperidin-1-yl]pyridin-3-yl}-6-methyl-1H-pyrrolo[2,3-c]pyridin-7(6H)-one (SLU-2119)
Scheme 57
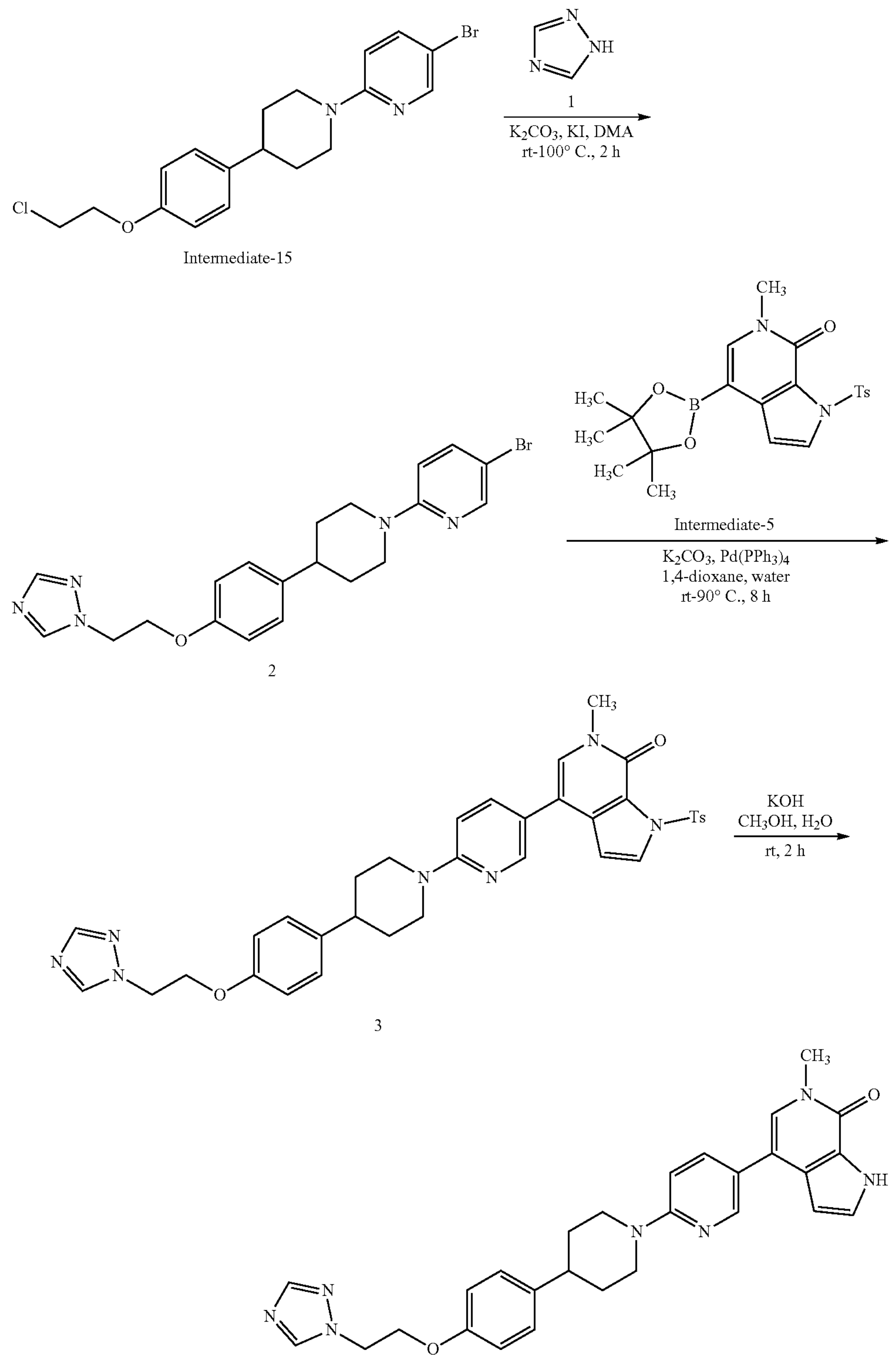
Intermediate-15
2
3
SLU-2119

2-{4-[4-(2-(1H-1,2,4-triazol-1-yl)ethoxy)phenyl] piperidin-1-yl}-5-bromopyridine (2)

To a stirred solution of Intermediate-15 (0.30 g, 0.76 mmol), 1H-1,2,4-triazole 1 (0.063 g, 0.91 mmol), KI (0.061 g, 0.38 mmol) and $K_2CO_3$ (0.314 g, 2.28 mmol) in DMA (5.0 mL) at room temperature and heated at 100° C. for 2 h. TLC indicated at which time the reaction gone to completion. The reaction mixture was diluted with water (15 mL) and extracted with EtOAc (3×20 mL). Combined organic layers were dried over anhydrous $Na_2SO_4$ and concentrated under reduced pressure. The crude product was purified by combiflash chromatography (Hexanes:EtOAc=70:30) to afford 2 (0.165 g, 51%) as colourless liquid.

$^1$H NMR (300 MHz, DMSO-$d_6$): δ ppm 9.11 (d, J=10.2 Hz, 1H), 8.87 (d, J=9.6 Hz, 1H), 8.41-8.44 (m, 1H), 8.20-8.23 (m, 2H), 8.03 (d, J=7.8 Hz, 2H), 7.69-7.75 (m, 1H), 7.48-7.51 (m, 1H), 5.46 (br.s., 2H), 5.231-5.24 (m, 4H), 3.77-3.87 (m, 2H), 3.56-3.65 (m, 1H), 2.78-2.82 (m, 2H), 2.51 (s, 2H).

4-{6-[4-(4-(2-(1H-1,2,4-triazol-1-yl)ethoxy)phenyl) piperidin-1-yl]pyridin-3-yl}-6-methyl-1-tosyl-1H-pyrrolo[2,3-c]pyridin-7(6H)-one (3)

To a stirred solution of 2 (0.165 g, 0.38 mmol), Intermediate-5 (0.165 g, 0.38 mmol8), $K_2CO_3$ (0.157 g, 1.14 mmol) in dioxane (4.0 mL), water (1.0 mL) degassed it with argon for 5 min at room temperature and $Pd(pph_3)_4$ (0.022 g, 0.01 mmol) and degassed it with argon for 2 min at room temperature and heated at 90° C. for 8 h. TLC indicated at which time the reaction gone to completion. The reaction mixture was diluted with water (15 mL) and extracted with EtOAc (3×20 mL). Combined organic layers were dried over anhydrous $Na_2SO_4$ and concentrated under reduced pressure. The crude product was purified by reverse phase chromatography (ACN:$H_2O$=60:40) to afford 3 (0.085 g) as a gummy solid.

$^1$H NMR (400 MHz, DMSO-$d_6$): δ ppm 8.53-8.56 (m, 1H), 8.20-8.23 (m, 1H), 7.92-8.02 (m, 4H), 7.61-7.66 (m, 1H), 7.39-7.53 (m, 3H), 7.10-7.16 (m, 2H), 6.91-6.97 (m, 1H), 6.78-6.84 (m, 2H), 6.63-6.68 (m, 1H), 4.27-4.30 (m, 2H), 4.08-4.11 (m, 2H), 3.33 (s, 3H), 2.82-2.89 (m, 2H), 2.71 (d, J=7.2 Hz, 1H), 2.37 (d, J=9.4 Hz, 5H), 1.79 (br.s., 2H), 1.57 (d, J=8.7 Hz, 2H).

4-{6-[4-(4-(2-(1H-1,2,4-triazol-1-yl)ethoxy)phenyl) piperidin-1-yl]pyridin-3-yl}-6-methyl-1H-pyrrolo[2,3-c]pyridin-7(6H)-one (SLU-2119)

To a stirred solution of 3 (0.085 g, 0.13 mmol) in $CH_3OH$ (3.0 mL), water (1.0 mL) was charged with potassium hydroxide (0.22 g, 3.9 mmol) and the reaction mixture was stirred for 2 h at room temperature. The reaction mixture was evaporated, diluted with water (5.0 mL) and extracted with EtOAc (3×20 mL). Combined organic layers were dried over anhydrous $Na_2SO_4$ and concentrated under reduced pressure. The crude product was purified by reverse phase chromatography (ACN:$H_2O$=60:40) to afford SLU-2119 (0.025 g, 39%) as an off-white solid.

$^1$H NMR (400 MHz, DMSO-$d_6$): δ ppm 12.12 (s, 1H), 8.56 (s, 1H), 8.30 (d, J=2.4 Hz, 1H), 7.98 (s, 1H), 7.74 (dd, J=2.4, 8.8 Hz, 1H), 7.33 (d, J=2.4 Hz, 1H), 7.30 (s, 1H), 7.16 (d, J=8.8 Hz, 2 H), 6.96 (d, J=8.8 Hz, 1H), 6.83 (d, J=8.4 Hz, 2H), 6.40 (d, J=2.8 Hz, 1H), 4.56 (t, J=4.8 Hz, 2H), 4.47 (d, J=13.2 Hz, 2H), 4.30 (t, J=5.2 Hz, 2H), 3.56 (s, 3H), 2.89 (t, J=12.4 Hz, 2H), 2.67-2.76 (m, 1H), 1.82 (d, J=12.8 Hz, 2H), 1.54-1.63 (m, 2H).

ESI-MS m/z $[C_{28}H_{29}N_7O_2+H]^+$ 496.2.

HPLC (Method D) 97.3% (AUC), $t_R$=6.4 min.

Synthesis of 4-[6-(2,8-diazaspiro[4.5]decan-8-yl) pyridin-3-yl]-6-methyl-1H-Pyrrolo[2,3-c]pyridin-7 (6H)-one (SLU-2120)

Scheme 58

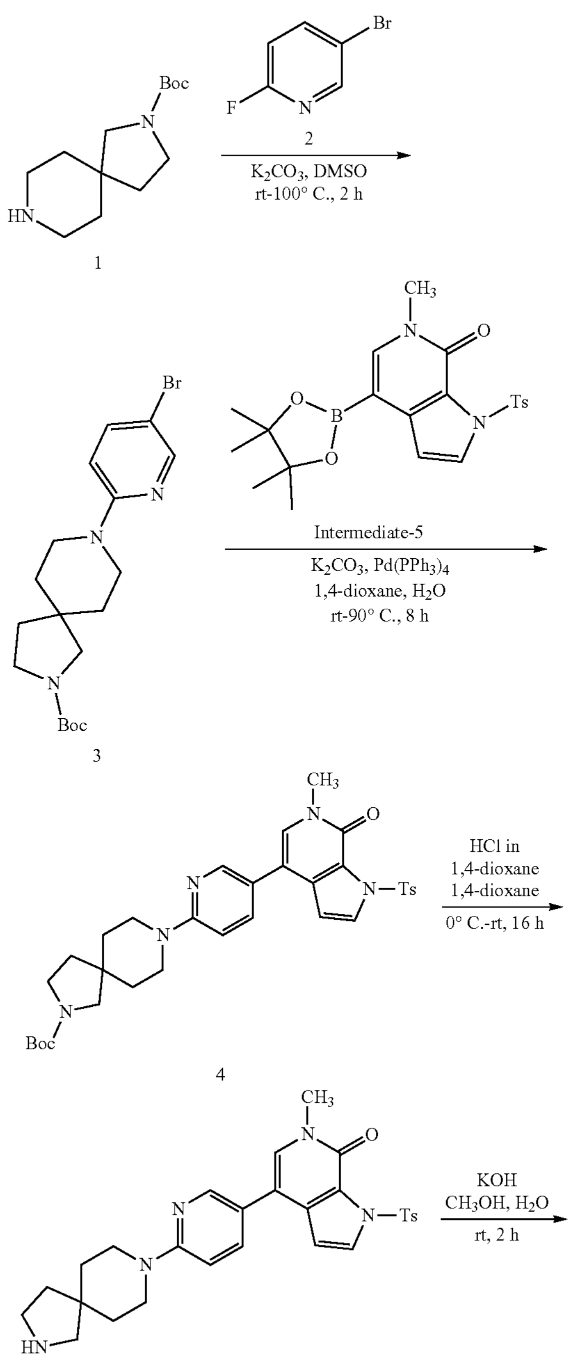

1

2

3

4

5

-continued

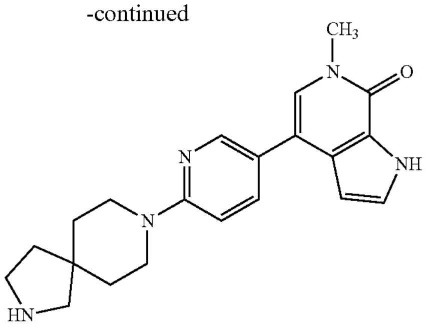

SLU-2120 tert-butyl 8-(5-bromopyridin-2-yl)-2,8-diazaspiro[4.5]decane-2-carboxylate (3)

To a stirred solution of 1 (0.05 g, 0.20 mmol), 5-bromo-2-fluoropyridine 2 (0.037 g, 0.20 mmol), $K_2CO_3$ (0.086 g, 0.624 mmol) in DMSO (3.0 mL) at room temperature and heated at 100° C. for 2 h. TLC indicated at which time the reaction gone to completion. The reaction mixture was diluted with water (5.0 mL) and extracted with EtOAc (3×8 mL). Combined organic layers were dried over anhydrous $Na_2SO_4$ and concentrated under reduced pressure. The crude product was purified by combiflash chromatography (Hexanes:EtOAc=85:15) to afford 3 (0.045 g, 55%) as an off-white solid.

$^1$H NMR (300 MHz, DMSO-$d_6$): δ ppm 8.14 (d, J=2.1 Hz, 1H), 7.64 (dd, J=2.1, 9.0 Hz, 1H), 6.83 (d, J=9.3 Hz, 1H), 3.48-3.53 (m, 4H), 3.27-3.30 (m, 2H), 3.11 (s, 2H), 1.73 (t, J=6.9 Hz, 2H), 1.51 (br.s., 4H), 1.39 (s, 9H).

tert-butyl 8-[5-(6-methyl-7-oxo-1-tosyl-6,7-dihydro-1H-pyrrolo[2,3-c]pyridin-4-yl)pyridin-2-yl]-2,8-diazaspiro[4.5]decane-2-carboxylate (4)

To a stirred solution of 3 (0.025 g, 0.06 mmol), Intermediate-5 (0.027 g, 0.06 mmol), $K_2CO_3$ (0.025 g, 0.18 mmol) in dioxane (2.0 mL), water (0.5 mL) and degassed it with argon for 2 min at room temperature. $Pd(PPh_3)_4$ (0.003 g, 0.003 mmol) was added to the reaction mixture and degassed it with argon for 1 min at room temperature and heated at 90° C. for 8 h. TLC indicated at which time the reaction gone to completion. The reaction mixture was diluted with water (5.0 mL) and extracted with EtOAc (3×8 mL). Combined organic layers were dried over anhydrous $Na_2SO_4$ and concentrated under reduced pressure. The crude product was purified by combiflash chromatography (Hexanes:EtOAc=60:40) to afford 4 (0.001 g) as an off-white solid.

$^1$H NMR (300 MHz, DMSO-$d_6$): δ ppm 8.21 (d, J=1.8 Hz, 1H), 8.01 (d, J=3.6 Hz, 1H), 7.96 (d, J=8.4 Hz, 1H), 7.59-7.65 (m, 2H), 7.51-7.57 (m, 2H), 6.93 (d, J=8.1 Hz, 1H), 6.65 (d, J=3.3 Hz, 1H), 3.55-3.58 (m, 4H), 3.44 (s, 3H), 3.14 (s, 2H), 2.38 (s, 3H), 1.75 (t, J=5.7 Hz, 2H), 1.53 (br.s., 4H), 1.40 (s, 9H), 1.23 (s, 2H).

tert-butyl 8-[5-(6-methyl-7-oxo-1-tosyl-6,7-dihydro-1H-pyrrolo[2,3-c]pyridin-4-yl)pyridin-2-yl]-2,8-diaza spiro[4.5]decane-2-carboxylate (5)

To a stirred solution of 4 (0.28 g, 0.45 mmol) in dioxane (4.0 mL), HCl in dioxane (5.0 mL) was charged at 0° C. and stirred for 16 h at room temperature. TLC indicated at which time the reaction gone to completion. The reaction mixture was concentrated to afford 5 (0.17 g) as a gummy solid. This crude was used for next step.

ESI-MS m/z $[C_{28}H_{31}N_5O_3S+H]^+$ 518.2.

4-[6-(2,8-diazaspiro[4.5]decan-8-yl)pyridin-3-yl]-6-methyl-1H-pyrrolo[2,3-c]pyridin-7(6H)-one (SLU-2120)

To a stirred solution of 5 (0.15 g, 0.29 mmol) in $CH_3OH$ (3.0 mL), water (1.0 mL) was charged with potassium hydroxide (0.15 g, 4.35 mmol) and stirred for 2 h at room temperature. The reaction mixture was evaporated, diluted with water (5.0 mL) and extracted with EtOAc (3×20 mL). Combined organic layers were dried over anhydrous $Na_2SO_4$ and concentrated under reduced pressure. The crude product was purified by reverse phase chromatography ($H_2O$:ACN=30:70) to afford SLU-2120 (0.013 g, 12%) as an off-white solid.

$^1$H NMR (300 MHz, DMSO-$d_6$): δ ppm 12.12 (s, 1H), 8.29 (d, J=5.7 Hz, 1H), 7.59-7.69 (m, 1H), 7.26-7.32 (m, 2H), 6.90 (br.s., 1H), 6.36 (d, J=7.2 Hz, 1H), 4.09 (s, 1H), 3.52-3.55 (m, 4H), 3.26 (s, 3H), 3.16 (s, 2H), 2.72-2.80 (m, 2H), 2.18-2.32 (m, 2H), 1.51 (br.s., 4H).

ESI-MS m/z $[C_{21}H_{25}N_5O+H]^+$ 364.2.

HPLC (Method D) 93.0% (AUC), $t_R$=5.9 min.

Synthesis of 4-(6-(2,8-diazaspiro[4.5]decan-2-yl)pyridin-3-yl)-6-methyl-1H-pyrrolo[2,3-c]pyridin-7(6H)-one (SLU-2214)

Scheme 59

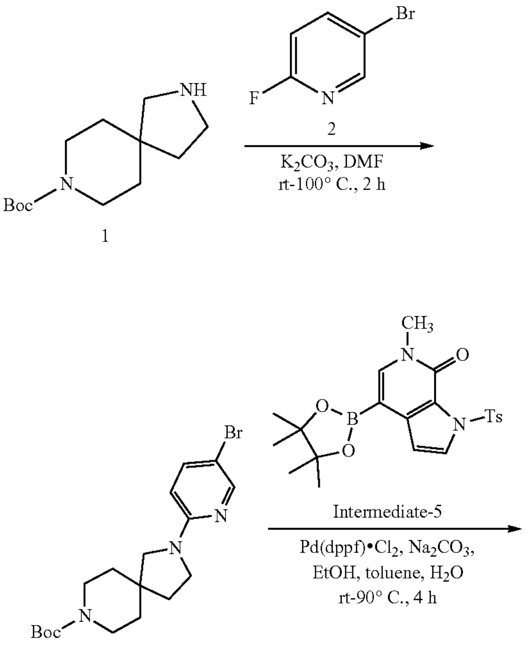

-continued

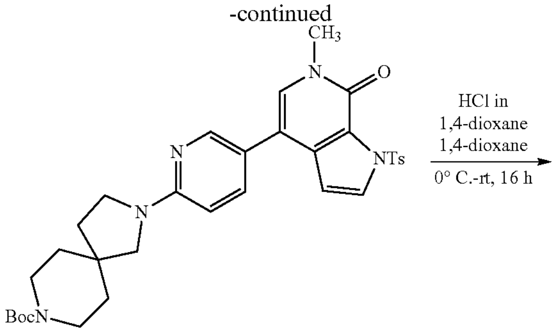

4

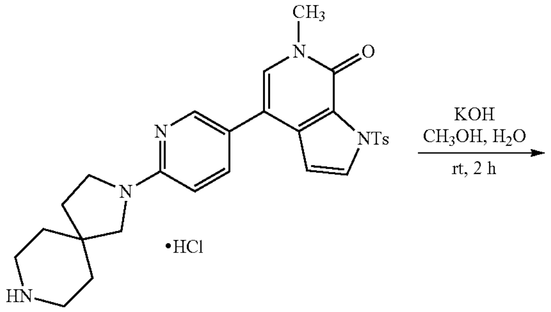

5

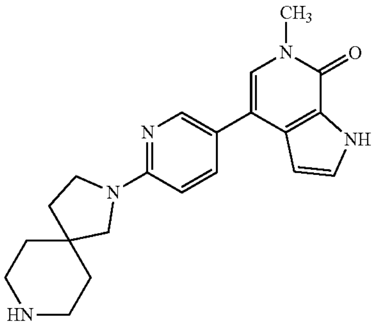

SLU-2214 tert-butyl 2-(5-bromopyridin-2-yl)-2,8-diazaspiro [4.5]decane-8-carboxylate (3)

To a stirred solution of 1 (0.05 g, 0.20 mmol), 5-bromo-2-fluoropyridine 2 (0.037 g, 0.20 mmol), $K_2CO_3$ (0.086 g, 0.624 mmol) in DMF (3.0 mL) at room temperature and was heated at 100° C. for 2 h. TLC indicated at which time the reaction gone to completion. The reaction mixture was diluted with water (5.0 mL) and extracted with EtOAc (3×8 mL). Combined organic layers were dried over anhydrous $Na_2SO_4$ and concentrated under reduced pressure. The crude product was purified by combiflash chromatography (Hexanes:EtOAc=85:15) to afford 3 (0.035 g, 43%3) as an off-white solid.

$^1$H NMR (300 MHz, DMSO-$d_6$): δ ppm 8.10 (s, 1H), 7.61-7.63 (m, 1H), 6.42-6.43 (m, 1H), 3.40 (s, 4H), 3.25 (br.s., 4H), 1.84 (br.s., 2H), 1.41 (s, 4H), 1.39 (s, 9H).

tert-butyl 2-[5-(6-methyl-7-oxo-1-tosyl-6,7-dihydro-1H-pyrrolo[2,3-c]pyridin-4-yl)pyridin-2-yl]-2,8-diazaspiro[4.5]decane-8-carboxylate (4)

To a stirred solution of 3 (0.30 g, 0.75 mmol), Intermediate-5 (0.323 g, 0.75 mmol), $Na_2CO_3$ (0.238 g, 2.25 mmol) in ethanol (5.0 mL), toluene (5.0 mL), water (2.0 mL) and degassed it with argon for 3 min at room temperature. Pd(dppf)$Cl_2$ (0.055 g, 0.075 mmol) was added to the reaction mixture and degassed it with argon for 2 min at room temperature and heated at 90° C. for 4 h. TLC indicated at which time the reaction gone to completion. The reaction mixture was diluted with water (10 mL) and extracted with EtOAc (3×20 mL). Combined organic layers were dried over anhydrous $Na_2SO_4$ and concentrated under reduced pressure. The crude product was purified by combiflash chromatography ($CH_2Cl_2$:$CH_3OH$=95:5) to afford 4 (0.150 g5) as an off-white solid.

$^1$H NMR (300 MHz, DMSO-$d_6$): δ ppm 8.16 (br.s., 1H), 7.95-8.01 (m, 3H), 7.61 (d, J=9.3 Hz, 1H), 7.41-7.50 (m, 3H), 6.63 (d, J=4.4 Hz, 1H), 6.52-6.55 (m, 1H), 3.9 (s, 6H), 3.44 (s, 5H), 2.83 (s, 3H) 1.73-1.87 (m, 2H), 1.48 (s, 4H), 1.40 (s, 9H).

tert-butyl 8-[5-(6-methyl-7-oxo-1-tosyl-6,7-dihydro-1H-pyrrolo[2,3-c]pyridin-4-yl)pyridin-2-yl]-2,8-diazaspiro[4.5]decane-2-carboxylate (4)

To a stirred solution of 4 (0.15 g, 0.27 mmol5) in dioxane (5.0 mL), HCl in dioxane (5.0 mL) was charged at 0° C. and stirred for 16 h at room temperature. TLC indicated at which time the reaction gone to completion. The reaction mixture was concentrated to afford 5 (0.09 g7) as a gummy solid. This crude was used for next step.

$^1$H NMR (300 MHz, DMSO-$d_6$): δ ppm 9.11-9.21 (m, 2H), 8.05 (s, 4H), 7.45-7.53 (m, 4H), 7.11 (br.s., 1H), 6.92 (br.s., 1H), 4.75-4.83 (m, 3H), 3.04-3.12 (m, 5H), 2.01 (s, 2H), 1.79 (br.s., 4H), 1.23-1.25 (m, 2H), 1.88 (br.s., 1H).

4-[6-(2,8-diazaspiro[4.5]decan-2-yl)pyridin-3-yl]-6-methyl-1H-pyrrolo[2,3-c]pyridin-7(6H)-one (SLU-2214)

To a stirred solution of 5 (0.09 g, 0.17 mmol6) in $CH_3OH$ (3.0 mL) and water (1 mL) was added potassium hydroxide (0.15 g, 2.55 mmol) the reaction mixture stirred for 2 h at room temperature. The reaction mixture was evaporated, diluted with water (5.0 mL) and extracted with EtOAc (3×20 mL). Combined organic layers were dried over anhydrous $Na_2SO_4$ and concentrated under reduced pressure. The crude product was purified by reverse phase chromatography ($H_2O$:ACN=60:40) to afford SLU-2214 (0.016 g, 30%) as an off-white solid.

$^1$H NMR (400 MHz, $CD_3OD$): δ ppm 8.15 (d, J=2.4 Hz, 1H), 7.69 (dd, J=2.0, 8.4 Hz, 1H), 7.28 (d, J=2.8, 1H), 7.15 (s, 1H), 6.55 (d, J=8.4 Hz, 1H), 6.36 (d, J=2.8 Hz, 1H), 3.59 (s, 3H), 3.50 (t, J=7.2 Hz, 2H), 3.37 (s, 2H), 3.11-3.22 (m, 4H), 1.96 (t, J=7.2 Hz, 2H), 1.75-1.85 (m, 4H).

ESI-MS m/z $[C_{21}H_{25}N_5O+H]^+$ 364.2.

HPLC (Method B) 93.0% (AUC), $t_R$=8.7 min.

Synthesis of 4-{6-[6-(2-hydroxyethoxy)pyridin-3-yl]quinolin-2-yl}-6-methyl-1H-pyrrolo[2,3-c]pyridin-7(6H)-one (SLU-2232)

Scheme 60

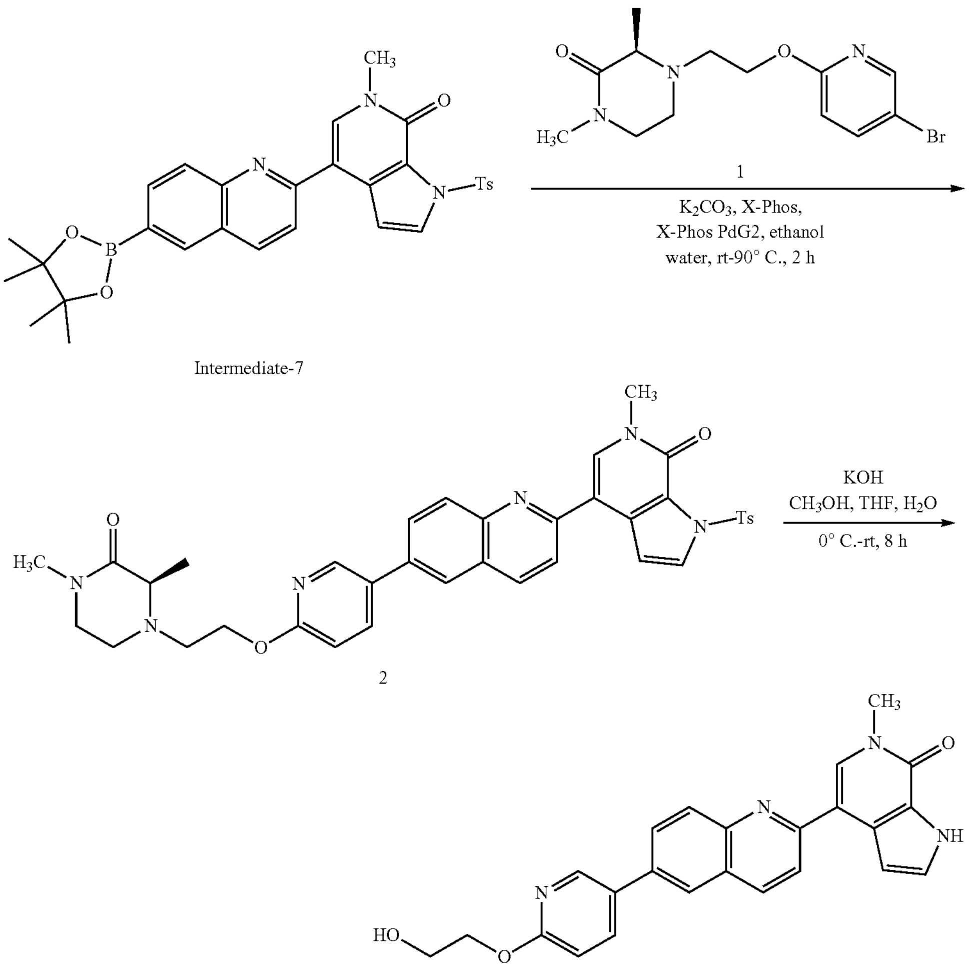

Intermediate-7

1

2

SLU-2232

4-{6-[6-(2-hydroxyethoxy)pyridin-3-yl]quinolin-2-yl}-6-methyl-1-tosyl-1H-pyrrolo[2,3-c]pyridin-7(6H)-one (2)

To a stirred solution of Intermediate-7 (0.070 g, 0.12 mmol3), in ethanol (3.0 mL) were charged with 1 (0.049 g, 0.15 mmol), $K_2CO_3$ (0.050 g, 0.36 mmol) at room temperature and degassed it with argon for 5 min. X-Phos (0.011 g, 0.024 mmol), X-PhosPdG2 (0.009 g, 0.012 mmol) was added to the reaction mixture at room temperature and was heated at 90° C. for 2 h. TLC indicated at which time the reaction gone to completion. The reaction mixture was diluted with water (10 mL) and extracted with EtOAc (3×20 mL). Combined organic layers were dried over anhydrous $Na_2SO_4$ and concentrated under reduced pressure. The crude product was purified by combiflash chromatography ($CH_2Cl_2$: $CH_3OH$=94:6) to afford 2 (0.050 g2) as an off-white solid. This crude was used for next step.

ESI-MS m/z $[C_{31}H_{26}N_4O_5S+H]^+$ 567.1.

4-{6-[6-(2-hydroxyethoxy)pyridin-3-yl]quinolin-2-yl}-6-methyl-1H-pyrrolo[2,3-c]pyridin-7(6H)-one (SLU-2232)

To a stirred solution of 2 (0.050 g, 0.07 mmol2) in $CH_3OH$ (1.0 mL), $H_2O$ (1.0 mL), THF (1.0 mL) was charged with potassium hydroxide (0.016 g, 0.29 mmol) at 0° C. and stirred for 8 h at room temperature. The reaction mixture was evaporated, diluted with water (10 mL) and extracted with $CH_2Cl_2$ (3×15 mL). Combined organic layers were dried over anhydrous $Na_2SO_4$ and concentrated under reduced pressure. The crude product was purified by reverse phase chromatography (ACN:$H_2O$=70:30). Pure compound was not obtained by purification with preparative TLC plate mobile phase (THF:$CH_3COOH$=99:1) to afford SLU-2232 (0.002 g, 5%) as an off-white solid.

$^1H$ NMR (400 MHz, $CD_3OD$): δ ppm 8.31 (d, J=8.8 Hz, 1H), 7.98-8.06 (m, 4H), 7.88-7.91 (m, 2H), 7.83 (s, 1H), 7.36 (d, J=2.8 Hz, 1H), 6.98 (d, J=2.8 Hz, 1H), 6.63 (d, J=9.2 Hz, 1H), 4.14 (t, J=4.8 Hz, 2H), 3.81 (t, J=5.2 Hz, 2H), 3.69 (s, 3H).

ESI-MS m/z $[C_{24}H_{20}N_4O_3+H]^+$ 413.1.

HPLC (Method C) 97.6% (AUC), $t_R$=8.4 min.

Synthesis of 6-methyl-4-{2-[4-(2-morpholinoethoxy)phenyl]quinolin-6-yl}-1,6-dihydro-7H-pyrrolo[2,3-c]pyridin-7-one (SLU-2234)

Scheme 61

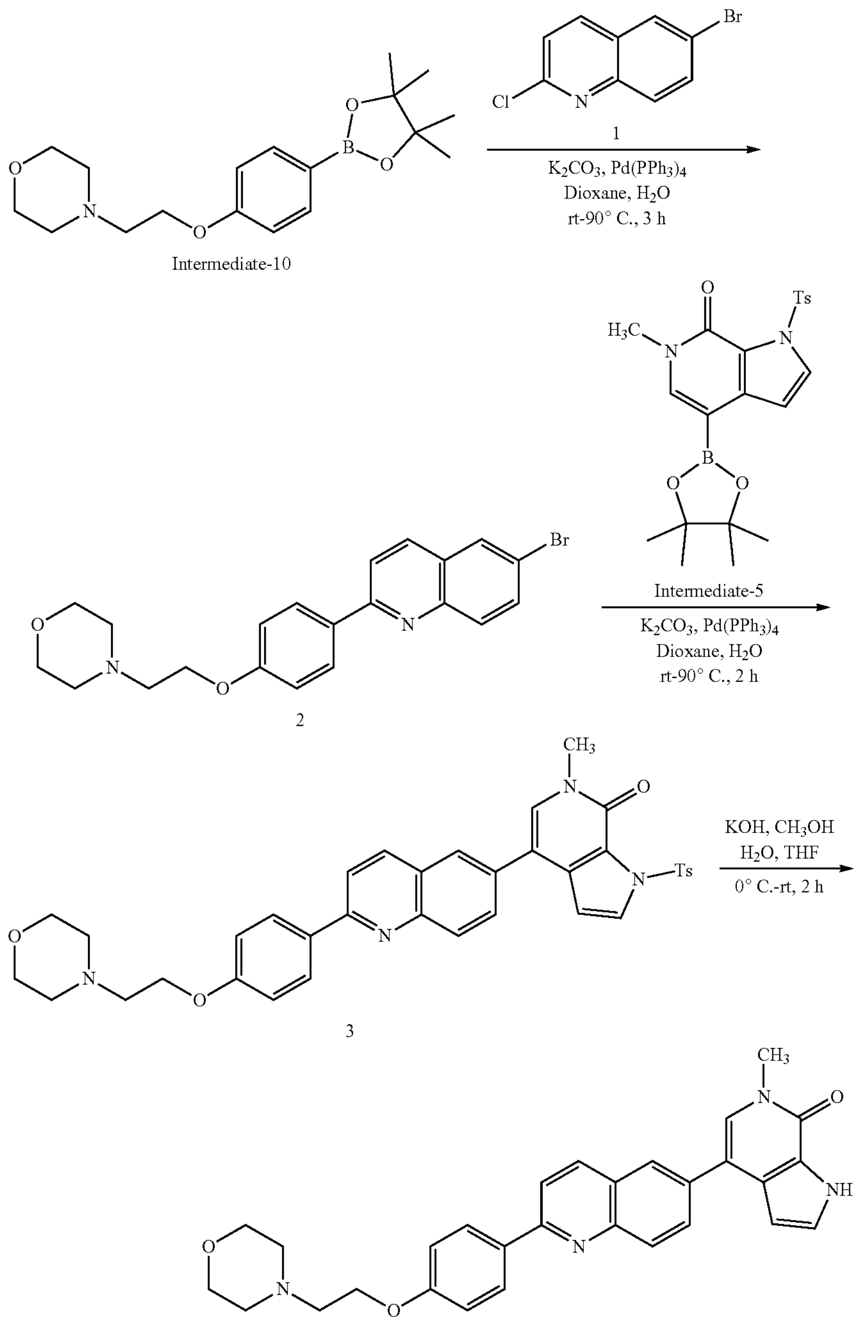

SLU-2234

4{-2-[4-(6-bromoquinolin-2-yl)phenoxy]ethyl}morpholine (2)

To a stirred solution of Intermediate-10 (0.480 g, 1.44 mmol7), in dioxane (8.0 mL) were charged with 6-bromo-2-chloroquinoline 1 (0.347 g, 1.44 mmol), $K_2CO_3$ (0.397 g, 2.88 mmol) at room temperature and degassed it with argon for 5 min. $Pd(PPh_3)_4$ (0.162 g, 0.14 mmol) at room temperature and was heated at 90° C. for 3 h. TLC indicated at which time the reaction gone to completion. The reaction mixture was diluted with water (20 mL) and extracted with EtOAc (3x35 mL). Combined organic layers were dried over anhydrous $Na_2SO_4$ and concentrated under reduced pressure. The crude product was purified by combiflash chromatography (EtOAc:Hexanes=80:20) to afford 2 (0.185 g, 31%0) as a light brown solid.

$^1$H NMR (400 MHz, DMSO-$d_6$): δ ppm 8.07-8.10 (m, 2H), 7.95-8.00 (m, 2H), 7.85 (d, J=8.8 Hz, 1H), 7.76 (dd, J=2.0, 8.8 Hz, 1H), 7.05 (d, J=8.8 Hz, 2H), 6.76 (d, J=6.4 Hz, 1H), 4.20 (t, J=5.6 Hz, 2H), 3.74-3.77 (m, 4H), 2.85 (t, J=5.6 Hz, 2H), 2.60-2.62 (m, 4H).

6-methyl-4-{2-[4-(2-morpholinoethoxy)phenyl]quinolin-6-yl}-1-tosyl-1,6-dihydro-7H-pyrrolo[2,3-c]pyridin-7-one (3)

To a stirred solution of 2 (0.185 g, 0.37 mmol0) in dioxane (4.0 mL) were charged with Intermediate-5 (0.161 g, 0.37 mmol), $K_2CO_3$ (0.102 g, 0.74 mmol), at room temperature and degassed it with argon for 5 min. $Pd(PPh_3)_4$ (0.043 g, 0.03 mmol) was added to the reaction mixture at room temperature and heated at 90° C. for 2 h. TLC indicated at which time the reaction gone to completion. The reaction mixture was diluted with water (20 mL) and extracted with EtOAc (2×30 mL). Combined organic layers were dried over anhydrous $Na_2SO_4$ and concentrated under reduced pressure. The crude product was purified by combi-flash ($CH_2Cl_2$:$CH_3OH$=97:3) to afford 3 (0.065 g, 26%6) as an off-white solid.

$^1$H NMR (400 MHz, DMSO-$d_6$): δ ppm 8.2 (d, J=2.0 Hz, 1H), 8.18 (d, J=2.4 Hz, 1H), 8.14-8.16 (m, 1H), 8.06 (d, J=8.4 Hz, 2H), 7.98 (d, J=3.6 Hz, 1H), 7.87-7.89 (m, 1H), 7.83 (d, J=1.6 Hz, 1H), 7.77 (dd, J=2.0, 8.4 Hz, 1H), 7.33 (d, J=8.4 Hz, 2H), 7.20 (s, 1H), 7.06 (d, J=8.8 Hz, 2H), 6.76 (d, J=7.2 Hz, 1H), 6.66 (d, J=3.6 Hz, 1H), 4.21 (t, J=5.6 Hz, 2H), 3.72-3.77 (m, 4H), 3.62 (s, 3H), 2.86 (t, J=5.6 Hz, 2H), 2.62 (t, J=4.4 Hz, 4H), 2.43 (s, 3H).

6-methyl-4-{2-[4-(2-morpholinoethoxy)phenyl]quinolin-6-yl}-1,6-dihydro-7H-pyrrolo[2,3-c]pyridin-7-one (SLU-2234)

To a stirred solution of 3 (0.065 g, 0.09 mmol6) in MeOH (3.0 mL), $H_2O$ (1.0 mL), THF (2.0 mL) was charged with potassium hydroxide (0.027 g, 0.48 mmol) at 0° C. The reaction mixture was stirred for 2 h at room temperature. The reaction mixture was evaporated, diluted with water (8.0 mL) and extracted with EtOAc (3×10 mL). Combined organic layers were dried over anhydrous $Na_2SO_4$ and concentrated under reduced pressure. The crude product was purified by reverse phase chromatography (ACN:$H_2O$=60:40) to afford SLU-2234 (0.017 g, 35%) as a pale yellow solid.

$^1$H NMR (400 MHz, DMSO-$d_6$): δ ppm 12.22 (s, 1H), 8.46 (d, J=8.8 Hz, 1H), 8.26 (d, J=8.8 Hz, 2H), 8.08-8.18 (m, 3H), 8.01 (dd, J=2.0, 8.8 Hz, 1H), 7.60 (s, 1H), 7.41 (t, J=2.4, 1H), 7.12 (d, J=9.2 Hz, 2H), 6.62 (t, J=1.6 Hz, 1H), 4.19 (t, J=5.6 Hz, 2H), 3.63 (s, 3H), 3.60 (t, J=4.8 Hz, 4H), 2.74 (t, J=5.6 Hz, 2H), 2.45-2.54 (m, 4H).

ESI-MS m/z $[C_{29}H_{28}N_4O_3+H]^+$ 481.2.

HPLC (Method C) 95.1% (AUC), $t_R$=8.4 min.

Synthesis of (R)-4-{6-[6-(2-(2,4-dimethyl-3-oxopiperazin-1-yl)ethoxy)pyridin-3-yl]quinolin-2-yl}-6-methyl-1H-pyrrolo[2,3-c]pyridin-7(6H)-one (SLU-2235)

Scheme 62

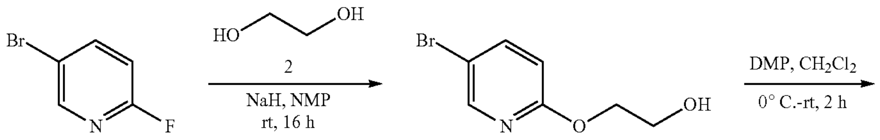

1

3

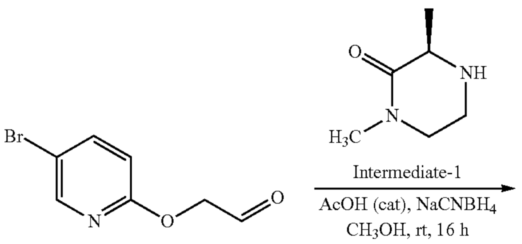

4

-continued

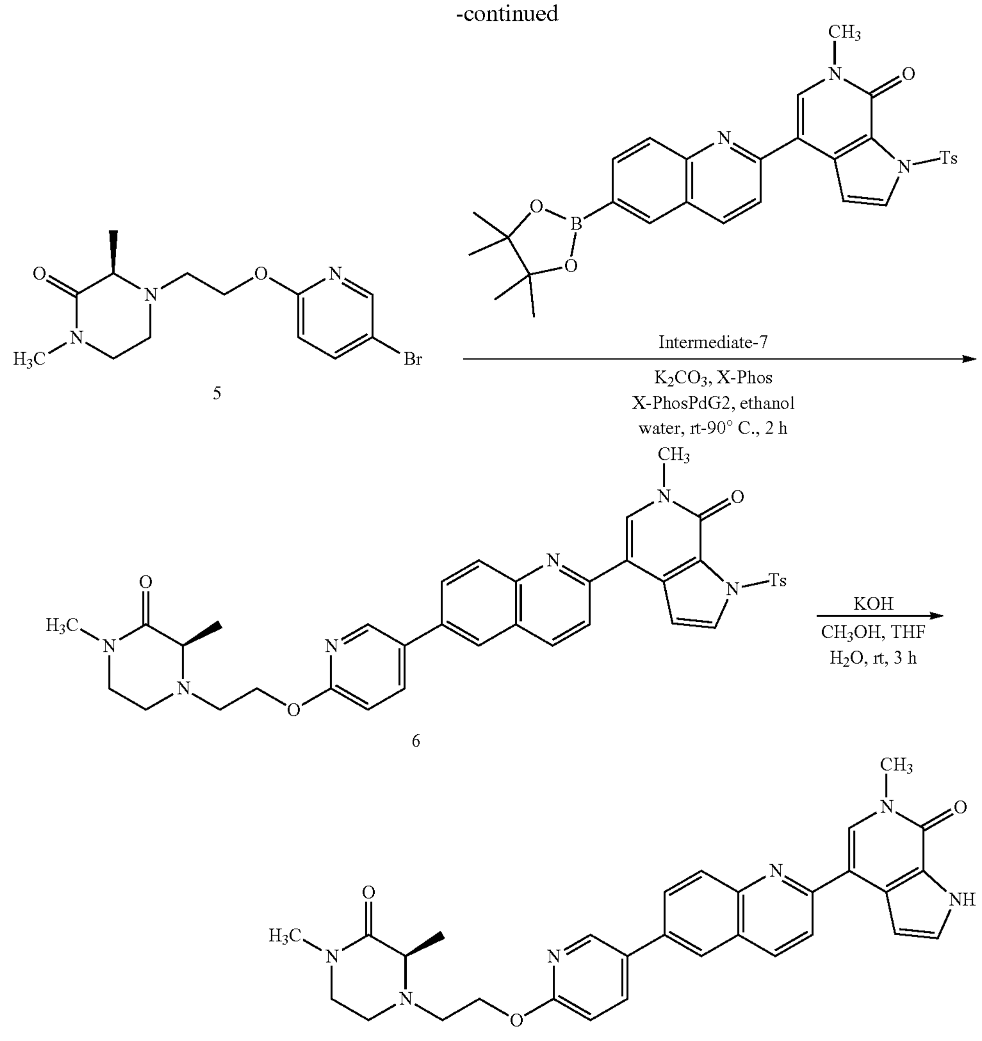

5

6

SLU-2235

2-((5-bromopyridin-2-yl)oxy)ethanol (3)

To a stirred solution of ethylene glycol 2 (3.54 g, 57.1 mmol) in N-methyl-2-pyrrolidone (20 mL), NaH (2.28 g, 57.1 mmol) was charged portion wise at 0° C. and stirred for 1 h at room temperature. 5-bromo-2-fluoropyridine 1 (2.00 g, 11.4 mmol) was added to the reaction mixture dropwise at 0° C. and stirred for 16 h at room temperature. The reaction mixture was diluted with water (150 mL) and extracted with EtOAc (3×150 mL). Organic layer was separated, dried over anhydrous $Na_2SO_4$ and concentrated under reduced pressure. The crude product was purified by combiflash chromatography (Hexanes:EtOAc=70:30) to afford 3 (1.10 g, 44%) as an off-white solid.

$^1$H NMR (400 MHz, $CDCl_3$): δ ppm 8.17 (d, J=2.4 Hz, 1H), 7.67 (dd, J=2.8, 8.8 Hz, 1H), 6.72 (d, J=8.8 Hz, 1H), 4.42-4.44 (m, 2H), 3.94 (s, 2H), 2.89 (s, 1H).

2-[(5-bromopyridin-2-yl)oxy]acetaldehyde (4)

To a stirred solution of 3 (0.5 g, 2.3 mmol1) in $CH_2Cl_2$ (5.0 mL) was cooled to 0° C. and Dess-Martin periodinane (3.9 g, 9.2 mmol) was charged portionwise at 0° C. and stirred for 2 h at room temperature. TLC indicated at which time the reaction gone to completion. The reaction mixture was diluted with saturated $NaHCO_3$ (20 mL) and extracted with EtOAc (3×50 mL). Organic layer was separated, dried over anhydrous $Na_2SO_4$ and concentrated under reduced pressure to afford 4 (0.4 g) as a gummy solid which was used for next step.

ESI-MS m/z $[C_7H_6NO_2Br+H]^+$ 216.0.

(R)-4-{2-[(5-bromopyridin-2-yl)oxy]ethyl}-1,3-dimethylpiperazin-2-one (5)

To a stirred solution of 4 (0.40 g, 1.86 mmol9) in $CH_3OH$ (10 mL), Intermediate-1 (0.71 g, 5.58 mmol3), AcOH (catalytic) were charged and stirred for 15 min at room temperature. $NaCNBH_3$ (0.35 g, 5.58 mmol) was added portion wise at room temperature and stirred for 16 h at room temperature. TLC indicated at which time the reaction gone to completion. The reaction mixture was concentrated, diluted with water (25 mL) and extracted with EtOAc (3×40 mL). Organic layer was separated, dried over anhydrous $Na_2SO_4$ and concentrated under reduced pressure. The crude product was purified by reverse phase combiflash chromatography (ACN:$H_2O$=60:40) to afford 5 (0.09 g, 15%0) as colourless liquid.

$^1$H NMR (400 MHz, $CDCl_3$): δ ppm 8.17 (d, J=2.8 Hz, 1H), 7.64 (dd, J=2.4, 8.8 Hz, 1H), 6.66 (d, J=9.2 Hz, 1H), 4.40 (q, J=5.6 Hz, 2H), 3.29-3.39 (m, 1H), 3.29-3.28 (m, 2H), 3.09-3.15 (m, 1H), 2.99-3.06 (m, 1H), 2.94 (s, 3H), 2.70-2.82 (m, 2H), 1.39 (d, J=6.8 Hz, 3H).

(R)-4-{6-[6-(2-(2,4-dimethyl-3-oxopiperazin-1-yl) ethoxy)pyridin-3-yl]quinolin-2-yl}-6-methyl-1-tosyl-1H-pyrrolo[2,3-c]pyridin-7(6H)-one (6)

To a stirred solution of Intermediate-7 (0.10 g, 0.18 mmol3), (R)-4-{2-[(5-bromopyridin-2-yl)oxy]ethyl}-1,3-dimethylpiperazin-2-one 5 (0.07 g, 0.22 mmol0), $K_2CO_3$ (0.074 g, 0.54 mmol) at room temperature and degassed it with argon for 5 min. X-Phos (0.017 g, 0.036 mmol), X-PhosPdG$_2$ (0.014 g, 0.018 mmol) was added to the reaction mixture at room temperature and degassed it with argon for 2 min. and heated at 90° C. for 2 h. TLC indicated at which time the reaction gone to completion. The reaction mixture was diluted with water (10 mL) and extracted with EtOAc (3×20 mL). Organic layer was separated, dried over anhydrous $Na_2SO_4$ and concentrated under reduced pressure. The crude product was purified by reverse phase chromatography (ACN:$H_2O$=70:30) to afford 6 (0.065 g, 40%4) as an off-white solid.

$^1$H NMR (400 MHz, DMSO-d$_6$): δ ppm 8.66 (d, J=2.4 Hz, 1H), 8.42 (d, J=8.8 Hz, 1H), 8.39 (s, 1H), 8.26 (s, 1H), 8.19 (dd, J=2.4, 8.4 Hz, 1H), 8.11-8.15 (m, 3H), 8.03 (d, J=8.8 Hz, 1H), 7.97 (d, J=8.4 Hz, 2H), 7.75 (d, J=3.6 Hz, 1H), 7.44 (d, J=8.8 Hz, 2H), 6.97 (d, J=8.8 Hz, 1H), 4.44 (q, J=5.6 Hz, 2H), 4.33-4.36 (m, 1H), 3.55 (s, 3H), 3.24-3.27 (m, 3H), 3.21-3.24 (m, 1H), 3.10-3.17 (m, 2H), 2.95-3.08 (m, 2H), 2.81 (s, 3H), 2.65-2.75 (m, 1H), 2.39 (s, 3H).

(R)-4-{6-[6-(2-(2,4-dimethyl-3-oxopiperazin-1-yl) ethoxy)pyridin-3-yl]quinolin-2-yl}-6-methyl-1H-pyrrolo[2,3-c]pyridin-7(6H)-one (SLU-2235)

To a stirred solution of 6 (0.065 g, 0.09 mmol4) in $CH_3OH$ (3.0 mL), water (1.5 mL), THF (2.0 mL) was charged with potassium hydroxide (0.027 g, 0.48 mmol) and stirred for 3 h at room temperature. The reaction mixture was evaporated, diluted with water (10 mL) and extracted with EtOAc (3×10 mL). Organic layer was dried over anhydrous $Na_2SO_4$ and concentrated under reduced pressure. The crude product was purified by reverse phase chromatography (ACN:$H_2O$=70:30) to afford SLU-2235 (0.014 g, 28%) as an off-white solid.

$^1$H NMR (400 MHz, DMSO-d$_6$): δ ppm 12.17 (s, 1H), 8.66 (d, J=2.4 Hz, 1H), 8.4 (d, J=8.8 Hz, 1H), 8.26 (s, 1H), 8.21 (s, 1H), 8.19 (d, J=2.4 Hz, 1H), 8.08-8.13 (m, 3H), 7.42 (t, J=2.8, 1H), 7.35 (t, J=2.8 Hz, 1H), 6.97 (d, J=8.8 Hz, 1H), 4.45 (q, J=6.0 Hz, 2H), 3.68 (s, 3H), 3.25-3.28 (m, 2H), 3.06-3.18 (m, 2H), 2.95-3.00 (m, 1H), 2.81 (s, 3H), 2.74-2.83 (m, 1H), 2.67-2.73 (m, 1H), 1.25 (d, J=6.8 Hz, 3H).

ESI-MS m/z $[C_{30}H_{30}N_6O_3+H]^+$ 523.2.

HPLC (Method A) 97.3% (AUC), $t_R$=6.03 min.

Synthesis of (R)-4-{2-[6-(2-(2,4-dimethyl-3-oxopiperazin-1-yl)ethoxy)pyridin-3-yl]quinolin-6-yl}-6-methyl-1,6-dihydro-7H-pyrrolo[2,3-c]pyridin-7-one (SLU-2240)

Scheme 63

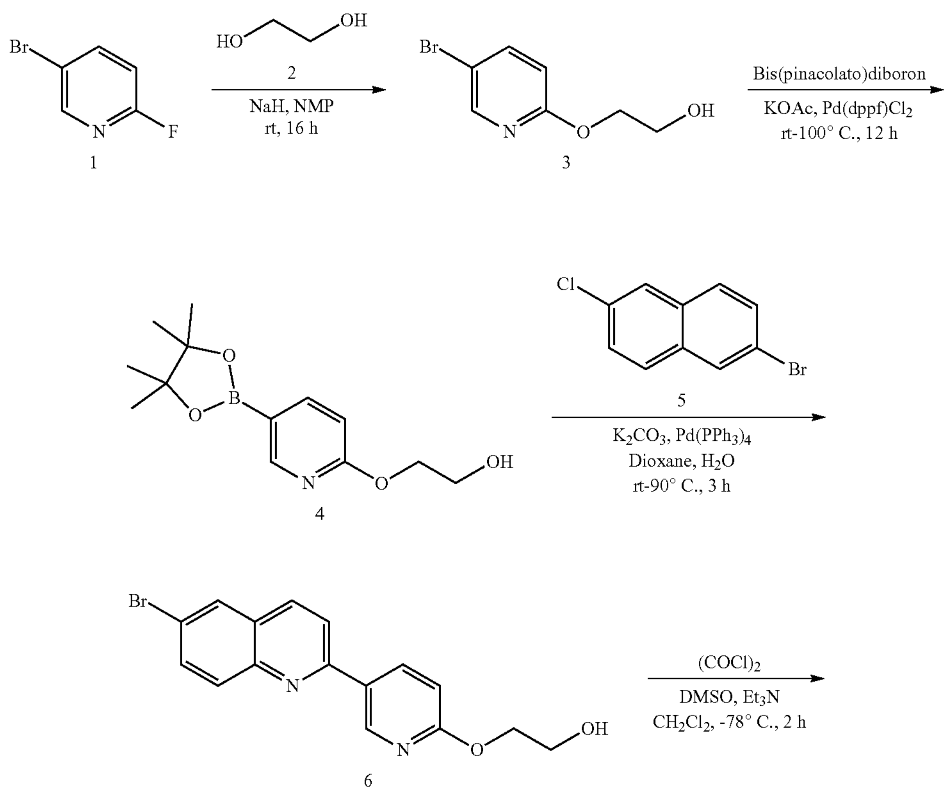

-continued

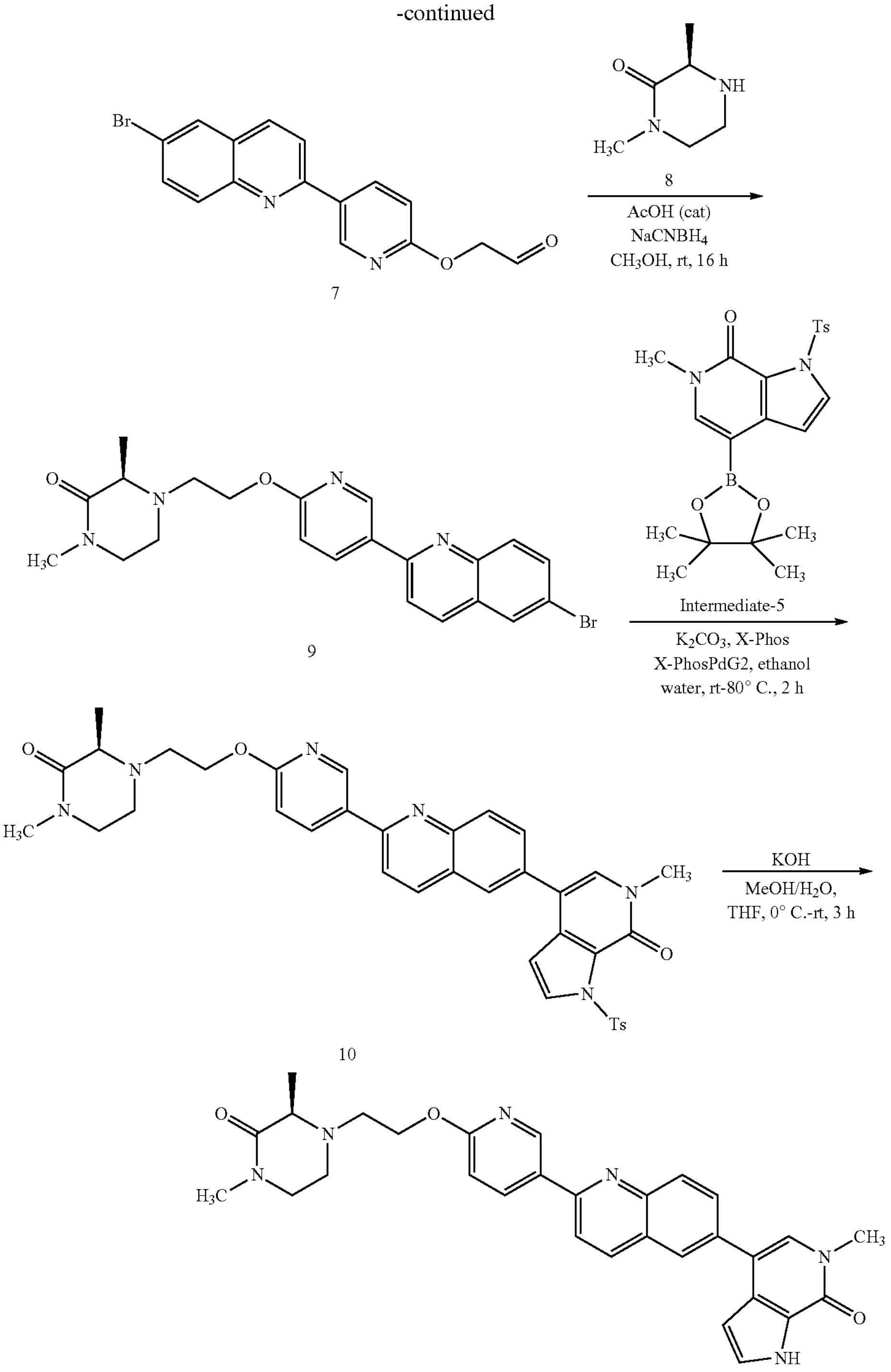

7

9

10

SLU-2240

2-[(5-bromopyridin-2-yl)oxy]ethan-1-ol (3)

To a stirred solution of ethylene glycol 2 (3.54 g, 57.1 mmol) in N-methyl-2-pyrrolidone, were charged with NaH (2.28 g, 57.1 mmol) was added portionwise at 0° C. and stirred for 1 h at room temperature. 5-bromo-2-fluoropyridine 1 (2.0 g, 11.4 mmol) was added to the reaction mixture dropwise at 0° C. and stirred for 24 h at room temperature. TLC indicated at which time the reaction gone to completion. The reaction mixture was diluted with water (150 mL) and extracted with EtOAc (3×150 mL). Combined organic layers were dried over anhydrous $Na_2SO_4$ and concentrated under reduced pressure. The crude product was purified by combiflash chromatography (Hexanes:EtOAc=70:30) to afford 3 (1.10 g, 44%) as an off-white solid.

$^1H$ NMR (400 MHz, $CDCl_3$): δ ppm 8.17 (d, J=2.4 Hz, 1H), 7.67 (dd, J=2.8, 8.8 Hz, 1H), 6.72 (d, J=8.8 Hz, 1H), 4.42-4.44 (m, 2H), 3.94 (s, 2H), 2.89 (s, 1H).

2-{[5-(4,4,5,5-tetramethyl-1,3,2-dioxaborolan-2-yl) pyridin-2-yl]oxy}ethan-1-ol (4)

To a stirred solution of 3 (5.0 g, 23.0 mmol) in dioxane (50 mL) were charged with bis(pincolato)diboron (7.0 g, 27.6 mmol), KOAc (4.5 g, 46.0 mmol) at room temperature and degassed it with argon for 10 min. Pd(dppf)$Cl_2$ (0.840 g, 1.15 mmol) was added to the reaction mixture at room temperature and degassed it with argon for 5 min and was heated at 100° C. for 12 h. TLC indicated at which time the reaction gone to completion. The reaction mixture was diluted with water (200 mL) and extracted with EtOAc (3×250 mL). Combined organic layers were dried over anhydrous $Na_2SO_4$ and concentrated under reduced pressure. The crude product was purified by combiflash chromatography (EtOAc:Hexanes=70:30) to afford 4 (3.5 g, 57%) as colourless liquid.

$^1$H NMR (400 MHz, $CDCl_3$) δ ppm 8.5 (d, J=1.2 Hz, 1H), 7.96 (dd, J=2.0, 8.4 Hz, 1H), 6.77 (d, J=9.2 Hz, 1H), 4.48-4.50 (m, 2H), 3.93-3.95 (m, 2H), 1.33 (s, 12H).

2-{[(5-(6-bromoquinolin-2-yl)pyridin-2-yl] oxy}ethan-1-ol (6)

To a stirred solution of 4 (3.5 g, 13.20 mmol4) in 1,4-dioxane (30 mL), $H_2O$ (4.0 mL) were charged with 6-bromo-2-chloroquinoline 5 (3.19 g, 13.20 mmol), $K_2CO_3$ (3.6 g, 26.4 mmol) at room temperature and degassed it with for 10 min. Pd$(pph_3)_4$ (1.5 g, 1.32 mmol) was added to the reaction mixture and heated at 90° C. for 3 h, at which TLC indicated the reaction gone to completion. The reaction mixture was diluted with water (200 mL) and extracted with EtOAc (3×250 mL). Combined organic layers were dried over anhydrous $Na_2SO_4$ and concentrated under reduced pressure. The crude product was purified by combiflash chromatography (EtOAc:Hexanes=70:30) to afford 6 (2.30 g, 48%) as an off-white solid.

$^1$H NMR (400 MHz, DMSO-$d_6$): δ ppm 9.04 (d, J=2.4 Hz, 1H), 8.59 (dd, J=1.6, 8.8 Hz, 1H), 8.44 (d, J=8.8 Hz, 1H), 8.29 (d, J=2.4 Hz, 1H), 8.22 (d, J=8.8 Hz, 1H), 7.99 (d, J=8.8 Hz, 1H), 7.89 (dd, J=2.4, 9.2 Hz, 1H), 6.99 (d, J=8.8 Hz, 1H), 4.88 (t, J=5.6 Hz, 1H), 4.37 (t, J=5.2 Hz, 2H), 3.75 (q, J=5.2 Hz, 2H).

2-[5-(6-bromoquinolin-2-yl)pyridin-2-yl] oxy}acetaldehyde (7)

A solution of $(COCl)_2$ (0.5 g, 1.74 mmol7) in $CH_2Cl_2$ (5.0 mL) was cooled to −78° C. and DMSO (0.226 g, 2.9 mmol) was added dropwise and stirred for 15 min. 6 (0.5 g, 1.45 mmol) in $CH_2Cl_2$ (5.0 mL) was added to above solution dropwise at −78° C. stirred for 2 h at the same temperature followed by the addition of $Et_3N$ (0.97 mL, 7.25 mmol) and stirred for 30 min at the same temperature. The reaction mixture was diluted with water (50 mL) and extracted with EtOAc (3×50 mL). Combined organic layers were dried over anhydrous $Na_2SO_4$ and concentrated under reduced pressure to afford 7 (0.4 g) as off-white solid which was used for next step.

ESI-MS m/z $[C_{16}H_{11}N_2O_2Br+H]^+$ 343.0

(R)-4-{2-[(5-(6-bromoquinolin-2-yl)pyridin-2-yl) oxy]ethyl}-1,3-dimethylpiperazin-2-one (9)

To a stirred solution of 7 (0.4 g, 13.31 mmol1) in $CH_3OH$ (10 mL) were charged with 8 (0.336 g, 2.63 mmol), AcOH (catalytic) and stirred for 15 min at room temperature. $NaCNBH_3$ (0.247 g, 3.93 mmol) was added to the reaction mixture portion wise and stirred for 16 h at room temperature. TLC indicated at which time the reaction gone to completion. The reaction mixture was concentrated, diluted with water (50 mL) and extracted with EtOAc (3×100 mL). Combined organic layers were dried over anhydrous $Na_2SO_4$ and concentrated under reduced pressure. The crude product was purified by combiflash chromatography ($CH_2Cl_2$:$CH_3OH$=97:3) to afford 9 (0.130 g, 22%) as off-white solid.

$^1$H NMR (400 MHz, DMSO-$d_6$): δ ppm 9.04 (d, J=2.0 Hz, 1H), 8.59 (dd, J=1.6, 8.8 Hz, 1H), 8.44 (d, J=8.8 Hz, 1H), 8.30 (d, J=2.4 Hz, 1H), 8.23 (d, J=8.8 Hz, 1H), 7.99 (d, J=8.8 Hz, 1H), 7.89 (dd, J=2.4, 9.2 Hz, 1H), 6.99 (d, J=8.8 Hz, 1H), 4.47-4.49 (m, 2H), 3.23-3.27 (m, 2H), 3.15 (d, J=8.0 Hz, 1H), 3.05-3.12 (m, 2H), 2.95-3.02 (m, 1H), 2.80 (s, 3H), 2.67-2.71 (m, 1H), 1.24 (d, J=6.8 Hz, 3H).

(R)-4-{2-[6-(2-(2,4-dimethyl-3-oxopiperazin-1-yl) ethoxy)pyridin-3-yl]quinolin-6-yl}-6-methyl-1-tosyl-1,6-dihydro-7H-pyrrolo[2,3-c]pyridin-7-one (10)

To a stirred solution of 9 (0.130 g, 0.35 mmol6) in ethanol (3.0 mL), $H_2O$ (1 mL) were charged with Intermediate-5 (0.181 g, 0.42 mmol), $K_2CO_3$ (0.145 g, 1.05 mmol) at room temperature and degassed it with argon for 5 min. X-Phos (0.033 g, 0.06 mmol), X-phosPd$G_2$ (0.028 g, 0.035 mmol) was added to the reaction mixture at room temperature and stirred at 80° C. for 2 h. The reaction mixture was diluted with water (20 mL) and extracted with EtOAc (3×50 mL). Combined organic layers were dried over anhydrous $Na_2SO_4$ and concentrated under reduced pressure. The crude product was purified by reverse phase chromatography (ACN:$H_2O$=60:40) to afford 10 (0.125 g, 43%) as white solid.

$^1$H NMR (400 MHz, DMSO-$d_6$): δ ppm 9.08 (s, 1H), 8.61 (d, J=8.0 Hz, 1H), 8.50 (d, J=8.4 Hz, 1H), 8.20 (d, J=8.4 Hz, 1H), 8.10-8.13 (m, 3H), 7.99 (d, J=8.0 Hz, 2H), 7.93 (d, J=8.8 Hz, 1H), 7.81 (s, 1H), 7.45 (d, J=8.0 Hz, 2H), 6.99 (d, J=8.4 Hz, 1H), 6.88 (d, J=3.6 Hz, 1H), 4.48 (br.s., 2H), 3.52 (s, 2H), 3.26 (br.s., 2H), 3.07-3.17 (m, 3H), 2.97-3.01 (m, 1H), 2.81 (s, 3H), 2.61-2.68 (m, 2H), 2.40 (s, 3H), 1.24 (d, J=6.8 Hz, 3H).

(R)-4-{2-[6-(2-(2,4-dimethyl-3-oxopiperazin-1-yl) ethoxy)pyridin-3-yl]quinolin-6-yl}-6-methyl-1,6-dihydro-7H-pyrrolo[2,3-c]pyridin-7-one (SLU-2240)

To a stirred solution of 10 (0.125 g, 0.18 mmol) in $CH_3OH$ (3.0 mL), $H_2O$ (1.5 mL), THF (2.0 mL) was charged with potassium hydroxide (0.052 g, 0.92 mmol) at 0° C. The reaction mixture stirred for 3 h at room temperature, was evaporated, diluted with water (10 mL) and extracted with 10% $CH_3OH$ in $CH_2Cl_2$ (3×20 mL). Combined organic layers were dried over anhydrous $Na_2SO_4$ and concentrated under reduced pressure. The crude product was purified by reverse phase chromatography (ACN:$H_2O$=70:30) to afford SLU-2240 (0.65 g, 68%) as an off-white solid.

$^1$H NMR (400 MHz, DMSO-$d_6$): δ ppm 12.23 (s, 1H), 9.07 (d, J=2.0 Hz, 1H), 8.62 (dd, J=2.4, 8.8 Hz, 1H), 8.51 (d, J=8.8 Hz, 1H), 8.18-8.21 (m, 2H), 8.12 (d, J=8.8 Hz, 1H), 8.02-8.05 (m, 1H), 7.63 (s, 1H), 7.41 (t, J=2.8, 1H), 6.99 (d, J=8.4 Hz, 1H), 6.62 (m, 1H), 4.48 (d, J=4.4 Hz, 2H), 3.63 (s, 3H), 3.26 (m, 2H), 3.16 (d, J=6.8 Hz, 1H), 3.08-3.11 (m, 1H), 3.01-2.98 (m, 1H), 2.81 (s, 4H), 2.69-2.72 (m, 1H), 1.25 (d, J=6.8 Hz, 3H).

ESI-MS m/z $[C_{30}H_{30}N_6O_3+H]^+$ 523.4.

HPLC (Method A) 94.6% (AUC), $t_R$=6.13 min.

Synthesis of 6-methyl-4-{2-[4-(2-(4-methyl-5-oxo-1,4-diazepan-1-yl)ethoxy)phenyl]quinolin-6-yl}-1,6-dihydro-7H-pyrrolo[2,3-c]pyridin-7-one (SLU-2277)
Scheme 64
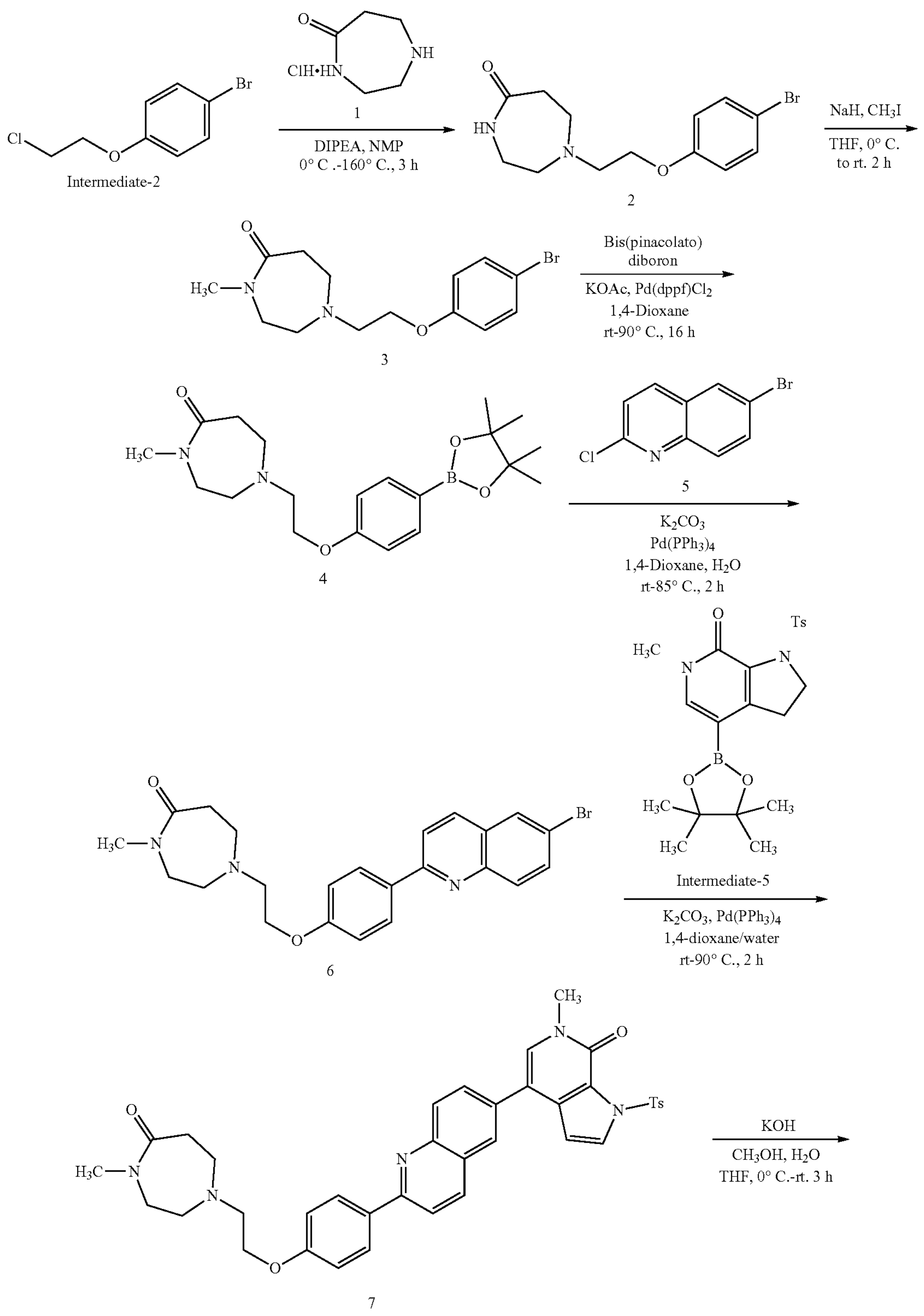

-continued

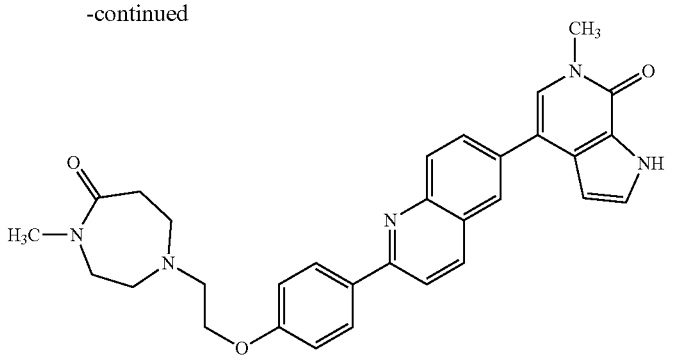

SLU-2277

1-(2-(4-bromophenoxy)ethyl)-1,4-diazepan-5-one (2)

To a stirred solution of Intermediate-2 (0.3 g, 27 mmoll) in NMP (5.0 mL) were charged with 1,4-diazepan-5-one hydrochloride 1 (0.230 g, 1.53 mmol), DIPEA (0.85 mL, 5.08 mmol) at 0° C. and heated at 160° C. for 3 h in sealed tube and sand bath. The reaction mixture was diluted with water (20 mL) and extracted with EtOAc (3×25 mL). Combined organic layers were dried over anhydrous $Na_2SO_4$ and concentrated under reduced pressure. The crude product was purified by combiflash chromatography ($CH_2Cl_2$:$CH_3OH$=97:3) to afford 2 (0.160 g, 40%) as an off-white solid.

$^1$H NMR (400 MHz, $CDCl_3$): δ ppm 7.37 (d, J=8.8 Hz, 2H), 6.77 (d, J=9.2 Hz, 2H), 6.15 (br.s., 1H), 4.05 (t, J=5.6 Hz, 2H), 3.29-3.31 (m, 2H), 2.93 (t, J=5.6 Hz, 2H), 2.76-2.80 (m, 4H), 2.64-2.65 (m, 2H).

1-[2-(4-bromophenoxy)ethyl]-4-methyl-1,4-diazepan-5-one (3)

To a stirred solution of 2 (0.160 g, 3.8 mmol7) in THF (10 mL), NaH (0.169 g 4.1 mmol) was charged portion wise at 0° C. and stirred for 15 min at same temperature followed by addition of $CH_3I$ (0.26 mL, 4.2 mmol) and stirred at room temperature for 2 h. TLC indicated at which time the reaction gone to completion. The mixture was diluted with water (150 mL) and extracted with EtOAc (3×150 mL). Combined organic layers were dried over anhydrous $Na_2SO_4$ and concentrated under reduced pressure. The crude product was purified by combiflash chromatography ($CH_2Cl_2$:$CH_3OH$=97:3) to afford 3 (0.980 g, 79%) as colourless liquid.

$^1$H NMR (400 MHz, DMSO-$d_6$): δ ppm 7.41 (d, J=8.4 Hz, 2H), 6.91 (d, J=8.4 Hz, 2H), 4.05 (t, J=5.6 Hz, 2H), 3.39-3.41 (m, 2H), 2.83 (s, 3H), 2.80 (t, J=5.6 Hz, 2H), 2.59-2.65 (m, 4H) 2.51 (s, 2H).

4-methyl-1-{2-[4-(4,4,5,5-tetramethyl-1,3,2-dioxaborolan-2-yl)phenoxy]ethyl}-1,4-diazepan-5-one (4)

To a stirred solution of 3 (0.980 g, 3.0 mmol9) in dioxane (15 mL) were charged with bis(pincolato)diboron (0.915 g, 3.61 mmol), KOAc (0.588 g, 6.0 mmol) at room temperature and degassed it with for 8 min. Pd(dppf)$Cl_2$ (0.219 g, 0.30 mmol) was added to the reaction mixture and heated at 90° C. for 16 h. TLC indicated at which time the reaction gone to completion. The reaction mixture was diluted with water (70 mL) and extracted with EtOAc (3×100 mL). Combined organic layers were dried over anhydrous $Na_2SO_4$ and concentrated under reduced pressure. The crude product was purified by combiflash chromatography ($CH_2Cl_2$:$CH_3OH$=95:5) to afford 4 (0.980 g, 66%) as a gummy solid.

$^1$H NMR (400 MHz, DMSO-$d_6$): δ ppm 7.59 (d, J=8.4 Hz, 2H), 6.91 (d, J=8.4 Hz, 2H), 4.09 (t, J=5.6 Hz, 2H), 3.39-3.42 (m, 2H), 2.83 (s, 3H), 2.80 (t, J=5.6 Hz, 2H), 2.62-2.66 (m, 4H) 2.52 (s, 2H), 1.27 (s, 12H).

1-{2-[4-(6-bromoquinolin-2-yl)phenoxy]ethyl}-4-methyl-1,4-diazepan-5-one (6)

To a stirred solution of 4 (0.980 g, 1.72 mmol2) in dioxane (8.0 mL), $H_2O$ (2.0 mL) were charged with 6-bromo-2-chloroquinoline 5 (0.415 g, 1.72 mmol), $K_2CO_3$ (0.474 g, 3.44 mmol) at room temperature and degassed it with for 5 min. Pd($PPh_3$)$_4$ (0.196 g, 0.17 mmol) was added to the reaction mixture and heated at 85° C. for 2 h. The reaction mixture was diluted with water (70 mL) and extracted with EtOAc (3×75 mL). Combined organic layers were dried over anhydrous $Na_2SO_4$ and concentrated under reduced pressure. The crude product was purified by combiflash chromatography ($CH_2Cl_2$:$CH_3OH$=96:4) to afford 6 (0.450 g, 58%) as an off-white solid.

$^1$H NMR (400 MHz, DMSO-$d_6$): δ ppm 8.38 (d, J=8.8 Hz, 1H), 8.23-8.26 (m, 3H), 8.16 (d, J=8.8 Hz, 1H), 7.96 (d, J=9.2 Hz, 1H), 7.86 (dd, J=2.4, 9.2 Hz, 1H), 7.11 (d, J=8.8 Hz, 2H), 4.17 (t, J=5.6 Hz, 2H), 3.42-3.44 (m, 2H), 2.69-2.87 (m, 5H), 2.63-2.68 (m, 4H), 2.52-2.56 (m, 2H).

6-methyl-4-{2-[4-(2-(4-methyl-5-oxo-1,4-diazepan-1-yl)ethoxy)phenyl]quinolin-6-yl}-1-tosyl-1,6-dihydro-7H-pyrrolo[2,3-c]pyridin-7-one (7)

To a stirred solution of 6 (0.450 g, 0.66 mmol8) in dioxane (8.0 mL), $H_2O$ (2.0 mL) were charged with Intermediate-5 (0.282 g, 0.66 mmol8), $K_2CO_3$ (0.182 g, 1.32 mmol) at room temperature and degassed it with argon for 5 min. Pd($PPh_3$)$_4$ (0.069 g, 0.06 mmol) was added to the reaction mixture and heated at 90° C. for 2 h. TLC indicated at which time the reaction gone to completion. The reaction mixture was diluted with water (30 mL) and extracted with EtOAc (3×50 mL). Combined organic layers were dried over anhydrous $Na_2SO_4$ and concentrated under reduced pressure. The crude product was purified by combiflash chromatography ($CH_2Cl_2$:$CH_3OH$=97:3) to afford 7 (0.125 g, 28%) as an off-white solid.

$^1H$ NMR (400 MHz, DMSO-$d_6$) δ ppm 8.45 (d, J=8.8 Hz, 1H), 8.26 (d, J=8.8 Hz, 2H), 8.15 (d, J=8.4 Hz, 1H), 8.09-8.11 (m, 3H), 7.99 (d, J=8.4 Hz, 2H), 7.90 (dd, J=1.6, 8.8 Hz, 1H), 7.80 (s, 1H), 7.45 (d, J=8.4 Hz, 2H), 7.12 (d, J=8.8 Hz, 2H), 6.87 (d, J=3.6 Hz, 1H), 4.18 (t, J=5.6 Hz, 2H), 3.51 (s, 3H), 3.43-3.45 (m, 2H), 2.85-2.88 (m, 5H), 2.64-2.70 (m, 4H), 2.52-2.56 (m, 2H), 2.40 (s, 3H).

6-methyl-4-{2-[4-(2-(4-methyl-5-oxo-1,4-diazepan-1-yl)ethoxy)phenyl]quinolin-6-yl}-1,6-dihydro-7H-pyrrolo[2,3-c]pyridin-7-one (SLU-2277)

To a stirred solution of 7 (0.125 g, 0.18 mmol2) in $CH_3OH$ (3.0 mL), $H_2O$ (1.5 mL), THF (2.0 mL) was charged with potassium hydroxide (0.052 g, 0.92 mmol) at 0° C. and stirred for 3 h at room temperature. The reaction mixture was evaporated, diluted with water (10 mL) and extracted with EtOAc (3×20 mL). Combined organic layers were dried over anhydrous $Na_2SO_4$ and concentrated under reduced pressure. The crude product was purified by reverse phase chromatography (ACN:$H_2O$=70:30) to afford SLU-2277 (0.065 g, 68%) as an off-white solid.

$^1H$ NMR (400 MHz, DMSO-$d_6$) δ ppm 12.22 (s, 1H), 8.46 (d, J=8.8 Hz, 1H), 8.26 (d, J=8.8 Hz, 2H), 8.08-8.18 (m, 3H), 8.01 (dd, J=2.0, 8.8 Hz, 1H), 7.59 (s, 1H), 7.41 (d, J=2.8, 1H), 7.12 (d, J=8.8 Hz, 2H), 6.61 (d, J=2.8 Hz, 1H), 4.18 (t, J=5.6 Hz, 2H), 3.63 (s, 3H), 3.43-3.45 (m, 2H), 2.88 (d, J=5.6 Hz, 2H), 2.70 (s, 3H), 2.64-2.69 (m, 4H), 2.53-2.55 (m, 2H).

ESI-MS m/z $[C_{31}H_{31}N_5O_3+H]^+$ 522.3.

HPLC (Method A) 96.8% (AUC), $t_R$=6.02 min.

Synthesis of 6-methyl-4-{6-[4-(2-morpholinoethoxy)phenyl]quinolin-2-yl}-1,6-dihydro-7H-pyrrolo[2,3-c]pyridin-7-one (SLU-2278)

Scheme 65

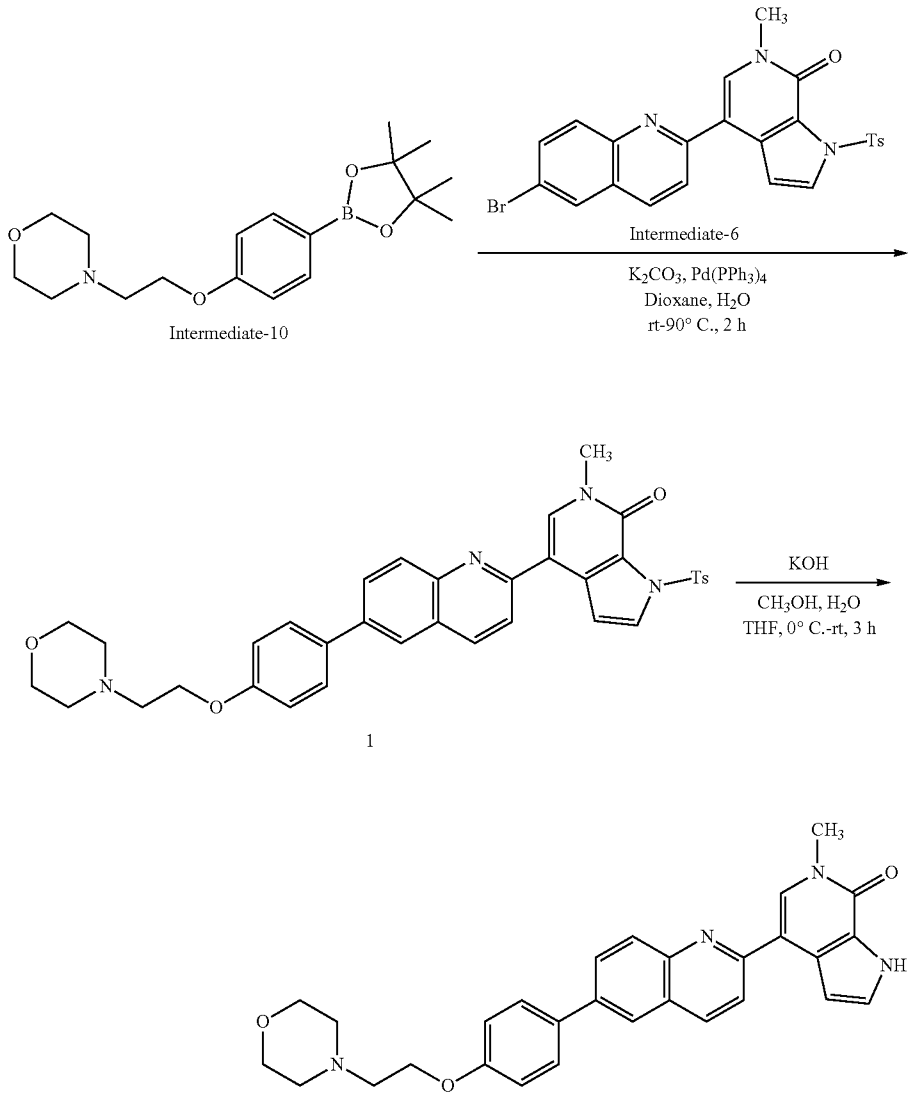

Intermediate-10

Intermediate-6

1

SLU-2278

6-methyl-4-(6-(4-(2-morpholinoethoxy)phenyl)quinolin-2-yl)-1-tosyl-1,6-dihydro-7H-pyrrolo[2,3-c]pyridin-7-one (1)

To a stirred solution of Intermediate-10 (0.5 g, 0.60 mmol1) in dioxane (4.0 mL), $H_2O$ (1.0 mL) were charged with Intermediate-6 (0.335 g, 0.66 mmol6), $K_2CO_3$ (0.166 g, 1.20 mmol) at room temperature and degassed it with argon for 5 min. $Pd(PPh_3)_4$ (0.069 g, 0.06 mmol), $K_2CO_3$ (0.166 g, 1.20 mmol) was added to the reaction mixture at room temperature and was heated at 90° C. for 2 h. TLC indicated at which time the reaction gone to completion. The reaction mixture was diluted with water (20 mL) and extracted with EtOAc (3×25 mL). Combined organic layers were dried over anhydrous $Na_2SO_4$ and concentrated under reduced pressure. The crude product was purified by reverse phase chromatography (ACN:$H_2O$=80:20) to afford 1 (0.175 g, 31%) as an off-white solid.

$^1$H NMR (400 MHz, DMSO-$d_6$): δ ppm 8.42 (d, J=8.8 Hz, 1H), 8.37 (s, 1H), 8.20 (s, 1H), 8.08-8.11 (m, 3H), 7.96-8.01 (m, 3H), 7.99 (d, J=8.8 Hz, 2H), 7.75 (d, J=8.4 Hz, 1H), 7.44 (d, J=8.0 Hz, 2H), 7.10 (d, J=8.8 Hz, 2H), 4.16 (t, J=5.6 Hz, 2H), 3.59 (t, J=4.8 Hz, 4H), 3.55 (s, 3H), 2.73 (t, J=5.6 Hz, 2H), 2.39 (s, 3H).

6-methyl-4-{6-[4-(2-morpholinoethoxy)phenyl]quinolin-2-yl}-1,6-dihydro-7H-pyrrolo[2,3-c]pyridin-7-one (SLU-2278)

To a stirred solution of 1 (0.175 g, 0.27 mmol6) in MeOH (4.0 mL), $H_2O$ (1.0 mL), THF (2.0 mL) was charged with potassium hydroxide (0.078 g, 1.38 mmol) at 0° C. The reaction mixture was stirred for 3 h at room temperature. The reaction mixture was evaporated, diluted with water (10 mL) and extracted with EtOAc (3×20 mL). Combined organic layers were dried over anhydrous $Na_2SO_4$ and concentrated under reduced pressure. The crude product was purified by reverse phase chromatography ($CH_2Cl_2$:$CH_3OH$=96:4) to afford SLU-2278 (0.091 g, 68%) as an off-white solid.

$^1$H NMR (400 MHz, DMSO-$d_6$) δ ppm 12.16 (s, 1H), 8.4 (d, J=8.8 Hz, 1H), 8.19 (s, 2H), 8.04-8.10 (m, 3H), 7.78 (d, J=8.8, 2H), 7.41 (d, J=2.4 Hz, 1H), 7.34 (d, J=2.8 Hz, 1H), 7.10 (d, J=8.8 Hz, 2H), 4.16 (t, J=5.6 Hz, 2H), 3.68 (s, 3H), 3.59 (t, J=4.8 Hz, 4H), 2.73 (t, J=5.6 Hz, 2H), 2.52 (m, 4H).

ESI-MS m/z $[C_{28}H_{28}N_4O_3+H]^+$ 481.3.

HPLC (Method A) 98.4% (AUC), $t_R$=6.1 min.

Synthesis of (S)-4-{2-[4-(2-(2,4-dimethyl-5-oxopiperazin-1-yl)ethoxy)phenyl]quinolin-6-yl}-6-methyl-1H-pyrrolo[2,3-c]pyridin-7(6H)-one (SLU-2287)

Scheme 66

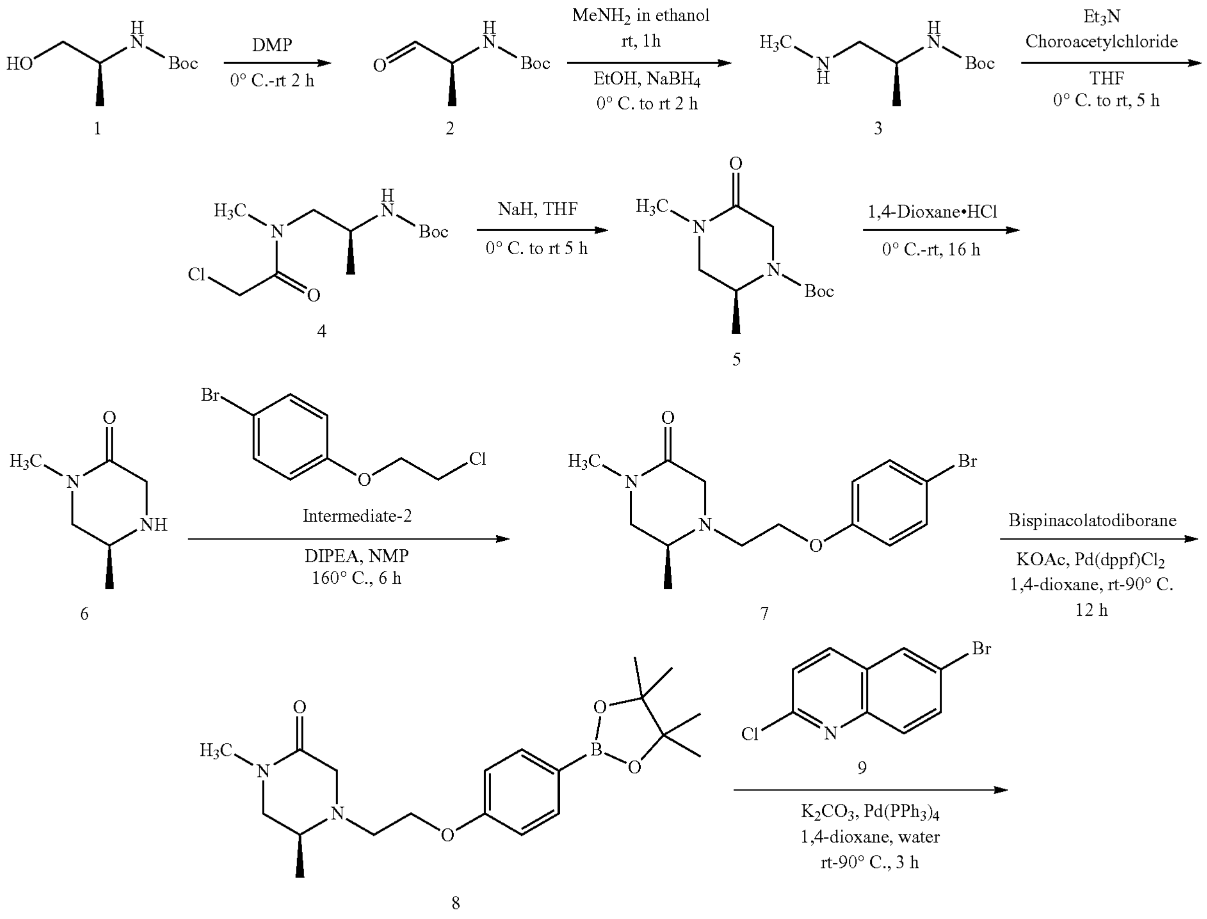

-continued

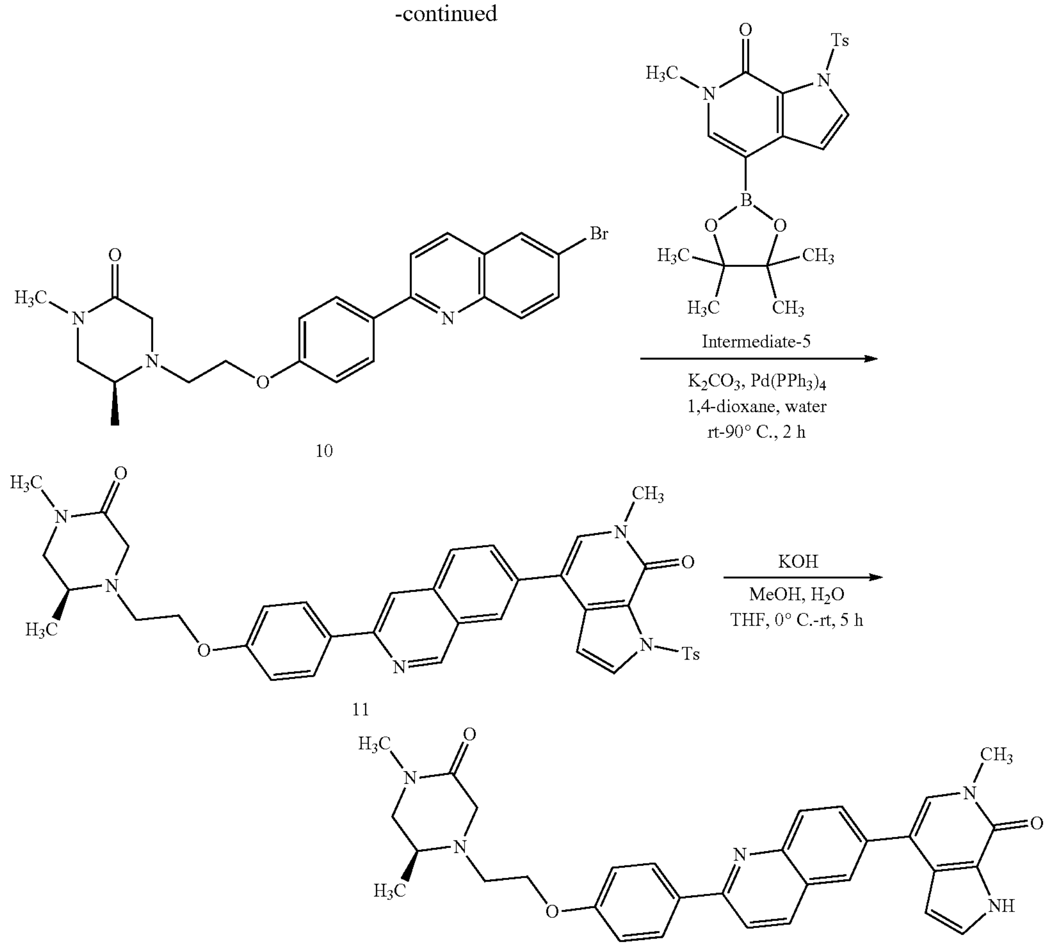

10

11

SLU-2287 tert-butyl (S)-(1-oxopropan-2-yl)carbamate (2)

To a stirred solution 1 (5.0 g, 28.5 mmol) in $CH_2Cl_2$ (100 mL) was charged with Dess-Martin periodinane (13.3 g, 31.4 mmol) portion wise at 0° C. The reaction mixture was stirred for 2 h at room temperature. TLC indicated at which time the reaction gone to completion. The mixture was filtered through celite bed and washed with $CH_2Cl_2$ (200 mL). The crude product was purified by combiflash chromatography (Hexanes:EtOAc=70:30) to afford 2 (4.10 g, 81%) as an off-white solid.

$^1$H NMR (400 MHz, $CDCl_3$) δ ppm 9.56 (s, 1H), 5.15 (s, 1H), 4.24 (t, J=6.8 Hz, 1H), 1.45 (s, 9H), 1.34 (d, J=6.8 Hz, 3H).

tert-butyl (S)-[1-(methylamino)propan-2-yl]carbamate (3)

To a stirred solution of 2 (4.1 g, 23.6 mmol1) in ethanol (40 mL), methyl amine in $C_2H_5OH$ (2 M, 17 mL, 35.5 mmol) was charged dropwise at room temperature and stirred for 1 h. $NaBH_4$ (1.74 g, 47.2 mmol) was added to the reaction mixture portion wise at 0° C. and stirred for 2 h at room temperature. TLC indicated at which time the reaction gone to completion. Reaction mixture was concentrated, diluted with water (100 mL) and extracted with EtOAc (3×100 mL). Combined organic layers were dried over anhydrous $Na_2SO_4$ and concentrated under reduced pressure to afford 3 (3.3 g5) as a gummy solid. This crude was used for next step.

$^1$H NMR (400 MHz, $CD_3OD$) δ ppm 3.61-3.68 (m, 1H), 2.42-2.48 (m, 2H), 2.25 (s, 3H), 1.33 (s, 9H), 1.00 (d, J=6.8 Hz, 3H).

tert-butyl (S)-[1-(2-chloro-N-methylacetamido)propan-2-yl]carbamate (4)

To a stirred solution of 3 (3.3 g, 17.5 mmol5) in THF (40 mL) were charged with $Et_3N$ (14.14 mL, 105.0 mmol), chloroacetylchloride (4.15 mL, 52.6 mmol) dropwise at 0° C. and stirred for 5 h at room temperature. The reaction mixture was diluted with water (100 mL) and extracted with EtOAc (3×100 mL). Combined organic layers were dried over anhydrous $Na_2SO_4$, concentrated under reduced pressure and crude residue was purified by combiflash chromatography (EtOAc:Hexanes=1:1) to afford 4 (2.5 g, 68%) as colourless liquid.

$^1$H NMR (400 MHz, $CDCl_3$): δ ppm 4.69-4.71 (m, 1H), 3.85-3.90 (m, 1H), 3.75-3.81 (m, 1H), 3.12 (s, 3H), 3.05-3.08 (m, 2H), 1.47 (s, 9H), 1.14 (d, J=6.4 Hz, 3H).

tert-butyl (S)-2,4-dimethyl-5-oxopiperazine-1-carboxylate (5)

To a stirred solution of 4 (2.50 g, 12.0 mmol8) in THF (40 mL) was charged with NaH (0.86 g, 36.0 mmol) portion wise at 0° C. and stirred for 5 h at room temperature. The reaction mixture was diluted with ice cold water (250 mL) and extracted with EtOAc (3×150 mL). Combined organic layers were dried over anhydrous $Na_2SO_4$ and concentrated under reduced pressure to afford 5 (1.50 g0) as a gummy solid which was used for next step without any purification.

$^1$H NMR (400 MHz, DMSO-$d_6$): δ ppm 4.22 (br.s., 1H), 3.96-4.00 (m, 1H), 3.55-3.66 (m, 2H), 3.09 (dd, J=2.8, 12.8 Hz, 1H), 2.86 (s, 3H), 1.40 (s, 9H), 1.11 (d, J=6.4 Hz, 3H).

(S)-1,5-dimethylpiperazin-2-one (6)

To a stirred solution of 5 (1.50 g, 6.5 mmol0) in 1,4-dioxane (15 mL), HCl in 1,4-dioxane (15 mL) was charged dropwise at 0° C. and stirred for 16 h at room temperature. TLC indicated at which time the reaction gone to completion. The reaction mixture was concentrated to afford 6 (1.1 g3) as a gummy solid. This crude was used for next step.

$^1$H NMR (400 MHz, DMSO-$d_6$) δ ppm 10.28 (br.s., 1H), 10.15 (br.s., 1H), 6.68 (br.s., 2H), 3.68-3.74 (m, 1H), 3.61 (d, J=4.0 Hz, 1H), 3.45 (d, J=8.0 Hz, 2H), 2.85 (s, 3H), 1.31 (d, J=6.4 Hz, 3H).

(S)-4-[2-(4-bromophenoxy)ethyl]-1,5-dimethylpiperazin-2-one (7)

A solution of Intermediate-2 (1.3 g, 5.5 mmol), 6 (0.8 g, 6.6 mmol3), DIPEA (3.7 mL, 22 mmol) in NMP (10 mL) was heated at 160° C. for 6 h in a sealed tube and sand bath. The reaction mixture was diluted with water (100 mL) and extracted with EtOAc (3×150 mL). Combined organic layers were dried over anhydrous $Na_2SO_4$ and concentrated under reduced pressure. The crude product was purified by combiflash chromatography ($CH_2Cl_2$:$CH_3OH$=95:5) to afford 7 (0.5 g, 25%) as a gummy solid.

$^1$H NMR (400 MHz, $CDCl_3$): δ ppm 7.36 (d, J=9.2 Hz, 2H), 6.77 (d, J=9.2 Hz, 2H), 4.03 (t, J=5.6 Hz, 2H), 3.47-3.51 (m, 1H), 3.27-3.31 (m, 2H), 3.08-3.11 (m, 3H), 2.94 (s, 3H), 2.74-2.81 (m, 1H), 1.17 (d, J=6.4 Hz, 3H).

(S)-1,5-dimethyl-4-{2-[4-(4,4,5,5-tetramethyl-1,3,2-dioxaborolan-2-yl)phenoxy]ethyl}piperazin-2-one (8)

To a stirred solution of 7 (0.5 g, 1.22 mmol4) in 1,4-dioxane (10 mL), were charged with bis(pincolato)diboron (0.372 g, 1.47 mmol), KOAc (0.239 g, 2.44 mmol) at room temperature and degassed it with argon for 10 min. Pd(dppf)$Cl_2$·$CH_2Cl_2$ (0.088 g, 0.12 mmol) was added to the reaction mixture at room temperature and degassed it with argon for 5 min and was heated at 90° C. for 12 h. The reaction mixture was diluted with water (30 mL), extracted with EtOAc (3×50 mL). Combined organic layers were dried over anhydrous $Na_2SO_4$, concentrated under reduced pressure and crude residue was purified by combiflash chromatography ($CH_2Cl_2$:$CH_3OH$=96:4) to afford 8 (0.380 g, 83%) as a gummy solid.

$^1$H NMR (400 MHz, $CDCl_3$) δ ppm 7.74 (dd, J=1.6, 6.8 Hz, 2H), 6.77 (dd, J=2.0, 6.8 Hz, 2H), 4.08-4.11 (m, 2H), 3.49-3.52 (m, 1H), 3.25-3.31 (m, 2H), 3.08-3.11 (m, 3H), 2.94 (s, 3H), 2.78-2.81 (m, 1H), 1.33 (s, 12H), 1.17 (d, J=6.0 Hz, 3H).

(S)-4-{2-[4-(6-bromoquinolin-2-yl)phenoxy]ethyl}-1,5-dimethylpiperazin-2-one (10)

A solution of 8 (0.380 g, 0.88 mmol7) in 1,4-dioxane (8.0 mL) were charged with 6-bromo-2-chloroquinoline 9 (0.213 g, 0.88 mmol), $K_2CO_3$ (0.243 g, 1.76 mmol) at room temperature and degassed it with argon for 5 min. Pd($PPh_3$)$_4$ (0.092 g, 0.08 mmol) was added to the reaction mixture and allowed to stir at 90° C. for 3 h. TLC indicated at which time the reaction gone to completion; the reaction mixture was diluted with water (20 mL) and extracted with EtOAc (3×30 mL). Combined organic layers were dried over anhydrous $Na_2SO_4$ and concentrated under reduced pressure. The crude product was purified by combiflash chromatography ($CH_2Cl_2$:$CH_3OH$=96:4) to afford 10 (0.170 g, 37%) as a gummy solid.

$^1$H NMR (300 MHz, DMSO-$d_6$) δ ppm 8.26-8.37 (m, 1H), 8.15-8.23 (m, 4H), 7.95-7.98 (m, 1H), 7.84-7.87 (m, 1H), 7.11 (d, J=8.4 Hz, 2H), 4.17 (br.s., 2H), 3.16-3.28 (m, 3H), 3.32-3.37 (m, 3H), 3.07-3.10 (m, 4H), 1.10 (br.s., 3H).

(S)-4-{2-[4-(2-(2,4-dimethyl-5-oxopiperazin-1-yl)ethoxy)phenyl]quinolin-6-yl}-6-methyl-1-tosyl-1,6-dihydro-7H-pyrrolo[2,3-c]pyridin-7-one (11)

To a stirred solution of 10 (0.170 g, 0.37 mmol2) in 1,4-dioxane (4.0 mL), water (1.0 mL), Intermediate-5 (0.160 g, 0.37 mmol), $K_2CO_3$ (0.102 g, 0.74 mmol) were added at room temperature and degassed it with argon for 5 min followed by addition of Pd($PPh_3$)$_4$ (0.043 g, 0.03 mmol) Then, the reaction mixture was heated at 90° C. for 2 h. The reaction mixture was diluted with water (10 mL) and extracted with EtOAc (3×25 mL). Combined organic layers were dried over anhydrous $Na_2SO_4$, concentrated under reduced pressure and crude residue was purified by combiflash chromatography ($CH_2Cl_2$:$CH_3OH$=96:4) to afford 11 (0.135 g, 53%) as an off-white solid.

$^1$H NMR (400 MHz, DMSO-$d_6$) δ ppm 8.40 (d, J=8.4 Hz, 1H), 8.26 (d, J=8.8 Hz, 2H), 8.09-8.16 (m, 4H), 7.99 (d, J=8.0 Hz, 2H), 7.90 (dd, J=2.0, 8.8 Hz, 1H), 7.80 (s, 1H), 7.45 (d, J=8.0 Hz, 2H), 7.12 (d, J=8.8 Hz, 2H), 6.86 (d, J=3.6 Hz, 1H), 4.17 (t, J=5.6 Hz, 2H), 3.51 (s, 3H), 3.27-3.36 (m, 1H), 2.94-3.04 (m, 3H), 2.81 (s, 3H), 2.72-2.77 (m, 1H), 2.44-2.54 (m, 1H), 2.39 (s, 3H), 1.09 (d, J=6.4 Hz, 3H).

(S)-4-{2-[4-(2-(2,4-dimethyl-5-oxopiperazin-1-yl)ethoxy)phenyl]quinolin-6-yl}-6-methyl-1,6-dihydro-7H-pyrrolo[2,3-c]pyridin-7-one (SLU-2287)

A solution of 11 (0.135 g, 0.20 mmol7) in MeOH (3.0 mL), $H_2O$ (1.0 mL), THF (2.0 mL) was charged with potassium hydroxide (0.056 g, 1.00 mmol) at 0° C. and stirred at room temperature for 5 h. The solvent was evaporated from the reaction mixture, diluted with water (10 mL) and extracted with EtOAc (3×20 mL). Combined organic layers were dried over anhydrous $Na_2SO_4$ and concentrated under reduced pressure. The crude product was purified by combiflash chromatography ($CH_2Cl_2$:$CH_3OH$=96:4) to afford SLU-2287 (0.058 g, 58%) as an off-white solid.

$^1$H NMR (400 MHz, DMSO-$d_6$) δ ppm 12.23 (s, 1H), 8.46 (d, J=8.8 Hz, 1H), 8.26 (d, J=8.8 Hz, 2H), 8.09-8.18 (m, 3H), 8.01 (dd, J=2.0, 8.8 Hz, 1H), 7.60 (s, 1H), 7.41 (d, J=2.8, 1H), 7.12 (d, J=9.2 Hz, 2H), 6.61 (d, J=2.8 Hz, 1H), 4.17 (t, J=6.0 Hz, 2H), 3.63 (s, 3H), 3.28-3.36 (m, 2H), 3.14 (d, J=16.8 Hz, 1H), 2.95-3.05 (m, 3H), 2.81 (s, 3H), 2.73-2.78 (m, 1H), 1.09 (d, J=6.0 Hz, 3H).

ESI-MS m/z $[C_{31}H_{31}N_5O_3+H]^+$ 522.3.

HPLC (Method A) 97.6% (AUC), $t_R$=6.07 min.

Synthesis of {6-methyl-4-[2-(4-(2-(4-methylpiperazin-1-yl)ethoxy)phenyl]quinolin-6-yl}-1-tosyl-1H-pyrrolo[2,3-c]pyridin-7(6H)-one (SLU-2288)
Scheme 67
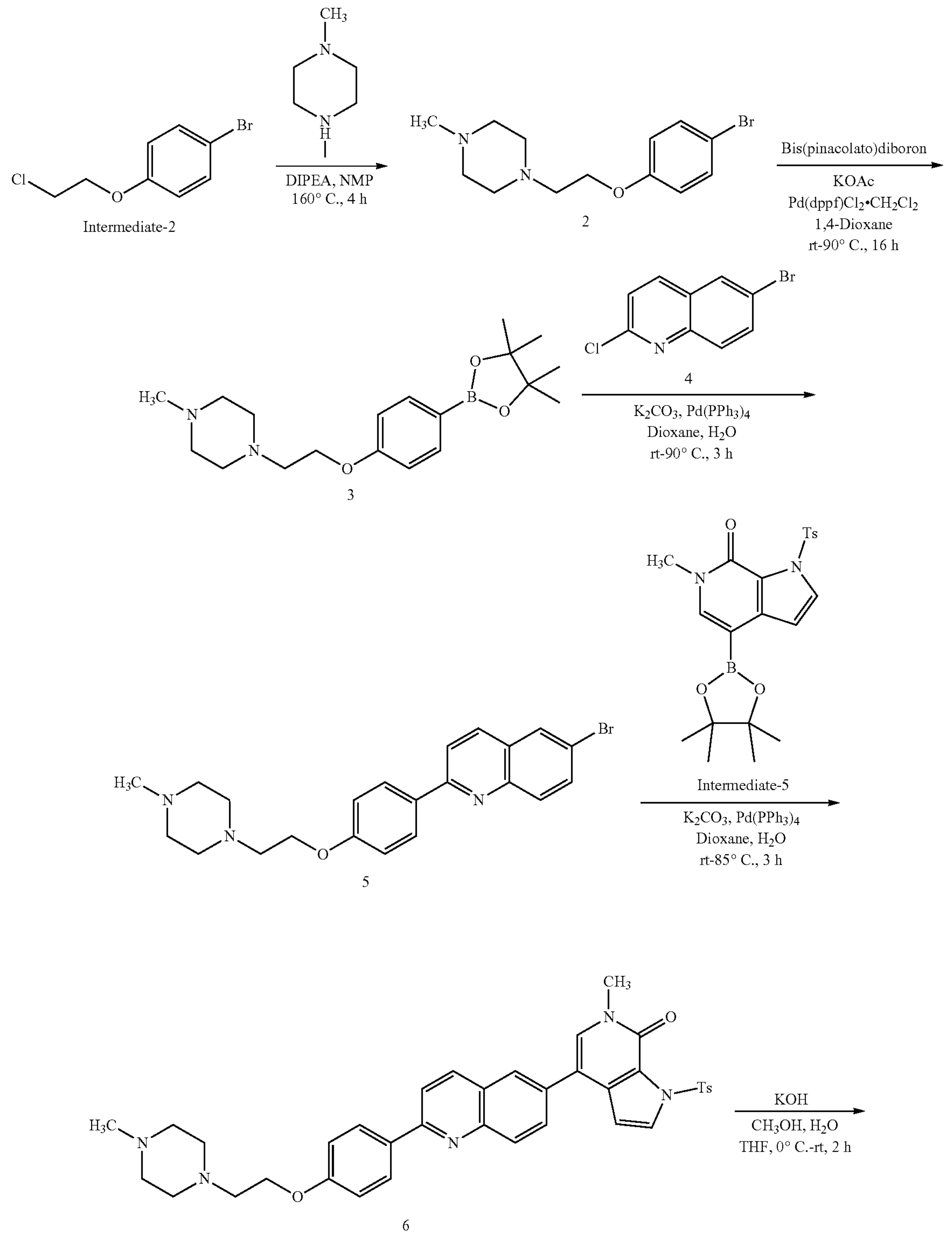

-continued

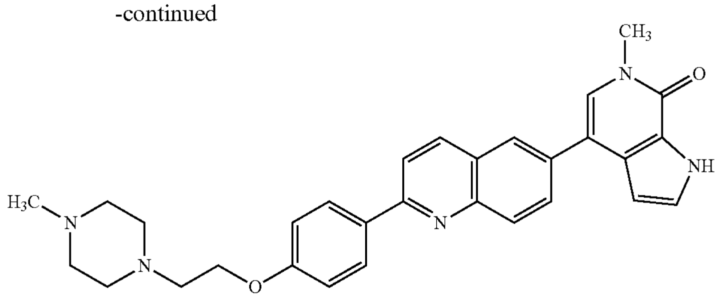

SLU-2288

(R)-benzyl {1-[2-(4-bromophenoxy)ethyl}-4-methylpiperazine (2)

To a stirred solution of Intermediate-2 (1.0 g, 4.2 mmol) in NMP (10 mL) in sealed tube, 4-methyl piperazine 1 (0.510 g, 5.1 mmol), DIPEA (3.0 mL, 16.8 mmol) were added and allowed to stir at 160° C. for 4 h in sand bath. TLC indicated at which time the reaction gone to completion. The reaction mixture was diluted with water (50 mL) and extracted with EtOAc (3×80 mL). Combined organic layers were dried over anhydrous $Na_2SO_4$, concentrated under reduced pressure and crude product was purified by combiflash chromatography ($CH_2Cl_2$:$CH_3OH$=95:5) to afford 2 (0.750 g, 54%) as an off-white solid.

$^1$H NMR (400 MHz, $CDCl_3$): δ ppm 7.36 (d, J=8.8 Hz, 2H), 6.78 (d, J=8.8 Hz, 2H), 4.06 (t, J=5.6 Hz, 2H), 3.38 (t, J=7.2 Hz, 1H), 2.84 (s, 1H), 2.80 (t, J=6.30 Hz, 2H), 2.62 (br.s., 3H), 2.47 (br.s., 3H), 2.29 (s, 3H).

1-methyl-4-{2-(4-(4,4,5,5-tetramethyl-1,3,2-dioxaborolan-2-yl)phenoxyl][ethyl}piperazine (3)

A solution of 2 (0.750 g, 2.18 mmol0) in 1,4-dioxane (10 mL) were charged with bis(pincolato)diboron (0.662 g, 2.61 mmol), KOAc (0.427 g, 4.36 mmol) at room temperature and degassed it with argon for 5 min. $Pd(dppf)Cl_2 \cdot CH_2Cl_2$ (0.153 g, 0.21 mmol) was added to the reaction mixture and heated at 90° C. for 16 h. The reaction mixture was diluted with water (50 mL) and extracted with EtOAc (3×80 mL). Combined organic layers were dried over anhydrous $Na_2SO_4$, concentrated under reduced pressure and was purified by combiflash chromatography ($CH_2Cl_2$:$CH_3OH$=96:4) to afford 3 (0.385 g, 44%) as a gummy solid.

$^1$H NMR (400 MHz, $CDCl_3$): δ ppm 7.74 (d, J=8.4 Hz, 2H), 6.89 (d, J=8.8 Hz, 2H), 4.13 (t, J=6.0 Hz, 2H), 2.82 (t, J=6.0 Hz, 1H), 2.64 (br.s., 3H), 2.50 (br.s., 3H), 2.31 (s, 3H), 1.32 (s, 12H).

{6-bromo-2-[4-(2-(4-methylpiperazin-1-yl)ethoxy) phenyl}quinoline (5)

To a stirred solution of 3 (0.385 g, 0.57 mmol4) in 1,4-dioxane (8.0 mL), $H_2O$ (2.0 mL), 6-bromo-2-chloroquinoline 4 (0.140 g, 0.57 mmol), $K_2CO_3$ (0.157 g, 1.1 mmol) were added at room temperature and degassed it with argon for 5 min. $Pd(PPh_3)_4$ (0.058 g, 0.05 mmol) was added to the reaction mixture and heated at 90° C. for 3 h. The reaction mixture was diluted with water (20 mL) and extracted with EtOAc (3×25 mL). Combined organic layers were dried over anhydrous $Na_2SO_4$ and concentrated under reduced pressure. The crude product was purified by combiflash chromatography ($CH_2Cl_2$:$CH_3OH$=96:4) to afford 5 (0.130 g, 42%) as a light brown solid.

$^1$H NMR (400 MHz, DMSO-$d_6$): δ ppm 8.38 (d, J=8.4 Hz, 2H), 8.23-8.27 (m, 3H), 8.17 (d, J=8.8 Hz, 2H), 7.96 (d, J=8.8 Hz, 1H), 7.86 (d, J=2.0, 8.8 Hz, 1H), 7.10 (d, J=8.8 Hz, 2H), 4.16 (t, J=5.6 Hz, 2H), 2.72 (t, J=5.6 Hz, 2H), 2.54 (br.s., 2H), 2.33-2.37 (m, 4H), 2.18 (s, 3H).

6-methyl-4-{2-[4-(2-(4-methylpiperazin-1-yl) ethoxy)phenyl]quinolin-6-yl}-1-tosyl-1H-pyrrolo[2, 3-c]pyridin-7(6H)-one (6)

A solution of 5 (0.130 g, 0.28 mmol8) in 1,4-dioxane (4.0 mL), $H_2O$ (1.0 mL) were charged with Intermediate-5 (0.120 g, 0.28 mmol), $K_2CO_3$ (0.075 g, 0.56 mmol) at room temperature and degassed it with argon for 5 min. $Pd(PPh_3)_4$ (0.031 g, 0.02 mmol) was added to the reaction mixture and allowed to stir at 85° C. for 3 h. After completion of the reaction, reaction mixture was diluted with water (10 mL) and extracted with EtOAc (3×20 mL). Combined organic layers were dried over anhydrous $Na_2SO_4$ and concentrated under reduced pressure. The crude product was purified by combiflash chromatography ($CH_2Cl_2$:$CH_3OH$=96:4) to afford 6 (0.085 g, 43%) as an off-white solid.

$^1$H NMR (400 MHz, DMSO-$d_6$) δ ppm 8.40 (d, J=8.4 Hz, 1H), 8.14 (d, J=8.8 Hz, 2H), 8.08-8.11 (m, 4H), 7.99 (d, J=8.4 Hz, 1H), 7.90 (dd, J=2.0, 8.8 Hz, 1H), 7.79 (s, 1H), 7.44 (d, J=8.4 Hz, 2H), 7.12 (d, J=8.8 Hz, 2H), 6.87 (d, J=3.6 Hz, 1H), 4.17 (t, J=5.6 Hz, 2H), 3.51 (s, 3H), 2.74 (t, J=5.6 Hz, 2H), 2.39 (s, 3H), 2.20 (s, 3H), 1.23 (s, 6H).

6-methyl-4-{2-[4-(2-(4-methylpiperazin-1-yl) ethoxy)phenyl]quinolin-6-yl}-1-tosyl-1H-pyrrolo[2, 3-c]pyridin-7(6H)-one (SLU-2288)

A solution of 6 (0.085 g, 0.13 mmol3) in MeOH (3.0 mL), $H_2O$ (1.0 mL), THF (2.0 mL) was charged with KOH (0.037 g, 0.66 mmol) at 0° C. The reaction mixture was stirred for 2 h at room temperature, evaporated, diluted with water (10 mL) and extracted with $CH_2Cl_2$ (3×20 mL). Combined organic layers were dried over anhydrous $Na_2SO_4$, concentrated under reduced pressure and crude product was purified by reverse phase chromatography (ACN:$H_2O$=95:5) to afford SLU-2288 (0.36 g, 56%) as an off-white solid.

$^1$H NMR (400 MHz, DMSO-$d_6$) δ ppm 12.21 (s, 1H), 8.46 (d, J=8.8 Hz, 1H), 8.26 (d, J=8.8 Hz, 2H), 8.08-8.17 (m, 3H), 8.00 (dd, J=2.0, 8.8 Hz, 1H), 7.59 (s, 1H), 7.41 (d, J=2.8, 1H), 7.12 (d, J=9.2 Hz, 2H), 6.62 (d, J=2.8 Hz, 1H), 4.17 (t, J=5.6 Hz, 2H), 3.63 (s, 3H), 2.73 (t, J=6.0 Hz, 2H), 2.52 (m, 4H), 2.32-2.33 (m, 4H), 2.15 (s, 3H);

ESI-MS m/z $[C_{30}H_{31}N_5O_2+H]^+$ 494.3.

HPLC (Method A) 99.6% (AUC), $t_R$=5.97 min.

Synthesis of (R)-4-{6-[4-(2-(2,4-dimethyl-3-oxopiperazin-1-yl)ethoxy)phenyl]quinolin-2-yl}-6-methyl-1H-pyrrolo[2,3-c]pyridin-7(6H)-one (SLU-2112)
Scheme 68
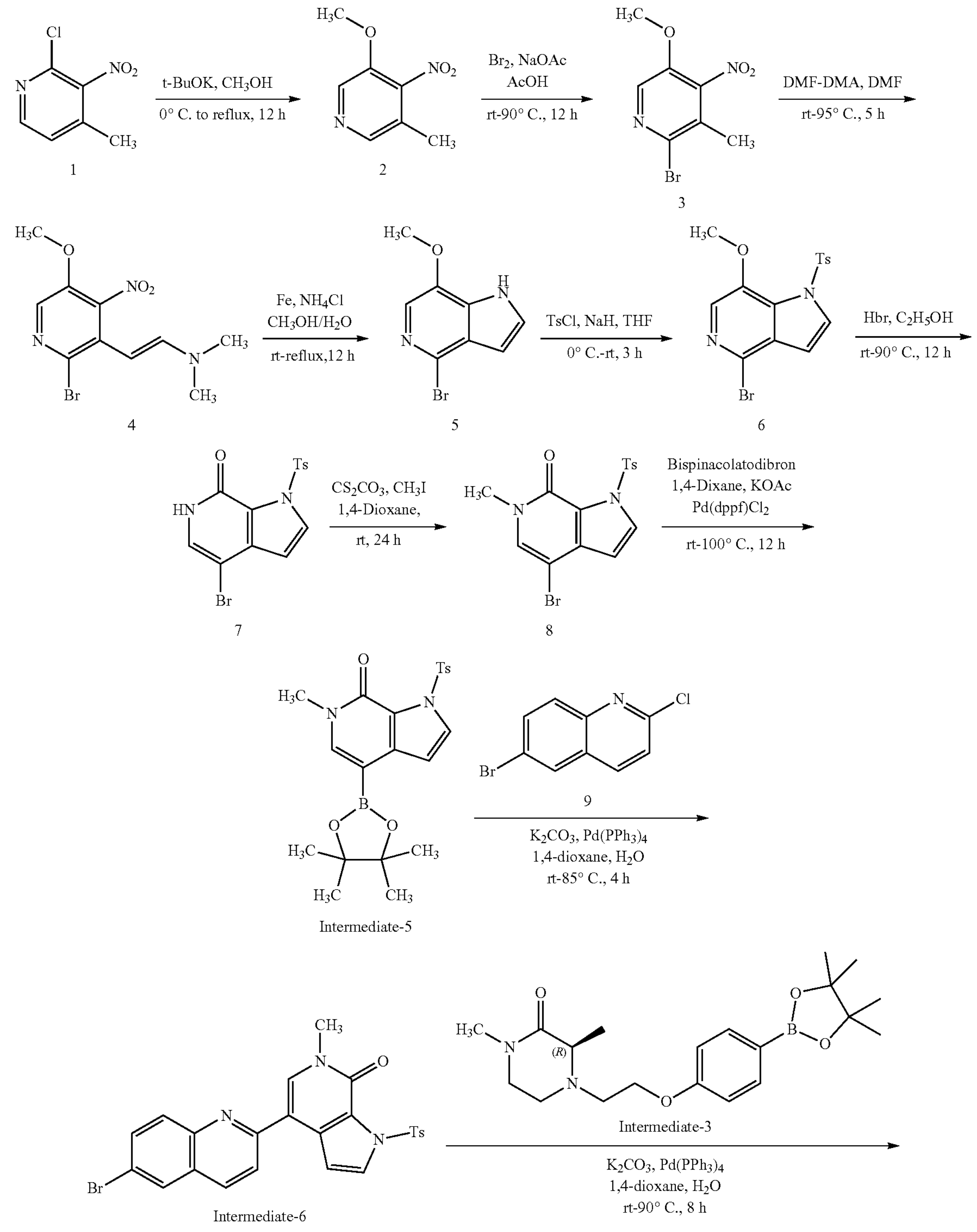

-continued

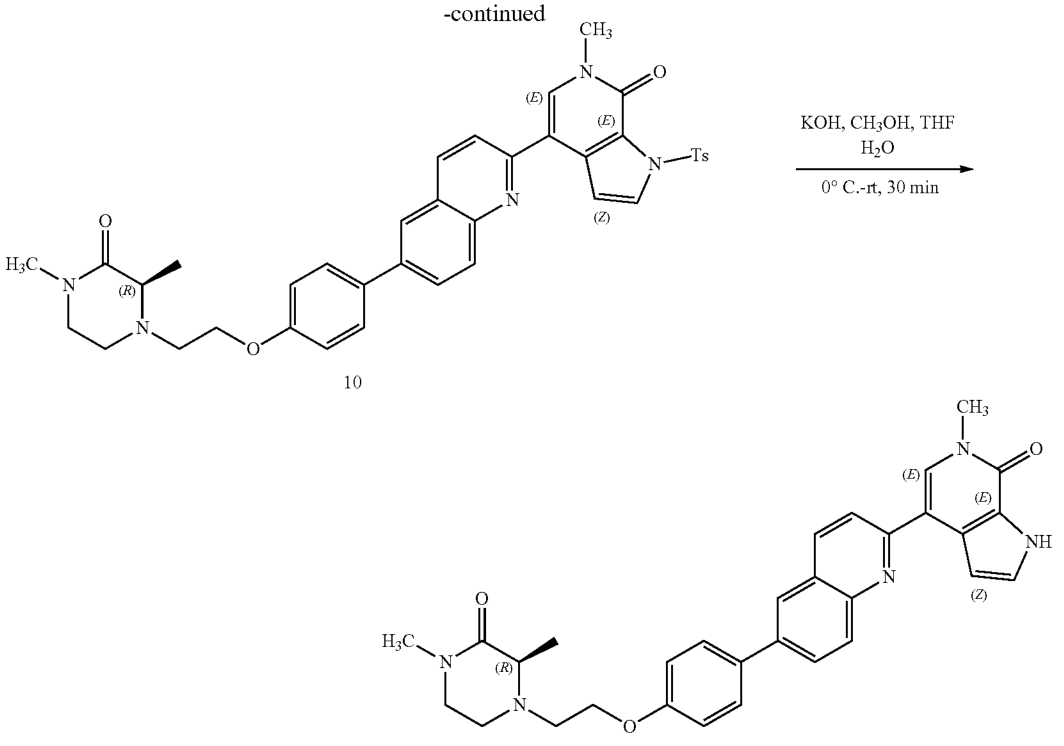

10

SLU-2112

2-methoxy-4-methyl-3-nitropyridine (2)

To a stirred solution of 2-chloro-4-methyl-3-nitropyridine (1, 25.0 g, 145.30 mmol) in methanol (300 mL) at 0° C. t-BuOK (32.5 g, 290.60 mmol) was charged portionwise and heated slowly to reflux for 12 h. The reaction mixture was concentrated under reduced pressure to a volume of (250 mL) and quenched by addition of $H_2O$ (200 mL). The resulting solid was collected by filtration, washed with water and dried under pressure to afford 2 (24.0 g, 48.0%) as a brown solid.

$^1H$ NMR (400 MHz, DMSO-$d_6$): δ 8.25 (d, J=5.2 Hz, 1H), 7.13 (d, J=5.2 Hz, 1H), 3.96 (s, 3H), 2.30 (s, 3H).

5-bromo-2-methoxy-4-methyl-3-nitropyridine (3)

Sodium acetate (43.9 g, 535.60 mmol) was charged to a stirred solution of 2-methoxy-4-methyl-3-nitropyridine (2, 24.0 g, 148.80 mmol) in acetic acid (200 mL) at ambient temperature. $Br_2$ (61.5 g, 386.90 mmol) was added dropwise for 30 min. Upon addition, the reaction mixture was heated at 90° C. for 12 h. TLC indicated at which time the reaction gone to completion, the reaction mixture was cooled to 0° C. and quenched by sequential addition of saturated aqueous sodium sulphite (10%, 300 mL). The resulting solid was collected by filtration, washed with water and dried under reduced pressure to afford 3 (29.0 g, 82%) as a light yellow solid.

$^1H$ NMR (400 MHz, DMSO-$d_6$): δ ppm 8.57 (s, 1H), 3.97 (s, 3H), 2.32 (s, 3H).

(E)-2-(5-bromo-2-methoxy-3-nitropyridin-4-yl)-N, N-dimethylethenamine (4)

DMF-DMA (300 mL) was charged to a solution of 5-bromo 2-methoxy-4-methyl-3-nitro pyridine (3, 58.0 g, 236.70 mmol) in DMF (500 mL) at room temperature. Upon addition, the reaction mixture was heated at 95° C. for 5 h. The reaction mixture was cooled to room temperature and poured into ice cold water (1.0 L). The resulting red solid was collected by filtration, washed with water and dried under reduced pressure to afford 4 (60.0 g, 84.0%) as a red solid.

$^1H$ NMR (400 MHz, DMSO-$d_6$): δ ppm 8.24 (s, 1H), 7.04 (d, J=13.6 Hz, 1H), 4.80 (d, J=13.6 Hz, 1H), 3.88 (s, 3H), 2.90 (s, 6H).

4-bromo-7-methoxy-1H-pyrrolo[2,3-c]pyridine (5)

A mixture of 4 (20.0 g, 66.20 mmol3), Fe (20.0 g, 357.60 mmol) and $NH_4Cl$ (20.0 g, 377.60 mmol) in $CH_3OH/H_2O$ (400/100 mL) was charged at room tyemperature and refluxed for 12 h. TLC indicated at which time the reaction gone to completion, the reaction mixture was filtered while hot and the cake was washed with methanol (3×300 mL). The combined filtrates were concentrated under reduced pressure and the resulting residue was triturated with acetonitrile to afford 5 (20.0 g, 90.0%) as a light brown solid.

$^1H$ NMR (400 MHz, DMSO-$d_6$): δ ppm δ 12.1 (br.s., 1H), 7.75 (s, 1H), 7.55 (t, J=2.8 Hz, 1H), 6.43 (t, J=2.4 Hz, 1H), 4.01 (s, 3H).

4-bromo-7-methoxy-1-tosyl-1H-pyrrolo[2,3-c]pyridine (6)

A solution of 5 (17.0 g, 74.50 mmol4) in tetrahydrofuran (300 mL), sodium hydride (60%, 5.3 g, 223.60 mmol) was charged portionwise at 0° C. Upon addition, the reaction mixture was stirred at room temperature and again cooled to 0° C. Tosyl chloride (21.2 g, 111.80 mmol) in THF (200 mL) was added dropwise and the resulting mixture was stirred at ambient temperature for 3 h. The reaction was quenched with saturated aqueous $NH_4Cl$ (500 mL) and extracted with EtOAc (3×200 mL). The combined organic layers were dried over $Na_2SO_4$, concentrated under reduced pressure and the residue was triturated with acetonitrile to afford 6 (25.0 g, 87%) as a brown solid.

$^1$H NMR (400 MHz, $CDCl_3$): δ ppm 7.97 (d, J=3.6 Hz, 1H), 7.89 (s, 1H), 7.77 (d, J=8.4 Hz, 2H), 7.29 (d, J=8.0 Hz, 2H), 6.68 (d, J=3.6 Hz, 1H), 3.88 (s, 3H), 2.40 (s, 3H).

4-bromo-1-tosyl-1H-pyrrolo[2,3-c]pyridin-7(6H)-one (7)

Hydrogen bromide (40% aqueous, 500 mL) was charged to a solution of 6 (50.0 g, 131.90 mmol3) in ethanol (100 mL) at room temperature. Upon addition, the reaction mixture was heated at 90° C. for 12 h. TLC indicated at which time the reaction had gone to completion. The reaction mixture was cooled to 0° C. and the resulting white solid was collected by filtration. The resulting mixture was washed with water and dried under vacuum to afford 7 (45.0 g, 93%) as an off-white solid.

$^1$H NMR (400 MHz, DMSO-$d_6$): δ ppm δ 11.5 (br.s., 1H), 8.03 (d, J=3.4 Hz, 1H), 7.93 (d, J=8.4 Hz, 2H), 7.41 (d, J=8.0 Hz, 2H), 7.36 (d, J=4.48 Hz, 1H), 6.59 (d, J=3.4 Hz, 1H), 2.37 (s, 3H).

4-bromo-6-methyl-1-tosyl-1H-pyrrolo[2,3-c]pyridin-7(6H)-one (8)

Methyl iodide (29.5 g, 207.8 mmol) was charged dropwise to stirred suspension of 7 (20.0 g, 54.70 mmol6) and cesium carbonate (53.3 g, 164.10 mmol) in 1,4-dioxane (300 mL) at room temperature. Upon addition, the reaction mixture was stirred at room temperature for 24 h. The solvent was evaporated under reduced pressure from the reaction mixture, diluted with $H_2O$ (200 mL) and extracted with EtOAc (5×150 mL). The combined organic layers dried over anhydrous $Na_2SO_4$ and concentrated under reduced pressure to afford 8 (20.0 g, 96%) as an off-white solid.

$^1$H NMR (400 MHz, $CDCl_3$): δ ppm δ 8.03 (d, J=8.3 Hz, 2H), 7.93 (d, J=3.4 Hz, 1H), 7.30 (d, J=8.3 Hz, 2H), 7.17 (s, 1H), 6.50 (d, J=3.4 Hz, 1H), 3.49 (s, 3H), 2.40 (s, 3H).

6-methyl-4-(4,4,5,5-tetramethyl-1,3,2-dioxaborolan-2-yl)-1-tosyl-1H-pyrrolo[2,3-c]pyridin-7(6H-one (Intermediate-5)

A mixture of 8 (12.0 g,31.6 mmol) and bis(pinacolato) diboron (9.60 g,37.9 mmol) in 1,4-dioxane (200 mL) was charged with potassium acetate (4.64 g, 47.4 mmol) at room temperature and degassed it with argon for 10 min. Pd(dppf)$Cl_2$ (1.15 g, 1.58 mmol) was added to the reaction mixture and heated at 100° C. for 12 h. Upon cooled, the reaction mixture was diluted with $H_2O$ (150 mL) and extracted with EtOAc (3×100 mL). Combined organic layers were dried over sodium sulphate and concentrated under reduced pressure. The crude product was purified by combi flash chromatography (Hexanes:EtOAc=1:1) to afford Intermediate-5 (6.00 g, 32%) as a yellow semi-solid.

$^1$H NMR (400 MHz, $CDCl_3$): δ ppm 7.96 (d, J=8.4 Hz, 2H), 7.88 (d, J=3.4 Hz, 1H), 7.51 (s, 1H), 7.32 (d, J=3.1 Hz, 2H), 6.69 (d, J=3.4 Hz, 1H), 3.52 (s, 3H), 2.38 (s, 3H), 1.32 (s, 12H).

4-(6-bromoquinolin-2-yl)-6-methyl-1-tosyl-1H-pyrrolo[2,3-c]pyridin-7(6H)-one (Intermediate-6)

To a stirred mixture of Intermediate-5 (0.75 g, 1.75 mmol) and 6-bromo-2-chloroquinoline (9, 0.42 g, 1.75 mmol) in 4:1 mixture of 1,4-dioxane, $H_2O$ (24 mL), $K_2CO_3$ (0.48 g, 3.50 mmol) was charged at room temperature. The solution was purged with argon for 10 min followed by addition of $Pd(PPh_3)_4$ (0.20 g, 0.17 mmol) and reaction mixture was heated at 85° C. for 4 h. The solvent was evaporated under reduced pressure and crude product was purified by combi flash chromatography ($CH_2Cl_2$:$CH_3OH$=97:3) to afford Intermediate-6 (0.45 g, 50%) as an off-white solid.

$^1$H NMR (400 MHz, DMSO-$d_6$): δ ppm 8.39 (d, J=2.0 Hz, 1H), 8.36 (s, 1H), 8.25 (d, J=2.0 Hz, 1H), 8.09 (d, J=3.2 Hz, 1H), 7.95-8.06 (m, 4H), 7.88 (dd, J=2.4, 9.2 Hz, 1H), 7.72 (d, J=3.2 Hz, 1H), 7.43 (d, J=8.0 Hz, 2H), 3.92 (s, 3H), 2.38 (s, 3H).

ESI-MS m/z $[C_{24}H_{18}BrN_3O_3S+H]^+$ 510.2

(R)-4-{6-[4-(2-(2,4-dimethyl-3-oxopiperazin-1-yl) ethoxy)phenyl]quinolin-2-yl}-6-methyl-1-tosyl-1H-pyrrolo[2,3-c]pyridin-7(6H)-one (10)

To a stirred mixture of Intermediate-6 (0.45 g, 0.88 mmol) and Intermediate-3 (0.34 g, 0.97 mmol) in 4:1 mixture of 1,4-dioxane, $H_2O$ (36 mL), $K_2CO_3$ (0.24 g, 1.77 mmol) was charged at room temperature and purged with argon for 15 min. $Pd(PPh_3)_4$ (0.10 g, 8.88 mmol) was added to the reaction mixture at room temperature and allowed to stirred at 90° C. for 8 h. The reaction mixture was filtered through celite pad and the celite pad was washed with EtOAc (2×100 mL). The filtrate was concentrated under reduced pressure and crude residue was purified by combi flash chromatography ($CH_2Cl_2$:$CH_3OH$=95:5) to afford 10 (0.34 g, 57%) as a brown solid.

$^1$H NMR (400 MHz, DMSO-$d_6$): δ ppm 8.42 (d, J=9.2 Hz, 2H), 8.37 (s, 1H), 8.21 (s, 1H), 8.09-8.11 (m, 3H), 7.97 (d, J=8.0 Hz, 2H), 7.79 (d, J=8.8 Hz, 2H), 7.75 (d, 3.6 Hz, 1H), 7.44 (d, J=8.0 Hz, 2H), 7.10 (d, J=8.8 Hz, 2H), 4.16 (t, J=5.6 Hz, 2H), 3.55 (s, 3H), 3.23-3.27 (m, 2H), 3.15-3.20 (m, 1H), 3.05-3.13 (m, 1H), 2.95-3.02 (m, 1H), 2.82 (s, 3H), 2.67-2.75 (m, 2H), 2.39 (s, 3H), 1.26 (d, J=6.8 Hz, 3H).

ESI-MS m/z $[C_{38}H_{37}N_5O_5S+H]^+$ 676.4.

(R)-4-{6-[4-(2-(2,4-dimethyl-3-oxopiperazin-1-yl) ethoxy)phenyl]quinolin-2-yl}-6-methyl-1H-pyrrolo [2,3-c]pyridin-7(6H)-one (SLU-2112)

To a stirred solution 10 (0.44 g, 0.65 mmol) in 2:2:1 mixture of $CH_3OH$, THF, $H_2O$ (25 mL), KOH (0.18 g, 3.25 mmol) was charged at 0° C. and left to room temperature for 30 min. The reaction mixture was concentrated under reduced pressure and crude product was purified by combi flash chromatography ($CH_2Cl_2$:$CH_3OH$=93:7) to afford SLU-2112 (0.25 g, 73%) as an off-white solid.

$^1$H NMR (400 MHz, DMSO-$d_6$): δ ppm 12.16 (s, 1H), 8.39 (d, J=8.8 Hz, 1H), 8.19 (s, 2H), 8.05-8.08 (m, 3H), 7.79 (d, J=8.8 Hz, 2H), 7.41 (t, J=2.4 Hz, 1H), 7.34 (t, J=2.0 Hz, 1H), 7.09 (d, J=8.8 Hz, 2H), 4.15 (t, J=5.6 Hz, 2H), 3.68 (s, 3H), 3.26 (t, J=7.2 Hz, 2H), 3.18 (q, J=6.8 Hz, 1 H), 3.06-3.12 (m, 1H), 2.95-3.01 (m, 1H), 2.83-2.85 (m, 1H), 2.82 (s, 3H), 2.69-2.75 (m, 1H), 1.26 (d, J=6.8 Hz, 3H).

ESI-MS m/z $[C_{31}H_{31}N_5O_3+H]^+$ 522.4.

HPLC (Method A) 95.9% (AUC), $t_R$=6.09 min.

Synthesis of (R)-4-{2-[4-(2-(2,4-dimethyl-3-oxopiperazin-1-yl)ethoxy)phenyl]quinolin-6-yl}-6-methyl-1H-pyrrolo[2,3-c]pyridin-7(6H)-one (SLU-2106)
Scheme 69
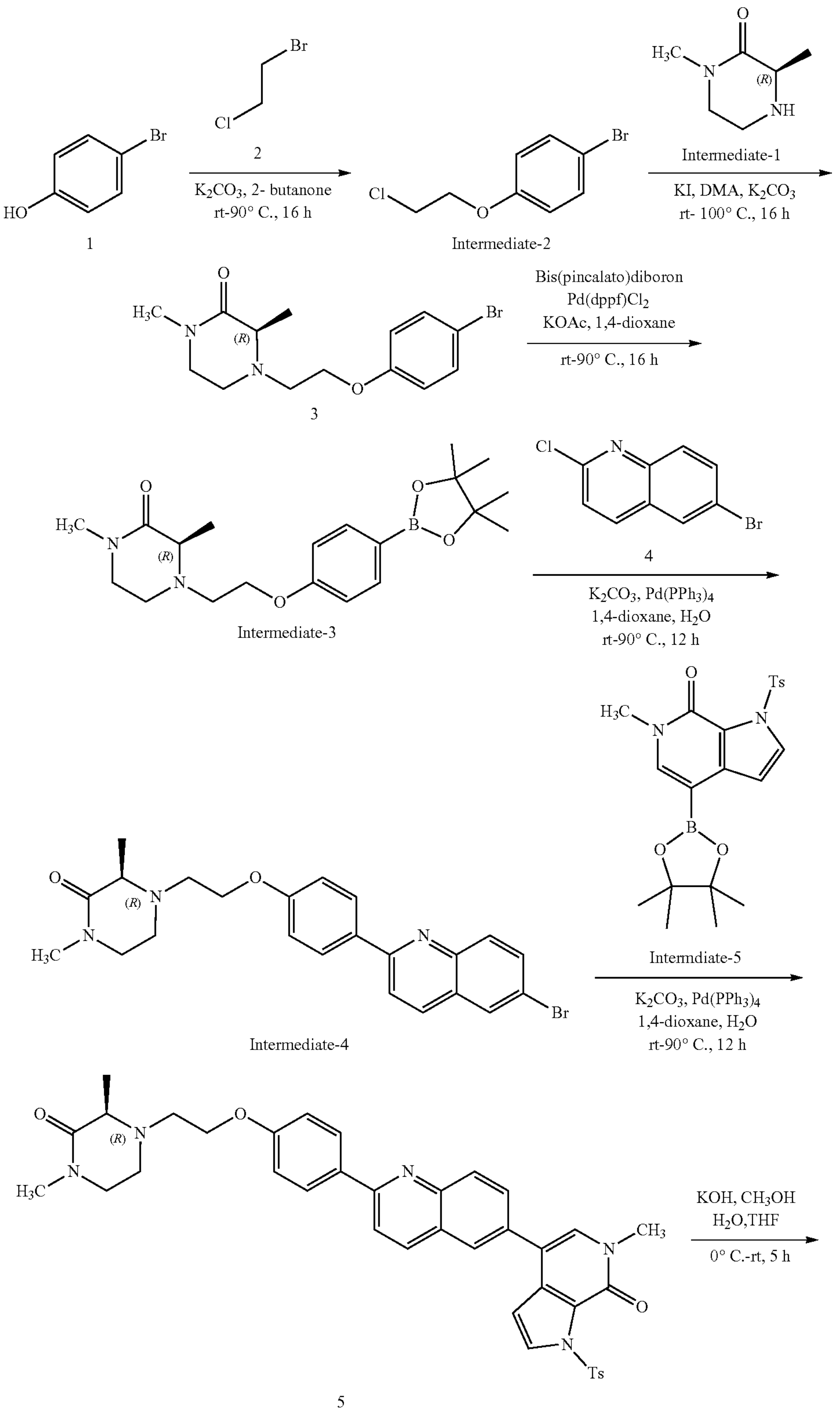

-continued

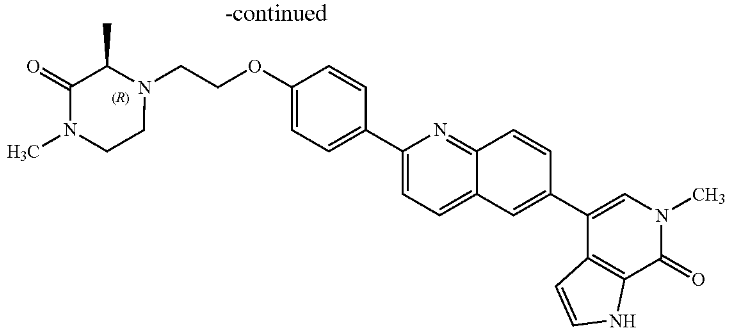

SLU-2106

1-bromo-4-(2-chloroethoxy)benzene (Intermediate-2)

To a stirred solution of 4-bromo phenol (1, 4.00 g, 23.1 mmol) in 2-butanone (40 mL), $K_2CO_3$ (6.3 g, 46.2 mmol) was charged at room temperature, followed by the addition of 1-bromo-2-chloroethane (2, 20 mL, 5.0 vol) at room temperature. The reaction mixture was heated at 90° C. for 16 h. The reaction mixture was allowed to ambient temperature and diluted with water EtOAc (100 mL), extracted with EtOAc (3×50 mL) and followed by brine (1×100 mL). Organic layer was dried over anhydrous $Na_2SO_4$ and concentrated under reduced pressure to afford Intermediate-2 (4.50 g, 84%) as a white solid.

$^1$H NMR (400 MHz, $CDCl_3$): δ ppm 7.38 (d, J=8.9 Hz, 2H), 6.80 (d, J=9.0 Hz, 2H), 4.19 (t, J=5.6 Hz, 2H), 3.80 (t, J=6.0 Hz, 2H).

(R)-4-[2-(4-bromophenoxy)ethyl]-1,3-dimethylpiperazin-2-one (3)

To a stirred solution of Intermediate-2 (4.50 g, 19.23 mmol,), Intermediate-1 (2.46 g, 19.23 mmol), KI (1.59 g, 9.6 mmol) and $K_2CO_3$ (6.3 g, 46.2 mmol) in dimethylacetamide (50 mL) at room temperature was heated at 100° C. for 16 h. TLC indicated at which time the reaction gone to completion. The mixture was diluted with water (100 mL) and extracted with EtOAc (3×150 mL), combined organic layers were dried over anhydrous $Na_2SO_4$ and concentrated under reduced pressure. The crude product was purified by combi flash chromatography (EtOAc:Hexanes=80:20) to afford 3 (3.0 g, 48%) as an off-white solid.

$^1$H NMR (400 MHz, $CDCl_3$): δ ppm 7.37 (d, J=9.0 Hz, 2H), 6.77 (d, J=8.7 Hz, 2H), 4.06-4.11 (m, 2H), 3.33-3.39 (m, 1H), 3.24-3.31 (m, 2H), 3.10-3.18 (m, 1H), 2.97-3.06 (s, 4H), 2.82-2.89 (m, 1H), 2.74-2.80 (m, 1H), 1.40 (d, J=6.8 Hz, 3H).

Preparation of (R)-1,3-dimethyl-4-{2-[4-(4,4,5,5-tetramethyl-1,3,2-dioxaborolan-2-yl)phenoxy]ethyl}piperazin-2-one (Intermediate-3)

To a stirred solution of compound 3 (3.00 g, 9.1 mmol), bis(pincolato)diboron (2.70 g, 10.9 mmol), $Pd(dppf)Cl_2$ (0.66 g, 0.91 mmol), KOAc (1.7 g, 18.2 mmol) in dioxane (50 mL) at room temperature and was heated at 90° C. for 16 h. TLC indicated at which time the reaction had gone to completion. The reaction mixture was diluted with water (50 mL) and extracted with EtOAc (3×40 mL). Combined organic layers were dried over anhydrous $Na_2SO_4$ and concentrated under reduced pressure. The crude product was purified by combi flash chromatography ($CH_2Cl_2$:$CH_3OH$=97:3) to afford Intermediate-3 (2.70 g, 73%) as a gummy solid.

$^1$H NMR (400 MHz, $CDCl_3$): δ ppm 7.74 (d, J=8.5 Hz, 2H), 6.88 (d, J=8.5 Hz, 2H), 4.07-4.16 (m, 2H), 3.33-3.39 (m, 1H), 3.23-3.31 (m, 2H), 3.13-3.17 (m, 1H), 3.01-3.07 (m, 1H), 2.94 (s, 3H), 2.84-2.90 (m, 1H), 2.75-2.81 (m, 1H), 1.41 (s, 3H), 1.33 (s, 12H).

(R)-4-{2-[4-(6-chloroquinolin-2-yl)phenoxy]ethyl}-1,3-dimethylpiperazin-2-one (Intermediate-4)

To a stirred solution of Intermediate-3 (1.5 g, 4.0 mmol) in 1,4-dioxane (35 mL), $H_2O$ (15 mL) were charged with 6-bromo-2-chloroquinoline (4, 0.966 g, 4.0 mmol), potassium carbonate (1.1 g, 8.0 mmol) at room temperature and degassed it with argon for 5 min. $Pd(PPh_3)_4$ (0.462 g, 0.4 mmol) was added to the reaction mixture and heated at 90° C. for 12 h. The reaction mixture was diluted with water (20 mL) and extracted with EtOAc (2×30 mL). Combined organic layers were dried over anhydrous $Na_2SO_4$ and concentrated under reduced pressure to obtain the crude. The crude material was purified by combi flash chromatography ($CH_2Cl_2$:MeOH=95:5) to afford Intermediate-4 (1.20 g, 66%) as an off-white solid.

$^1$H NMR (400 MHz, $CDCl_3$): δ ppm 8.00-8.06 (m, 3H), 7.92 (d, J=8.9 Hz, 1H), 7.88 (d, J=2.1 Hz, 1H), 7.78 (d, J=8.6 Hz, 1H), 7.69 (dd, J=2.2, 8.9 Hz, 1H), 6.96 (d, J=8.8 Hz, 2H), 4.06-4.13 (m, 2H), 3.19-3.33 (m, 3H), 3.07-3.13 (m, 1H), 2.98-3.04 (m, 1H), 2.81-2.88 (m, 4H), 2.71-2.77 (m, 1H), 1.36 (d, J=6.8 Hz, 3H).

(R)-4-{2-[4-(2-(2,4-dimethyl-3-oxopiperazin-1-yl)ethoxy)phenyl]quinolin-6-yl}-6-methyl-1-tosyl-1H-pyrrolo[2,3-c]pyridin-7(6H)-one (5)

To a stirred solution of Intermediate-4 (1.00 g, 2.2 mmol) in 1,4-dioxane (20 mL), $H_2O$ (5.0 mL) were charged with intermediate-5 (0.940 g, 2.2 mmol8), $K_2CO_3$ (0.607 g, 4.4 mmol) at room temperature and degassed it with argon for 10 min. $Pd(PPh_3)_4$ (0.254 g, 0.22 mmol) was added to the reaction mixture and heated at 90° C. for 12 h. The reaction mixture was diluted with water (30 mL) and extracted with EtOAc (2×50 mL). Combined organic layers were dried over anhydrous $Na_2SO_4$ and concentrated under reduced pressure. The crude product was purified by combi flash chromatography ($CH_2Cl_2$:$CH_3OH$=95:5) to afford 5 (1.00 g, 58%) as an off-white solid. The crude material was used for next step without further purification.

$^1H$ NMR (400 MHz, $CDCl_3$): δ ppm 8.14-8.20 (m, 4H), 8.05 (d, J=8.4 Hz, 2H), 7.97 (d, J=3.4 Hz, 1H),), 7.88 (d, J=8.6 Hz, 1H), 7.83 (d, J=1.7 Hz, 1H), 7.78 (dd, J=1.9, 8.7 Hz, 1H), 7.33 (d, J=8.2 Hz, 1H), 7.20 (s, 1H), 7.05 (d, J=8.8 Hz, 2H), 6.65 (d, J=3.4 Hz, 2H), 4.16-4.23 (m, 2H), 3.62 (s, 3H), 3.27-3.44 (m, 3H), 3.16-3.21 (m, 1H), 3.06-3.12 (m, 1H), 2.89-2.96 (m, 4H), 2.79-2.85 (m, 1H), 1.43 (d, J=6.8 Hz, 3H).

(R)-4-{2-[4-(2-(2,4-dimethyl-3-oxopiperazin-1-yl) ethoxy)phenyl]quinolin-6-yl}-6-methyl-1H-pyrrolo [2,3-c]pyridin-7(6H)-one (SLU-2106)

To a stirred solution of 5 (1.00 g, 1.48 mmol) in MeOH (15 mL), $H_2O$ (5.0 mL), THF (5.0 mL) were charged with potassium hydroxide (0.400 g, 7.4 mmol) at 0° C. The reaction mixture was stirred for 5 h at room temperature, evaporated, diluted with water (50 mL) and extracted with $CH_2Cl_2$ (3×40 mL). Combined organic layers were dried over anhydrous $Na_2SO_4$ and concentrated under reduced pressure. The crude product was triturated with (20 mL) acetonitrile, stirred, filtered and dried under vacuum to afford SLU-2106 (0.500 g, 64%) as an off-white solid.

ESI-MS m/z $[C_{31}H_{31}N_5O_3+H]^+$ 522.1.

HPLC (Method B) 96.2% (AUC), $t_R$=6.09 min.

$^1H$ NMR (300 MHz, DMSO-$d_6$): δ ppm 12.22 (br.s., 1H), 8.46 (d, J=8.7 Hz, 1H), 8.26 (d, J=8.7 Hz, 2H), 8.08-8.17 (m, 3H), 8.03 (d, J=10.5 Hz, 1H), 7.60 (s, 1H), 7.41 (t, J=2.4 Hz, 1H), 7.12 (d, J=9.0 Hz, 2H), 6.62 (s, 1H), 4.18 (t, J=5.4 Hz, 2H), 3.63 (s, 3H), 3.26 (t, J=6.0 Hz, 2H), 3.12-3.21 (m, 1H), 2.95-3.09 (m, 2H), 2.79-2.87 (m, 4H), 2.68-2.76 (m, 1H), 1.26 (d, J=6.9 Hz, 3H).

Synthesis of (R)-4-{6-[4-(4-(2-(2,4-dimethyl-3-oxopiperazin-1-yl)ethoxy)phenyl)piperidin-1-yl] pyridin-3-yl}-6-methyl-1H-pyrrolo[2,3-c]pyridin-7 (6H)-one (SLU-2089)

Scheme 70

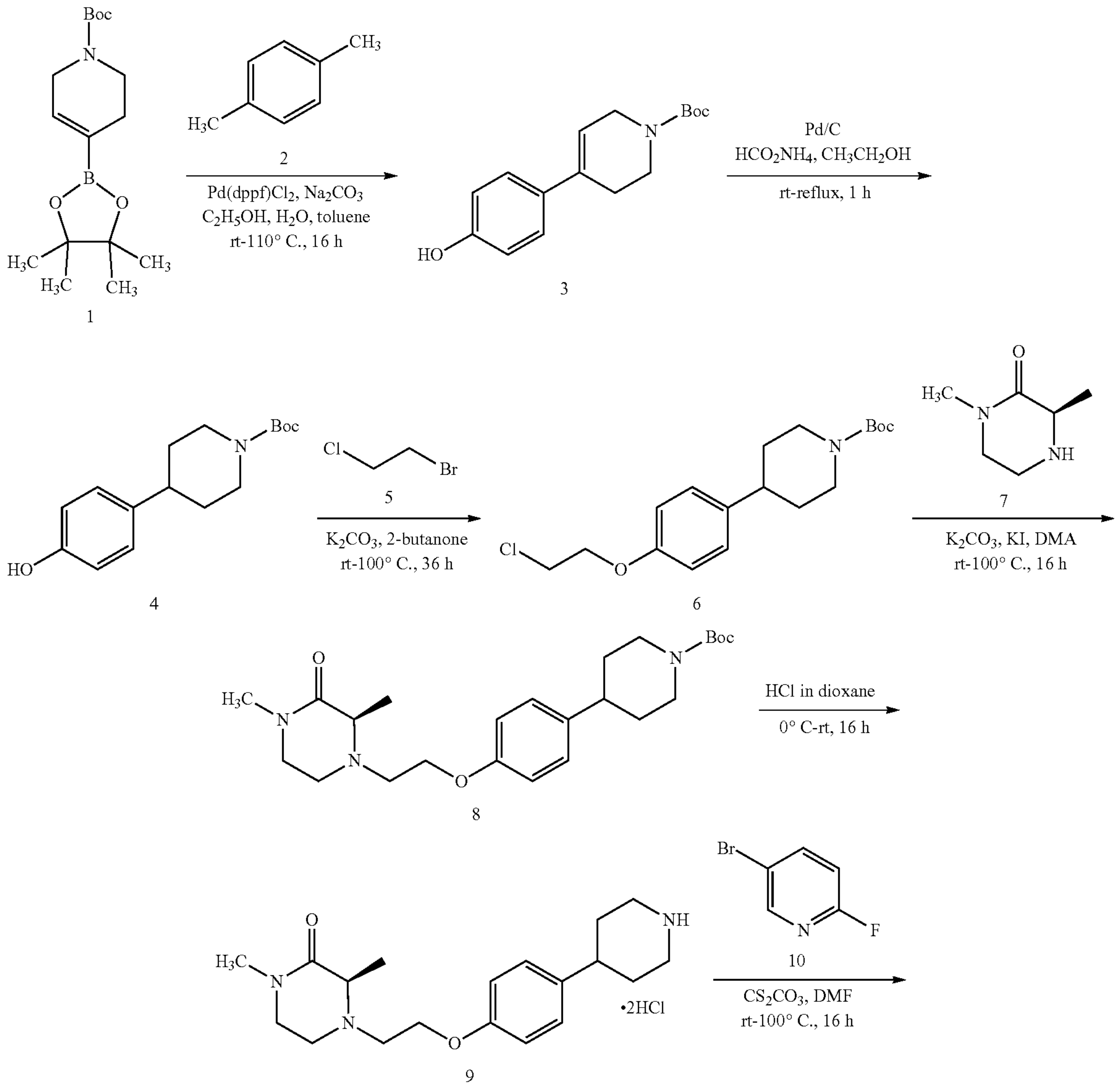

-continued

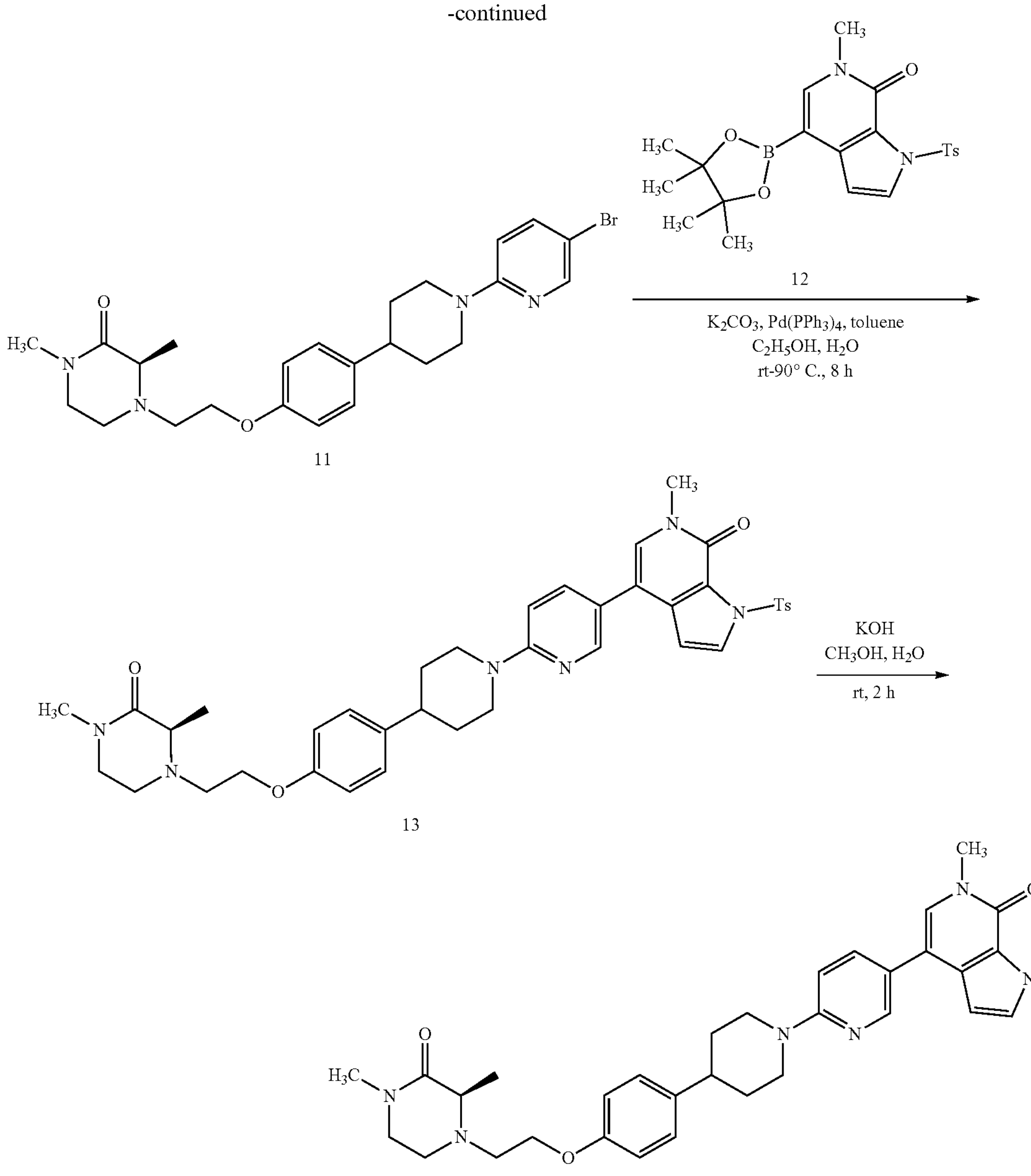

11

13

SLU-2089 tert-butyl 4-(4-hydroxyphenyl)-5,6-dihydropyridine-1(2H)-carboxylate (3)

A solution of tert-butyl 4-(4,4,5,5-tetramethyl-1,3,2-dioxaborolan-2-yl)-5,6-dihydropyridine-1(2H)-carboxylate (1, 40.0 g, 128.0 mmol), 4-bromo phenol (2, 22.0 g, 128.0 mmol), $Na_2CO_3$ (41.0 g, 388.0 mmol) in ethanol (200 mL), toluene (200 mL), water (200 mL) were charged at room temperature and was degassed with argon for 5 min. $Pd(dppf)Cl_2$ (9.4 g, 12.8 mmol) was added at room temperature. The reaction mixture was heated at 110° C. for 16 h, diluted with water (800 mL) and extracted with EtOAc (3×800 mL). Combined organic layers were dried over anhydrous $Na_2SO_4$, concentrated under reduced pressure and purified by combi flash chromatography (Hexanes: EtOAc=70:30) to afford 3 (22.01 g, 60%).as an off-white solid.

ESI-MS m/z $[C_{16}H_{21}NO_3+H]^+$ 176.0 (minus Boc)

tert-butyl 4-(4-hydroxyphenyl)piperidine-1-carboxylate (4)

A solution of tert-butyl 4-(4-hydroxyphenyl)-5,6-dihydropyridine-1(2H)-carboxylate (3, 21.0 g, 75.5 mmol), Pd/C (4.50 g) and $HCOONH_4$ (47.4 g, 753.0 mmol) in ethanol (450 mL) were charged at room temperature and refluxed to 1 h. The reaction mixture was filtered through celite bed, washed with ethanol (2×150 mL) and concentrated. The resulting mixture was diluted with water (700 mL) and extracted with EtOAc (3×700 mL). Combined organic layers were dried over anhydrous $Na_2SO_4$ and concentrated under reduced pressure to afford 4 (14.0 g, 73%) as an off-white solid.

ESI-MS m/z $[C_{16}H_{23}NO_3+H]^+$ 178.1 (minus Boc)

tert-butyl 4-[4-(2-chloroethoxy)phenyl]piperidine-1-carboxylate (6)

To a stirred solution of 4 (14.0 g, 50.4 mmol), 1-bromo-2-chloroethane (5, 36.0 g, 252 mmol) and $K_2CO_3$ (20.8 g, 151.2 mmol) in 2-butanone (140 mL) at room temperature and was stirred at 100° C. for 36 h. TLC indicated at which time the reaction had gone to completion. The reaction mixture was diluted with water (400 mL) and extracted with EtOAc (3×250 mL). Combined organic layers were dried over anhydrous $Na_2SO_4$ and concentrated under reduced pressure. The crude product was purified by combi flash chromatography (Hexanes:EtOAc=85:15) to afford 6 (8.60 g, 51%) as an off-white solid.

ESI-MS m/z $[C_{18}H_{26}ClNO_3+H]^+$ 240.1 (minus Boc)

(R)-tert-butyl 4-{4-[2-(2,4-dimethyl-3-oxopiperazin-1-yl)ethoxy]phenyl}piperidine-1-carboxylate (8)

To a stirred solution of 6 (8.00 g, 23.4 mmol), Intermediate-1 (3.70 g, 29.0 mmol) in DMA (80 mL), KI (1.96 g, 11.6 mmol) and $K_2CO_3$ (9.6 g, 70.6 mmol) was charged at room temperature and stirred for 100° C. for 16 h. TLC indicated at which time the reaction had gone to completion. The reaction mixture was diluted with water (400 mL) and extracted with EtOAc (3×350 mL). Combined organic layers were dried over anhydrous $Na_2SO_4$ and concentrated under reduced pressure. The crude product was purified by combi flash chromatography ($CH_2Cl_2$:$CH_3OH$=97:3) to afford 7 (4.10 g, 41%) as colourless liquid.

HCl Salt of (R)-1,3-dimethyl-4-{2-[4-(piperidin-4-yl)phenoxy]ethyl}piperazin-2-one (9)

To a stirred solution of 7 (4.10 g, 9.5 mmol) in dioxane and HCl in dioxane (20 mL) were charged at 0° C. and stirred for 16 h at room temperature. TLC indicated at which time the reaction had gone to completion. The reaction mixture was concentrated to afford 8 (3.50 g) as a gummy solid. The crude was used for next step.

$^1H$ NMR (400 MHz, DMSO-$d_6$): δ ppm 7.11 (d, J=8.4 Hz, 2H), 6.84 (d, J=7.8 Hz, 2H), 4.03 (t, J=5.7 Hz, 1H), 3.93 (t, J=5.1 Hz, 1H), 3.68 (t, J=4.8 Hz, 1H), 3.23 (t, J=5.4 Hz, 1H), 3.02-3.10 (m, 4H), 2.96-3.02 (m, 2H) 2.70 (s, 3H), 2.65-2.73 (m, 1H), 2.53-2.57 (m, 3H) 1.63 (d, J=11.7 Hz, 2H), 1.41-1.46 (m, 2H), 1.23 (d, J=6.6 Hz, 3H).

(R)-4-{2-[4-(1-(5-bromopyridin-2-yl)piperidin-4-yl)phenoxy]ethyl}-1,3-dimethylpiperazin-2-one (11)

To a stirred solution of 8 (2.80 g, 8.4 mmol) in DMF (25 mL) were charged with 5-bromo-2-chloropyridine (9, 1.48 g, 8.4 mmol) and $Cs_2CO_3$ (7.9 g, 25.2 mmol) at room temperature and heated at 100° C. for 16 h. TLC indicated at which time the reaction had gone to completion. The reaction mixture was diluted with water (150 mL) and extracted with EtOAc (3×200 mL). Combined organic layers were dried over anhydrous $Na_2SO_4$ and concentrated under reduced pressure. The crude product was purified by combi flash chromatography ($CH_2Cl_2$:$CH_3OH$=97:3) to afford 10 (1.28 g, 32%) as colourless liquid.

$^1H$ NMR (300 MHz, DMSO-$d_6$): δ ppm 8.15 (d, J=2.1 Hz, 1H), 7.65 (dd, J=2.4, 9.0 Hz, 1H), 7.14 (d, J=8.4 Hz, 2H), 6.84-6.87 (m, 3H), 4.38 (d, J=12.9 Hz, 2H), 4.03 (t, J=5.7 Hz, 2H), 3.22-3.25 (m, 2H), 3.10-3.17 (m, 2H), 3.02-3.07 (m, 1H), 2.87 (s, 1H) 2.82-2.84 (m, 1H), 2.78 (s, 3H), 2.70-2.77 (m, 1H), 2.66-2.69 (m, 2H), 1.79 (d, J=12.9 Hz, 2H), 1.52-1.60 (m, 2H), 1.23 (d, J=6.6 Hz, 3H).

(R)-4-{6-[4-(4-(2-(2,4-dimethyl-3-oxopiperazin-1-yl)ethoxy)phenyl)piperidin-1-yl]pyridin-3-yl}-6-methyl-1-tosyl-1H-pyrrolo[2,3-c]pyridin-7(6H)-one (13)

To a stirred solution of 10 (0.60 g, 1.23 mmol) in ethanol (5.0 mL), toluene (5.0 mL), $H_2O$ (2.0 mL) were charged with Intermediate-5 (0.58 g, 1.35 mmol8), $K_2CO_3$ (0.39 g, 3.69 mmol) at room temperature and degassed it with argon for 5 min. Pd(dppf)$Cl_2$ (0.088 g, 0.12 mmol) was added to the reaction mixture at room temperature and heated at 90° C. for 8 h. TLC indicated at which time the reaction had gone to completion. The reaction mixture was diluted with water (15 mL) and extracted with EtOAc (2×35 mL). Combined organic layers were dried over anhydrous $Na_2SO_4$ and concentrated under reduced pressure. The crude product was purified by combi flash chromatography ($CH_2Cl_2$:$CH_3OH$=95:5) to afford 11 (0.21 g, 24%) as an off-white solid.

$^1H$ NMR (400 MHz, DMSO-$d_6$): δ ppm 8.23 (d, J=2.4 Hz, 1H), 8.02 (d, J=3.6 Hz, 1H), 7.97 (d, J=8.4 Hz, 2H), 7.65 (dd, J=2.4, 8.8 Hz, 1H), 7.53 (s, 1H), 7.43 (d, J=8.4 Hz, 2H), 7.16 (d, J=8.4 Hz, 2H), 6.97 (d, J=9.2 Hz, 1H), 6.86 (d, J=8.4 Hz, 2H), 6.67 (d, J=3.2 Hz, 1H), 4.48 (d, J=13.2 Hz, 2H), 4.03 (t, J=5.6 Hz, 2H), 3.45 (s, 3H), 3.22-3.25 (m, 2H), 3.11-3.17 (m, 1H), 3.03-3.08 (m, 1H), 2.90-2.93 (m, 3H), 2.80 (s, 3H) 2.67-2.77 (m, 3H), 2.4 (s, 3H), 1.83 (d, J=11.6 Hz, 2H), 1.54-1.62 (m, 2H), 1.23 (d, J=6.8 Hz, 3H).

(R)-4-{6-[4-(4-(2-(2,4-dimethyl-3-oxopiperazin-1-yl)ethoxy)phenyl)piperidin-1-yl]pyridin-3-yl}-6-methyl-1H-pyrrolo[2,3-c]pyridin-7(6H)-one (SLU-2089)

To a stirred solution of 11 (0.210 g, 0.29 mmol) in $CH_3OH$ (5.0 mL), water (2.0 mL) was charged with potassium hydroxide (0.32 g, 8.8 mmol) were charged at room temperature and the stirred for 2 h at room temperature. The reaction mixture was evaporated, diluted with water (15.0 mL) and extracted with EtOAc (3×30 mL). Combined organic layers were dried over anhydrous $Na_2SO_4$ and concentrated under reduced pressure. The crude product was purified by reverse phase chromatography (2 times) (ACN: $H_2O$=80:20) to afford SLU-2089 (0.10 g, 25%) as a white solid.

ESI-MS m/z $[C_{32}H_{38}N_6O_3+H]^+$ 555.3.

HPLC (Method D) 98.9% (AUC), $t_R$=6.18 min.

$^1H$ NMR (400 MHz, DMSO-$d_6$): δ ppm 12.12 (s, 1H), 8.33 (d, J=2.0 Hz, 1H), 7.74 (dd, J=2.4, 8.8 Hz, 1H), 7.33 (t, J=2.8 Hz, 1H), 7.31 (s, 1H), 7.17 (d, J=8.4 Hz, 2H), 6.97 (d, J=8.8 Hz, 1H), 6.87 (d, J=8.8 Hz, 2H), 6.40 (t, J=2.0 Hz, 1H), 4.48 (d, J=12.4 Hz, 2H), 4.04 (t, J=5.6 Hz, 2 H), 3.56 (s, 3H), 3.24 (d, J=4.4 Hz, 2H), 3.13-3.17 (m, 1H), 3.03-3.07 (m, 1H), 2.90 (t, J=10.8 Hz, 3H) 2.80 (s, 3H), 2.69-2.77 (m, 2H), 1.83 (d, J=12.4 Hz, 2H), 1.56-1.64 (m, 2H), 1.37 (br.s., 1H), 1.23 (d, J=6.8 Hz, 3H).

Synthesis of (R)-6-(difluoromethyl)-4-{6-[4-(2-(2,4-dimethyl-3-oxopiperazin-1-yl)ethoxy)phenyl]quinolin-2-yl}-1H-pyrrolo[2,3-c]pyridin-7(6H)-one (SLU-2325)
Scheme 71
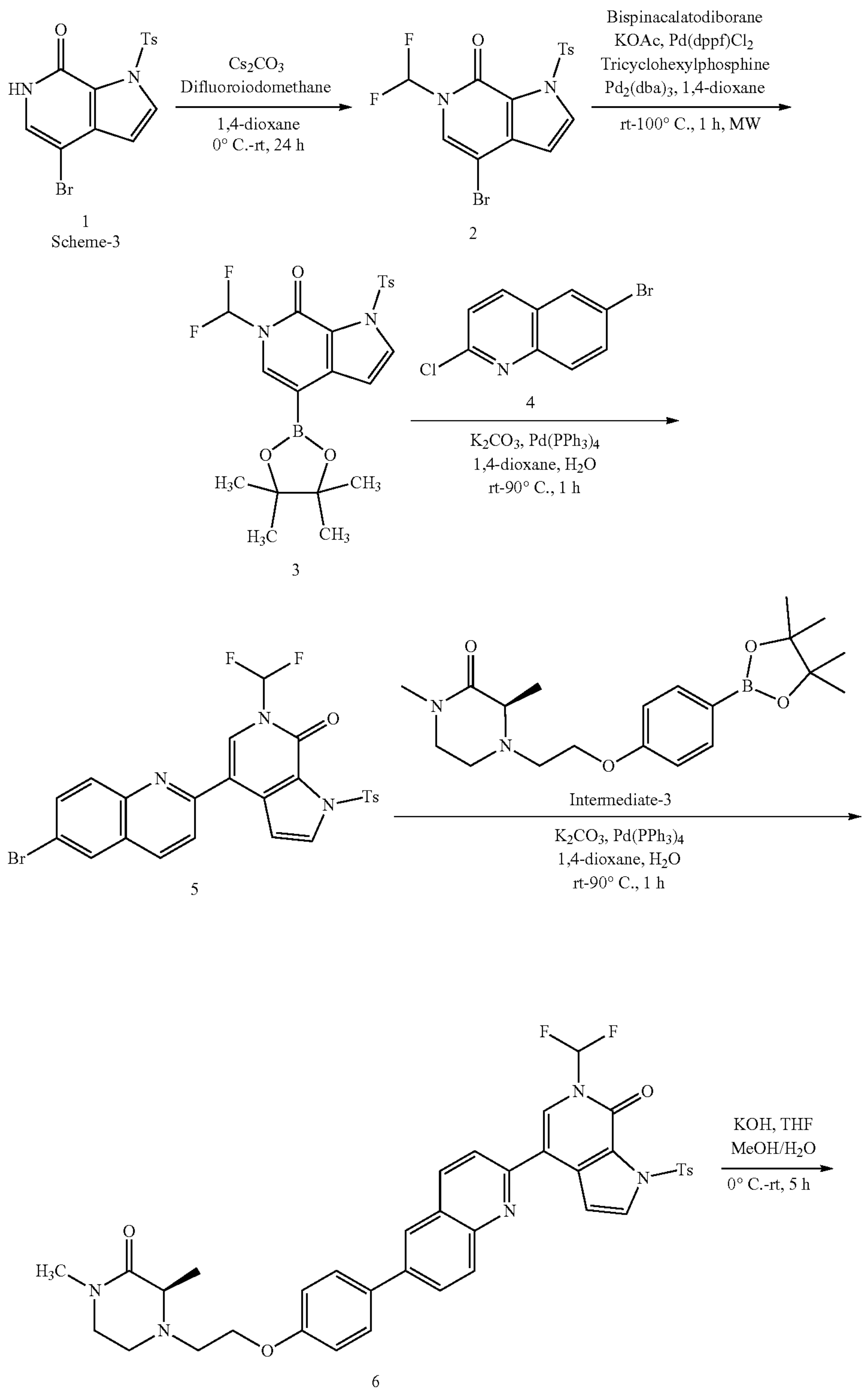

-continued

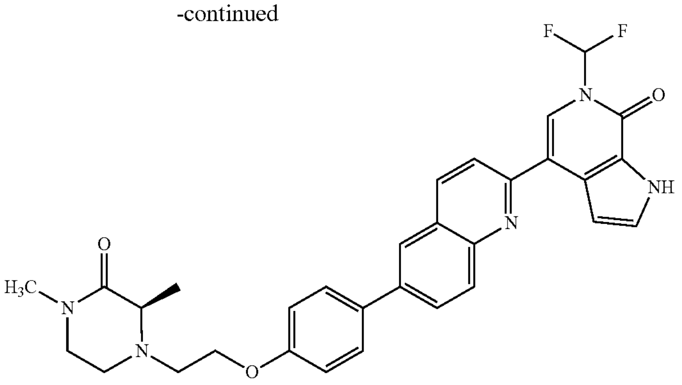

SLU-2325

NOTE: 1 was available in Scheme 3

4-bromo-6-(difluoromethyl)-1-tosyl-1H-pyrrolo[2,3-c]pyridin-7(6H)-one (2)

Difluoroiodomethane (≈3.62 g, 20.5 mmol) gas was passed to the stirred suspension of 1 (5.00 g, 13.6. mmol6) and cesium carbonate (13.2 g, 40.8 mmol) in 1,4-dioxane (50 mL) was charged at 0° C. in sealed tube. Upon addition, the reaction mixture was stirred at room temperature for 24 h. The solvent was evaporated under reduced pressure from the reaction mixture, diluted with $H_2O$ (30 mL) and extracted with EtOAc (3x30 mL). The combined organic layers dried over anhydrous $Na_2SO_4$ and concentrated under reduced pressure. The crude product was purified by combi flash chromatography (Hexanes:EtOAc=85:15) to afford 2 (2.00 g, 35%) as an off-white solid.

$^1$H NMR (400 MHz, $CDCl_3$): δ ppm δ 7.99-8.02 (m, 3H), 7.68 (t, J=59.9 Hz, 1H), 7.35 (d, J=8.3 Hz, 3H), 6.58 (d, J=3.4 Hz, 1H), 2.44 (s, 3H).

6-[(difluoromethyl)-4-(4,4,5,5-tetramethyl-1,3,2-dioxaborolan-2-yl)]-1-tosyl-1H-pyrrolo[2,3-c]pyridin-7(6H)-one (3)

A mixture of 2 (1.00 g, 2.4 mmol8) and bis(pinacolato) diboron (0.649 g, 2.6 mmol) in 1,4-dioxane (10 mL) was charged with potassium acetate (0.460 g, 4.8 mmol), tricyclohexylphosphine (0.134 g, 0.48 mmol) at room temperature and degassed it with argon for 10 min. $Pd_2(dba)_3$ (0.219 g, 0.24 mmol) was added to the reaction mixture at room temperature and heated at 100° C. for 1 h in microwave. Upon cooled, the reaction mixture was diluted with $H_2O$ (50 mL) and was extracted with EtOAc (3x50 mL). The combined organic layers were dried over sodium sulphate and concentrated under reduced pressure. The crude product was purified by combi flash chromatography (Hexanes: EtOAc=85:15) to afford 3 (0.350 g, 33% as an off-white solid.

$^1$H NMR (400 MHz, $CDCl_3$): δ ppm 7.93-7.95 (m, 3H), 7.55-7.86 (m, 2H), 7.30 (d, J=8.2, 2H), 7.95 (d, J=3.4 Hz, 1H), 2.40 (s, 3H), 1.33 (s, 12H).

4-[(6-bromoquinolin-2-yl)-6-(difluoromethyl)]-1-tosyl-1H-pyrrolo[2,3-c]pyridin-7(6H)-one (5)

To a stirred mixture of 3 (0.200 g, 0.43 mmol) and 6-bromo-2-chloroquinoline 4 (0.115 g, 0.47 mmol) in 4:1 mixture of 1,4-dioxane, $H_2O$ (20 mL), $K_2CO_3$ (0.118 g, 0.86 mmol) was charged at room temperature. The solution was purged with argon for 10 min followed by addition of $Pd(PPh_3)_4$ (0.049 g, 0.043 mmol) and reaction mixture was heated at 90° C. for 1 h. The reaction mixture diluted with water (20 mL) and extracted with EtOAc (2x30 mL). The combined organic layers were dried over anhydrous $Na_2SO_4$ and concentrated under reduced pressure. The crude product was purified by combi flash chromatography (Hexanes: EtOAc=80:20) to afford 5 (0.250 g, 80%) as an off-white solid.

$^1$H NMR (400 MHz, $CDCl_3$): ppm δ 8.15 (d, J=8.5, 1H), 8.08 (d, J=3.4, 1H), 7.99-8.02 (m, 4H), 7.65-7.36 (m, 3H), 7.27 (d, J=3.4 Hz, 1H), 2.43 (s, 3H).

(R)-6-(difluoromethyl)-4-{6-[4-(2-(2,4-dimethyl-3-oxopiperazin-1-yl)ethoxy)phenyl]quinolin-2-yl}-1-tosyl-1H-pyrrolo[2,3-c]pyridin-7(6H)-one (6)

To a stirred mixture of 5 (0.200 g, 0.36 mmol) and Intermediate-3 (0.137 g, 0.36 mmol in 4:1 mixture of 1,4-dioxane, $H_2O$ (20 mL), $K_2CO_3$ (0.099 g, 0.72 mmol) was charged at room temperature. The solution was purged with argon for 10 min followed by addition of $Pd(PPh_3)_4$ (0.041 g, 0.036 mmol) and reaction mixture was heated at 90° C. for 1 h. The reaction mixture diluted with water (20 mL) and extracted with EtOAc (2x30 mL). The combined organic layers were dried over anhydrous $Na_2SO_4$ and concentrated under reduced pressure. The crude material was purified by combi flash chromatography ($CH_2Cl_2$: MeOH=95:5) to afford 6 (0.150 g, 48%) as an off-white solid.

$^1$H NMR (400 MHz, $CDCl_3$): δ ppm 8.27 (d, J=8.4 Hz, 1H), 8.17 (d, J=8.8 Hz, 1H), 8.08 (d, J=3.2 Hz, 1H), 7.98-8.01 (m, 4H), 7.67-7.96 (m, 5H), 7.38 (d, J=3.6 Hz, 1H), 7.34 (d, J=8.0 Hz, 2H), 7.04 (d, J=8.0 Hz, 2H), 4.14-4.20 (m, 2H), 3.27-3.42 (m, 3H), 3.16-3.20 (m, 1H), 3.04-3.12 (m, 1H), 2.90-2.96 (m, 4H), 2.77-2.85 (m, 1H), 2.43 (s, 3H), 1.44 (d, J=6.8 Hz, 3H).

(R)-6-(difluoromethyl)-4-{6-[4-(2-(2,4-dimethyl-3-oxopiperazin-1-yl)ethoxy)phenyl]quinolin-2-yl}-1H-pyrrolo[2,3-c]pyridin-7(6H)-one (SLU-2325)

To a stirred solution of 6 (0.150 g, 0.21 mmol) in MeOH (10 mL), $H_2O$ (5.0 mL), THF (5.0 mL) were charged with potassium hydroxide (0.058 g, 1.05 mmol) at 0° C. The reaction mixture was stirred for 5 h at room temperature, evaporated, diluted with water (30 mL) and extracted with EtOAc (3×30 mL). The combined organic layers were dried over anhydrous $Na_2SO_4$ and concentrated under reduced pressure. The crude product was triturated with (10 mL) acetonitrile, stirred, filtered and dried to afford SLU-2325 (0.060 g, 51%) as an off-white solid.

ESI-MS m/z $[C_{31}H_{29}F_2N_5O_3+H]^+$ 558.3

HPLC (Method B) 97.2% (AUC), $t_R$=6.93 min.

$^1$H NMR (400 MHz, DMSO-$d_6$): δ ppm 12.67 (br.s., 1H), 8.47 (d, J=8.8 Hz, 1H), 8.00-8.30 (m, 6H), 7.81 (d, J=8.8 Hz, 2H), 7.59 (t, J=2.0 Hz, 1H), 7.31 (s, 1H), 7.11 (d, J=8.8 Hz, 2H), 4.19 (t, J=5.6 Hz, 2H), 3.26-3.29 (m,2H), 3.18 (q, J=6.8 Hz, 1H), 3.07-3.12 (m, 1H), 2.95-3.02 (m, 1H), 2.79-2.85 (m, 4H), 2.69-2.77 (m, 1H), 1.26 (d, J=6.8 Hz, 3H).

Synthesis of (R)-6-(difluoromethyl)-4-{2-[4-(2-(2,4-dimethyl-3-oxopiperazin-1-yl)ethoxy)phenyl]quinolin-6-yl}-1H-pyrrolo[2,3-c]pyridin-7(6H)-one: (SLU-2297)

Scheme 72

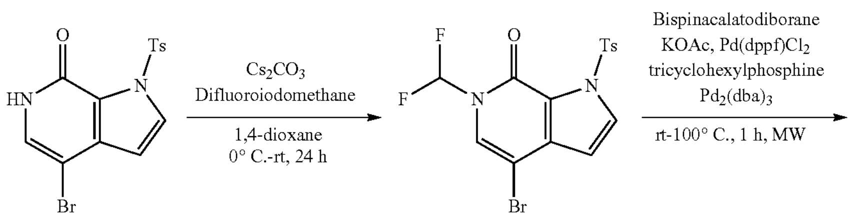

1
Scheme-3

2

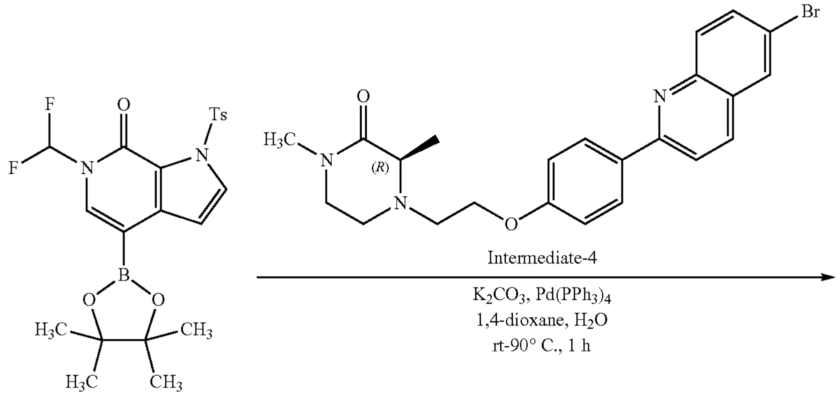

3

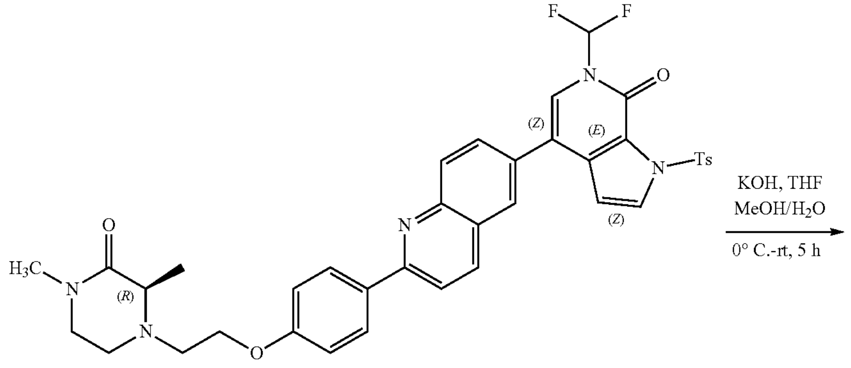

4

-continued

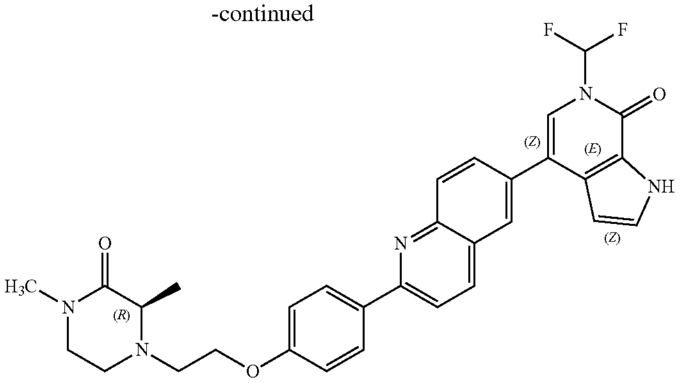

SLU-2297

NOTE: 1 is available in Scheme 3

4-bromo-6-(difluoromethyl)-1-tosyl-1H-pyrrolo[2,3-c]pyridin-7(6H)-one (2)

Difluoroiodomethane (3.62 g, 20.5 mmol) gas passed to stirred suspension of 1 (5.00 g, 13.6 mmol6) and cesium carbonate (13.2 g, 40.8 mmol) in 1,4-dioxane (50 mL) at 0° C. in sealed tube. Upon addition, reaction mixture was stirred at room temperature for 24 h. The solvent was evaporated under reduced pressure from the reaction mixture, diluted with $H_2O$ (30 mL) and extracted with EtOAc (3×30 mL). The combined organic layers dried over anhydrous $Na_2SO_4$ and concentrated under reduced pressure. The crude product was purified by combi flash chromatography (Hexanes:EtOAc=85:15) to afford 2 (2.00 g, 35%) as an off-white solid.

$^1$H NMR (400 MHz, $CDCl_3$): δ ppm δ 7.99-8.02 (m, 3H), 7.68 (t, J=59.9 Hz, 1H), 7.35 (d, J=8.3 Hz, 3H), 6.58 (d, J=3.4 Hz, 1H), 2.44 (s, 3H).

6-(difluoromethyl)-4-(4,4,5,5-tetramethyl-1,3,2-dioxaborolan-2-yl)-1-tosyl-1H-pyrrolo[2,3-c]pyridin-7(6H)-one (3)

A mixture of 2 (1.0 g, 2.4 mmol8) and bis(pinacolato) diboron (0.649 g, 2.6 mmol) in 1,4-dioxane (10 mL) was charged with potassium acetate (0.460 g, 4.8 mmol), tricyclohexylphosphine (0.134 g, 0.48 mmol) at room temperature and degassed it with argon for 10 min. $Pd_2(dba)_3$ (0.219 g, 0.24 mmol) was added to the reaction mixture at room temperature, and heated at 100° C. for 1 h in microwave. Upon cooled, the mixture was diluted with $H_2O$ (50 mL) and extracted with EtOAc (3×50 mL), combined organic layers were dried over sodium sulphate and concentrated under reduced pressure. The crude product was purified by combi flash chromatography (Hexanes:EtOAc=85:15) to afford compound 3 (0.350 g, 33% as off white solid.

$^1$H NMR (400 MHz, $CDCl_3$): δ ppm 7.93-7.95 (m, 3H), 7.55-7.86 (m, 2H), 7.30 (d, J=8.2, 2H), 7.95 (d, J=3.4 Hz, 1H), 2.40 (s, 3H), 1.33 (s, 12H).

(R)-6-(difluoromethyl)-4-{2-[4-(2-(2,4-dimethyl-3-oxopiperazin-1-yl)ethoxy)phenyl]quinolin-6-yl}-1-tosyl-1H-pyrrolo[2,3-c]pyridin-7(6H)-one (4)

To a stirred mixture of 3 (0.153 g, 0.33 mmol and Intermediate-4 (0.150 g, 0.33 mmol in 4:1 mixture of 1,4-dioxane, $H_2O$ (24 mL), $K_2CO_3$ (0.091 g, 0.66 mmol) was charged at room temperature. The solution was purged with argon for 10 min followed by addition of $Pd(PPh_3)_4$ (0.038 g, 0.033 mmol) and reaction mixture was heated at 90° C. for 1 h. Upon cooled, the reaction mixture was diluted with $H_2O$ (50 mL) and extracted with EtOAc (3×50 mL). Combined organic layers were dried over sodium sulphate and concentrated under reduced pressure to afford 4 [0.200 g (crude)] as a brown solid.

ESI-MS m/z $[C_{38}H_{35}F_2N_5O_5S+H]^+$ 712.3.

Preparation (R)-6-(difluoromethyl)-4-{2-[4-(2-(2,4-dimethyl-3-oxopiperazin-1-yl)ethoxy)phenyl]quinolin-6-yl}-1H-pyrrolo[2,3-c]pyridin-7(6H)-one (SLU-2297)

To a stirred solution of 4 (0.150 g, 0.21 mmol) in MeOH (10 mL), $H_2O$ (5.0 mL), THF (5.0 mL) were charged with potassium hydroxide (0.058 g, 1.4 mmol) at 0° C. The reaction mixture was stirred for 5 h at room temperature, evaporated, diluted with water (30 mL) and extracted with EtOAc (3×30 mL). Combined organic layers were dried over anhydrous $Na_2SO_4$ and concentrated under reduced pressure. The crude product was triturated with (20 mL) acetonitrile, stirred, filtered and dried to afford SLU-2297 (0.035 g, 30%) as an off-white solid.

ESI-MS m/z $[C_{32}H_{33}N_5O_3+H]^+$ 558.3.

HPLC (Method B) >99% (AUC), $t_R$=6.85 min.

$^1$H NMR (400 MHz, DMSO-$d_6$): δ ppm 12.71 (s, 1H), 8.50 (d, J=8.4 Hz, 1H), 8.28 (d, J=9.2 Hz, 2H), 8.23 (s, 1H), 7.97-8.17 (m, 4H), 7.57 (t, J=2.4 Hz, 1H), 7.49 (s, 1H), 7.12 (d, J=8.8 Hz, 2H), 6.61-6.64 (m, 1H), 4.19 (t, J=5.6 Hz, 2H), 3.29-3.26 (m, 2H), 3.18 (q, J=6.8 Hz, 1H), 3.08-3.13 (m, 1H), 3.03-2.96 (m, 1H), 2.86-2.82 (m, 4H), 2.69-2.75 (m, 1H), 1.26 (d, J=6.8 Hz, 3H).

Synthesis of 4-{6-[4-(4-(isopentyloxy)phenyl)piperidin-1-yl]pyridin-3-yl}-6-methyl-1H-pyrrolo[2,3-c]pyridin-7(6H)-one (SLU-2124)
Scheme 73
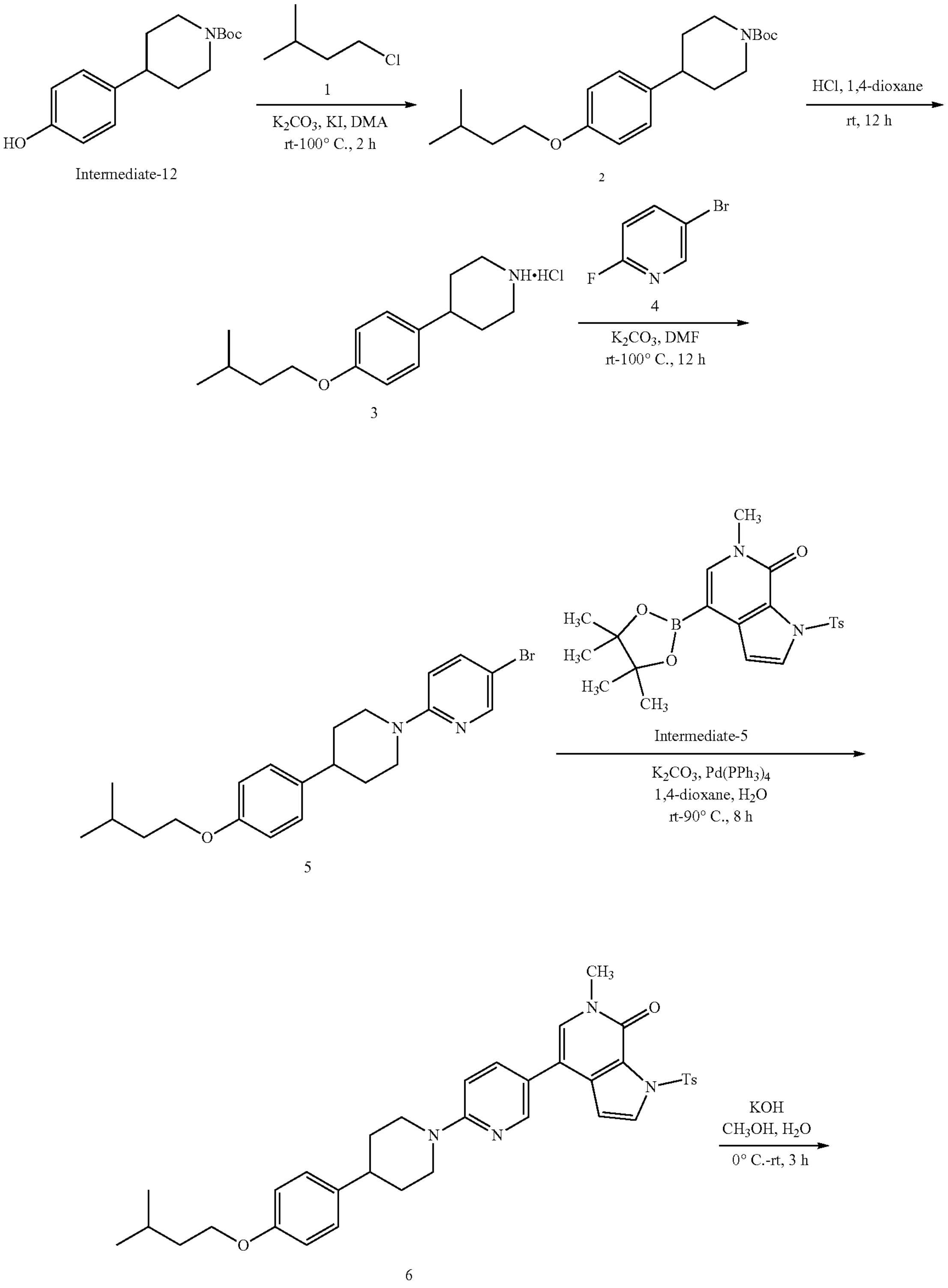

-continued

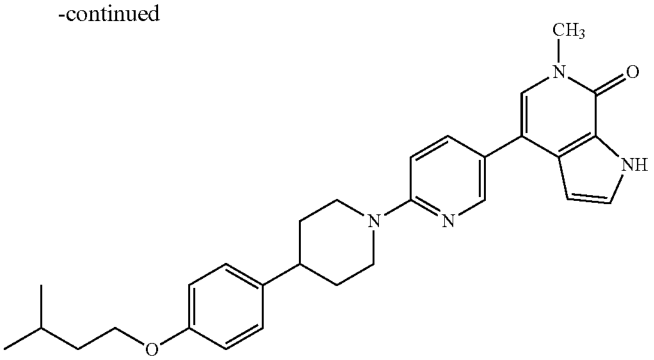

SLU-2124 tert-butyl 4-[4-(isopentyloxy)phenyl]piperidine-1-carboxylate (2)

To a stirred solution of Intermediate-12 (1.00 g, 3.5 mmol) in N,N-dimethyl acetamide, (15 mL), $K_2CO_3$ (1.40 g, 10.5 mmol), KI (0.298 g, 1.79 mmol) was charged and followed by the addition of 1-chloro-3-methylbutane 1 (20 mL, 5.0 vol) at room temperature. The reaction mixture was heated at 100° C. for 2 h. The reaction mixture was allowed to ambient temperature, diluted with water (30 mL), extracted with EtOAc (3×30 mL) and followed by brine (1×100 mL). Organic layer was dried over anhydrous $Na_2SO_4$ and concentrated under reduced pressure to afford 2 [1.00 g (crude)] as an off-white solid. The crude product was used for next step without any further purification.

$^1$H NMR (400 MHz, $CDCl_3$): δ ppm 7.10 (d, J=8.4 Hz, 2H), 6.84 (d, J=8.4 Hz, 2H), 3.96 (t, J=6.8 Hz, 2H), 2.82-2.71 (m, 2H), 2.61-2.55 (m, 1H), 1.86-1.52 (m, 6H), 1.49 (s, 9H), 0.95 (d, J=6.4 Hz, 6H).

4-[4-(isopentyloxy)phenyl]piperidine hydrochloride (3)

To a stirred solution of 2 (1.00 g, 2.8 mmol) in 1,4-dioxane (3 mL) were charged with HCl in 1,4-dioxane (10 mL) at room temperature and stirred for 12 h at room temperature. TLC indicated at which time the reaction gone to completion. The mixture was evaporated under reduced pressure to afford 3 [0.700 g (crude)] as an off-white solid. The crude product was used for next step without any further purification.

$^1$H NMR (400 MHz, DMSO-$d_6$): δ ppm 9.22 (br.s., 2H), 7.12 (d, J=8.4 Hz, 2H). 6.88 (d, J=8.4 Hz, 2H), 3.95 (t, J=4.0 Hz, 2H), 3.30 (d, J=12.0 Hz, 2H), 2.96-2.92 (m, 2H), 2.83-2.70 (m, 1H), 1.89-1.73 (m, 5H), 1.59 (q, J=6.8 Hz, 2H), 0.91 (d, J=6.8 Hz, 6H).

5-bromo-2-{4-[4-(isopentyloxy)phenyl]piperidin-1-yl}pyridine (5)

To a stirred solution of 3 (0.700 g, 2.83 mmol) in DMF (10 mL) were charged with 5-bromo-2-chloropyridine 6 (0.504 g, 2.61 mmol), $K_2CO_3$ (1.17 g, 8.49 mmol) at room temperature and heated at 100° C. for 12 h. TLC indicated at which time the reaction gone to completion. The reaction mixture was diluted with water (20 mL) and extracted with EtOAc (3×50 mL). Combined organic layers were dried over anhydrous $Na_2SO_4$ and concentrated under reduced pressure to afford 5 [0.500 g (crude)] as an off-white solid. The crude product was used for next step without any further purification.

$^1$H NMR (400 MHz, $CDCl_3$): δ ppm 8.18 (d, J=2.0 Hz, 1H), 7.51 (dd, J=2.8, 9.2 Hz, 1H), 7.12 (d, J=6.8 Hz, 2H), 6.84 (d, J=6.4 Hz, 2H), 6.59 (d, J=8.8 Hz, 1H), 4.36 (d, J=12.8 Hz, 2H), 3.96 (t, J=6.4 Hz, 2H), 2.94-2.87 (m, 2H), 2.72-2.65 (m, 1H), 1.91 (d, J=12.8 Hz, 2H), 1.86-1.65 (m, 5H), 0.95 (d, J=6.4 Hz, 6H).

4-{6-[4-(4-(isopentyloxy)phenyl)piperidin-1-yl]pyridin-3-yl}-6-methyl-1-tosyl-1H-pyrrolo[2,3-c]pyridin-7(6H)-one (6)

To a stirred solution of 5 (0.300 g, 0.74 mmol) in 1,4-dioxane (10 mL), $H_2O$ (5 mL) were charged with intermediate-5 (0.319 g, 0.74 mmol), $K_2CO_3$ (0.3.6 g, 2.22 mmol) at room temperature and degassed it with argon for 10 min. $Pd(PPh_3)_4$ (0.042 g, 0.037 mmol) was added to the reaction mixture and heated at 90° C. for 8 h. The reaction mixture was diluted with water (20 mL) and extracted with EtOAc (2×30 mL). Combined organic layers were dried over anhydrous $Na_2SO_4$ and concentrated under reduced pressure to afford 6 [0.400 g (crude)] as an off-white solid. The crude material was used for next step without further purification.

ESI-MS m/z $[C_{36}H_{40}N_4O_4S+H]^+$ 625.2.

4-{6-[4-(4-(isopentyloxy)phenyl)piperidin-1-yl]pyridin-3-yl}-6-methyl-1H-pyrrolo[2,3-c]pyridin-7(6H)-one (SLU-2124)

To a stirred solution of 6 (0.400 g, 0.64 mmol) in MeOH (10 mL), $H_2O$ (5.0 mL) were charged with potassium hydroxide (0.208 g, 3.2 mmol) at 0° C. The reaction mixture was stirred for 3 h at room temperature, evaporated, diluted with water (50 mL) and extracted with $CH_2Cl_2$ (3×40 mL). Combined organic layers were dried over anhydrous $Na_2SO_4$ and concentrated under reduced pressure. The crude material was purified by combi flash chromatography ($CH_2Cl_2$:MeOH=95:5) to afford SLU-2124 (0.050 g, 16%) as an off-white solid.

ESI-MS m/z $[C_{29}H_{34}N_4O_2+H]^+$ 471.2.

HPLC (Method F) 98.6% (AUC), $t_R$=7.46 min.

$^1$H NMR (300 MHz, DMSO-$d_6$): δ ppm 12.12 (s, 1H), 8.33 (d, J=2.4 Hz, 1H), 7.74 (dd, J=2.1, 8.7 Hz, 1H), 7.33 (t, J=2.4 Hz, 1H), 7.30 (s, 1H), 7.15 (d, J=8.4 Hz, 2H), 6.96 (d, J=8.7 Hz, 1H), 6.85 (d, J=8.4 Hz, 2H), 6.40 (s, 1H), 4.48 (d, J=12.9 Hz, 2H), 3.94 (t, J=6.6 Hz, 2H), 3.56 (s, 3H), 2.89 (t, J=12.6 Hz, 2H), 2.73 (t, J=10.5 Hz, 1H), 1.70-1.99 (m, 3H), 1.55-1.62 (m, 4H), 0.92 (d, J=6.5 Hz, 6H).

Synthesis of (R)-4-{2-[4-(2-(2,4-dimethyl-3-oxopiperazin-1-yl)ethoxy)phenyl)quinolin-6-yl)-6-ethyl-1H-pyrrolo[2,3-c]pyridin-7(6H)-one (SLU-2296)
Scheme 74
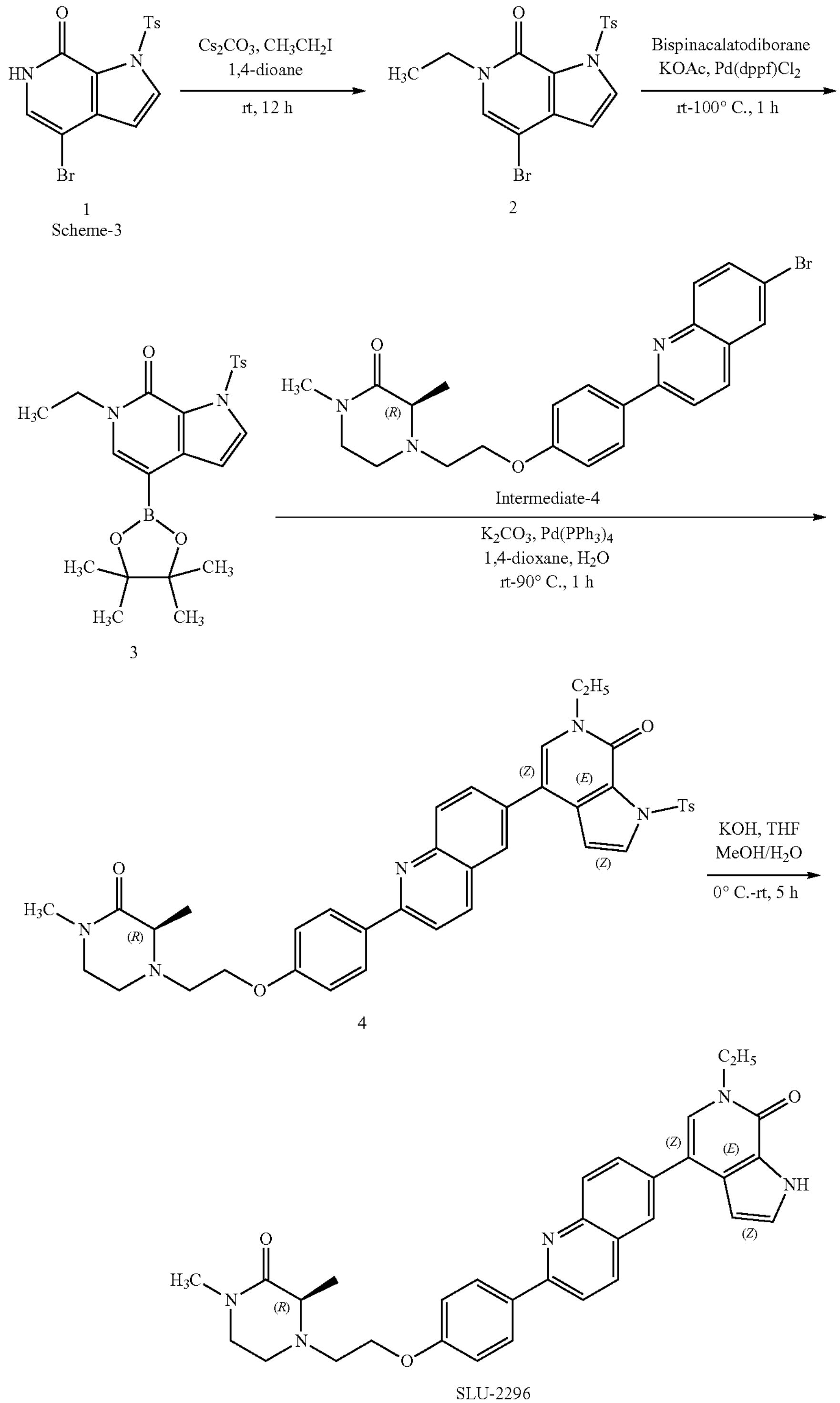
1
Scheme-3
2
3
4
SLU-2296
NOTE: 1 is available in Scheme 3

4-bromo-6-ethyl-1-tosyl-1H-pyrrolo[2,3-c]pyridin-7(6H)-one (2)

Ethyl iodide (1.70 g, 10.9 mmol) was charged dropwise to stirred suspension of 1 (2.00 g, 5.4 mmol6) and cesium carbonate (5.26 g, 16.2 mmol) in 1,4-dioxane (20 mL) at room temperature. Upon addition, the reaction mixture was stirred at room temperature for 12 h. The solvent was evaporated under reduced pressure from the reaction mixture, diluted with $H_2O$ (30 mL) and extracted with EtOAc (3×30 mL). The combined organic layers dried over anhydrous $Na_2SO_4$ and concentrated under reduced pressure to afford 2 [2.10 g (crude)1] as an off-white solid.

$^1H$ NMR (400 MHz, $CDCl_3$): δ ppm 7.99 (d, J=8.3 Hz, 2H), 7.91 (d, J=3.4 Hz, 1H), 7.29 (d, 8.0 Hz, 2H), 7.16 (s, 1H), 6.50 (d, J=3.4 Hz, 1H), 3.95 (q, J=7.2 Hz, 2H), 2.40 (s, 3H), 1.27 (t, J=7.1 Hz, 3H).

6-ethyl-4-(4,4,5,5-tetramethyl-1,3,2-dioxaborolan-2-yl)-1-tosyl-1H-pyrrolo[2,3-c]pyridin-7(6H-one (3)

A mixture of 2 (2.0 g, 5.0 mmol1) and bis(pinacolato) diboron (1.41 g, 5.5 mmol) in 1,4-dioxane (30 mL) was charged with potassium acetate (0.960 g, 10.0 mmol) at room temperature and degassed it with argon for 10 min. $Pd(dppf)Cl_2$ (0.360 g, 0.50 mmol) was added to the reaction mixture at room temperature and heated at 100° C. for 12 h. Upon cooled, the reaction mixture was diluted with $H_2O$ (50 mL) and extracted with EtOAc (3×50 mL). Combined organic layers were dried over sodium sulphate and concentrated under reduced pressure. The crude product was purified by combi flash chromatography (EtOAc:Hexanes=1:1) to afford compound 3 (0.700 g, 31%) as an off-white solid.

$^1H$ NMR (400 MHz, $CDCl_3$): δ ppm 7.95 (d, J=8.4 Hz, 2H), 7.87 (d, J=3.4 Hz, 2H), 7.50 (s, 1H), 6.89 (d, J=3.4 Hz, 1H), 3.98 (q, J=7.2 Hz, 2H), 2.38 (s, 3H), 1.24-1.32 (m, 15H).

(R)-4-(2-(4-(2-(2,4-dimethyl-3-oxopiperazin-1-yl)ethoxy)phenyl)quinolin-6-yl)-6-ethyl-1-tosyl-1H-pyrrolo[2,3-c]pyridin-7(6H)-one (4)

To a stirred mixture of 3 (0.200 g, 0.44 mmol) and Intermediate-4 (0.200 g, 0.44 mmol in 4:1 mixture of 1,4-dioxane, $H_2O$ (24 mL), $K_2CO_3$ (0.121 g, 0.88 mmol) was charged at room temperature. The solution was purged with argon for 10 min followed by the addition of $Pd(PPh_3)_4$ (0.050 g, 0.044 mmol) and reaction mixture was heated at 90° C. for 1 h. The solvent was evaporated under reduced pressure and crude product was purified by combi flash chromatography ($CH_2Cl_2$:$CH_3OH$=97:3) to afford 4 (0.200 g, 54% as an off-white solid.

$^1H$ NMR (400 MHz, $CDCl_3$): δ ppm 8.13-8.21 (m, 4H), 8.05 (d, J=8.3 Hz, 2H), 7.97 (d, J=3.5 Hz, 1H), 7.88 (d, J=8.6 Hz, 1H), 7.83 (d, J=1.8 Hz, 1H), 7.78 (dd, J=2.0, 8.6 Hz, 1H), 7.32 (d, J=8.1 Hz, 2H), 7.19 (s, 1H), 7.05 (d, J=8.8 Hz, 2H), 6.64 (d, J=3.4 Hz, 1H), 4.11-4.23 (m, 2H), 4.08 (q, J=7.3 Hz, 2H), 3.27-3.42 (m, 1H), 3.06-3.13 (m, 1H), 2.89-2.96 (m, 4H), 2.79-2.88 (m, 1H), 2.41 (s, 3H), 1.43 (d, J=6.7 Hz, 3H), 1.35 (t, J=7.1 Hz, 3H).

(R)-4-{2-[4-(2-(2,4-dimethyl-3-oxopiperazin-1-yl)ethoxy)phenyl]quinolin-6-yl}-6-ethyl-1H-pyrrolo[2,3-c]pyridin-7(6H)-one (SLU-2296)

To a stirred solution of 4 (0.200 g, 0.290 mmol in MeOH (10 mL), $H_2O$ (5.0 mL), THF (5.0 mL) were charged with potassium hydroxide (0.079 g, 1.4 mmol) at 0° C. The reaction mixture was stirred for 5 h at room temperature, evaporated, diluted with water (30 mL) and extracted with $CH_2Cl_2$ (3×30 mL). Combined organic layers were dried over anhydrous $Na_2SO_4$ and concentrated under reduced pressure. The crude product was triturated with (20 mL) acetonitrile, stirred, filtered and dried to afford SLU-2296 (0.128 g, 80%) as an off-white solid.

ESI-MS m/z $[C_{32}H_{33}N_5O_3+H]^+$ 536.3.

HPLC (Method B) 97.4% (AUC), $t_R$=6.76 min.

$^1H$ NMR (400 MHz, DMSO-$d_6$): δ ppm 12.2 (s, 1H), 8.46 (d, J=8.8 Hz, 1H), 8.27 (d, J=8.8 Hz, 2H), 8.18 (d, J=1.2 Hz, 1H), 8.09-8.14 (m, 2H), 8.02 (dd, J=1.6, 8.8 Hz, 1H), 7.59 (s, 1H), 7.41 (t, J=2.8 Hz, 1H), 7.12 (d, J=8.8 Hz, 2H), 6.61 (t, J=2.4 Hz, 1H), 4.19 (t, J=6.0 Hz, 2H), 4.12 (q, J=6.4 Hz, 2H), 3.26-3.29 (m, 2H), 3.18 (q, J=6.4 Hz, 1H), 3.07-3.13 (m, 1H), 2.96-3.02 (m, 1H), 2.86-2.82 (m, 4H), 2.69-2.75 (m, 1H), 1.32 (t, J=6.8 Hz, 3H), 1.26 (d, J=6.8 Hz, 3H).

Synthesis of (R)-4-{6-[4-(2-(2,4-dimethyl-3-oxopiperazin-1-yl)ethoxy)phenyl]quinolin-2-yl}-6-ethyl-1H-pyrrolo[2,3-c]pyridin-7(6H)-one (SLU-2295)

Scheme 75

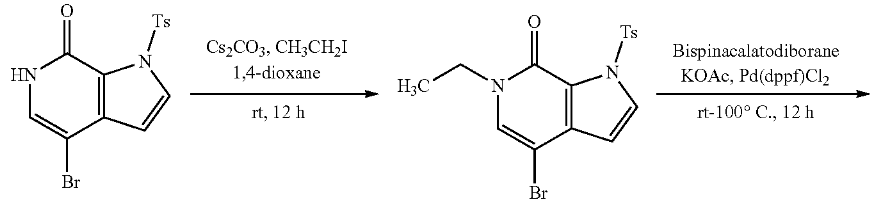

1
Scheme-3

2

-continued

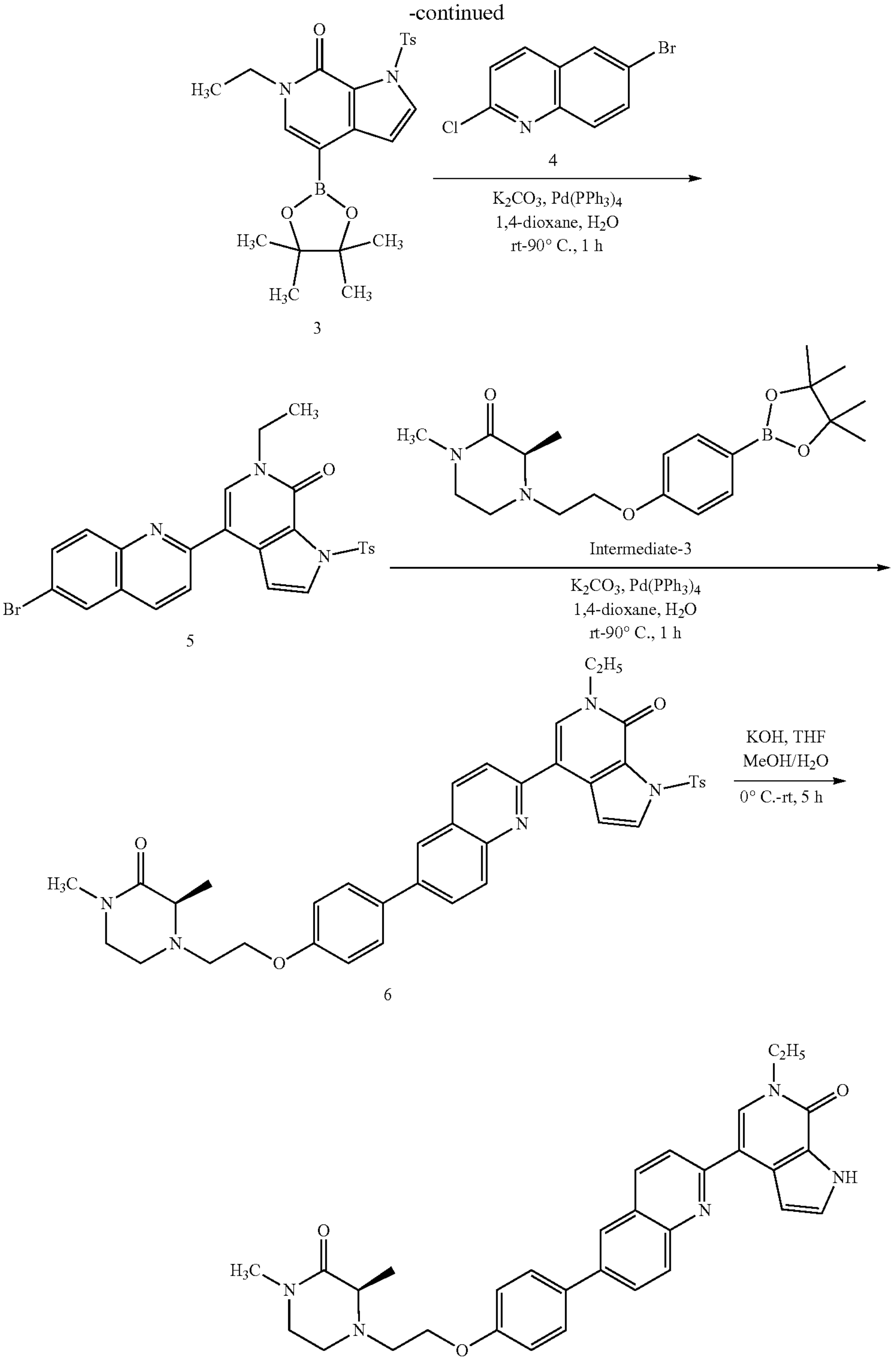

SLU-2295

NOTE: 1 was available in Scheme 3

4-bromo-6-ethyl-1-tosyl-1H-pyrrolo[2,3-c]pyridin-7 (6H)-one (2)

Ethyl iodide (1.70 g, 10.9 mmol) was charged dropwise to stirred suspension of 1 (2.00 g, 5.4. mmol6) and cesium carbonate (5.26 g, 16.2 mmol) in 1,4-dioxane (20 mL) at room temperature, Upon addition, the reaction mixture was stirred at room temperature for 12 h. The solvent was evaporated under reduced pressure from the reaction mixture, diluted with $H_2O$ (30 mL) and extracted with EtOAc (3x30 mL). The combined organic layers dried over anhydrous $Na_2SO_4$ and concentrated under reduced pressure to afford 2 [2.10 g, (crude)1] as an off-white solid.

$^1H$ NMR (400 MHz, $CDCl_3$): δ ppm 7.99 (d, J=8.3 Hz, 2H), 7.91 (d, J=3.4 Hz, 1H), 7.29 (d, 8.0 Hz, 2H) 7.16 (s, 1H), 6.50 (d, J=3.4 Hz, 1H), 3.95 (q, J=7.2 Hz, 2H), 2.40 (s, 3H), 1.27 (t, J=7.1 Hz, 3H).

6-ethyl-4-(4,4,5,5-tetramethyl-1,3,2-dioxaborolan-2-yl)-1-tosyl-1H-pyrrolo[2,3-c]pyridin-7(6H-one (3)

A mixture of 2 (2.0 g, 5.0 mmol1) and bis(pinacolato) diboron (1.41 g, 5.5 mmol) in 1,4-dioxane (30 mL) was charged with potassium acetate (0.960 g, 10.0 mmol) at room temperature, and degassed it with argon for 10 min. Pd(dppf)$Cl_2$ (0.360 g, 0.50 mmol) was added to the reaction mixture and heated at 100° C. for 12 h. Upon cooled, the mixture was diluted with $H_2O$ (50 mL) and extracted with EtOAc (3×50 mL). Combined organic layers were dried over sodium sulphate and concentrated under reduced pressure. The crude product was purified by combi flash chromatography (EtOAc:Hexanes=1:1) to afford compound 3 (0.700 g, 31%) as an off-white solid.

$^1H$ NMR (400 MHz, $CDCl_3$): δ ppm 7.95 (d, J=8.4 Hz, 2H), 7.87 (d, J=3.4 Hz, 2H), 7.50 (s, 1H), 6.89 (d, J=3.4 Hz, 1H), 3.98 (q, J=7.2 Hz, 2H), 2.38 (s, 3H), 1.24-1.32 (m, 15H).

4-(6-bromoquinolin-2-yl)-6-ethyl-1-tosyl-1H-pyrrolo[2,3-c]pyridin-7(6H)-one (5)

To a stirred mixture of 3 (0.300 g, 0.66 mmol) and 6-bromo-2-chloroquinoline 4 (0.200 g, 0.72 mmol) in 4:1 mixture of 1,4-dioxane, $H_2O$ (30 mL), $K_2CO_3$ (0.182 g, 1.32 mmol) was charged at room temperature. The solution was purged with argon for 10 min followed by addition of $Pd(PPh_3)_4$ (0.076 g, 0.066 mmol) and reaction mixture was heated at 90° C. for 1 h. The reaction mixture diluted with water (20 mL) and extracted with EtOAc (2×30 mL). Combined organic layers were dried over anhydrous $Na_2SO_4$ and concentrated under reduced pressure. The crude product was triturated with MTBE (10 mL) filtered and dried to afford 5 [0.200 g (crude)3] as an off-white solid.

$^1H$ NMR (400 MHz, DMSO-$d_6$): ppm δ 8.37-8.39 (m, 2H), 8.25 (d, J=2.0 Hz, 1H), 8.08-8.10 (m, 2H), 8.01 (d, J=9.0 Hz, 1H), 7.96 (d, J=8.3 Hz, 1H), 7.82-7.89 (m, 2H), 7.71 (d, J=3.4 Hz, 1H), 7.43 (d, J=8.3 Hz, 2H), 7.26 (t, J=6.8 Hz, 1H), 4.03 (q, J=6.8 Hz, 2H), 2.38 (s, 3H), 1.23 (t, J=6.9 Hz, 2H).

(R)-4-{6-[4-(2-(2,4-dimethyl-3-oxopiperazin-1-yl) ethoxy)phenyl]quinolin-2-yl}-6-ethyl-1-tosyl-1H-pyrrolo[2,3-c]pyridin-7(6H)-one (6)

To a stirred mixture of 5 (0.069 g, 0.13 mmol3) and Intermediate-3 (0.050 g, 0.13 mmol) in 4:1 mixture of 1,4-dioxane, $H_2O$ (10 mL), $K_2CO_3$ (0.035 g, 0.26 mmol) was charged at room temperature. The solution was purged with argon for 10 min followed by addition of $Pd(PPh_3)_4$ (0.015 g, 0.013 mmol) and reaction mixture was heated at 90° C. for 1 h. The reaction mixture diluted with water (20 mL) and extracted with EtOAc (2×30 mL). Combined organic layers were dried over anhydrous $Na_2SO_4$ and concentrated under reduced pressure. The crude product was purified by combi flash chromatography ($CH_2Cl_2$: $CH_3OH$=97:3) to afford 6 [0.060 g (crude) as an off-white solid.

ESI-MS m/z $[C_{39}H_{39}N_5O_5S+H]^+$ 690.4.

(R)-4-{6-[4-(2-(2,4-dimethyl-3-oxopiperazin-1-yl) ethoxy)phenyl]quinolin-2-yl}-6-ethyl-1H-pyrrolo[2,3-c]pyridin-7(6H)-one (SLU-2295)

To a stirred solution of 6 (0.100 g, 0.40 mmol in MeOH (10 mL), $H_2O$ (5.0 mL), THF (5.0 mL) were charged with potassium hydroxide (0.039 g, 1.4 mmol) at 0° C. The reaction mixture was stirred for 5 h at room temperature, evaporated, diluted with water (30 mL) and extracted with $CH_2Cl_2$ (3×30 mL). Combined organic layers were dried over anhydrous $Na_2SO_4$ and concentrated under reduced pressure. The crude product was triturated with (10 mL) acetonitrile, stirred, filtered and dried to afford SLU-2295 (0.050 g, 64%) as an off-white solid.

ESI-MS m/z $[C_{32}H_{33}N_5O_3+H]^+$ 536.3.

HPLC (Method B) >99% (AUC), $t_R$=6.75 min.

$^1H$ NMR (400 MHz, DMSO-$d_6$) δ 12.1 (s, 1H), 8.40 (d, J=8.8 Hz, 1H), 8.20 (d, J=2.0 Hz, 1H), 8.18 (s, 1H), 8.0-8.10 (m, 3H), 7.79 (d, J=8.8 Hz, 2H), 7.41 (t, J=2.8 Hz, 1H), 7.34 (t, J=2.4 Hz, 1H), 7.10 (d, J=8.8 Hz, 2H), 4.15-4.19 (m, 4H), 3.25-3.29 (m, 2H), 3.18 (q, J=6.4 Hz, 1H), 3.07-3.12 (m, 1H), 2.95-3.01 (m, 1H), 2.79-2.85 (m, 4H), 2.69-2.75 (m, 1H), 1.34 (t, J=7.2 Hz, 3H), 1.26 (d, J=6.8 Hz, 3H).

Synthesis of 6-methyl-4-(quinolin-6-yl)-1H-pyrrolo[2,3-c]pyridin-7(6H)-one: (SLU-2298)

Scheme 76

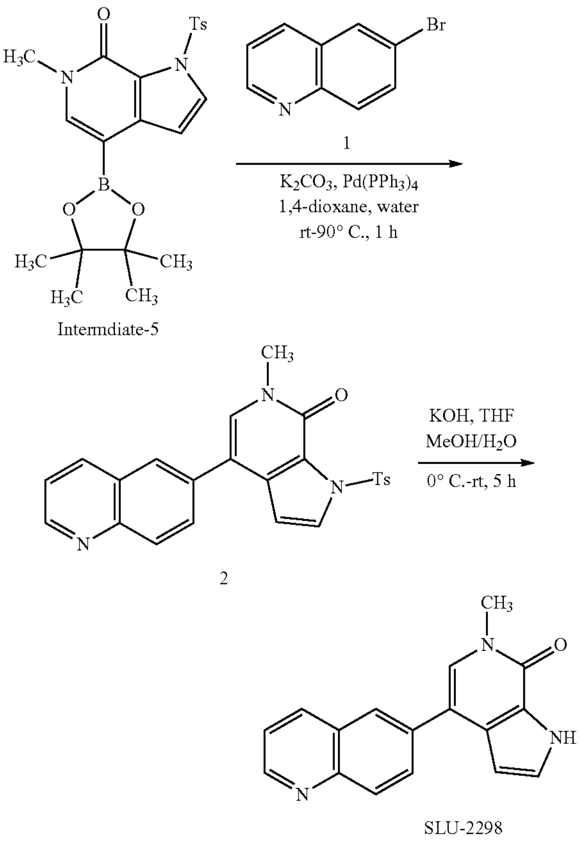

Intermdiate-5

1

2

SLU-2298

6-methyl-4-(quinolin-6-yl)-1-tosyl-1H-pyrrolo[2,3-c]pyridin-7(6H)-one (2)

To a stirred mixture of Intermediate-5 (0.200 g, 0.46 mmol8) and 6-bromoquinoline 1 (0.097 g, 0.46 mmol) in 4:1 mixture of 1,4-dioxane, $H_2O$ (15 mL), $K_2CO_3$ (0.126 g, 0.92 mmol) was charged at room temperature. The solution was purged with argon for 10 min followed by addition of $Pd(PPh_3)_4$ (0.053 g, 0.046 mmol) and reaction mixture was heated at 90° C. for 1 h. The reaction mixture diluted with water (20 mL), extracted with EtOAc (2x30 mL). Combined organic layers were dried over anhydrous $Na_2SO_4$ and concentrated under reduced pressure. The crude product was purified by combi flash chromatography ($CH_2Cl_2$: MeOH=95:5) to afford 2 (0.120 g, 60%) as an off-white solid.

$^1$H NMR (400 MHz, $CDCl_3$): δ ppm 8.94 (dd, J=1.6, 4.2 Hz, 1H), 8.18 (d, J=8.7 Hz, 2H), 8.05 (d, J=8.3 Hz, 2H), 7.97 (d, J=3.4 Hz, 1H), 7.85 (d, J=1.8 Hz, 1H), 7.79 (dd, J=2.0, 8.7 Hz, 1H), 7.46 (dd, J=4.2, 8.2 Hz, 1H), 7.33 (d, J=8.16 Hz, 2H), 7.19 (s, 1H), 6.63 (d, J=3.4 Hz, 1H), 3.61 (s, 3H), 2.42 (s, 3H).

Preparation 6-methyl-4-(quinolin-6-yl)-1H-pyrrolo[2,3-c]pyridin-7(6H)-one (SLU-2298)

To a stirred solution of 2 (0.120 g, 0.21 mmol) in MeOH (10 mL), $H_2O$ (5.0 mL), THF (5.0 mL) were charged with potassium hydroxide (0.084 g, 1.5 mmol) at 0° C. The reaction mixture was stirred for 5 h at room temperature, evaporated, diluted with water (20 mL) and extracted with EtOAc (3x20 mL). Combined organic layers were dried over anhydrous $Na_2SO_4$ and concentrated under reduced pressure. The crude product was triturated with (10 mL) acetonitrile, stirred, filtered and dried to afford SLU-2298 (0.033 g, 43%) as an off-white solid.

ESI-MS m/z $[C_{17}H_{13}N_3O+H]^+$ 276.1.

HPLC (Method B) 96.6% (AUC), $t_R$=6.63 min.

$^1$H NMR (400 MHz, DMSO-$d_6$): δ ppm 12.2 (s, 1H), 8.89 (d, J=2.8 Hz, 1H), 8.43 (d, J=7.2 Hz, 2H), 8.19 (s, 1H), 8.09 (d, J=8.4 Hz, 2H), 8.02 (dd, J=1.6, 8.8 Hz, 1H), 7.59 (s, 1H), 7.54-7.57 (m, 1H), 7.40 (t, J=2.8 Hz, 1H), 6.58-6.62 (m, 1H), 3.63 (s, 3H).

Synthesis of (R)-4-{7-[4-(2-(2,4-dimethyl-3-oxopiperazin-1-yl)ethoxy)phenyl]isoquinolin-3-yl}-6-methyl-1H-pyrrolo[2,3-c]pyridin-7(6H)-one (SLU-2219)

Scheme 77

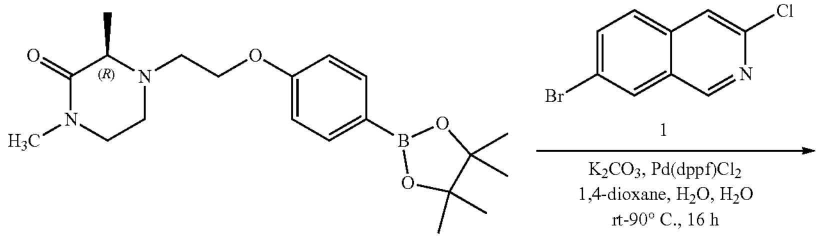

intermediate-3

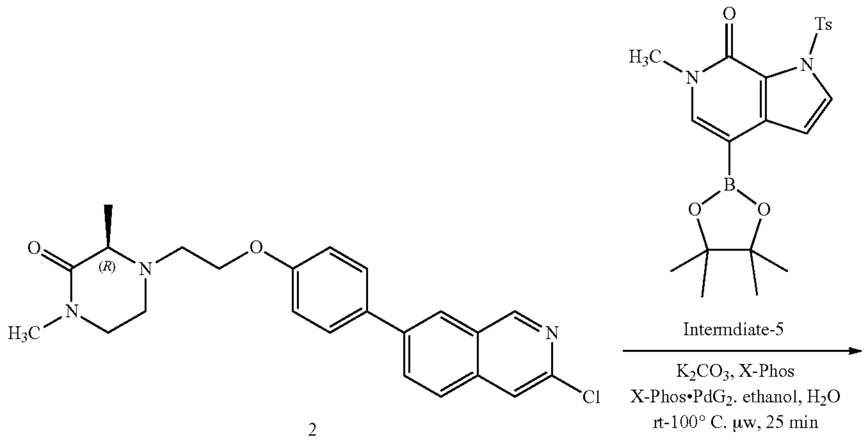

2

-continued

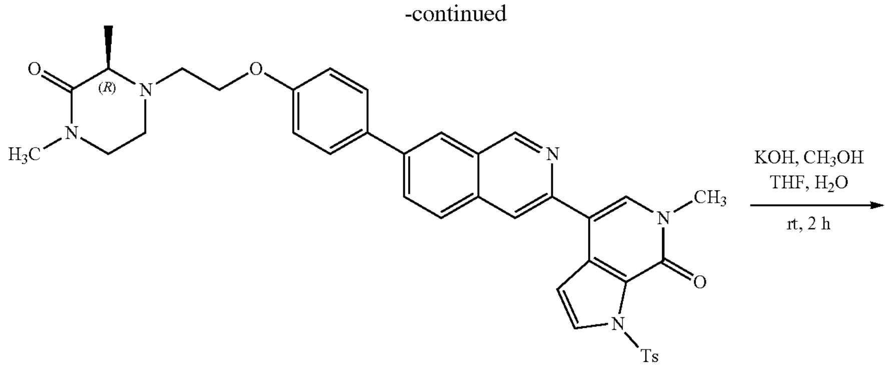

3

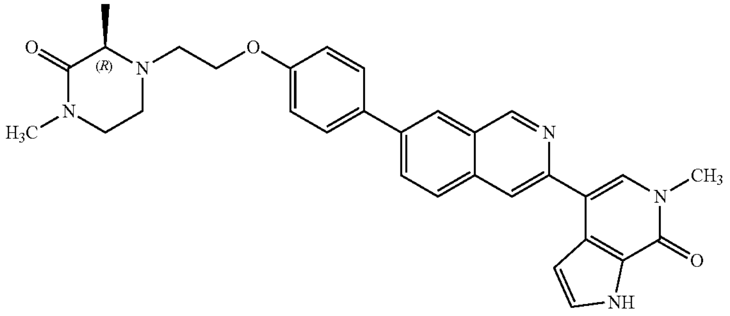

SLU-2219

(R)-4-{2-[4-(3-chloroisoquinolin-7-yl)phenoxy]ethyl}-1,3-dimethylpiperazin-2-one (2)

To a stirred solution of Intermediate-3 (0.60 g, 01.60 mmol8) in 4:1 of dioxane, $H_2O$ (20 mL), 7-bromo-3-chloroisoquinoline 1 (0.38 g, 1.60 mmol) and $K_2CO_3$ (0.44 g, 3.20 mmol) were charged at room temperature and purged with argon for 5 min. Pd(dppf)$Cl_2$ (0.11 g, 0.16 mmol) was added followed to the reaction mixture at room temperature. The reaction mixture was heated at 90° C. for 16 h. The reaction mixture was allowed to room temperature and concentrated under reduced pressure. The crude product was purified by combiflash chromatography ($CH_2Cl_2$:$CH_3OH$=92:3) to afford 2 (0.22 g, 33%) as brown colour gum.

$^1H$ NMR (400 MHz, $CDCl_3$): δ ppm δ 9.09 (s, 1H), 8.08 (s, 1H), 7.95 (d, J=8.4 Hz, 1H), 7.81 (d, J=8.8 Hz, 1H), 7.72 (s, 1H), 7.63 (d, J=8.8 Hz, 2H), 7.03 (d, J=8.4 Hz, 2H).

(R)-4-{7-[4-(2-(2,4-dimethyl-3-oxopiperazin-1-yl)ethoxy)phenyl]isoquinolin-3-yl}-6-methyl-1-tosyl-1H-pyrrolo[2,3-c]pyridin-7(6H)-one (3)

In a microwave vial, to a stirred solution of 4 (0.10 g, 0.24 mmol) in 4:1 of 1,4-dioxane, $H_2O$ (7.5 mL), intermediate-5 (0.15 g, 0.36 mmol) was charged at room temperature. $K_2CO_3$ (0.10 g, 0.73 mmol) was added followed to the reaction mixture at room temperature and purged with argon for 5 min. Then X-Phos (0.02 g, 0.04 mmol) and X-Phos·Pd$G_2$ were added at room temperature and purged with argon for 5 min. The reaction mixture was heated at 100° C. for 25 min in microwave and allowed to room temperature to concentrated under reduced pressure. The crude product was purified by combi flash chromatography ($CH_2Cl_2$:MeOH=95:5) to afford 3 (0.05 g, 15%) as a brown solid.

ESI-MS m/z $[C_{38}H_{37}N_5O_5S+H]^+$ 676.4.

(R)-4-{7-[4-(2-(2,4-dimethyl-3-oxopiperazin-1-yl)ethoxy)phenyl]isoquinolin-3-yl}-6-methyl-1H-pyrrolo[2,3-c]pyridin-7(6H)-one (SLU-2219)

To a stirred solution of 3 (0.05 g, 0.07 mmol0) in MeOH (2.0 mL), $H_2O$ (0.5 mL) and THF (2.0 mL) was charged with potassium hydroxide (0.01 g, 0.22 mmol) at room temperature for 2 h. The reaction mixture was diluted with EtOAc (200 mL), dried over anhydrous $Na_2SO_4$ and concentrated under reduced pressure. The crude product was purified by reverse phase column chromatography ($CH_3CN$:$H_2O$=70:30) as eluent. The obtained solid was stirred in $CH_3CN$ (0.5 mL) and filtered to afford SLU-2219 (0.02 g, 64%) as an off-white solid.

$^1H$ NMR (400 MHz, DMSO-$d_6$): δ ppm 12.21 (s, 1H), 9.41 (s, 1H), 8.38 (s, 1H), 8.24 (s, 1H), 8.11 (br.s., 2H), 7.81 (s, 1H), 7.82 (d, J=8.8 Hz, 2H), 7.43 (t, J=2.8 Hz, 1H), 7.11 (d, J=9.2 Hz, 2H), 7.01 (t, J=2.4 Hz, 1H), 4.17 (t, J=5.6 Hz, 2H), 3.67 (s, 3H), 3.26-3.27 (m, 2H), 3.16-3.20 (m, 1H), 3.07-3.12 (m, 1H), 2.92-3.02 (m, 1H), 2.82-2.84 (m, 1H), 2.82 (s, 3H), 2.69-2.84 (m, 1H), 1.23-1.33 (m, 3H).

ESI-MS m/z $[C_{31}H_{31}N_5O_3+H]^+$ 522.3.

HPLC (Method B) 98.4% (AUC), $t_R$=6.13 min.

Synthesis of (R)-4-{2-[3-(2-(2,4-dimethyl-3-oxopiperazin-1-yl)ethoxy)phenyl]quinolin-6-yl}-6-methyl-1H-pyrrolo[2,3-c]pyridin-7(6H)-one (SLU-2301)
Scheme 78
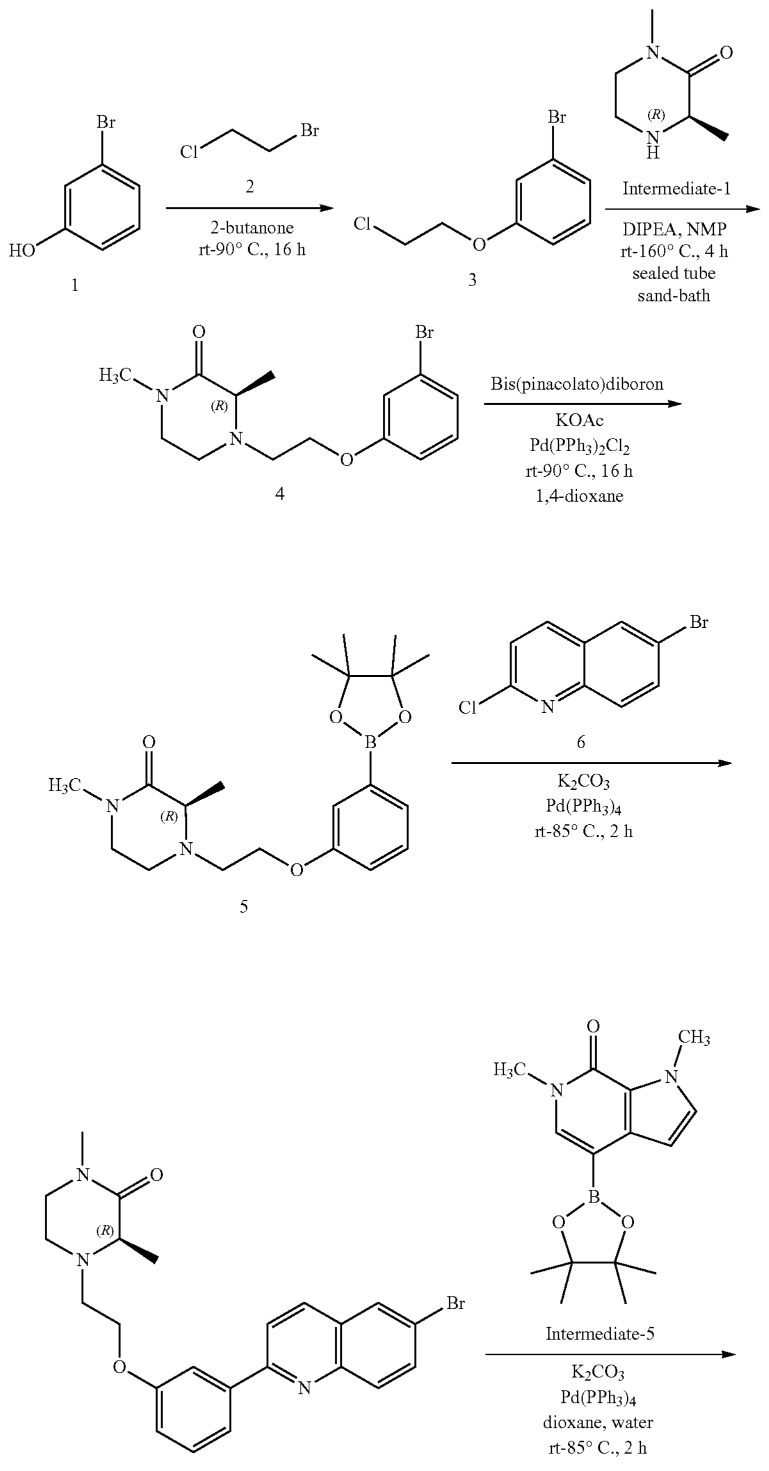
1
3
4
5
7

-continued

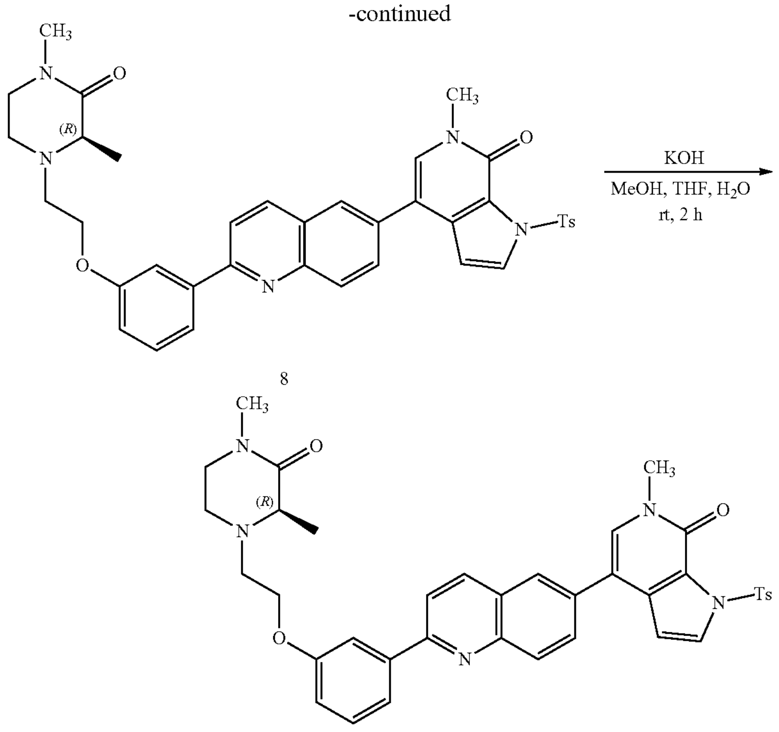

8

SLU-2301

1-bromo-3-(2-chloroethoxy)benzene (3)

To a stirred solution of 3-bromo phenol 1 (3.00 g, 17.3 mmol) in 2-butanone (30 mL), $K_2CO_3$ (7.21 g, 51.02 mmol) and 1-bromo-2-chloroethane 2 (9.91 g, 69.02 mmol) were charged at room temperature and heated at 90° C. for 16 h. The reaction mixture was allowed to room temperature and diluted with $CH_2Cl_2$ (500 mL). The organic layer was washed with water (2×100 mL) and brine (1×50 mL). The organic layer was dried over anhydrous $Na_2SO_4$ and concentrated under reduced pressure. The crude product was purified by combi flash chromatography (hexanes: EtOAc=97:3) to afford 3 (2.50 g, 65%) as colourless liquid.

$^1$H NMR (400 MHz, $CDCl_3$): δ ppm 7.07-7.15 (m, 3H), 6.84-6.86 (m, 1H), 4.21 (t, J=5.6 Hz, 2H), 3.80 (t, J=5.6 Hz, 2H).

(R)-4-[2-(3-bromophenoxy)ethyl]-1,3-dimethylpiperazin-2-one (4)

To a stirred solution of 3 (2.50 g, 10.04 mmoll) in NMP (8.0 mL) was charged with DIPEA (4.96 mL, 30.12 mmol) and intermediate-1 (1.38 g, 10.04 mmol) in a sealed tube and heated at 160° C. for 4 h on a sand bath. The reaction mixture was allowed to room temperature, diluted with water (100 mL) and extracted with EtOAc (3×200 mL). The combined organic layers were washed with cold water (2×50 mL), brine (1×50 mL), dried over anhydrous $Na_2SO_4$ and concentrated under reduced pressure. The crude product was purified by combi flash chromatography ($CH_2Cl_2$: $CH_3OH$=95:5) to afford 4 (1.50 g, 45%) as a colourless gum.

$^1$H NMR (400 MHz, $CDCl_3$): δ ppm 7.05-7.15 (m, 3H), 6.81-6.84 (m, 1H), 4.02-4.07 (m, 2H), 3.31-3.39 (m, 1H), 3.23-3.29 (m, 2H), 3.10-3.16 (m, 1H), 3.00-3.05 (m, 1H), 2.99 (s, 3H), 2.85-2.94 (m, 1H), 2.74-2.80 (m, 1H), 1.40 (t, J=6.8 Hz, 3H).

ESI-MS m/z $[C_{14}H_{19}BrN_2O_2+H]^+$ 327.4.

(R)-1,3-dimethyl-4-{2-[3-(4,4,5,5-tetramethyl-1,3,2-dioxaborolan-2-yl)phenoxy]ethyl}piperazin-2-one (5)

To a stirred solution of 4 (1.00 g, 3.00 mmol4) in 1,4-dioxane (40 mL) was charged with potassium acetate (0.58 g, 6.00 mmol), bis(pinacolato)diboron (0.97 g, 3.80 mmol) and purged with argon for 10 min at room temperature. $Pd(PPh_3)_2Cl_2$ (0.21 g, 0.03 mmol) was added at room temperature and purged with argon for 10 min. The reaction mixture was heated at 90° C. for 16 h. The reaction mixture was filtered through celite pad and concentrated under reduced pressure. The crude product was purified by combi flash chromatography (100% EtOAc) to afford 5 (0.40 g, 38%) as a colourless gum.

$^1$H NMR (400 MHz, $CDCl_3$): δ ppm 7.40 (d, J=7.2 Hz, 1H), 7.32 (d, J=2.8 Hz, 1H), 7.28 (s, 1H), 6.98-7.01 (m, 1H), 4.10-4.14 (m, 2H), 3.34-3.40 (m, 1H), 3.23-3.32 (m, 2H), 3.11-3.18 (m, 1H), 2.99-3.07 (m, 1H), 2.94 (s, 3H), 2.37-2.90 (m, 2H), 1.41 (d, J=7.6 Hz, 3H), 1.34 (s, 12H).

ESI-MS m/z $[C_{20}H_{31}BN_2O_4+H]^+$ 375.3.

(R)-4-{2-[3-(6-bromoquinolin-2-yl)phenoxy]ethyl}-1,3-dimethylpiperazin-2-one (7)

To a stirred solution of 5 (0.30 g, 0.80 mmol6) in 1,4-dioxane (20 mL) and $H_2O$ (4.0 mL) was charged with 6-bromo2-chloroquinoline 6 (0.19 g, 0.80 mmol), potassium carbonate (0.22 g, 1.60 mmol) at room temperature and degassed it with argon for 5 min. $Pd(PPh_3)_4$ (0.09 g, 0.08 mmol) was added to the reaction mixture and heated at 85° C. for 2 h. The reaction mixture was concentrated under reduced pressure. The crude product was purified by reverse phase column chromatography ($CH_3CN:H_2O$=60:40) to afford 7 (0.20 g, 41%) as a colourless gum.

$^1$H NMR (400 MHz, DMSO-$d_6$): δ ppm 8.44 (d, J=8.8 Hz, 1H), 8.30 (d, J=2.4 Hz, 1H), 8.22 (d, J=8.4 Hz, 1H), 8.01 (d, J=9.2 Hz, 1H), 7.89 (dd, J=2.4, 8.8 Hz, 1H), 7.83 (d, J=1.6 Hz, 2H), 7.46 (t, J=8.4 Hz, 1H), 7.08-7.11 (m, 1H), 4.21 (t, J=5.6 Hz, 2H), 3.24-3.29 (m, 2H), 3.19 (q, J=6.8 Hz, 1H), 3.09-3.14 (m, 1H), 2.97-3.03 (m, 1H), 2.83-2.87 (m, 1H), 2.81 (s, 3H), 2.70-2.76 (m, 1H), 1.27 (d, J=6.8 Hz, 3H).

ESI-MS m/z $[C_{23}H_{24}BrN_3O_2+H]^+$ 454.3.

(R)-4-{2-[3-(2-(2,4-dimethyl-3-oxopiperazin-1-yl) ethoxy)phenyl]quinolin-6-yl}-6-methyl-1-tosyl-1H-pyrrolo[2,3-c]pyridin-7(6H)-one (8)

To a stirred solution of 7 (0.17 g, 0.37 mmol4) in 1,4-dioxane (30.0 mL) and $H_2O$ (6.0 mL) was charged with Intermediate-5 (0.19 g, 0.44 mmol), potassium carbonate (0.10 g, 0.74 mmol) at room temperature and degassed it with argon for 5 min. $Pd(PPh_3)_4$ (0.04 g, 0.03 mmol) was added to the reaction mixture and heated at 85° C. for 2 h. The reaction mixture was concentrated under reduced pressure. The crude product was purified by combi flash chromatography ($CH_2Cl_2$:MeOH=97:3) to afford 8 (0.12 g, 44%) as light green gum.

ESI-MS m/z $[C_{38}H_{37}N_5O_5S+H]^+$ 676.3.

(R)-4-{2-[3-(2-(2,4-dimethyl-3-oxopiperazin-1-yl) ethoxy)phenyl]quinolin-6-yl}-6-methyl-1H-pyrrolo [2,3-c]pyridin-7(6H)-one (SLU-2301)

To a stirred solution of 8 (0.10 g, 0.14 mmol8) in MeOH (10.0 mL), $H_2O$ (5.0 mL), THF (10.0 mL) was charged with potassium hydroxide (0.04 g, 0.74 mmol) at room temperature and stirred for 2 h at room temperature. The reaction mixture was evaporated, diluted with EtOAc (100 mL), dried over anhydrous $Na_2SO_4$ and concentrated under reduced pressure. The crude product was purified by combi flash chromatography ($CH_2Cl_2$:MeOH=95:5). The obtained solid was stirred in MTBE (50 mL) and filtered-off to afford SLU-2301 (0.06 g, 70%) as an off-white solid.

$^1$H NMR (400 MHz, DMSO-$d_6$): δ ppm 12.23 (s, 1H), 8.51 (d, J=8.8 Hz, 1H), 8.14-8.22 (m, 3H), 8.04 (dd, J=2.0, 8.8 Hz, 1H), 7.86-7.88 (m, 2H), 7.62 (s, 1H), 7.47 (t, J=8.0 Hz, 1H), 7.42 (t, J=2.8 Hz, 1H), 7.08-7.10 (m, 1H), 6.63 (t, J=2.0 Hz, 1H), 4.22 (t, J=6.0 Hz, 2H), 3.64 (s, 3H), 3.29 (t, J=4.8 Hz, 2H), 3.20 (q, J=4.8 Hz, 1H), 3.11-3.15 (m, 1H) 2.98-3.09 (m, 1H), 2.86 (t, J=6.8 Hz, 1H), 2.82 (s, 3H), 2.71-2.77 (m, 1H), 1.28 (d, J=6.8 Hz, 3H).

ESI-MS m/z $[C_{31}H_{31}N_5O_3+H]^+$ 521.24.

HPLC (Method B) 98.2% (AUC), $t_R$=6.77 min.

Synthesis of (R)-4-{2-[4-(3-(2,4-dimethyl-3-oxopiperazin-1-yl)propoxy)phenyl]quinolin-6-yl}-6-methyl-1H-pyrrolo[2,3-c]pyridin-7(6H)-one (SLU-2299)

Scheme 79

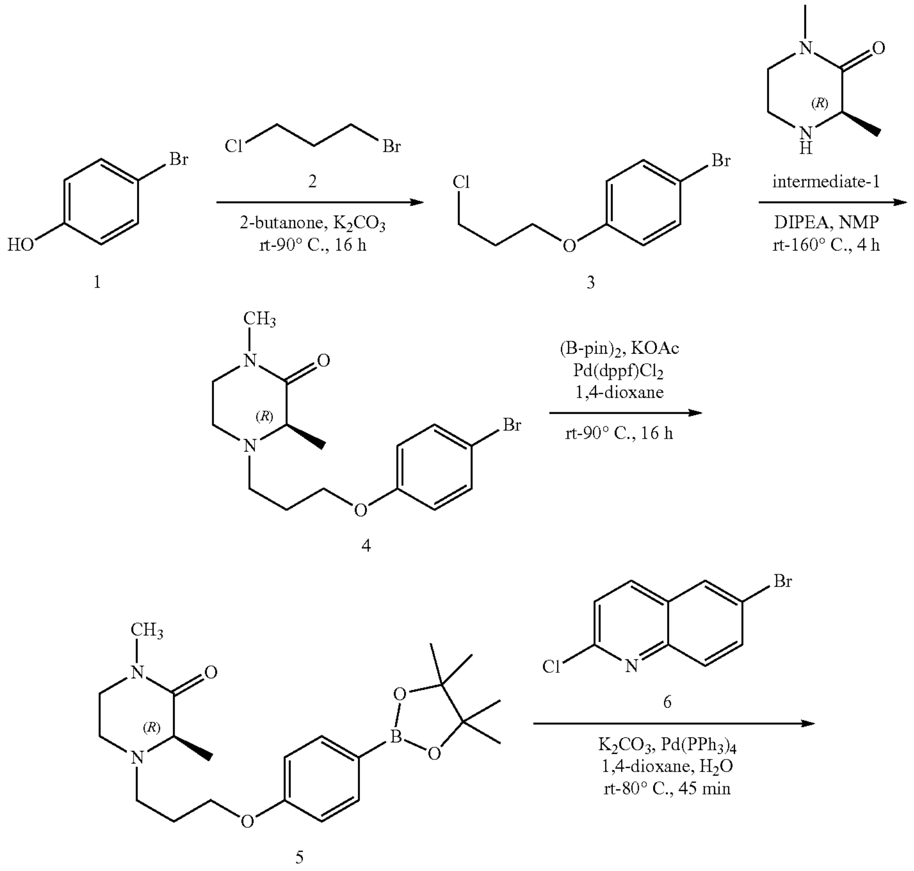

-continued

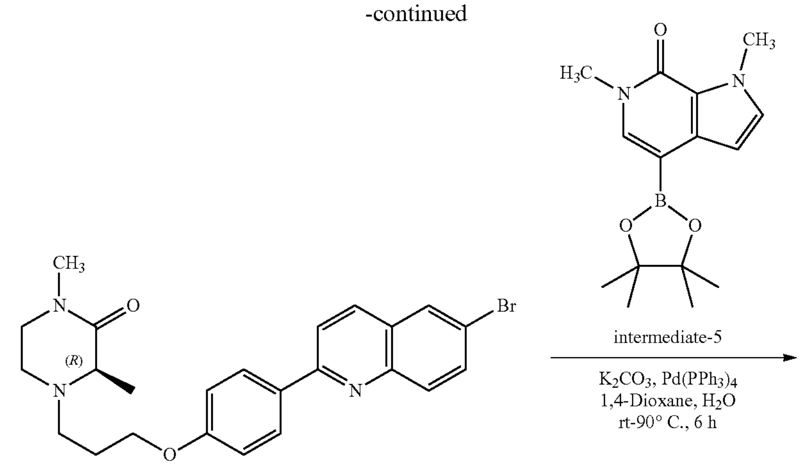

7

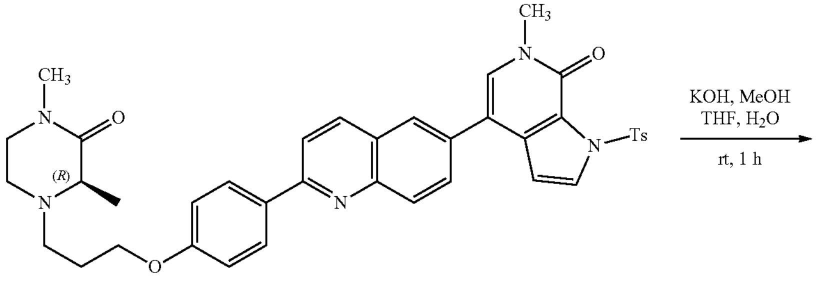

8

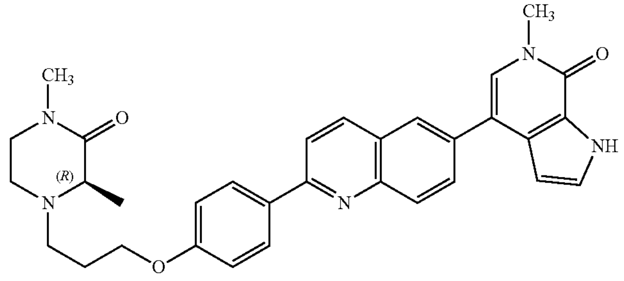

SLU-2299

1-bromo-4-(3-chloropropoxy)benzene (3)

To a stirred solution of 1 (3.00 g, 17.3 mmol) in 2-butanone (30 mL), $K_2CO_3$ (7.16 g, 52.02 mmol), 1-bromo-3-chloropropane 2 (5.70 mL, 52.02 mmol) were charged at room temperature and heated at 90° C. for 16 h. The reaction mixture was allowed to room temperature and diluted with $CH_2Cl_2$ (500 mL). The organic layer was washed with water (2×100 mL) and brine (1×50 mL). The organic layer was dried over anhydrous $Na_2SO_4$ and concentrated under reduced pressure. The crude product was purified by combi flash chromatography (hexanes:EtOAc=97:3) to afford 3 (2.50 g, 58%) as light green liquid.

$^1H$ NMR (400 MHz, $CDCl_3$): δ ppm 7.37 (d, J=9.2 Hz, 2H), 6.78 (d, J=8.8 Hz, 2H), 4.08 (t, J=5.6 Hz, 2H), 3.73 (t, J=6.0 Hz, 2H), 2.19-2.25 (m, 2H).

(R)-4-(3-(4-bromophenoxy)propyl)-1,3-dimethylpiperazin-2-one (4)

To a stirred solution of 3 (2.50 g, 10.04 mmol0) in NMP (8.0 mL) was charged with DIPEA (4.96 mL, 30.12 mmol) and intermediate-1 (1.28 g, 10.04 mmol) in a sealed tube and heated at 160° C. for 4 h on a sand bath. The reaction mixture was allowed to room temperature, diluted with water (100 mL) and extracted with EtOAc (5×150 mL). The combined organic layers were washed with cold water (3×20 mL), brine (1×20 mL), dried over anhydrous $Na_2SO_4$, and concentrated under reduced pressure. The crude product was purified by combi flash chromatography ($CH_2Cl_2$: $CH_3OH$=96:4) to afford 4 (1.40 g, 44%) as a colourless gum.

$^1H$ NMR (400 MHz, $CDCl_3$): δ ppm 7.36 (d, J=11.5 Hz, 2H), 7.70 (d, J=11.5 Hz, 2H), 3.98 (t, J=6.0 Hz, 2H), 3.16-3.35 (m, 3H), 3.00-3.05 (m, 1H), 2.95 (s, 3H), 2.78-2.85 (m, 1H), 2.50-2.61 (m, 2H), 1.89-1.96 (m, 2H), 1.34 (d, J=6.8 Hz, 3H).

ESI-MS m/z $[C_{15}H_{21}BrN_2O_2+H]^+$ 341.4.

(R)-1,3-dimethyl-4-{3-[4-(4,4,5,5-tetramethyl-1,3,2-dioxaborolan-2-yl)phenoxy]propyl}piperazin-2-one (5)

To a stirred solution of 4 (1.25 g, 3.67 mmol3) in 1,4-dioxane (30 mL) was charged with potassium acetate (0.53 g, 5.51 mmol), bis(pinacolato)diboron (1.40 g, 5.51 mmol) and purged with argon for 10 min at room temperature. Pd(dppf)$Cl_2$ (0.26 g, 0.36 mmol) was added to the reaction mixture at room temperature and purged with argon for 10 min. The reaction mixture was heated at 90° C. for 16 h. The reaction mixture was filtered through celite pad and concentrated under reduced pressure. The crude product was purified by combi flash chromatography ($CH_2Cl_2$: $CH_3OH$=95:5) to afford 5 (1.10 g, 68%) as a brown gum.

$^1$H NMR (400 MHz, $CDCl_3$): δ ppm 7.73 (d, J=8.4 Hz, 2H), 6.87 (d, J=8.4 Hz, 2H), 4.04 (t, J=6.0 Hz, 2H), 3.18-3.26 (m, 3H), 3.00-3.06 (m, 1H), 2.94 (s, 3H), 2.79-2.86 (m, 1H), 2.52-2.62 (m, 2H), 1.90-1.98 (m, 2H), 1.35 (d, J=6.8 Hz, 3H), 1.33 (s, 12H).

ESI-MS m/z $[C_{21}H_{33}BN_2O_4+H]^+$ 389.4.

(R)-4-{3-[4-(6-bromoquinolin-2-yl)phenoxy]propyl}-1,3-dimethyl piperazin-2-one (7)

To a stirred solution of 5 (0.50 g, 1.28 mmol0) in 1,4-dioxane (30 mL), $H_2O$ (5.0 mL) was charged with 6-bromo2-chloroquinoline 6 (0.31 g, 1.28 mmol), potassium carbonate (0.26 g, 1.93 mmol) at room temperature and degassed it with argon for 5 min. Pd$(PPh_3)_4$ (0.14 g, 0.12 mmol) was added to the reaction mixture and heated at 80° C. for 45 min. The reaction mixture was concentrated under reduced pressure. The crude product was purified by reverse phase column chromatography ($CH_3CN$:$H_2O$=60:40) to afford 7 (0.20 g, 32%) as an off-white solid.

$^1$H NMR (400 MHz, DMSO-$d_6$): δ ppm 8.38 (d, J=8.8 Hz, 1H), 8.22-8.26 (m, 3H), 8.16 (d, J=8.8 Hz, 1H), 7.96 (d, J=9.2 Hz, 1H), 7.86 (dd, J=2.0, 8.8 Hz, 1H), 7.09 (d, J=8.8 Hz, 2H), 4.11 (t, J=6.4 Hz, 2H), 3.25-3.27 (m, 2H), 2.97-3.05 (m, 2H), 2.79 (s, 3H), 2.74-2.77 (m, 1H), 2.45-2.46 (m, 2H), 1.90 (t, J=6.8 Hz, 2H), 1.21 (d, J=6.8 Hz, 3H).

ESI-MS m/z $[C_{24}H_{26}BrN_3O_2+H]^+$ 470.1

(R)-4-{2-[4-(3-(2,4-dimethyl-3-oxopiperazin-1-yl) propoxy)phenyl]quinolin-6-yl}-6-methyl-1-tosyl-1H-pyrrolo[2,3-c]pyridin-7(6H)-one (8)

To a stirred solution of 7 (0.15 g, 0.32 mmol6) in 1,4-dioxane (20.0 mL) and $H_2O$ (5.0 mL) was charged with Intermediate-5 (0.15 g, 0.35 mmol1), potassium carbonate (0.08 g, 0.64 mmol) at room temperature and degassed it with argon for 10 min. Pd$(PPh_3)_4$ (0.03 g, 0.03 mmol) was added to the reaction mixture and heated at 90° C. for 6 h. The reaction mixture was concentrated under reduced pressure. The crude product was purified by combi flash chromatography ($CH_2Cl_2$:$CH_3OH$=97:3) to afford 8 (0.10 g, 45%) as an off-white solid.

$^1$H NMR (400 MHz, DMSO-$d_6$): δ ppm 8.45 (d, J=8.8 Hz, 1H), 8.38 (d, J=8.8 Hz, 1H), 8.25 (d, J=8.8 Hz, 2H), 8.09-8.17 (m, 3H), 7.84-8.00 (m, 3H), 7.79 (s, 1H), 7.44 (d, J=8.0 Hz, 2H), 7.10 (dd, J=3.6, 8.8 Hz, 2H), 6.86 (d, J=3.6 Hz, 1H), 4.11 (t, J=6.0 Hz, 2H), 3.51 (s, 3H), 3.26 (t, J=3.6 Hz, 2H), 2.99-3.05 (m, 2H), 2.81 (s, 3H), 2.74-2.78 (m, 2H), 2.43-2.45 (m, 1H), 2.40 (s, 3H), 1.91 (br.s., 2H), 1.20-1.22 (m, 3H).

(R)-4-{2-[4-(3-(2,4-dimethyl-3-oxopiperazin-1-yl) propoxy)phenyl]quinolin-6-yl}-6-methyl-1H-pyrrolo [2,3-c]pyridin-7(6H)-one (SLU-2299)

To a stirred solution of 8 (0.08 g, 0.11 mmol3) in MeOH (5.0 mL), $H_2O$ (2.0 mL) and THF (5.0 mL) was charged with potassium hydroxide (0.03 g, 0.58 mmol) at room temperature and stirred for 1 h at room temperature. The reaction mixture was evaporated, diluted with EtOAc (100 mL) and $H_2O$ (10 mL). The organic layer was separated, dried over anhydrous $Na_2SO_4$ and concentrated under reduced pressure. The crude product was purified by combi flash chromatography ($CH_2Cl_2$:MeOH=94:6). The obtained solid was stirred in $CH_3CN$ (10 mL) and filtered-off to afford SLU-2299 (0.05 g, 66%) as an off-white solid.

$^1$H NMR (400 MHz, DMSO-$d_6$): δ ppm 12.21 (s, 1H), 8.45 (d, J=8.8 Hz, 1H), 8.25 (d, J=8.8 Hz, 2H), 8.17 (d, J=1.6 Hz, 1H), 8.11 (t, J=8.8 Hz, 2H), 8.01 (dd, J=2.0, 8.8 Hz, 1H), 7.59 (s, 1H), 7.41 (t, J=2.4 Hz, 1H), 7.10 (d, J=8.8 Hz, 2H), 6.61 (t, J=2.4 Hz, 1H), 4.11 (t, J=6.0 Hz, 2H), 3.63 (s, 3H), 3.26 (q, J=4.8 Hz, 2H), 2.98-3.06 (m, 2H), 2.81 (s, 3H), 2.76 (t, J=7.2 Hz, 1H), 2.45-2.55 (m, 2H), 1.89-1.91 (m, 2H), 1.22 (d, J=6.8 Hz, 3H).

ESI-MS m/z $[C_{32}H_{33}N_5O_3+H]^+$ 536.3.

HPLC (Method A) 99.5% (AUC), $t_R$=6.13 min.

Synthesis of 6-methyl-4-{2-[4-(2-(4-methyl-3-oxo-1,4-diazepan-1-yl)ethoxy)phenyl]quinolin-6-yl}-1H-pyrrolo[2,3-c]pyridin-7(6H)-one (SLU-2300)

Scheme 80

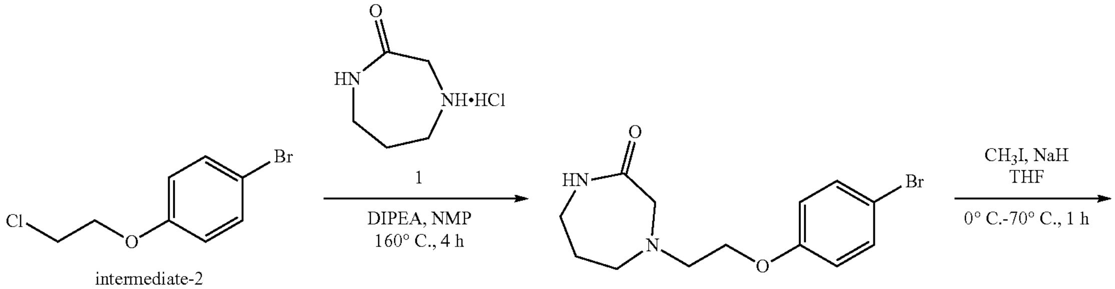

intermediate-2

2

-continued
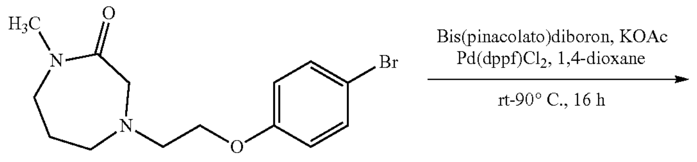
3
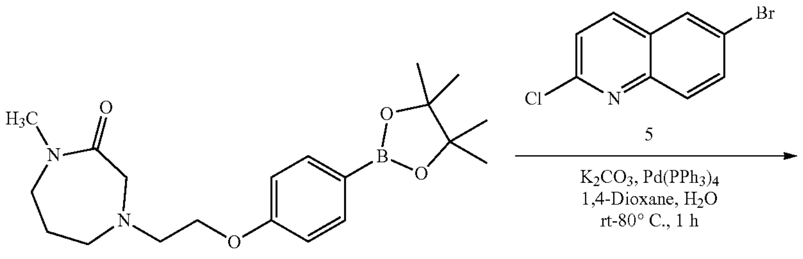
4
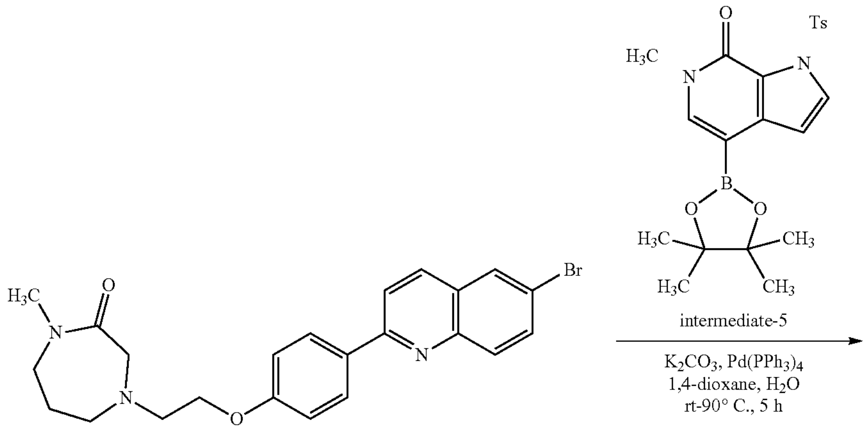
6
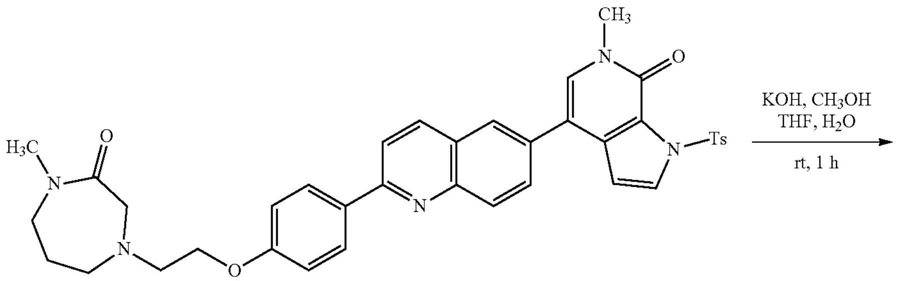
7
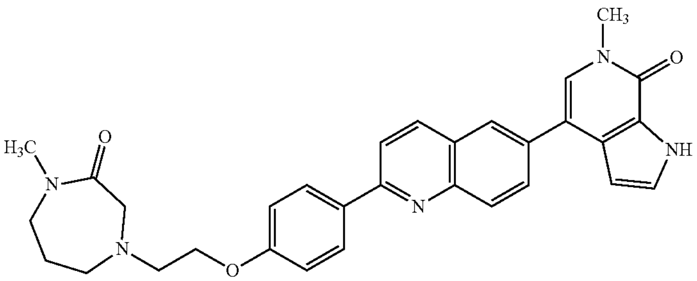
SLU-2300

4-[2-(4-bromophenoxy)ethyl]-1,4-diazepan-2-one (2)

To a stirred solution of Intermediate-2 (1.50 g, 6.38 mmol1) in NMP (7.0 mL) was charged with DIPEA (4.28 mL, 25.53 mmol) and 1,4-diazepan-2-one hydrochloride 1 (1.0 g, 6.38 mmol) in a sealed tube and heated at 160° C. for 4 h on a sand bath. The reaction mixture was diluted with water (200 mL) and extracted with EtOAc (5×150 mL). The combined organic layers were washed with water (3×50 mL), brine (1×50 mL), dried over anhydrous $Na_2SO_4$, and concentrated under reduced pressure. The obtained crude was washed with n-hexanes (2×50 mL) to afford 2 (1.35 g, 67%) as an off-white solid.

$^1$H NMR (400 MHz, DMSO-$d_6$): δ ppm 7.55 (br.s., 1H), 7.43 (d, J=8.8 Hz, 2H), 6.91 (d, J=8.8 Hz, 2H), 4.03 (t, J=6.0 Hz, 2H), 3.31 (s, 2H), 3.11 (q, J=5.2 Hz, 2H), 2.95 (t, J=5.2 Hz, 2H), 2.86 (t, J=5.2 Hz, 2H), 1.59 (t, J=4.8 Hz, 2H).

ESI-MS m/z $[C_{13}H_{17}BrN_2O_2+H]^+$ 315.2.

4-[2-(4-bromophenoxy)ethyl]-1-methyl-1,4-diazepan-2-one (3)

To a stirred solution of 2 (1.35 g, 4.30 mmol, IN-SKA-Q-142) in THF (50 mL) at 0° C. under inert atmosphere, NaH (60% in mineral oil, 0.34 g, 8.60 mmol) was charged and stirred for 10 min. $CH_3I$ (0.4 mL, 6.40 mmol) was added to the reaction mixture and slowly heated at 70° C. for 1 h. The reaction mixture allowed to room temperature, poured in to ice-cold water (100 mL) and extracted into EtOAc (3×200 mL). The combined organic layers were washed with brine (1×50 mL). The organic layer was dried over anhydrous $Na_2SO_4$ and concentrated under reduced pressure to afford 3 [0.95 g, 68%] as a colorless gum.

ESI-MS m/z $[C_{14}H_{19}BrN_2O_2+H]^+$ 327.3.

1-methyl-4-{2-[4-(4,4,5,5-tetramethyl-1,3,2-dioxaborolan-2-yl)phenoxy]ethyl}-1,4-diazepan-2-one (4)

To a stirred solution of 3 (0.95 g, 2.91 mmol3) in 1,4-dioxane (20 mL) was charged with potassium acetate (0.57 g, 5.82 mmol), bis(pinacolato)diboron (1.10 g, 4.37 mmol) and purged with argon for 10 min at room temperature. Pd(dppf)$Cl_2$ (0.21 g, 0.29 mmol) was added to the reaction mixture at room temperature and purged with argon for 10 min. The reaction mixture was heated at 90° C. for 16 h. The reaction mixture was filtered through celite pad and concentrated under reduced pressure. The crude product was purified by combi flash chromatography ($CH_2Cl_2$:$CH_3OH$=96:4) to afford 4 (0.62 g, 56%) as a colourless gum.

$^1$H NMR (400 MHz, DMSO-$d_6$): δ ppm 7.59 (d, J=8.4 Hz, 2H), 6.92 (d, J=8.4 Hz, 2H), 4.06 (t, J=6.0 Hz, 2H), 3.46 (s, 3H), 3.39-3.42 (m, 2H), 2.92 (t, J=5.2 Hz, 2H), 2.84-2.82 (m, 4H), 1.64 (br.s., 2H), 1.27 (s, 12H).

ESI-MS m/z $[C_{20}H_{31}BN_2O_4+H]^+$ 375.3.

4-{2-[4-(6-bromoquinolin-2-yl)phenoxy]ethyl}-1-methyl-1,4-diazepan-2-one (6)

To a stirred solution of 4 (0.50 g, 1.28 mmol4) in 1,4-dioxane (10 mL), $H_2O$ (2.5 mL) was charged with 6-bromo2-chloroquinoline 5 (0.34 g, 1.41 mmol), potassium carbonate (0.35 g, 2.56 mmol) at room temperature and degassed it with argon for 5 min. Pd$(PPh_3)_4$ (0.14 g, 0.12 mmol) was added to the reaction mixture and heated at 80° C. for 1 h. The reaction mixture was concentrated under reduced pressure. The crude product was purified by reverse phase column chromatography ($CH_3CN$:$H_2O$=70:30) to afford 6 (0.20 g, 34%) as an off-white solid.

$^1$H NMR (400 MHz, DMSO-$d_6$): δ ppm 8.38 (d, J=8.4 Hz, 1H), 8.23-8.26 (m, 3H), 8.16 (d, J=8.8 Hz, 1H), 7.96 (d, J=8.8 Hz, 1H), 7.86 (dd, J=2.4, 9.2 Hz, 1H), 7.10 (d, J=8.8 Hz, 2H), 4.14 (t, J=6.0 Hz, 2H), 3.49 (s, 2H), 3.40 (s, 3H), 2.96 (t, J=5.6 Hz, 2H), 2.88-2.90 (m, 4H), 1.68 (m, 2H).

ESI-MS m/z $[C_{23}H_{24}BrN_3O_2+H]^+$ 454.1.

6-methyl-4-{2-[4-(2-(4-methyl-3-oxo-1,4-diazepan-1-yl)ethoxy)phenyl]quinolin-6-yl}-1-tosyl-1H-pyrrolo[2,3-c]pyridin-7(6H)-one (7)

To a stirred solution of 6 (0.180 g, 0.33 mmol0) in 1,4-dioxane (20.0 mL), $H_2O$ (5.0 mL) was charged with Intermediate-5 (0.15 g, 0.36 mmol1), potassium carbonate (0.09 g, 0.66 mmol) at room temperature and degassed it with argon for 10 min. Pd$(PPh_3)_4$ (0.03 g, 0.03 mmol) was added to the reaction mixture and heated at 90° C. for 5 h. The reaction mixture was concentrated under reduced pressure. The crude product was purified by combi flash chromatography ($CH_2Cl_2$:MeOH=97:3) to afford 7 (0.11 g, 37%4) as an off-white solid.

$^1$H NMR (400 MHz, DMSO-$d_6$) δ ppm 8.45 (d, J=8.4 Hz, 1H), 8.26 (d, J=8.8 Hz, 2H), 8.08-8.15 (m, 4H), 7.79 (s, 1H), 7.44 (d, J=8.0 Hz, 2H), 7.11 (d, J=8.8 Hz, 2H), 6.87 (d, J=3.6 Hz, 1H), 4.14 (t, J=3.2 Hz, 2H), 3.91 (s, 3H), 3.50-3.51 (m, 2H), 3.42-3.44 (m, 2H), 2.96 (t, J=4.8 Hz, 2H), 2.89 (t, J=2.0 Hz, 2H), 2.86 (S, 3H), 2.39 (S, 3H), 1.67 (br.s., 2H).

ESI-MS m/z $[C_{38}H_{37}N_5O_5S+H]^+$ 676.3.

6-methyl-4-{2-[4-(2-(4-methyl-3-oxo-1,4-diazepan-1-yl)ethoxy)phenyl]quinolin-6-yl}-1H-pyrrolo[2,3-c]pyridin-7(6H)-one (SLU-2300)

To a stirred solution of 7 (0.09 g, 0.13 mmol4) in MeOH (5.0 mL), $H_2O$ (2.0 mL), THF (5.0 mL) was charged with potassium hydroxide (0.03 g, 0.66 mmol) at room temperature and stirred for 1 h at room temperature. The reaction mixture was evaporated, diluted with EtOAc (100 mL) and $H_2O$ (10 mL). The organic layer was separated, dried over anhydrous $Na_2SO_4$ and concentrated under reduced pressure. The crude product was purified by combi flash chromatography ($CH_2Cl_2$:MeOH=92:8). The obtained solid was stirred in $CH_3CN$ (10 mL) and filtered-off to afford SLU-2300 (0.05 g, 64%) as an off-white solid.

$^1$H NMR (400 MHz, DMSO-$d_6$): δ ppm 12.21 (s, 1H), 8.46 (d, J=8.8 Hz, 1H), 8.26 (d, J=8.8 Hz, 2H), 8.17 (d, J=1.6 Hz, 1H), 8.09-8.14 (m, 2H), 8.01 (dd, J=1.6, 8.4 Hz, 1H), 7.59 (s, 1H), 7.41 (t, J=2.8 Hz, 1H), 7.11 (d, J=8.8 Hz, 2H), 6.61 (t, J=2.4 Hz, 1H), 4.15 (t, J=6.0 Hz, 2H), 3.63 (s, 3H), 3.50 (s, 2H), 3.43 (t, J=4.0 Hz, 2H), 2.96 (t, J=5.2 Hz, 2H), 2.89 (t, J=6.0 Hz, 2H), 2.86 (s, 3H), 1.68 (br.s., 2H).

ESI-MS m/z $[C_{31}H_{31}N_5O_3+H]^+$ 522.5.

HPLC (Method A) 96.8% (AUC), $t_R$=6.07 min.

Synthesis of (R)-4-{2-[4-(2-(2,4-dimethyl-3-oxopiperazin-1-yl)ethoxy)phenyl]quinolin-6-yl}-1H-pyrrolo[2,3-c]pyridin-7(6H)-one (SLU-2302)

Scheme 81

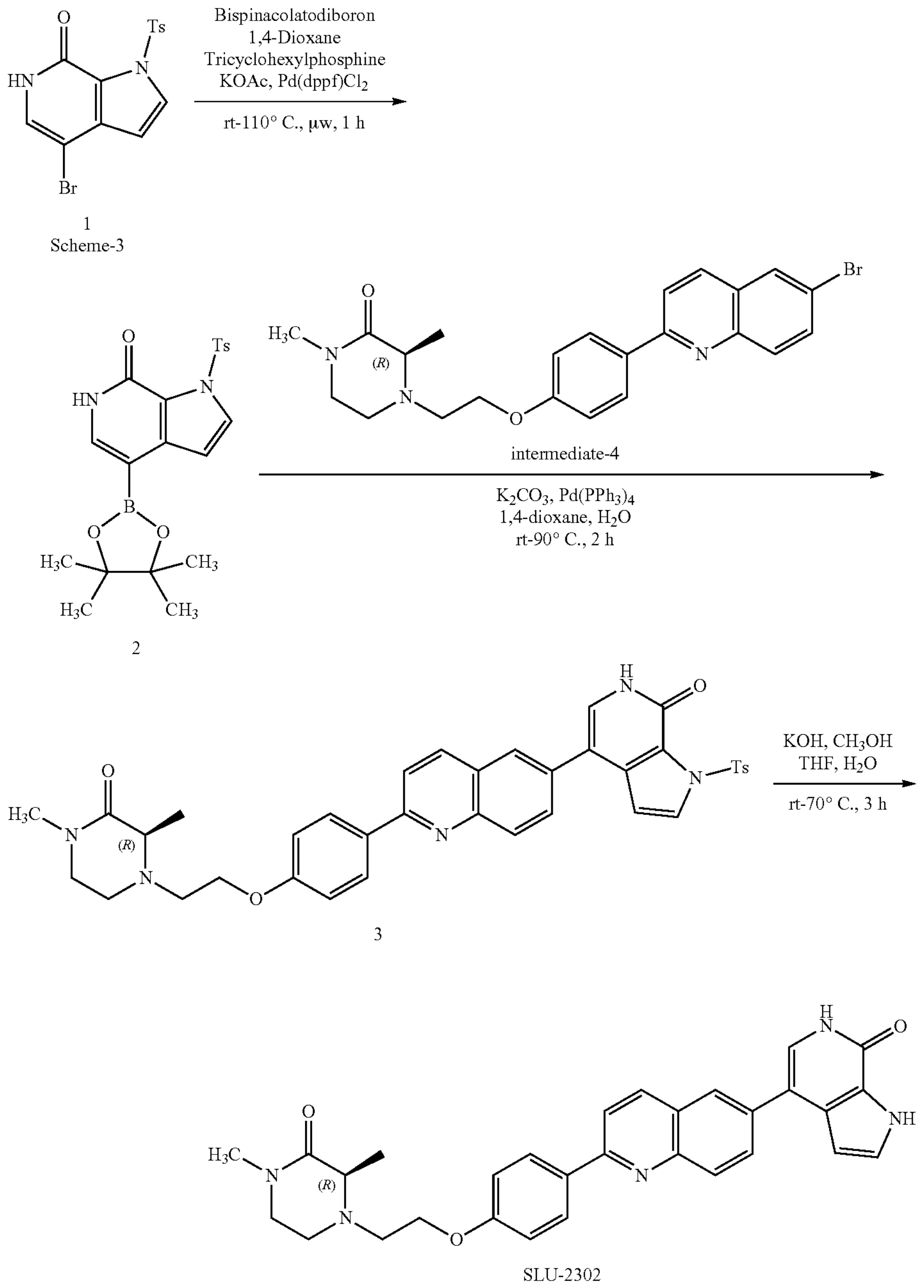

Note: compound 1 was available in Scheme 3

4-(4,4,5,5-tetramethyl-1,3,2-dioxaborolan-2-yl)-1-tosyl-1H-pyrrolo[2,3-c]pyridin-7(6H)-one (2)

A mixture of 1 (1.60 g, 4.3 mmol7) and bis(pinacolato) diboron (1.18 g, 4.8 mmol) in 1,4-dioxane (30 mL) was charged with potassium acetate (0.835 g, 8.6 mmol), tricyclohexylphosphine (0.242 g, 0.86 mmol) at room temperature and degassed it with argon for 10 min. $Pd_2(dba)_3$ (0.433 g, 0.47 mmol) was added to the reaction mixture and heated at 110° C. for 1 h in microwave. Upon cooled, the reaction mixture was diluted with $H_2O$ (50 mL) and extracted with EtOAc (3×50 mL). The combined organic layers were dried over sodium sulphate and concentrated under reduced pressure. The crude product was purified by combi flash chromatography (EtOAc:Hexanes=80:20) to afford compound 2 (0.480 g, 26%) as a light brown solid.

(R)-4-{2-[4-(2-(2,4-dimethyl-3-oxopiperazin-1-yl) ethoxy)phenyl]quinolin-6-yl}-1-tosyl-1H-pyrrolo[2, 3-c]pyridin-7(6H)-one (3)

To a stirred solution of 2 (0.16 g, 0.39 mmol7) in 1,4-dioxane (20.0 mL) and $H_2O$ (4.0 mL) was charged with Intermediate-4 (0.15 g, 0.33 mmol), potassium carbonate (0.09 g, 0.66 mmol) at room temperature and degassed it with argon for 5 min. $Pd(PPh_3)_4$ (0.03 g, 0.03 mmol) was added to the reaction mixture and heated at 90° C. for 2 h. The reaction mixture was concentrated under reduced pressure. The crude product was purified by combi flash chromatography ($CH_2Cl_2$:MeOH=97:3) to afford 3 (0.13 g, 44%) as a brown red solid.

$^1H$ NMR (400 MHz, DMSO-$d_6$): δ ppm 11.58 (d, J=6.0 Hz, 1H), 8.44 (d, J=8.8 Hz, 1H), 8.26 (d, J=8.8 Hz, 2H), 8.14 (d, J=8.8 Hz, 1H), 8.06-8.09 (m, 2H), 7.98 (d, J=8.4 Hz, 2H), 7.98 (d, J=8.4 Hz, 2H), 7.88 (dd, J=2.0, 8.8 Hz, 1H), 7.43 (d, J=8.0 Hz, 2H), 7.34 (d, J=6.0 Hz, 2H), 7.12 (d, J=9.2 Hz, 2H), 6.84 (d, J=3.6 Hz, 1H), 4.18 (t, J=6.0 Hz, 2H), 3.25-3.29 (m, 2H), 3.18 (q, J=6.8 Hz, 1H), 3.07-3.12 (m, 1H), 2.96-3.02 (m, 1H), 2.83-2.84 (m, 1H), 2.81 (s, 3H), 2.54-2.75 (m, 1H), 2.39 (s, 3H), 1.26 (d, J=5.2 Hz, 3H).

(R)-4-{2-[4-(2-(2,4-dimethyl-3-oxopiperazin-1-yl) ethoxy)phenyl]quinolin-6-yl}-1H-pyrrolo[2,3-c] pyridin-7(6H)-one (SLU-2302)

To a stirred solution of 3 (0.10 g, 0.15 mmol3) in MeOH (10.0 mL), $H_2O$ (5.0 mL) and THF (10.0 mL) was charged with potassium hydroxide (0.04 g, 0.75 mmol) at room temperature and heated at 70° C. for 3 h. The reaction mixture was evaporated, diluted with $CH_2Cl_2$ (100 mL), dried over anhydrous $Na_2SO_4$ and concentrated under reduced pressure. The crude product was purified by combi flash chromatography ($CH_2Cl_2$:MeOH=94:6) to afford SLU-2302 (0.03 g, 30%) as a white solid.

$^1H$ NMR (400 MHz, DMSO-$d_6$): δ ppm 12.21 (s, 1H), 11.27 (d, J=6.0 Hz, 1H), 8.46 (d, J=8.8 Hz, 1H), 8.26 (d, J=8.8 Hz, 2H), 8.16 (d, J=2.0 Hz, 1H), 8.13 (d, J=8.8 Hz, 1H), 8.08 (d, J=8.8 Hz, 1H), 7.98 (dd, J=2.0, 8.8 Hz, 1H), 7.41 (t, J=2.8 Hz, 1H), 7.18 (d, J=6.0 Hz, 1H), 7.12 (d, J=8.8 Hz, 2H), 6.61 (t, J=2.4 Hz, 1H), 4.18 (t, J=6.0 Hz, 2H), 3.27 (t, J=8.0 Hz, 2H), 3.18 (q, J=6.8 Hz, 1H), 3.07-3.13 (m, 1H), 2.96-3.02 (m, 1H), 2.84 (t, J=5.6 Hz, 1H), 2.96 (s, 3H), 2.55-2.75 (m, 1H), 1.26 (d, J=8.8 Hz, 3H).

ESI-MS m/z $[C_{30}H_{29}N_5O_3+H]^+$ 508.3.

HPLC (Method B) 99.9% (AUC), $t_R$=6.64 min.

Synthesis of (R)-4-{2-[4-(2-(2,4-dimethyl-3-oxopiperazin-1-yl)ethoxy)phenyl]quinolin-6-yl}-1H-pyrrolo[2,3-c]pyridin-7(6H)-one (SLU-2327)

Scheme 82

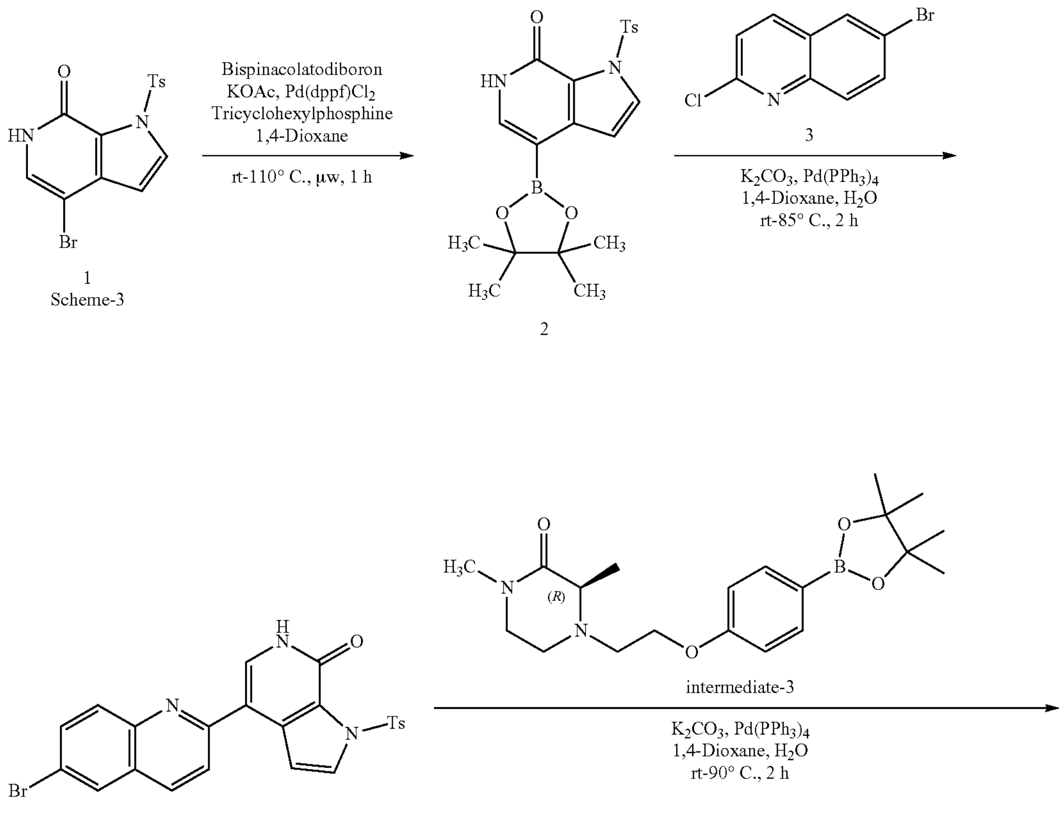

1
Scheme-3

2

3

4

-continued

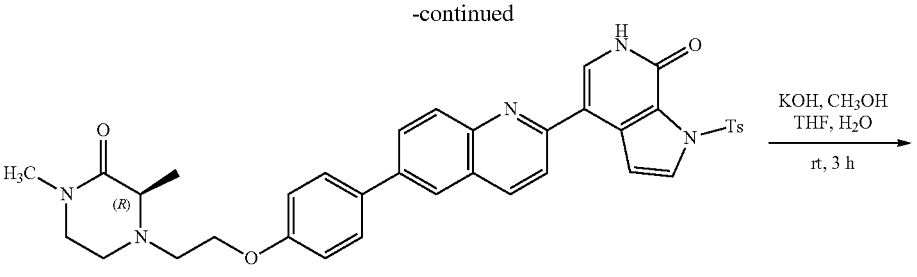

5

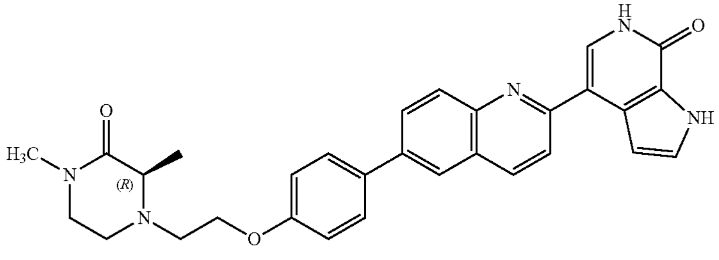

SLU-2327

Note: compound 1 is available in Scheme 3

Preparation of 4-(4,4,5,5-tetramethyl-1,3,2-dioxaborolan-2-yl)-1-tosyl-1H-pyrrolo[2,3-c]pyridin-7(6H)-one (2)

A mixture of 1 (1.60 g, 4.3 mmol6), bis(pinacolato) diboron (1.18 g, 4.8 mmol) in 1,4-dioxane (30 mL) was charged with potassium acetate (0.835 g, 8.6 mmol), tricyclohexylphosphine (0.242 g, 0.86 mmol) at room temperature and degassed it with argon for 10 min. $Pd_2(dba)_3$ (0.433 g, 0.47 mmol) was added to the reaction mixture and heated at 110° C. for 1 h in microwave. Upon cooled, the reaction mixture was diluted with $H_2O$ (50 mL) and extracted with EtOAc (3×50 mL). The combined organic layers were dried over sodium sulphate and concentrated under reduced pressure. The crude product was purified by combi flash chromatography (EtOAc:Hexanes=80:20) to afford 2 (0.480 g, 26%) as a light brown solid.

$^1H$ NMR (400 MHz, $CDCl_3$): δ ppm δ 10.6 (br.s., 1H), 7.95 (d, J=8.3 Hz, 2H), 7.92 (d, J=3.4 Hz, 1H), 7.45 (d, J=5.0 Hz, 1H), 7.26 (d, J=8.0 Hz, 2H), 6.96 (d, J=3.3 Hz, 1H), 2.37 (s, 3H), 1.34 (s, 12H).

4-(6-bromoquinolin-2-yl)-1-tosyl-1H-pyrrolo[2,3-c]pyridin-7(6H)-one (10)

To a stirred solution of 2 (0.20 g, 0.48 mmol7) in 4:1 of dioxane, $H_2O$ (50 mL), 6-bromo-2-chloroquinoline 3 (0.12 g, 0.53 mmol), $K_2CO_3$ (0.13 g, 0.96 mmol) were charged at room temperature and purged with argon for 5 min. $Pd(PPh_3)_4$ (0.05 g, 0.04 mmol) was added followed to the reaction mixture at room temperature. The reaction mixture was heated at 85° C. for 2 h. The reaction mixture was allowed to room temperature and concentrated under reduced pressure. The crude product was purified by combi flash chromatography (EtOAc:Hexanes=80:20) to afford 4 (0.14 g, 60%) as a brown solid.

$^1H$ NMR (400 MHz, $CDCl_3$): δ ppm δ 9.57 (s, 1H), 8.11-8.14 (m, 1H), 8.00-8.05 (m, 4H), 7.80-7.81 (m, 1H), 7.66-7.69 (m, 1H), 7.60 (br.s., 1H), 7.37 (t, J=4.4 Hz, 1H), 7.28-7.30 (m, 3H), 2.38 (s, 3H).

ESI-MS m/z $[C_{23}H_{16}BrN_3O_3S+H]^+$ 496.05.

(R)-4-{6-[4-(2-(2,4-dimethyl-3-oxopiperazin-1-yl)ethoxy)phenyl]naphthalen-2-yl}-1-tosyl-1H-pyrrolo[2,3-c]pyridin-7(6H)-one (5)

To a stirred solution of 4 (0.14 g, 0.28 mmol0) in 4:1 of 1,4-dioxane, $H_2O$ (36 mL), intermediate-3 (0.10 g, 0.28 mmol) and $K_2CO_3$ (0.07 g, 0.56 mmol) were charged at room temperature and purged with argon for 5 min. $Pd(PPh_3)_4$ (0.03 g, 0.028 mmol) was added followed to the reaction mixture at room temperature. The reaction mixture was heated at 90° C. for 2 h. The reaction mixture was allowed to room temperature and concentrated under reduced pressure. The crude product was purified by combi flash chromatography ($CH_2Cl_2$:MeOH=95:5) to afford 5 (0.15 g, 66%) as a brown solid.

$^1H$ NMR (400 MHz, DMSO-$d_6$): δ ppm 11.74 (d, J=4.4 Hz, 1H), 8.39 (d, J=8.8 Hz, 1H), 8.21 (s, 1H), 8.09 (d, J=4.4 Hz, 3H), 7.91-8.00 (m, 4H), 7.74-7.80 (m, 3H), 7.42 (d, J=8.0 Hz, 2H), 7.10 (d, J=8.4 Hz, 2H), 4.16 (t, J=5.6 Hz, 2H), 3.25-3.26 (m, 2H), 3.18 (q, J=6.8 Hz, 1H), 3.06-3.12 (m, 1H), 2.95-3.01 (m, 1H), 2.82 (s, 3H), 2.67-2.75 (m, 2H), 2.38 (s, 3H), 1.26 (d, J=6.8 Hz, 3H).

ESI-MS m/z $[C_{37}H_{35}N_5O_5S+H]^+$ 662.3.

(R)-4-{2-[4-(2-(2,4-dimethyl-3-oxopiperazin-1-yl)ethoxy)phenyl]quinolin-6-yl}-1H-pyrrolo[2,3-c]pyridin-7(6H)-one (SLU-2327)

To a stirred solution of 5 (0.12 g, 0.18 mmol4) in MeOH (10 mL), $H_2O$ (5.0 mL), THF (10.0 mL) was charged with potassium hydroxide (0.05 g, 0.9 mmol) at room temperature for 3 h. The reaction mixture was diluted with EtOAc (200 mL), dried over anhydrous $Na_2SO_4$ and concentrated under reduced pressure. The crude product was purified by reverse phase column chromatography ($CH_3CN$:$H_2O$=70:30) as an eluent to afford SLU-2327 (0.01 g, 9%) as a white solid.

$^1$H NMR (400 MHz, DMSO-$d_6$) δ ppm 12.13 (br.s., 1H), 11.47 (br.s., 1H), 8.37 (d, J=8.8 Hz, 1H), 8.19 (br.s., 1H), 8.02-8.09 (m, 3H), 7.79 (d, J=8.4 Hz, 3H), 7.42 (d, J=2.4 Hz, 1H), 7.34 (d, J=2.8 Hz, 1H), 7.10 (d, J=8.0 Hz, 2H), 4.16 (t, J=5.6 Hz, 2H), 3.26-3.29 (m, 2H), 3.18 (q, J=6.8 Hz, 1H), 3.07-3.12 (m, 1H), 2.95-3.01 (m, 1H), 2.84-2.85 (m, 1H), 2.82 (s, 3H), 2.69-2.75 (m, 1H), 1.26 (d, J=6.8 Hz, 3H).

ESI-MS m/z $[C_{30}H_{29}N_5O_3+H]^+$ 508.3.

HPLC (Method A) 95.7% (AUC), $t_R$=5.98 min.

Synthesis of (R)-4-{2-[3-(2,4-dimethyl-3-oxopiperazin-1-yl)propoxyl]quinolin-6-yl}-6-methyl-1H-pyrrolo[2,3-c]pyridin-7(6H)-one (SLU-2347)

Scheme 83

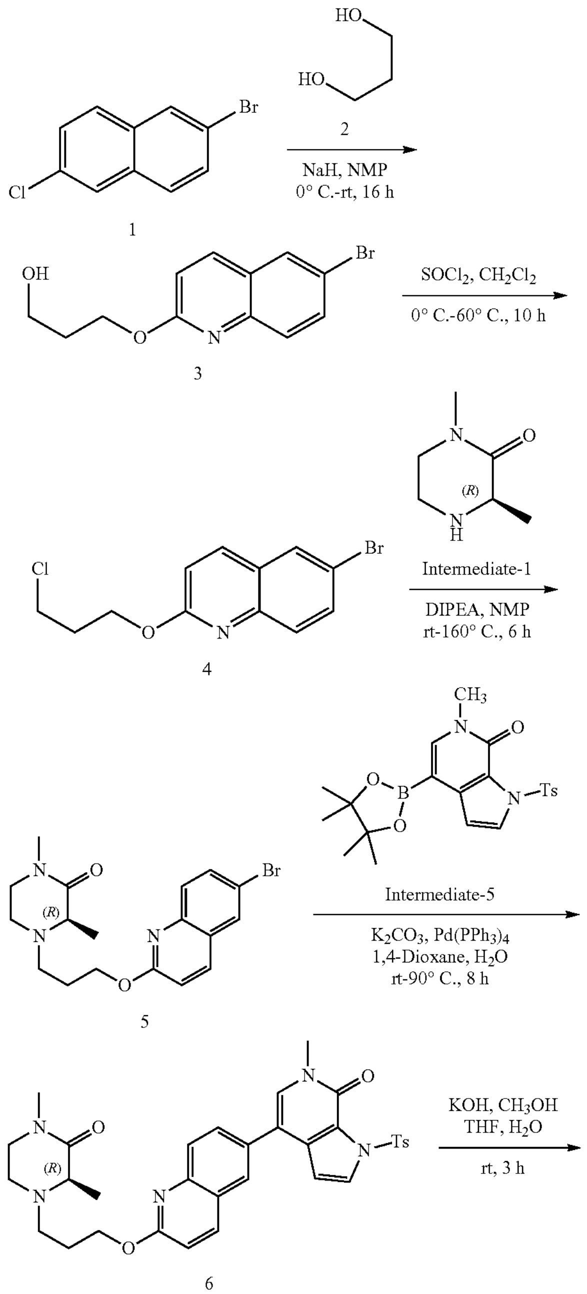

-continued

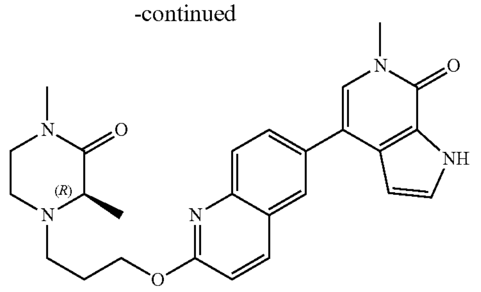

SLU-2347

3-[(6-bromoquinolin-2-yl)oxy]propan-1-ol (3)

To a stirred solution of propane-1,3-diol 2 (3.00 g, 12.39 mmol) in NMP (60 mL) under inert atmosphere NaH (60% in mineral oil, 2.47 g, 61.98 mmol) was charged at 0° C. as portion wise for 5 min. Upon 15 min, at same temperature a solution of 6-bromo-2-chloroquinoline in NMP (15 mL) was slowly added to the reaction mixture dropwisely for 15 min and left at room temperature for 16 h. The reaction mixture was poured in to ice-cold water (200 mL) and organic compound was extracted in to EtOAc (3×200 mL). The combined organic layers were washed with ice-cold water (3×50 mL), brine (1×50 mL), dried over anhydrous $Na_2SO_4$ and concentrated under reduced pressure. The crude product was purified by column chromatography (EtOAc: n-hexanes=60:40) to afford 3 (2.30 g, 66%) as a white solid.

$^1$H NMR (400 MHz, $CDCl_3$): δ ppm 7.91 (d, J=8.8 Hz, 1H), 7.86 (d, J=1.2 Hz, 1H), 7.67-7.68 (m, 2H), 6.92 (d, J=8.8 Hz, 1H), 4.68 (t, J=5.6 Hz, 2H), 3.70-3.71 (m, 2H), 3.54-3.55 (m, 1H), 2.02-2.05 (m, 2H).

ESI-MS m/z $[C_{12}H_{12}BrNO_2+H]^+$ 282.1.

6-bromo-2-(3-chloropropoxy)quinolone (4)

To a stirred solution of 3 (1.50 g, 5.31 mmol9) in $CH_2Cl_2$ (20 mL) at 0° C. $SOCl_2$ (10 mL) was added dropwise to the reaction mixture for 10 min. The reaction mixture was heated to 60° C. for 10 h. The reaction mixture was evaporated under reduced pressure. The crude material was washed with n-hexanes (3×20 mL) and dried under vacuum to afford 4 (1.27 g, 80% as an off-white solid.

$^1$H NMR (400 MHz, DMSO-$d_6$): δ ppm 8.00 (d, J=2.0 Hz, 1H), 7.89 (d, J=9.6 Hz, 1H), 7.76 (dd, J=2.4, 9.2 Hz, 1H), 7.55 (d, J=8.8 Hz, 1H), 6.67 (d, J=9.6 Hz, 1H), 4.33 (t, J=7.2 Hz, 2H), 3.77 (t, J=6.4 Hz, 2H), 2.02-2.08 (m, 2H).

ESI-MS m/z $[C_{12}H_{11}BrClNO+H]^+$ 302.1.

(R)-4-{3-[(6-bromoquinolin-2-yl)oxy]propyl}-1,3-dimethylpiperazin-2-one (5)

To a stirred solution of 4 (0.65 g, 2.16 mmol, intermediate-1 (0.41 g, 3.24 mmol in N-methyl-2-pyrrolidone (3.0 mL), DIPEA (1.42 mL, 8.64 mmol) was charged at room temperature in a sealed tube and heated at 160° C. on a sand bath for 6 h. The reaction mixture was allowed to room temperature and poured in to water (100 mL). The organic compound was extracted in to EtOAc (5×100 mL). The combined organic layers were washed with ice-cold water (2×50 mL), brine (1×50 mL), dried over anhydrous $Na_2SO_4$ and concentrated under reduced pressure. The crude product was purified by column chromatography ($CH_2Cl_2$: $CH_3OH$=95:5) to afford 5 (0.30 g, 35%) as a brown gum.

$^1$H NMR (400 MHz, DMSO-$d_6$): δ ppm 7.99 (d, J=2.4 Hz, 1H), 7.88 (d, J=9.6 Hz, 1H), 7.75 (dd, J=2.4, 9.2 Hz, 1H), 7.56 (d, J=9.2 Hz, 1H), 6.65 (d, J=9.6 Hz, 1H), 4.16-4.30 (m, 2H), 3.23-3.24 (m, 2H), 2.81 (s, 3H), 2.66-2.73 (m, 2H), 2.39-2.47 (m, 2H), 1.70-1.77 (m, 2H), 1.20 (d, J=7.2 Hz, 3H).

ESI-MS m/z $[C_{18}H_{22}BrN_3O_2+H]^+$ 392.1.

(R)-4-{2-[3-(2,4-dimethyl-3-oxopiperazin-1-yl)propoxy]quinolin-6-yl}-6-methyl-1-tosyl-1H-pyrrolo[2,3-c]pyridin-7(6H)-one (6)

To a stirred solution of 5 (0.27 g, 0.68 mmol) in 4:1 of dioxane, $H_2O$ (25 mL), intermediate-5 (0.32 g), $K_2CO_3$ (0.18 g, 0.75 mmol) were charged at room temperature and purged with argon for 5 min. $Pd(PPh_3)_4$ (0.07 g, 0.06 mmol) was added to the reaction mixture at room temperature. The reaction mixture was heated at 90° C. for 8 h and was filtered through celite pad. The resulting mixture was washed with EtOAc (2×50 mL), dried over anhydrous $Na_2SO_4$, concentrated under reduced pressure and purified by combi flash chromatography ($CH_2Cl_2$:$CH_3OH$=95:5) to afford 6 (0.12 g, 28%) as a brown gum.

ESI-MS m/z $[C_{33}H_{35}N_5O_5S+H]^+$ 614.4.

(R)-4-{2-[3-(2,4-dimethyl-3-oxopiperazin-1-yl)propoxy]quinolin-6-yl}-6-methyl-1H-pyrrolo[2,3-c]pyridin-7(6H)-one (SLU-2347)

To a stirred solution of 6 (0.10 g, 0.16 mmol) in $CH_3OH$ (5.0 mL), $H_2O$ (2.0 mL), THF (5.0 mL) was charged with potassium hydroxide (0.04 g, 0.81 mmol) at room temperature for 3 h. The reaction mixture was diluted with $CH_2Cl_2$ (100 mL), dried over anhydrous $Na_2SO_4$ and concentrated under reduced pressure. The crude product was purified by combi flash chromatography ($CH_2Cl_2$:$CH_3OH$=92:8) to afford SLU-2347 (0.03 g, 46%) as a white solid.

$^1$H NMR (400 MHz, DMSO-$d_6$): δ ppm 12.17 (s, 1H), 7.98 (d, J=9.6 Hz, 1H), 7.95 (d, J=2.0 Hz, 1H), 7.84 (dd, J=2.0, 8.8 Hz, 1H), 7.69 (d, J=9.2 Hz, 1H), 7.44 (s, 1H), 7.37 (t, J=2.8 Hz, 1H), 6.64 (d, J=9.6 Hz, 1H), 6.51 (t, J=2.0 Hz, 1H), 4.23-4.37 (m, 2H), 3.60 (s, 3H), 3.27 (t, J=5.6 Hz, 2H), 2.98-3.12 (m, 2H), 2.82 (s, 3H), 2.66-2.79 (m, 1H), 2.53-2.56 (m, 2H), 1.75-1.80 (m, 2H), 1.23 (d, J=6.8 Hz, 3H).

ESI-MS m/z $[C_{26}H_{29}N_5O_3+H]^+$ 460.3.

HPLC (Method A) 98.6% (AUC), $t_R$=6.01 min.

Synthesis of (R)-4-{2-[4-(2-(4-ethyl-2-methyl-3-oxopiperazin-1-yl)ethoxy)phenyl]quinolin-6-yl}-6-methyl-1H-pyrrolo[2,3-c]pyridin-7(6H)-one (SLU-2611)

Scheme 84

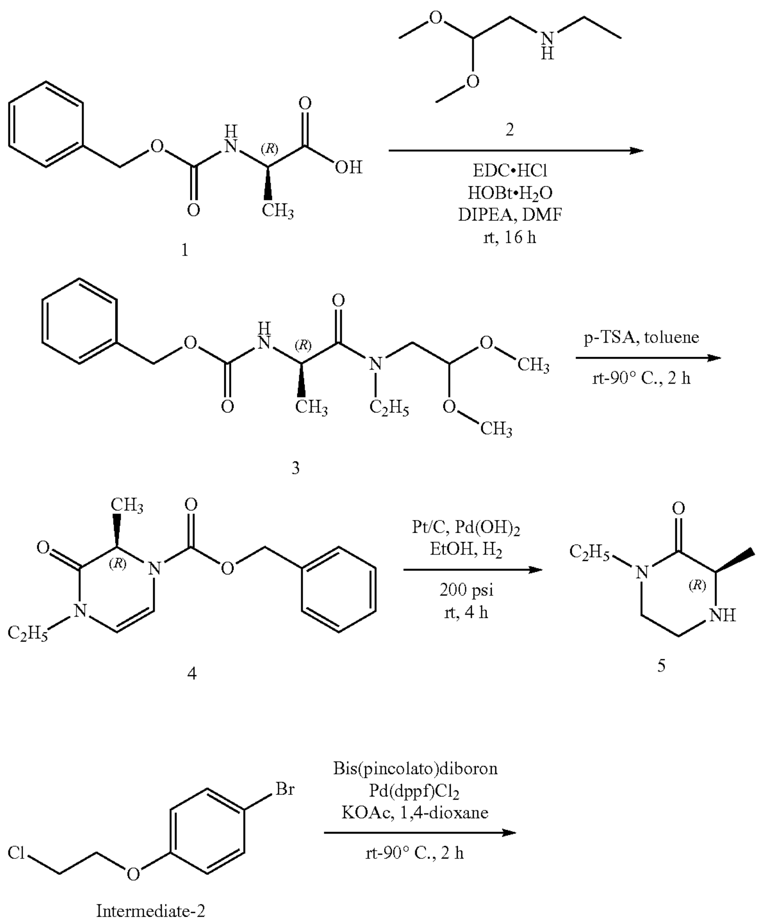

-continued
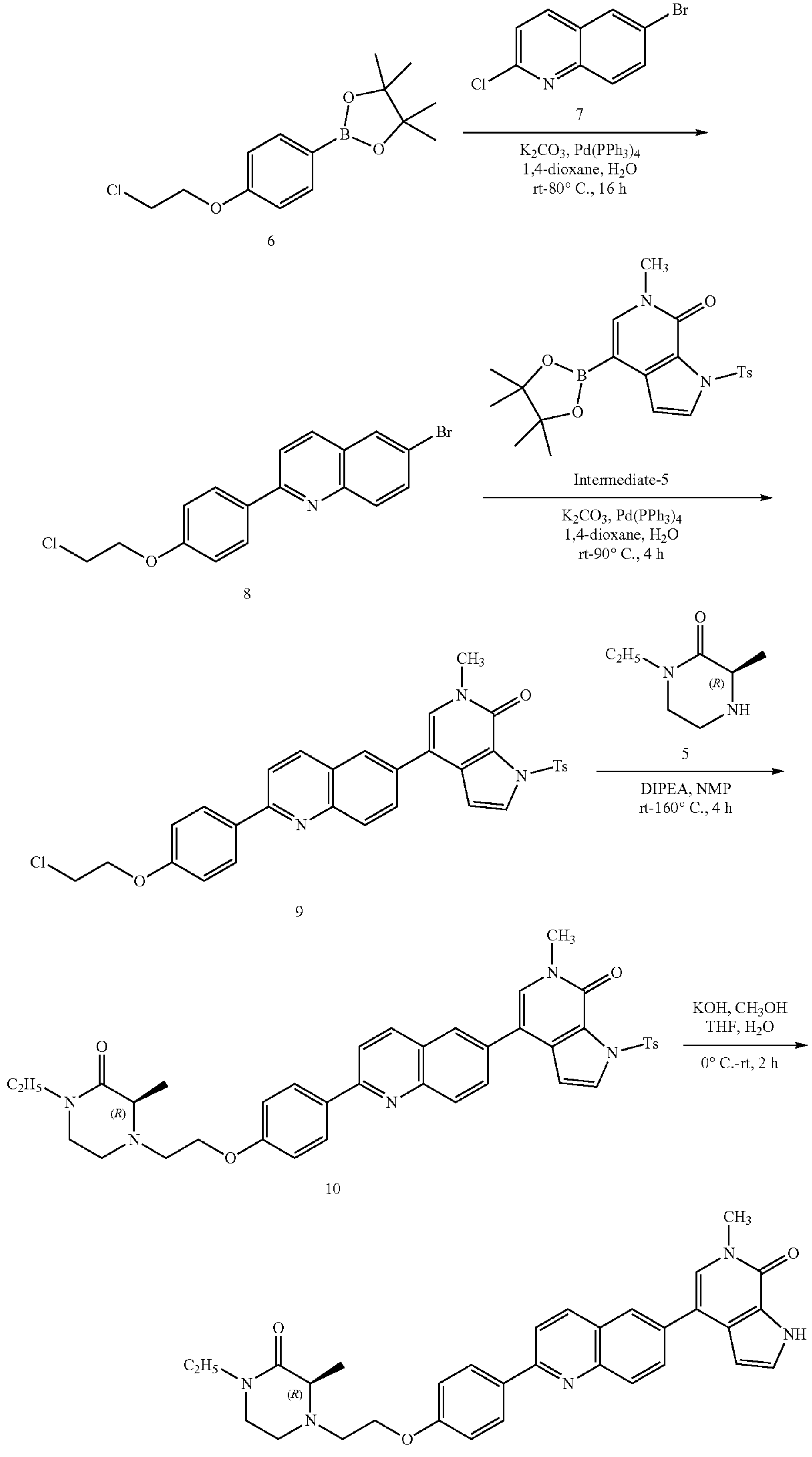
SLU-2611

(R)-benzyl {1-[(2,2-dimethoxyethyl)(ethyl)amino]-1-oxopropan-2-yl}carbamate (3)

To a stirred solution of 1 (0.90 g, 4.03 mmol) in DMF (20 mL), N-ethyl-2,2-dimethoxyethanamine 2 (0.52 g, 4.43 mmol) was charged at room temperature. DIPEA (1.33 mL, 8.06 mmol), EDC·HCl (0.84 g, 4.43 mmol) and HOBt·$H_2O$ (0.59 g, 4.43 mmol) was added to the reaction mixture at room temperature. The reaction mixture was stirred at ambient temperature for 16 h. The reaction mixture was poured in to water (100 mL) and extracted with EtOAc (3×100 mL). The combined organic layers were dried over anhydrous $Na_2SO_4$ and concentrated under reduced pressure. The crude product was purified by combi flash column chromatography (EtOAc:n-hexanes=60:40) as an eluent to afford 3 (0.72 g, 53%) as a colourless gum.

$^1$H NMR (400 MHz, $CDCl_3$): δ ppm 7.29-7.35 (m, 5H), 5.61-5.69 (m, 1H), 5.05-5.13 (m, 2H), 4.62-4.75 (m, 1H), 4.44-4.49 (m, 1H), 3.56-3.61 (m, 1H), 3.44-3.50 (m, 2H), 3.39-3.40 (m, 7H), 3.19-3.24 (m, 1H), 1.30-1.36 (m, 2H), 1.25-1.27 (m, 1H), 1.19-1.24 (m, 2H).

(R)-benzyl 4-ethyl-2-methyl-3-oxo-3,4-dihydropyrazine-1(2H)-carboxylate (4)

To a stirred solution of 3 (0.72 g, 2.13 mmol) in toluene (20 mL), P-TSA (0.23 g, 1.06 mmol) was charged portion-wise for 5 min at room temperature and heated at 90° C. for 2 h. The reaction mixture was cooled to room temperature and toluene was evaporated under reduced pressure. The crude was dissolved in EtOAc (200 mL) and washed with saturated $NaHCO_3$ solution (2×50 mL). The organic layer was dried over anhydrous $Na_2SO_4$ and concentrated under reduced pressure. The crude product was purified by combi flash column chromatography (EtOAc:n-hexanes=60:40) to afford 4 (0.48 g, 82%) as brown gum.

$^1$H NMR (400 MHz, $CDCl_3$): δ ppm 7.33-7.36 (m, 5H), 6.22-6.35 (m, 1H), 5.48-5.60 (m, 1H), 5.20 (s, 2H), 4.79-4.90 (m, 1H), 3.58-3.67 (m, 1H), 3.37-3.47 (m, 1H), 1.27-1.31 (m, 3H), 1.16 (t, J=7.2 Hz, 3H).

(R)-1-ethyl-3-methylpiperazin-2-one (5)

In a (75 mL) capacity of auto clave vessel was charged with stirred solution of 4 (0.48 g, 1.75 mmol) in ethanol (20 mL), platinum on carbon (5%, 0.07 g) was added at room temperature. Palladium hydroxide on charcoal (20%, 0.07 g) was added to the reaction mixture at room temperature. The reaction mixture was stirred at room temperature at 200 psi under hydrogen atmosphere for 4 h. The reaction mixture was filtered through celite pad and washed with methanol (200 mL). The filtrate was concentrated under reduced pressure to afford 5 (0.18 g, 68%) as a brown gum.

$^1$H NMR (400 MHz, $CDCl_3$): δ ppm 3.50-3.55 (m, 1H), 3.37-3.47 (m, 3H), 3.17-3.25 (m, 2H), 3.01-3.08 (m, 1H), 2.31-2.37 (m, 1H), 1.40 (d, J=6.8 Hz, 3H), 1.13 (t, J=7.2 Hz, 3H).

2-[4-(2-chloroethoxy)phenyl]-4,4,5,5-tetramethyl-1,3,2-dioxaborolane (6)

A mixture of intermediate-2 (18.0 g, 76.53 mmol), bis(pinacolato)diboron (25.2 g, 99.40 mmol) in 1,4-dioxane (300 mL) was charged with potassium acetate (11.10 g, 114.79 mmol) at room temperature and degassed it with argon for 10 min. Pd(dppf)$Cl_2$ (2.77 g, 3.88 mmol) was added to the reaction mixture and heated at 90° C. for 2 h. The reaction mixture was evaporated under reduced pressure, diluted with $H_2O$ (150 mL) and extracted with EtOAc (3×500 mL). The combined organic layers were dried over anhydrous $Na_2SO_4$ and concentrated under reduced pressure. The crude product was purified by combi flash chromatography (Hexanes:EtOAc=98:2) to afford compound 6 (10.0 g, 45%) as a brown solid.

$^1$H NMR (400 MHz, $CDCl_3$): δ ppm 7.58 (dd, J=2.4, 6.4 Hz, 2H), 6.90 (dd, J=2.0, 6.8 Hz, 2H), 4.25 (t, J=6.0 Hz, 2H), 3.81 (t, J=6.0 Hz, 2H), 1.33 (s, 12H).

6-bromo-2-[4-(2-chloroethoxy)phenyl]quinolone (8)

To a stirred solution of 6 (0.50 g, 1.76 mmol) in 4:1 of dioxane, $H_2O$ (30 mL), 6-bromo-2-chloroquinoline 7 (0.42 g, 1.76 mmol), $K_2CO_3$ (0.48 g, 3.52 mmol) were charged at room temperature and purged with argon for 15 min. Pd$(PPh_3)_4$ (0.14 g, 12.3 mmol) was added to the reaction mixture at room temperature. The reaction mixture was heated slowly at 80° C. for 16 h. The reaction mixture was allowed to room temperature and concentrated under reduced pressure. The crude product was purified by combi flash chromatography (Hexanes:EtOAc=80:20) to afford 8 (0.4 g, 65%) as an off-white solid.

$^1$H NMR (400 MHz, $CDCl_3$): δ ppm 7.99-8.10 (m, 3H), 7.96-7.99 (m, 2H), 7.85 (d, J=8.4 Hz, 1H), 7.76 (dd, J=2.4, 8.8 Hz, 1H), 7.05-7.07 (m, 2H), 4.32 (t, J=6.0 Hz, 2H), 3.86 (t, J=5.6 Hz, 2H).

ESI-MS m/z $[C_{17}H_{13}BrClNO+H]^+$ 362.0.

4-{2-[4-(2-chloroethoxy)phenyl]quinolin-6-yl}-6-methyl-1-tosyl-1H-pyrrolo[2,3-c]pyridin-7(6H-one (9)

To a stirred solution of 8 (0.10 g, 0.275 mmol) in 4:1 of 1,4-dioxane, $H_2O$ (7.5 mL), intermediate-5 (0.11 g, 0.27 mmol), $K_2CO_3$ (0.07 g, 0.55 mmol) were charged at room temperature and purged with argon for 5 min. Pd$(PPh_3)_4$ (0.03 g, 0.027 mmol) was added to the reaction mixture at room temperature. The reaction mixture was heated at 90° C. for 4 h. The reaction mixture was allowed to room temperature and filtered through celite pad. The filtrate was concentrated under reduced pressure. The crude product was purified by combi flash chromatography (n-hexanes:EtOAc=60:40) as an eluent to afford 9 (0.14 g, 87%) as an off-white solid.

$^1$H NMR (400 MHz, $CDCl_3$): δ ppm 8.15-8.21 (m, 4H), 8.05 (d, J=8.4 Hz, 2H), 7.98 (d, J=3.2 Hz, 1H), 7.87-7.89 (m, 1H), 7.83 (d, J=2.0 Hz, 1H), 7.78 (dd, J=2.0, 8.8 Hz, 1H), 7.33 (d, J=8.0 Hz, 2H), 7.20 (s, 1H), 7.07 (d, J=8.8 Hz, 2H), 6.65 (d, J=3.6 Hz, 1H), 4.33 (t, J=6.0 Hz, 2H), 3.88 (t, J=6.0 Hz, 2H), 3.62 (m, 3H), 2.42 (t, J=14.8 Hz, 3H).

ESI-MS m/z $[C_{32}H_{26}ClN_3O_4S+H]^+$ 584.1.

(R)-4-{2-[4-(2-(4-ethyl-2-methyl-3-oxopiperazin-1-yl)ethoxy)phenyl]quinolin-6-yl}-6-methyl-1-tosyl-1H-pyrrolo[2,3-c]pyridin-7(6H)-one (10)

To a stirred solution of 9 (0.10 g, 0.17 mmol) in NMP (3.0 mL) was charged with DIPEA (0.08 mL, 0.68 mmol), (R)-1-ethyl-3-methylpiperazin-2-one 5 (0.03 g, 0.18 mmol) in a sealed tube at room temperature and heated at 160° C. for 4 h on a sand bath. The reaction mixture was diluted with water (50 mL) and extracted with EtOAc (5×100 mL). The combined organic layers were dried over anhydrous $Na_2SO_4$ and concentrated under reduced pressure. The crude material purified by combi flash chromatography ($CH_2Cl_2$: $CH_3OH$=92:8) as an eluent to afford 10 (0.08 g, 48%) as a brown gum.

ESI-MS m/z $[C_{39}H_{39}N_5O_5S+H]^+$ 690.3.

(R)-4-{2-[4-(2-(4-ethyl-2-methyl-3-oxopiperazin-1-yl)ethoxy)phenyl]quinolin-6-yl}-6-methyl-1H-pyrrolo[2,3-c]pyridin-7(6H)-one (SLU-2611)

To a stirred solution of 10 (0.07 g, 0.10 mmol) in MeOH (4.0 mL), $H_2O$ (2.0 mL), THF (4.0 mL) was charged with potassium hydroxide (0.01 g, 0.40 mmol) at 0° C. and left at room temperature for 3 h. The reaction mixture was evaporated, diluted with EtOAc (150 mL), dried over anhydrous $Na_2SO_4$ and concentrated under reduced pressure. The crude product was purified by combi flash chromatography ($CH_2Cl_2$:MeOH=92:8) followed by reverse phase column chromatography ($CH_3CN$:$H_2O$=50:50) as an eluent to afford SLU-2611 (0.01 g, 16%) as an off-white solid.

$^1H$ NMR (400 MHz, DMSO-$d_6$): δ ppm 12.22 (s, 1H), 8.46 (d, J=8.4 Hz, 1H), 8.26 (d, J=8.8 Hz, 2H), 8.09-8.18 (m, 3H), 8.01 (dd, J=1.6, 8.4 Hz, 1H), 7.60 (s, 1H), 7.41 (t, J=2.8 Hz, 1H), 7.12 (d, J=8.8 Hz, 2H), 6.61 (t, J=2.0 Hz, 1H), 4.19 (t, J=6.0 Hz, 2H), 3.63 (s, 3H), 3.27 (t, J=8.8 Hz, 4H), 3.08-3.18 (m, 2H), 2.96-3.02 (m, 1H), 2.80-2.86 (m, 1H), 2.67-2.73 (m, 1H), 1.26 (d, J=6.8 Hz, 3H), 1.02 (t, J=7.2 Hz, 3H).

ESI-MS m/z $[C_{32}H_{33}N_5O_3+H]^+$ 536.3.

HPLC (Method A) 99.7% (AUC), $t_R$=6.11 min.

Synthesis of (R)-4-{2-[3-(2,4-dimethyl-3-oxopiperazin-1-yl)propoxy]quinolin-6-yl}-6-methyl-1H-pyrrolo[2,3-c]pyridin-7(6H)-one (SLU-2348)

Scheme 85

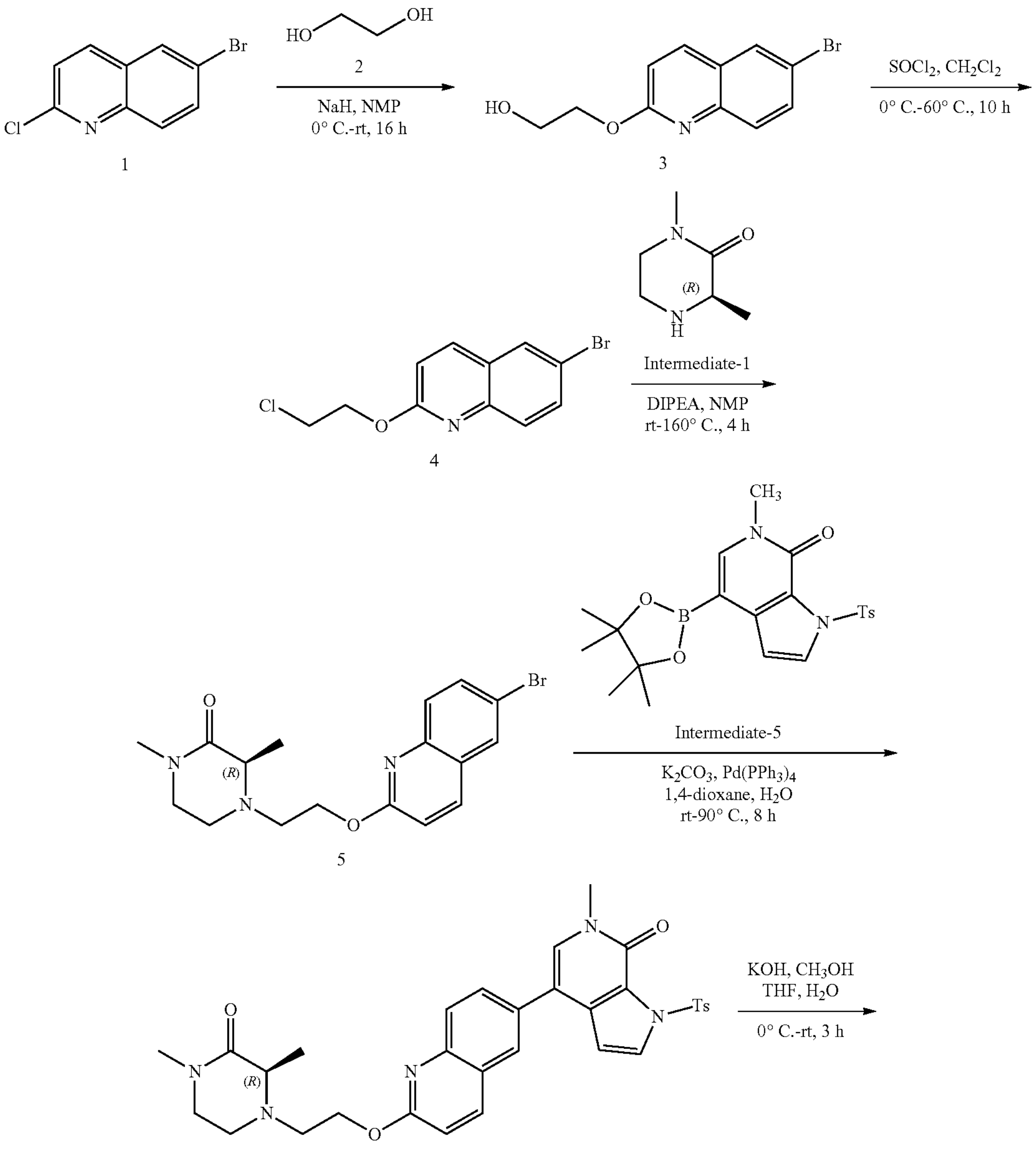

1

3

4

5

6

-continued

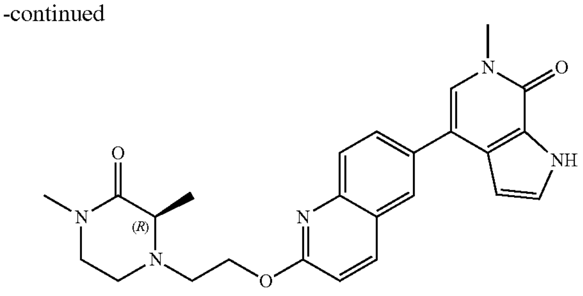

SLU-2348

2-[(6-bromoquinolin-2-yl)oxy]ethanol (3)

To a stirred solution of ethane-1,2-diol 2 (1.91 g, 30.91 mmol) in NMP (20 mL) at 0° C. under inert atmosphere NaH (60% in mineral oil, 1.23 g, 30.91 mmol) was charged portionwise for 5 min. Upon 15 min, at same temperature a solution of 6-bromo-2-chloroquinoline in NMP (10 mL) was slowly added to the reaction mixture as dropwise for 5 min and left at room temperature for 16 h. The reaction mixture was poured in to ice-cold water (200 mL) and organic compound was extracted in to EtOAc (3×200 mL). The combined organic layers were washed with ice-cold water (3×50 mL), brine (1×50 mL), dried over anhydrous $Na_2SO_4$ and concentrated under reduced pressure. The crude product was purified by column chromatography (EtOAc:n-hexanes=60:40) to afford 3 (0.85 g, 77%) as a white solid.

$^1$H NMR (400 MHz, DMSO-$d_6$): δ ppm 8.22 (d, J=8.8 Hz, 1H), 8.16 (d, J=2.0 Hz, 1H), 7.77 (dd, J=2.4, 8.8 Hz, 1H), 7.69 (d, J=8.8 Hz, 1H), 7.07 (d, J=8.8 Hz, 1H), 4.86 (t, J=5.6 Hz, 1H), 4.42 (t, J=4.8 Hz, 2H), 3.77 (m, 2H).

ESI-MS m/z $[C_{11}H_{10}BrNO_2+H]^+$ 268.0.

6-bromo-2-(2-chloroethoxy)quinoline (4)

To a stirred solution of 3 (0.50 g, 1.86 mmol) in $CH_2Cl_2$ (30 mL) was charged at 0° C. $SOCl_2$ (10 mL) was added to the reaction mixture as dropwise for 10 min. The reaction mixture was heated at 60° C. for 10 h. The reaction mixture was evaporated under reduced pressure. The crude material was washed with n-hexanes (3×20 mL) and dried under vacuum to afford 4 (0.32 g, 57%) as a white solid.

(R)-4-{2-[(6-bromoquinolin-2-yl)oxy]ethyl}-1,3-dimethylpiperazin-2-one (5)

To a stirred solution of 4 (0.32 g, 1.19 mmol), intermediate-1 (0.16 g, 1.31 mmol in N-methyl-2-pyrrolidone (5.0 mL), DIPEA (0.98 mL, 5.97 mmol) was charged at room temperature in a sealed tube and heated at 160° C. on a sand bath for 4 h. The reaction mixture was allowed to room temperature and poured in to water (100 mL). The organic compound was extracted in to EtOAc (5×200 mL). The combined organic layers were dried over anhydrous $Na_2SO_4$ and concentrated under reduced pressure. The crude product was purified by column chromatography ($CH_2Cl_2$:$CH_3OH$=95:5) to afford 5 (0.25 g, 56%) as an off-white solid.

$^1$H NMR (400 MHz, DMSO-$d_6$): δ ppm 7.98 (d, J=2.4 Hz, 1H), 7.88 (d, J=9.2 Hz, 1H), 7.73 (dd, J=2.4, 9.2 Hz, 1H), 7.55 (d, J=9.2 Hz, 1H), 6.66 (d, J=9.6 Hz, 1H), 4.27-(m, 2H), 3.20-3.23 (m, 2H), 3.10-3.16 (m, 1H), 3.03-3.08 (m, 1H), 2.81-2.84 (m, 1H), 2.78 (s, 3H), 2.55-2.68 (m, 2H), 1.05 (d, J=6.8 Hz, 3H).

(R)-4-{2-[2-(2,4-dimethyl-3-oxopiperazin-1-yl) ethoxy]quinolin-6-yl}-6-methyl-1-tosyl-1H-pyrrolo [2,3-c]pyridin-7(6H)-one (6)

To a stirred solution of 5 (0.25 g, 0.65 mmol) in 4:1 of dioxane, $H_2O$ (25 mL), intermediate-5 (0.31 g), $K_2CO_3$ (0.17 g, 1.30 mmol) were charged at room temperature and purged with argon for 5 min. $Pd(PPh_3)_4$ (0.07 g, 0.06 mmol) was added to the reaction mixture at room temperature. The reaction mixture was heated at 90° C. for 8 h. The reaction mixture was filtered through celite pad, washed with EtOAc (2×50 mL), dried over anhydrous $Na_2SO_4$, concentrated under reduced pressure and purified by combi flash chromatography ($CH_2Cl_2$:$CH_3OH$=95:5) to afford 6 (0.17 g, 44%) as a brown gum.

ESI-MS m/z $[C_{32}H_{33}N_5O_5S+H]^+$ 600.3.

(R)-4-{2-[2-(2,4-dimethyl-3-oxopiperazin-1-yl) ethoxy]quinolin-6-yl}-6-methyl-1H-pyrrolo[2,3-c] pyridin-7(6H)-one (SLU-2348)

To a stirred solution of 6 (0.15 g, 0.25 mmol) in $CH_3OH$ (6.0 mL), $H_2O$ (2.0 mL), THF (6.0 mL) was charged with potassium hydroxide (0.07 g, 1.25 mmol) at 0° C. and stirred at room temperature for 3 h. The reaction mixture was diluted with $CH_2Cl_2$ (100 mL) and $H_2O$ (15 mL). The organic layer was separated, dried over anhydrous $Na_2SO_4$ and concentrated under reduced pressure. The crude product was purified by combi flash chromatography ($CH_2Cl_2$:$CH_3OH$=92:8) as an eluent followed by reverse phase column chromatography ($CH_3CN$:$H_2O$=55:45) to afford SLU-2348 (0.01 g, 16%) as a white solid.

$^1$H NMR (400 MHz, DMSO-$d_6$): δ ppm 12.18 (s, 1H), 7.99 (d, J=9.6 Hz, 1H), 7.94 (d, J=2.0 Hz, 1H (t, J=5.2 Hz, 2H), 3.08-3.19 (m, 2H), 2.84-2.89 (m, 1H), 2.79 (s, 3H), 2.61-2.74 (m, 2H), 1.11 (d, J=6.8 Hz, 3H).

ESI-MS m/z $[C_{25}H_{27}N_5O_3+H]^+$ 446.4.

HPLC (Method A) 93.3% (AUC), $t_R$=5.97 min.

Synthesis of (R)-4-{2-[3-(3-(2,4-dimethyl-3-oxopiperazin-1-yl)propoxy)phenyl]quinolin-6-yl}-6-methyl-1H-pyrrolo[2,3-c]pyridin-7(6H)-one (SLU-2292)
Scheme 86
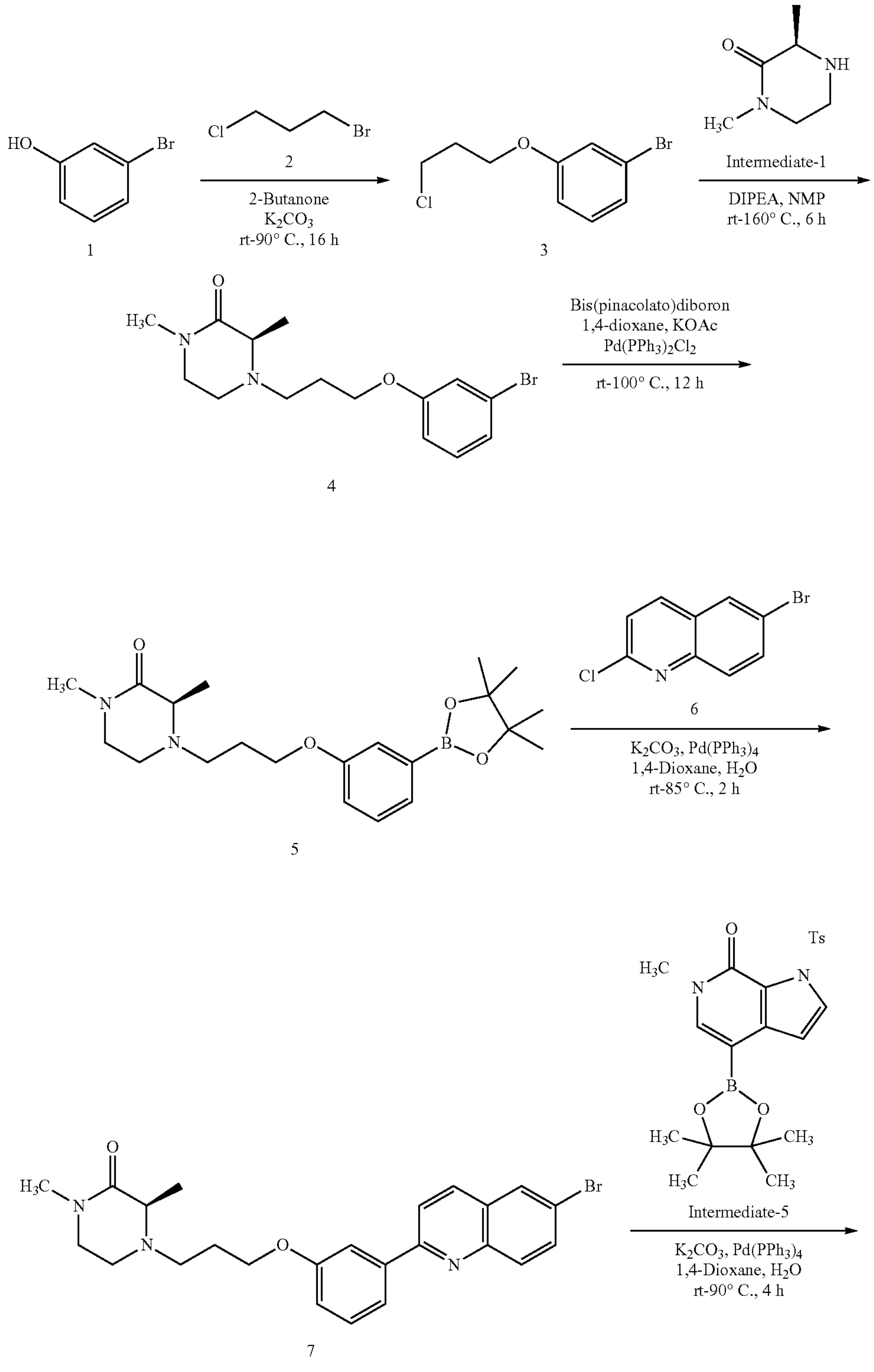
1 3 4 5 7

-continued

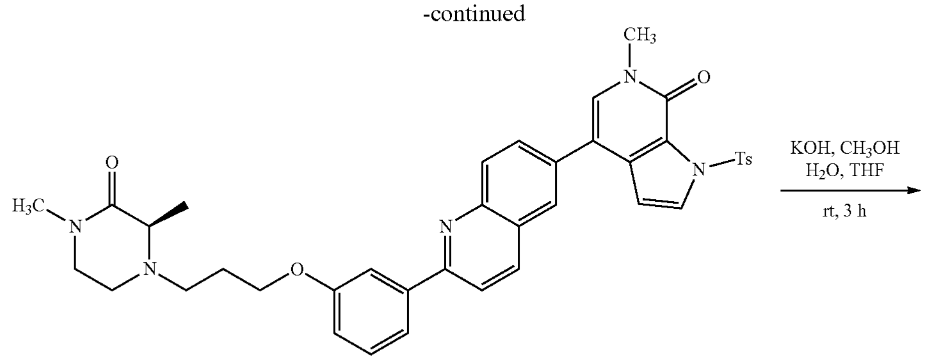

8

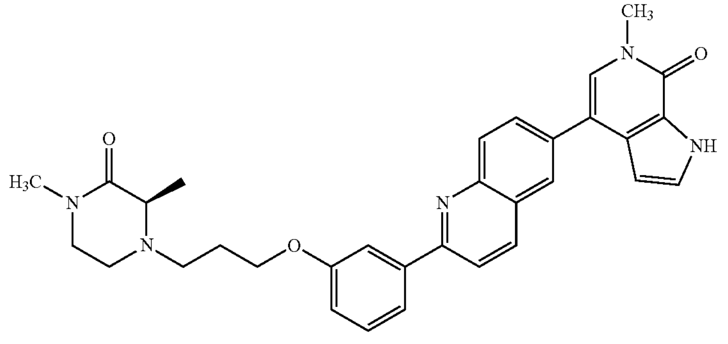

SLU-2292

1-bromo-3-(3-chloropropoxy)benzene (3)

To a stirred solution of 3-bromo phenol 1 (2.00 g, 11.5 mmol) in 2-butanone (40 mL), $K_2CO_3$ (4.76 g, 34.5 mmol), 1-bromo-3-chloropropane 2 (6.0 mL, 57.8 mmol) were charged at room temperature and heated at 90° C. for 16 h. The reaction mixture was allowed to room temperature and diluted with water (50 mL) and extracted with EtOAc (3×50 mL). The combined organic layers were dried over anhydrous $Na_2SO_4$ and concentrated under reduced pressure.to afford 3 (1.90 g, 63%) as colorless liquid.

$^1$H NMR (400 MHz, $CDCl_3$): δ ppm 7.07-7.16 (m, 1H), 7.03-7.07 (m, 2H), 6.82-6.84 (m, 1H), 4.09 (t, J=5.6 Hz, 2H), 3.73 (t, J=6.4 Hz, 2H), 2.23 (q, J=6.0 Hz, 2H).

(R)-4-[3-(3-bromophenoxy)propyl]-1,3-dimethylpiperazin-2-one (4)

To a stirred solution of 3 (1.90 g, 7.6 mmol) and Intermediate-1 (1.17 g, 9.1 mmol) in N-methyl-2-pyrrolidone (15 mL), DIPEA (3.9 mL, 22.8 mmol) was charged at room temperature in a sealed tube and heated at 160° C. on a sand bath for 6 h. The reaction mixture was allowed to room temperature and poured in to water (50 mL). The organic compound was extracted in to EtOAc (3×50 mL). The combined organic layers were washed with ice-cold water (3×50 mL), brine (1×50 mL), dried over anhydrous $Na_2SO_4$ and concentrated under reduced pressure. The resulting compound was purified by combi flash chromatography ($CH_2Cl_2$:$CH_3OH$=97:3) to afford 4 (0.90 g, 37%) as an off-white solid.

$^1$H NMR (400 MHz, DMSO-$d_6$) δ ppm 7.29 (d, J=7.6 Hz, 1H), 7.23 (d, J=6.8 Hz, 1H), 7.14 (d, J=2.4 Hz, 1H), 7.04 (dd, J=1.6, 8.0 Hz, 1H), 4.00 (t, J=6.8 Hz, 2H), 3.22-3.26 (m, 2H), 2.96-3.01 (m, 2H), 2.80 (s, 3H), 2.71-2.76 (m, 1H), 2.40-2.47 (m, 2H), 1.83-1.86 (m, 2H), 1.19 (d, J=6.8 Hz, 3H).

(R)-1,3-dimethyl-4-{3-[3-(4,4,5,5-tetramethyl-1,3,2-dioxaborolan-2-yl)phenoxy]propyl}piperazin-2-one (5)

To a stirred solution of 5 (0.90 g, 2.78 mmol) in 1,4-dioxane (5.0 mL), bis(pincolato)diboron (0.84 g, 3.34 mmol), Pd(dppf)$Cl_2$ (0.18 g, 0.27 mmol) and KOAc (0.54 g, 5.56 mmol) were charged at room temperature and heated at 100° C. for 12 h. The reaction mixture was diluted with water (40 mL) and extracted with EtOAc (3×50 mL). The combined organic layers were dried over anhydrous $Na_2SO_4$, concentrated under reduced pressure and crude product was purified by combi flash chromatography ($CH_2Cl_2$:$CH_3OH$=95:5) to afford 5 (0.35 g, 32%) as colourless liquid.

(R)-4-{3-[3-(6-bromoquinolin-2-yl)phenoxy]propyl}-1,3-dimethyl piperazin-2-one (7)

A solution of 5 (0.35 g, 0.90 mmol) in 1,4-dioxane (8.0 mL), $H_2O$ (2.0 mL) were charged with 6-bromo-2-chloroquinoline 6 (0.21 g, 0.90 mmol), potassium carbonate (0.24 g, 1.8 mmol) at room temperature and degassed it with argon for 5 min. Pd($PPh_3$)$_4$ (0.10 g, 0.09 mmol) was added to the reaction mixture and stirred at 85° C. for 2 h. The reaction mixture was diluted with water (20 mL) and extracted with EtOAc (2×30 mL). The combined organic layers were dried over anhydrous $Na_2SO_4$, concentrated under reduced pressure and crude material was purified by combi flash chromatography ($CH_2Cl_2$:MeOH=95:5) to afford 7 (0.20 g, 49%) as an off-white solid.

$^1H$ NMR (400 MHz, DMSO-$d_6$) δ ppm 8.44 (d, J=8.4 Hz, 1H), 8.31 (d, J=2.0 Hz, 1H), 8.22 (d, J=8.8 Hz, 1H), 8.01 (d, J=8.8 Hz, 1H), 7.89 (dd, J=2.4, 9.2 Hz, 1H), 7.82 (d, J=2.4 Hz, 2H), 7.46 (t, J=8.0 Hz, 1H), 7.07-7.10 (m, 1H), 4.14 (t, J=6.0 Hz, 2H), 3.23-3.27 (m, 2H), 2.99-3.06 (m, 2H), 2.75-2.85 (m, 4H), 2.54-2.56 (m, 1H), 2.44-2.47 (m, 1H), 1.90-1.94 (m, 2H), 1.22 (d, J=6.8 Hz, 3H).

(R)-4-{2-[3-(3-(2,4-dimethyl-3-oxopiperazin-1-yl) propoxy)phenyl]quinolin-6-yl}-6-methyl-1-tosyl-1H-pyrrolo[2,3-c]pyridin-7(6H)-one (8)

A solution of 7 (0.230 g, 0.50 mmol) in 1,4-dioxane (8.0 mL), $H_2O$ (2.0 mL) were charged with Intermediate-5 (0.23 g, 0.55 mmol), potassium carbonate (0.13 g, 1.0 mmol) at room temperature and degassed it with argon for 5 min. $Pd(PPh_3)_4$ (0.05 g, 0.05 mmol) was added to the reaction mixture and stirred at 90° C. for 4 h. The reaction mixture was diluted with water (20 mL) and extracted with EtOAc (2×30 mL). The combined organic layers were dried over anhydrous $Na_2SO_4$, concentrated under reduced pressure and crude material was purified by combi flash chromatography ($CH_2Cl_2$:MeOH=95:5) to afford 8 (0.115 g, 33%) as a gummy solid.

$^1H$ NMR (400 MHz, DMSO-$d_6$) δ ppm 8.50 (d, J=8.8 Hz, 1H), 8.14-8.20 (m, 3H), 8.09 (d, J=3.6 Hz, 1H), 7.99 (d, J=8.4 Hz, 2H), 7.93 (dd, J=2.4, 8.8 Hz, 1H), 7.84-7.86 (m, 2H), 7.81 (s, 1H), 7.44-7.48 (m, 3H), 7.08 (dd, J=1.6, 7.6 Hz, 1H), 6.88 (d, J=3.2 Hz, 1H), 4.15 (t, J=5.6 Hz, 2H), 3.52 (s, 3H), 3.24-3.28 (m, 2H), 3.00-3.05 (m, 2H), 2.80 (s, 4H), 2.55-2.57 (m, 2H), 2.40 (s, 3H), 1.89-1.93 (m, 2H), 1.22 (d, J=6.8 Hz, 3H).

(R)-4-{2-[3-(3-(2,4-dimethyl-3-oxopiperazin-1-yl) propoxy)phenyl]quinolin-6-yl}-6-methyl-1H-pyrrolo [2,3-c]pyridin-7(6H)-one (SLU-2292)

To a stirred solution of 8 (0.115 g, 0.16 mmol) in $CH_3OH$ (5.0 mL), THF (2.0 mL), water (2.0 mL) was charged with potassium hydroxide (0.05 g, 0.83 mmol) and stirred for 3 h at room temperature. The reaction mixture was evaporated, diluted with water (15 mL) and extracted with EtOAc (3×20 mL). The combined organic layers were dried over anhydrous $Na_2SO_4$ and concentrated under reduced pressure. The crude product was purified by reverse phase chromatography (ACN:$H_2O$=70:30) to afford SLU-2292 (0.057 g, 64%) as an off-white solid.

ESI-MS m/z $[C_{32}H_{33}N_5O_3+H]^+$ 536.3.

HPLC (Method B) 97.7% (AUC), $t_R$=6.80 min.

$^1H$ NMR (400 MHz, DMSO-$d_6$) δ ppm 12.23 (s, 1H), 8.51 (d, J=8.8 Hz, 1H), 8.13-8.22 (m, 3H), 8.05 (dd, J=2.0, 8.8 Hz, 1H), 7.84-7.86 (m, 2H), 7.62 (s, 1H), 7.46 (t, J=8.0, 1H), 7.42 (t, J=2.4 Hz, 1H), 7.08 (dd, J=2.0, 8.4 Hz, 1H), 6.63 (t, J=2.4, 1H), 4.15 (t, J=6.0 Hz, 2H), 3.64 (s, 3H), 3.24-3.28 (m, 2H), 3.00-3.05 (m, 2H), 2.77-2.84 (m, 4H), 2.45-2.55 (m, 2H), 1.89-1.93 (m, 2H), 1.23 (d, J=6.8 Hz, 3H).

Synthesis of (R)-4-{2-[4-(3-(2,4-dimethyl-3-oxopiperazin-1-yl)propyl)piperazin-1-yl]quinolin-6-yl}-6-methyl-1H-pyrrolo[2,3-c]pyridin-7(6H)-one (SLU-2346)

Scheme 87

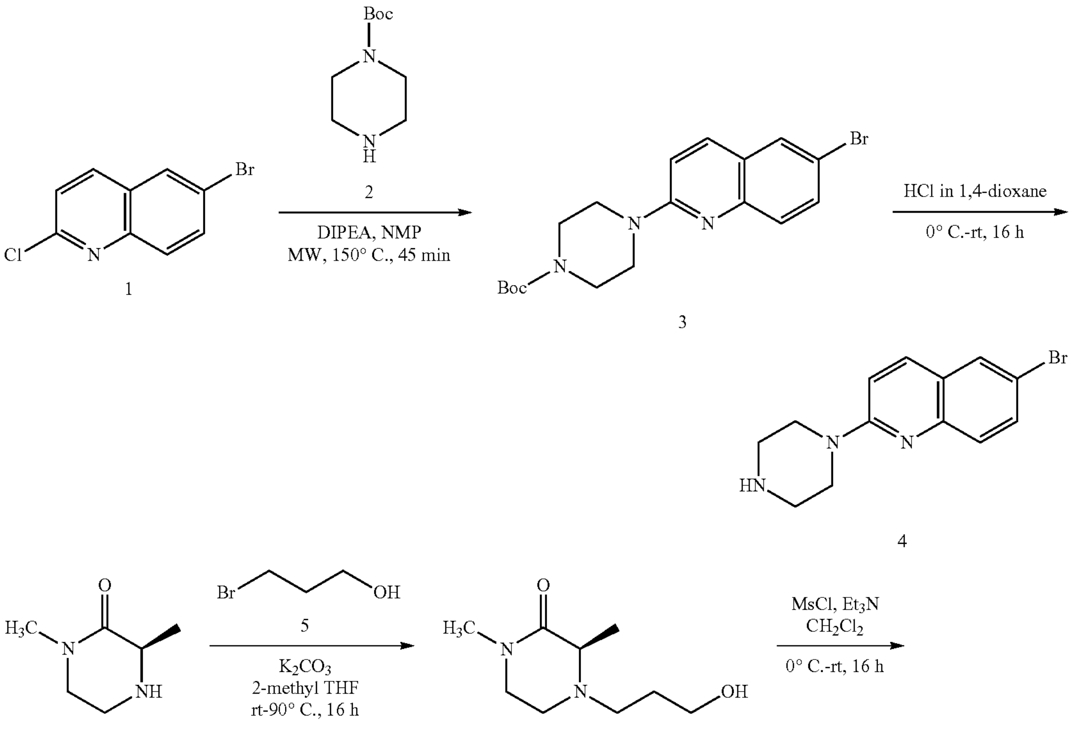

1
3
4
Intermediate-1
6

-continued
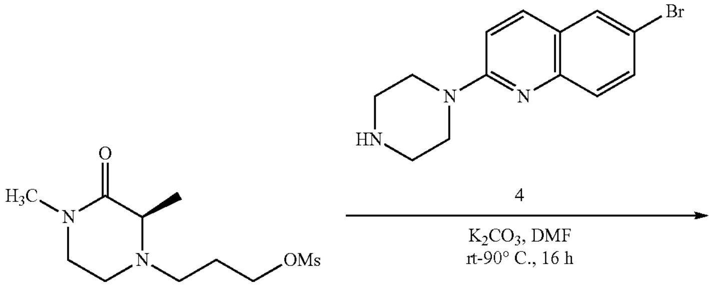
7
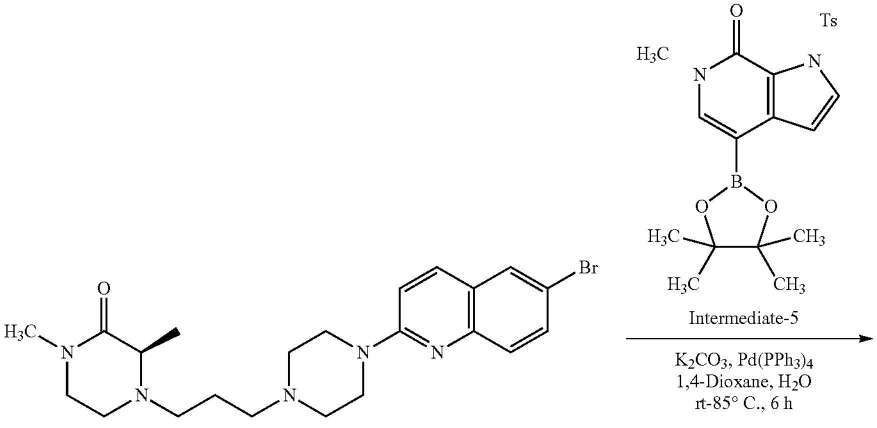
8
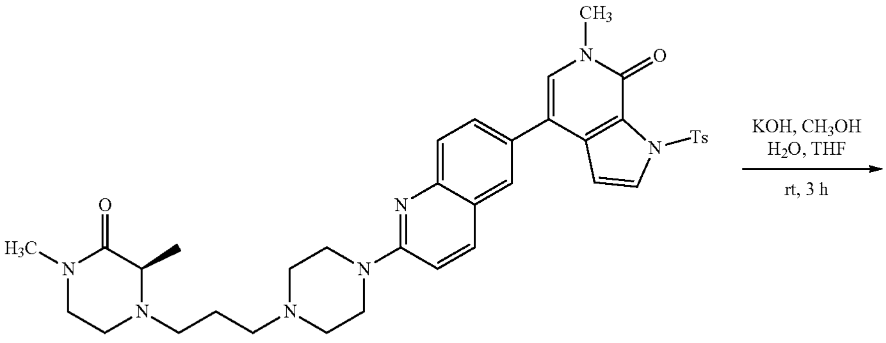
9
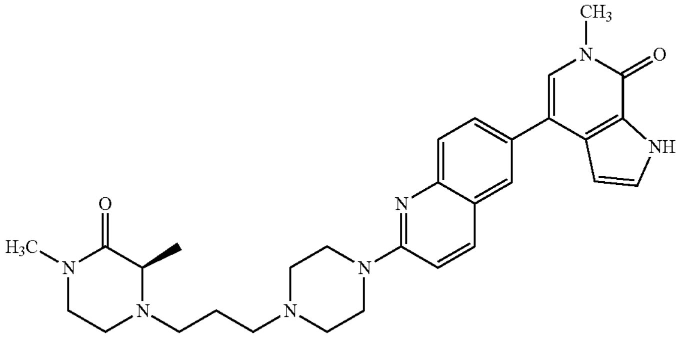
SLU-2346 tert-butyl 4-(6-bromoquinolin-2-yl)piperazine-1-carboxylate (3)

To a stirred solution of 6-bromo-2-chloroquinoline 1 (0.10 g, 0.41 mmol) in NMP (2.0 mL) tert-butyl piperazine-1-carboxylate (0.092 g, 0.49 mmol), DIPEA (0.2 mL, 1.23 mmol) were charged at room temperature and stirred for 150° C. for 45 min in microwave. The reaction mixture was allowed to room temperature and diluted with water (5.0 mL) and extracted with EtOAc (3×5 mL). The combined organic layers were dried over anhydrous $Na_2SO_4$ and concentrated under reduced pressure to afford 3 (0.085 g, 53%) as an off-white solid.

$^1$H NMR (400 MHz, DMSO-$d_6$): δ ppm 7.81 (d, J=9.2 Hz, 1H), 7.74 (d, J=2.0 Hz, 1H), 7.54-7.61 (m, 2H), 6.97 (d, J=9.2 Hz, 1H), 3.71-3.74 (m, 4H), 3.56-3.58 (m, 4H), 1.48 (s, 9H).

6-bromo-2-(piperazin-1-yl)quinoline (4)

To a stirred solution of 3 (0.81 g, 2.06 mmol) in dioxane (5.0 mL) was charged with HCl in dioxane (5.0 mL) at 0° C. and stirred for 16 h at room temperature. The reaction mixture was concentrated and diluted with water (20 mL). The reaction mixture was basified with saturated $NaHCO_3$ ($p^H$~8) and extracted with EtOAc (3×30 mL). The combined organic layers were dried over anhydrous $Na_2SO_4$ and concentrated under reduced pressure to afford 4 [0.58 g (crude %)] as an off-white solid.

$^1$H NMR (400 MHz, DMSO-$d_6$): δ ppm 9.4 (br.s., 2H), 8.25 (d, J=9.2 Hz, 1H), 8.11 (s, 1H), 7.79 (d, J=7.6 Hz, 1H), 7.49 (d, J=8.8 Hz, 1H), 4.07 (br.s., 4H), 3.26 (br.s., 4H).

(R)-4-(3-hydroxypropyl)-1,3-dimethylpiperazin-2-one (6)

To a stirred solution of intermediate-1 (1.0 g, 7.8 mmol) in 2-methyl THF (15 mL), $K_2CO_3$ (3.2 g, 23.4 mmol) and 3-bromo propanol 5 (1.60 g, 11.7 mmol) were charged at room temperature and heated at 90° C. for 16 h. The reaction mixture was allowed to room temperature, diluted with water (50 mL) and extracted with [($CHCl_3$:IPA=80:20), (3×50 mL)]. The combined organic layers were dried over anhydrous $Na_2SO_4$ and concentrated under reduced pressure to afford 6 (0.565 g, 17%) as colourless liquid.

$^1$H NMR (400 MHz, DMSO-$d_6$): δ ppm 4.4 (br.s., 1H), 3.42-3.45 (m, 2H), 3.20-3.23 (m, 1H), 2.92-2.98 (m, 2H), 2.58-2.65 (m, 1H), 2.44-2.47 (m, 4H), 2.30-2.37 (m, 1H), 1.52-1.57 (m, 2H), 1.19 (d, J=6.8 Hz, 3H).

(R)-3-(2,4-dimethyl-3-oxopiperazin-1-yl)propyl methanesulfonate (7)

To a stirred solution of 6 (0.10 g, 0.53 mmol) in $CH_2Cl_2$ (5.0 mL), $Et_3N$ (0.2 mL, 1.59 mmol), methanesulfonyl chloride (0.09 g, 0.80 mmol) were charged at 0° C. The reaction mixture warmed to room temperature and stirred for 16 h. The reaction mixture was diluted with water (5.0 mL) and extracted with [($CHCl_3$:$CH_3CH_2CH_2OH$=80:20), (3×10 mL)]. The combined organic layers were dried over anhydrous $Na_2SO_4$ and concentrated under reduced pressure to afford 7 [0.1 g (crude)] as colorless liquid.

$^1$H NMR (400 MHz, DMSO-$d_6$): δ ppm 4.27-4.32 (m, 2H), 3.75-3.77 (m, 2H), 3.14-3.20 (m, 2H), 3.05-3.09 (m, 2H), 2.86-2.89 (m, 2H), 2.35 (s, 3H), 2.19 (br.s., 2H), 1.58 (d, J=6.4 Hz, 2H). 1.32 (d, J=6.4 Hz, 3H).

(R)-4-{3-[4-(6-bromoquinolin-2-yl)piperazin-1-yl]propyl}-1,3-dimethylpiperazin-2-one (8)

To a stirred solution of 7 (0.50 g, 1.89 mmol) in DMF (8.0 mL), $K_2CO_3$ (0.78 g, 5.67 mmol) and 6-bromo-2-(piperazin-1-yl)quinoline 4 (0.55 g, 1.89 mmol) were charged at room temperature and heated at 90° C. for 16 h. The reaction mixture was allowed to room temperature and diluted with water (50 mL) and extracted with [($CHCl_3$:$CH_3CH_2CH_2OH$=80:20) (3×50 mL)]. The combined organic layers were dried over anhydrous $Na_2SO_4$, concentrated under reduced pressure and purified by combi flash chromatography ($CH_2Cl_2$:$CH_3OH$=90:10) to afford 8 (0.27 g, 31%) as a gummy solid.

$^1$H NMR (400 MHz, DMSO-$d_6$): δ ppm 8.01 (d, J=9.6 Hz, 1H), 7.94 (d, J=2.4 Hz, 1H), 7.60 (dd, J=2.0, 8.8 Hz, 1H), 7.47 (d, J=9.2 Hz, 1H), 7.29 (d, J=9.2 Hz, 1H), 3.68 (br.s., 4H), 3.33 (s, 2H), 3.22-3.25 (m, 2H), 2.95-2.99 (m, 2H), 2.80 (s, 3H), 2.58-2.65 (m, 1H), 2.47-2.49 (m, 3H), 2.33-2.36 (m, 3H), 1.54-1.64 (m, 2H), 1.20 (d, J=6.8 Hz, 3H).

(R)-4-{2-[4-(3-(2,4-dimethyl-3-oxopiperazin-1-yl)propyl)piperazin-1-yl]quinolin-6-yl}-6-methyl-1-tosyl-1H-pyrrolo[2,3-c]pyridin-7(6H)-one (9)

A solution of 8 (0.220 g, 0.47 mmol) in 1,4-dioxane (8.0 mL), $H_2O$ (2.0 mL) were charged with Intermediate-5 (0.22 g, 0.52 mmol), potassium carbonate (0.13 g, 0.94 mmol) at room temperature and degassed it with argon for 5 min. $Pd(PPh_3)_4$ (0.05 g, 0.047 mmol) was added to the reaction mixture and stirred at 85° C. for 6 h. The reaction mixture was diluted with water (20 mL), extracted with [($CH_2Cl_2$:MeOH=90:10), (3×30 mL)]. The combined organic layers were dried over anhydrous $Na_2SO_4$, concentrated under reduced pressure and crude material was purified by combi flash chromatography ($CH_2Cl_2$:MeOH=90:10) to afford 9 (0.08 g, 25%) as an off white solid.

$^1$H NMR (400 MHz, DMSO-$d_6$): δ ppm 8.05-8.10 (m, 2H), 7.97 (d, J=8.8 Hz, 2H), 7.83 (s, 1H), 7.65 (d, J=8.8 Hz, 3H), 7.44 (d, J=8.4 Hz, 2H), 7.28 (d, J=9.2 Hz, 1H), 6.77 (d, J=3.2 Hz, 1H), 3.69 (br.s., 4H), 3.48 (s, 3H), 3.24 (br.s., 2H), 2.96-3.0 (m, 2H), 2.81 (s, 3H), 2.59-2.67 (m, 2H), 2.39 (s, 3H), 2.32-2.35 (m, 5H), 1.61-1.62 (m, 2H), 1.22 (d, J=4.0 Hz, 3H).

(R)-4-{2-[4-(3-(2,4-dimethyl-3-oxopiperazin-1-yl)propyl)piperazin-1-yl]quinolin-6-yl}-6-methyl-1H-pyrrolo[2,3-c]pyridin-7(6H)-one (SLU-2346)

To a stirred solution of 9 (0.06 g, 0.08 mmol) in $CH_3OH$ (3.0 mL), THF (1.0 mL), water (1.0 mL) was charged with potassium hydroxide (0.025 g, 0.44 mmol) and stirred for 3 h at room temperature. The reaction mixture was evaporated, diluted with water (5.0 mL) and extracted with EtOAc (3×20 mL). The combined organic layers were dried over anhydrous $Na_2SO_4$ and concentrated under reduced pressure. The crude product was purified by reverse phase chromatography (ACN:$H_2O$=80:20) to afford SLU-2346 (0.021 g, 34%) as an off-white solid.

ESI-MS m/z $[C_{30}H_{37}N_7O_2+H]^+$ 528.3.

HPLC (Method A) 99.6% (AUC), $t_R$=5.75 min.

$^1$H NMR (400 MHz, $CDCl_3$) δ ppm 10.21 (s, 1H), 7.93 (d, J=9.2 Hz, 1H), 7.77 (br.s., 3H), 7.31 (t, J=2.4 Hz, 1H), 7.08 (s, 1H), 7.02 (d, J=9.2, 1H), 6.58 (t, J=2.4 Hz, 1H), 3.78 (t, J=4.4 Hz, 4H), 3.74 (s, 3H), 3.31-3.36 (m, 2H), 3.28 (q, J=4.8 Hz, 1H), 3.16-3.21 (m, 1H), 2.95 (s, 3H), 2.68-2.75 (m, 1H), 2.60-2.63 (m, 6H), 2.43-2.47 (m, 4H), 1.37 (d, J=6.4 Hz, 3H).

Synthesis of 4-{6-[8-(2-hydroxyacetyl)-2,8-diazaspiro[4.5]decan-2-yl]pyridin-3-yl}-6-methyl-1H-pyrrolo[2,3-c]pyridin-7(6H)-one (SLU-2218)

Scheme 88

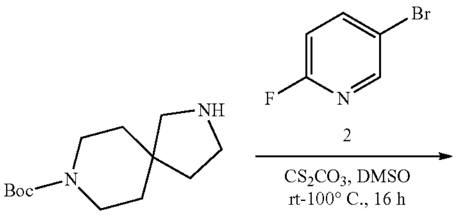

1

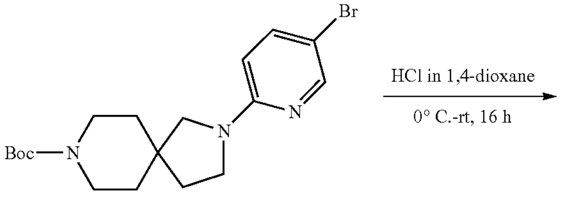

3

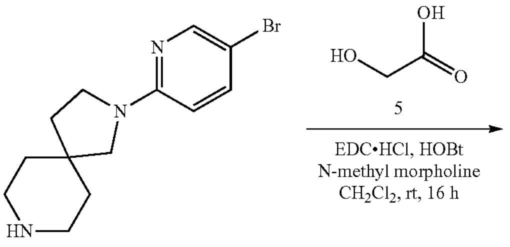

4

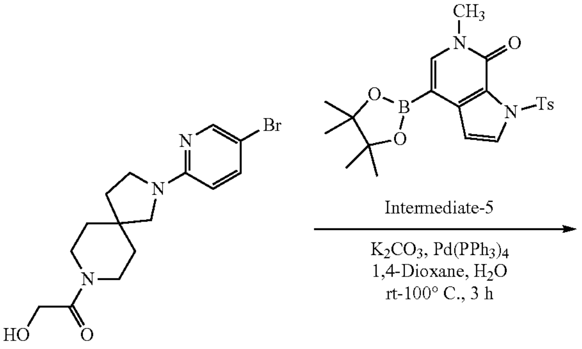

6

-continued

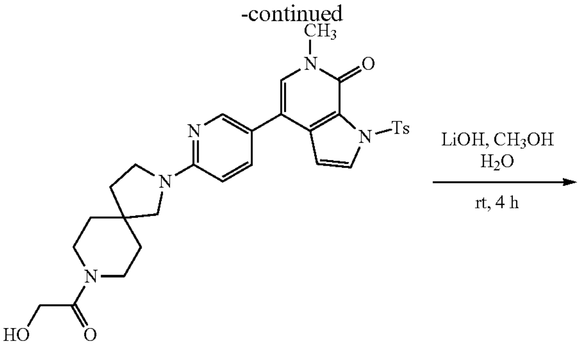

7

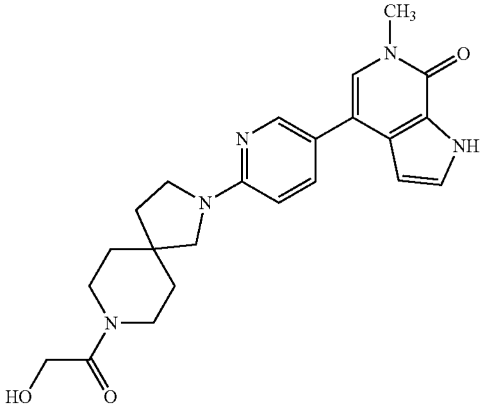

SLU-2218 tert-butyl 2-(5-bromopyridin-2-yl)-2,8-diazaspiro[4.5]decane-8-carboxylate (3)

To a stirred solution of 1 (1.00 g, 4.1 mmol), 5-bromo-2-fluoropyridine 2 (0.74 g, 4.1 mmol), $Cs_2CO_3$ (4.0 g, 12.3 mmol) in DMF (10.0 mL) at room temperature and heated at 100° C. for 16 h. TLC indicated at which time the reaction had gone to completion. The reaction mixture was diluted with water (50 mL) and extracted with EtOAc (3x80 mL). The combined organic layers were dried over anhydrous $Na_2SO_4$ and concentrated under reduced pressure. The crude product was purified by combi flash chromatography (Hexanes:EtOAc=85:15) to afford 3 (0.845 g, 52% as gummy liquid.

$^1$H NMR (400 MHz, $CDCl_3$): δ ppm 8.15 (d, J=2.0 Hz, 1H), 7.48 (dd, J=2.8, 9.2 Hz, 1H), 6.25 (d, J=9.2 Hz, 1H), 3.52-3.55 (m, 2H), 3.46 (t, J=6.8 Hz, 2H), 3.30-3.36 (m, 4H), 1.90 (t, J=7.2 Hz, 2H), 1.47 (s, 9H).

2-(5-bromopyridin-2-yl)-2,8-diazaspiro[4.5]decane (4)

To a stirred solution of 3 (0.40 g, 1.0 mmol) in dioxane (4.0 mL), HCl in dioxane (5.0 mL) was charged at 0° C. and stirred for 16 h at room temperature. TLC indicated at which time the reaction had gone to completion. The reaction mixture was concentrated to afford 4 (0.30 g) as a gummy solid. The crude was used for next step.

1-[2-(5-bromopyridin-2-yl)-2,8-diazaspiro[4.5]decan-8-yl]-2-hydroxyethanone (6)

To a stirred solution of 4 (0.17 g, 0.67 mmol) in $CH_2Cl_2$ (10 mL) EDC·HCl (0.19 g, 1.0 mmol), HOBT (0.108 g, 0.8 mmol), N-methyl morpholine (0.16 g, 1.67 mmol) were charged room temperature and stirred at room temperature for 16 h. The reaction mixture was diluted with water (20 mL) and extracted with EtOAc (3×20 mL). The combined organic layers were dried over anhydrous $Na_2SO_4$, concentrated under reduced pressure and crude material was purified by combi flash chromatography ($CH_2Cl_2$:$CH_3OH$=95:5) to afford 6 (0.115 g, 57%) as an off-white solid.

$^1$H NMR (400 MHz, DMSO-$d_6$): δ ppm 8.10 (d, J=2.4 Hz, 1H), 7.62 (dd, J=2.4, 11.6 Hz, 1H), 6.43 (d, J=11.6 Hz, 1H), 4.47 (t, J=7.2 Hz, 1H), 4.07 (d, J=6.8 Hz, 2H), 3.55 (br.s., 1H), 3.41 (t, J=9.2 Hz, 4H), 3.27 (s, 3H), 1.87 (t, J=9.2 Hz, 2H), 1.51-1.53 (m, 4H).

4-{6-[8-(2-hydroxyacetyl)-2,8-diazaspiro[4.5]decan-2-yl]pyridin-3-yl}-6-methyl-1-tosyl-1H-pyrrolo[2,3-c]pyridin-7(6H)-one (7)

To a stirred solution of 6 (0.115 g, 0.31 mmol), Intermediate-5 (0.16 g, 0.37 mmol), $K_2CO_3$ (0.105 g, 0.77 mmol) in dioxane (5.0 mL), water (1.0 mL) was charged at room temperature and degassed it with argon for 2 min at room temperature. $Pd(PPh_3)_4$ (0.018 g, 0.015 mmol) was added to the reaction mixture, degassed it with argon for 2 min at room temperature and heated at 100° C. for 3 h. TLC indicated at which time the reaction had gone to completion. The reaction mixture was diluted with water (10.0 mL) and extracted with EtOAc (3×15 mL). The combined organic layers were dried over anhydrous $Na_2SO_4$ and concentrated under reduced pressure. The crude product was purified by combi flash chromatography ($CH_2Cl_2$:$CH_3OH$=95:5) to afford 7 (0.07 g, 37%) as an off-white solid.

$^1$H NMR (400 MHz, DMSO-$d_6$): δ ppm 8.16 (d, J=2.4 Hz, 1H), 8.00 (d, J=3.2 Hz, 1H), 7.96 (d, J=8.4 Hz, 2H), 7.61 (dd, J=2.4, 8.8 Hz, 1H), 7.47 (s, 1H), 7.42 (d, J=8.0 Hz, 2H), 6.63 (d, J=3.2 Hz, 1H), 6.54 (d, J=8.8 Hz, 1H), 4.47 (t, J=5.6 Hz, 1H), 4.08-4.09 (m, 2H), 3.56-3.62 (m, 1H), 3.48 (t, J=6.8 Hz, 2H), 3.45 (s, 4H), 3.35 (s, 3H), 3.16 (d, J=5.2 Hz, 1H), 2.38 (s, 3H), 1.89 (t, J=7.2 Hz, 2H), 1.50-1.55 (m, 4H).

4-{6-[8-(2-hydroxyacetyl)-2,8-diazaspiro[4.5]decan-2-yl]pyridin-3-yl}-6-methyl-1H-pyrrolo[2,3-c]pyridin-7(6H)-one (SLU-2218)

To a stirred solution of 7 (0.06 g, 0.1 mmol) in $CH_3OH$ (2.0 mL), water (0.5 mL) was charged with lithium hydroxide (0.022 g, 0.5 mmol) at room temperature and stirred for 4 h at room temperature. The reaction mixture was evaporated, diluted with water (5.0 mL) and extracted with EtOAc (3×10 mL). The combined organic layers were dried over anhydrous $Na_2SO_4$ and concentrated under reduced pressure. The crude product was purified by reverse phase chromatography ($H_2O$:ACN=40:60) to afford SLU-2218 (0.07 g, 14%) as off-white solid.

ESI-MS m/z $[C_{23}H_{27}N_5O_3+H]^+$ 422.3.

HPLC (Method B) 95.7% (AUC), $t_R$=6.54 min.

$^1$H NMR (400 MHz, $CD_3OD$): δ ppm 8.23 (d, J=2.0 Hz, 1H), 7.77 (dd, J=2.4, 8.4 Hz, 1H), 7.38 (d, J=2.8, 1H), 7.19 (s, 1H), 6.63 (d, J=8.8 Hz, 1H), 6.47 (d, J=2.8 Hz, 1H), 4.24 (s, 2H), 3.72-3.77 (m, 1H), 3.69 (s, 3H), 3.53-3.65 (m, 3H), 3.45-3.48 (m, 1H), 3.43 (s, 3H), 2.01 (t, J=6.8 Hz, 2H), 1.63-1.68 m, 4H).

Synthesis of 4-{6-[8-(2-hydroxyacetyl)-2,8-diazaspiro[4.5]decan-2-yl]pyridin-3-yl}-6-methyl-1H-pyrrolo[2,3-c]pyridin-7(6H)-one (SLU-2127)

Scheme 89

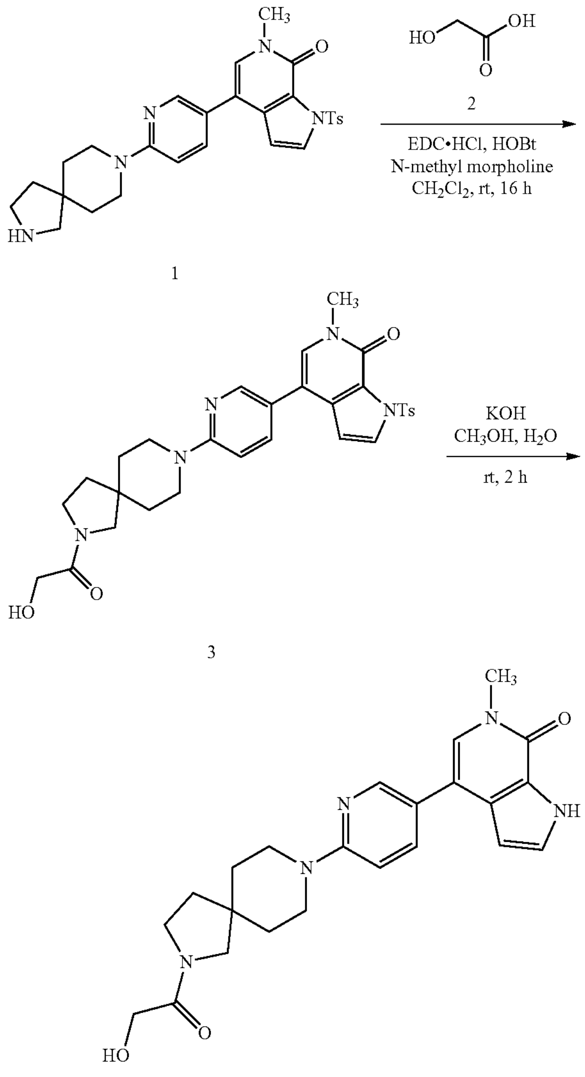

SLU-2127

Note: 1 is available in Scheme 58, comound 5

4-{6-[2-(2-hydroxyacetyl)-2,8-diazaspiro[4.5]decan-8-yl]pyridin-3-yl}-6-methyl-1-tosyl-1H-pyrrolo[2,3-c]pyridin-7(6H-one (3)

To a stirred solution of 1 (0.30 g, 0.77 mmol) in $CH_2Cl_2$ (10 mL) EDC·HCl (0.22 g, 1.15 mmol), HOBT (0.125 g, 0.92 mmol), N-methyl morpholine (0.19 g, 1.92 mmol) were charged at room temperature and stirred at room temperature for 16 h. The reaction mixture was diluted with water (20 mL) and extracted with EtOAc (3×20 mL). The combined organic layers were dried over anhydrous $Na_2SO_4$, concentrated under reduced pressure and crude material was purified by combi flash chromatography ($CH_2Cl_2$:$CH_3OH$=92:8) to afford 3 (0.10 g, 520%) as an off-white solid.

$^1H$ NMR (300 MHz, DMSO-$d_6$) δ ppm 8.21 (br.s., 1H), 7.95-8.01 (m, 4H), 7.71 (d, J=7.8 Hz, 1H), 7.52 (br.s., 1H), 7.39 (d, J=8.7 Hz, 3H), 6.94 (d, J=9.0 Hz, 1H), 6.65 (d, J=3.3 Hz, 1H), 4.49-4.50 (m, 1H), 4.09 (br.s., 1H), 3.90 (s, 5H), 3.62-3.66 (m, 2H), 3.44 (s, 3H), 2.42 (s, 3H), 1.83-1.90 (m, 1H), 1.72-1.76 (m, 1H), 1.54 (br. s., 3H).

4-{6-[2-(2-hydroxyacetyl)-2,8-diazaspiro[[4.5]decan-8-yl]pyridin-3-yl}-6-methyl-1H-pyrrolo[2,3-c]pyridin-7(6H)-one (SLU-2127)

To a stirred solution of 3 (0.10 g, 0.3 mmol) in $CH_3OH$ (5.0 mL), water (2.0 mL) was charged with potassium hydroxide (0.32 g, 9.13 mmol) at room temperature and stirred for 2 h at room temperature. The reaction mixture was evaporated, diluted with water (5.0 mL) and extracted with EtOAc (3×20 mL). The combined organic layers were dried over anhydrous $Na_2SO_4$ and concentrated under reduced pressure. The crude product was purified by reverse phase chromatography ($H_2O$:ACN=30:70) to afford SLU-2127 (0.022 g, 30%) as a white solid.

ESI-MS m/z $[C_{23}H_{27}N_5O_3+H]^+$ 422.1.

HPLC (Method F) 97.4% (AUC), $t_R$=6.04 min.

$^1H$ NMR (300 MHz, DMSO-$d_6$) δ ppm 12.1 (s, 1H), 8.32 (s, 1H), 7.72 (d, J=7.5 Hz, 1H), 7.33 (br.s., 1H), 7.29 (s, 1H), 6.94 (d, J=8.4 Hz, 1H), 6.38 (s, 1H), 4.49 (br.s., 1H), 4.00 (s, 2H), 3.62-3.64 (m, 2H), 3.56 (s, 4H), 3.43-3.45 (m, 3H), 3.26-3.28 (m, 2H), 1.84 (t, J=6.6 Hz, 1H), 1.75 (t, J=6.9 Hz, 1H), 1.55 (s, 4H).

Synthesis of (R)-6-allyl-4-{6-[4-(2-(2,4-dimethyl-3-oxopiperazin-1-yl)ethoxy)phenyl]quinolin-2-yl}-1H-pyrrolo[2,3-c]pyridin-7(6H)-one (SLU-2326)

Scheme 90

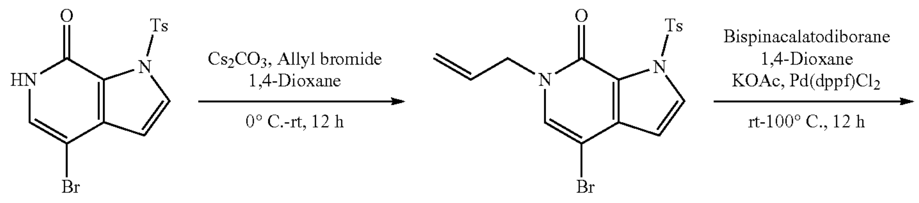

1
Scheme 3

2

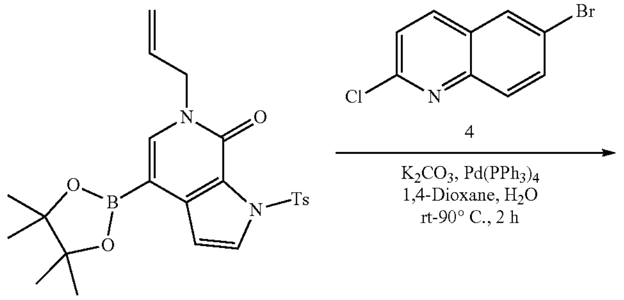

4

3

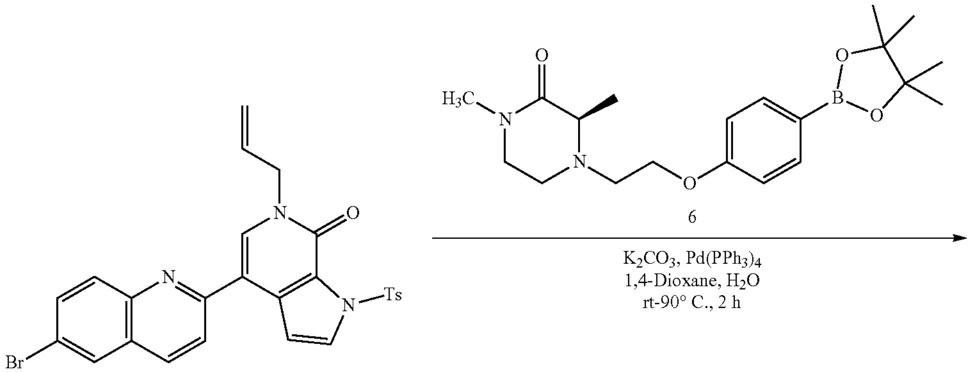

6

5

-continued

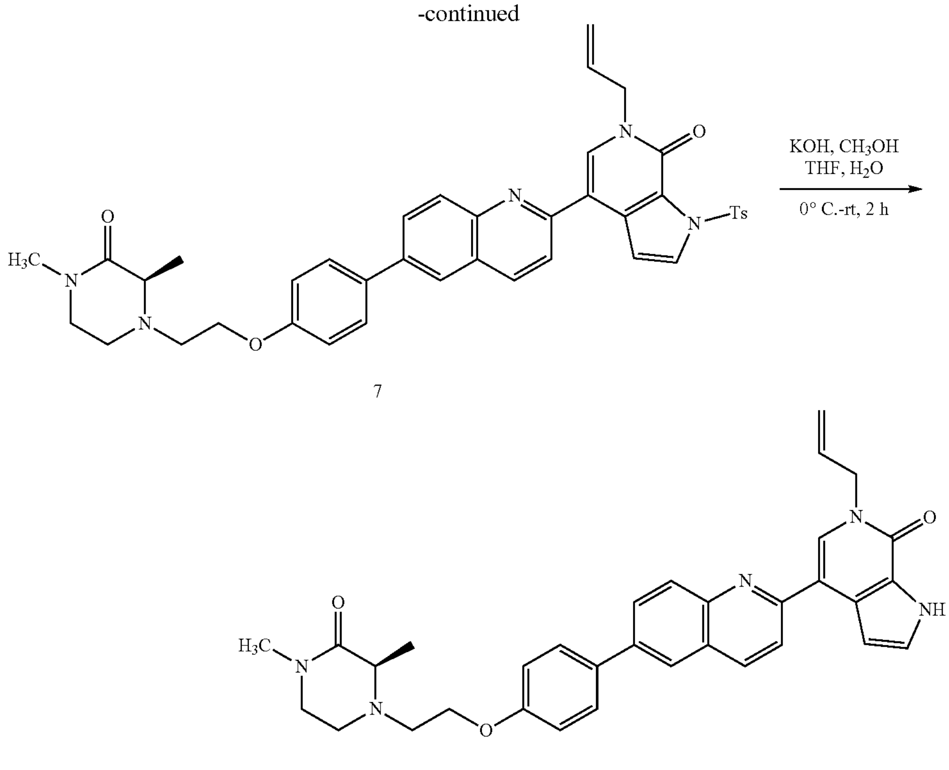

7

SLU-2326

Note: 1 available in Scheme 3

6-allyl-4-bromo-1-tosyl-1H-pyrrolo[2,3-c]pyridin-7(6H)-one (2)

Allyl bromide (1.30 g, 10.9 mmol) was charged dropwisely to stirred suspension of 1 (2.00 g, 5.4 mmol6), $Cs_2CO_3$ (5.2 g, 16.2 mmol) in 1,4-dioxane (20 mL) at 0° C. Upon addition, reaction mixture was stirred at room temperature for 12 h. The solvent was evaporated under reduced pressure from the reaction mixture, diluted with $H_2O$ (30 mL) and extracted with EtOAc (3×30 mL). The combined organic layers dried over anhydrous $Na_2SO_4$ and concentrated under reduced pressure afford 2 [2.20 g (crude)] as an off-white solid.

$^1H$ NMR (400 MHz, $CDCl_3$): δ ppm δ 7.99 (d, J=8.3 Hz, 2H), 7.93 (d, J=3.4 Hz, 2H), 7.29 (d, J=8.0 Hz, 2H), 7.13 (s, 1H). 6.50 (d, J=3.4 Hz, 1H), 5.90-5.80 (m, 1H). 5.29-5.13 (s, 2H). 4.06-4.01 (m, 2H), 2.40 (s, 3H).

Preparation 6-allyl-4-(4,4,5,5-tetramethyl-1,3,2-dioxaborolan-2-yl)-1-tosyl-1H-pyrrolo[2,3-c]pyridin-7(6H)-one (3)

To a stirred solution of 2 (1.60 g, 3.9 mmol), bis(pinco-lato)diboron (1.10 g, 4.3 mmol), KOAc (0.940 g, 7.88 mmol) in dioxane (50 mL) was charged at room temperature and degassed it with argon for 10 min. Pd(dppf)$Cl_2$ (0.288 g, 0.39 mmol) was added to the reaction mixture and heated at 100° C. for 12 h. TLC indicated at which time the reaction had gone to completion. The reaction mixture was diluted with water (50 mL) and extracted with EtOAc (3×40 mL). The combined organic layers were dried over anhydrous $Na_2SO_4$ and concentrated under reduced pressure. The crude product was purified by combi flash chromatography (Hexanes:EtOAc=70:30) to afford 3 (0.600 g, 27%) as an off white solid.

$^1H$ NMR (400 MHz, $CDCl_3$): δ ppm δ 7.95 (d, J=8.2 Hz, 2H), 7.88 (d, J=3.4 Hz, 1H), 7.46 (s, 1H), 7.26 (d, J=8.0 Hz, 1H), 6.91 (d, J=3.4 Hz, 1H), 5.93-5.83 (m, 1H), 5.17-5.06 (m, 2H), 4.56 (d, J=5.6 Hz, 2H), 4.52 (s, 1H), 2.38 (s, 3H), 1.32 (s, 12H).

6-allyl-4-(6-bromoquinolin-2-yl)-1-tosyl-1H-pyrrolo[2,3-c]pyridin-7(6H)-one (5)

A solution of 6-bromo-2-chloroquinoline 4 (0.266 g, 1.10 mmol) in 1,4-dioxane (8.0 mL), $H_2O$ (2.0 mL) were charged with 3 (0.500 g, 1.10 mmol), potassium carbonate (0.304 g, 2.20 mmol) at room temperature and degassed it with argon for 5 min. $Pd(PPh_3)_4$ (0.115 g, 0.1 mmol) was added to the reaction mixture and stirred at 90° C. for 2 h. The reaction mixture was diluted with water (20 mL), extracted with EtOAc (2×30 mL). The combined organic layers were dried over anhydrous $Na_2SO_4$, concentrated under reduced pressure and crude material was purified by combi flash chromatography (Hexanes:EtOAc=95:5) to afford 5 (0.185 g, 32%) as an off-white solid.

$^1H$ NMR (400 MHz, DMSO-$d_6$) δ ppm 8.39 (d, J=8.4 Hz, 1H), 8.31 (s, 1H), 8.26 (d, J=2.0 Hz, 1H), 8.11 (d, J=3.6 Hz, 1H), 8.03 (t, J=8.4 Hz, 2H), 7.94 (d, J=8.0 Hz, 2H), 7.89 (dd, J=2.4, 8.8 Hz, 1H), 7.71 (d, J=3.6 Hz, 1H), 7.42 (d, J=8.4 Hz, 2H), 5.90-6.00 (m, 1H), 5.15 (d, J=10.4 Hz, 1H), 5.06 (d, J=17.6 Hz, 1H), 4.63 (d, J=5.2 Hz, 2H), 2.38 (s, 3H).

(R)-6-allyl-4-[6-[4-(2-(2,4-dimethyl-3-oxopiperazin-1-yl)ethoxy)phenyl]quinolin-2-yl}-1-tosyl-1H-pyrrolo[2,3-c]pyridin-7(6H)-one (6)

A solution of 5 (0.185 g, 0.34 mmol) in 1,4-dioxane (8.0 mL), $H_2O$ (2.0 mL) were charged with Intermediate-3 (0.130 g, 0.34 mmol), potassium carbonate (0.094 g, 0.68 mmol) at room temperature and degassed it with argon for 5 min. $Pd(PPh_3)_4$ (0.035 g, 0.03 mmol) was added to the reaction mixture and stirred at 90° C. for 2 h. The reaction mixture was diluted with water (20 mL) and extracted with EtOAc (2×30 mL). The combined organic layers were dried over anhydrous $Na_2SO_4$, concentrated under reduced pressure and crude material was purified by combi flash chromatography ($CH_2Cl_2$:$CH_3OH$=95:5) to afford 6 (0.108 g, 32%) as a pale yellow solid.

$^1H$ NMR (400 MHz, DMSO-$d_6$) δ ppm 8.43 (d, J=8.8 Hz, 1H), 8.28 (s, 1H), 8.21 (br.s., 1H), 8.09-8.12 (m, 3H), 7.94-8.00 (m, 3H), 7.79 (d, J=8.4 Hz, 2H), 7.74 (d, J=3.6 Hz, 1H), 7.43 (d, J=8.0 Hz, 2H), 7.10 (d, J=8.8 Hz, 2H), 5.90-5.95 (m, 1H), 5.16 (dd, J=1.2, 10.0 Hz, 1H), 5.08 (dd, J=1.6, 17.2 Hz, 1H), 4.64 (d, J=5.2 Hz, 2H), 4.16 (t, J=5.6 Hz, 2H), 3.27-3.30 (m, 2H), 3.16-3.24 (m, 1H), 3.08-3.15 (m, 1H), 2.93-3.01 (m, 1H), 2.75-2.85 (m, 4H), 2.67-2.74 (m, 1H), 2.38 (s, 3H), 1.26 (d, J=6.8 Hz, 3H).

(R)-6-allyl-4-{6-[4-(2-(2,4-dimethyl-3-oxopiperazin-1-yl)ethoxy)phenyl]quinolin-2-yl}-1H-pyrrolo[2,3-c]pyridin-7(6H)-one (SLU-2326)

To a stirred solution of 12 (0.105 g, 0.14 mmol) in $CH_3OH$ (5.0 mL), THF (2.0 mL), water (2.0 mL) was charged with potassium hydroxide (0.042 g, 0.74 mmol) at room temperature. The reaction mixture was stirred for 2 h at room temperature. The reaction mixture was evaporated, diluted with water (15.0 mL) and extracted with EtOAc (3×20 mL). The combined organic layers were dried over anhydrous $Na_2SO_4$ and concentrated under reduced pressure. The crude product was purified by reverse phase chromatography (ACN:$H_2O$=70:30) to afford SLU-2326 (0.042 g, 51%) as an off-white solid.

ESI-MS m/z $[C_{33}H_{33}N_5O_3+H]^+$ 548.3.

HPLC (Method B) 99.4% (AUC), $t_R$=6.8 min.

$^1H$ NMR (400 MHz, DMSO-$d_6$) δ ppm 12.19 (br.s., 1H), 8.40 (d, J=8.8 Hz, 1H), 8.20 (d, J=2.0 Hz, 1H), 8.03-8.11 (m, 4H), 7.80 (d, J=8.8 Hz, 2H), 7.43 (t, J=2.8, 1H), 7.34 (t, J=2.0 Hz, 1H), 7.10 (d, J=8.8 Hz, 2H), 6.04-6.11 (m, 1H), 5.12-5.21 (m, 2H), 4.77 (d, J=5.2 Hz, 2H), 4.16 (t, J=6.0 Hz, 2H), 3.27-3.29 (m, 2H), 3.15-3.25 (m, 1H), 3.07-3.12 (m, 1H), 2.97-3.01 (m, 1H), 2.79-2.85 (m, 4H), 2.66-2.75 (m, 1H), 1.26 (d, J=6.8 Hz, 3H).

Synthesis of (R)-6-allyl-4-{2-[4-(2-(2,4-dimethyl-3-oxopiperazin-1-yl)ethoxy)phenyl]quinolin-6-yl}-1H-pyrrolo[2,3-c]pyridin-7(6H)-one (SLU-2293)

Scheme 91

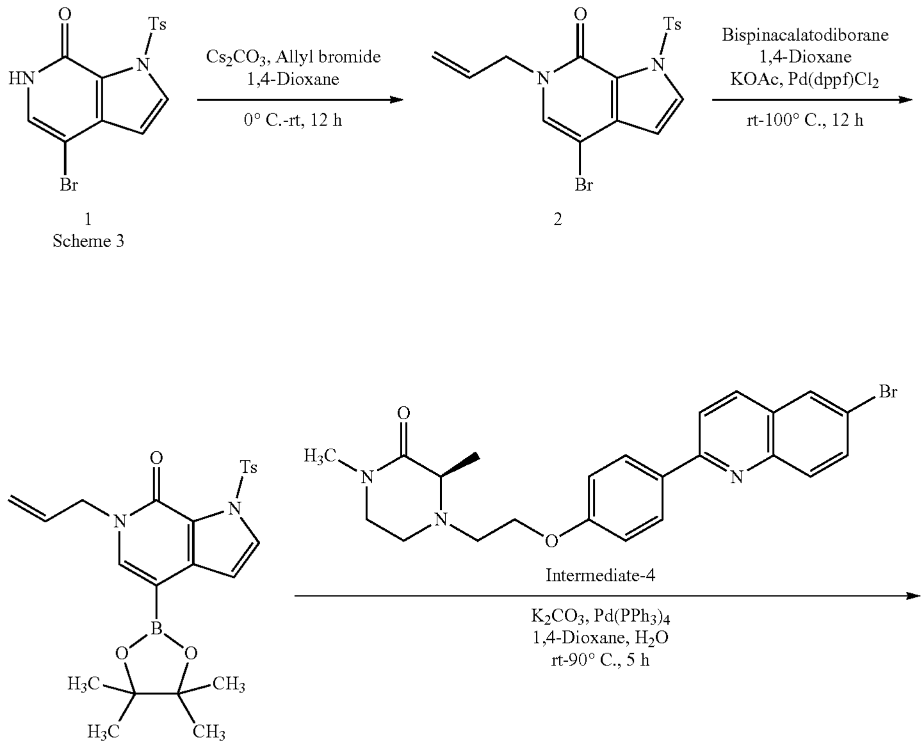

1 Scheme 3

2

3

-continued

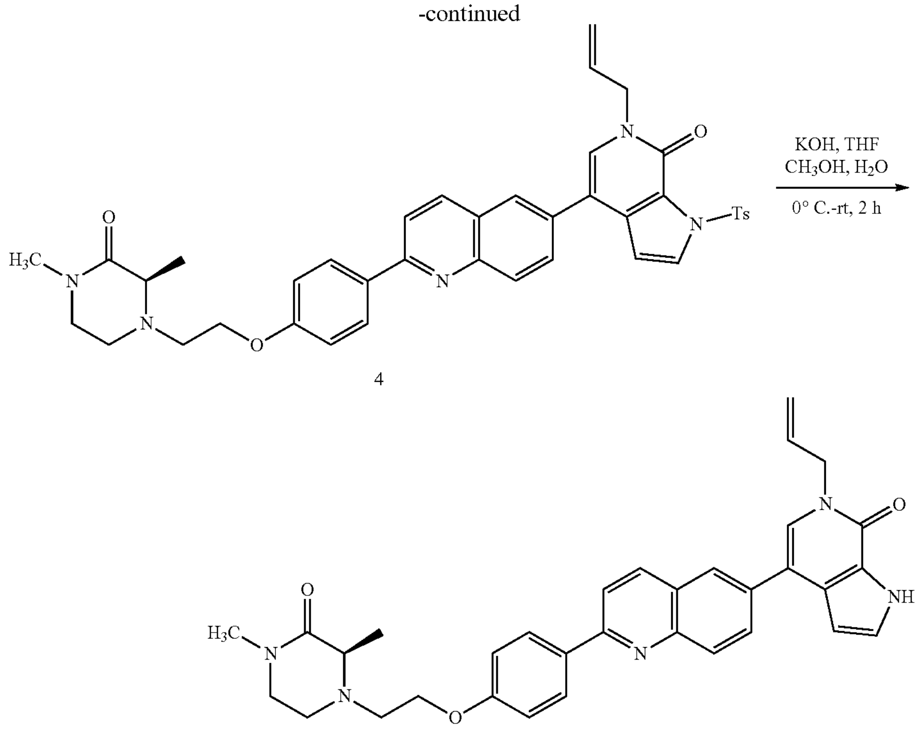

4

SLU-2293

Note: 1 available in Scheme 3

6-allyl-4-bromo-1-tosyl-1H-pyrrolo[2,3-c]pyridin-7(6H)-one (2)

Allyl bromide (1.30 g, 10.9 mmol) was charged dropwisely to stirred suspension of 1 (2.00 g, 5.4. mmol6), $Cs_2CO_3$ (5.2 g, 16.2 mmol) in 1,4-dioxane (20 mL) at 0° C. Upon addition, reaction mixture was stirred at room temperature for 12 h. The solvent was evaporated under reduced pressure from the reaction mixture, diluted with $H_2O$ (30 mL) and extracted with EtOAc (3×30 mL). The combined organic layers dried over anhydrous $Na_2SO_4$ and concentrated under reduced pressure afford 2 [2.20 g (crude)2] as an off-white solid.

$^1$H NMR (400 MHz, $CDCl_3$): δ ppm 7.99 (d, J=8.3 Hz, 2H), 7.93 (d, J=3.4 Hz, 2H), 7.29 (d, J=8.0 Hz, 2H), 7.13 (s, 1H). 6.50 (d, J=3.4 Hz, 1H), 5.90-5.80 (m, 1H). 5.29-5.13 (s, 2H). 4.06-4.01 (m, 2H), 2.40 (s, 3H).

Preparation 6-allyl-4-(4,4,5,5-tetramethyl-1,3,2-dioxaborolan-2-yl)-1-tosyl-1H-pyrrolo[2,3-c]pyridin-7(6H)-one (3)

To a stirred solution of 2 (1.60 g, 3.9 mmol), bis(pinco-lato)diboron (1.10 g, 4.3 mmol), KOAc (0.940 g, 7.88 mmol) in dioxane (50 mL) was charged at room temperature and degassed it with argon for 10 min. Pd(dppf)$Cl_2$ (0.288 g, 0.39 mmol) was added to the reaction mixture and heated at 100° C. for 12 h. TLC indicated at which time the reaction had gone to completion. The reaction mixture was diluted with water (50 mL) and extracted with EtOAc (3×40 mL). The combined organic layers were dried over anhydrous $Na_2SO_4$ and concentrated under reduced pressure. The crude product was purified by combi flash chromatography (Hexanes:EtOAc=70:30) to afford 3 (0.600 g, 27%) as an off white solid.

$^1$H NMR (400 MHz, $CDCl_3$): δ ppm 7.95 (d, J=8.2 Hz, 2H), 7.88 (d, J=3.4 Hz, 1H), 7.46 (s, 1H), 7.26 (d, J=8.0 Hz, 1H), 6.91 (d, J=3.4 Hz, 1H), 5.93-5.83 (m, 1H), 5.17-5.06 (m, 2H), 4.56 (d, J=5.6 Hz, 2H), 4.52 (s, 1H), 2.38 (s, 3H), 1.32 (s, 12H).

(R)-6-allyl-4-(2-(4-(2-(2,4-dimethyl-3-oxopiperazin-1-yl)ethoxy)phenyl)quinolin-6-yl)-1-tosyl-1H-pyrrolo[2,3-c]pyridin-7(6H)-one (4)

A solution of Intermediate-4 (0.150 g, 0.33 mmol) in 1,4-dioxane (8.0 mL), $H_2O$ (2.0 mL) were charged with 9 (0.176 g, 0.39 mmol), potassium carbonate (0.091 g, 0.66 mmol) at room temperature and degassed it with argon for 5 min. $Pd(PPh_3)_4$ (0.035 g, 0.03 mmol) was added to the reaction mixture and stirred at 90° C. for 2 h. The reaction mixture was diluted with water (10 mL) and extracted with EtOAc (2×30 mL). The combined organic layers were dried over anhydrous $Na_2SO_4$, concentrated under reduced pressure and crude material was purified by combi flash chromatography ($CH_2Cl_2$:MeOH=95:5) to afford 10 (0.105 g, 34%) as a pale yellow solid.

$^1$H NMR (400 MHz, DMSO-$d_6$) δ ppm 8.46 (d, J=8.8 Hz, 1H), 8.27 (d, J=8.8 Hz, 2H), 8.09-8.16 (m, 4H), 7.98 (d, J=8.4 Hz, 2H), 7.88 (dd, J=2.0, 8.4 Hz, 1H), 7.70 (s, 1H), 7.44 (d, J=8.4 Hz, 2H), 7.12 (d, J=8.4 Hz, 2H), 6.87 (d, J=3.6 Hz, 1H), 5.90-5.97 (m, 1H), 5.08-5.17 (m, 2H), 4.60 (d, J=5.2 Hz, 1H), 4.18 (t, J=6.0 Hz, 2H), 3.26-3.29 (m, 2H), 3.16-3.20 (m, 2H), 3.07-3.12 (m, 1H), 2.96-3.02 (m, 1H), 2.83-2.86 (m, 4H), 2.67-2.75 (m, 1H) 2.39 (s, 3H), 1.26 (d, J=6.8 Hz, 3H).

(R)-6-allyl-4-{2-[4-(2-(2,4-dimethyl-3-oxopiperazin-1-yl)ethoxy)phenyl]quinolin-6-yl}-1H-pyrrolo[2,3-c]pyridin-7(6H)-one (SLU-2293)

To a stirred solution of 10 (0.105 g, 0.14 mmol) in $CH_3OH$ (5.0 mL), THF (2.0 mL), water (2.0 mL) was charged with potassium hydroxide (0.042 g, 0.74 mmol) at room temperature. The reaction mixture was stirred for 2 h at room temperature. The reaction mixture was evaporated, diluted with water (15.0 mL) and extracted with EtOAc (3×20 mL). The combined organic layers were dried over anhydrous $Na_2SO_4$ and concentrated under reduced pressure. The crude product was purified by reverse phase chromatography (ACN:$H_2O$=70:30) to afford SLU-2293 (0.030 g, 35%) as an off-white solid.

ESI-MS m/z $[C_{33}H_{33}N_5O_3+H]^+$ 548.3.

HPLC (Method B) 99.2% (AUC), $t_R$=6.79 min.

$^1H$ NMR (400 MHz, DMSO-$d_6$): δ ppm 12.25 (s, 1H), 8.47 (d, J=8.8 Hz, 1H), 8.27 (d, J=8.8 Hz, 2H), 8.09-8.17 (m, 3H), 7.99 (dd, J=1.6, 8.4 Hz, 1H), 7.50 (s, 1H), 7.43 (t, J=2.8, 1H), 7.12 (d, J=8.8 Hz, 2H), 6.62 (s, 1H), 6.00-6.10 (m, 1H), 5.13-5.21 (m, 2H), 4.73 (d, J=5.2 Hz, 2H), 4.19 (t, J=5.6 Hz, 2H), 3.26-3.29 (m, 2H), 3.2 (q, J=8.0 Hz, 1H), 3.08-3.15 (m, 1H), 2.97-3.07 (m, 1H), 2.83-2.86 (m, 4H), 2.67-2.75 (m, 1H), 1.26 (d, J=6.8 Hz, 3H).

Synthesis of 4-(2-methoxyquinolin-6-yl)-6-methyl-1H-pyrrolo[2,3-c]pyridin-7(6H)-one (SLU-2294)

Scheme 92

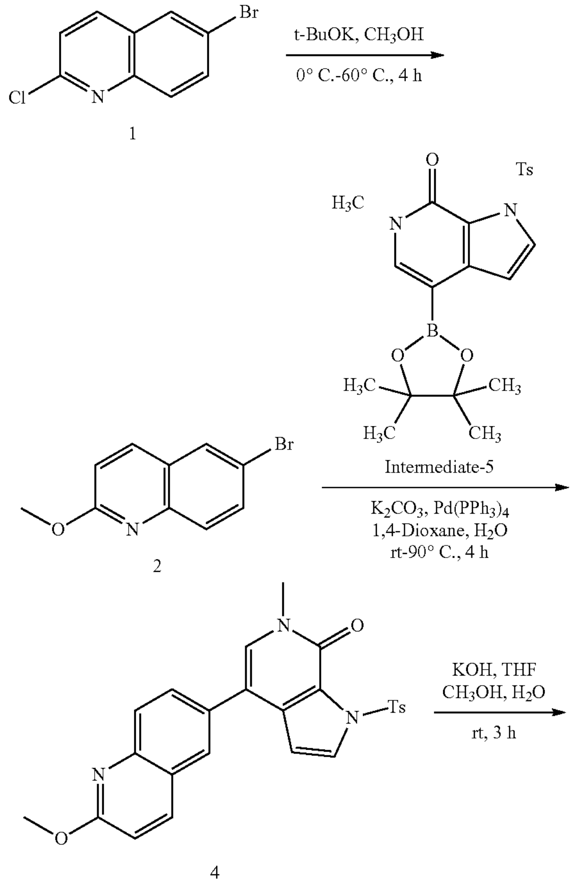

-continued

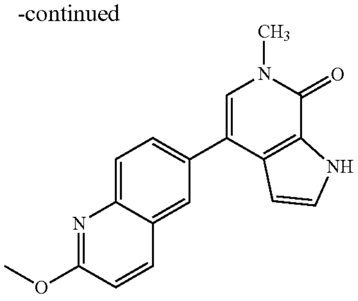

SLU-2294

1-bromo-3-(3-chloropropoxy)benzene (2)

To a stirred solution of 6-bromo-2-chloroquinoline 1 (0.05 g, 0.2 mmol) in $CH_3OH$ (3.0 mL), t-BuOK (0.046 g, 0.4 mmol) was charged portionwise at 0° C. The reaction mixture was heated at 60° C. for 4 h. The reaction mixture was allowed to room temperature and diluted with water (5.0 mL) and and extracted with EtOAc (3×10 mL). The combined organic layers were dried over anhydrous $Na_2SO_4$ and concentrated under reduced pressure (Hexane:EtOAc=95:5) to afford 2 [0.05 g (crude)] as a gummy solid.

$^1H$ NMR (400 MHz, $CDCl_3$): δ ppm 7.85-7.89 (m, 2H), 7.66-7.73 (m, 2H), 6.91 (d, J=8.8 Hz, 1H), 4.06 (s, 3H).

4-(2-methoxyquinolin-6-yl)-6-methyl-1-tosyl-1H-pyrrolo[2,3-c]pyridin-7(6H)-one (4)

A solution of 2 (0.120 g, 0.51 mmol) in 1,4-dioxane (4.0 mL), $H_2O$ (1.0 mL) were charged with Intermediate-5 (0.218 g, 0.51 mmol), potassium carbonate (0.141 g, 1.02 mmol) at room temperature and degassed it with argon for 5 min. $Pd(PPh_3)_4$ (0.058 g, 0.05 mmol) was added to the reaction mixture and stirred at 90° C. for 4 h. The reaction mixture was diluted with water (10 mL), extracted with EtOAc (2×20 mL). The combined organic layers were dried over anhydrous $Na_2SO_4$, concentrated under reduced pressure and crude material was purified by combi flash chromatography Hexane:EtOAc=70:30) to afford 4 (0.095 g, 41%) as an off-white solid.

$^1H$ NMR (400 MHz, $CDCl_3$): δ ppm 8.05 (d, J=8.8 Hz, 2H), 7.95-8.00 (m, 2H), 7.91 (d, J=8.4 Hz, 1H), 7.74 (d, J=1.6 Hz, 1H), 7.68 (dd, J=2.0, 8.4 Hz, 1H), 7.33 (d, J=8.0 Hz, 2H), 7.14 (s, 1H), 6.95 (d, J=9.2 Hz, 1H), 6.61 (d, J=3.6 Hz, 1H), 4.09 (s, 3H), 3.60 (s, 3H), 2.42 (s, 3H).

[4-(2-methoxyquinolin-6-yl)]-6-methyl-1H-pyrrolo[2,3-c]pyridin-7(6H)-one (SLU-2294)

To a stirred solution of 4 (0.075 g, 0.16 mmol) in $CH_3OH$ (3.0 mL), THF (1.0 mL), water (1.0 mL) was charged with potassium hydroxide (0.045 g, 0.83 mmol) at room temperature. The reaction mixture was stirred for 3 h at room temperature. The reaction mixture was evaporated, diluted with water (10.0 mL) and extracted with EtOAc (3×20 mL). The combined organic layers were dried over anhydrous $Na_2SO_4$ and concentrated under reduced pressure. The crude product was purified by reverse phase chromatography (ACN:$H_2O$=70:30) to afford SLU-2294 (0.044 g, 88%) as an off-white solid.

ESI-MS m/z $[C_{18}H_{15}N_3O_2+H]^+$ 306.1.

HPLC (Method B) 97.0% (AUC), $t_R$=7.89 min.

1H NMR (400 MHz, DMSO-$d_6$) δ ppm 12.20 (s, 1H), 8.31 (d, J=8.8 Hz, 1H), 8.10 (d, J=2.0 Hz, 1H), 7.91 (dd, J=2.0, 8.8 Hz, 1H), 7.86 (d, J=8.4, 1H), 7.51 (s, 1H), 7.39 (t, J=2.8, 1H), 7.05 (d, J=8.8, 1H), 6.55 (t, J=2.0, 1H), 4.00 (s, 3H), 3.61 (s, 3H).
Synthesis of (R)-4-{3-[4-(2-(2,4-dimethyl-3-oxopiperazin-1-yl)ethoxy)phenyl]isoquinolin-7-yl}-6-methyl-1H-pyrrolo[2,3-c]pyridin-7(6H)-one (SLU-2217)
Scheme 93
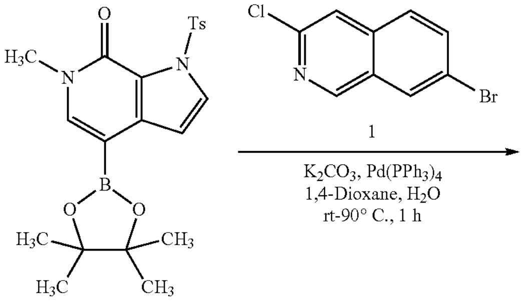
Intermediate-5
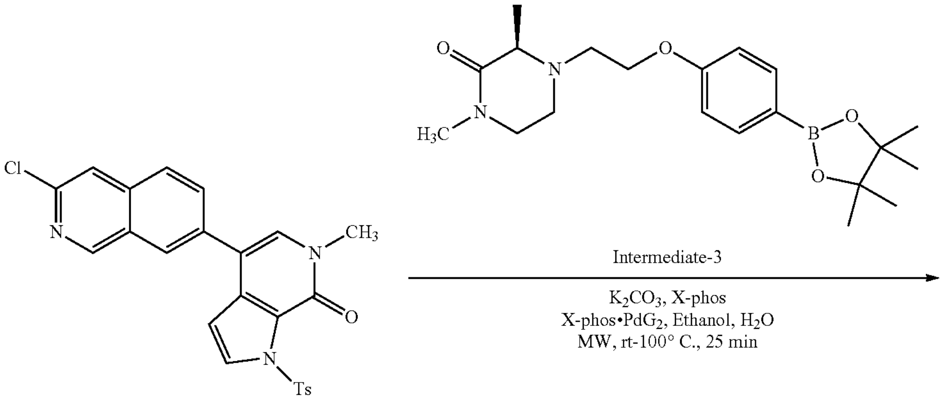
2
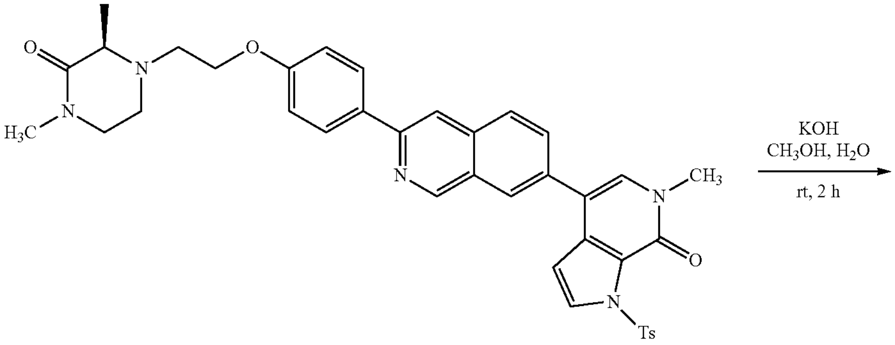
3
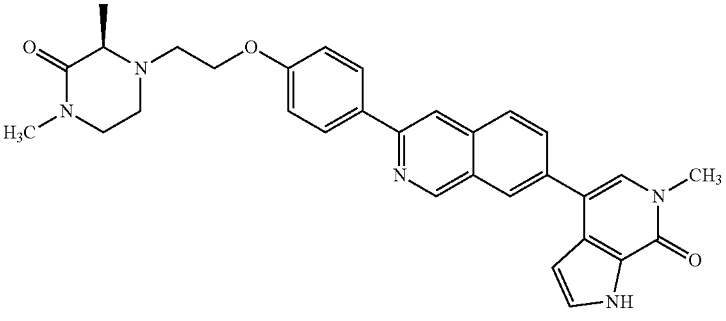
SLU-2217

4-(3-chloroisoquinolin-7-yl)-6-methyl-1-tosyl-1H-pyrrolo[2,3-c]pyridin-7(6H)-one (2)

To a stirred solution of Intermediate-5 (0.40 g, 0.8 mmol), 1 (0.22 g, 0.96 mmol), $K_2CO_3$ (0.32 g, 2.4 mmol) in dioxane (8.0 mL), water (2.0 mL) was charged at room temperature and degassed it with argon for 5 min at room temperature. $Pd(pph_3)_4$ (0.040 g, 0.04 mmol) was added to the reaction mixture and degassed it with argon for 2 min at room temperature. The reaction mixture was heated at 90° C. for 1 h. TLC indicated at which time the reaction had gone to completion. The reaction mixture was diluted with water (25 mL) and extracted with EtOAc (3×40 mL). The combined organic layers were dried over anhydrous $Na_2SO_4$ and concentrated under reduced pressure. The crude product was purified by combi flash chromatography ($CH_2Cl_2$: $CH_3OH$=95:5) to afford 2 (0.130 g) as an off-white solid.

$^1$H NMR (400 MHz, DMSO-$d_6$): δ ppm 9.27 (s, 1H), 8.31 (br.s., 1H), 8.06-8.10 (m, 2H), 7.97-8.01 (m, 2H), 7.82 (s, 1H), 7.59-7.64 (m, 1H), 7.53-7.57 (m, 1H), 7.44 (d, J=8.0 Hz, 2H), 6.88 (d, J=3.2 Hz, 1H), 3.51 (s, 3H), 2.39 (s, 3H).

(R)-4-{3-[4-(2-(2,4-dimethyl-3-oxopiperazin-1-yl)ethoxy)phenyl]isoquinolin-7-yl}-6-methyl-1-tosyl-1H-pyrrolo[2,3-c]pyridin-7(6H)-one (3)

To a stirred solution of 2 (0.11 g, 0.23 mmol), Intermediate-3 (0.178 g, 0.47 mmol), $K_2CO_3$ (0.095 g, 0.69 mmol) in ethanol (4.0 mL), water (1.0 mL) was charged at room temperature and degassed it with argon for 5 min at room temperature.

X-phos (0.022 g, 0.046 mmol), X-phos·$PdG_2$ (0.018 g, 0.023 mmol) was added to the reaction mixture and degassed it with argon for 2 min at room temperature. The reaction mixture was heated at 100° C. for 25 min in microwave. TLC indicated at which time the reaction had gone to completion. The reaction mixture was diluted with water (10 mL) and extracted with EtOAc (3×15 mL). The combined organic layers were dried over anhydrous $Na_2SO_4$ and concentrated under reduced pressure. ($CH_2Cl_2$: $CH_3OH$=95:5) to afford 3 [0.130 g (crude)] as a gummy solid.

$^1$H NMR (400 MHz, DMSO-$d_6$): δ ppm 9.41 (s, 1H), 8.46 (s, 1H), 8.27 (s, 1H), 8.19 (d, J=8.4 Hz, 1H), 8.07-8.10 (m, 2H), 8.02 (d, J=12.0 Hz, 2H), 7.92 (d, J=8.4 Hz, 1H), 7.82 (s, 1H), 7.52 (d, J=8.4 Hz, 1H), 7.45 (d, J=8.4 Hz, 1H), 7.10 (d, J=8.4 Hz, 2H), 6.99 (d, J=8.4 Hz, 1H), 6.88 (d, J=3.2 Hz, 1H), 4.17 (br. s., 2H), 4.08-4.11 (m, 3H), 3.51 (s, 3H), 3.24-3.26 (m, 2H), 3.04-3.13 (m, 2H), 2.92-3.02 (m, 2H), 2.67-2.77 (m, 2H), 2.39 (s, 3H), 1.23-1.27 (m, 3H).

(R)-4-{3-[4-(2-(2,4-dimethyl-3-oxopiperazin-1-yl)ethoxy)phenyl]isoquinolin-7-yl}-6-methyl-1H-pyrrolo[2,3-c]pyridin-7(6H)-one (SLU-2217)

To a stirred solution of 3 (0.07 g, 0.1 mmol) in $CH_3OH$ (3.0 mL), water (1.0 mL) was charged with potassium hydroxide (0.030 g, 0.5 mmol) at room temperature. The reaction mixture was stirred for 2 h at room temperature. The reaction mixture was evaporated, diluted with water (5.0 mL) and extracted with EtOAc (3×20 mL). The combined organic layers were dried over anhydrous $Na_2SO_4$ and concentrated under reduced pressure. The crude product was purified by reverse phase chromatography ($CH_2Cl_2$: $CH_3OH$=96:4) to afford SLU-2217 (0.032 g, 60%) as a white solid.

ESI-MS m/z $[C_{31}H_{31}N_5O_3+H]^+$ 522.2.

HPLC (Method B) 99.6% (AUC), $t_R$=6.11 min.

$^1$H NMR (400 MHz, DMSO-$d_6$): δ ppm 12.24 (s, 1H), 9.42 (s, 1H), 8.36 (s, 1H), 8.31 (s, 1H), 8.19 (d, J=8.8 Hz, 2H), 8.04 (q, J=8.4 Hz, 2H), 7.62 (s, 1H), 7.42 (t, J=2.8, 1H), 7.10 (d, J=8.8 Hz, 2H), 6.63 (t, J=2.4 Hz, 1H), 4.17 (t, J=5.6 Hz, 2H), 3.63 (s, 3H), 3.26-3.29 (m, 2H), 3.17 (q, J=6.8 Hz, 1H), 3.07-3.13 (m, 1H), 2.95-3.02 (m, 1H), 2.84-2.85 (m, 1H), 2.82 (s, 3H), 2.71-2.75 (m, 1H), 1.26 (d, J=6.8 Hz, 3H).

Example 2: Materials and Methods

Cells and Cell Culture. Primary human myoblast cell lines, immortalized by retroviral transduction of cyclin-dependent kinase 4 (CDK4) and human telomerase reverse transcriptase (hTERT) (Stadler, et al., 2011), were obtained from the Fields Center at the University of Rochester (world-wide-web at urmc.rochester.edu/fields-center.aspx). Immortalized myoblasts were grown in Ham's F-10 Nutrient Mix (Gibco, Waltham, MA, USA) supplemented with 20% HyClone Fetal Bovine Serum (GE Healthcare Life Sciences, Pittsburgh, PA, USA), 100 U/100 µg penicillin/streptomycin (Gibco), 10 ng/ml recombinant human fibroblast growth factor (Promega Corporation, Madison, WI, USA) and 1 µM dexamethasone (Sigma-Aldrich). Differentiation of myoblasts into myotubes was achieved by switching the fully confluent myoblast monolayer into Dulbecco's Modified Eagle Medium (DMEM) (Gibco) containing 1% horse serum (Gibco), 100 U/100 µg penicillin/streptomycin, 10 µg/ml insulin (Sigma-Aldrich) and 10 µg/ml transferrin (Sigma-Aldrich) (HS/IT media) or DMEM:F12 Nutrient Mixture (1:1, Gibco) supplemented with 2% KnockOut Serum Replacement (Gibco), 100 U/100 µg penicillin/streptomycin, 10 µg/ml insulin and 10 µg/ml transferrin (KSR media) for 2-6 days.

Screening: qPCR analysis of DUX4 target genes MBD3L2. For screening compounds, differentiating MB200 FSHD2 muscle cells were exposed to BET inhibitors at a variety of concentrations for 40 hours to determine the effects of the drugs on DUX4 expression. Cell lysates were prepared using Cells-to-Ct Bulk Lysis Reagents (Invitrogen, Waltham, MA, USA). Gene expression was measured by quantitative polymerase chain reaction (qPCR) was carried out on a QuantStudio 5 (Applied Biosystems, Waltham, MA, USA) using TaqMan Gene Expression Assays (Applied Biosystems) and TaqMan Fast Virus 1-Step Master Mix (Invitrogen). The relative expression levels of DUX4 target gene methyl-CpG binding domain protein 3 like 2 (MBD3L2), was normalized to that of the reference gene ribosomal protein L30 (RPL30), which was included in multiplex (two gene) PCR reactions. TaqMan Gene Expression Assay ID numbers: MBD3L2, Hs00544743_m1; RPL30, Hs00265497_m1. Data is expressed as relative expression with the expression in absence of inhibitors set to one.

Measurement of DUX4 and DUX4 target gene expression in FSHD1 and FSHD2 myotubes. FSHD1 and FSHD2 myoblasts were induced to differentiate into myotubes for 40 hours in the presence of BET inhibitors. Total RNA was extracted from whole cells using the RNeasy Mini Kit (Qiagen, Hilden, Germany) according to the manufacturer's instructions. Isolated RNA was treated with DNase I (Thermo Fisher Scientific), heat inactivated and reverse transcribed into cDNA using Superscript III (Thermo Fisher Scientific) and oligo(dT) primers (Invitrogen) following the manufacturer's protocol. qPCR was performed on cDNA to measure expression of DUX4, MBD3L2, ZSCAN4, LEUTX, MYOG, and MYH2 using TaqMan Gene Expression Assay ID numbers: MBD3L2, Hs00544743_m1; MYH2, Hs00430042_m1; MYOG, Hs01072232_m1; RPL30, Hs00265497_m1; LEUTX, Hs01028718_m1; ZSCAN4, Hs00537549_m1; or DUX4 with primers GCCGGCCCAGGTACCA and CAGCGAGCTCCCTTGCA with probe 6FAM-CAGTGCGCACCCCGMGBNFQ.

Analysis of DUX4 expression in mice. Human MB200 FSHD2 myoblasts were co-injected with barium chloride into the tibialis anterior muscles of immunodeficient mice (Hardy, et al., 2016). The grafted myoblasts became part of mature muscle myofibers in the mouse tibialis anterior muscle while retaining the genomic organization of human FSHD cells and the FSHD-specific regulation of DUX4. MB200 FSHD2 xenografted mice were administered SLU-2106 by oral gavage at 2, 4, 6 and 8 mpk BID, beginning immediately after FSHD myoblast implantation. Four days post implantation, RNA was isolated from TA muscles. Purified RNA was analyzed for human specific gene expression by qRT-PCR using primers directed to hZSCAN, hMBD3L2, hLEUTXas described above. Relative mRNA levels were normalized to that of the vehicle control group.

Example 3: Treatment with BET Inhibitors Decreases DUX4 Expression

Analysis of MBD3L2 expression in cultured FSHD2 cells. DUX4 mRNA is present in very low levels, even in differentiating FSHD2 myoblasts, so DUX4 target gene MBD3L2 was used as a surrogate marker of DUX4 expression. FSHD2 patient derived muscle cells were analyzed to determine whether BET inhibitors affect MBD3L2 expression, indicating a reduction in DUX4 expression. As shown in Table 1, treatment with a variety of SLU BET inhibitors causes reductions in MBD3L2 with $IC_{50S}$ in the nanomolar range.

SLU-2106 reduces DUX4 expression in FSHD myoblast xenografts. To further demonstrate the potential clinical utility of BET inhibition for FSHD, SLU-2106 was tested in a mouse pharmacology model of human FSHD gene regulation wherein FSHD myoblasts were engrafted into the mouse tibialis anterior muscles (Hardy, et al., 2016). The grafted human myoblasts become part of mature muscle myofibers in the mouse TA muscle, yet retain the genomic organization of human FSHD cells and maintain the unique FSHD-specific regulation of DUX4. Treatment of mice containing human MB200 FSHD2 xenografts with SLU-2106 results in significant dose-dependent decreases in the expression of DUX4 target genes (FIGS. 1A-C), supporting the concept of systemic administration of a SLU BET inhibitor to target DUX4 expression in muscle tissue for the treatment of FSHD.

TABLE 1

| Compound | DUX4* MT FSHD2 $IC_{50}$ (nM) |
|---|---|
| SLU-2089 | 4.8 |
| SLU-2090 | 43 |
| SLU-2091 | 20 |
| SLU-2096 | 180 |
| SLU-2097 | 120 |
| SLU-2098 | 310 |
| SLU-2102 | 130 |
| SLU-2104 | 43 |
| SLU-2106 | 24 |
| SLU-2107 | 48 |
| SLU-2108 | 280 |
| SLU-2109 | 33 |
| SLU-2110 | 16 |
| SLU-2111 | 29 |
| SLU-2112 | 40 |
| SLU-2114 | 330 |
| SLU-2115 | 97 |
| SLU-2116 | 270 |
| SLU-2117 | 91 |
| SLU-2118 | 261 |
| SLU-2119 | 130 |
| SLU-2120 | 350 |
| SLU-2124 | 1300 |
| SLU-2127 | 37 |
| SLU-2130 | 120 |
| SLU-2131 | 62 |
| SLU-2211 | 62 |
| SLU-2212 | 86 |
| SLU-2213 | 41 |
| SLU-2214 | 95 |
| SLU-2217 | 22 |
| SLU-2218 | 41 |
| SLU-2219 | 95 |
| SLU-2225 | 35 |
| SLU-2226 | 47 |
| SLU-2227 | 69 |
| SLU-2232 | 97 |
| SLU-2233 | 290 |
| SLU-2234 | 69 |
| SLU-2235 | 12 |
| SLU-2236 | 13 |
| SLU-2240 | 35 |
| SLU-2241 | 110 |
| SLU-2242 | 93 |
| SLU-2243 | 110 |
| SLU-2244 | 28 |
| SLU-2277 | 20 |
| SLU-2278 | 120 |
| SLU-2279 | 420 |
| SLU-2280 | 120 |
| SLU-2281 | 130 |
| SLU-2282 | 54 |
| SLU-2283 | 160 |
| SLU-2284 | 90 |
| SLU-2285 | 570 |
| SLU-2286 | 63 |
| SLU-2287 | 108 |
| SLU-2288 | 250 |
| SLU-2292 | 25 |
| SLU-2293 | 18 |
| SLU-2294 | 59 |
| SLU-2295 | 51 |
| SLU-2296 | 58 |
| SLU-2297 | 1600 |
| SLU-2298 | 113 |
| SLU-2299 | 3.4 |
| SLU-2300 | 49 |
| SLU-2301 | 13 |
| SLU-2302 | 1800 |
| SLU-2325 | 290 |
| SLU-2326 | 130 |
| SLU-2327 | 1100 |
| SLU-2346 | 41 |
| SLU-2347 | 85 |
| SLU-2348 | 140 |
| SLU-2611 | 41 |

*DUX4 expression inferred from surrogate marker MBD3L2 expression (see Example 2)

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the disclosure. All variations and modifications apparent to those skilled in the art are deemed to be within the spirit, scope, and concept of the disclosure as defined by the appended claims.

VIII. REFERENCES

The following references to the extent that they provide exemplary procedural or other details supplementary to those set forth herein, are specifically incorporated herein by reference.

US 2002/0118671
US 2003/0232831
US 2004/0254236
US 2004/0267012
US 2004/0102636
US 2004/0132729
US 2005/0020590
US 2005/0020540
US 2006/0122221
US 2007/0185175
US 2007/0213300
US 2008/0171741
US 2009/0143422
US 2009/0136596
US 2009/0118272
US 2011/0190292
US 2011/0077243
U.S. Pat. No. 5,945,418
WO 1999/032463
WO 1999/000357
WO 2000/012497
WO 2000/012074
WO 2003/068747
WO 2003/093248
WO 2004/010995
WO 2005/012241
WO 2005/073189
WO 2009/155388
WO 2009/155388
WO 2010/067131
WO 2012/031057
Anderson, *Practical Process Research & Development*—A Guide for Organic Chemists, 2nd ed., Academic Press, New York, 2012.
*Handbook of Pharmaceutical Salts: Properties, and Use*, Stahl and Wermuth Eds., Verlag Helvetica Chimica Acta, 2002.
Smith, *March's Advanced Organic Chemistry*: Reactions, Mechanisms, and Structure, 7th Ed., Wiley, 2013.
Balog et al., *Epigenetics,* 10:1133-1142, 2015.
Bosnakovski et al., *EMBO J,* 27:2766-2779, 2008.
Cuadrado et al., *Biochem J.;* 429(3):403-17, 2010.
Das & Chadwick, *PLoS One,* 11:e0160022, 2016.
Daxinger et al., *Curr Opin Genet Dev,* 33:56-61, 2015.
De Iaco et al., *Nat Genet,* 49:941-945, 2017.
Feng et al., *Elife,* 4, 2015.
Fisk et al., *Am. J Cardiovasc. Drugs,* 14:155-165, 2014.
Gangwal et al, *Current Topics in Medicinal Chemistry,* 13(9):1015-1035, 2013.
Geng et al., *Dev Cell,* 22:38-51, 2012.
Hardy et al., *PLoS One,* 11:e0147198, 2016.
Hendrickson et al., *Nat Genet,* 49:925-934, 2017.
Karcher and Laufer, *Curr. Top. Med. Chem.,* 9(7):655-676, 2009.
Kimble et al., *Endocrinol.,* 136:3054-61, 1995.
Kostenko et al., *World J Biol Chem.* 26; 2(5):73-89, 2011
Kowaljow et al., *Neuromuscul Disord,* 17:611-623, 2007.
Kumar et al., *Nat. Rev. Drug Discov.,* 2(9):717-726, 2003.
Lee et al., *Immunopharmacology,* 47(2-3):185-201, 2000.
Lemmers et al., *Science,* 329:1650-1653, 2010.
Lemmers et al., *Nat. Genet.,* 44:1370-1374, 2012.
Lim et al., *Hum Mol Genet,* 24:4817-4828, 2015.
Marber et al., *J Mol Cell Cardiol.;* 51(4):485-90, 2011.
Norman, *Expert Opin. Investig. Drugs,* 24(3):383-392, 2015.
Reagan-Shaw et al., *FASEB J.,* 22(3):659-661, 2008
Rickard et al., *Hum Mol Genet,* 24:5901-5914, 2015.
Shadle et al., *PLoS Genet,* 13:e1006658, 2017.
Snider et al., *Hum Mol Genet,* 18:2414-2430, 2009.
Snider et al., *PLoS Genet,* 6:e1001181, 2010.
Tawil et al., *Skelet Muscle,* 4:12, 2014.
van den Boogaard et al., *Am. J. Hum. Genet.,* 98:1020-1029, 2016.
van Overveld et al., *Nat Genet,* 35:315-317, 2003.
Wallace et al., *Ann Neurol,* 69:540-552, 2011.
Whiddon et al., *Nat Genet,* 49:935-940, 2017.
Winokur et al., *Hum Mol Genet,* 12:2895-2907, 2003.
Yong et al., *Expert Opin. Investig. Drugs,* 18(12):1893-1905, 2009.
Young et al., *PLoS Genet,* 9:e1003947, 2013.
Zeng et al., *PLoS Genet,* 5:e1000559, 2009.

What is claimed is:

1. A compound of the formula:

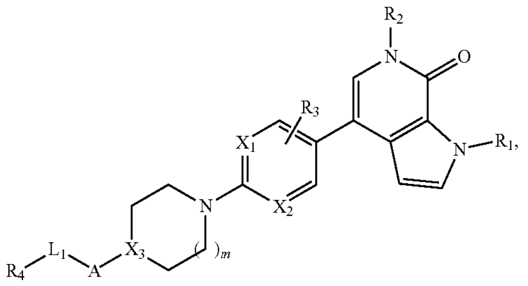

(I)

wherein:

m is 0 or 1;

$R_1$ and $R_2$ are each independently hydrogen; or alkyl$_{(C\leq12)}$, alkenyl$_{(C\leq12)}$, alkynyl$_{(C\leq12)}$, cycloalkyl$_{(C\leq12)}$, aralkyl$_{(C\leq12)}$, acyl$_{(C\leq12)}$, —S(O)$_2$-aryl$_{(C\leq12)}$, or a substituted version of any of these groups;

$X_1$, $X_2$, and $X_3$ are each independently CH or N;

$R_3$ is hydrogen, hydroxy, amino, or halo; or alkoxy$_{(C\leq12)}$, alkylamino$_{(C\leq12)}$, dialkylamino$_{(C\leq12)}$, or a substituted version of any of these groups;

A is arenediyl$_{(C\leq12)}$, substituted arenediyl$_{(C\leq12)}$, heteroarenediyl$_{(C\leq12)}$, or substituted heteroarenediyl$_{(C\leq12)}$;

$L_1$ is a covalent bond; or alkanediyl$_{(C\leq12)}$, —O-alkanediyl$_{(C\leq12)}$-, —C(O)-alkanediyl$_{(C\leq12)}$-, —OC(O)-alkanediyl$_{(C\leq12)}$-, —C(O)-alkanediyl$_{(C\leq12)}$-O-alkanediyl$_{(C\leq12)}$-, —OC(O)-alkanediyl$_{(C\leq12)}$-O-alkanediyl$_{(C\leq12)}$-, or a substituted version of any of these groups; and $R_4$ is hydrogen, hydroxy, or amino; or alkoxy$_{(C\leq 12)}$, alkylamino$_{(C\leq 12)}$, dialkylamino$_{(C\leq 12)}$, cycloalkyl$_{(C\leq 12)}$, heterocycloalkyl$_{(C\leq 12)}$, aryl$_{(C\leq 12)}$, heteroaryl$_{(C\leq 12)}$, or a substituted version of any of these groups; or a group of the formula:

(Ia)

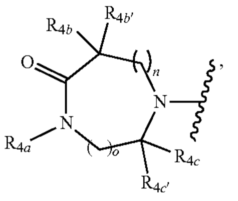

wherein:

n is 0 or 1;

o is 1 or 2;

$R_{4a}$ is hydrogen; or alkyl$_{(C\leq 12)}$, alkenyl$_{(C\leq 12)}$, alkynyl$_{(C\leq 12)}$, acyl$_{(C\leq 12)}$, or a substituted version of any of these groups; and $R_{4b}$, $R_{4b'}$, $R_{4c}$, and $R_{4c'}$ are each independently hydrogen, alkyl$_{(C\leq 12)}$, or substituted alkyl$_{(C\leq 12)}$; or a compound of the formula:

(II)

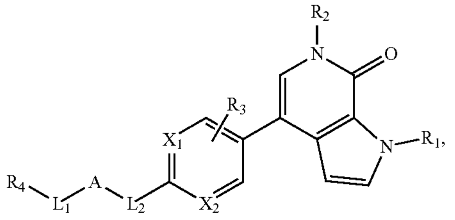

wherein:

$R_1$, $R_2$, $R_3$, $R_4$, $X_1$, $X_2$, and $L_1$ are as defined above;

A is a covalent bond, arenediyl$_{(C\leq 12)}$, substituted arenediyl$_{(C\leq 12)}$, heteroarenediyl$_{(C\leq 12)}$, or substituted heteroarenediyl$_{(C\leq 12)}$; and $L_2$ is a group of the formula:

(IIa)

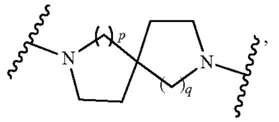

wherein:

p is 1, 2, or 3; and q is 1, 2, or 3; or a compound of the formula:

(III)

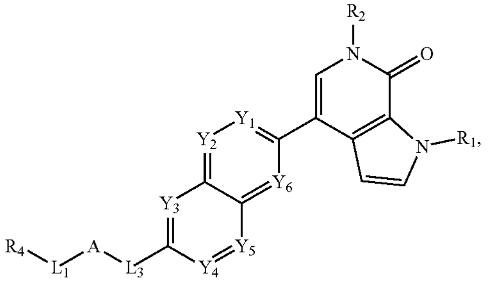

wherein:

$R_1$, $R_2$, $R_4$, and $L_1$ are as defined above;

$L_3$ is a covalent bond; or alkanediyl$_{(C\leq 12)}$, alkenediyl$_{(C\leq 12)}$, alkynediyl$_{(C\leq 12)}$, cycloalkanediyl$_{(C\leq 12)}$, heterocycloalkanediyl$_{(C\leq 12)}$, or a substituted version of any of these groups;

or a group of formula (IIa) as defined above;

A is a covalent bond, arenediyl$_{(C\leq 12)}$, substituted arenediyl$_{(C\leq 12)}$, heteroarenediyl$_{(C\leq 12)}$, or substituted heteroarenediyl$_{(C\leq 12)}$; and $Y_1$, $Y_2$, $Y_3$, $Y_4$, $Y_5$, and $Y_6$ are each independently CH or N;

wherein when any of these terms are used with the "substituted" modifier one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$;

or a pharmaceutically acceptable salt of any one of these formulas.

2. The compound of claim 1, wherein the compound is further defined as:

(IV)

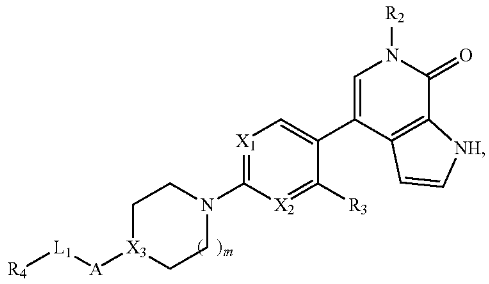

wherein:

m is 0 or 1;

$R_2$ is hydrogen, alkyl$_{(C\leq 12)}$, substituted alkyl$_{(C\leq 12)}$, alkenyl$_{(C\leq 12)}$, or substituted alkenyl$_{(C\leq 12)}$;

$X_1$, $X_2$, and $X_3$ are each independently CH or N;

$R_3$ is hydrogen, alkoxy$_{(C\leq 12)}$, or substituted alkoxy$_{(C\leq 12)}$;

A is arenediyl$_{(C\leq 12)}$, substituted arenediyl$_{(C\leq 12)}$, heteroarenediyl$_{(C\leq 12)}$, or substituted heteroarenediyl$_{(C\leq 12)}$;

$L_1$ is a covalent bond; or alkanediyl$_{(C\leq 12)}$, —O-alkanediyl$_{(C\leq 12)}$-, —C(O)-alkanediyl$_{(C\leq 12)}$-, —OC(O)-alkanediyl$_{(C\leq 12)}$-, —C(O)-alkanediyl$_{(C\leq 12)}$-O-alkanediyl$_{(C\leq 12)}$-, —OC(O)-alkanediyl$_{(C\leq 12)}$-O-alkanediyl$_{(C\leq 12)}$-, or a substituted version of any of these groups; and $R_4$ is hydrogen, hydroxy, or amino; or alkoxy$_{(C\leq 12)}$, alkylamino$_{(C\leq 12)}$, dialkylamino$_{(C\leq 12)}$, cycloalkyl$_{(C\leq 12)}$, heterocycloalkyl$_{(C\leq 12)}$, aryl$_{(C\leq 12)}$, heteroaryl$_{(C\leq 12)}$, or a substituted version of any of these groups; or a group of the formula:

(Ia)

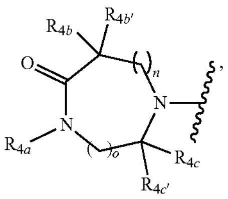

wherein:

n is 0 or 1;

o is 1 or 2;

$R_{4a}$ is hydrogen; or alkyl$_{(C\leq 12)}$, alkenyl$_{(C\leq 12)}$, alkynyl$_{(C\leq 12)}$, acyl$_{(C\leq 12)}$, or a substituted version of any of these groups; and $R_{4b}$, $R_{4b'}$, $R_{4c}$, and $R_{4c'}$ are each independently hydrogen, alkyl$_{(C\leq 12)}$, or substituted alkyl$_{(C\leq 12)}$;

or a pharmaceutically acceptable salt thereof.

3. The compound of claim 1, wherein the compound is further defined as:

(V)

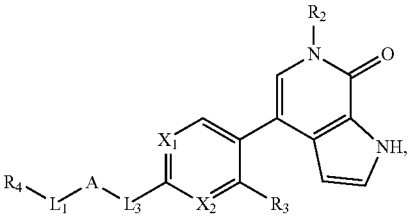

wherein:

$R_2$ is hydrogen, alkyl$_{(C\leq 12)}$, substituted alkyl$_{(C\leq 12)}$, alkenyl$_{(C\leq 12)}$, or substituted alkenyl$_{(C\leq 12)}$;

$X_1$ and $X_2$ are each independently CH or N;

$R_3$ is hydrogen, alkoxy$_{(C\leq 12)}$, or substituted alkoxy$_{(C\leq 12)}$;

A is a covalent bond, arenediyl$_{(C\leq 12)}$, substituted arenediyl$_{(C\leq 12)}$, heteroarenediyl$_{(C\leq 12)}$, or substituted heteroarenediyl$_{(C\leq 12)}$;

$L_1$ is a covalent bond; or alkanediyl$_{(C\leq 12)}$, —O-alkanediyl$_{(C\leq 12)}$-, —C(O)-alkanediyl$_{(C\leq 12)}$-, —OC(O)-alkanediyl$_{(C\leq 12)}$-, —C(O)-alkanediyl$_{(C\leq 12)}$-O-alkanediyl$_{(C\leq 12)}$-, —OC(O)-alkanediyl$_{(C\leq 12)}$-O-alkanediyl$_{(C\leq 12)}$-, or a substituted version of any of these groups;

$R_4$ is hydrogen, hydroxy, or amino; or alkoxy$_{(C\leq 12)}$, alkylamino$_{(C\leq 12)}$, dialkylamino$_{(C\leq 12)}$, cycloalkyl$_{(C\leq 12)}$, heterocycloalkyl$_{(C\leq 12)}$, aryl$_{(C\leq 12)}$, heteroaryl$_{(C\leq 12)}$, or a substituted version of any of these groups; or a group of the formula:

(Ia)

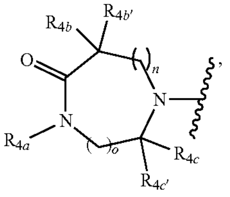

wherein:

n is 0 or 1;

o is 1 or 2;

$R_{4a}$ is hydrogen; or alkyl$_{(C\leq 12)}$, alkenyl$_{(C\leq 12)}$, alkynyl$_{(C\leq 12)}$, acyl$_{(C\leq 12)}$, or a substituted version of any of these groups; and $R_{4b}$, $R_{4b'}$, $R_{4c}$, and $R_{4c'}$ are each independently hydrogen, alkyl$_{(C\leq 12)}$, or substituted alkyl$_{(C\leq 12)}$; and $L_2$ is a group of the formula:

(IIa)

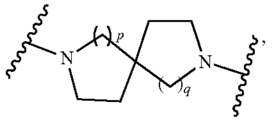

wherein:

p is 1, 2, or 3; and q is 1, 2, or 3;

or a pharmaceutically acceptable salt thereof.

4. The compound of claim 1, wherein the compound is further defined as:

(VI)

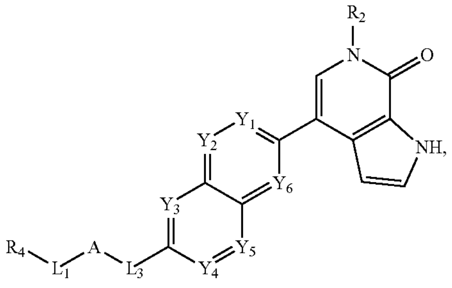

wherein:

$R_2$ is hydrogen, alkyl$_{(C\leq 12)}$, substituted alkyl$_{(C\leq 12)}$, alkenyl$_{(C\leq 12)}$, or substituted alkenyl$_{(C\leq 12)}$;

A is a covalent bond, arenediyl$_{(C\leq 12)}$, substituted arenediyl$_{(C\leq 12)}$, heteroarenediyl$_{(C\leq 12)}$, or substituted heteroarenediyl$_{(C\leq 12)}$;

$L_1$ is a covalent bond; or alkanediyl$_{(C\leq 12)}$, —O-alkanediyl$_{(C\leq 12)}$-, —C(O)-alkanediyl$_{(C\leq 12)}$-, —OC(O)-alkanediyl$_{(C\leq 12)}$-, —C(O)-alkanediyl$_{(C\leq 12)}$-O-alkanediyl$_{(C\leq 12)}$-, —OC(O)-alkanediyl$_{(C\leq 12)}$-O-alkanediyl$_{(C\leq 12)}$-, or a substituted version of any of these groups;

$R_4$ is hydrogen, hydroxy, or amino; or alkoxy$_{(C\leq12)}$, alkylamino$_{(C\leq12)}$, dialkylamino$_{(C\leq12)}$, cycloalkyl$_{(C\leq12)}$, heterocycloalkyl$_{(C\leq12)}$, aryl$_{(C\leq12)}$, heteroaryl$_{(C\leq12)}$, or a substituted version of any of these groups; or a group of the formula:

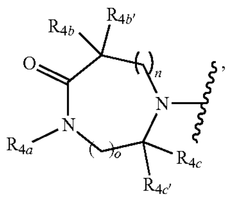

(Ia)

wherein:

n is 0 or 1;

o is 1 or 2;

$R_{4a}$ is hydrogen; or alkyl$_{(C\leq12)}$, alkenyl$_{(C\leq12)}$, alkynyl$_{(C\leq12)}$, acyl$_{(C\leq12)}$, or a substituted version of any of these groups; and $R_{4b}$, $R_{4b'}$, $R_{4c}$, and $R_{4c'}$ are each independently hydrogen, alkyl$_{(C\leq12)}$, or substituted alkyl$_{(C\leq12)}$;

$L_3$ is a covalent bond; or alkanediyl$_{(C\leq12)}$, alkenediyl$_{(C\leq12)}$, alkynediyl$_{(C\leq12)}$, cycloalkanediyl$_{(C\leq12)}$, heterocycloalkanediyl$_{(C\leq12)}$, or a substituted version of any of these groups; or a group of formula (IIa) as defined above; and $Y_1$, $Y_2$, $Y_3$, $Y_4$, $Y_5$, and $Y_6$ are each independently CH or N;

or a pharmaceutically acceptable salt thereof.

5. The compound of claim 1, wherein $R_2$ is alkyl$_{(C\leq12)}$, substituted alkyl$_{(C\leq12)}$, alkenyl$_{(C\leq12)}$, or substituted alkenyl$_{(C\leq12)}$.

6. The compound of claim 1, wherein A is arenediyl$_{(C\leq12)}$, substituted arenediyl$_{(C\leq12)}$, heteroarenediyl$_{(C\leq12)}$, or substituted heteroarenediyl$_{(C\leq12)}$.

7. The compound of claim 1, wherein $L_1$ is alkanediyl$_{(C\leq12)}$, —O-alkanediyl$_{(C\leq12)}$-, —C(O)-alkanediyl$_{(C\leq12)}$-, —C(O)-alkanediyl$_{(C\leq12)}$-O-alkanediyl$_{(C\leq12)}$-, or a substituted version of any of these groups.

8. The compound of claim 1, wherein $R_4$ is dialkyl amino$_{(C\leq12)}$ or substituted dialkylamino$_{(C\leq12)}$.

9. The compound of claim 1, wherein $R_4$ is heteroaryl$_{(C\leq12)}$ or substituted heteroaryl$_{(C\leq12)}$.

10. The compound of claim 1, wherein $R_4$ is heterocycloalkyl$_{(C\leq12)}$ or substituted heterocycloalkyl$_{(C\leq12)}$.

11. The compound of claim 1, wherein $R_4$ is a group of formula (Ia).

12. The compound of claim 1, wherein $L_3$ is heterocycloalkanediyl$_{(C\leq12)}$ or substituted heterocycloalkanediyl$_{(C\leq12)}$.

13. The compound of claim 1, wherein the compound is further defined as:

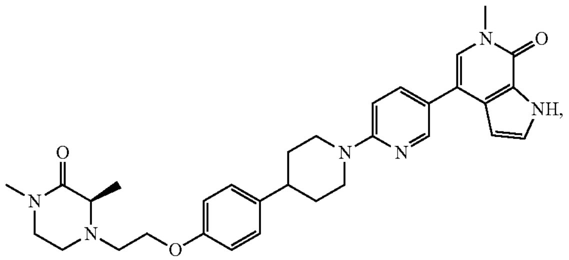

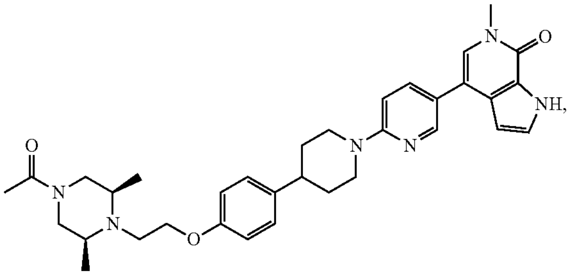

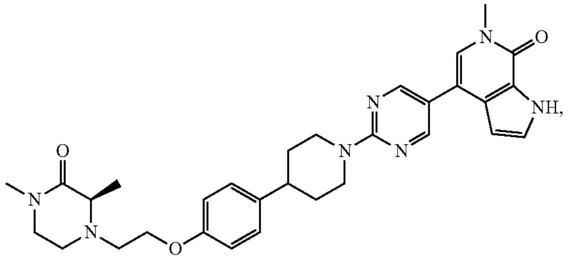

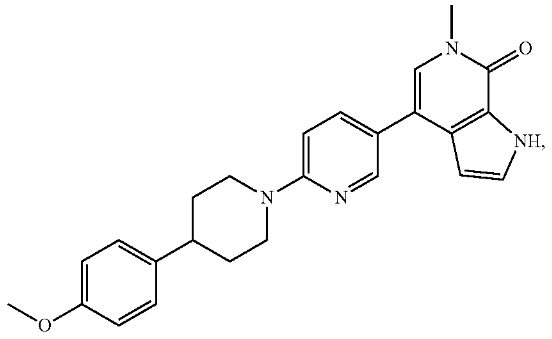

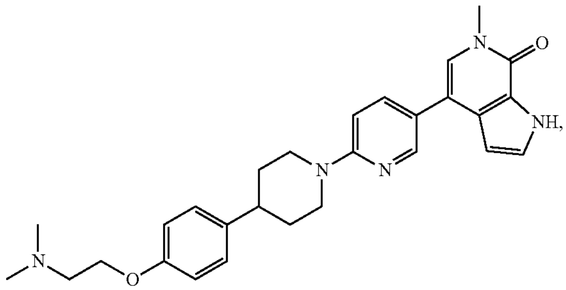

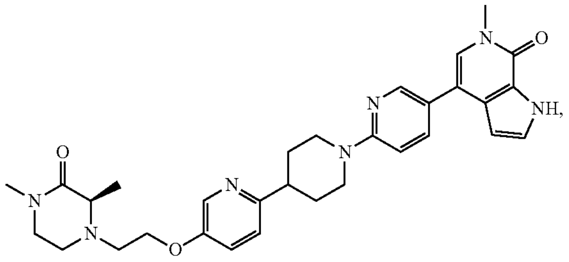

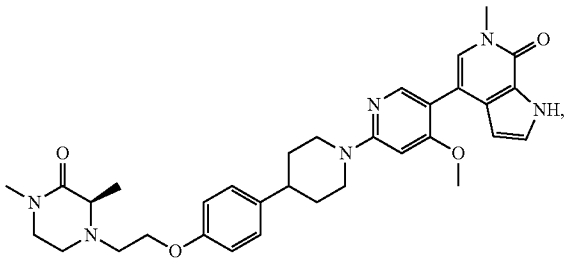
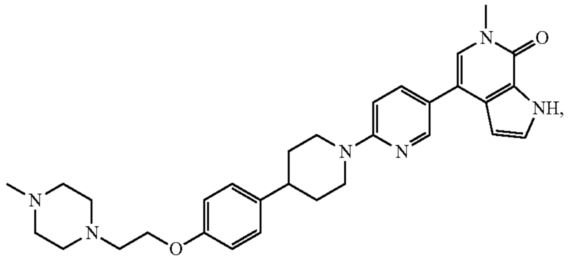
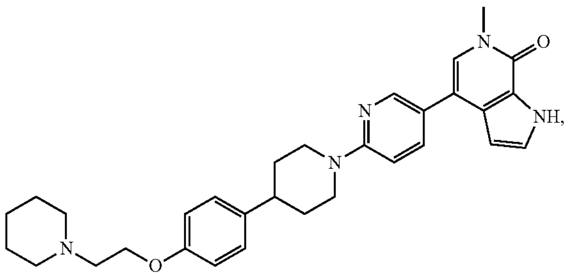
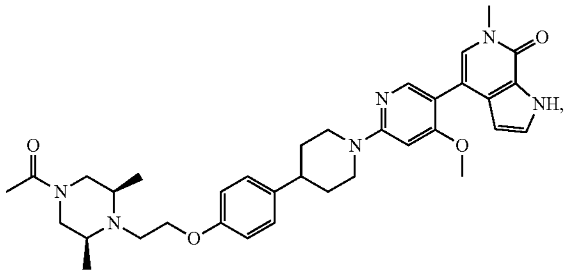
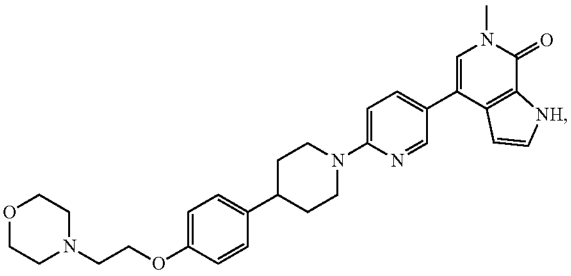
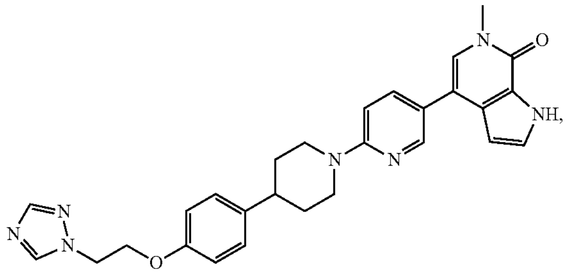
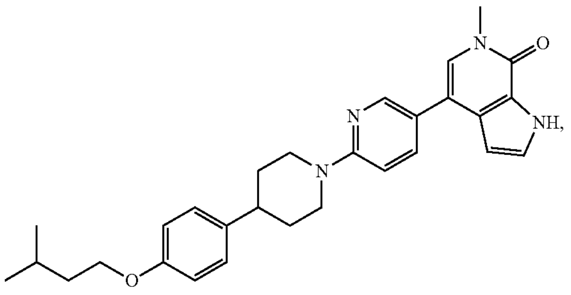
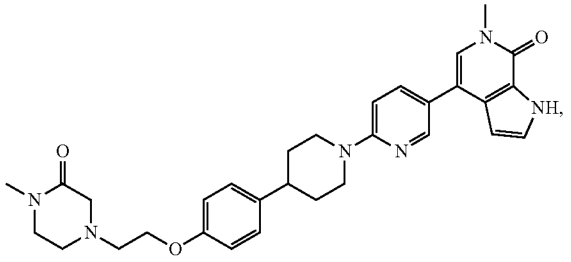
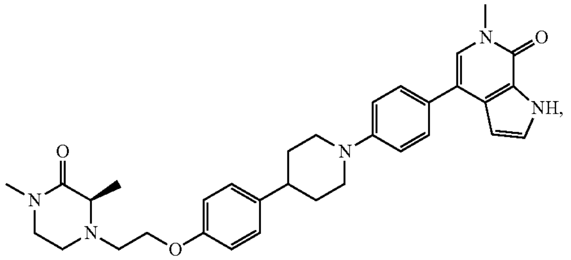
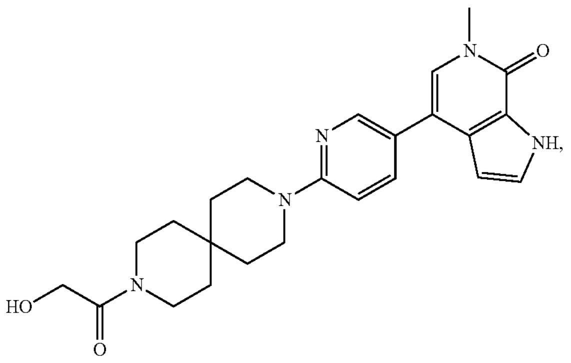
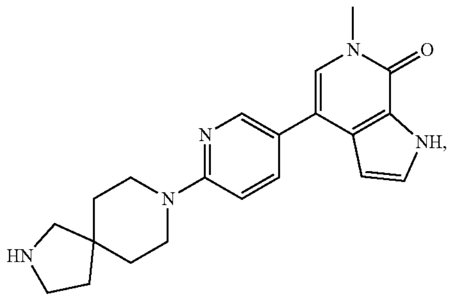

-continued
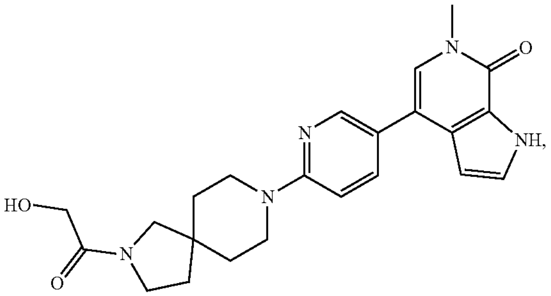
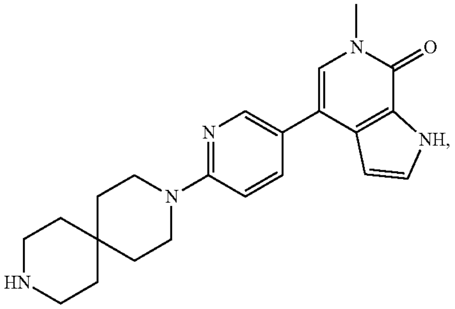
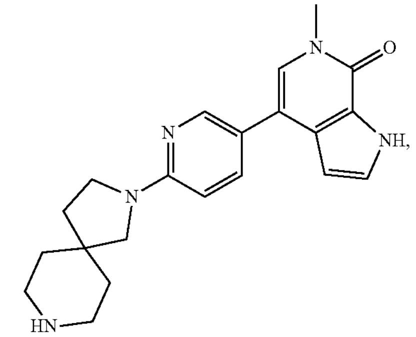
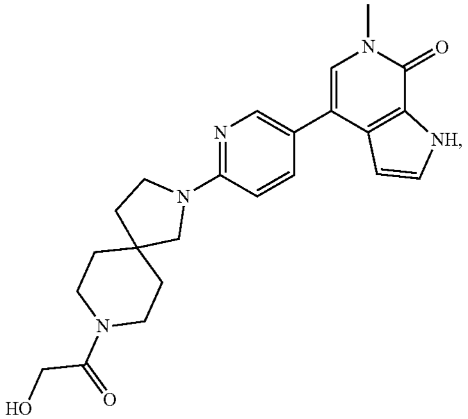
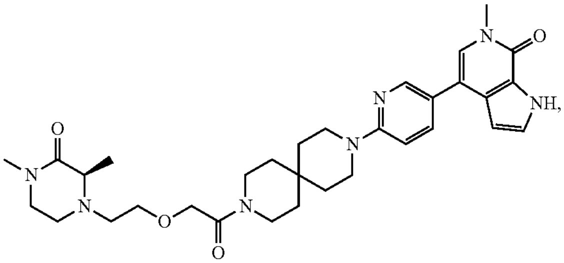
-continued
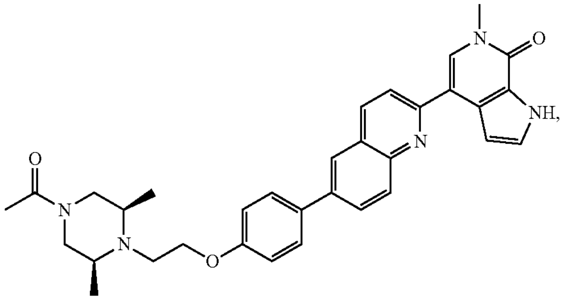
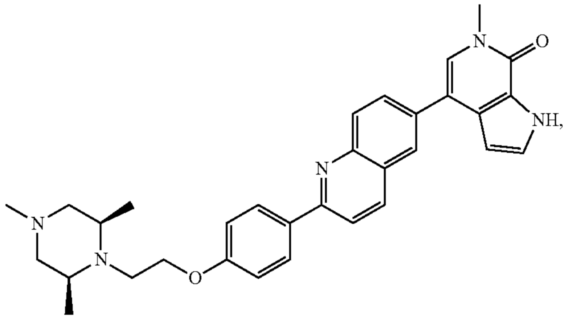
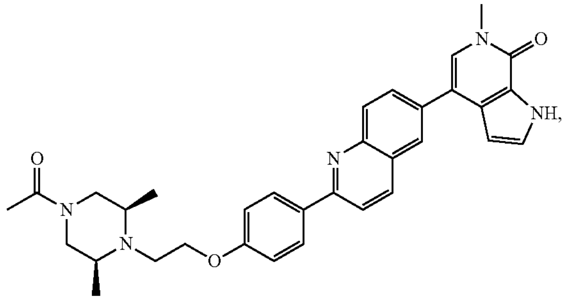
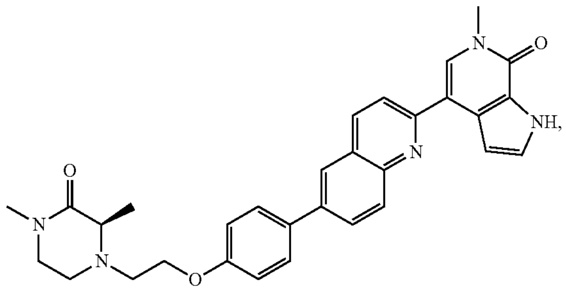
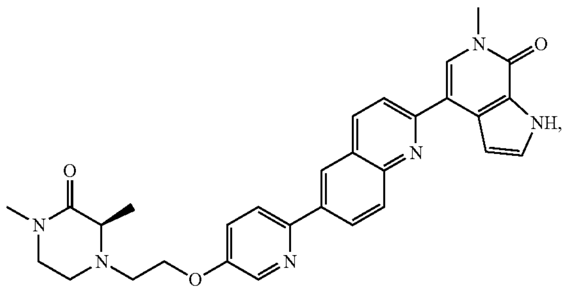

-continued
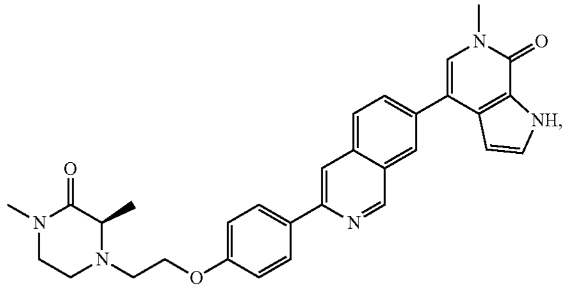
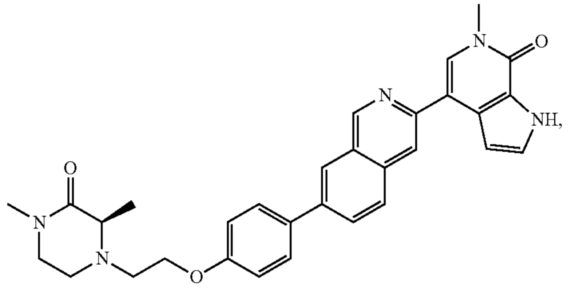
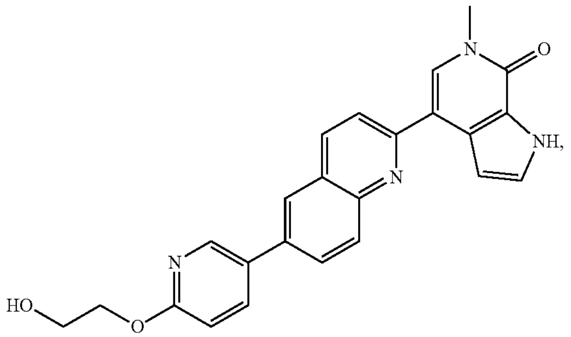
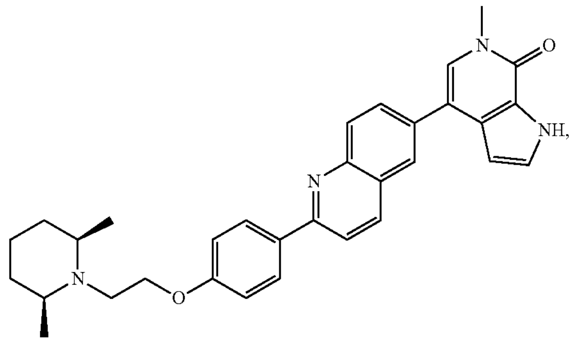
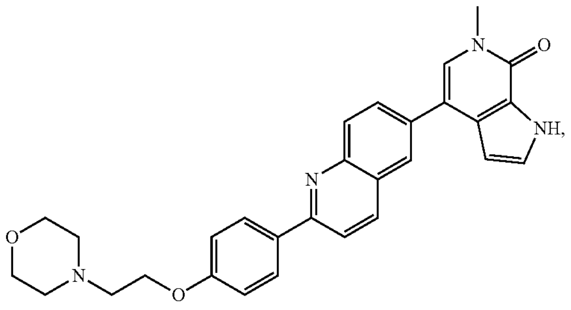
-continued
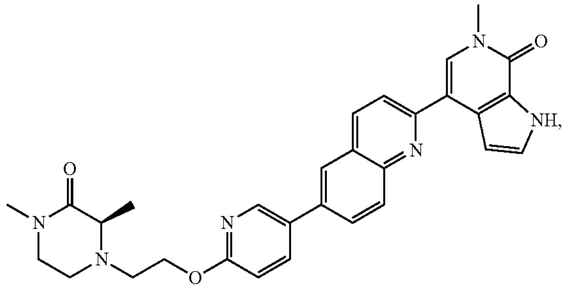
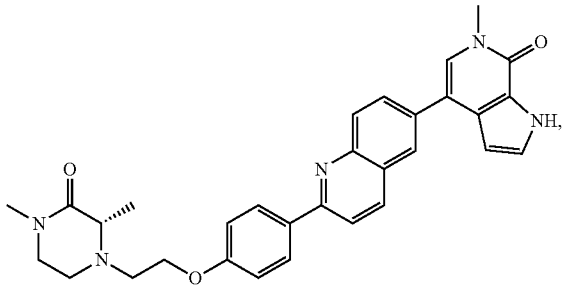
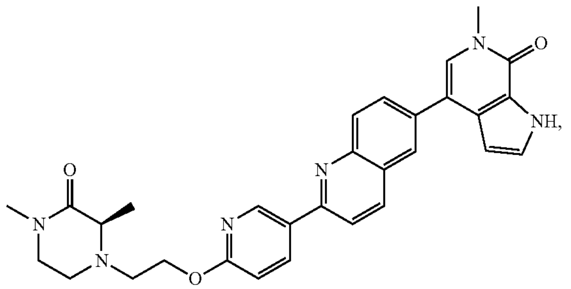
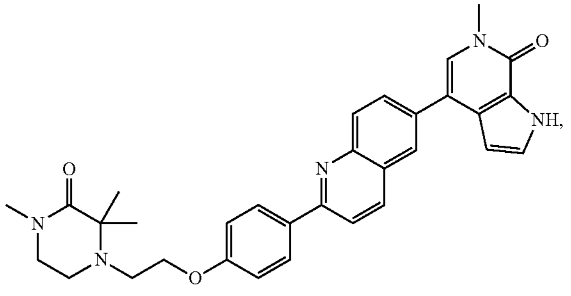
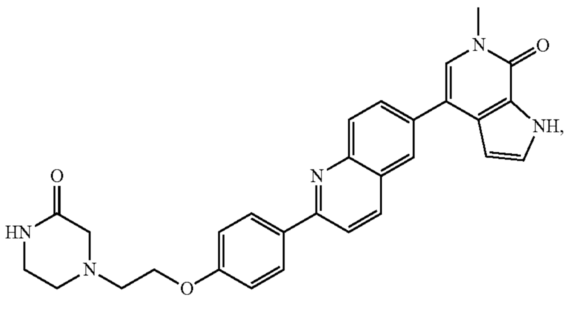

-continued
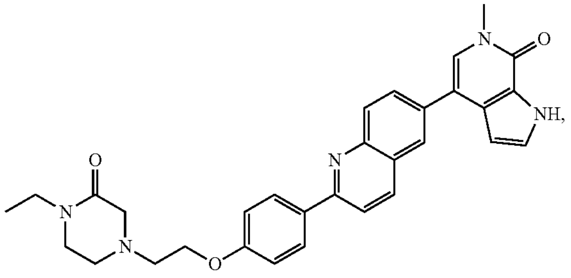
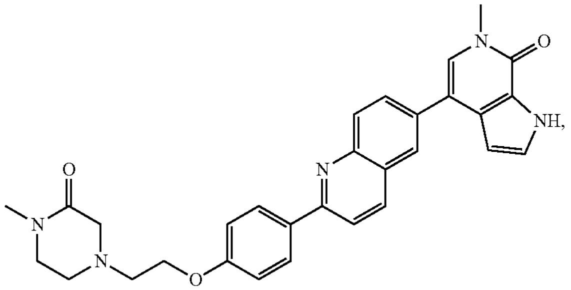
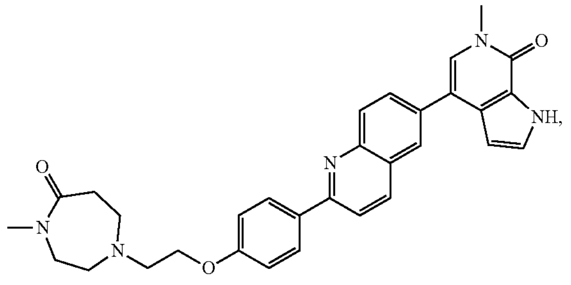
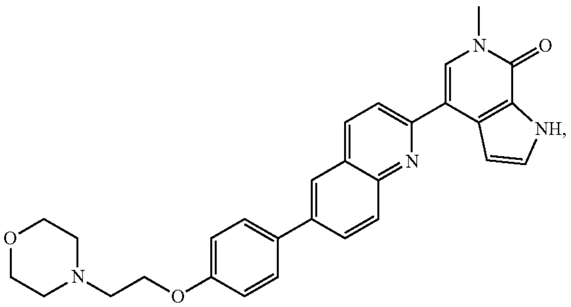
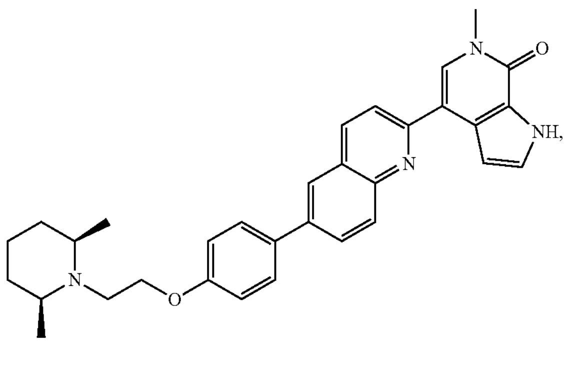
-continued
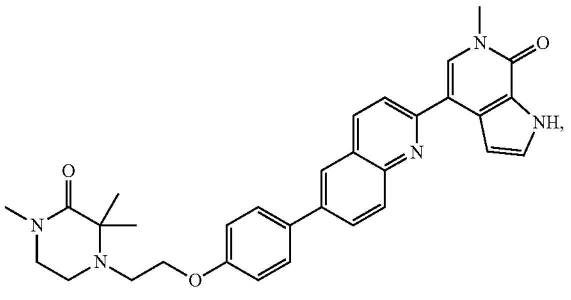
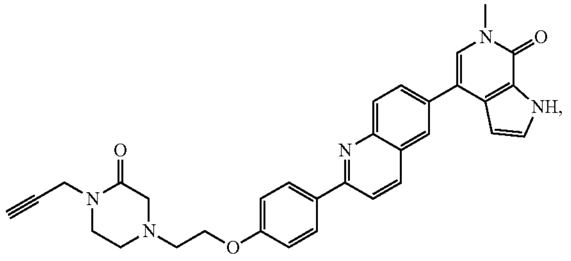
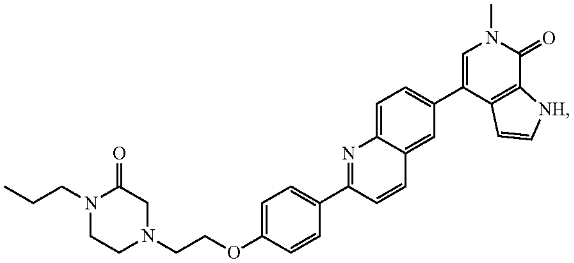
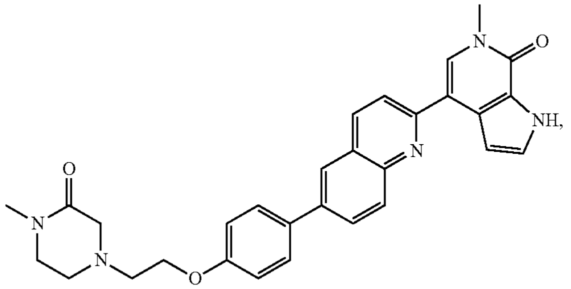
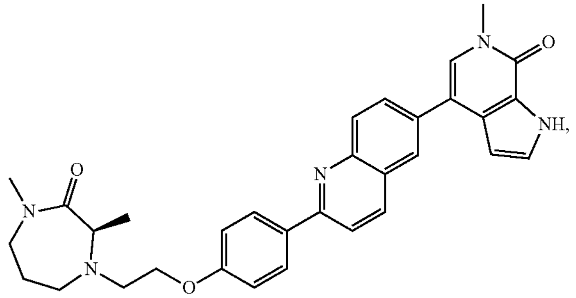
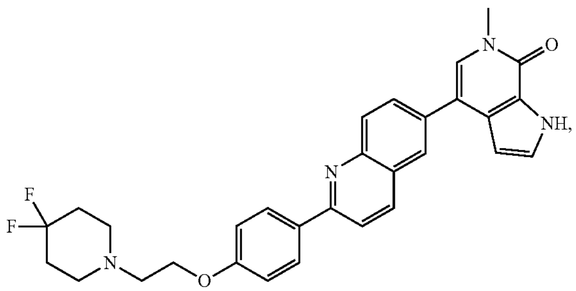

-continued
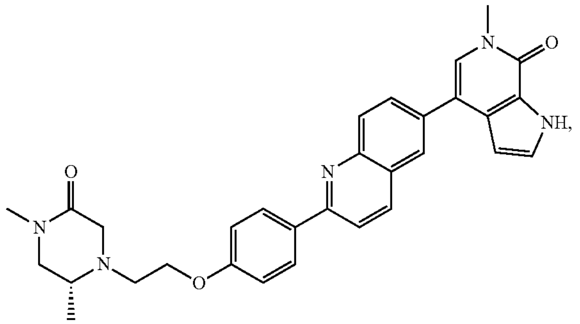
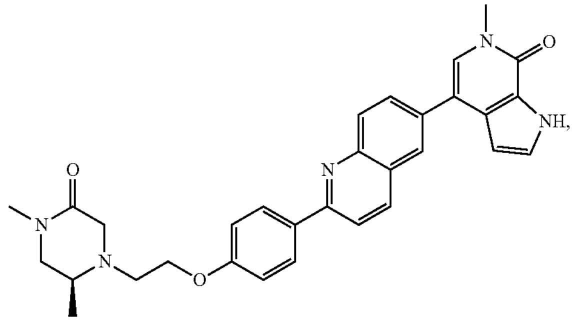
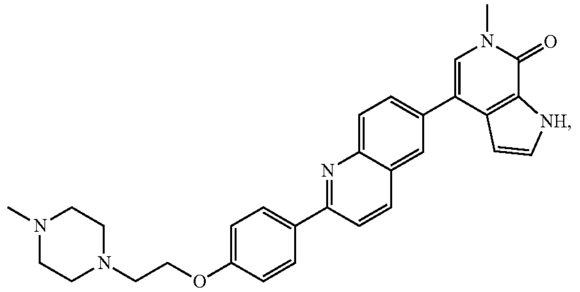
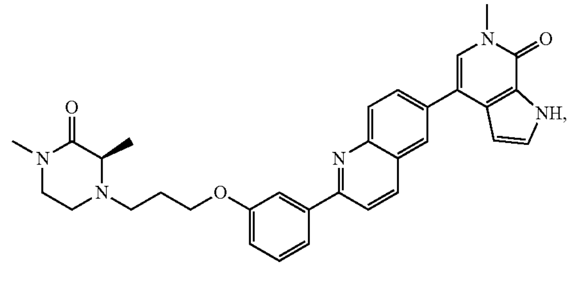
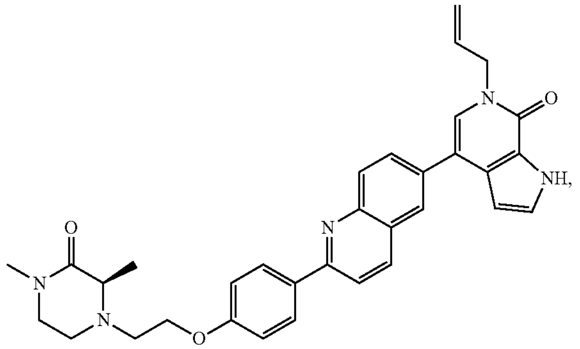
-continued
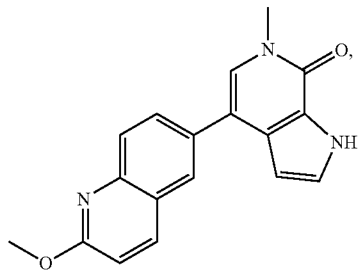
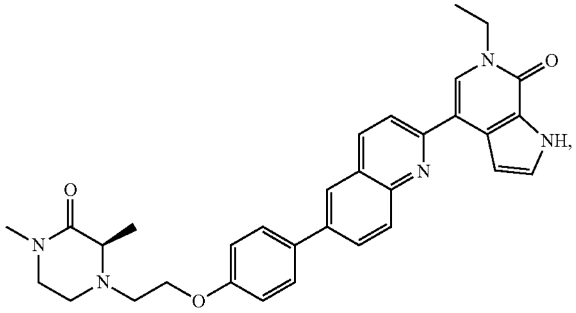
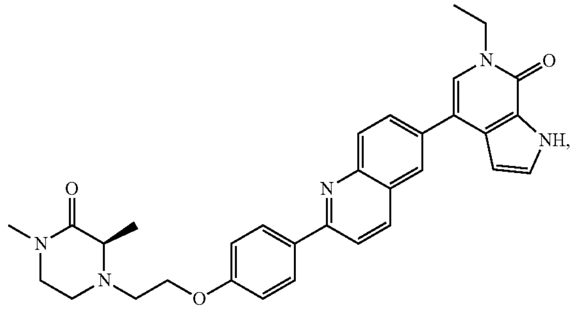
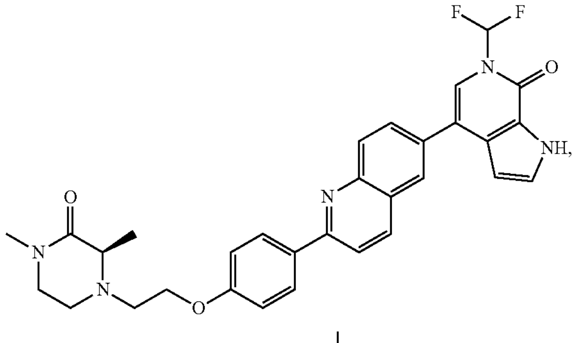
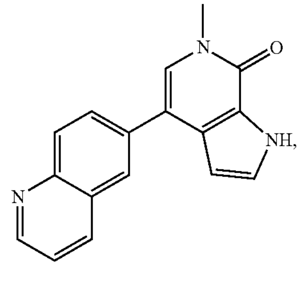

-continued

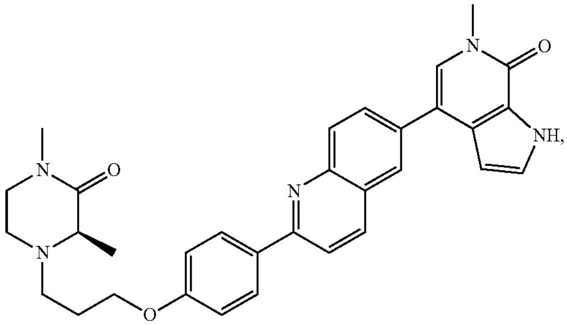
,

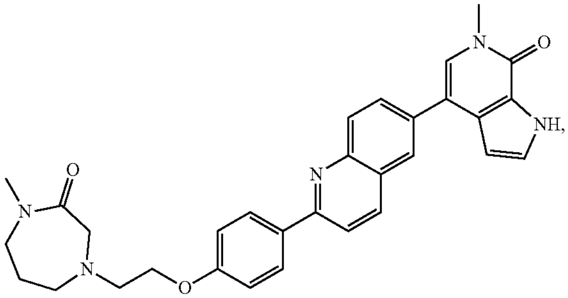
,

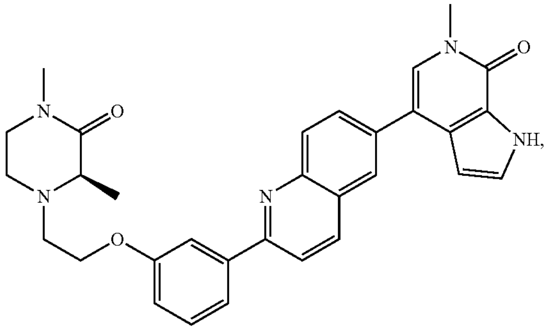
,

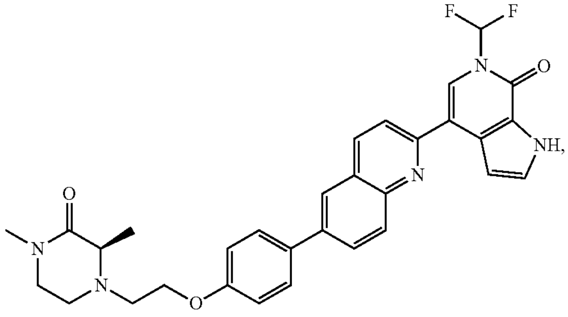
,

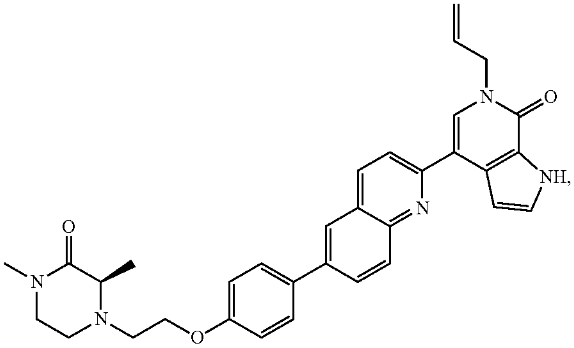
,

-continued

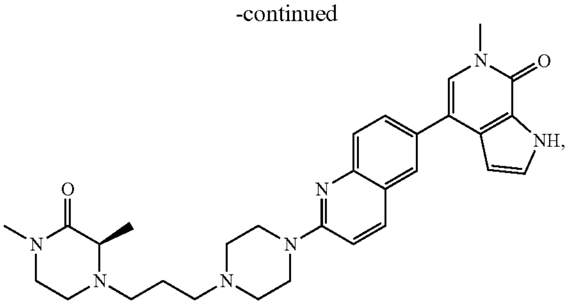
,

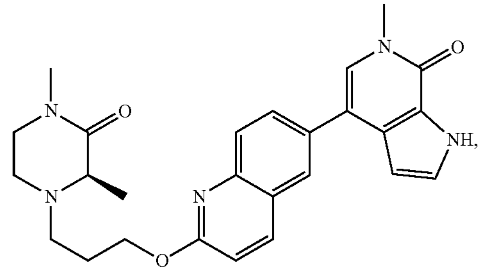
,

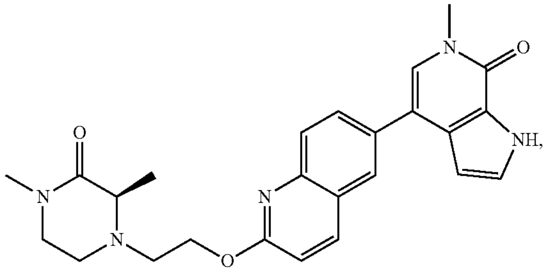
,

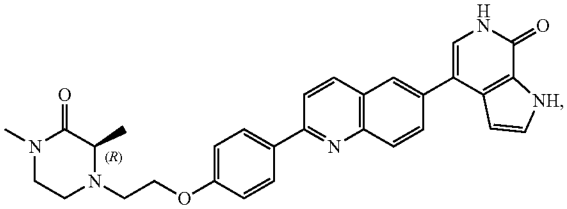
,

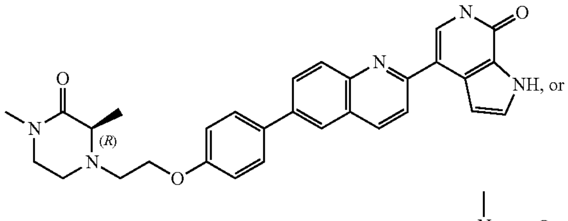
, or

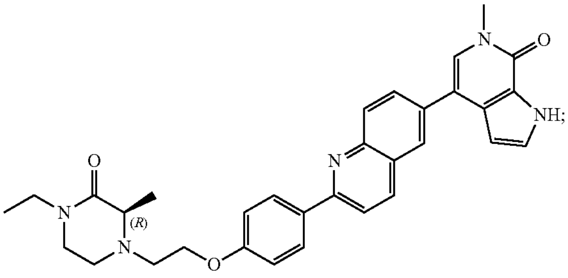
;

or a pharmaceutically acceptable salt thereof.

14. A pharmaceutical composition comprising:

a) the compound of claim 1; and b) an excipient and/or a pharmaceutically acceptable carrier.

15. A method of treating a patient with facioscapulohumeral muscular dystrophy (FSHD) comprising administering to the patient a therapeutically effective amount of an inhibitor of a bromo- and extra-terminal (BET) domain protein, wherein the inhibitor is the compound of claim 1.

16. The method of claim 15, wherein the method further comprises administering a second therapy for FSHD.

17. The method of claim 16, wherein the second therapy is administered before the inhibitor of BET.

18. The method of claim 16, wherein the second therapy is a β-2 adrenergic receptor agonist.

19. The method of claim 16, wherein the second therapy is an inhibitor of p38 is an inhibitor of p38α and p38β.

* * * * *